(12) United States Patent
Javanbakht et al.

(10) Patent No.: US 12,281,307 B2
(45) Date of Patent: Apr. 22, 2025

(54) OLIGOMERS AND OLIGOMER CONJUGATES

(71) Applicant: Hoffmann-La Roche Inc., Little Falls, NJ (US)

(72) Inventors: Hassan Javanbakht, Basel (CH); Søren Ottosen, Glostrup (DK); Morten Lindow, Copenhagen (DK)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 18/114,626

(22) Filed: Feb. 27, 2023

(65) Prior Publication Data

US 2024/0035032 A1    Feb. 1, 2024

Related U.S. Application Data

(60) Division of application No. 17/013,374, filed on Sep. 4, 2020, now Pat. No. 11,591,598, which is a division of application No. 16/530,765, filed on Aug. 2, 2019, now Pat. No. 10,767,181, which is a continuation of application No. 14/714,004, filed on May 15, 2015, now Pat. No. 10,421,967.

(30) Foreign Application Priority Data

May 15, 2014   (GB) ..................... 1408623

(51) Int. Cl.
| | | |
|---|---|---|
| C12N 15/113 | (2010.01) | |
| A61K 31/713 | (2006.01) | |
| A61K 47/54 | (2017.01) | |
| C12N 15/11 | (2006.01) | |
| C12N 15/36 | (2006.01) | |
| C12N 15/51 | (2006.01) | |

(52) U.S. Cl.
CPC ........ *C12N 15/1131* (2013.01); *A61K 31/713* (2013.01); *A61K 47/549* (2017.08); *A61K 47/554* (2017.08); *C12N 15/1133* (2013.01); *C12N 2310/11* (2013.01); *C12N 2310/315* (2013.01); *C12N 2310/3231* (2013.01); *C12N 2310/3341* (2013.01); *C12N 2310/346* (2013.01); *C12N 2310/351* (2013.01); *C12N 2310/3515* (2013.01); *C12N 2320/30* (2013.01)

(58) Field of Classification Search
CPC .. A61P 31/20; A61P 1/16; A61P 31/12; A61P 3/00; A61K 31/713
See application file for complete search history.

(56) References Cited

U.S. PATENT DOCUMENTS

| | | |
|---|---|---|
| 4,587,044 A | 9/1986 | Miller et al. |
| 4,667,025 A | 5/1987 | Miyoshi et al. |
| 4,740,463 A | 4/1988 | Weinberg et al. |
| 4,934,210 A | 4/1990 | Levenson et al. |
| 4,948,882 A | 8/1990 | Ruth |
| 4,962,029 A | 10/1990 | Levenson et al. |
| 5,108,921 A | 4/1992 | Low et al. |
| 5,132,963 A | 5/1992 | Pieles et al. |
| 5,138,045 A | 8/1992 | Cook et al. |
| 5,245,022 A | 9/1993 | Weis et al. |
| 5,254,469 A | 10/1993 | Warren, II et al. |
| 5,391,723 A | 2/1995 | Priest |
| 5,486,603 A | 1/1996 | Buhr |
| 5,510,475 A | 4/1996 | Agrawal et al. |
| 5,512,667 A | 4/1996 | Reed et al. |
| 5,525,465 A | 6/1996 | Haralambidis et al. |
| 5,541,313 A | 7/1996 | Ruth |
| 5,545,730 A | 8/1996 | Urdea et al. |
| 5,552,538 A | 9/1996 | Urdea et al. |
| 5,574,141 A | 11/1996 | Seliger et al. |
| 5,580,731 A | 12/1996 | Chang et al. |
| 5,608,046 A | 3/1997 | Cook et al. |
| 5,684,142 A | 11/1997 | Mishra |
| 5,770,716 A | 6/1998 | Khan et al. |
| 5,856,438 A | 1/1999 | Little, II |
| 5,885,968 A | 3/1999 | Biessen |
| 5,994,517 A | 11/1999 | Ts'o et al. |
| 6,086,900 A | 7/2000 | Draper |
| 6,096,875 A | 8/2000 | Klan et al. |
| 6,166,089 A | 12/2000 | Kozak |
| 6,335,432 B1 | 1/2002 | Segev |
| 6,335,437 B1 | 1/2002 | Manoharan |
| 7,087,229 B2 | 8/2006 | Zhao et al. |
| 7,399,843 B2 | 7/2008 | Seth et al. |
| 8,598,334 B2 | 12/2013 | Hamatake |
| 8,642,752 B2 | 2/2014 | Swayze et al. |
| 10,421,967 B2 | 9/2019 | Javanbakh et al. |

(Continued)

FOREIGN PATENT DOCUMENTS

| | | |
|---|---|---|
| CA | 2921162 | 11/2014 |
| EP | 1222309 | 7/2002 |

(Continued)

OTHER PUBLICATIONS

U.S. Appl. No. 60/977,409, Hansen et al., filed Oct. 4, 2007.
*Antisense Research and Applications*, S. T. Crooke and B. Lebleu, Eds., CRC Press, Boca Raton. Fla., 1993, p. 303-350.
Asseline et al. "Nucleic acid-binding molecules with high affinity and base sequence specificity; Interealating agents covalently linked to oligodeoxy nucleotides," Proc. Natl. Acad. Sci. USA, Jun. 1984, 81:3297-3301.
Baenziger et al., "Galactose and N-acetylgalactosamine-specific endocytosis of glycopeptides by isolated hepatocytes." Cell, Nov. 1980. 22(2):611-620.

(Continued)

*Primary Examiner* — Barry A Chestnut
(74) *Attorney, Agent, or Firm* — Bradley E. Davis

(57) ABSTRACT

The present invention relates to an oligomer conjugate for use in the treatment of a viral disorder. The oligomer conjugate comprises: a) an oligomer capable of modulating a target sequence in HBx and/or HBsAg of Hepatitis B Virus (HBV) to treat said viral disorder; and b) a carrier component capable of delivering the oligomer to the liver which is linked, preferably conjugated, to the oligomer.

1 Claim, 25 Drawing Sheets

Specification includes a Sequence Listing.

(56) References Cited

U.S. PATENT DOCUMENTS

| | | |
|---|---|---|
| 10,767,181 B2 | 9/2020 | Javanbakh et al. |
| 2002/0058639 A1 | 5/2002 | Manoharan |
| 2003/0148983 A1 | 8/2003 | Morrissey et al. |
| 2003/0206887 A1 | 11/2003 | Morrissey et al. |
| 2004/0054156 A1 | 3/2004 | Draper et al. |
| 2004/0127446 A1 | 7/2004 | Blatt et al. |
| 2012/0207709 A1 | 8/2012 | Hamatake |
| 2013/0035366 A1 | 2/2013 | Swayze et al. |
| 2020/0024603 A1 | 1/2020 | Javanbakh et al. |

FOREIGN PATENT DOCUMENTS

| | | |
|---|---|---|
| EP | 1495769 | 1/2005 |
| EP | 2512491 | 10/2012 |
| JP | 2004512810 | 4/2004 |
| JP | 2004532022 | 10/2004 |
| JP | 2012524096 | 10/2012 |
| JP | 2013507933 | 3/2013 |
| JP | 2014504295 | 2/2014 |
| WO | WO 91/04733 | 4/1991 |
| WO | WO 93/01286 | 1/1993 |
| WO | WO 95/17414 | 6/1995 |
| WO | WO 93/19433 | 7/1995 |
| WO | WO 96/11205 | 4/1996 |
| WO | WO 96/39502 | 12/1996 |
| WO | WO 96/40961 | 12/1996 |
| WO | WO 97/03211 | 1/1997 |
| WO | WO 98/03533 | 1/1998 |
| WO | WO 98/52614 | 11/1998 |
| WO | WO 99/02673 | 1/1999 |
| WO | WO 99/14226 | 3/1999 |
| WO | WO 99/64449 | 12/1999 |
| WO | WO 99/65925 | 12/1999 |
| WO | WO 00/15265 | 3/2000 |
| WO | WO 01/16312 | 3/2001 |
| WO | WO 2001/23613 | 4/2001 |
| WO | WO 02/081494 | 10/2002 |
| WO | WO 2004/046160 | 6/2004 |
| WO | WO 2005/921800 | 3/2005 |
| WO | WO 2007/031091 | 3/2007 |
| WO | WO 2007/134181 | 11/2007 |
| WO | WO 2007/146511 | 12/2007 |
| WO | WO 2008/034122 | 3/2008 |
| WO | WO 2008/34123 | 3/2008 |
| WO | WO 2008/113832 | 9/2008 |
| WO | WO 2008/150729 | 12/2008 |
| WO | WO 2008/154401 | 12/2008 |
| WO | WO 2009/006478 | 1/2009 |
| WO | WO 2009/06764 | 5/2009 |
| WO | WO 2009/360316 | 5/2009 |
| WO | WO 200 7901 | 7/2009 |
| WO | WO 2009/100320 | 8/2009 |
| WO | WO 2009/124238 | 10/2009 |
| WO | WO 2009/124295 | 10/2009 |
| WO | WO 2009/126933 | 10/2009 |
| WO | WO 2010/036698 | 4/2010 |
| WO | WO 2010/120861 | 10/2010 |
| WO | WO 2011/017521 | 2/2011 |
| WO | WO 2011/085102 | 2/2011 |
| WO | WO 2011/047312 | 4/2011 |
| WO | WO 2011/115818 | 9/2011 |
| WO | WO 2012/024170 | 2/2012 |
| WO | WO 2012/082046 | 6/2012 |
| WO | WO 2012/083046 | 6/2012 |
| WO | WO 2012/089332 | 7/2012 |
| WO | WO 2012/145674 | 10/2012 |
| WO | WO 2012/145697 | 10/2012 |
| WO | WO 2013/003520 | 1/2013 |
| WO | WO 2013/040429 | 3/2013 |
| WO | WO 2014/076195 | 5/2014 |
| WO | WO 2014/076196 | 5/2014 |
| WO | WO 2014/118267 | 8/2014 |
| WO | WO 2014/179620 | 11/2014 |
| WO | WO 2014/179627 | 11/2014 |
| WO | WO 2014/207232 | 12/2014 |
| WO | WO 2016/055601 | 4/2016 |

OTHER PUBLICATIONS

Bhat et al, "RG-101 a GalNAC-conjugated anti-miR employing a unique mechanism of action by targeting host factor microRNA-122 (miR-122), demonstrates potent activity and reduction of HCV in preclinical studies." AASLD Liverlearning®Neben S. Nov. 4, 2013; 42786, Retrieved from the Internet: URL<http://www.reguhusrx.com/wp-content/uploads/2013/11/RT13-002-Neben_AASLD-LFPfinal.pdf>, 1 page.

Bhat et al., "RG-101, a GalNAC-conjugated anti-mR employing a unique mechanism of action by targeting host factor microRNA-122 (miR-122), demonstrates potent actvity and redaction of HCV in preclinical studies," Hepatology, 64 Annual meeting of the american association for the study of liver diseases, 2013, vol. 58:13934.

Bhat et al., "RG-101, & GalNAC-conjugated anti-miR employing a unique mechanism of action by targeting host factor microRNA-122 (HR-122), demonstrates polent activity and reduction of HCV in preclinical studies, " Hepatology: 64 Annual meeting of the american association for the study of liver diseases. Nov. 1-5, 2013. 1 page, poster.

Biessen et al., "Synthesis of Cluster Galactosides with High Affinity for the Hepatic Asialoglycoprotein Receptor" J. Med. Chem, Apr. 1995, 39:1538-1546.

Biessen et al., "Targeted delivery of oligodeoxynucleotides to parenchymal liver cells in vivo." Biochemical Journal, Jun. 1999. 340(3):783-792.

Bramsen et al.. "Development of therapeutic-grade small interfering RNAs by chemical engineering " Frontiers in Genetics. Aug. 2012, 3(article 154):1-22.

Chen et al., "RNAI for Treating Hepatitis B Viral Infection. " Pharmaceutical Research, Jan. 2008. 25(1):72-86.

Christensen et al., "Intercalating nucleic acids containing insertions of 1-0-(1-pyrenylmethyl)glycerol: stabilisation of dsDNA and discrimination of DNA over RNA," Nacl. Acids. Res., Nov. 15, 2002 430(22):4918-4925.

Connolly et al., "Binding and Endocytosis of Cluster Glycosides by Rabbit: Hepatocytes," Journal of Biological Chemistry, Jan. 1982, 257(2):939-945.

Delong et al., "Novel cationic amphiphiles as delivery agents for antisense oligonucleotides." Nuel. Acid Res. Aug. 15, 1999, 27(16)3334-3341.

Ebi.ac.uk [online]. "Sequence U95531.1: Hepatitis B virus subtype ayw, complete genome," first public Jun. 8, 1997, Retrievied from the Internet: URL <https://www.ebi.ac.uk/ena/data/view/U95551>, 1 page.

Felgner et al., "Lipofection: A highly efficient, lipid-mediated DNA-transfection procedure," Proc. Natl. Acad. Sci., Nov. 1987, 84:7413-7417.

Fluiter et al., "Filling the gap in LNA antisense oligo gapmers: the effects of unlocked nucleic acid. (UNA) and 40-C-hydroxymethyl-DNA modifications on RNase H recmitment and efficacy of as LNA gapmer," Mol. Biosyst., Aug. 2009, 5:838-843.

Freier et al., "The ups and downs of nucleic acid duplex stability; structure-stability studies on chemically modified DNA RNA duplexes," Nucl. Acid Res., Nov. 1997, 25(22):4429-4443.

Glen Research Catalogue No. 10-1920-xx, http://www.glenresearch.com/ProductFiles/Product.php?item=10-1920, 2 pages.

Glen Research Catalogue No. 10-1922-xx, http://www.glenresearch.com/ProductFiles/Product.php?item=10-1922, 2 pages.

Glen Research Catalogue No. 10-1925-xx, http://www.glenresearch.com/ProductFiles/Product.php?item=10-1925, 2 pages.

Hangeland et al., "Cell-Type Specific and Liganel Specific Enhancement of Cellular Uptake of Oligodeoxynucleoside-Methylphosphonates Covalently Linked with a Neoglycopeptide, YEE(ah- GalNAc)." Bioconjug Chem, Nov.-Dec. 1995, 6(6)695-701.

(56) References Cited

OTHER PUBLICATIONS

Iobst et al. "Selective Sugar Binding to the Carbohydrate Recognition Domains of the Rat Hepatic and Macrophage Asialoglycoprotein Receptors," The Journal of Biological Chemistry, Mar. 22, 1996, 271(12):6686-6693.

Klein et al., "Inhibitation of Hepatitis B Venas Replication In Vivo by Nucleoside Analogues and siRNA," Gastroenterology, Jul. 2003, 125(1):9-18.

Korba et al., "Antisense oligonucleotides are effective inhibitors of hepatitis B virus replication in vitro,"Antiviral Research, Nov. 1995, 28(3):225-242.

Kreig, et al, "Uptake of Oligodeoxyribonucleoides by Lymphoid Cells Is Heterogeneous and Inducible," Antisense Research and Development, Summer, 1(2):161-171.

Kumar et al. "The first analogues of LNA (locked nucleic acids): phosphorothioate-LNA and 2'-thio-LNA," Bioorg, & Med. Chem. Lett., Aug. 18, 1998, 8:2219-2222.

Langer, "New methods of drug delivery," Science, Sep. 1990, 249(4976):1527-1533.

Leamon et al., "Delivery of macromolecules into living cells: A method that expolits folate receptor endocytosis," Proc. Natl. Acad. Sci. Jul. 1991, 88(13):5572-5576.

Lamaitre et al, "Specific antiviral activity of a poly(L-lysine)-conjugated oligodeoxyribonucleotide sequence complementary to vescular stomatitis virus N protein mRNA initiation site," Proc. Natl. Acd. Sci. USA, Feb. 1987, 84(3):648-652.

Malone et al., "Catonic liposome-mediated RNA transfection,"Proc. Natl. Acad. Sci., Aug. 1989, 86(16):6077-6081.

Manoharan et al., "Novel Functionalization of the Sugar Moiety of Nucleic Acids for Multiple Labeling in the Minor Groove," Tetrahedron Letter, Dec. 1991, 32(49):7171-7174.

Merwin et al., "Targeted delivery of DNA using YEE(GaINAcAH)3, a synthetic glycopeptide ligand for the asiatoglycoprotein receptor," Bioconjug Chem, Nov.-Dec. 1994 5(6):612-20.

Minshull et al. "The use of single-stranded DNA and RNase H to promote quantitive 'hybrid arrest of translation" of mRNA/DNA hybrids in reticulocyte lysanre cell-free translations," Nucleic Acids Research, Aug. 1986, 14(16):6433-6451.

Oh et al. "Inhibition of Hepatitis B Virus Expression by the Antisense Oligodeoxyribonucleotides," Korean Journal of Biochemistry, 1993, 25(2)115-120.

Plank et al., "Gene Transfer into Hepatocytes Using Asialoglycoprotein Receptor Mediated Endocytosis of DNA Completed with an Artificial Tetra-Antennary Galatose Ligard," Bioconjug Chem. Nov.-Dec. 1992, 3(6):533-539.

Reinis et al., "Inhibition of hepatistis B virus surface gene expression by antisense oligodeoxynucleotides in a human hepatoma cell line," Folia Biologica, 1993, 39(5):262-269.

Seth et al., "Synthesis and biophysical evaluation of 2',4'-constrained 2'O-methoxyethyl and 2',4'-constrained 2'O-ethyl nucleic acid analogues," J Org Chem. Mar. 2010, 75(5):1569-1581.

Singh et al., "LNA (locked nucleic acids): synthesis and high-affinity nucleic acid recognition," Chem. Commun, 1998, 4:455-456.

Szostak et al., "Hybridization with synthetic Oligonucleotides," Meth. Enzymol, Jan. 1979, 68:419-428.

Uhlmann, "Recent advances in the medincal chemistry of antisense Oligonucleotides," Curr. Opinion in Drug Development. mar. 2000. 3(2):203-213.

Vester et al., "Chemically modified oligonucleotides with efficient RNase H response," Bioorg Med Chem Lett, Apr. 1, 2008 18(7):2296-300.

Vives et al. "Lipophilic pro-oligonucleotides ar erapidly and efficiently internalized in HeLa cells," Nucl. Acids Res. Oct. 1999, 27(20):4071-4076.

Wagner et al., "Transferrin-polycation conjugates as carriers for DNA uptake into cells," Proc. Natl. Acad. Sci. USA, May 1990, 87(9):3410-3414.

Winkler, "Oligonucleotides conjugates for therepeutic applications," Therepeutic delivery, Jul. 2013, 4(7):791-809.

Wolfram et al, "Mechanisms and optimization of in vivo delivery of lipophilic siRNAs," Nature Biotechnology, Oct. 2007, 25(10):1149-1157.

Woodell et al., "Hepatocyte-targeted RNAi Therapeutics for the Treatment of Chronic Hepatitis B Virus Infection," Molecular Therapy, May 2013, 21(5):973-985.

Wu et al., "Specific Inhibition of Hepatitis B Viral Gene Expression in Vitro by targeted antisense oligonucleotides," J of BioChem, 1992 267(18):12436-12439.

Yang et al., "A mouse model for HBV immunotolerance and immunotherapy," Cellular & Molecular Immunology, Jan. 2014, 11:71-78.

Yang et al., "HPMA Polymer-based Site-specific Delivery of Oligonucleotides to Hapatic Stellate Cells," Bioconjug Chem, Feb. 2009 20(2): 213-21.

Ying et al., "Hepatitis B virus is inhibited by RNA interference in cell culture and in mice," Antiviral Research Jan. 2207. 73(1):21-30.

Zatseptin et al., "Synthesis and Applications of Oligonucleotide Carbohydrate Conjugates," Chem Biodivers, Oct. 2004, 1(10): 1401-1417.

Zheng et al., "Distribution and anti-HBV effects of antisense pro-oligodeoxynu-cleotides conjugated to galactosylated poly-L-lysine," World J Gastroenterol., 2003, 9(6):1250-1255.

Conj 3=

Conj 4=

Conj 1a= GalNAc1

Conj 2a = GalNAc2

Conj 3a=

Phosphorthioate    2'-O-Methyl    2'-MOE    2'-Fluoro

2'-AP    HNA    CeNA    PNA

Morpholino    2'-F-ANA    2'-(3-hydroxy)propyl    3'-Phosphoramidate

Boranophosphates

SEQ ID NO: 808

SEQ ID NO: 814

SEQ ID NO: 815

SEQ ID NO: 825

SEQ ID NO: 826

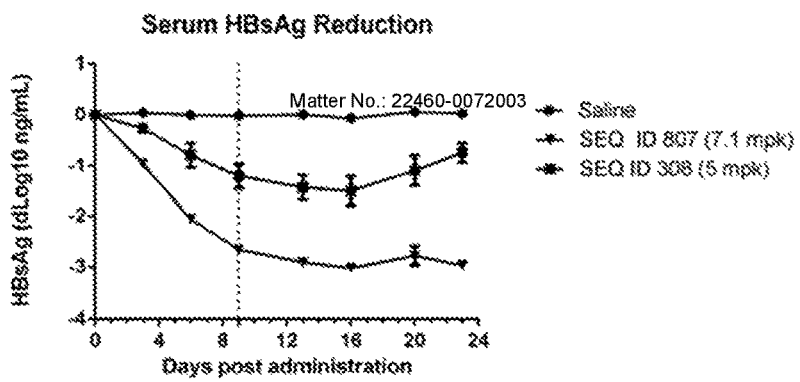
FIG. 15A
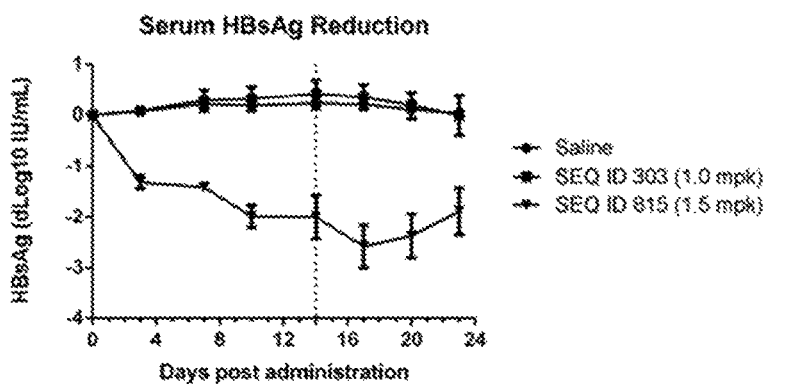
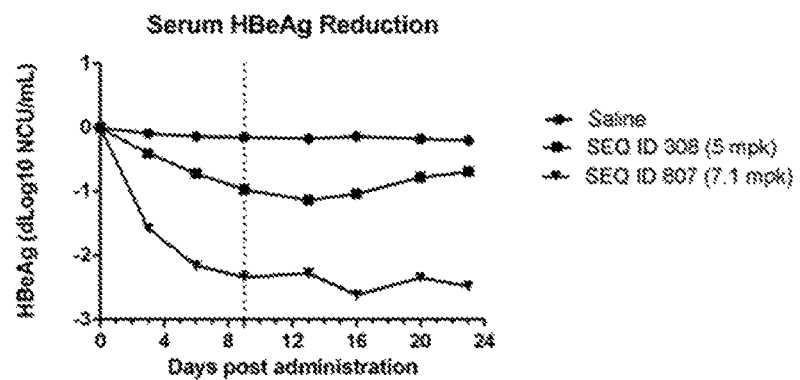
FIG. 15B
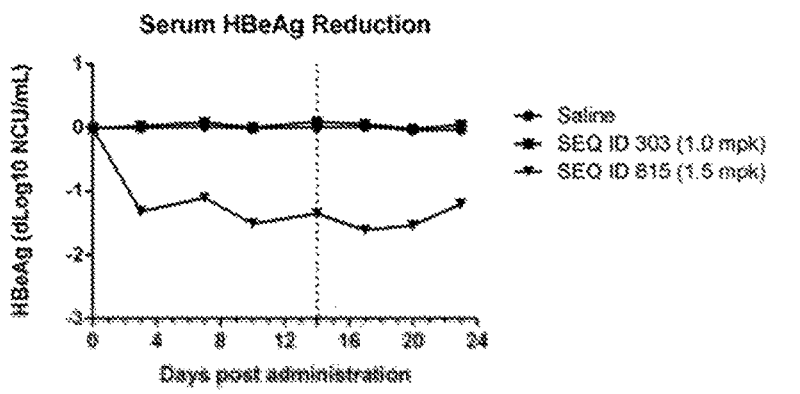

OLIGOMERS AND OLIGOMER CONJUGATES

CROSS REFERENCE TO RELATED APPLICATIONS

This application is a divisional and claims priority to U.S. application Ser. No. 17/013,374, filed Sep. 4, 2020, which is a divisional and claims priority to U.S. application Ser. No. 16/530,765, filed Aug. 2, 2019, which is a continuation and claims priority to U.S. application Ser. No. 14/714,004, filed May 15, 2015, which claims priority benefit of Great Britain Patent Application No. 1408623.5 having a filing date of May 15, 2014, the entire contents of which are incorporated herein by reference in its entirety.

SEQUENCE LISTING

This application contains a Sequence Listing that has been submitted electronically as an XML file named 22460-0072004.xml. The XML file, created on May 30, 2023, is 1,859,345 bytes in size. The material in the XML file is hereby incorporated by reference in its entirety.

FIELD OF INVENTION

The invention relates to the field of oligomer therapeutics, and in particular to oligomers and oligomer conjugates targeting Hepatitis B Virus (HBV). In particular, the invention relates to the field of oligomer conjugates therapeutics wherein antisense oligonucleotides are attached to a carrier component. In certain aspects, the invention relates to the field of oligomer conjugates therapeutics wherein antisense oligonucleotides are covalently attached to a carrier component by means of physiologically labile linkers.

More specifically, the present invention relates to oligomers, in particular oligomer conjugates therapeutics, that target HBV mRNA in a cell leading to treatment of the viral disorders.

BACKGROUND

Molecular strategies are being developed to modulate unwanted gene expression that either directly causes, participates in, or aggravates a disease state. One such strategy involves inhibiting gene expression with oligonucleotides complementary in sequence to the messenger RNA of a deleterious target gene. The messenger RNA strand is a copy of the coding DNA strand and is therefore, as the DNA strand, called the sense strand. Oligonucleotides that hybridize to the sense strand are called antisense oligonucleotides. Binding of these strands to mRNA interferes with the translation process and consequently with gene expression.

Certain nucleotide-based compounds have been utilized in various therapeutic applications. In particular, various oligonucleotides have been investigated including single-stranded and double-stranded oligonucleotides, and analogues. To be useful in in vivo applications, an oligonucleotide must have a plethora of properties including the ability to penetrate a cell membrane, have good resistance to extra- and intracellular nucleases, have high affinity and specificity for the target and preferably have the ability to recruit endogenous enzymes such as RNAseH, RNAaseIII, RNAseL etc.

A fundamental property of oligonucleotides that underlies many of their potential therapeutic applications is their ability to recognize and hybridize specifically to complementary single stranded nucleic acids employing either Watson-Crick hydrogen bonding (A-T and G-C) or other hydrogen bonding schemes such as the Hoogsteen/reverse Hoogsteen mode. Affinity and specificity are properties commonly employed to characterize hybridization characteristics of a particular oligonucleotide. Affinity is a measure of the binding strength of the oligonucleotide to its complementary target (expressed as the rmostability (Tm) of the duplex). Each nucleobase pair in the duplex adds to the rmostability and thus affinity increases with increasing size (number of nucleobases) of the oligonucleotide. Specificity is a measure of the ability of the oligonucleotide to discriminate between a fully complementary and a mismatched target sequence.

Modified nucleic acids are known to be used to improve for example stabilisation of the oligonucleotides, in particular for the gapmer designs, such as when 1 or more modified nucleotides are present in either or both of the wing regions. Examples of modifications include 2'-O-alkyl-RNA units, 2'-amino-DNA units, 2'-fluoro-DNA units, LNA units, arabino nucleic acid (ANA) units, 2'-fluoro-ANA units, HNA units, INA (intercalating nucleic acid—Christensen, 2002. Nucl. Acids. Res. 2002 30: 4918-4925, hereby incorporated by reference) units, 2'MOE units, ENA (ethylene nucleic acid), UNA (Unlocked Nucleic Acid, Fluiter et al., Mol. Biosyst., 2009, 10, 1039), Tricyclo DNA (R. Steffens & C. J. Leumann, J. Am. Chem. Soc, 1997, 119, 11548-49), cET-LNA (shown herein), and LNA. FIG. 4 presents drawings of some of these analogues.

A particular efficacious modified nucleic acid is referred to as a Locked Nucleic Acids (LNA). LNAs have been reported in the art—for example see International Patent Application WO 99/14226; P. Nielsen et al, J. Chem. Soc., Perkin Trans. 1, 1997, 3423; P. Nielsen et al., Chem. Commun., 1997, 9, 825; N. K. Christensen et al., J. Am. Chem. Soc., 1998, 120, 5458; A. A. Koshkin et al., J. Org. Chem., 1998, 63, 2778; A. A Koshkin et al. J. Am. Chem. Soc. 1998, 120, 13252-53; Kumar et al. Bioorg, & Med. Chem. Lett., 1998, 8, 2219-2222; and S. Obika et al., Bioorg. Med. Chem. Lett., 1999, 515. Interestingly, incorporation of LNA units containing a 2'-O,4'-C-methylene bridge into an oligonucleotide sequence leads to an unprecedented improvement in the hybridization stability of the modified oligonucleotide (see above and e.g., S. K. Singh et al., Chem. Commun, 1998, 455). Oligonucleotides comprising the 2'-O,4'-C-methylene bridge (LNA) units and also the corresponding 2'-thio-LNA (thio-LNA), 2'-HN-LNA (amino-LNA), and 2'-N(R)-LNA (amino-R-LNA) analogue, form duplexes with complementary DNA and RNA with thermal stabilities not previously observed for bi- and tri-cyclic nucleosides modified oligonucleotides. The increase in Tm per modification varies from +3 to +11° C., and furthermore, the selectivity is also improved. No other DNA analogue has reproducibly shown such high affinity for nucleic acids.

In a particular aspect, the present invention relates to hepatitis B virus (HBV) therapies. Hepatitis B is a viral disease caused by the hepatitis B virus (HBV). It is transmitted parenterally by contaminated material such as blood and blood products, contaminated needles, sexually and vertically from infected or carrier mothers to their offspring. In those areas of the world where the disease is common vertical transmission at an early age results in a high proportion of infected individuals becoming chronic carriers of hepatitis B. It is estimated by the World Health Organization that more than 2 billion people have been infected worldwide, with about 4 million acute cases per year, 1 million deaths per year, and 350-400 million chronic carriers. Approximately 25% of carriers die from chronic hepatitis, cirrhosis, or liver cancer and nearly 75% of chronic carriers are Asian. Hepatitis B virus is the second most significant carcinogen behind tobacco, causing from 60% to 80% of all primary liver cancer. HBV is 100 times more contagious than HIV.

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes and via the specific binding of HBV surface antigens (HBV sAg). Once the virion has entered the cell, the viral cores and the encapsidated RC DNA are transported by host factors, via a nuclear localization signal, into the nucleus through the Impp/Impa nuclear transport receptors. Inside the nucleus, host DNA repair enzymes convert the RC DNA into cccDNA. cccDNA acts as the template for all viral mRNAs and as such, is responsible for HBV persistence in infected individuals. The transcripts produced from cccDNA are grouped into two categories; pgRNA and subgenomic RNA. Subgenomic transcripts encode for the three envelope (L, M and S) and X proteins, and pgRNA encodes for Pre-Core, Core, and Pol proteins. Inhibition of HBV gene expression or HBV RNA synthesis leads to the inhibition of HBV viral replication and antigens production. For instance, IFN-α was shown to inhibit HBV replication and viral HBsAg production by decreasing the transcription of pregenomic RNA (pgRNA) and subgenomic RNA from the HBV covalently closed circular DNA (cccDNA) minichromosome. All HBV viral mRNAs are capped and polyadenylated, and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence. The mature nucleocapsids containing RC DNA are enveloped with cellular lipids and viral L, M, and S proteins and then the infectious HBV particles are then released by budding at the intracellular membrane. Interestingly, non-infectious particles are also produced that greatly outnumber the infectious virions. These empty, enveloped particles (L, M and S), are referred to as subviral particles. Importantly, since subviral particles share the same envelope proteins and as infectious particles, it has been surmised that they act as decoys to the host immune system and have been used for HBV vaccines. The S, M, and L envelope proteins are expressed from a single ORF that contains three different start codons. All three proteins share a 226aa sequence, the S-domain, at their C-termini. M and L have additional pre-S domains, Pre-S2 and Pre-S2 and Pre-S1, respectively. However, it is the S-domain that has the HBsAg epitope.

Hepatitis B viral infections are a continuing medical problem because, like any rapidly-replicating infectious agent, there are continuing mutations that help some subpopulations of HBV become resistant to current treatment regimens. Currently the recommended therapies for chronic HBV infection by the American Association for the Study of Liver Diseases (AASLD) and the European Association for the Study of the Liver (EASL) include interferon alpha (INFa), pegylated interferon alpha-2a (Peg-IFN2a), entecavir, and tenofovir. However, typical interferon therapy is 48-weeks and results in serious and unpleasant side effects, and HBeAg seroconversion, 24 weeks after therapy has ceased, ranges from only 27-36%. Seroconversion of HBsAg is even lower—only 3% observed immediately after treatment ceases, with an increase to upwards of 12% after 5 years.

The secretion of antiviral cytokines in response to HBV infection by the hepatocytes and/or the intra-hepatic immune cells plays a central role in the viral clearance of infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). In particular, SVPs could contribute to the absence of antigen presentation by dendritic cells together with the lack of HBV-specific T cell immune activation to enable viral persistence. HBsAg quantification is a significant biomarker to predict the infection outcome; however the achievement of HBsAg seroconversion is rarely observed in chronically infected patients. The reduction of the SVP and HBsAg burden is thought as a pathway to recover anti-viral immune function and the seroconversion to HBsAg-negative after antiviral therapy can be seen as an indication as a functional cure and remains the ultimate goal of therapy. Therefore, targeting HBV gene expression leading to reduction of HBsAg together with HBV DNA levels in CHB patients may significantly improve CHB patient immune reactivation and remission.

The nucleoside and nucleotide therapies entecavir and tenofovir are successful at reducing viral load, but the rates of HBeAg seroconversion and HBsAg loss are even lower than those obtained using IFNa therapy. Other similar therapies, including lamivudine (3TC), telbivudine (LdT), and adefovir are also used, but for nucleoside/nucleotide therapies in general, the emergence of resistance limits therapeutic efficacy.

U.S. Pat. No. 8,598,334 and WO 2012/145697 mention the use of antisense oligonucleotides to target HBV.

The control of viral infection needs a tight surveillance of the host innate immune system which could respond within minutes to hours after infection to impact on the initial growth of the virus and limit the development of a chronic and persistent infection. Despite the available current treatments based on IFN and nucleos(t)ide analogues, the Hepatitis B virus (HBV) infection remains a major health problem worldwide which concerns an estimated 350 million chronic carriers who have a higher risk of liver cirrhosis and hepatocellular carcinoma.

There is a need for new anti-viral therapies, in particular anti-HBV therapies. There is also a need to have a therapeutic strategy that enables one to target different types of HBV genotypes.

SUMMARY OF INVENTION

The present invention relates to oligomer conjugates, uses thereof, methods using same, that are suitable for use in medicine, such as the treatment of a viral disorder.

In particular, the present invention provides an oligomer or an oligomer conjugate—that is suitable for use in the treatment of a viral disorder—wherein said oligomer or said oligomer of the oligomer conjugate is capable of modulating a target sequence of Hepatitis B Virus (HBV), preferably HBx or HBsAg of HBV. In certain embodiments a carrier component is conjugated to the oligomer.

The invention provides an oligomer or an oligomer conjugate as herein defined wherein the oligomer or oligomer component of the oligomer conjugate comprises at least 6, preferably at least 7, preferably at least 8, preferably at least 9, preferably at least 10 units, preferably at least 11 units, preferably at least 12 units, preferably at least 13 units, preferably at least 14 units, preferably at least 15 units, preferably at least 16 units that are at least 80% identical, preferably at least 85% identical, preferably at least 90% identical, preferably at least 91% identical, preferably at least 92% identical, preferably at least 93% identical, preferably at least 94% identical, preferably at least 95% identical, preferably at least 96% identical, preferably at least 97% identical, preferably at least 98% identical, preferably at least 99% identical, preferably identical to a region corresponding to a HBV HBx gene or HBsAg gene or to the reverse complement of a target region of a nucleic acid which encodes a HBV HBx or HBV HBsAg.

The invention provides an oligomer or an oligomer conjugate as herein defined wherein the oligomer or oligomer component of the oligomer conjugate comprises at least 6, preferably at least 7, preferably at least 8, preferably at least 9, preferably at least 10 units that are identical to a region corresponding to a HBV HBx gene or HBsAg gene or to the reverse complement of a target region of a nucleic acid which encodes a HBV HBx or HBV HBsAg.

For certain embodiments, the invention provides an oligomer or an oligomer conjugate as herein defined wherein the oligomer or oligomer component of the oligomer conjugate comprises less than 20 units, such as less than 19 units, such as less than 18 units, such as less than 17 units, such as 16 or less units.

For certain embodiments, the invention provides an oligomer or an oligomer conjugate as herein defined wherein the oligomer or oligomer component of the oligomer conjugate comprises 15 units or 16 units.

The invention provides a conjugate comprising the oligomer according to the invention, and at least one non-nucleotide or non-polynucleotide moiety covalently attached to said oligomer.

The invention provides a pharmaceutical composition comprising the oligomer or the conjugate according to the invention, and a pharmaceutically acceptable diluent (such as water or saline), carrier, salt or adjuvant.

The invention provides the oligomer or the conjugate according to the invention for use as a medicament, such as for the treatment of a viral disorder.

The invention provides the use of an oligomer or the conjugate according to the invention for the manufacture of a medicament for the treatment of a viral disorder.

The invention provides a method of treating a viral disorder, said method comprising administering an effective amount of, an oligomer, an oligomer conjugate or a pharmaceutical composition according to the invention, to an animal suffering from, or likely to suffer from a viral disorder (such as an animal suffering from or susceptible to the disease or disorder).

The invention provides a method of treating a viral disorder, said method comprising administering an effective amount of, an oligomer, an oligomer conjugate or a pharmaceutical composition according to the invention, to a non-human animal suffering from, or likely to suffer from a viral disorder (such as a non-human animal suffering from or susceptible to the disease or disorder).

The invention provides a method of treating a viral disorder, said method comprising administering an effective amount of, an oligomer, an oligomer conjugate or a pharmaceutical composition according to the invention, to a human patient suffering from, or likely to suffer from a viral disorder (such as a human patient suffering from or susceptible to the disease or disorder).

Also disclosed are methods of treating an animal (a non-human animal or a human) suspected of having, or susceptible to, a disease or condition, associated with expression, or over-expression of HBx or HBsAg by administering to the non-human animal or human a therapeutically or prophylactically effective amount of one or more of the oligomers, conjugates or pharmaceutical compositions of the invention. Further, methods of using oligomers for the inhibition of expression of HBx or HBsAg, and for treatment of diseases associated with activity of HBx or HBsAg are provided.

The invention further provides a pharmaceutical system comprising a pharmaceutical composition according to the invention and an additional pharmaceutical entity/therapeutic entity. The additional pharmaceutical entity may be an oligomer or oligomer conjugate according to the present invention. The additional pharmaceutical entity may be an oligomer or oligomer conjugate capable of modulating a target sequence in HBV which is not within HBx or HBsAg. For example, at least one oligomer or oligomer conjugate may be capable of modulating a target sequence within the gene or mRNA for HBV HBsAg, HBeAg, or DNA polymerase.

In one embodiment, a plurality of oligomers or conjugates according to the invention are administered to a subject in need of treatment. The oligomers or conjugates may administered with additional pharmaceutical/therapeutic agents.

In one embodiment, the disease or disorder or condition is associated with overexpression of HBx or HBsAg.

The invention provides for methods for modulating the expression of HBx or HBsAg in a cell or a tissue, the method comprising the step of contacting the cell or tissue, in vitro or in vivo, with an effective amount of one or more oligomers, conjugates, or pharmaceutical compositions thereof, to effect modulation of expression of HBx or HBsAg.

The invention provides for methods of inhibiting (e.g., by down-regulating) the expression of HBx in a cell or a tissue, the method comprising the step of contacting the cell or tissue, in vitro or in vivo, with an effective amount of one or more oligomers, conjugates, or pharmaceutical compositions thereof, to effect down-regulation of expression of HBx or HBsAg.

The invention provides for a method for the inhibition of HBx or HBsAg in a cell which is expressing HBx or HBsAg, said method comprising administering an oligomer, or a conjugate according to the invention to said cell so as to affect the inhibition of HBx or HBsAg in said cell.

Further provided are methods of down-regulating the expression of HBx or HBsAg in cells or tissues comprising contacting said cells or tissues, in vitro or in vivo, with an effective amount of one or more of the oligomers, oligomer conjugates or compositions of the invention.

Aspects of the present invention are now provided.

In one aspect, the present invention provides an oligomer conjugate for use in the treatment of a viral disorder, wherein said oligomer conjugate comprises:

a) at least one first oligomer region capable of modulating a target sequence of Hepatitis B Virus (HBV), preferably HBx or HBsAg of HBV, to treat said viral disorder; and
b) a carrier component. Preferably, for delivering said first oligomer to the liver.

In one aspect, the present invention provides an oligomer conjugate suitable for the treatment of a viral disorder, wherein said oligomer conjugate comprises:
a) at least one first oligomer region capable of modulating a target sequence of Hepatitis B Virus (HBV), preferably HBx or HBsAg of HBV, to treat said viral disorder; and
b) a carrier component. Preferably, for delivering said first oligomer to the liver.

In one aspect, the present invention provides a composition suitable for the treatment of a viral disorder, wherein said composition comprises an oligomer conjugate and at least one additional different oligonucleotide; wherein said oligomer conjugate comprises:
a) at least one first oligomer region capable of modulating a target sequence of Hepatitis B Virus (HBV), preferably HBx or HBsAg of HBV, to treat said viral disorder; and
b) a carrier component. Preferably, for delivering said first oligomer to the liver.

In one aspect, the present invention provides an oligomer or the oligomer component of the oligomer conjugate that hybridize to a target sequence selected from the group consisting of any one or more of positions: 1530 to 1598; 1264-1278 and 670 to 706 of SEQ ID NO: 3.

In one aspect, the present invention provides an oligomer based on a core motif selected from the group consisting of any one or more of:

GCGTAAAGAGAGG; (SEQ ID NO: 13)

GCGTAAAGAGAGGT; (SEQ ID NO: 11)

AGCGAAGTGCACACG; (SEQ ID NO: 20)

AGGTGAAGCGAAGTG; (SEQ ID NO: 26)

AGCGAAGTGCACACGG; (SEQ ID NO 18)

CGAACCACTGAACA; (SEQ ID NO: 7)

GAACCACTGAACAAA; (SEQ ID NO 4)

CGAACCACTGAACAAA; (SEQ ID NO 5)

CGAACCACTGAACAA; (SEQ ID NO 6)

CGAACCACTGAAC (SEQ ID NO 8)

CCGCAGTATGGATCG (SEQ ID NO 9)

CGCAGTATGGATC; (SEQ ID NO: 10)

CGCGTAAAGAGAGGT; (SEQ ID NO 12)

AGAAGGCACAGACGG; (SEQ ID NO 14)

GAGAAGGCACAGACGG (SEQ ID NO 15)

GAAGTGCACACGG; (SEQ ID NO 16)

GCGAAGTGCACACGG; (SEQ ID NO 17)

CGAAGTGCACACG; (SEQ ID NO 19)

AGGTGAAGCGAAGT; (SEQ ID NO 27)
and

TAGTAAACTGAGCCA, (SEQ ID NO: 852)

which is capable of modulating a target sequence in HBx or HBsAg of HBV to treat a viral disorder.

In one aspect, the present invention provides a composition suitable for the treatment of a viral disorder, wherein said composition comprises an oligomer and at least one additional different oligonucleotide; wherein said oligomer comprises at least one first oligomer region capable of modulating a target sequence of Hepatitis B Virus (HBV), preferably HBx or HBsAg of HBV, to treat said viral disorder.

In one aspect, the present invention provides a method for treating a viral disorder, said method comprising administering to a subject in need of treatment an effective amount of an oligomer conjugate according to the invention.

In one aspect, the present invention provides a method for treating a viral disorder, said method comprising administering to a subject in need of treatment an effective amount of a composition according to the invention.

In one aspect, the present invention provides a method for treating a viral disorder, said method comprising administering to a subject in need of treatment an effective amount of an oligomer according to the invention.

In one aspect, the present invention provides a pharmaceutical composition comprising an oligomer conjugate according to the invention; and one or more pharmaceutically acceptable diluents, carriers, salts or adjuvants.

In one aspect, the present invention provides a pharmaceutical composition comprising a composition according to the invention; and one or more pharmaceutically acceptable diluents, carriers, salts or adjuvants.

In one aspect, the present invention provides a pharmaceutical composition comprising an oligomer according to the invention; and one or more pharmaceutically acceptable diluents, carriers, salts or adjuvants.

In one aspect, the present invention provides a pharmaceutical system comprising a pharmaceutical composition according to the invention and an additional pharmaceutical entity.

In one aspect, the present invention provides a motif selected from the group consisting of any one or more of:

GCGTAAAGAGAGG;           (SEQ ID NO: 13)

GCGTAAAGAGAGGT;          (SEQ ID NO: 11)

AGCGAAGTGCACACG;         (SEQ ID NO: 20)

AGGTGAAGCGAAGTG;         (SEQ ID NO: 26)

AGCGAAGTGCACACGG;        (SEQ ID NO 18)

for constructing an oligomer conjugate according to the invention.

In one aspect, the present invention provides a motif selected from the group consisting of any one or more of: NO: 13) GCGTAAAGAGAGGT (SEQ ID NO: 11) and CGCGTAAAGAGAGGT (SEQ ID NO 12) for constructing a composition according to the invention.

In one aspect, the present invention provides a motif selected from the group consisting of any one or more of: AGCGAAGTGCACACG (SEQ ID NO: 20); AGGTGAAGCGAAGTG (SEQ ID NO: 26); AGCGAAGTGCACACGG (SEQ ID NO 18); GAAGTGCACACGG (SEQ ID NO 16); GCGAAGTGCACACGG (SEQ ID NO 17); CGAAGTGCACACG (SEQ ID NO 19) and AGGTGAAGCGAAGT (SEQ ID NO 27) for constructing an oligomer according to the invention.

In one aspect, the present invention provides a method of manufacturing an oligomer conjugate according to the invention, comprising conjugating one or more oligomers according to the invention with a carrier component according to the invention.

In one aspect, the present invention provides a method of manufacturing a composition according to the invention, comprising admixing an oligomer conjugate according to the invention with a pharmaceutically acceptable diluents, carriers, salts or adjuvants.

BRIEF DESCRIPTION OF FIGURES

FIG. 14A) presents HBsAG reduction. FIG. 14B) presents HBeAG reduction. FIG. 14C) presents DNA reduction FIGS. 15A, 15B and 15C: Presents results on unconjugated oligomers (■) (SEQ ID NO:308 and 303) and conjugated oligomers (▼) (SEQ ID NO: 807 and 815) tested at equimolar oligomer dosages. FIG. 15A) presents HBsAG reduction. FIG. 15B) presents HBeAG reduction. FIG. 15C) presents DNA reduction.

DEFINITIONS/ELEMENTS OF THE INVENTION

Figure 1:
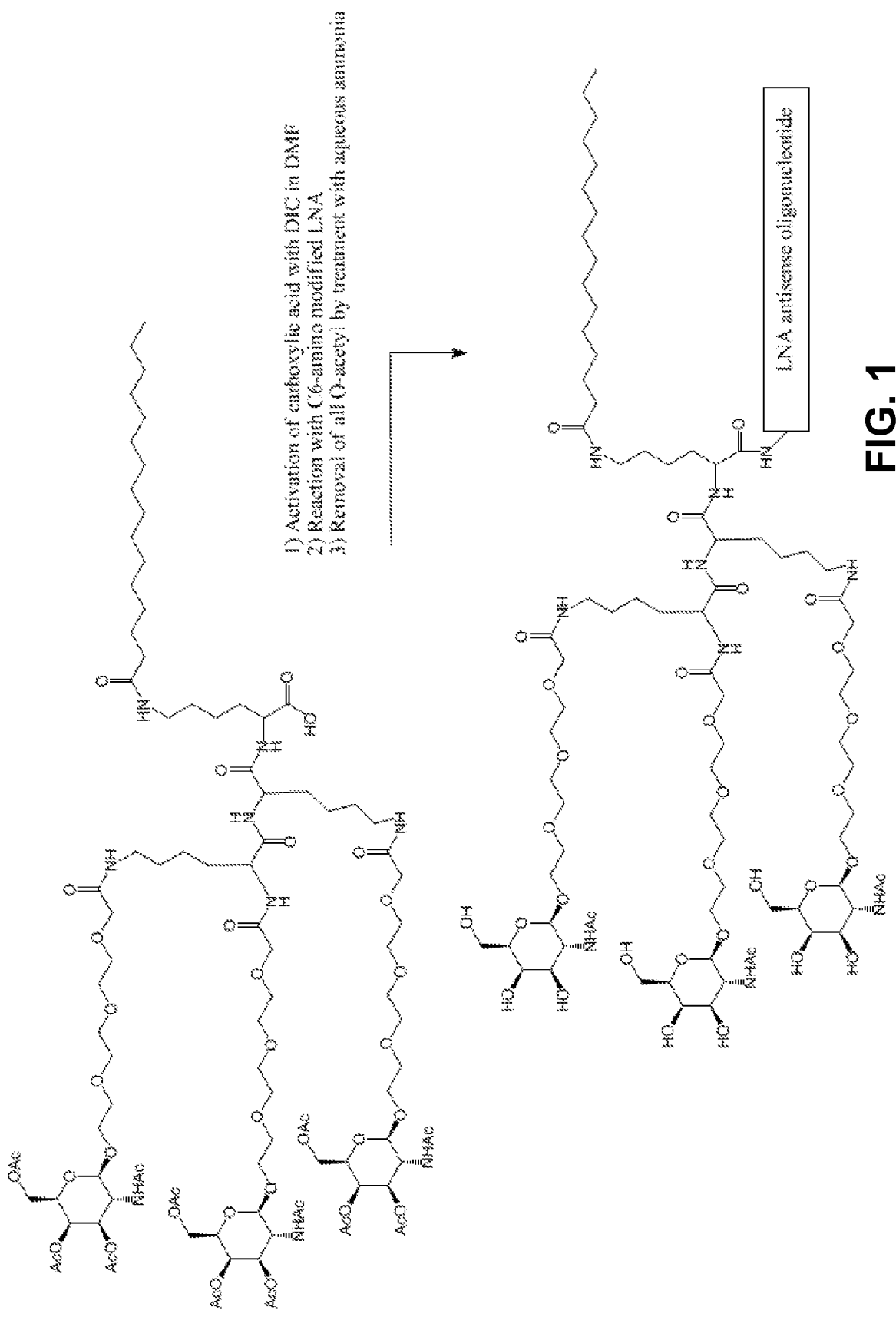
FIG. 1: Presents a scheme for a LNA oligomer GalNAc conjugation step.

The following presents definitions of terms that apply to all aspects of the present invention. These definitions are not mutually exclusive. These definitions also teach additional embodiments regarding all aspects of the present invention.
Oligomer/Oligonucleotide In the context of the present invention, references to "oligomer" and "oligonucleotide" as used herein also apply to the first oligomer region and/or the second oligomer region—such as when the first oligomer region is in the oligomer conjugate or when it is not in the free form (i.e. when not in the oligomer conjugate).

The term "oligomer" refers to a molecule formed by covalent linkage of two or more nucleotides (i.e. an oligonucleotide). Therefore as used herein, the terms "oligomer" and "oligonucleotide" are interchangeable and have identical meaning. Herein, a single nucleotide (unit) may also be referred to as a monomer or unit. In some embodiments, the terms "nucleoside", "nucleotide", "unit" and "monomer" are used interchangeably. It will be recognised that when referring to a sequence of nucleotides or units, what is referred to is the sequence of bases, such as A, T, G, C or U.

As used herein, the terms "oligomer" and "oligonucleotide" include linear or circular oligomers of natural and/or modified units or linkages, including deoxyribonucleosides, ribonucleosides, substituted and alpha-anomeric forms thereof, peptide nucleic acids (PNA), and the like, capable of specifically binding to a target polynucleotide by way of a regular pattern of unit-to-unit interactions, such as Watson-Crick type of base pairing, Hoogsteen or reverse Hoogsteen types of base pairing, or the like.

The oligonucleotide may be composed of a single region or may be composed of several regions. The oligonucleotide may be "chimeric", that is, composed of different regions. In the context of this invention "chimeric" antisense compounds are antisense compounds, particularly oligonucleotides, which contain two or more chemical regions, for example, DNA region(s), RNA region(s), PNA region(s) etc. Each chemical region is made up of at least one unit, i.e., a nucleotide in the case of an oligonucleotide compound. These oligonucleotides typically contain at least one region wherein the oligonucleotide is modified in order to exhibit one or more sought properties. The sought properties of the oligonucleotide might be to increased resistance to nuclease degradation, increased cellular uptake, and/or increased binding affinity for the target nucleic acid. Different regions of the oligonucleotide may therefore have different properties. One ore more regions of the oligonucleotide may serve as a substrate for enzymes capable of cleaving RNA:DNA or RNA:RNA hybrids. There are several enzymes with such catalytic effect. A method of digesting RNA at a specific location with an antisense oligonucleotide and an RNase H has been demonstrated by Minshull et al. (Nucleic Acids Research, 14:6433-6451 (1986)). Rnase H is a cellular endonuclease which cleaves the RNA strand of an RNA: DNA duplex. Therefore, activation of RNase H results in cleavage of the RNA target. The efficiency of oligonucleotide inhibition of gene expression might therefore be enhanced. Other enzymes capable of cleaving are Rnase L and Rnase P.

Nucleobase

The term "nucleobase" refers to the base moiety of a nucleotide and covers both naturally occurring a well as non-naturally occurring variants.

Thus, "nucleobase" covers not only the known purine and pyrimidine heterocycles but also heterocyclic analogues and tautomeres thereof.

Examples of nucleobases include, but are not limited to adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

In some embodiments, at least one of the nucleobases present in the oligomer is a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

Units

As used herein, the term "units" or "monomers" typically indicates nucleoside units linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphornates, phosphoroselenoate, phosphoramidate, and the like.

Nucleosides and Nucleoside Analogues

In some embodiments, the terms "nucleoside analogue" and "nucleotide analogue" are used interchangeably.

The term "nucleotide" as used herein, refers to a glycoside comprising a sugar moiety, a base moiety and a covalently linked group (linkage group), such as a phosphate or phosphorothioate internucleotide linkage group, and covers both naturally occurring nucleotides, such as DNA or RNA, and non-naturally occurring nucleotides comprising modified sugar and/or base moieties, which are also referred to as "nucleotide analogues" herein. Herein, a single nucleotide (unit) may also be referred to as a monomer or nucleic acid unit.

In field of biochemistry, the term "nucleoside" is commonly used to refer to a glycoside comprising a sugar moiety and a base moiety, and may therefore be used when referring to the nucleotide units, which are covalently linked by the internucleotide linkages between the nucleotides of the oligomer.

In the field of biotechnology, the term "nucleotide" is often used to refer to a nucleic acid monomer or unit, and as such in the context of an oligonucleotide may refer to the base—such as the "nucleotide sequence"- and typically may refer to the nucleobase sequence (i.e. the presence of the sugar backbone and internucleoside linkages are implicit).

Likewise, particularly in the case of oligonucleotides where one or more of the internucleoside linkage groups are modified, the term "nucleotide" may refer to a "nucleoside" for example the term "nucleotide" may be used, even when specifying the presence or nature of the linkages between the nucleosides.

As one of ordinary skill in the art would recognise, the 5' terminal nucleotide of an oligonucleotide does not comprise a 5' internucleotide linkage group, although may or may not comprise a 5' terminal group.

Non-naturally occurring nucleotides include nucleotides which have modified sugar moieties, such as bicyclic nucleotides or 2' modified nucleotides, such as 2' substituted nucleotides.

"Nucleotide analogues" are variants of natural nucleotides, such as DNA or RNA nucleotides, by virtue of modifications in the sugar and/or base moieties. Analogues could in principle be merely "silent" or "equivalent" to the natural nucleotides in the context of the oligonucleotide, i.e. have no functional effect on the way the oligonucleotide works to inhibit target gene expression. Such "equivalent" analogues may nevertheless be useful if, for example, they are easier or cheaper to manufacture, or are more stable to storage or manufacturing conditions, or represent a tag or label. Preferably, however, the analogues will have a functional effect on the way in which the oligomer works to inhibit expression; for example by producing increased binding affinity to the target and/or increased resistance to intracellular nucleases and/or increased ease of transport into the cell. Specific examples of nucleoside analogues are described by e.g. Freier & Altmann; Nucl. Acid Res., 1997, 25, 4429-4443 and Uhlmann; Curr. Opinion in Drug Development, 2000, 3(2), 293-213, and in Scheme 1 presented in FIG. 4.

Linker/Linker Group etc.

The terms "linker group", "linkage group", "linker", "linker molecule" or "internucleoside linkage" are intended to mean a group capable of covalently coupling together two entities, such as nucleotides. Specific examples include phosphate groups and phosphorothioate groups. Such linkers may contain a spacer molecule covalently attached to one or more activated groups or functional groups. Optionally, the functional group of the linker molecule can be treated with a coupling agent to form an activated group. Such linkers also include tether molecules as described herein.

The term "brancher region" is intended to mean a group or region capable of covalently coupling together two or more entities, such as nucleotides or for the generation of carrier component clusters such as galctose clusters.

Alternatively, "linker groups" and "brancher regions" as described herein may be used to covalently couple nucleotide regions and non-nucleotide regions, such a linker group is termed L. For example, a linker group may be used to conjugate an oligomer of the invention to a carrier component described herein. For example, a brancher region may be used to conjugate an oligomer of the invention to one or more carrier components described herein. For example, a brancher region may be used to conjugate one or more oligomers of the invention to a carrier component described herein. For example, a brancher region may be used to conjugate one or more oligomers of the invention to one or more carrier components described herein.

Oligomer Conjugate

The term "oligomer conjugate" is intended to indicate a heterogenous molecule formed by the attachment ("conjugation"), such as by the covalent attachment, of the oligomer as described herein to a carrier component.

The linkage, such as covalent conjugation, may be chemical in nature, such as via a linker group, or genetic in nature for example by recombinant genetic technology, such as in a fusion protein with for example a reporter molecule (e.g. green fluorescent protein, β-galactosidase, Histag, etc. Alternatively, the oligomer may be conjugated to the carrier component directly without the need for any tether molecule or linker group.

Carrier Component

As used herein, the term "carrier component" relates to a molecular vehicle which is intended to carry or convey the oligomers of the invention to their desired location, such as desired anatomical location.

Carrier components according to the present invention may be used to enhance the activity, cellular distribution and/or cellular uptake of the oligomers.

Any suitable carrier component may be used.

The carrier component may be polynucleotide. However, typically, the carrier component is a non-nucleotide moiety or a non-polynucleotide moiety.

Examples of non-nucleotide or non-polynucleotide moieties include macromolecular agents selected from the group consisting of carbohydrates, cell surface receptor ligands, drug substances, hormones, lipophilic substances, polymers, proteins, peptides, toxins (e.g. bacterial toxins), vitamins, viral proteins, or combinations thereof. Typical polymers may be polyethylene glycol and/or polypropylene glycol (PPG).

In some embodiments, the carrier component may be an amino acid, a protein, a peptide or polypeptide. Typically proteins may be enzymes, serum proteins (e.g. human serum albumin (HSA), transferrin or glycoproteins), receptors, antibodies or antibody derivatives thereof like single-chain variable fragments, bispecific antibodies, tribodies etc designed to bind a desired target antigen.

Examples of peptide carrier components are poly(L-lysine), that significantly increases cell penetration, and the antennapedia transport peptide. Such conjugates are described by Lemaitre et al, "Specific antiviral activity of a poly(L-lysine)-conjugated oligodeoxyribonucleotide sequence complementary to vesicular stomatitis virus N protein mRNA initiation site," Proc. Natl. Acad. Sci. USA, 84:648-652, 1987; U.S. Pat. Nos. 6,166,089 and 6,086,900. The procedure in the above publication requires that the 3'-terminal nucleotide be a ribonucleotide. The resulting aldehyde groups are then randomly coupled to the epsilon-amino groups of lysine residues of poly(L-lysine) by Schiff base formation, and then reduced with sodium cyanoborohydride. This procedure converts the 3'-terminal ribose ring into morpholine structure antisense oligomers. The peptide segment can also be synthesized by strategies which are compatible with DNA/RNA synthesis e.g. Mmt/Fmoc strategies. In that case the peptide can be synthesized directly before or after the oligonucleotide segment. Also methods exist to prepare the peptide oligonucleotide conjugate post synthetically, e.g., by formation of a disulfide bridge.

In some embodiments, the conjugate moiety may be or comprise a lipophilic conjugate moiety. Lipophilic conjugate moieties may be selected from the group consisting of sterols, stanols, steroids, polycyclic aromatic groups, aliphatic groups, lipids, phospholipids, lipophilic alcohols, fatty acids and fatty esters. In some embodiments, the conjugate moiety comprises cholesterol.

The carrier component may be or comprise a pharmacokinetic modulator, such as a lipophilic or hydrophobic moieties. Such moieties are disclosed within the context of siRNA conjugates in WO2012/082046. The hydrophobic moiety may comprise a C8-C36 fatty acid, which may be saturated or un-saturated. In some embodiments, C10, C12, C14, C16, C18, C20, C22, C24, C26, C28, C30, C32 and C34 fatty acids may be used. The hydrophobic group may have 16 or more carbon atoms. Exemplary suitable hydrophobic groups may be selected from the group comprising: sterol, cholesterol, palmitoyl, hexadec-8-enoyl, oleyl, (9E, 12E)-octadeca-9,12-dienoyl, dioctanoyl, and C16-C20 acyl. According to WO2012/082046, hydrophobic groups having fewer than 16 carbon atoms are less effective in enhancing polynucleotide targeting, but they may be used in multiple copies (e.g. 2×, such as 2× C8 or C10, C12 or C14) to enhance efficacy. Pharmacokinetic modulators useful as polynucleotide targeting moieties may be selected from the group consisting of: cholesterol, alkyl group, alkenyl group, alkynyl group, aryl group, aralkyl group, aralkenyl group, and aralkynyl group, each of which may be linear, branched, or cyclic. Pharmacokinetic modulators are preferably hydrocarbons, containing only carbon and hydrogen atoms. However, substitutions or heteroatoms which maintain hydrophobicity, for example fluorine, may be permitted.

WO2007/031091 provides examples of other suitable ligands and carrier components, which are hereby incorporated by reference.

In some embodiments, the carrier component is or comprises a carbohydrate moiety. Carbohydrate conjugate moieties include, but is not limited to, galactose, lactose, n-acetylgalactosamine, mannose and mannose-6-phosphate. Carbohydrate conjugates may be used to enhance delivery or activity in a range of tissues, such as liver and/or muscle. See, for example, EP1495769, WO99/65925, Yang et al., Bioconjug Chem (2009) 20(2): 213-21. Zatsepin & Oretskaya Chem Biodivers. (2004) 1(10): 1401-17.

In addition, the oligomer may further comprise one or more additional conjugate moieties, of which lipophilic or hydrophobic moieties are particularly interesting. These may for example, act as pharmacokinetic modulators, and may be covalently linked to either the carbohydrate conjugate, a linker linking the carbohydrate conjugate to the oligomer or a linker linking multiple carbohydrate conjugates (multi-valent) conjugates, or to the oligomer, optionally via a linker, such as a physiologically labile linker.

In some embodiments, the carrier component comprises an asiaglycoprotein receptor (ASGP-R) targeting moiety with affinity equal to or greater than that of galactose. The ASPG-R targeting moiety may be selected from the group consisting of galactose, galactosamine, N-formyl-galactosamine, N-acetylgalactosamine (GalNAc), N-propionyl-galactosamine, N-n-butanoyl-galactosamine, and N-isobutanoylgalactos-amine. In some embodiments the asialoglycoprotein receptor targeting conjugate moiety is mono-valent. In other embodiments the carrier component comprises a galactose cluster, such as a di-valent, tri-valent or tetra-valent asialoglycoprotein receptor targeting conjugate moiety (i.e. containing 1, 2, 3 or 4 terminal carbohydrate moieties capable of binding to the asialoglycoprotein receptor). In some embodiments, the carrier component comprises a GalNAc (N-acetylgalactosamine), such as a mono-valent, di-valent, tri-valent of tetra-valent GalNAc. GalNAc conjugates may be used to target the compound to the liver. A preferred carrier component is a N-acetylgalactosamine trimer. GalNAc conjugates have been used with methylphosphonate and PNA antisense oligonucleotides (e.g. U.S. Pat. No. 5,994,517 and Hangeland et al., Bioconjug Chem. 1995 November-December; 6(6):695-701) and siRNAs (e.g. WO2009/126933, WO2012/089352 and WO2012/083046) and with LNA and 2'-MOE modified nucleosides WO 2014/076196 WO 2014/207232, WO 2014/179620 and WO 2014/179627. The GalNAc references and the specific conjugates used therein are hereby incorporated by reference. WO2012/083046 discloses siRNAs with GalNAc conjugate moieties which comprise cleavable pharmacokinetic modulators, which are suitable for use in the present invention, the preferred pharmacokinetic modulators are C16 hydrophobic groups such as palmitoyl, hexadec-8-enoyl, oleyl, (9E, 12E)-octadeca-9,12-dienoyl, dioctanoyl, and C16-C20 acyl. The WO2012/083046 cleavable pharmacokinetic modulators may also be cholesterol.

The carrier component may be selected from the group consisting of: galactose, galactosamine, N-formyl-galactosamine, N-acetylgalactosamine, Npropionyl-galactosamine, N-n-butanoyl-galactosamine, N-iso-butanoylgalactos-amine, galactose cluster, and N-acetylgalactosamine trimer and may have a pharmacokinetic modulator selected from the group consisting of: hydrophobic group having 16 or more carbon atoms, hydrophobic group having 16-20 carbon atoms, palmitoyl, hexadec-8-enoyl, oleyl, (9E,12E)-octadeca-9,12dienoyl, dioctanoyl, and C16-C20 acyl, and cholesterol. Certain GalNac clusters disclosed in '046 include: (E)-hexadec-8-enoyl (C16), oleyl (C18), (9E,12E)-octadeca-9,12-dienoyl (C18), octanoyl (C8), dodececanoyl (C12), C-20 acyl, C24 acyl, dioctanoyl (2×C8). The carrier component-pharmacokinetic modulator may be linked to the polynucleotide via a physiologically labile bond or, e.g. a disulfide bond (PO-linker), or a PEG linker. The invention also relates to the use of phosphodiester linkers between the oligomer and the carrier component (suitably are positioned between the oligomer and the carbohydrate conjugate group).

In one embodiments of the present invention, the oligomer is linked, preferably conjugated, to a carrier component, which may be used to deliver oligomers to the liver of a subject e.g. by increasing the cellular uptake of oligomers.

Figure 2:
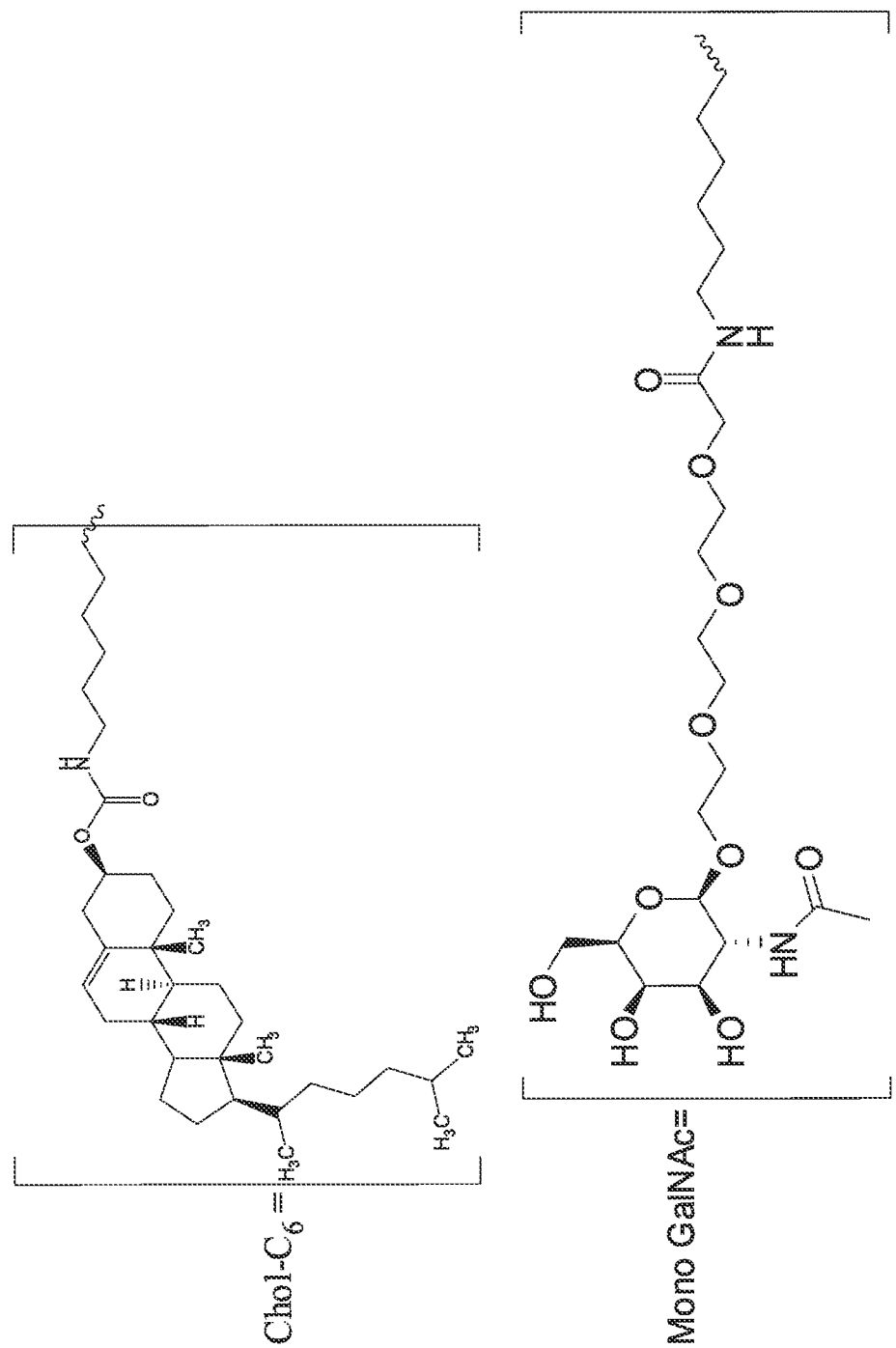
FIG. 2: Presents examples of a cholesterol or mono-GalNAc carrier components including a C6 linker moiety (region E) which is used to link the carrier component to the oligomer (region A or to a physiologically labile linker region PL, such as a PO linker). The wavy line represents the covalent link to the oligomer or region PL.
Figure 3:
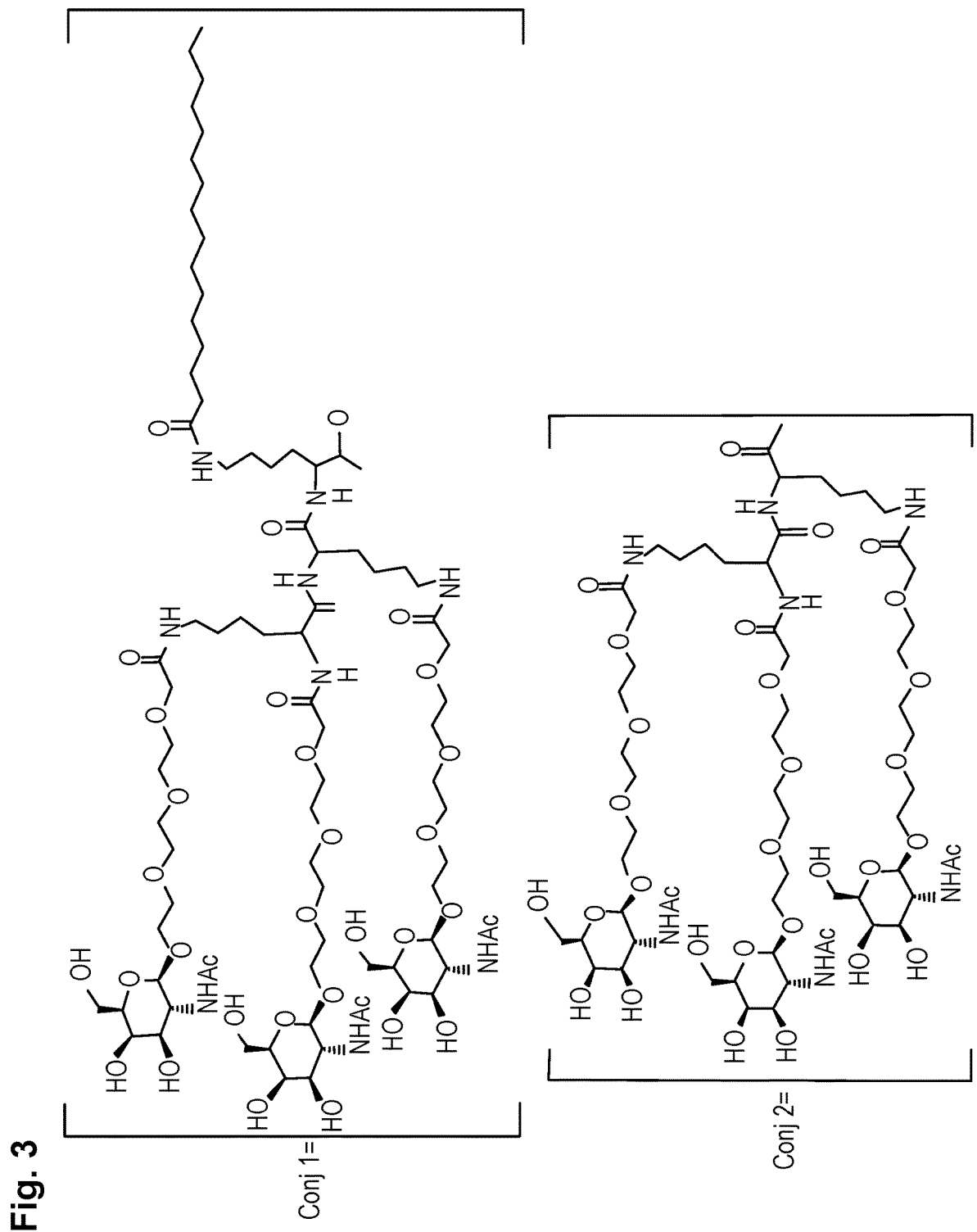
FIG. 3: Presents examples of tri-GalNAc carrier components. Conjuagtes 1-4 illustrate 4 suitable GalNAc carrier components, and conjugates 1a-4a refer to the same carrier components with an additional C6 linker moiety (region E) which is used to link the carrier component to the oligomer (region A or to a physiologically labile linker, region PL, such as a PO linker). The wavy line represents the covalent link to the oligomer or region PL.
Figure 3:
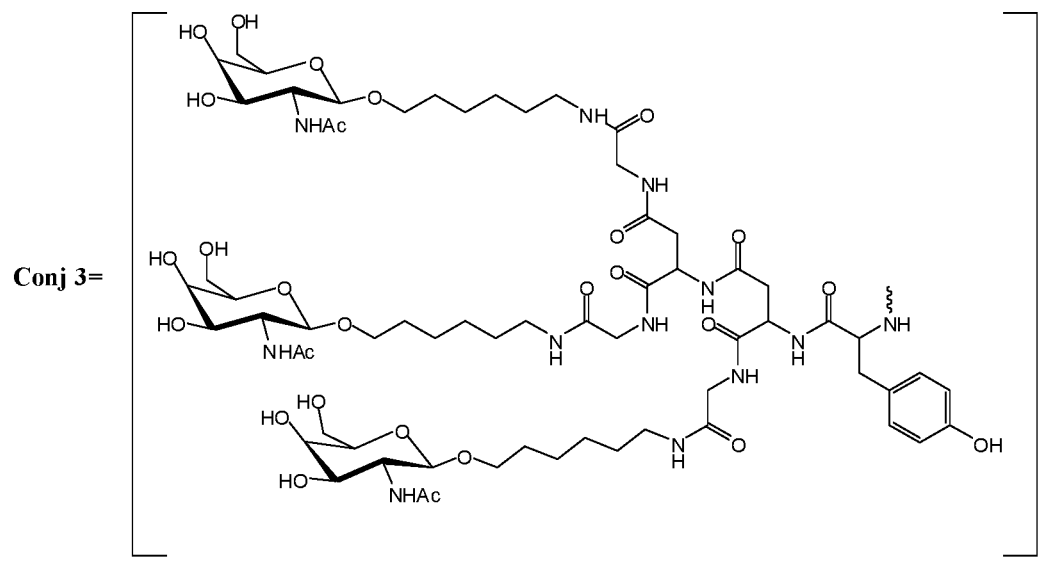
Figure 3:
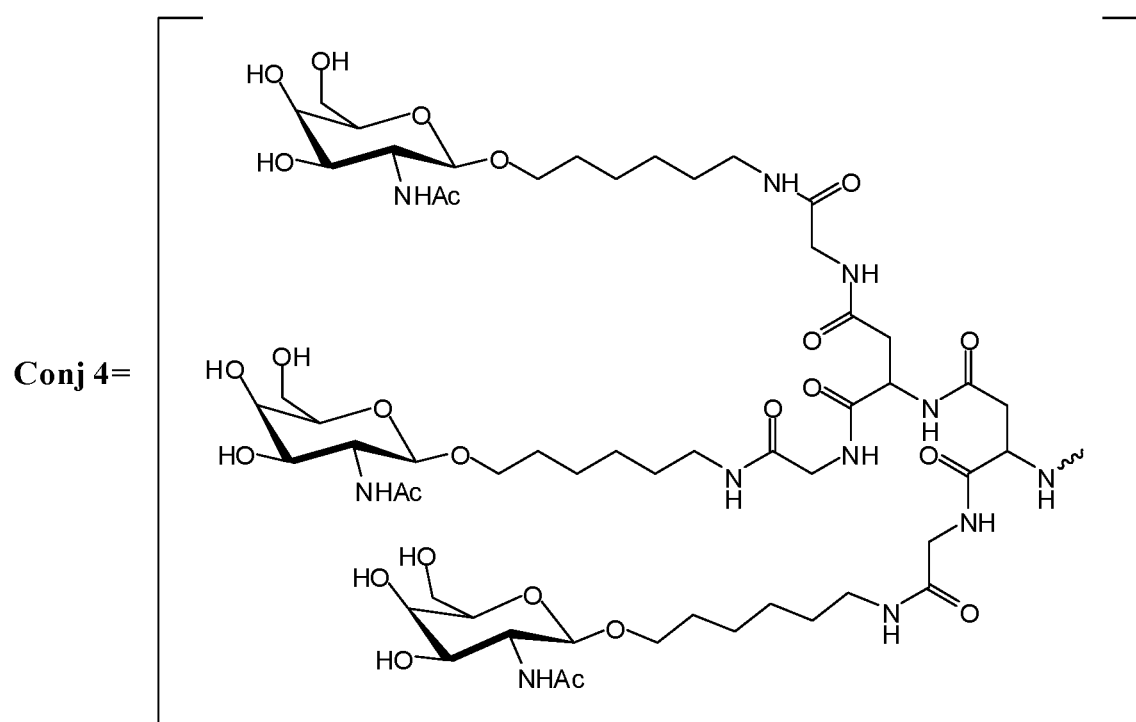
Figure 3:
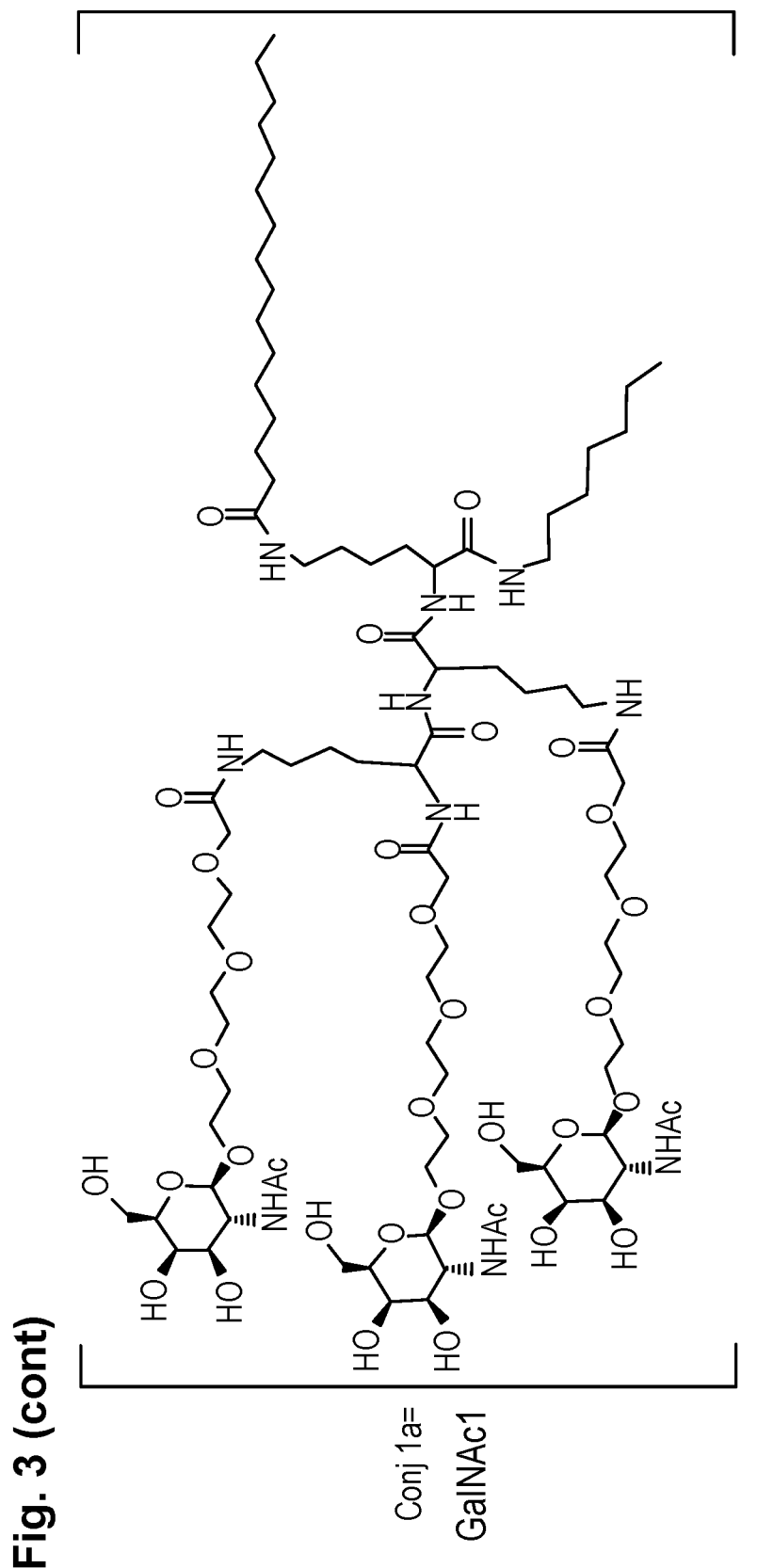
Figure 3:
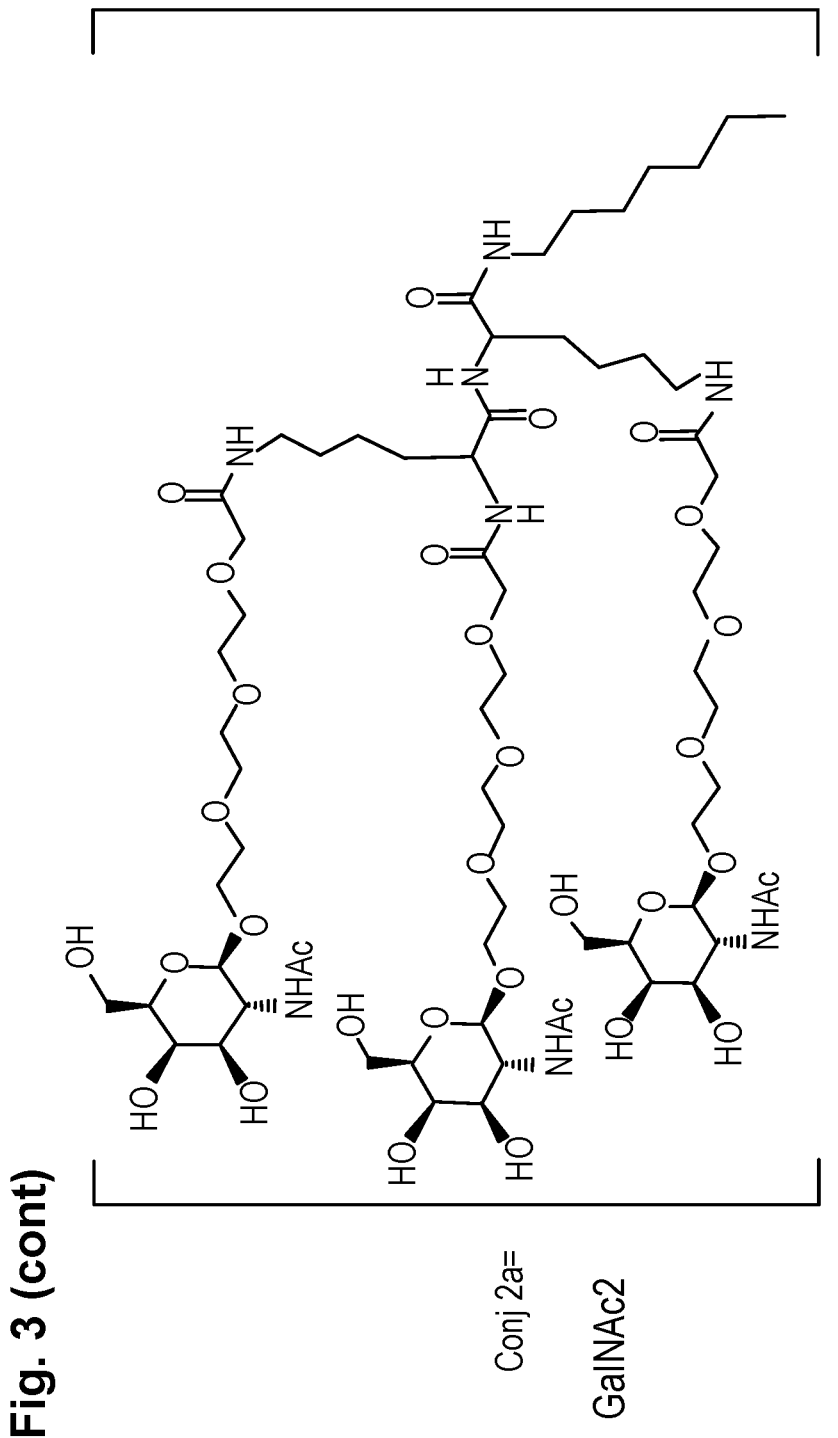
Figure 3:
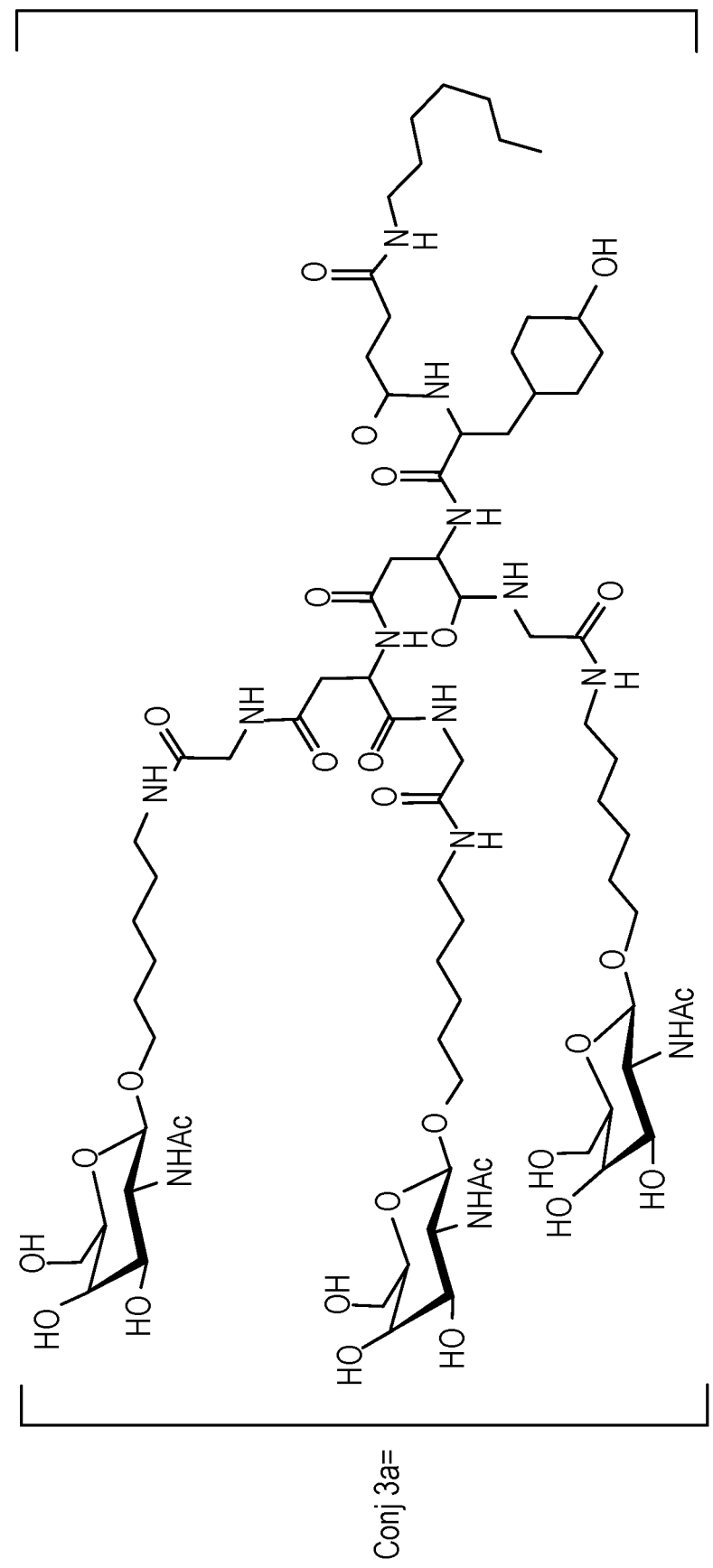
Figure 3:
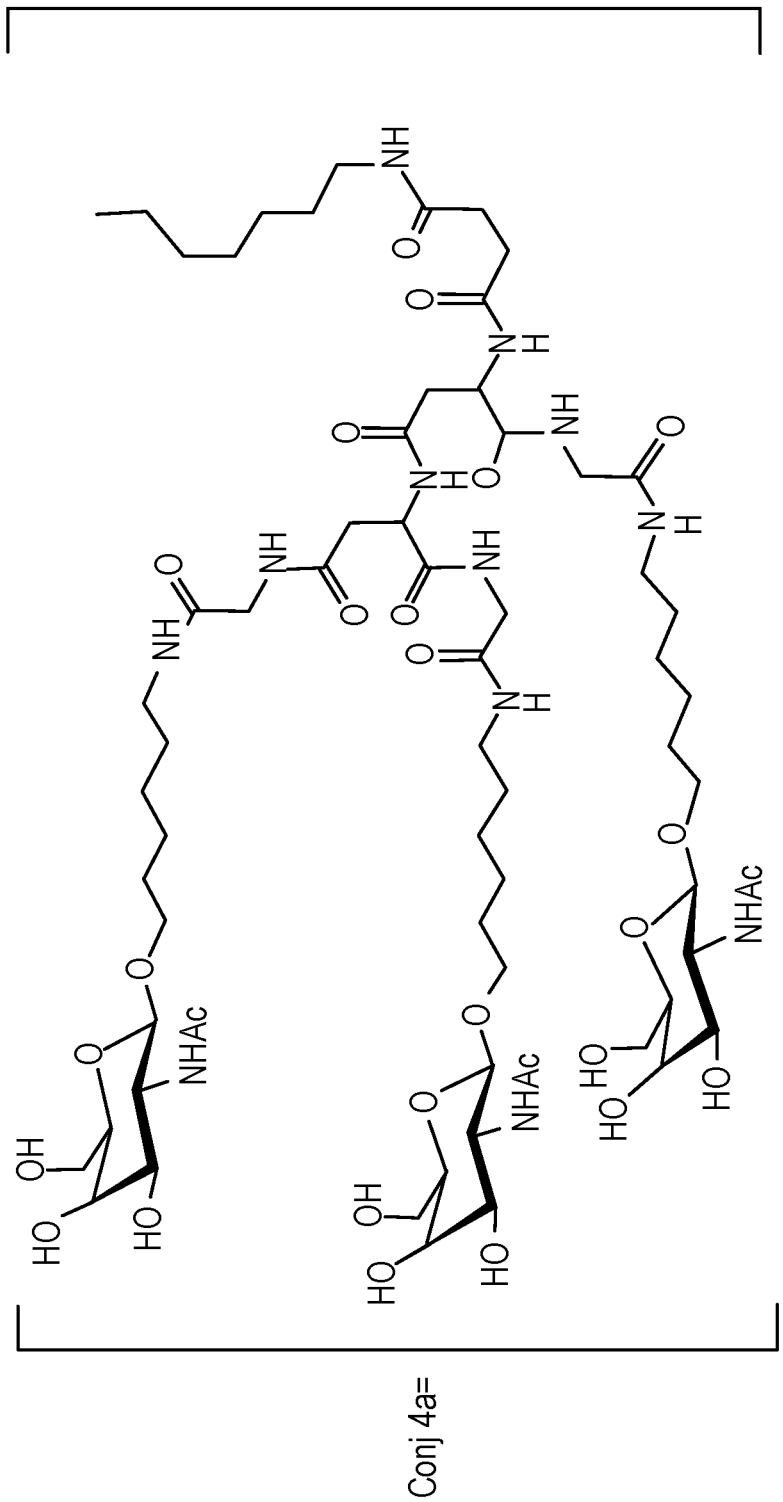

In a particular embodiment, the carrier component may be GalNAc or a GalNAc cluster. FIGS. 2 and 3 presents some carier components.

For targeting hepatocytes in liver, a preferred targeting ligand is a galactose cluster.

A galactose cluster comprises a molecule having e.g. comprising two to four terminal galactose derivatives. As used herein, the term galactose derivative includes both galactose and derivatives of galactose having affinity for the ASGP-R equal to or greater than that of galactose. A terminal galactose derivative is attached to a molecule through its C—I carbon. The ASGP-R is unique to hepatocytes and binds branched galactose-terminal glycoproteins. A preferred galactose cluster has three terminal galactosamines or galactosamine derivatives each having affinity for the asialoglycoprotein receptor. A more preferred galactose cluster has three terminal N-acetyl-galactosamines. Other terms common in the art include tri-antennary galactose, tri-valent galactose and galactose trimer. It is known that tri-antennary galactose derivative clusters are bound to the ASGP-R with greater affinity than bi-antennary or mono-antennary galactose derivative structures (Baenziger and Fiete, 1980, Cell, 22, 611-620; Connolly et al., 1982, 1. Biol. Chern., 257, 939-945). Multivalency is required to achieve nM affinity.

A preferred galactose derivative is an N-acetyl-galactosamine (GalNAc). Other saccharides having affinity for the asialoglycoprotein receptor may be selected from the list comprising: galactosamine, N-n-butanoylgalactosamine, and N-iso-butanoylgalactosamine. The affinities of numerous galactose derivatives for the asialoglycoprotein receptor have been studied (see for example: Jobst, S. T. and Drickamer, K. J B. C. 1996, 271,6686) or are readily determined using methods typical in the art.

A galactose cluster may comprise two or preferably three galactose derivatives each linked to a central branch point. The galactose derivatives are attached to the central branch point through the C—I carbons of the saccharides. The galactose derivative is preferably linked to the branch point via linkers or spacers. A preferred spacer is a flexible hydrophilic spacer (U.S. Pat. No. 5,885,968; Biessen et al. J. Med. Chern. 1995 Vol. 39 p. 1538-1546). A preferred flexible hydrophilic spacer is a PEG spacer. A preferred PEG spacer is a PEG3 spacer (three ethylene units). The branch point can be any small molecule which permits attachment of the three galactose derivatives and further permits attachment of the branch point to the oligomer. Each galactose derivative (carbohydrate moiety) in a GalNAc cluster (e.g. GalNAc) may be joined to the oligomer via a spacer, such as (poly)ethylene glycol linker (PEG), such as a di, tri, tetra, penta, hexa-ethylene glycol linker. The PEG moiety may form a spacer between the galactose derivative sugar moiety and a peptide (di-lysine is shown) linker. An exemplary branch point group is a di-lysine. A di-lysine molecule contains three amine groups through which three galactose derivatives may be attached and a carboxyl reactive group through which the di-lysine may be attached to the oligomer (se for example FIG. 4).

The carbohydrate conjugate (e.g. GalNAc), or carbohydrate-linker moiety (e.g. carbohydrate-PEG moiety) may be covalently joined (linked) to the oligomer via a branch point group such as, an amino acid, or peptide, which suitably comprises two or more amino groups (such as 3, 4, or 5), such as lysine, di-lysine or tri-lysine or tetra-lysine. A tri-lysine molecule contains four amine groups through which three carbohydrate conjugate groups, such as galactose & derivatives (e.g. GalNAc) and a further conjugate such as a hydrophobic or lipophilic moiety/group may be attached and a carboxyl reactive group through which the tri-lysine may be attached to the oligomer. The further conjugate, such as lipophilic/hyrodphobic moiety may be attached to the lysine residue that is attached to the oligomer.

In some embodiments, the GalNac cluster comprises a peptide linker, e.g. a Tyr-Asp(Asp) tripeptide or Asp(Asp) dipeptide, which is attached to the oligomer via a biradical linker, for example the GalNac cluster may comprise biradical linkers such as those illustrated as Conj 3, 3a, 4 and 4a in FIG. 3.

Alternative brancher molecules may be selected from the from the group consisting of 1,3-bis-[5-(4,4'-dimethoxytrityloxy)pentylamido]propyl-2-[(2-cyanoethyl)-(N,N-diisopropyl)]phosphoramidite (Glen Research Catalogue Number: 10-1920-xx), tris-2,2,2-[3-(4,4'-dimethoxytrityloxy)propyloxymethyl]ethyl-[(2-cyanoethyl)-(N,N-diisopropyl)]-phosphoramidite (Glen Research Catalogue Number: 10-1922-xx), tris-2,2,2-[3-(4,4'-dimethoxytrityloxy)propyloxymethyl]methyleneoxypropyl-[(2-cyanoethyl)-(N,N-diisopropyl)]-phosphoramidite and 1-[5-(4,4'-dimethoxy-trityloxy)pentylamido]-3-[5-fluorenomethoxy-carbonyl-oxypentylamido]-propyl-2-[(2-cyanoethyl)-(N,N-diisopropyl)]-phosphoramidite (Glen Research Catalogue Number: 10-1925-xx). WO 2014/179620 and European application No. 14188444.5 describes the generation of various GalNAc conjugate moieties (hereby incorporated by reference). Attachment of the branch point to oligomer may occur through a linker or spacer. A preferred spacer is a flexible hydrophilic spacer. A preferred flexible hydrophilic spacer is a PEG spacer or C6 linker. A preferred PEG spacer is a PEG3 spacer (three ethylene units). In a preferred embodiment the linker is a physiologically labile linker. The galactose cluster may be attached to the 3' or 5' end of the oligomer using methods known in the art. In preferred embodiments the asialoglycoprotein receptor targeting conjugate moiety is linked to the 5'-end of the oligonucleotide.

A preferred galactose cluster comprises three terminal GalNAc moieties linked via a PEG spacer to a di-lysine brancher molecule (a GalNAc cluster). Preferably, the PEG spacer is a 3PEG spacer. Preferred GalNAc clusters are Conj 1, 1a, 2 and 2a. Most preferred is Conj2a (also termed GalNAc2).

Galactose Clusters are Presented in FIG. 3. Carrier Component Linker

The carrier component may be linked to the first oligomer region, and/or the second oligomer region, by means of a linker (L). Any suitable linker may be used.

A carbohydrate conjugate (e.g. GalNAc) may be linked to the oligomer via a biocleavable linker also termed a physiologically labile linker.

As used herein, a physiologically labile bond is a labile bond that is cleavable under conditions normally encountered or analogous to those encountered within a mammalian body (also referred to as a physiologically labile linker). Physiologically labile linkage groups are selected such that they undergo a chemical transformation (e.g., cleavage) when present in certain physiological conditions. Mammalian intracellular conditions include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic or hydrolytic enzymes Chemical transformation (cleavage of the labile bond) may be initiated by the addition of a pharmaceutically acceptable agent to the cell or may occur spontaneously when a molecule containing the labile bond reaches an appropriate intra- and/or extra-cellular environment. For example, a pH labile bond may be cleaved when the molecule enters an acidified endosome.

Thus, a pH labile bond may be considered to be an endosomal cleavable bond. Enzyme cleavable bonds may be cleaved when exposed to enzymes such as those present in an endosome or lysosome or in the cytoplasm. A disulfide bond may be cleaved when the molecule enters the more reducing environment of the cell cytoplasm. Thus, a disulfide may be considered to be a cytoplasmic cleavable bond. As used herein, a pH-labile bond is a labile bond that is selectively broken under acidic conditions (pH<7). Such bonds may also be termed endosomally labile bonds, since cell endosomes and lysosomes have a pH less than 7. An example of another physiologically labile linker is a di-lysine as used in the GalNAc clusters in FIG. 3.

In some embodiments, the oligomer conjugate of the invention comprises a physiologically labile linker (region PL, also referred to as a biocleavable linker or nuclease susceptible linker), which joins the oligomer (region A) of the invention to the carrier component (or region C).

For physiologically labile linkers associated with a carrier component for targeted delivery it is preferred that, the cleavage rate seen in the target tissue (for example muscle, liver, kidney or a tumor) is greater than that found in blood serum. Suitable methods for determining the level (%) of cleavage in target tissue versus serum are described in the "Tissue specific In vitro linker cleavage assay" section. In some embodiments, the physiologically labile linker (also referred to as the biocleavable linker, or nuclease susceptible linker) in a compound of the invention, are at least about 20% cleaved, such as at least about 30% cleaved, such as at least about 40% cleaved, such as at least about 50% cleaved, such as at least about 60% cleaved, such as at least about 70% cleaved, such as at least about 75% cleaved in the "Tissue specific In vitro linker cleavage assay" in the "Materials and methods" section. In some embodiments, the cleavage (%) in serum, as used in the "Tissue specific In vitro linker cleavage assay", is less than about 20%, such as less than about 10%, such as less than 5%, such as less than about 1%.

In some embodiments, the oligomer conjugate of the invention comprises three regions: i) a first region (region A), which comprises 10-18 contiguous nucleotides; ii) a second region (region PL) which comprises a physiologically labile linker and iii) a third region (C) which comprises a carrier component, wherein the third region is covalent linked to the second region which is covalently linked to the first region.

In some embodiments region A and region PL is covalently linked via a phosphate nucleoside linkage (e.g. phosphodiester, phosphorothioate, phosphodithioate, boranophosphate or methylphosphonate) or a triazol group. In some embodiments region PL and region C is covalently linked via a phosphate nucleoside linkage (e.g. phosphodiester, phosphorothioate, phosphodithioate, boranophosphate or methylphosphonate) or a triazol group. In some embodiments region PL and region C is covalently linked via a second linker such as region E linkers described below.

In some embodiments, the physiologically labile linker may be situated either at the 5' end and/or the 3'-end of the oligomer (region A). In a preferred embodiment the physiologically labile linker is at the 5'-end.

In some embodiments, the physiologically labile linker is attached at its 3'-end to the 5'-end of region A and the carrier component (region C) is attached to the 5'-end or the physiologically labile linker (e.g. PO-linker), optionally via an additional linker region E.

Nuclease Susceptible Linker—Phosphodiester Linker (PO-Linker)

In some embodiments, the physiologically labile linker is susceptible to nuclease(s) which may for example, be expressed in the target cell—and as such, as detailed herein, the linker may be a short region (e.g. 1-10) phosphodiester linked nucleosides, such as DNA nucleosides.

In some embodiments, which may be the same or different, the physiologically labile linker (region PL) is susceptible to S1 nuclease cleavage. Susceptibility to S1 cleavage may be evaluated using the S1 nuclease assay described in the "S1 nuclease cleavage assay" section. In some embodiments, the physiologically labile linker (also referred to as the physiologically labile linker, or nuclease susceptible linker), such as region PL, in a compound of the invention, are at least about 30% cleaved, such as at least about 40% cleaved, such as at least about 50% cleaved, such as at least about 60% cleaved, such as at least about 70% cleaved, such as at least about 80% cleaved, such as at least about 90% cleaved, such as at least 95% cleaved after 120 min incubation with S1 nuclease as described in the "S1 nuclease cleavage assay in the "Materials and methods" section.

In some embodiments, the physiologically labile linker (region PL) is a nuclease susceptible linker, which comprises between 1 and 10 nucleosides, such as 1, 2, 3, 4, 5, 6, 7, 8, 9 or 10 nucleosides, more preferably between 2 and 6 nucleosides and most preferably between 2 and 4 linked nucleosides. In some embodiments, the nuclease susceptible linker is a phosphodiester nucleotide linker, such a linker is also termed a PO-linker. In preferred embodiments the nuclease susceptible linker (PO-linker) comprises at least one phosphodiester linked nucleoside. Preferably, the nuclease susceptible PO-linker comprises at least two consecutive phosphodiester linkages, such as at least 3 or 4 or 5 consecutive phosphodiester linkages.

In some embodiments, the nucleosides in the PO-linker are (optionally independently) selected from the group consisting of DNA and RNA or modifications thereof which do not interfere with nuclease cleavage. Modifications of DNA and RNA nucleosides which do not interfere with nuclease cleavage may be non-naturally occurring nucleobases. Certain sugar-modified nucleosides may also allow nuclease cleavage such as an alpha-L-oxy-LNA. In some embodiments, all the nucleosides of the PO-linker comprise (optionally independently) either a 2'-OH ribose sugar (RNA) or a 2'-H sugar—i.e. RNA or DNA. In some embodiments, the nucleosides of the PO-linker are DNA nucleosides. In some embodiments, at least two consecutive nucleosides of the PO-linker are DNA or RNA nucleosides (such as at least 3 or 4 or 5 consecutive DNA or RNA nucleosides). Preferably the PO-linker consists of between 1 to 5 or 1 to 4, such as 2, 3, 4 consecutive phosphodiester linked DNA nucleosides. In preferred embodiments the PO-linker is so short that it does not recruit RNAseH. In some embodiments, the PO-linker comprises no more than 3 or no more than 4 consecutive phospodiester linked DNA and/or RNA nucleosides (such as DNA nucleosides).

In some embodiments, the PO-linker is not complementary to the target nucleic acid sequence or to the oligomer in region A.

In some embodiments, the PO-linker is complementary with the target nucleic acid sequence. In this respect region A and the PO-linker together may form a single contiguous sequence which is complementary to the target sequence.

In some embodiments, region A and the PO-linker form a single contiguous nucleotide sequence of 10-22, such as 12-20 nucleotides in length. In this context region A can be differentiated from the PO-linker in that it starts with at least one, preferably at least two, modified nucleosides with increased binding affinity to the target nucleic acid (e.g. LNA or nucleosides with a 2' substituted sugar moiety) and region A on its own is capable of modulation of the expression the target nucleic acid in a relevant cell line. Furthermore, if region A comprises DNA or RNA nucleosides these are linked with nuclease resistant internucleoside linkage, such phosphorothioate or boranophosphate.

In some aspects the internucleoside linkage between the first (region A) and the second region (the PO-linker) may be considered part of the second region.

In some embodiments, the sequence of bases in the PO-linker is selected to provide an optimal endonuclease cleavage site, based upon the predominant endonuclease cleavage enzymes present in the target tissue or cell or sub-cellular compartment. In this respect, by isolating cell extracts from target tissues and non-target tissues, endonuclease cleavage sequences for use in the PO-linker may be selected based upon a preferential cleavage activity in the desired target cell (e.g. liver/hepatocytes) as compared to a non-target cell (e.g. kidney). In this respect, the potency of the compound for target down-regulation may be optimized for the desired tissue/cell.

In some embodiments the PO-linker comprises a dinucleotide of sequence AA, AT, AC, AG, TA, TT, TC, TG, CA, CT, CC, CG, GA, GT, GC, or GG, wherein C may be 5-methylcytosine, and/or T may be replaced with U. Preferably, the internucleoside linkage is a phosphodiester linkage. In a preferred embodiment the PO-linker is a CA dinucleotide with at least two phosphodiester linkages (one being to Region A). In some embodiments the PO-linker comprises a trinucleotide of sequence AAA, AAT, AAC, AAG, ATA, ATT, ATC, ATG, ACA, ACT, ACC, ACG, AGA, AGT, AGC, AGG, TAA, TAT, TAC, TAG, TTA, TTT, TTC, TAG, TCA, TCT, TCC, TCG, TGA, TGT, TGC, TGG, CAA, CAT, CAC, CAG, CTA, CTG, CTC, CTT, CCA, CCT, CCC, CCG, CGA, CGT, CGC, CGG, GAA, GAT, GAC, CAG, GTA, GTT, GTC, GTG, GCA, GCT, GCC, GCG, GGA, GGT, GGC, and GGG wherein C may be 5-methylcytosine and/or T may be replaced with U.

Preferably, the internucleoside linkages are phosphodiester linkages. In some embodiments the PO-linker comprises a trinucleotide of sequence AAAX, AATX, AACX, AAGX, ATAX, ATTX, ATCX, ATGX, ACAX, ACTX, ACCX, ACGX, AGAX, AGTX, AGCX, AGGX, TAAX, TATX, TACX, TAGX, TTAX, TTTX, TTCX, TAGX, TCAX, TCTX, TCCX, TCGX, TGAX, TGTX, TGCX, TGGX, CAAX, CATX, CACX, CAGX, CTAX, CTGX, CTCX, CTTX, CCAX, CCTX, CCCX, CCGX, CGAX, CGTX, CGCX, CGGX, GAAX, GATX, GACX, CAGX, GTAX, GTTX, GTCX, GTGX, GCAX, GCTX, GCCX, GCGX, GGAX, GGTX, GGCX, and GGGX, wherein X may be selected from the group consisting of A, T, U, G, C and analogues thereof, wherein C may be 5-methylcytosine and/or T may be replaced with U. Preferably, the internucleoside linkages are phosphodiester linkages. It will be recognized that when referring to (naturally occurring) nucleobases A, T, U, G, C, these may be substituted with nucleobase analogues which function as the equivalent natural nucleobase (e.g. base pair with the complementary nucleoside).

In some embodiments, region PL is a phosphodiester nucleotide linker (PO-linker) covalently attached to a lipophilic conjugate moiety, such as a lipid, a fatty acid, sterol, such as cholesterol or tocopherol. In some embodiments, region PL is a phosphodiester nucleotide linker (PO-linker) covalently attached to a asialoglycoprotein receptor targeting moiety, such as a GalNAc carrier component.

Figure 4:
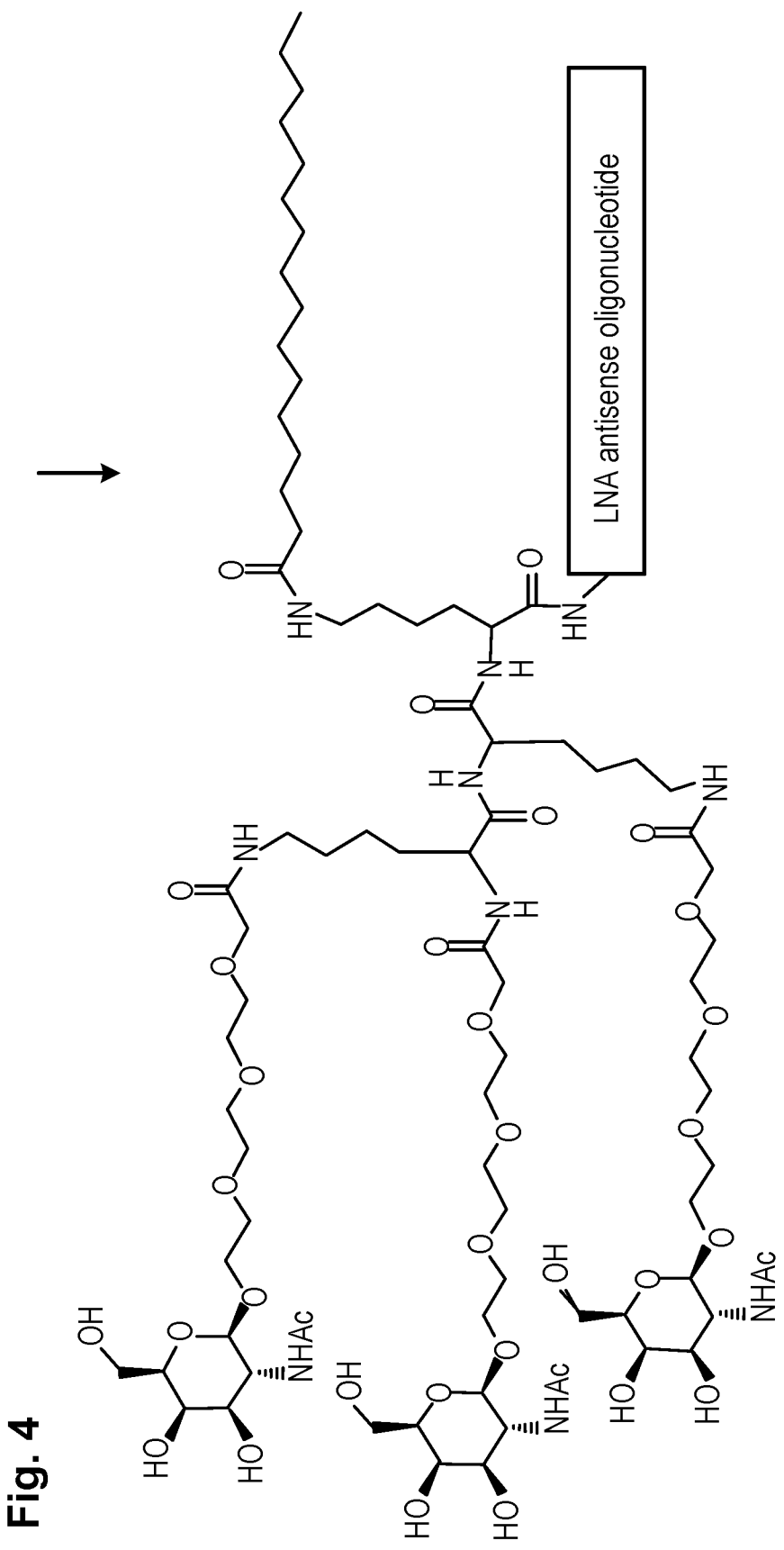
FIG. 4: Presents examples of oligomer conjugates with trivalent GalNAc carrier components.
Figure 4:
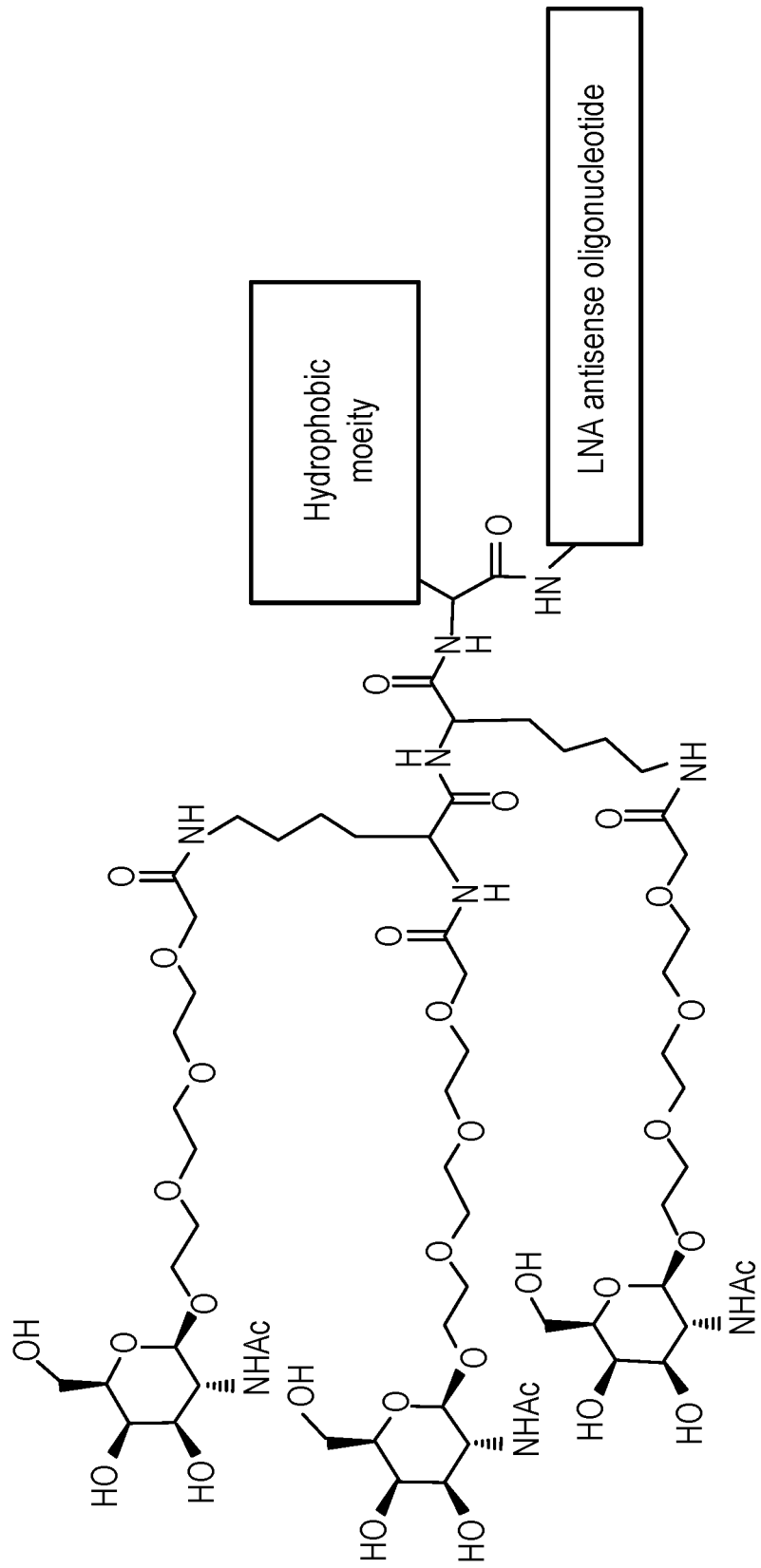
Figure 4:
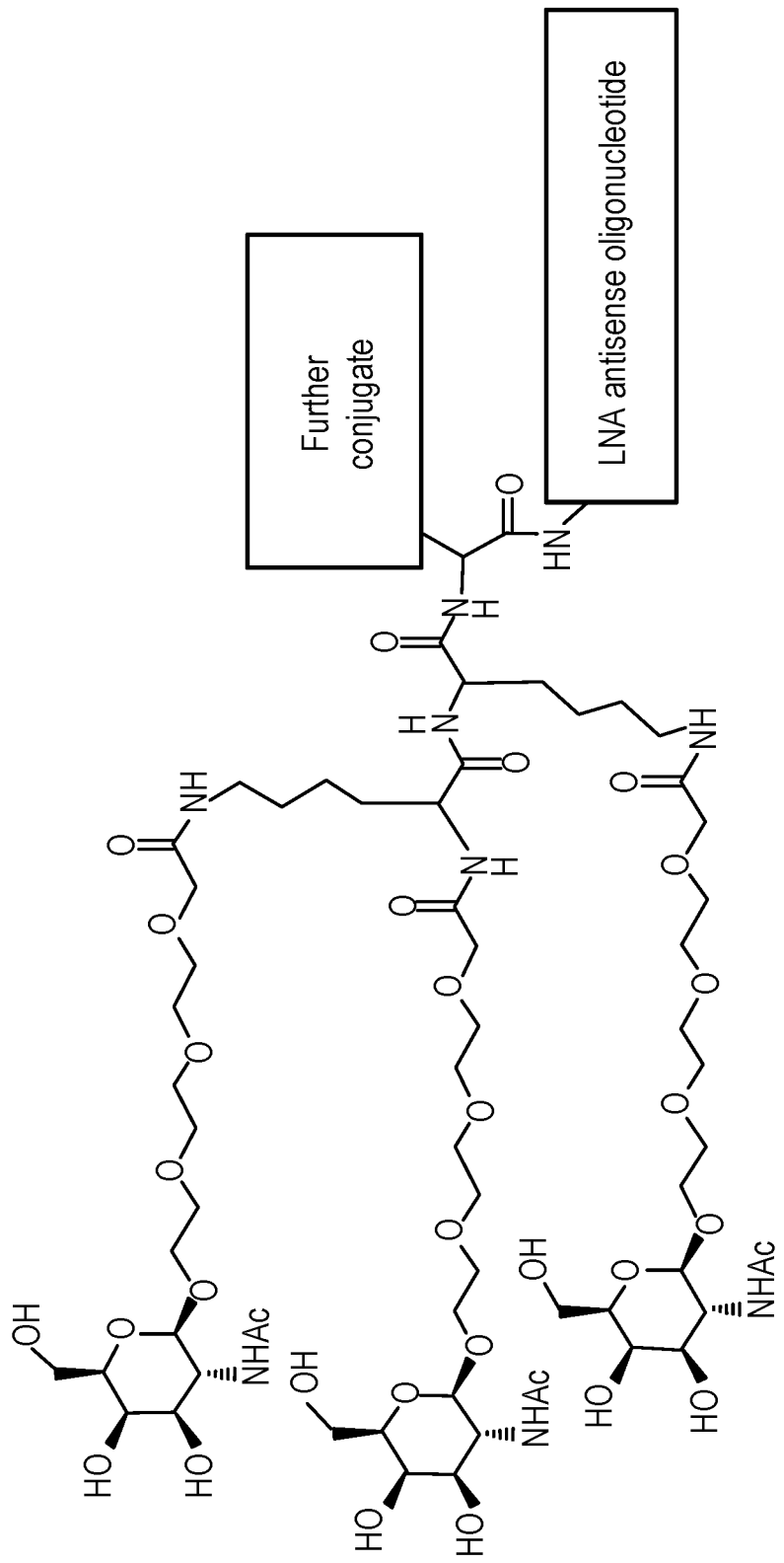
Figure 4:
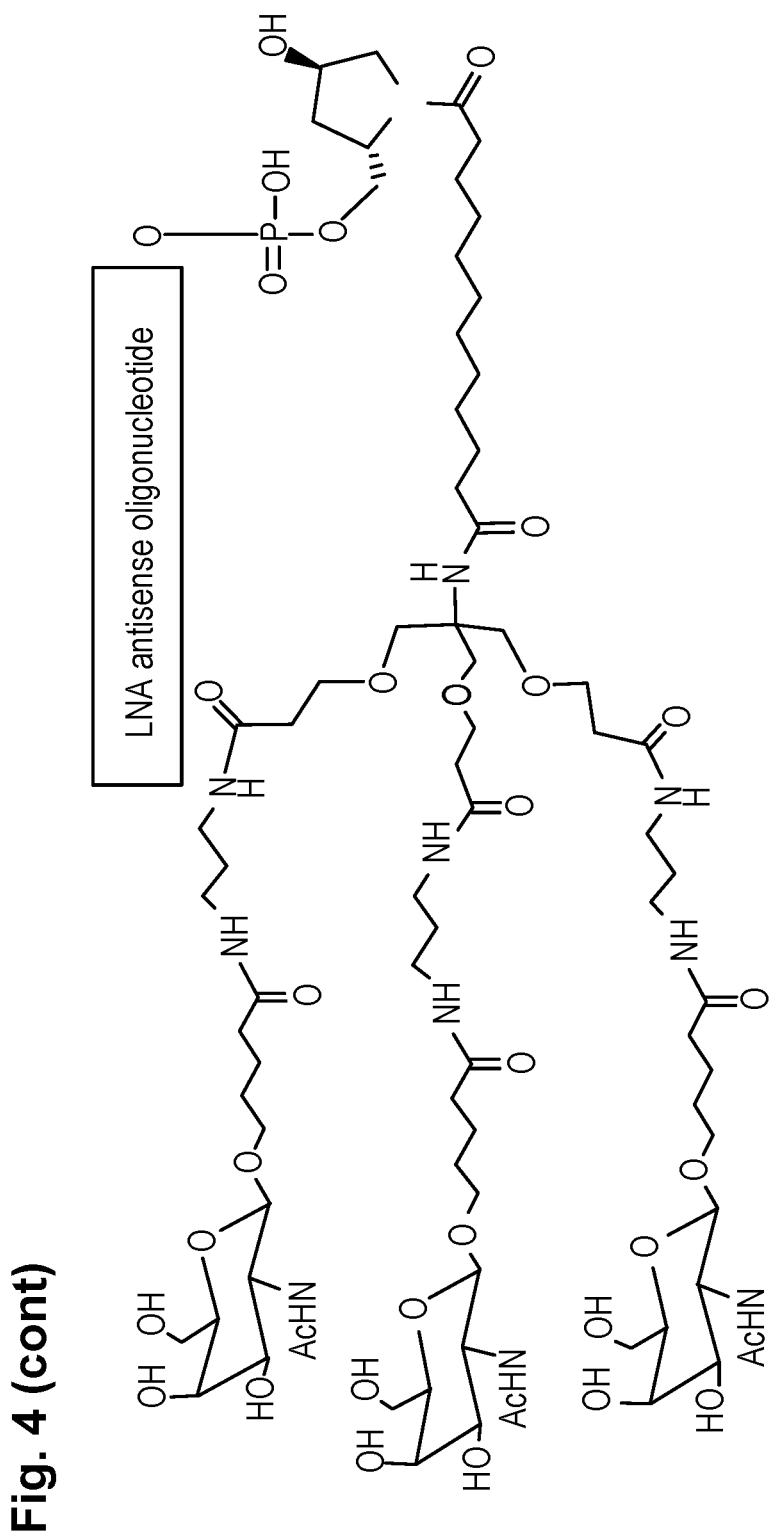

The concept of inserting a physiologically labile linker between the oligomer and the carrier component is described in detail in WO 2014/076195 (hereby incorporated by reference, in particular FIGS. 3 and 4 are incorporated by reference).

Alternative Linkers (Region E)

In some instances linkers are not necessarily physiologically labile but primarily serves to covalently connect a third region, e.g. a carrier component (region C), to an oligomer (region A). Herein these linkers are also termed region E. The oligomer conjugates of the present invention can be constructed of the following regional elements A-C/C-A, A-PL-C/C-PL-A, A-PL-E-C/C-E-PL-A, A-E-PL-C/C-PL-E-A or A-E-C/C-E-A.

In some embodiments, the linker E comprises a chain structure or an oligomer of repeating units such as ethylene glycol, amino acid units or amino alkyl groups. The linker E can have at least two functionalities, one for attaching to the oligomer (optionally with a physiologically labile linker) and the other for attaching to the carrier component. Example linker functionalities can be electrophilic for reacting with nucleophilic groups on the oligomer or carrier component, or nucleophilic for reacting with electrophilic groups. In some embodiments, linker functionalities include amino, hydroxyl, carboxylic acid, thiol, phosphoramidate, phosphorothioate, phosphate, phosphite, unsaturations (e.g., double or triple bonds), and the like. For example, a carbohydrate carrier component (e.g. GalNAc) may be linked to the oligomer via a linker, such as (poly)ethylene glycol linker (PEG), such as a di, tri, tetra, penta, hexa-ethylene glycol linker.

In some embodiments the linker (region E) is an amino alkyl, such as a C2-C36 amino alkyl group, including, for example C6 to C12 amino alkyl groups. In a preferred embodiment the linker (region E) is a C6 amino alkyl group. The amino alkyl group may be added to the oligomer (region A or region A-L/L-A) as part of standard oligomer synthesis, for example using a (e.g. protected) amino alkyl phosphoramidite. The linkage group between the amino alkyl and the oligomer may for example be a phosphorothioate or a phosphodiester, or one of the other nucleoside linkage groups referred to herein. The amino alkyl group is covalently linked to the 5' or 3'-end of the oligomer. Commercially available amino alkyl linkers are for example 3'-Amino-Modifier reagent for linkage at the 3'-end of the oligomer and for linkage at the 5'-end of an oligomer 5'-Amino-Modifier C6 is available. These reagents are available from Glen Research Corporation (Sterling, Va.). These compounds or similar ones were utilized by Krieg, et al, Antisense Research and Development 1991, 1, 161 to link fluorescein to the 5'-terminus of an oligomer. A wide variety of further linker groups are known in the art and can be useful in the attachment of carrier components to oligomers. A review of many of the useful linker groups can be found in, for example, Antisense Research and Applications, S. T. Crooke and B. Lebleu, Eds., CRC Press, Boca Raton, Fla., 1993, p. 303-350. Other compounds such as acridine have been attached to the 3'-terminal phosphate group of an oligomer via a polymethylene linkage (Asseline, et al., Proc. Natl. Acad. Sci. USA 1984, 81, 3297). Any of the above groups can be used as a single linker (region E) or in combination with one or more further linkers (region E-E' or region E-L or L-E).

Linkers and their use in preparation of conjugates of oligomers are provided throughout the art such as in WO 96/11205 and WO 98/52614 and U.S. Pat. Nos. 4,948,882; 5,525,465; 5,541,313; 5,545,730; 5,552,538; 5,580,731; 5,486,603; 5,608,046; 4,587,044; 4,667,025; 5,254,469; 5,245,022; 5,112,963; 5,391,723; 5,510475; 5,512,667; 5,574,142; 5,684,142; 5,770,716; 6,096,875; 6,335,432; and 6,335,437, WO 2012/083046 each of which is incorporated by reference in its entirety. FIG. 3 present example GalNAc clusters, Conj 1, 2, 3, 4 and Conj1a, 2a, 3a and 4a having an optional C6 linker which joins the GalNac cluster to the oligomer.

Asiaglycoprotein Receptor (ASGP-R) Targeting Moiety

As used herein, the term "asiaglycoprotein receptor (ASGP-R) targeting moiety" relates to a moiety which interacts with ASGP-R and thereby brings an oligomer into contact with, or into proximity to, a cell expressing surface ASGP-R.

Conjugate Moiety

In some embodiments, the carrier component is a conjugate moiety.

In addition, one or more conjugate moieties may be attached to the oligomer or the oligomer conjugate in addition to the carrier component.

In some embodiments, one or more conjugate moieties may be attached to the oligomer of the present invention.

The conjugate moiety may be a non-nucleotide moiety or a non-polynucleotide moiety.

The conjugate moiety may enhance the activity, cellular distribution or cellular uptake of the oligomer of the invention. Such moieties include, but are not limited to, antibodies, polypeptides, lipid moieties such as a cholesterol moiety, cholic acid, a thioether, e.g. Hexyl-s-tritylthiol, a thiocholesterol, an aliphatic chain, e.g., dodecandiol or undecyl residues, a phospholipids, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

The oligomers of the invention may also be conjugated to active drug substances for example, aspirin, ibuprofen, a sulfa drug, an antidiabetic, an antibacterial or an antibiotic.

In certain embodiments the conjugated moiety is a sterol, such as cholesterol.

In various embodiments, the conjugate moiety comprises or consists of a positively charged polymer, such as a positively charged peptides of, for example from 1-50, such as 2-20 such as 3-10 amino acid residues in length, and/or polyalkylene oxide such as polyethylglycol (PEG) or polypropylene glycol—see WO 2008/034123, hereby incorporated by reference. Suitably the positively charged polymer, such as a polyalkylene oxide may be attached to the oligomer of the invention via a linker such as the releasable linker described in WO 2008/034123.

The oligomers and oligomer conjugates of the present invention may include—as a conjugate moiety—an appropriate ligand-binding molecule. For example, the oligonucleotides may be conjugated for therapeutic administration to ligand-binding molecules which recognize cell-surface molecules, such as according to International Patent Application WO 91/04753. The ligand-binding molecule may comprise, for example, an antibody against a cell surface antigen, an antibody against a cell surface receptor, a growth factor having a corresponding cell surface receptor, an antibody to such a growth factor, or an antibody which recognizes a complex of a growth factor and its receptor. Methods for conjugating ligand-binding molecules to oligonucleotides are detailed in WO 91/04753. Further, conjugation methods and methods to improve cellular uptake which may be used are described in the following international patent applications WO 9640961, WO9964449, WO9902673, WO9803533, WO0015265 and U.S. Pat. Nos. 5,856,438 and 5,138,045.

By way of a further example, the conjugate moiety may be a growth factor such as transferrin or folate. Transferrin-polylysine-oligonucleotide complexes or folate-polylysine-oligonucleotide complexes may be prepared for uptake by cells expressing high levels of transferrin or folate receptor. The preparation of transferrin complexes as carrier components facilitating oligonucleotide uptake into cells is described by Wagner et al., *Proc. Natl. Acad. Sci. USA* 87, 3410-3414 (1990). Cellular delivery of folate-macromolecule conjugates via folate receptor endocytosis, including delivery of an antisense oligonucleotide, is described by Low et al., U.S. Pat. No. 5,108,921. Also see, Leamon et al., *Proc. Natl. Acad. Sci.* 88, 5572 (1991).

Target Nucleic Acid/Target Sequence

In preferred aspects, the terms "target nucleic acid" and "target sequence", as used herein refer to the DNA or RNA encoding a HBx or HBsAg polypeptide, such as a sequence contained within any of SEQ ID No. 1 or SEQ ID No. 2. The terms "target nucleic acid" and "target sequence" therefore include HBx- or HBsAg-encoding nucleic acids or naturally occurring variants thereof, and RNA nucleic acids derived therefrom, preferably mRNA, such as pre-mRNA, although preferably mature mRNA. In some embodiments, for example when used in research or diagnostics the "target nucleic acid" or "target sequence" may be a cDNA or a synthetic oligonucleotide derived from the above DNA or RNA nucleic acid targets. The oligomer according to the invention is preferably capable of hybridising to the target nucleic acid.

Identity/Homology

As used herein, the terms "homologous" and "homology" are interchangeable with the terms "identity" and "identical".

Corresponding to/Corresponds to

The terms "corresponding to" and "corresponds to" refer to the comparison between the nucleotide sequence of the oligomer (i.e. the nucleobase or base sequence) or a contiguous nucleotide sequence thereof and the equivalent contiguous nucleotide sequence of a further sequence selected from either i) a sub-sequence of the reverse complement of the nucleic acid target, such as the mRNA which encodes the target sequence protein, such as any sequence within SEQ ID No. 1 or SEQ ID No. 2 or SEQ ID No. 3 and/or ii) the sequence of any of the specific nucleotide sequences provided herein, or sub-sequence thereof. Nucleotide analogues are compared directly to their equivalent or corresponding nucleotides. A sequence which corresponds to a further sequence under i) or ii) typically is identical to that sequence over the length of the first sequence (such as the contiguous nucleotide sequence) or, as described herein may, in some embodiments, is at least 80% homologous to a corresponding sequence, such as at least 85%, at least 90%, at least 91%, at least 92% at least 93%, at least 94%, at least 95%, at least 96% homologous, such as 100% homologous (identical). The percentage sequence identity may be calculated by counting the number of aligned bases that are identical between the 2 sequences, dividing by the total number of units in the oligomer, and multiplying by 100.

The terms "corresponding nucleotide analogue" and "corresponding nucleotide" are intended to indicate that the nucleotide in the nucleotide analogue and the naturally occurring nucleotide are identical. For example, when the 2-deoxyribose unit of the nucleotide is linked to an adenine, the "corresponding nucleotide analogue" contains a pentose unit (different from 2-deoxyribose) linked to an adenine.

Complementary

The term, "complementary" means that two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. Normally, the complementary sequence of the oligonucleotide has at least 90%, preferably 95%, most preferably 100%, complementarity to a defined sequence.

In determining the degree of "complementarity" between oligomers of the invention (or regions thereof) and the target sequence, such as the HBx or HBsAg target sequence, the degree of "complementarity" (also, "homology" or "identity") is expressed as the percentage identity (or percentage homology) between the sequence of the oligomer (or region thereof) and the sequence of the target region (or the reverse complement of the target region) that best aligns therewith. The percentage is calculated by counting the number of aligned bases that are identical between the 2 sequences, dividing by the total number of contiguous units in the oligomer, and multiplying by 100. In such a comparison, if gaps exist, it is preferable that such gaps are merely mismatches rather than areas where the number of units within the gap differs between the oligomer of the invention and the target region.

In particular, the term "complementary" means the capacity for pairing between nucleobases of a first nucleic acid and a second nucleic acid. Two sequences are complementary when the sequence of one can bind to the sequence of the other in an anti-parallel sense wherein the 3'-end of each sequence binds to the 5'-end of the other sequence and each nucleobase A, T(U), G, and C of one sequence is then aligned with a T(U), A, C, and G, respectively, of the other sequence. In determining the degree of complementarity between oligomers of the invention (or regions thereof) and the target sequence, such as the HBx or HBsAg target sequence, the degree of complementarity is expressed as the percentage complementarity between the sequence of the oligomer (or region thereof) and the sequence of the target region that best aligns therewith. The percentage is calculated by counting the number of aligned bases that form pairs between the 2 sequences, dividing by the total number of contiguous units in the oligomer, and multiplying by 100. In such a comparison a nucleobase/nucleotide which does not align is termed a mismatch. Normally, the complementary sequence of a oligonucleotide of the present invention has at least 80%, preferably 85%, preferably 90%, more preferably 95%, most preferably 100%, complementarity to a defined sequence.

The term "complementary sequence" as it refers to a polynucleotide sequence, relates to the base sequence in another nucleic acid molecule by the base-pairing rules. More particularly, the term or like term refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 95% of the nucleotides of the other strand, usually at least about 98%, and more preferably from about 99 to about 100%. Complementary polynucleotide sequences can be identified by a variety of approaches including use of well-known computer algorithms and software, for example the BLAST program.

Reverse Complement/Reverse Complementary/Reverse Complementarity

The terms "reverse complement", "reverse complementary" and "reverse complementarity" as used herein are interchangeable with the terms "complement", "complementary" and "complementarity".

Mismatch

The term "mismatch"—that is sometimes referred to as a non-complementary nucleobase—refers to a nucleobase or nucleotide at a given position in a first nucleic acid that does not make Watson-Crick base paring with the corresponding nucleobase or nucleotide in a second nucleic acid when the first nucleic acid is aligned with thee second nucleic acid. The first nucleic acid can for example be an oligomer or oligomer conjugate according to the invention and the second nucleic acid can for example be a target sequence. In the oligomer or the oligomer conjugate containing multiple mismatches, the mismatches can either be adjacent to each other or interspersed.

Naturally Occurring Variant Thereof

The term "naturally occurring variant thereof" refers to variants of the target sequence which exist naturally within the defined taxonomic group, such as HBV genotypes A-H. Typically, when referring to "naturally occurring variants" of a polynucleotide the term may also encompass any allelic variant of the target sequence encoding genomic DNA which are found by chromosomal translocation or duplication, and the RNA, such as mRNA derived therefrom. "Naturally occurring variants" may also include variants derived from alternative splicing of the target sequence mRNA. When referenced to a specific polypeptide sequence, e.g., the term also includes naturally occurring forms of the protein which may therefore be processed, e.g. by co- or post-translational modifications, such as signal peptide cleavage, proteolytic cleavage, glycosylation, etc.

Downstream

As used herein, the term "downstream" when used in reference to a direction along a nucleotide sequence means in the direction from the 5' to the 3' end. Similarly, the term "upstream" means in the direction from the 3' to the 5' end.

LNA

The term "LNA" refers to a bicyclic nucleoside analogue, known as "Locked Nucleic Acid". It may refer to an LNA unit, or, when used in the context of an "LNA oligonucleotide", LNA refers to an oligonucleotide containing one or more such bicyclic nucleotide analogues. LNA nucleotides are characterised by the presence of a linker group (such as a bridge) between C2' and C4' of the ribose sugar ring—for example as shown as the biradical $R^{4*}$-$R^{2*}$ as described below.

As used herein, the terms "LNA oligonucleotide" and "LNA-modified oligonucleotide" include any oligonucleotide either fully or partially modified with LNA units. Thus, an LNA-modified oligonucleotide may be composed entirely of LNA units, or a LNA-modified oligonucleotide may comprise one LNA unit.

The LNA used in the oligonucleotide compounds of the invention preferably has the structure of the general formula I

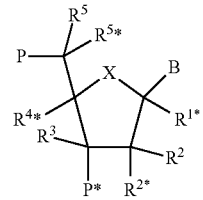

Formula 1 wherein for all chiral centers, asymmetric groups may be found in either R or S orientation;

wherein X is selected from —O—, —S—, —N($R^{N*}$)—, —C($R^6R^{6*}$)—, such as, in some embodiments —O—;

B is selected from hydrogen, optionally substituted $C_{1-4}$-alkoxy, optionally substituted $C_{1-4}$-alkyl, optionally substituted $C_{1-4}$-acyloxy, nucleobases including naturally occurring and nucleobase analogues, DNA intercalators, photochemically active groups, thermochemically active groups, chelating groups, reporter groups, and ligands; preferably, B is a nucleobase or nucleobase analogue;

P designates an internucleotide linkage to an adjacent unit, or a 5-terminal group, such internucleotide linkage or 5-terminal group optionally including the substituent $R^5$ or equally applicable the substituent $R^{5*}$;

P* designates an internucleotide linkage to an adjacent unit, or a 3'-terminal group; $R^{4*}$ and $R^{2*}$ together designate a bivalent linker group consisting of 1-4 groups/atoms selected from —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, optionally substituted $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl) amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=CH$_2$), wherein for all chiral centers, asymmetric groups may be found in either R or S orientation, and;

each of the substituents $R^{1*}$, $R^2$, $R^3$, $R^5$, $R^{5*}$, $R^6$ and $R^{6*}$, which are present is independently selected from hydrogen, optionally substituted $C_{1-12}$-alkyl, optionally substituted $C_{2-12}$-alkenyl, optionally substituted $C_{2-12}$- alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene; wherein $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl; and basic salts and acid addition salts thereof. For all chiral centers, asymmetric groups may be found in either R or S orientation.

In some embodiments, $R^{4*}$ and $R^{2*}$ together designate a biradical consisting of functional groups selected from the group consisting of $C(R^aR^b)$—$C(R^aR^b)$—, $C(R^aR^b)$—O—, $C(R^aR^b)$—$NR^a$—, $C(R^aR^b)$—S—, and $C(R^aR^b)$—$C(R^aR^b)$—O—, wherein each $R^a$ and $R^b$ may optionally be independently selected. In some embodiments, $R^a$ and $R^b$ may be, optionally independently selected from the group consisting of hydrogen and $_{c1-6}$ alkyl, such as methyl, such as hydrogen.

In some embodiments, $R^{4*}$ and $R^{2*}$ together designate the biradical —O—CH($CH_2OCH_3$)— (2'O-methoxyethyl bicyclic nucleic acid—Seth at al., 2010, J. Org. Chem)—in either the R- or S-configuration.

In some embodiments, $R^{4*}$ and $R^{2*}$ together designate the biradical —O—CH($CH_2CH_3$)— (2'O-ethyl bicyclic nucleic acid—Seth at al., 2010, J. Org. Chem). —in either the R- or S-configuration.

In some embodiments, $R^{4*}$ and $R^{2*}$ together designate the biradical —O—CH($CH_3$)—. —in either the R- or S-configuration. In some embodiments, $R^{4*}$ and $R^{2*}$ together designate the biradical —O—$CH_2$—O—$CH_2$— (Seth at al., 2010, J. Org. Chem).

In some embodiments, $R^{4*}$ and $R^{2*}$ together designate the biradical —O—NR—$CH_3$— (Seth at al., 2010, J. Org. Chem).

In some embodiments, the LNA units have a structure selected from the following group:

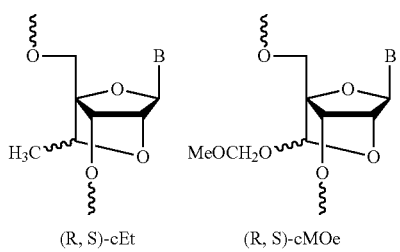

(R, S)-cEt    (R, S)-cMOe

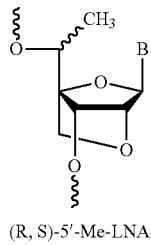

(R, S)-5'-Me-LNA

In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. For all chiral centers, asymmetric groups may be found in either R or S orientation.

In some embodiments, $R^{1*}$, $R^2$, $R^3$, $R^5$, $R^{5*}$ are hydrogen.

In some embodiments, $R^{1*}$, $R^2$, $R^3$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. For all chiral centers, asymmetric groups may be found in either R or S orientation.

In some embodiments, $R^{1*}$, $R^2$, $R^3$ are hydrogen.

In some embodiments, $R^5$ and $R^{5*}$ are each independently selected from the group consisting of H, —$CH_3$, —$CH_2$—$CH_3$, —$CH_2$—O—$CH_3$, and —CH═$CH_2$. Suitably in some embodiments, either $R^5$ or $R^{5*}$ are hydrogen, where as the other group ($R^5$ or $R^{5*}$ respectively) is selected from the group consisting of $C_{1-5}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl or substituted acyl (—C(═O)—); wherein each substituted group is mono or poly substituted with substituent groups independently selected from halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $OJ_1$, $SJ_1$, $NJ_1J_2$, $N_3$, $COOJ_1$, CN, O—C(═O)$NJ_1J_2$, N(H)C(═NH)NJ, $J_2$ or N(H)C(═X)N(H)$J_2$ wherein X is O or S; and each $J_1$ and $J_2$ is, independently, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$ aminoalkyl, substituted $C_{1-6}$ aminoalkyl or a protecting group. In some embodiments either $R^5$ or $R^{5*}$ is substituted $C_{1-6}$ alkyl. In some embodiments either $R^5$ or $R^{5*}$ is substituted methylene wherein preferred substituent groups include one or more groups independently selected from F, $NJ_1J_2$, $N_3$, CN, $OJ_1$, $SJ_1$, O—C(═O)$NJ_1J_2$, N(H)C(═NH)NJ, $J_2$ or N(H)C(O)N(H)$J_2$. In some embodiments each $J_1$ and $J_2$ is, independently H or $C_{1-6}$ alkyl. In some embodiments either $R^5$ or $R^{5*}$ is methyl, ethyl or methoxymethyl. In some embodiments either $R^5$ or $R^{5*}$ is methyl. In a further embodiment either $R^5$ or $R^{5*}$ is ethylenyl. In some embodiments either $R^5$ or $R^{5*}$ is substituted acyl. In some embodiments either $R^5$ or $R^{5*}$ is C(═O)$NJ_1J_2$. For all chiral centers, asymmetric groups may be found in either R or S orientation. Such 5' modified bicyclic nucleotides are disclosed in WO 2007/134181, which is hereby incorporated by reference in its entirety.

In some embodiments B is a nucleobase, including nucleobase analogues and naturally occurring nucleobases, such as a purine or pyrimidine, or a substituted purine or substituted pyrimidine, such as a nucleobase referred to herein, such as a nucleobase selected from the group consisting of adenine, cytosine, thymine, adenine, uracil, and/or a modified or substituted nucleobase, such as 5-thiazolo-uracil, 2-thio-uracil, 5-propynyl-uracil, 2'thio-thymine, 5-methyl cytosine, 5-thiozolo-cytosine, 5-propynyl-cytosine, and 2,6-diaminopurine.

In some embodiments, $R^{4*}$ and $R^{2*}$ together designate a biradical selected from —C($R^aR^b$)—O—, —C($R^aR^b$)—C($R^cR^d$)—O—, —C($R^aR^b$)—C($R^cR^d$)—C($R^eR^f$)—O—, —C($R^aR^b$)—O—C($R^cR^d$)—, —C($R^aR^b$)—O—C($R^cR^d$)—O—, —C($R^aR^b$)—C($R^cR^d$)—, —C($R^aR^b$)—C($R^cR^d$)—C($R^eR^f$)—, —C($R^a$)=C($R^b$)—C($R^cR^d$)—, —C($R^aR^b$)—N($R^c$)—, —C($R^aR^b$)—C($R^cR^d$)—N($R^e$)—, —C($R^aR^b$)—N($R^c$)—O—, and —C($R^aR^b$)—S—, —C($R^aR^b$)—C($R^cR^d$)—S—, wherein $R^a$, $R^b$, $R^c$, $R^d$, $R^e$, and $R^f$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=$CH_2$). For all chiral centers, asymmetric groups may be found in either R or S orientation.

In a further embodiment $R^{4*}$ and $R^{2*}$ together designate a biradical (bivalent group) selected from —$CH_2$—O—, —$CH_2$—S—, —$CH_2$—NH—, —$CH_2$—N($CH_3$)—, —$CH_2$—$CH_2$—O—, —$CH_2$—CH($CH_3$)—, —$CH_2$—$CH_2$—S—, —$CH_2$—$CH_2$—NH—, —$CH_2$—$CH_2$—$CH_2$—, —$CH_2$—$CH_2$—$CH_2$—O—, —$CH_2$—$CH_2$—CH($CH_3$)—, —CH=CH—$CH_2$—, —$CH_2$—O—$CH_2$—O—, —$CH_2$—NH—O—, —$CH_2$—N($CH_3$)—O—, —$CH_2$—O—$CH_2$—, —CH($CH_3$)—O—, and —CH($CH_3$)—O—$CH_3$)—O—, and/or, —$CH_2$—$CH_2$—, and —CH=CH— For all chiral centers, asymmetric groups may be found in either R or S orientation.

In some embodiments, $R^{4*}$ and $R^{2*}$ together designate the biradical C($R^aR^b$)—N($R^c$)—O—, wherein $R^a$ and $R^b$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen, and; wherein $R^c$ is selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ together designate the biradical C($R^aR^b$)—O—C($R^cR^d$)—O—, wherein $R^a$, $R^b$, $R^c$, and $R^d$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ form the biradical —CH(Z)—O—, wherein Z is selected from the group consisting of $C_{1-6}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl, acyl, substituted acyl, substituted amide, thiol or substituted thio; and wherein each of the substituted groups, is, independently, mono or poly substituted with optionally protected substituent groups independently selected from halogen, oxo, hydroxyl, $OJ_1$, $NJ_1J_2$, $SJ_1$, $N_3$, OC(=X)$J_1$, OC(=X)$NJ_1J_2$, $NJ^3$C(=X)$NJ_1J_2$ and CN, wherein each $J_1$, $J_2$ and $J_3$ is, independently, H or $C_{1-6}$ alkyl, and X is O, S or $NJ_1$. In some embodiments Z is $C_{1-6}$ alkyl or substituted $C_{1-6}$ alkyl. In some embodiments Z is methyl. In some embodiments Z is substituted $C_{1-6}$ alkyl. In some embodiments said substituent group is $C_{1-6}$ alkoxy. In some embodiments Z is $CH_3OCH_2$—. For all chiral centers, asymmetric groups may be found in either R or S orientation. Such bicyclic nucleotides are disclosed in U.S. Pat. No. 7,399,845 which is hereby incorporated by reference in its entirety. In some embodiments, $R^{1*}$, $R^2$, $R^3$, $R^5$, $R^{5*}$ are hydrogen. In some embodiments, $R^{1*}$, $R^2$, $R^{3*}$ are hydrogen, and one or both of $R^5$, $R^{5*}$ may be other than hydrogen as referred to above and in WO 2007/134181.

In some embodiments, $R^{4*}$ and $R^{2*}$ together designate a biradical which comprise a substituted amino group in the bridge such as consist or comprise of the biradical —$CH_2$—N($R^c$)—, wherein $R^c$ is $C_{1-12}$ alkyloxy. In some embodiments $R^{4*}$ and $R^{2*}$ together designate a biradical —$Cq_3q_4$-NOR—, wherein $q_3$ and $q_4$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl; wherein each substituted group is, independently, mono or poly substituted with substituent groups independently selected from halogen, $OJ_1$, $SJ_1$, $NJ_1J_2$, $COOJ_1$, CN, O—C(=O)$NJ_1J_2$, N(H)C(=NH)N $J_1J_2$ or N(H)C(=X=N(H)$J_2$ wherein X is 0 or S; and each of $J_1$ and $J_2$ is, independently, H, $C_{1-6}$ alkyl, $C_{2-6}$ alkenyl, $C_{2-6}$ alkynyl, $C_{1-6}$ aminoalkyl or a protecting group. For all chiral centers, asymmetric groups may be found in either R or S orientation. Such bicyclic nucleotides are disclosed in WO2008/150729 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181. In some embodiments $R^{4*}$ and $R^{2*}$ together designate a biradical (bivalent group) C($R^aR^b$)—O—, wherein $R^a$ and $R^b$ are each independently halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$; or $R^a$ and $R^b$ together are =C($q_3$)($q_4$); $q_3$ and $q_4$ are each, independently, H, halogen, $C_1$-$C_{12}$alkyl or substituted $C_1$-$C_{12}$ alkyl; each substituted group is, independently, mono or poly substituted with substituent groups independently selected from halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$, $SJ_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=O)NJ_1J_2$ or $N(H)C(=S)NJ_1J_2$ and; each $J_1$ and $J_2$ is, independently, H, C1-$C_6$ alkyl, substituted C1-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, C1-$C_6$ aminoalkyl, substituted C1-$C_6$ aminoalkyl or a protecting group. Such compounds are disclosed in WO2009006478A, hereby incorporated in its entirety by reference.

In some embodiments, $R^{4*}$ and $R^{2*}$ form the biradical -Q-, wherein Q is $C(q_1)(q_2)C(q_3)(q_4)$, $C(q_1)=C(q_3)$, $C[=C(q_1)(q_2)]-C(q_3)(q_4)$ or $C(q_1)(q_2)-C[=C(q_3)(q_4)]$; $q_1$, $q_2$, $q_3$, $q_4$ are each independently. H, halogen, $C_{1-12}$ alkyl, substituted $C_{1-12}$ alkyl, $C_{2-12}$ alkenyl, substituted $C_{1-12}$ alkoxy, $OJ_1$, $SJ_1$, $SOJ_1$, $SO_2J_1$, $NJ_1J_2$, $N_3$, CN, $C(=O)OJ_1$, $C(=O)-NJ_1J_2$, $C(=O)J_1$, $-C(=O)NJ_1J_2$, $N(H)C(=NH)NJ_1J_2$, $N(H)C(=O)NJ_1J_2$ or $N(H)C(=S)NJ_1J_2$; each $J_1$ and $J_2$ is, independently, H, $C_1$. 6 alkyl, $C_{2-6}$ alkenyl, $C_{2-6}$ alkynyl, $C_{1-6}$ aminoalkyl or a protecting group; and, optionally wherein when Q is $C(q_1)(q_2)(q_3)(q_4)$ and one of $q_3$ or $q_4$ is $CH_3$ then at least one of the other of $q_3$ or $q_4$ or one of $q_1$ and $q_2$ is other than H. In some embodiments, $R^{1*}$, $R^2$, $R^3$, $R^5$, $R^{5*}$ are hydrogen. For all chiral centers, asymmetric groups may be found in either R or S orientation. Such bicyclic nucleotides are disclosed in WO2008/154401 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181 or WO2009/067647 (alpha-L-bicyclic nucleic acids analogs).

Further bicyclic nucleoside analogues and their use in antisense oligonucleotides are disclosed in WO2011/115818, WO2011/085102, WO2011/017521, WO09/100320, WO10/036698, WO09/124295 & WO09/006478. Such nucleoside analogues may in some aspects be useful in the compounds of present invention.

In some embodiments the LNA used in the oligonucleotide compounds of the invention preferably has the structure of the general formula II:

Formula II

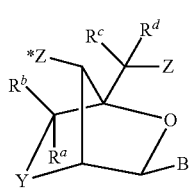

wherein Y is selected from the group consisting of —O—, —$CH_2$O—, —S—, —NH—, N($R^e$) and/or —$CH_2$—; Z and Z* are independently selected among an internucleotide linkage, RH, a terminal group or a protecting group; B constitutes a natural or non-natural nucleotide base moiety (nucleobase), and RH is selected from hydrogen and $C_{1-4}$-alkyl; $R^a$, $R^b$ $R^c$, $R^d$ and $R^e$ are, optionally independently, selected from the group consisting of hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=$CH_2$); and RH is selected from hydrogen and $C_{1-4}$-alkyl. In some embodiments $R^a$, $R^b$ $R^c$, $R^d$ and $R^e$ are, optionally independently, selected from the group consisting of hydrogen and $C_{1-6}$ alkyl, such as methyl. For all chiral centers, asymmetric groups may be found in either R or S orientation, for example, two exemplary stereochemical isomers include the beta-D and alpha-L isoforms, which may be illustrated as follows:

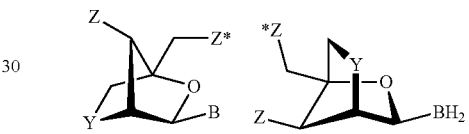

Specific exemplary LNA units are shown below:

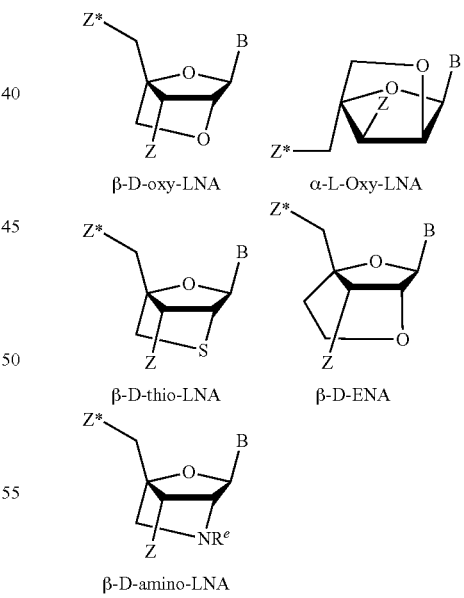

β-D-oxy-LNA  α-L-Oxy-LNA

β-D-thio-LNA  β-D-ENA

β-D-amino-LNA

The term "thio-LNA" comprises a locked nucleotide in which Y in the general formula above is selected from S or —$CH_2$—S—. Thio-LNA can be in both beta-D and alpha-L-configuration.

The term "amino-LNA" comprises a locked nucleotide in which Y in the general formula above is selected from —N(H)—, N(R)—, $CH_2$—N(H)—, and —$CH_2$—N(R)— where R is selected from hydrogen and $C_{1-4}$-alkyl. Amino-LNA can be in both beta-D and alpha-L-configuration.

The term "oxy-LNA" comprises a locked nucleotide in which Y in the general formula above represents —O—. Oxy-LNA can be in both beta-D and alpha-L-configuration.

The term "ENA" comprises a locked nucleotide in which Y in the general formula above is —$CH_2$—O— (where the oxygen atom of —$CH_2$—O— is attached to the 2'-position relative to the base B). $R^e$ is hydrogen or methyl.

In some exemplary embodiments LNA is selected from beta-D-oxy-LNA, alpha-L-oxy-LNA, beta-D-amino-LNA and beta-D-thio-LNA, in particular beta-D-oxy-LNA.

LNA-modified antisense oligonucleotides may be used in combinations. For instance, a cocktail of several different LNA modified oligonucleotides, directed against different regions of the same gene, may be administered simultaneously or separately.

Headmer

A "headmer" is defined as an oligomer that comprises a region X' and a region Y' that is contiguous thereto, with the 5'-most unit of region Y' linked to the 3'-most unit of region X'.

Region X' comprises a contiguous stretch of non-RNase recruiting nucleoside analogues and region Y' comprises a contiguous stretch (such as at least 7 contiguous units) of DNA units or nucleoside analogue units recognizable and cleavable by the RNase.

Tailmer

A "tailmer" is defined as an oligomer that comprises a region X" and a region Y" that is contiguous thereto, with the 5'-most unit of region Y" linked to the 3'-most unit of the region X". Region X" comprises a contiguous stretch (such as at least 7 contiguous units) of DNA units or nucleoside analogue units recognizable and cleavable by the RNase, and region X" comprises a contiguous stretch of non-RNase recruiting nucleoside analogues.

Chimeric Oligomers/Mixmers

"Chimeric" oligomers, called "mixmers", consist of an alternating composition of (i) DNA units or nucleoside analogue units recognizable and cleavable by RNase, and (ii) non-RNase recruiting nucleoside analogue units.

Photochemically Active Groups

In the present context, the term "photochemically active groups" refers to compounds which are able to undergo chemical reactions upon irradiation with light. Illustrative examples of functional groups herein are quinones, especially 6-methyl-1,4-naphtoquinone, anthraquinone, naphtoquinone, and 1,4-dimethyl-anthraquinone, diazirines, aromatic azides, benzophenones, psoralens, diazo compounds, and diazirino compounds.

Based on

As used herein, the term "based on" means that the oligomer or the oligomer of the oligomer conjugate comprises at least 80%, preferably at least 85%, preferably at least 90%, preferably at least 95%, preferably all of the nucleotides of the core motif or sequence and optionally wherein one or more of the nucleotides may be a modified nucleotide.

Accordingly, for certain embodiments, the term "based on" means that the oligomer or the oligomer of the oligomer conjugate comprises all of the nucleotides of the core motif or sequence and optionally wherein one or more of the nucleotides may be a modified nucleotide.

For certain embodiments, the term "based on" means that the oligomer or the oligomer of the oligomer conjugate comprises all of the nucleotides of the core motif or sequence and wherein one or more of the nucleotides is a modified nucleotide.

For certain embodiments, the term "based on" means that the oligomer or the oligomer of the oligomer conjugate comprises at least 80%, preferably at least 85%, preferably at least 90%, preferably at least 95%, preferably all of the nucleotides of the core motif or sequence and wherein one or more of the nucleotides may be a modified nucleotide; and wherein said oligomer is a gapmer of the motif X—Y—Z wherein each of X and Z is independently a wing comprising at least one modified nucleotide and Y is a central region of nucleotides.

Accordingly, for certain embodiments, the term "based on" means that the oligomer or the oligomer of the oligomer conjugate comprises all of the nucleotides of the core motif or sequence and wherein one or more of the nucleotides may be a modified nucleotide; and wherein said oligomer is a gapmer of the motif X—Y—Z wherein each of X and Z is independently a wing comprising at least one modified nucleotide and Y is a central region of nucleotides.

Stability

The term "stability" in reference to duplex or triplex formation generally designates how tightly an antisense oligonucleotide binds to its intended target sequence; more particularly, "stability" designates the free energy of formation of the duplex or triplex under physiological conditions. Melting temperature under a standard set of conditions, e.g., as described below, is a convenient measure of duplex and/or triplex stability. Preferably, antisense oligonucleotides of the invention are selected that have melting temperatures of at least 45° C. when measured in 100 mM NaCl, 0.1 mM EDTA and 10 mM phosphate buffer aqueous solution, pH 7.0 at a strand concentration of both the antisense oligonucleotide and the target nucleic acid of 1.5 µM. Thus, when used under physiological conditions, duplex or triplex formation will be substantially favored over the state in which the antisense oligonucleotide and its target are dissociated. It is understood that a stable duplex or triplex may in some embodiments include mismatches between base pairs and/or among base triplets in the case of triplexes. Preferably, LNA modified antisense oligonucleotides of the invention form perfectly matched duplexes and/or triplexes with their target nucleic acids.

Potent Inhibitor

In some embodiments the oligomer or oligomer conjugate is a potent inhibitor, in particular of HBx or HBsAg.

As used herein, the phrase "potent inhibitor" refers to an oligomer with an IC50 of less than 5 nM as determined by a lipofectamin transfection assay. In some embodiments, the IC50 is less than 4 nM, such as less than 2 nM.

A "potent inhibitor" as determined by "gymnosis", where gymnosis describes the delivery of the oligomer to the cultured cell without the use of a transfection agent, refers to an IC50 of less than 5 µm in a gymnosis assay or in a in vivo AAV/HBV Mouse Model. In some embodiments, the IC50 is less than 2 µm, such as less than 1 µm.

Treat/Treatment

The terms "treat"/"treatment" etc. include one or more of to cure, to alleviate, to prevent or to detect. In certain preferred embodiments, the terms "treat"/"treatment" etc. mean to cure or to alleviate. The term "alleviate" includes to alleviate the symptoms and/or the conditions attributed with or associated with a viral disorder.

Thus, in some aspects, the present invention relates to oligomers or oligomer conjugates suitable for, and uses thereof and methods using same, to cure, to alleviate, to prevent or to detect a viral disorder.

Accordingly, in certain aspects, the present invention relates to oligomers or oligomer conjugates suitable for, and uses thereof and methods using same, to cure or to alleviate a viral disorder.

In some embodiments, the term 'treatment' as used herein refers to both treatment of an existing disease (e.g. a disease or disorder as herein referred to), or prevention of a disease, i.e. prophylaxis. It will therefore be recognised that treatment as referred to herein may, In some embodiments, be prophylactic.

"Treating" a disease or condition in a subject or "treating" a subject having a disease or condition refers to subjecting the individual to a pharmaceutical treatment, e.g., the administration of a drug, such that at least one symptom of the disease or condition is decreased or stabilized.

A patient who is in need of treatment is a patient suffering from or likely to suffer from the disease or disorder.

By "treating prophyllactically" a disease or condition in a subject is meant reducing or eliminating the risk of developing (i.e., the incidence) of or reducing the severity of the disease or condition prior to the appearance of at least one symptom of the disease.

Agent

The term "agent" means any compound, for example, an antibody, or a therapeutic agent, a detectable label (e.g., a marker, tracer, or imaging compound).

Therapeutic Agent

The term "therapeutic agent" means any compound having a biological activity. Therapeutic agents may be useful for treating conditions or diseases. Specific therapeutic agents according to the invention may be oligomers. Specific therapeutic agents may be oligomers or oligomer conjugates according to the present invention.

Delivering Said Oligomer to the Liver

As used herein, the term "delivering said oligomer to the liver" relates to the process by which an oligomer is brought into contact with, or into proximity to the cells or tissues of the liver. This includes the delivery of the oligomer to the blood supply within or surrounding the liver. The oligomer may be delivered or carried from the site of entry into the body to the liver or tissues surrounding the liver.

Delivering Said Oligomer to a Hepatocyte

As used herein, the term "delivering said oligomer to a hepatocyte" relates to the process by which an oligomer is brought into contact with, or into proximity to, a hepatocyte of the liver. This includes the delivery of the oligomer to the blood supply within or surrounding a hepatocyte. The oligomer may be delivered or carried from the site of entry into the body to a hepatocyte.

Viral Disorder

The term "viral disorder" in the context of the present invention refers to any disorder or disease which is associated with viral infection.

Pharmaceutical Carriers/Pharmaceutically Acceptable Carriers

"Pharmaceutical carriers" or "pharmaceutically acceptable carriers" are to be distinguished from the "carrier component" of the invention as described above. "Pharmaceutical carrier" and "carrier component" are to be treated as mutually exclusive terms in the context of the present invention.

Administering/Administration

The terms "administering" and "administration" are intended to mean a mode of delivery including, without limitation, intra-arterially, intra-nasally, intra-peritoneally, intravenously, intramuscularly, sub-cutaneously, transdermally or per os. A daily dosage can be divided into one, two or more doses in a suitable form to be administered at one, two or more times throughout a time period.

DETAILED DESCRIPTION OF THE INVENTION

Introduction

The present invention relates to oligomers (also referred to as oligomeric molecules) and/or oligomer conjugates.

The oligomers and oligomer conjugates are useful for the treatment of a viral disorder.

In particular embodiments, the oligomers or oligomer conjugates of the invention are capable of modulating a target sequence in HBV HBx or HBsAg.

The oligomers of the invention may be conjugated to a carrier component.

Preferably, the carrier component may be capable of delivering the oligomer to the liver of a subject to be treated.

The present invention therefore employs oligomers or oligomer conjugates for use in modulating the function of nucleic acid molecules encoding HBV HBx or HBsAg, such as the HBV nucleic acid molecule presented as SEQ ID no 1 or SEQ ID No 2, and naturally occurring variants of such nucleic acid molecules encoding HBV HBx or HBV HBsAg.

Oliogomer Features

The oligomer or the oligomer of the oligomer conjugate may consist or comprise of a contiguous nucleotide sequence of from 8-50, 8-30, 8-25, 8-20, 8-18, 8-17, 8-16, 8-15, 8-14, 8-13, or 8-12 nucleotides in length, preferably 8-16 nucleotides in length, more preferably 10 to 20 nucleotides in length.

For some embodiments, the oligomer or the oligomer of the oligomer conjugate may comprise or consist of a contiguous nucleotide sequence of from 10-50, such as 10-30, 10-20, 10-18, 10-17, 10-16, 10-15, 10-14, 10-13, or 10-12 nucleotides in length, preferably 10-20 nucleotides in length, more preferably 10 to 18 nucleotides in length, most preferably 10 to 16 nucleotides in length.

For some embodiments, the oligomer or the oligomer of the oligomer conjugate may comprise or consist of a contiguous nucleotide sequence of from 12-50, such as 12-30, 12-20, 12-18, 12-17, 12-16, 12-15, 12-14 or 12-13 nucleotides in length, preferably 12-16 nucleotides in length.

For some embodiments, the oligomer or the oligomer of the oligomer conjugate may comprise or consist of a contiguous nucleotide sequence of 8, 9, 10, 11, 12, 13, 14, 15, 16, 17, 18, 19 or 20 nucleotides in length.

For some embodiments, the oligomers or the oligomer component of the oligomer conjugates of the present invention may comprise or consist of a contiguous nucleotide sequence of a total of 8, 9, 10, 11, 12, 13, 14, 15, 16, 17, 18, 19, 20, 21, 22, 23, 24, 25, 26, 27, 28, 29 or 30 contiguous nucleotides in length.

In some embodiments, the oligomer or the oligomer of the oligomer conjugate comprises or consists of a contiguous nucleotide sequence of a total of from 8-22, such as 8-20, such as 8-18, such as 8-17 or 8-16, contiguous nucleotides in length.

In some embodiments, the oligomer or the oligomer of the oligomer conjugate comprises or consists of a contiguous nucleotide sequence of a total of 8, 9, 10, 11, 12, 13, 14, 15, or 16 contiguous nucleotides in length.

In some embodiments, the oligomer or the oligomer of the oligomer conjugate comprises or consists of a contiguous nucleotide sequence of a total of 15 or 16 contiguous nucleotides in length.

In some embodiments, the oligomer or the oligomer of the oligomer conjugate according to the invention consists of no more than 22 nucleotides, such as no more than 20 nucleotides, such as no more than 18 nucleotides—such as 15, or 16 or 17 nucleotides.

In some embodiments, preferably the oligomer or the oligomer of the oligomer conjugate of the invention comprises less than 20 nucleotides.

It should be understood that when a range is given for an oligomer, or contiguous nucleotide sequence length it includes the lower an upper lengths provided in the range, for example from (or between) 10-30, includes both 10 and 30.

The length of the oligonucleotide moieties is sufficiently large to ensure that specific binding takes place only at the desired target polynucleotide and not at other fortuitous sites, as explained in many references, e.g., Rosenberg et al., International application PCT/US92/05305; or Szostak et al., *Meth. Enzymol,* 68:419-429 (1979). The upper range of the length is determined by several factors, including the inconvenience and expense of synthesizing and purifying oligomers greater than about 30-40 nucleotides in length, the greater tolerance of longer oligonucleotides for mismatches than shorter oligonucleotides, whether modifications to enhance binding or specificity are present, whether duplex or triplex binding is desired, and the like.

The oligomer or the oligomer of the oligomer conjugate may comprise or consist of a simple sequence of natural occurring nucleotides—preferably 2'-deoxynucleotides (referred to here generally as "DNA"), but also possibly ribonucleotides (referred to here generally as "RNA"), or a combination of such naturally occurring nucleotides and one or more non-naturally occurring nucleotides, i.e. nucleotide analogues. Such nucleotide analogues may suitably enhance the affinity of the oligomer for the target sequence.

Examples of suitable and preferred nucleotide analogues are provided by WO2007/031091 or are referenced therein.

Examples of nucleotide analogues include nucleotides that have been modified. Examples of such modifications include modifying the sugar moiety to provide a 2'-substituent group or to produce a bridged (locked nucleic acid) structure which enhances binding affinity and may also provide increased nuclease resistance. These modified nucleotide analogues can therefore be affinity-enhancing nucleotide analogues.

Incorporation of affinity-enhancing nucleotide analogues in the oligomer or the oligomer of the oligomer conjugate, such as LNA or 2'-substituted sugars, can allow the size of the specifically binding oligomer to be reduced, and may also reduce the upper limit to the size of the oligomer before non-specific or aberrant binding takes place.

In some embodiments, the oligomer or the oligomer of the oligomer conjugate comprises at least 1 nucleotide analogue. In some embodiments the oligomer or the oligomer of the oligomer conjugate comprises at least 2 nucleotide analogues. In some embodiments, the oligomer or the oligomer of the oligomer conjugate comprises from 2-8 nucleotide analogues, e.g. 6 or 7 nucleotide analogues. In the by far most preferred embodiments, at least one of said nucleotide analogues is a locked nucleic acid (LNA); for example at least 2, 3 or at least 4, or at least 5, or at least 6, or at least 7, or 8, of the nucleotide analogues may be LNA. In some embodiments all the nucleotides analogues may be LNA.

It will be recognised that when referring to a preferred nucleotide sequence motif or nucleotide sequence, which consists of only nucleotides, the oligomers or the oligomers of the oligomer conjugates of the invention which are defined by that sequence may comprise a corresponding nucleotide analogue in place of one or more of the nucleotides present in said sequence, such as LNA units or other nucleotide analogues, which raise the duplex stability/$T_m$ of the oligomer/target duplex (i.e. affinity enhancing nucleotide analogues).

A preferred nucleotide analogue is LNA, such as oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). Most preferred is beta-D-oxy-LNA.

In some embodiments the nucleotide analogues present within the oligomer or the oligomer of the oligomer conjugate of the invention (such as in region W and region Y for gapmers—as mentioned herein) are independently selected from, for example: 2'-O-alkyl-RNA units, 2'-amino-DNA units, 2'-fluoro-DNA units, LNA units, arabino nucleic acid (ANA) units, 2'-fluoro-ANA units, HNA units, INA (intercalating nucleic acid—Christensen, 2002. Nucl. Acids. Res. 2002 30: 4918-4925, hereby incorporated by reference) units and 2'MOE units. In some embodiments there is only one of the above types of nucleotide analogues present in the oligomer of the invention, or contiguous nucleotide sequence thereof.

In some embodiments the nucleotide analogues are 2'-O-methoxyethyl-RNA (2'MOE), 2'-fluoro-DNA units or LNA nucleotide analogues, and as such the oligonucleotide of the invention may comprise nucleotide analogues which are independently selected from these three types of analogue, or may comprise only one type of analogue selected from the three types. In some embodiments at least one of said nucleotide analogues is 2'-MOE-RNA, such as 2, 3, 4, 5, 6, 7, 8, 9 or 10 2'-MOE-RNA nucleotide units. In some embodiments at least one of said nucleotide analogues is 2'-fluoro DNA, such as 2, 3, 4, 5, 6, 7, 8, 9 or 10 2'-fluoro-DNA nucleotide units.

In some embodiments, the oligomer or the oligomer of the oligomer conjugate according to the invention comprises at least one Locked Nucleic Acid (LNA) unit, such as 1, 2, 3, 4, 5, 6, 7, or 8 LNA units, such as from 3-7 or 4 to 8 LNA units, or 3, 4, 5, 6 or 7 LNA units. In some embodiments, all the nucleotide analogues are LNA.

In some embodiments, the oligomer or the oligomer of the oligomer conjugate may comprise both beta-D-oxy-LNA, and one or more of the following LNA units: thio-LNA, amino-LNA, oxy-LNA, and/or ENA in either the beta-D or alpha-L configurations or combinations thereof. In some embodiments all LNA cytosine units are 5'methyl-Cytosine.

In some embodiments of the invention, the oligomer or the oligomer of the oligomer conjugate may comprise both LNA and DNA units. Preferably the combined total of LNA and DNA units is 10-25, such as 10-24, preferably 10-20, such as 10-18, even more preferably 12-16. In some embodiments of the invention, the nucleotide sequence of the oligomer, such as the contiguous nucleotide sequence consists of at least one LNA and the remaining nucleotide units are DNA units.

In some embodiments the oligomer or the oligomer of the oligomer conjugate comprises only LNA nucleotide analogues and naturally occurring nucleotides (such as RNA or DNA, most preferably DNA nucleotides), optionally with modified internucleotide linkages such as phosphorothioate.

In some embodiments, any mismatches between the nucleotide sequence of the oligomer and the target sequence are preferably found in regions outside the affinity enhancing nucleotide analogues. Examples of such regions outside the affinity enhancing nucleotide analogues in gapmers include region X as referred to herein and/or region V as referred to herein and/or region Z as referred to herein, and/or at the site of non modified nucleotides in the oligonucleotide, and/or in regions which are 5' or 3' to the contiguous nucleotide sequence.

In some embodiments, the oligomer or the oligomer of the oligomer conjugate of the invention does not comprise RNA (units). It is preferred that the oligomer or the oligomer of the oligomer conjugate according to the invention is a linear molecule or is synthesised as a linear molecule. Preferably the oligomer or the oligomer of the oligomer conjugate is a single stranded molecule, and preferably does not comprise short regions of, for example, at least 3, 4 or 5 contiguous nucleotides, which are complementary to equivalent regions within the same oligomer (i.e. duplexes). In this regard, the oligomer or the oligomer of the oligomer conjugate is not (essentially) double stranded. In some embodiments, the oligomer or the oligomer of the oligomer conjugate is essentially single stranded. In various embodiments, the oligomer or the oligomer of the oligomer conjugate of the invention may consist entirely of the contiguous nucleotide region. Thus, preferably the oligomer or the oligomer of the oligomer conjugate is not substantially self-complementary.

Hence, in certain aspects, the invention provides an oligomer or an oligomer conjugate having an oligomer component from 5-50, such as 5-30, or such as 5-20, such as 8-30, such as 8-20, such as 8-18, such as 8-16, such as 10-16, such as 10-15, such as 12-16, such as 12-15 nucleotides in length which comprises a contiguous nucleotide sequence (a first region) of a total of at least 5 such as at least 8 nucleotides, wherein said contiguous nucleotide sequence (a first region) is at least 80% (e.g., 85%, 90%, 95%, 98%, or 99%) homologous to a region corresponding to the reverse complement of a HBV HBx or HBsAg gene or mRNA, such any sequence within any of SEQ ID No. 1, SEQ ID No. 2 and SEQ ID No. 3 or naturally occurring variant thereof. Thus, for example, the oligomer or the oligomer component of the oligomer conjugate hybridizes to a single stranded nucleic acid molecule having the sequence of a portion of any of SEQ ID No. 1, SEQ ID No. 2 and SEQ ID No. 3, preferably within any of SEQ ID No. 1 and SEQ ID No. 2. The oligomer or oligomer component may hybridize to a single stranded nucleic acid molecule having the sequence of a portion sequence shown as position 200 to 1900 of SEQ ID No. 3). The oligomer or the oligomer component of the oligomer conjugate may hybridize to a single stranded nucleic acid molecule having the sequence shown as position 1264 to 1598 or 691 to 706 of SEQ ID NO: 3. The oligomer or the oligomer component of the oligomer conjugate may hybridize to a single stranded nucleic acid molecule with a sequence selected from the group consisting of the following positions in SEQ ID NO 3: position 1 to 1944, position 157 to 1840, position 1196 to 1941, position 1376 to 1840 and position 3158-3182. Preferably, the oligomer conjugate hybridize to a single stranded nucleic acid molecule with a sequence selected within position 1530 to 1598 of SEQ ID NO: 3, more preferable within position 1577 to 1598 of SEQ ID NO: 3 and most preferably within position 1530 to 1543 of SEQ ID NO: 3. An oligomer or the oligomer component of the oligomer conjugate may hybridize to a single stranded nucleic acid molecule selected from the group consisting of positions: 1264-1278; 1265-1277; 1530-1543; 1530-1544; 1531-1543; 1551-1565; 1551-1566; 1577-1589; 1577-1591; 1577-1592; 1578-1590; 1578-1592; 1583-1598; 1584-1598; and 1585-1598; or 670-706, 691-705; 691-706; 692-706; 693-706; and 694-706 of SEQ ID NO: 3. Preferably, an oligomer or the oligomer component of the oligomer conjugate may hybridize to a single stranded nucleic acid molecule within position 1530 to 1598 of SEQ ID NO: 3, more preferably withn positions 1530-1543 or positions 1577-1598 of SEQ ID NO: 3.

For certain embodiments, the invention provides an oligomer or an oligomer conjugate having an oligomer based on a core motif selected from the group consisting of any one or more of:

GCGTAAAGAGAGG; (SEQ ID NO: 13)

GCGTAAAGAGAGGT; (SEQ ID NO: 11)

AGCGAAGTGCACACG; (SEQ ID NO: 20)

AGGTGAAGCGAAGTG; (SEQ ID NO: 26)

AGCGAAGTGCACACGG; (SEQ ID NO 18)

CGAACCACTGAACA; (SEQ ID NO: 7)

GAACCACTGAACAAA; (SEQ ID NO 4)

CGAACCACTGAACAAA; (SEQ ID NO 5)

CGAACCACTGAACAA; (SEQ ID NO 6)

CGAACCACTGAAC (SEQ ID NO 8)

CCGCAGTATGGATCG (SEQ ID NO 9)

CGCAGTATGGATC; (SEQ ID NO: 10)

CGCGTAAAGAGAGGT; (SEQ ID NO 12)

AGAAGGCACAGACGG; (SEQ ID NO 14)

GAGAAGGCACAGACGG (SEQ ID NO 15)

GAAGTGCACACGG; (SEQ ID NO 16)

GCGAAGTGCACACGG; (SEQ ID NO 17)

CGAAGTGCACACG; (SEQ ID NO 19)

AGGTGAAGCGAAGT; (SEQ ID NO 27)
and

TAGTAAACTGAGCCA, (SEQ ID NO: 852)

which is capable of modulating a target sequence in HBx or HBsAg of HBV to treat a viral disorder.

The oligomer or the oligomer component of the oligomer conjugate may be based on a sequence selected from the group consisting of any one or more of:

```
                          (SEQ ID NO: 303)
GCGtaaagagaGG (SEQ ID NO: 301)
GCGtaaagagaGGT (SEQ ID NO: 618)
GCGtaaagagAGG;

(SEQ ID NO: 310)
AGCgaagtgcacACG (SEQ ID NO: 668)
AGgtgaagcgaAGTG;

(SEQ ID NO: 308)
AGCgaagtgcacaCGG;

(SEQ ID NO: 297)
CGAaccactgaACA;

(SEQ ID NO: 300)
CGCagtatggaTC;

(SEQ ID NO: 315)
AGGtgaagcgaagTGC;

(SEQ ID NO: 316)
AGGtgaagcgaaGTG;

(SEQ ID NO: 294)
GAAccactgaacAAA;

(SEQ ID NO: 295)
CGAaccactgaacAAA;

(SEQ ID NO: 296)
CGAaccactgaaCAA (SEQ ID NO: 298)
CGAaccactgaAC;

(SEQ ID NO: 299)
CCGcagtatggaTCG;

(SEQ ID NO: 302)
CGCgtaaagagaGGT;

(SEQ ID NO: 304)
AGAaggcacagaCGG;

(SEQ ID NO: 305)
GAGaaggcacagaCGG;

(SEQ ID NO: 306)
GAAgtgcacacGG;

(SEQ ID NO: 307)
GCGaagtgcacaCGG;

(SEQ ID NO: 309)
CGAagtgcacaCG;

(SEQ ID NO: 585)
GAAccactgaaCAAA;

(SEQ ID NO: 588)
CGAAccactgaacAAA (SEQ ID NO: 628)
GAAgtgcacaCGG;

(SEQ ID NO: 678)
TAGtaaactgagCCA;
```

-continued

```
                          (SEQ ID NO: 600)
CGAaccactgAAC;

(SEQ ID NO: 317)
AGGtgaagcgaAGT;
and (SEQ ID NO: 597)
CGAaccactgAACA,
``` wherein uppercase letters denote LNA units and lower case letters denote DNA units.

In certain embodiments, the oligomer, or additional oligomer, or oligomer component of the oligomer conjugate, or oligomer component of the additional oligomer conjugate may comprise a sequence based on a sequence selected from a list of:

```
                          (SEQ ID NO: 13)
GCGTAAAGAGAGG;

(SEQ ID NO: 11)
GCGTAAAGAGAGGT;

(SEQ ID NO 12)
CGCGTAAAGAGAGGT;

(SEQ ID NO 14)
AGAAGGCACAGACGG;

(SEQ ID NO 15)
GAGAAGGCACAGACGG;

(SEQ ID NO 18)
AGCGAAGTGCACACGG;

(SEQ ID NO 16)
GAAGTGCACACGG;

(SEQ ID NO 17)
GCGAAGTGCACACGG;

(SEQ ID NO: 20)
AGCGAAGTGCACACG;

(SEQ ID NO 19)
CGAAGTGCACACG;

(SEQ ID NO: 26)
AGGTGAAGCGAAGTG;
and (SEQ ID NO 27)
AGGTGAAGCGAAGT.
```

In another embodiment the motif sequence is selected from:

```
                          (SEQ ID NO: 13)
GCGTAAAGAGAGG;

(SEQ ID NO: 11)
GCGTAAAGAGAGGT;

(SEQ ID NO: 20)
AGCGAAGTGCACACG;

(SEQ ID NO: 26)
AGGTGAAGCGAAGTG;
and (SEQ ID NO 18)
AGCGAAGTGCACACGG
```

In another embodiment the motif sequence is selected from GCGTAAAGAGAGG (SEQ ID NO: 13)

GCGTAAAGAGAGGT (SEQ ID NO: 11) and CGCGTAAAGAGAGGT (SEQ ID NO 12).

In another embodiment the motif sequence is selected from AGCGAAGTGCACACG (SEQ ID NO: 20); AGGTGAAGCGAAGTG (SEQ ID NO: 26); AGCGAAGTGCACACGG (SEQ ID NO 18); GAAGTGCACACGG (SEQ ID NO 16); GCGAAGTGCACACGG (SEQ ID NO 17); CGAAGTGCACACG (SEQ ID NO 19) and AGGTGAAGCGAAGT (SEQ ID NO 27).

In another embodiment the motif sequence is selected from CGAACCACTGAACA (SEQ ID NO: 7); GAACCACTGAACAAA (SEQ ID NO 4); CGAACCACTGAACAAA (SEQ ID NO 5); CGAACCACTGAACAA (SEQ ID NO 6); CGAACCACTGAAC (SEQ ID NO 8) and TAGTAAACTGAGCCA (SEQ ID NO: 852).

In another embodiment the motif sequence is selected from CCGCAGTATGGATCG (SEQ ID NO 9) and CGCAGTATGGATC (SEQ ID NO: 10).

In another embodiment the motif sequence is selected from AGAAGGCACAGACGG (SEQ ID NO 14) and GAGAAGGCACAGACGG (SEQ ID NO 15).

In certain embodiments, the oligomer, or additional oligomer, or oligomer component of the oligomer conjugate, or oligomer component of the additional oligomer conjugate may comprise or consist of a sequence selected from the rou resented below:

GCGtaaagagaGG; (SEQ ID NO: 303)

GCGtaaagagaGGT; (SEQ ID NO: 301)

GCGtaaagagAGG; (SEQ ID NO: 618)

AGCgaagtgcacACG; (SEQ ID NO: 310)

AGgtgaagcgaAGTG; (SEQ ID NO: 668)

AGCgaagtgcacaCGG; (SEQ ID NO: 308)

CGAaccactgaACA; (SEQ ID NO: 297)

CGCagtatggaTC; (SEQ ID NO: 300)

AGGtgaagcgaagTGC; (SEQ ID NO: 315)

AGGtgaagcgaaGTG; (SEQ ID NO: 316)

GAAccactgaacAAA; (SEQ ID NO: 294)

CGAaccactgaacAAA; (SEQ ID NO: 295)

CGAaccactgaaCAA (SEQ ID NO: 296)

CGAaccactgaAC; (SEQ ID NO: 298)

CCGcagtatggaTCG; (SEQ ID NO: 299)

CGCgtaaagagaGGT; (SEQ ID NO: 302)

AGAaggcacagaCGG; (SEQ ID NO: 304)

GAGaaggcacagaCGG; (SEQ ID NO: 305)

GAAgtgcacacGG; (SEQ ID NO: 306)

GCGaagtgcacaCGG; (SEQ ID NO: 307)

CGAagtgcacaCG; (SEQ ID NO: 309)

GAAccactgaaCAAA; (SEQ ID NO: 585)

CGAAccactgaacAAA (SEQ ID NO: 588)

GAAgtgcacaCGG; (SEQ ID NO: 628)

TAGtaaactgagCCA; (SEQ ID NO: 678)

CGAaccactgAAC; (SEQ ID NO: 600)

AGGtgaagcgaAGT; (SEQ ID NO: 317)
and

CGAaccactgAACA. (SEQ ID NO: 597)

wherein uppercase letters denote affinity enhancing nucleotide analogues and lower case letters denote DNA units.

In another embodiment the sequence is selected from:

GCGtaaagagaGG; (SEQ ID NO: 303)

GCGtaaagagaGGT; (SEQ ID NO: 301)

GCGtaaagagAGG; (SEQ ID NO: 618)

CGCgtaaagagaGGT; (SEQ ID NO: 302)

AGAaggcacagaCGG; (SEQ ID NO: 304)

GAGaaggcacagaCGG; (SEQ ID NO: 305)

GAAgtgcacacGG; (SEQ ID NO: 306)

GCGaagtgcacaCGG; (SEQ ID NO: 307)

GAAgtgcacaCGG; (SEQ ID NO: 628)

AGCgaagtgcacaCGG; (SEQ ID NO: 308)

CGAagtgcacaCG; (SEQ ID NO: 309)

AGCgaagtgcacACG (SEQ ID NO: 310)

```
                                   (SEQ ID NO: 315)
AGGtgaagcgaagTGC;

(SEQ ID NO: 316)
AGGtgaagcgaaGTG;

(SEQ ID NO: 317)
AGGtgaagcgaAGT;
and (SEQ ID NO: 668)
AGgtgaagcgaAGTG.
```

In one embodiment the sequence is selected from:

```
                                   (SEQ ID NO: 303)
GCGtaaagagaGG;

(SEQ ID NO: 301)
GCGtaaagagaGGT;

(SEQ ID NO: 618)
GCGtaaagagAGG;

(SEQ ID NO: 310)
AGCgaagtgcacACG (SEQ ID NO: 668)
AGgtgaagcgaAGTG;
and (SEQ ID NO: 308)
AGCgaagtgcacaCGG.
```

In one embodiment the sequence is selected from GCGtaaagagaGG (SEQ ID NO: 303) GCGtaaagagaGGT (SEQ ID NO: 301); GCGtaaagagAGG (SEQ ID NO: 618) and CGCgtaaagagaGGT (SEQ ID NO: 302).

In another embodiment the sequence is selected from AGCgaagtgcacACG (SEQ ID NO: 310); AGGtgaagcgaagTGC (SEQ ID NO: 315); AGGtgaagcgaaGTG (SEQ ID NO: 316); GAAgtgcacaCGG (SEQ ID NO: 628); AGgtgaagcgaAGTG (SEQ ID NO: 668); AGCgaagtgcacaCGG (SEQ ID NO: 308); GAAgtgcacacGG (SEQ ID NO: 306); GCGaagtgcacaCGG (SEQ ID NO: 307); CGAagtgcacaCG (SEQ ID NO: 309); and AGGtgaagcgaAGT (SEQ ID NO: 317).

In another embodiment the sequence is selected from CGAaccactgaACA (SEQ ID NO: 297); GAAccactgaacAAA (SEQ ID NO: 294); CGAaccactgaacAAA (SEQ ID NO: 295); CGAaccactgaaCAA (SEQ ID NO: 296); CGAaccactgaAC (SEQ ID NO: 298); CGAaccactgAACA (SEQ ID NO: 597) and TAGtaaactgagCCA (SEQ ID NO: 678).

In another embodiment the sequence is selected from CCGcagtatggaTCG (SEQ ID NO: 299) and CGCagtatggaTC (SEQ ID NO: 300).

In another embodiment the sequence is selected from AGAaggcacagaCGG (SEQ ID NO: 304) and GAGaaggcacagaCGG (SEQ ID NO: 305).

The oligomer conjugate may be based on a sequence selected from the group consisting of any one or more of:

```
                                                        (SEQ ID NO: 815)
5'-GN2-C6  caG_s^mC_sG_st_sa_sa_sa_sg_sa_sg_sa_sG_sG-3'

(SEQ ID NO: 814)
5'-GN2-C6  caG_s^mC_sG_st_sa_sa_sa_sg_sa_sg_sasG_sT-3'

(SEQ ID NO: 825)
5'-GN2-C6  caG_s^mC_sG_st_sa_sa_sa_sg_sa_sg_sA_sG_sG-3'

(SEQ ID NO: 808)
5'-GN2-C6  caA_sG_s^mC_sg_sa_sa_sg_st_sg_sc_sa_sC_sA_s^mC_sG-3'

(SEQ ID NO: 826)
5'-GN2-C6  caA_sG_st_st_sg_sa_sa_sg_s^mc_sg_sa_sA_sG_sT_sG-3'

(SEQ ID NO: 807)
5'-GN2-C6  caA_sG_s^mC_sg_sa_sa_sg_st_sc_sa_sc_sa_s^mC_sG_sG-3'

(SEQ ID NO: 799)
5'-GN2-C6  caG_sA_sA_sc_sc_sa_sc_st_sg_sa_sa_sc_sA_sA_sA-3'

(SEQ ID NO: 800)
5'-GN2-C6  ca^mC_sG_sA_sa_sc_sc_sa_sc_st_sg_sa_sa_sc_sA_sA_sA-3'

(SEQ ID NO: 801)
5'-GN2-C6  ca^mC_sG_sA_sa_sc_sc_sa_sc_st_sg_sa_sa_s^mC_sA_sA-3'

(SEQ ID NO: 802)
5'-GN2-C6  ca^mC_s^mC_sG_sc_sa_sg_st_sa_st_sg_sg_sa_sT_s^mC_sG-3'

(SEQ ID NO: 803)
5'-GN2-C6  ca^mC_sG_s^mC_sg_st_sa_sa_sa_sg_sa_sg_sa_sG_sG_sT-3'

(SEQ ID NO: 804)
5'-GN2-C6  caA_sG_sA_sa_sg_sg_sc_sa_sc_sa_sg_sa_s^mC_sG_sG-3'

(SEQ ID NO: 805)
5'-GN2-C6  caG_sA_sG_sa_sa_sg_sg_sc_sa_sc_sa_sg_sa_s^mC_sG_sG-3'

(SEQ ID NO: 806)
5'-GN2-C6  caG_s^mC_sG_sa_sa_sg_st_sg_sc_sa_sc_sa_s^mC_sG_sG-3'

(SEQ ID NO: 809)
5'-GN2-C6  caA_sG_sG_st_sg_sa_sa_sg_s^mc_sg_sa_sa_sg_sT_sG_s^mC-3'

(SEQ ID NO: 810)
5'-GN2-C6  caA_sG_sG_st_sg_sa_sa_sg_s^mc_sg_sa_sa_sG_sT_sG-3'

(SEQ ID NO: 811)
5'-GN2-C6  ca^mC_sG_sA_sa_sc_sc_sa_sc_st_sg_sa_sA_s^mC_sA-3'

(SEQ ID NO: 812)
5'-GN2-C6  ca^mC_sG_sA_sa_sc_sc_sa_sc_st_sg_sa_sA_s^mC-3'

(SEQ ID NO: 813)
5'-GN2-C6  ca^mC_sG_s^mC_sa_sg_st_sa_st_sg_sg_sa_sT_s^mC-3'

(SEQ ID NO: 816)
5'-GN2-C6  caG_sA_sA_sg_st_sg_sc_sa_sc_sa_s^mC_sG_sG-3'

(SEQ ID NO: 817)
5'-GN2-C6  ca^mC_sG_sA_sa_sg_st_sg_sc_sa_sc_sa_s^mC_sG-3'

(SEQ ID NO: 818)
5'-GN2-C6  caA_sG_st_sg_sa_sa_sg_s^mc_sg_sa_sA_sG_sT-3'

(SEQ ID NO: 819)
5'-GN2-C6  caG_sA_sA_sc_sc_sa_sc_st_sg_sa_sa_s^mC_sA_sA_sA-3'

(SEQ ID NO: 820)
5'-GN2-C6  ca^mC_sG_sA_sA_sc_sc_sa_sc_st_sg_sa_sa_sc_sA_sA_sA-3'

(SEQ ID NO: 821)
5'-GN2-C6  caG_sA_sA_sg_st_sg_sc_sa_sc_sa_s^mC_sG_sG-3'

(SEQ ID NO: 822)
5'-GN2-C6  caT_sA_sG_st_sa_sa_sa_sc_st_sg_sa_sg_s^mC_s^mC_sA_s3'

(SEQ ID NO: 823)
5'-GN2-C6  ca^mC_sG_sA_sa_sc_sc_sa_sc_st_sg_sA_sA_s^mC-3'

(SEQ ID NO: 824)
5-GN2-C6  ca^mC_sG_sA_sa_sc_sc_sa_sc_st_sg_sA_sA_s^mC_sA-3'
``` wherein uppercase letters denote beta-D-oxy-LNA units; lowercase letters denote DNA units; the subscript "s" denotes a phosphorothioate linkage; superscript m denotes a a DNA or beta-D-oxy-LNA unit containing a 5-methylcytosine base; GN2-C6 denotes a GalNAc2 carrier component with a C6 linker.

In another embodiment the oligomer conjugate is selected from:

5'-GN2-C6 caG$_s$$^m$C$_s$G$_s$t$_s$a$_s$a$_s$a$_s$g$_s$a$_s$g$_s$a$_s$G$_s$G-3' (SEQ ID NO: 815)

5'-GN2-C6 caG$_s$$^m$C$_s$G$_s$t$_s$a$_s$a$_s$a$_s$g$_s$a$_s$g$_s$a$_s$G$_s$G$_s$T-3' (SEQ ID NO: 814)

5'-GN2-C6 caG$_s$$^m$C$_s$G$_s$t$_s$a$_s$a$_s$a$_s$g$_s$a$_s$g$_s$A$_s$G$_s$G-3' (SEQ ID NO: 825)

5'-GN2-C6 ca$^m$C$_s$G$_s$$^m$C$_s$g$_s$t$_s$a$_s$a$_s$a$_s$g$_s$a$_s$g$_s$a$_s$G$_s$G$_s$T-3' (SEQ ID NO: 803)

5'-GN2-C6 caA$_s$G$_s$A$_s$a$_s$g$_s$g$_s$c$_s$a$_s$c$_s$a$_s$g$_s$a$_s$$^m$C$_s$G$_s$G-3' (SEQ ID NO: 804)

5'-GN2-C6 caG$_s$A$_s$G$_s$a$_s$a$_s$g$_s$g$_s$c$_s$a$_s$c$_s$a$_s$g$_s$a$_s$$^m$C$_s$G$_s$G-3' (SEQ ID NO: 805)

5'-GN2-C6 caG$_s$A$_s$A$_s$g$_s$t$_s$g$_s$c$_s$a$_s$c$_s$a$_s$$^m$C$_s$G$_s$G-3' (SEQ ID NO: 816)

5'-GN2-C6 caG$_s$$^m$C$_s$G$_s$a$_s$a$_s$g$_s$t$_s$g$_s$c$_s$a$_s$c$_s$a$_s$$^m$C$_s$G$_s$G-3' (SEQ ID NO: 806)

5'-GN2-C6 caG$_s$A$_s$A$_s$g$_s$t$_s$g$_s$c$_s$a$_s$c$_s$a$_s$$^m$C$_s$G$_s$G-3' (SEQ ID NO: 821)

5'-GN2-C6 caA$_s$G$_s$$^m$C$_s$g$_s$a$_s$a$_s$g$_s$t$_s$g$_s$c$_s$a$_s$c$_s$a$_s$$^m$C$_s$G$_s$G-3' (SEQ ID NO: 807)

5'-GN2-C6 ca$^m$C$_s$G$_s$A$_s$a$_s$g$_s$t$_s$g$_s$c$_s$a$_s$c$_s$a$_s$$^m$C$_s$G-3' (SEQ ID NO: 817)

5'-GN2-C6 caA$_s$G$_s$$^m$C$_s$g$_s$a$_s$a$_s$g$_s$t$_s$g$_s$c$_s$a$_s$c$_s$a$_s$A$_s$$^m$C$_s$G-3' (SEQ ID NO: 808)

5'-GN2-C6 caA$_s$G$_s$t$_s$g$_s$a$_s$a$_s$g$_s$$^m$c$_s$g$_s$a$_s$a$_s$g$_s$T$_s$G$_s$$^m$C-3' (SEQ ID NO: 809)

5'-GN2-C6 caA$_s$G$_s$t$_s$g$_s$a$_s$a$_s$g$_s$$^m$c$_s$g$_s$a$_s$a$_s$G$_s$T$_s$G-3' (SEQ ID NO: 810)

5'-GN2-C6 caA$_s$G$_s$t$_s$g$_s$a$_s$a$_s$g$_s$$^m$c$_s$g$_s$a$_s$A$_s$G$_s$T-3' (SEQ ID NO: 818)

5'-GN2-C6 caA$_s$G$_s$t$_s$g$_s$a$_s$a$_s$g$_s$$^m$c$_s$g$_s$a$_s$A$_s$G$_s$T$_s$G-3' (SEQ ID NO: 826)

In another embodiment the oligomer conjugate is selected from:

5'-GN2-C6 caG$_s$$^m$C$_s$G$_s$t$_s$a$_s$a$_s$a$_s$g$_s$a$_s$g$_s$a$_s$G$_s$G-3' (SEQ ID NO: 815)

5'-GN2-C6 caG$_s$$^m$C$_s$G$_s$t$_s$a$_s$a$_s$a$_s$g$_s$a$_s$g$_s$a$_s$G$_s$G$_s$T-3' (SEQ ID NO: 814)

5'-GN2-C6 caG$_s$$^m$C$_s$G$_s$t$_s$a$_s$a$_s$a$_s$g$_s$a$_s$g$_s$A$_s$G$_s$G-3' (SEQ ID NO: 825)

5'-GN2-C6 caA$_s$G$_s$$^m$C$_s$g$_s$a$_s$a$_s$g$_s$t$_s$g$_s$c$_s$a$_s$c$_s$A$_s$$^m$C$_s$G-3' (SEQ ID NO: 808)

5'-GN2-C6 caA$_s$G$_s$t$_s$g$_s$a$_s$a$_s$g$_s$$^m$c$_s$g$_s$a$_s$A$_s$G$_s$T$_s$G-3' (SEQ ID NO: 826)

5'-GN2-C6 caA$_s$G$_s$$^m$C$_s$g$_s$a$_s$a$_s$g$_s$t$_s$g$_s$c$_s$a$_s$c$_s$a$_s$$^m$C$_s$G$_s$G-3' (SEQ ID NO: 827)

In another embodiment the oligomer conjugate is selected from:

5'-GN2-C6 caG$_s$$^m$C$_s$G$_s$t$_s$a$_s$a$_s$a$_s$g$_s$a$_s$g$_s$a$_s$G$_s$G-3' (SEQ ID NO: 815)

5'-GN2-C6 caG$_s$$^m$C$_s$G$_s$t$_s$a$_s$a$_s$a$_s$g$_s$a$_s$g$_s$a$_s$G$_s$G$_s$T-3' (SEQ ID NO: 814)

5'-GN2-C6 caG$_s$$^m$C$_s$G$_s$t$_s$a$_s$a$_s$a$_s$g$_s$a$_s$g$_s$A$_s$G$_s$G-3' (SEQ ID NO: 825)

5'-GN2-C6 ca$^m$C$_s$G$_s$$^m$C$_s$g$_s$t$_s$a$_s$a$_s$a$_s$g$_s$a$_s$g$_s$a$_s$G$_s$G$_s$T-3' (SEQ ID NO: 803)

5'-GN2-C6 caAsG$_s$$^m$C$_s$g$_s$a$_s$a$_s$g$_s$t$_s$g$_s$c$_s$a$_s$c$_s$A$_s$$^m$C$_s$G-3' (SEQ ID NO: 808)

5'-GN2-C6 caA$_s$G$_s$t$_s$g$_s$a$_s$a$_s$g$_s$$^m$c$_s$g$_s$a$_s$a$_s$g$_s$T$_s$G$_s$$^m$C-3' (SEQ ID NO: 809)

5'-GN2-C6 caA$_s$G$_s$t$_s$g$_s$a$_s$a$_s$g$_s$$^m$c$_s$g$_s$a$_s$a$_s$G$_s$T$_s$G-3' (SEQ ID NO: 810)

5'-GN2-C6 caG$_s$A$_s$A$_s$g$_s$t$_s$g$_s$c$_s$a$_s$c$_s$a$_s$$^m$C$_s$G$_s$G-3' (SEQ ID NO: 818)

5'-GN2-C6 caG$_s$A$_s$A$_s$g$_s$t$_s$g$_s$c$_s$a$_s$c$_s$a$_s$$^m$C$_s$G$_s$G-3' (SEQ ID NO: 821)

5'-GN2-C6 caA$_s$G$_s$t$_s$g$_s$a$_s$a$_s$g$_s$$^m$c$_s$g$_s$a$_s$A$_s$G$_s$T$_s$G-3' (SEQ ID NO: 826)

5'-GN2-C6 caA$_s$G$_s$$^m$C$_s$g$_s$a$_s$a$_s$g$_s$t$_s$g$_s$c$_s$a$_s$c$_s$a$_s$$^m$C$_s$G$_s$G-3' (SEQ ID NO: 807)

5'-GN2-C6 ca$^m$C$_s$G$_s$A$_s$a$_s$g$_s$t$_s$g$_s$c$_s$a$_s$c$_s$a$_s$$^m$C$_s$G-3' (SEQ ID NO: 817)

5'-GN2-C6 caG$_s$$^m$C$_s$G$_s$a$_s$a$_s$g$_s$t$_s$g$_s$c$_s$a$_s$c$_s$a$_s$$^m$C$_s$G$_s$G-3' (SEQ ID NO: 806)

5'-GN2-C6 caG$_s$A$_s$A$_s$g$_s$t$_s$g$_s$c$_s$a$_s$c$_s$a$_s$$^m$C$_s$G$_s$G-3' (SEQ ID NO: 816)

In another embodiment the oligomer conjugate is selected from:

5'-GN2-C6 caG$_s$A$_s$A$_s$c$_s$c$_s$a$_s$c$_s$t$_s$g$_s$a$_s$a$_s$c$_s$A$_s$A$_s$A-3' (SEQ ID NO: 799)

5'-GN2-C6 ca$^m$C$_s$G$_s$A$_s$a$_s$c$_s$c$_s$a$_s$c$_s$t$_s$g$_s$a$_s$a$_s$c$_s$A$_s$A$_s$A-3' (SEQ ID NO: 800)

5'-GN2-C6 ca$^m$C$_s$G$_s$A$_s$a$_s$c$_s$c$_s$a$_s$c$_s$t$_s$g$_s$a$_s$a$_s$$^m$C$_s$A$_s$A-3' (SEQ ID NO: 801)

5'-GN2-C6 ca$^m$C$_s$G$_s$A$_s$a$_s$c$_s$c$_s$a$_s$c$_s$t$_s$g$_s$a$_s$A$_s$$^m$C$_s$A-3' (SEQ ID NO: 811)

5'-GN2-C6ca$^m$C$_s$G$_s$A$_s$a$_s$c$_s$c$_s$a$_s$c$_s$t$_s$g$_s$a$_s$A$_s$$^m$C-3' (SEQ ID NO: 812)

5'-GN2-C6 ca$^m$C$_s$G$_s$A$_s$a$_s$c$_s$c$_s$a$_s$c$_s$t$_s$g$_s$A$_s$A$_s$$^m$C$_s$A-3' (SEQ ID NO: 824)

5'-GN2-C6 caT$_s$A$_s$G$_s$t$_s$a$_s$a$_s$a$_s$c$_s$t$_s$g$_s$a$_s$g$_s$$^m$C$_s$$^m$C$_s$A$_s$-3' (SEQ ID NO: 822)

In another embodiment the oligomer conjugate is selected from:

(SEQ ID NO: 802)
5'-GN2-C6 ca$^m$C$_s$$^m$CsG$_s$c$_s$a$_s$g$_s$t$_s$a$_s$t$_s$g$_s$g$_s$a$_s$T$_s$$^m$C$_s$G-3'

(SEQ ID NO: 813)
5'-GN2-C6 ca$^m$C$_s$G$_s$$^m$C$_s$a$_s$g$_s$t$_s$a$_s$t$_s$g$_s$g$_s$a$_s$T$_s$$^m$C-3;

In another embodiment the oligomer conjugate is selected from:

(SEQ ID NO: 804)
5'-GN2-C6 caA$_s$G$_s$A$_s$a$_s$g$_s$g$_s$c$_s$a$_s$c$_s$a$_s$g$_s$a$_s$$^m$C$_s$G$_s$G-3'

(SEQ ID NO: 805)
5'-GN2-C6 caG$_s$A$_s$G$_s$a$_s$a$_s$g$_s$g$_s$c$_s$a$_s$c$_s$a$_s$g$_s$a$_s$$^m$C$_s$G$_s$G-3'

In some embodiments the oligomer or oligomer conjugate according to the invention consists of or comprises or is based on the sequence motif GCGTAAAGAGAGG (SEQ ID NO: 13), or a sub-sequence of thereof.

In some embodiments the oligomer or oligomer conjugate according to the invention consists of or comprises or is based on the sequence motif AGCGAAGTGCACACG (SEQ ID NO: 20), or a sub-sequence of thereof.

In some embodiments the oligomer or oligomer conjugate according to the invention consists of or comprises or is based on the sequence motif GCGTAAAGAGAGGT (SEQ ID NO: 11), or a sub-sequence of thereof.

In some embodiments the oligomer or oligomer conjugate according to the invention consists of or comprises or is based on the sequence motif AGGTGAAGCGAAGTG (SEQ ID NO: 26), or a sub-sequence of thereof.

In some embodiments the oligomer or oligomer conjugate according to the invention consists of or comprises or is based on the sequence motif AGCGAAGTGCACACGG (SEQ ID NO 18), or a sub-sequence of thereof.

In some embodiments the oligomer or oligomer conjugate according to the invention consists of or comprises or is based on the sequence motif CGAACCACTGAACA (SEQ ID NO: 7), or a sub-sequence of thereof.

In some embodiments the oligomer or oligomer conjugate according to the invention consists of or comprises or is based on the sequence motif CCGCAGTATGGATCG (SEQ ID NO 9), or a sub-sequence of thereof.

In some embodiments the oligomer or oligomer conjugate according to the invention consists of or comprises or is based on GCGtaaagagaGG (SEQ ID NO: 303).

In some embodiments the oligomer or oligomer conjugate according to the invention consists of or comprises or is based on GCGtaaagagaGGT (SEQ ID NO: 301).

In some embodiments the oligomer or oligomer conjugate according to the invention consists of or comprises or is based on GCGtaaagagAGG (SEQ ID NO: 618).

In some embodiments the oligomer or oligomer conjugate according to the invention consists of or comprises or is based on AGCgaagtgcacACG (SEQ ID NO: 310).

In some embodiments the oligomer or oligomer conjugate according to the invention consists of or comprises or is based on AGgtgaagcgaAGTG (SEQ ID NO: 668).

In some embodiments the oligomer or oligomer conjugate according to the invention consists of or comprises or is based on AGCgaagtgcacaCGG (SEQ ID NO: 308).

In some embodiments the oligomer or oligomer conjugate according to the invention consists of or comprises or is based on CGAaccactgaACA (SEQ ID NO: 297).

In some embodiments the oligomer or oligomer conjugate according to the invention consists of or comprises or is based on CCGcagtatggaTCG (SEQ ID NO: 299)

In some embodiments the oligomer conjugate according to the invention consists of or comprises (SEQ ID NO: 815)
5'-GN2-C6 caG$_s$$^m$C$_s$G$_s$t$_s$a$_s$a$_s$a$_s$g$_s$a$_s$g$_s$a$_s$G$_s$G-3', In some embodiments the oligomer conjugate according to the invention consists of or comprises (SEQ ID NO: 814)
5'-GN2-C6 caG$_s$$^m$C$_s$G$_s$t$_s$a$_s$a$_s$a$_s$g$_s$a$_s$sg$_s$a$_s$G$_s$T-3'.

In some embodiments the oligomer conjugate according to the invention consists of or comprises (SEQ ID NO: 825)
5'-GN2-C6 caG$_s$$^m$C$_s$G$_s$t$_s$a$_s$a$_s$a$_s$g$_s$a$_s$g$_s$A$_s$G-3'.

In some embodiments the oligomer conjugate according to the invention consists of or comprises (SEQ ID NO: 808)
5'-GN2-C6 caA$_s$G$_s$$^m$C$_s$g$_s$a$_s$a$_s$g$_s$t$_s$g$_s$c$_s$a$_s$c$_s$A$_s$$^m$C$_s$G-3'.

In some embodiments the oligomer conjugate according to the invention consists of or comprises (SEQ ID NO: 826)
5'-GN2-C6 caA$_s$G$_s$g$_s$t$_s$g$_s$a$_s$a$_s$g$_s$$^m$c$_s$g$_s$a$_s$A$_s$G$_s$T$_s$G-3'.

In some embodiments the oligomer conjugate according to the invention consists of or comprises (SEQ ID NO: 807)
5'-GN2-C6 caA$_s$G$_s$$^m$C$_s$g$_s$a$_s$a$_s$g$_s$t$_s$g$_s$c$_s$a$_s$c$_s$a$_s$$^m$C$_s$G-3'.

In some embodiments the oligomer conjugate according to the invention consists of or comprises (SEQ ID NO: 811)
5'-GN2-C6 ca$^m$C$_s$G$_s$A$_s$a$_s$c$_s$c$_s$a$_s$c$_s$t$_s$g$_s$a$_s$A$_s$$^m$C$_s$A-3'

In some embodiments the oligomer conjugate according to the invention consists of or comprises (SEQ ID NO: 802)
5'-GN2-C6 ca$^m$C$_s$$^m$C$_s$G$_s$c$_s$a$_s$g$_s$t$_s$a$_s$t$_s$g$_s$g$_s$a$_s$T$_s$$^m$C$_s$G-3'.

Gapmer

Preferably, the oligomer or the oligomer component of the oligomer conjugate of the invention is a gapmer (sometimes referred to as a gapmer oligomer). Preferably, the oligomer region comprises a 2'-deoxyribonucleotide gap region flanked on each side by a wing, wherein each wing independently comprises one or more LNA units.

Typically, a gapmer oligomer of the present invention or the gapmer oligomer component of the oligomer conjugate of the invention can be represented by any one of the following formulae:

W—X—Y;
V—W—X—Y;
W—X—Y—Z;
V—W—X—Y—Z;

wherein for each formula:
W represents a region of one or more affinity enhancing nucleotide analogues (region W)
X represents a region comprising a stretch of nucleotides capable of recruiting an RNAse (region X)
Y represents a region of one or more affinity enhancing nucleotide analogues (region Y)
V represents a region of one or more nucleotide units (region V)
Z represents a region of one or more nucleotide units (region Z).

Any one of regions V, W, X, Y or Z may contain additional nucleotides or affinity enhancing nucleotide analogues.

Typically, therefore, a gapmer oligomer is an oligomer which comprises a contiguous stretch of nucleotides which is capable of recruiting an RNAse, such as RNAseH, such as a region of at least 6 or 7 DNA nucleotides that is region X; wherein region X is flanked both 5' and 3' by regions of affinity enhancing nucleotide analogues, such as from 1-6 nucleotide analogues 5' and 3' to the contiguous stretch of nucleotides which is capable of recruiting RNAse—these regions are region W and region Y respectively.

In some embodiments, the units which are capable of recruiting RNAse are selected from the group consisting of DNA units, alpha-L-LNA units, C4' alkylayted DNA units (see PCT/EP2009/050349 and Vester et al., Bioorg. Med. Chem. Lett. 18 (2008) 2296-2300, hereby incorporated by reference), and UNA (unlinked nucleic acid) nucleotides (see Fluiter et al., Mol. Biosyst., 2009, 10, 1039 hereby incorporated by reference). UNA is unlocked nucleic acid, typically where the C2-C3 C—C bond of the ribose has been removed, forming an unlocked "sugar" residue. Preferably the gapmer comprises a (poly)nucleotide sequence of formula (5' to 3'), W—X—Y, or optionally W—X—Y—Z or V—W—X—Y, wherein: region W (W) (5' region) consists or comprises at least one nucleotide analogue, such as at least one LNA unit, such as from 1-6 nucleotide analogues, such as LNA units, and; region X (X) consists or comprises at least five consecutive nucleotides which are capable of recruiting RNAse (when formed in a duplex with a complementary RNA molecule, such as the mRNA target), such as DNA nucleotides, and; region Y (Y) (3' region) consists or comprises at least one nucleotide analogue, such as at least one LNA unit, such as from 1-6 nucleotide analogues, such as LNA units, and; region V (V) and/or region Z (Z), when present consists or comprises 1, 2 or 3 nucleotide units, such as DNA nucleotides.

In some embodiments, region W consists of 1, 2, 3, 4, 5 or 6 nucleotide analogues, such as LNA units, such as from 2-5 nucleotide analogues, such as 2-5 LNA units, such as 3 or 4 nucleotide analogues, such as 2, 3 or 4 LNA units.

In some embodiments, region Y consists of 1, 2, 3, 4, 5 or 6 nucleotide analogues, such as LNA units, such as from 2-5 nucleotide analogues, such as 2-5 LNA units, such as 2, 3 or 4 nucleotide analogues, such as 3 or 4 LNA units.

In some embodiments, region X consists or comprises 5, 6, 7, 8, 9, 10, 11 or 12 consecutive nucleotides which are capable of recruiting RNAse, or from 6-10, or from 7-9, such as 8 consecutive nucleotides which are capable of recruiting RNAse.

In some embodiments region X consists or comprises at least one DNA nucleotide unit, such as 1-12 DNA units, preferably from 4-12 DNA units, more preferably from 6-10 DNA units, such as from 7-10 DNA units, most preferably 8, 9 or 10 DNA units.

In some embodiments, region W consist of 2, 3 or 4 nucleotide analogues, such as LNA, region X consists of 7, 8, 9 or 10 DNA units, and region Y consists of 2, 3 or 4 nucleotide analogues, such as LNA. Such designs include (W—X—Y) 3-10-3, 3-10-4, 4-10-3, 3-9-3, 3-9-4, 4-9-3, 3-8-3, 3-8-4, 4-8-3, 3-7-3, 3-7-4, 4-7-3, 3-10-2, 3-9-2, 3-8-2, 3-7-2, 4-10-2, 4-9-2, 4-8-2, 4-7-2; and may further include region V, which may have 1, 2 or 3 nucleotide units, such as DNA units and/or region Z, which may have 1, 2 or 3 nucleotide units, such as DNA units.

Further gapmer designs are disclosed in WO2004/046160, which is hereby incorporated by reference. WO2008/113832, which claims priority from U.S. provisional application 60/977,409 hereby incorporated by reference, refers to 'shortmer' gapmer oligomers. In some embodiments, oligomers presented here may be such shortmer gapmers.

In some embodiments the oligomer is consisting of a contiguous nucleotide sequence of a total of 10, 11, 12, 13 or 14 nucleotide units, wherein the contiguous nucleotide sequence is of formula (5'-3'), W—X—Y, or optionally W—X—Y—Z or V—W—X—Y, wherein; W consists of 1, 2 or 3 nucleotide analogue units, such as LNA units; X consists of 7, 8 or 9 contiguous nucleotide units which are capable of recruiting RNAse when formed in a duplex with a complementary RNA molecule (such as a mRNA target); and Y consists of 1, 2 or 3 nucleotide analogue units, such as LNA units. When present, V consists of 1 or 2 DNA units. When present, Z consists of 1 or 2 DNA units.

In some embodiments W consists of 1 LNA unit. In some embodiments W consists of 2 LNA units. In some embodiments W consists of 3 LNA units.

In some embodiments Y consists of 1 LNA unit. In some embodiments Y consists of 2 LNA units. In some embodiments Y consists of 3 LNA units.

In some embodiments X consists of 7 nucleotide units. In some embodiments X consists of 8 nucleotide units. In some embodiments X consists of 9 nucleotide units. In certain embodiments, region X consists of 10 nucleoside units. In certain embodiments, region X comprises 1-10 DNA units. In some embodiments X comprises from 1-9 DNA units, such as 2, 3, 4, 5, 6, 7, 8 or 9 DNA units. In some embodiments X consists of DNA units. In some embodiments X comprises at least one LNA unit which is in the alpha-L configuration, such as 2, 3, 4, 5, 6, 7, 8 or 9 LNA units in the alpha-L-configuration. In some embodiments X comprises at least one alpha-L-oxy LNA unit or wherein all the LNA units in the alpha-L-configuration are alpha-L-oxy LNA units.

In some embodiments the number of nucleotides present in W—X—Y are selected from the group consisting of (nucleotide analogue units—region X—nucleotide analogue units): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, 3-10-1, 3-10-2, 2-10-3, 3-10-3.

In some embodiments the number of nucleotides in W—X—Y are selected from the group consisting of: 2-7-1, 1-7-2, 2-7-2, 3-7-3, 2-7-3, 3-7-2, 3-7-4, and 4-7-3; in some embodiments preferred motifs are 3-10-3, 3-9-3, 3-8-3, 3-8-2.

In certain embodiments, each of regions W and Y consists of 2 or 3 LNA units, and region X consists of 8 or 9 or 10 nucleoside units, preferably DNA units.

In some embodiments both W and Y consist of 2 or 3 LNA units each, and X consists of 8 or 9 nucleotide units, preferably DNA units.

In various embodiments, other gapmer designs include those where regions W and/or Y consists of 3, 4, 5 or 6 nucleoside analogues, such as units containing a 2'-O-methoxyethyl-ribose sugar (2'-MOE) or units containing a 2'-fluoro-deoxyribose sugar, and region X consists of 8, 9, 10, 11 or 12 nucleosides, such as DNA units, where regions W—X—Y have 3-9-3, 3-10-3, 5-10-5 or 4-12-4 units.

Further gapmer designs are disclosed in WO 2007/146511A2, hereby incorporated by reference.

Accordingly, the oligomer or the oligomer component of the oligomer conjugate may comprise at least 1, at least 2 or at least 3 modified nucleotides at the 5' end of the above sequences. For example, one or more preferably all of the modified nucleotides may be LNA units.

The oligomer or the oligomer component of the oligomer conjugate may comprise at least 1, at least 2 or at least 3 modified nucleotides at the 3' end of the above sequences. For example, one or more preferably all of the modified nucleotides may be LNA units.

The oligomer or the oligomer component of the oligomer conjugate may comprise at least 1, at least 2 or at least 3 modified nucleotides at the 5' and/or 3' end of the sequences disclosed herein. For example, one or more preferably all of the modified nucleotides may be LNA units.

For certain embodiments, the oligomer or the oligomer component of the oligomer conjugate may comprise at least 2 or at least 3 modified nucleotides at the 5' and/or 3' end of the sequences disclosed herein. For example, two or more preferably all of the nucleotides may be LNA units.

For certain embodiments, the oligomer or the oligomer component of the oligomer conjugate may comprise at least 3 modified nucleotides at the 5' and/or 3' end of the sequences disclosed herein. For example, three or more preferably all of the modified nucleotides may be LNA units.

For certain embodiments, the oligomer or the oligomer component of the oligomer conjugate may comprise 3 modified nucleotides at the 5' and/or 3' end of the sequences disclosed herein.

For example the modified nucleotides may be LNA units.

For certain embodiments, the oligomer or the oligomer component of the oligomer conjugate may comprise 3 modified nucleotides at the 5' and at the 3' end of the sequences disclosed herein. For example one or more preferably all of the modified nucleotides may be LNA units.

For some embodiments, the oligomer may comprise an additional CA dinucleotide motif.

In certain aspects, preferably the oligomer is not GAGG-CATAGCAGCAGG (SEQ ID NO: 102).

For certain embodiments of the invention, the oligomer or oligomer component of the oligomer conjugate comprises any one of the motifs: 2-8-2, 3-8-3, 2-8-3, 3-8-2, 2-9-2, 3-9-3, 2-9-3, 3-9-2, 2-10-2, 3-10-3, 3-10-2, 2-10-3 wherein the first number is the number of LNA units in an LNA wing region, the second number is the number of nucleotides in the gap region, and the third number is the number of LNA units in an LNA wing region.

For certain embodiments of the invention, the oligomer or oligomer component of the oligomer conjugate comprises any one of the motifs 3-8-3, 3-8-2, 3-9-3, 3-9-2, 3-10-3, 3-10-2 wherein the first number is the number of LNA units in an LNA wing region, the second number is the number of nucleotides in the gap region, and the third number is the number of LNA units in an LNA wing region.

For certain embodiments, the invention provides an oligomer or an oligomer conjugate as herein defined wherein the oligomer or oligomer component of the oligomer conjugate is a gapmer, and wherein the overall sequence comprises at least 6, preferably at least 7, preferably at least 8, preferably at least 9, preferably at least 10 units, preferably at least 11 units, preferably at least 12 units that are at least 80%, at least 85%, at least 90%, at least 95%, at least 98% identical to a region corresponding to part of the HBV HBx gene, such as part of SEQ ID No. 1, or part of the HBsAg gene, such as SEQ ID No. 2, or to the reverse complement of a target region of a nucleic acid which encodes a HBV HBx or HBV HBsAg.

For certain embodiments, the invention provides an oligomer or an oligomer conjugate as herein defined wherein the oligomer or oligomer component of the oligomer conjugate is a gapmer, and wherein the sequence of the central region comprises at least 6, preferably at least 7, preferably at least 8, preferably at least 9, preferably at least 10 units, that are at least 80%, at least 85%, at least 90%, at least 95%, at least 98% identical to a region corresponding to part of the HBV HBx gene, such as part of SEQ ID No. 1, or part of the HBsAg gene, such as SEQ ID No. 2, or to the reverse complement of a target region of a nucleic acid which encodes a HBV HBx or HBV HBsAg.

For certain embodiments of the invention, the oligomer or the oligomer component of the oligomer conjugate may be based on a sequence selected from the group consisting of any one or more of:

GCGTAAAGAGAGG; (SEQ ID NO: 13)

GCGTAAAGAGAGGT; (SEQ ID NO: 11)

AGCGAAGTGCACACG; (SEQ ID NO: 20)

AGGTGAAGCGAAGTG; (SEQ ID NO: 26)

AGCGAAGTGCACACGG; (SEQ ID NO 18)

CGAACCACTGAACA; (SEQ ID NO: 7)

GAACCACTGAACAAA; (SEQ ID NO 4)

CGAACCACTGAACAAA; (SEQ ID NO 5)

CGAACCACTGAACAA; (SEQ ID NO 6)

CGAACCACTGAAC (SEQ ID NO 8)

CCGCAGTATGGATCG (SEQ ID NO 9)

CGCAGTATGGATC; (SEQ ID NO: 10)

CGCGTAAAGAGAGGT; (SEQ ID NO 12)

AGAAGGCACAGACGG; (SEQ ID NO 14)

GAGAAGGCACAGACGG; (SEQ ID NO 15)

GAAGTGCACACGG; (SEQ ID NO 16)

GCGAAGTGCACACGG; (SEQ ID NO 17)

CGAAGTGCACACG; (SEQ ID NO 19)

AGGTGAAGCGAAGT; (SEQ ID NO 27)
and

TAGTAAACTGAGCCA, (SEQ ID NO: 852)

wherein 1, 2, 3 or 4 of the three to four 5' terminal nucleotides are modified nucleotides, for example LNA units; and 1, 2, 3 or 4 of the three to four 3' terminal nucleotides are modified nucleotides, for example LNA units.

For certain embodiments of the invention, the oligomer or the oligomer component of the oligomer conjugate may be based on a sequence selected from the group consisting of any one or more of:

GCGTAAAGAGAGG; (SEQ ID NO: 13)

AGCGAAGTGCACACG; (SEQ ID NO: 20)

GCGTAAAGAGAGGT; (SEQ ID NO: 11)

AGGTGAAGCGAAGTG; (SEQ ID NO: 26)

AGCGAAGTGCACACGG; (SEQ ID NO 18)

CGAACCACTGAACA; (SEQ ID NO: 7)

GAACCACTGAACAAA; (SEQ ID NO 4)

CGAACCACTGAACAAA; (SEQ ID NO 5)

CGAACCACTGAACAA; (SEQ ID NO 6)

CGAACCACTGAAC (SEQ ID NO 8)

CCGCAGTATGGATCG (SEQ ID NO 9)

CGCAGTATGGATC; (SEQ ID NO: 10)

CGCGTAAAGAGAGGT; (SEQ ID NO 12)

AGAAGGCACAGACGG; (SEQ ID NO 14)

GAGAAGGCACAGACGG (SEQ ID NO 15)

GAAGTGCACACGG; (SEQ ID NO 16)

GAGAAGGCACAGACGG (SEQ ID NO: 15)

GAAGTGCACACGG; (SEQ ID NO: 16)

GCGAAGTGCACACGG; (SEQ ID NO: 17)

CGAAGTGCACACG; (SEQ ID NO: 19)

AGGTGAAGCGAAGT; (SEQ ID NO: 27)
and

TAGTAAACTGAGCCA, (SEQ ID NO: 852)

wherein
  2 or 3 of the three 5' terminal nucleotides are modified nucleotides, for example LNA units;
  2 or 3 of the three 3' terminal nucleotides are modified nucleotides, for example LNA units.

For certain embodiments of the invention, the oligomer or the oligomer component of the oligomer conjugate may be based on a sequence selected from the group consisting of any one or more of:

GCGTAAAGAGAGG; (SEQ ID NO: 13)

GCGTAAAGAGAGGT; (SEQ ID NO: 11)

AGCGAAGTGCACACG; (SEQ ID NO: 20)

AGGTGAAGCGAAGTG; (SEQ ID NO: 26)

AGCGAAGTGCACACGG; (SEQ ID NO 18)

CGAACCACTGAACA; (SEQ ID NO: 7)

GAACCACTGAACAAA; (SEQ ID NO 4)

CGAACCACTGAACAAA; (SEQ ID NO 5)

CGAACCACTGAACAA; (SEQ ID NO 6)

CGAACCACTGAAC (SEQ ID NO 8)

CCGCAGTATGGATCG (SEQ ID NO 9)

CGCAGTATGGATC; (SEQ ID NO: 10)

CGCGTAAAGAGAGGT; (SEQ ID NO 12)

AGAAGGCACAGACGG; (SEQ ID NO 14)

GAGAAGGCACAGACGG (SEQ ID NO 15)

GAAGTGCACACGG; (SEQ ID NO 16)

GCGAAGTGCACACGG;  (SEQ ID NO 17)

CGAAGTGCACACG;  (SEQ ID NO 19)

AGGTGAAGCGAAGT; and  (SEQ ID NO 27)

TAGTAAACTGAGCCA;  (SEQ ID NO: 852)

wherein
- the three 5' terminal nucleotides are modified nucleotides, for example LNA units;
- 2 or 3 of the three 3' terminal nucleotides are modified nucleotides, for example LNA units.

For certain embodiments of the invention, the oligomer or the oligomer component of the oligomer conjugate may be based on a sequence selected from the group consisting of any one or more of:

GCGtaaagagaGG;  (SEQ ID NO: 303)

GCGtaaagagaGGT;  (SEQ ID NO: 301)

GCGtaaagagAGG;  (SEQ ID NO: 618)

AGCgaagtgcacACG  (SEQ ID NO: 310)

AGgtgaagcgaAGTG;  (SEQ ID NO: 668)

AGCgaagtgcacaCGG;  (SEQ ID NO: 308)

CGAaccactgaACA;  (SEQ ID NO: 297)

CGCagtatggaTC;  (SEQ ID NO: 300)

AGGtgaagcgaagTGC  (SEQ ID NO: 315)

AGGtgaagcgaaGTG;  (SEQ ID NO: 316)

GAAccactgaacAAA;  (SEQ ID NO: 294)

CGAaccactgaacAAA;  (SEQ ID NO: 295)

CGAaccactgaaCAA;  (SEQ ID NO: 296)

CGAaccactgaAC;  (SEQ ID NO: 298)

CCGcagtatggaTCG;  (SEQ ID NO: 299)

CGCgtaaagagaGGT;  (SEQ ID NO: 302)

AGAaggcacagaCGG;  (SEQ ID NO: 304)

GAGaaggcacagaCGG;  (SEQ ID NO: 305)

GAAgtgcacacGG;  (SEQ ID NO: 306)

GCGaagtgcacaCGG;  (SEQ ID NO: 307)

CGAagtgcacaCG;  (SEQ ID NO: 309)

GAAccactgaaCAAA;  (SEQ ID NO: 585)

CGAAccactgaacAAA  (SEQ ID NO: 588)

GAAgtgcacaCGG;  (SEQ ID NO: 628)

TAGtaaactgagCCA;  (SEQ ID NO: 678)

CGAaccactgAAC;  (SEQ ID NO: 600)

AGGtgaagcgaAGT; and  (SEQ ID NO: 317)

CGAaccactgAACA,  (SEQ ID NO: 597)

wherein upper case letters denote nucleotides which may be modified nucleotides, for example LNA units.

For certain embodiments of the invention, the oligomer or the oligomer component of the oligomer conjugate may be based on a sequence selected from the group consisting of any one or more of:

5'-AM-C6 caG$_s$$^m$C$_s$G$_s$t$_s$a$_s$a$_s$a$_s$g$_s$a$_s$g$_s$a$_s$G$_s$G-3'  (SEQ ID NO: 303)

5'-AM-C6 caG$_s$$^m$C$_s$G$_s$t$_s$a$_s$a$_s$a$_s$g$_s$a$_s$g$_s$a$_s$G$_s$T-3'  (SEQ ID NO: 301)

5'-AM-C6 caG$_s$$^m$C$_s$G$_s$t$_s$a$_s$a$_s$a$_s$g$_s$a$_s$g$_s$A$_s$G$_s$G-3'  (SEQ ID NO: 618)

5'-AM-C6 caA$_s$G$_s$$^m$C$_s$g$_s$a$_s$a$_s$g$_s$t$_s$g$_s$c$_s$a$_s$c$_s$A$_s$$^m$C$_s$G-3'  (SEQ ID NO: 310)

5'-AM-C6 caA$_s$G$_s$g$_s$t$_s$g$_s$a$_s$a$_s$g$_s$$^m$c$_s$g$_s$a$_s$A$_s$G$_s$T$_s$G-3'  (SEQ ID NO: 668)

5'-AM-C6 caA$_s$G$_s$$^m$C$_s$g$_s$a$_s$a$_s$g$_s$t$_s$g$_s$c$_s$a$_s$c$_s$a$_s$$^m$C$_s$G-3'  (SEQ ID NO: 308)

5'-AM-C6 caG$_s$A$_s$A$_s$c$_s$c$_s$a$_s$c$_s$t$_s$g$_s$a$_s$a$_s$c$_s$A$_s$A$_s$A-3'  (SEQ ID NO: 294)

5'-AM-C6 ca$^m$C$_s$G$_s$A$_s$a$_s$c$_s$c$_s$a$_s$c$_s$t$_s$g$_s$a$_s$a$_s$c$_s$A$_s$A$_s$A-3'  (SEQ ID NO: 295)

5'-AM-C6 ca$^m$C$_s$G$_s$A$_s$a$_s$c$_s$c$_s$a$_s$c$_s$t$_s$g$_s$a$_s$a$_s$$^m$C$_s$A$_s$A-3'  (SEQ ID NO: 296)

5'-AM-C6 ca$^m$C$_s$$^m$C$_s$G$_s$c$_s$a$_s$g$_s$t$_s$a$_s$t$_s$g$_s$g$_s$a$_s$T$_s$$^m$C$_s$G-3'  (SEQ ID NO: 299)

5'-AM-C6 ca$^m$C$_s$G$_s$$^m$C$_s$g$_s$t$_s$a$_s$a$_s$a$_s$g$_s$a$_s$g$_s$a$_s$G$_s$G$_s$T-3'  (SEQ ID NO: 302)

5'-AM-C6 caA$_s$G$_s$A$_s$a$_s$g$_s$g$_s$c$_s$a$_s$c$_s$a$_s$g$_s$a$_s$$^m$C$_s$G$_s$G-3'  (SEQ ID NO: 304)

5'-AM-C6 caG$_s$A$_s$G$_s$a$_s$a$_s$g$_s$g$_s$c$_s$a$_s$c$_s$a$_s$g$_s$a$_s$$^m$C$_s$G$_s$G-3'  (SEQ ID NO: 305)

(SEQ ID NO: 307)
5'-AM-C6 caG$_s$$^m$C$_s$G$_s$a$_s$a$_s$g$_s$t$_s$g$_s$c$_s$a$_s$c$_s$a$_s$$^m$C$_s$G-3'

(SEQ ID NO: 315)
5'-AM-C6 caA$_s$G$_s$G$_s$t$_s$g$_s$a$_s$a$_s$g$_s$$^m$c$_s$g$_s$a$_s$a$_s$g$_s$T$_s$G$_s$$^m$C-3'

(SEQ ID NO: 316)
5'-AM-C6 caA$_s$G$_s$G$_s$t$_s$g$_s$a$_s$a$_s$g$_s$$^m$c$_s$g$_s$a$_s$a$_s$G$_s$T$_s$G-3'

(SEQ ID NO: 297)
5'-AM-C6 ca$^m$C$_s$G$_s$A$_s$a$_s$c$_s$c$_s$a$_s$c$_s$t$_s$g$_s$a$_s$A$_s$$^m$C$_s$A-3'

(SEQ ID NO: 298)
5'-AM-C6 ca$^m$C$_s$G$_s$A$_s$a$_s$c$_s$c$_s$a$_s$c$_s$t$_s$g$_s$a$_s$A$_s$$^m$C-3'

(SEQ ID NO: 300)
5'-AM-C6 ca$^m$C$_s$G$_s$$^m$C$_s$a$_s$g$_s$t$_s$a$_s$t$_s$g$_s$g$_s$a$_s$T$_s$$^m$C-3'

(SEQ ID NO: 306)
5'-AM-C6 caG$_s$A$_s$A$_s$g$_s$t$_s$g$_s$c$_s$a$_s$c$_s$a$_s$$^m$c$_s$G$_s$G-3'

(SEQ ID NO: 309)
5'-AM-C6 ca$^m$C$_s$G$_s$A$_s$a$_s$g$_s$t$_s$g$_s$c$_s$a$_s$c$_s$a$_s$$^m$C$_s$G-3'

(SEQ ID NO: 317)
5'-AM-C6 caA$_s$G$_s$G$_s$t$_s$g$_s$a$_s$a$_s$g$_s$$^m$c$_s$g$_s$a$_s$A$_s$G$_s$T-3'

(SEQ ID NO: 585)
5'-AM-C6 caG$_s$A$_s$A$_s$c$_s$c$_s$a$_s$c$_s$t$_s$g$_s$a$_s$a$_s$$^m$C$_s$A$_s$A$_s$A-3'

(SEQ ID NO: 588)
5'-AM-C6 ca$^m$C$_s$G$_s$A$_s$A$_s$c$_s$c$_s$a$_s$c$_s$t$_s$g$_s$a$_s$a$_s$c$_s$A$_s$A$_s$A-3'

(SEQ ID NO: 628)
5'-AM-C6 caG$_s$A$_s$A$_s$g$_s$t$_s$g$_s$c$_s$a$_s$c$_s$a$_s$$^m$C$_s$G$_s$G-3'

(SEQ ID NO: 678)
5'-AM-C6 caT$_s$A$_s$G$_s$t$_s$a$_s$a$_s$a$_s$c$_s$t$_s$g$_s$a$_s$g$_s$$^m$C$_s$$^m$C$_s$A$_s$3'

(SEQ ID NO: 600)
5'-AM-C6 ca$^m$C$_s$G$_s$A$_s$a$_s$c$_s$c$_s$a$_s$c$_s$t$_s$g$_s$A$_s$A$_s$$^m$C-3'

(SEQ ID NO: 597)
5'-AM-C6 ca$^m$C$_s$G$_s$A$_s$a$_s$c$_s$c$_s$a$_s$c$_s$t$_s$g$_s$A$_s$A$_s$$^m$C$_s$A-3' wherein
- uppercase letters denote beta-D-oxy-LNA units;
- lowercase letters denote DNA units;
- the subscript "s" denotes a phosphorothioate linkage;
- superscript m denotes a DNA or beta-D-oxy-LNA unit containing a 5-methylcytosine base;
- AM-C6 is an amino-C6 linker; wherein the 5' terminal group "AM-C6 c a" is optional.

AM-C6 is an amino-C6 linker: 6-aminohexanol in the 5'-end of the oligonucleotide linked via a phosphodiester or phorphothioate Accordingly, for certain embodiments of the invention, the oligomer or the oligomer component of the oligomer conjugate may be based on a sequence selected from the group consisting of any one or more of:

(SEQ ID NO: 303)
G$^m$CGtaaagagaGG;

(SEQ ID NO: 301)
G$^m$CGtaaagagaGGT;

(SEQ ID NO: 618)
G$^m$CGtaaagagAGG;

(SEQ ID NO: 310)
AG$^m$CgaagtgcacA$^m$CG;

(SEQ ID NO: 668)
AGgtgaag$^m$cgaAGTG;

(SEQ ID NO: 308)
AG$^m$Cgaagtgcaca$^m$CGG;

(SEQ ID NO: 297)
$^m$CGAaccactgaA$^m$CA;

(SEQ ID NO: 300)
$^m$CG$^m$CagtatggaT$^m$C;

(SEQ ID NO: 315)
AGGtgaagcgaagTGC;

(SEQ ID NO: 316)
AGGtgaag$^m$cgaaGTG;

(SEQ ID NO: 294)
GAAccactgaacAAA;

(SEQ ID NO: 295)
$^m$CGAaccactgaacAAA;

(SEQ ID NO: 296)
$^m$CGAaccactgaa$^m$CAA (SEQ ID NO: 298)
$^m$CGAaccactgaA$^m$C;

(SEQ ID NO: 299)
$^m$c$^m$CGcagtatggaT$^m$CG;

(SEQ ID NO: 302)
$^m$CG$^m$CgtaaagagaGGT;

(SEQ ID NO: 304)
AGAaggcacaga$^m$CGG;

(SEQ ID NO: 305)
GAGaaggcacaga$^m$CGG;

(SEQ ID NO: 306)
GAAgtgcaca$^m$cGG;

(SEQ ID NO: 307)
G$^m$CGaagtgcaca$^m$CGG;

(SEQ ID NO: 309)
$^m$CGAagtgcaca$^m$CG;

(SEQ ID NO: 585)
GAAccactgaa$^m$CAAA;

(SEQ ID NO: 588)
$^m$CGAAccactgaacAAA (SEQ ID NO: 628)
GAAgtgcaca$^m$CGG;

(SEQ ID NO: 678)
TAGtaaactgag$^m$C$^m$CA;

(SEQ ID NO: 600)
$^m$CGAaccactgAA$^m$C;

(SEQ ID NO: 317)
AGGtgaag$^m$cgaAGT;
and (SEQ ID NO: 597)
$^m$CGAaccactgAA$^m$CA, wherein
- uppercase letters denote beta-D-oxy-LNA units;
- lowercase letters denote DNA units;
- all internucleoside linkages are phosphorothioate linkages;
- superscript m denotes a DNA or beta-D-oxy-LNA unit containing a 5-methylcytosine base.

In certain preferred aspects, the oligomer or oligomer component of the oligomer conjugate comprises any one of the motifs: 3-10-3, 3-10-2, 3-9-3, 3-9-2, 3-8-3, 3-8-2 wherein the first number is the number of modified nucleotides in the wing region, preferably at least one being an LNA unit, preferably all being an LNA unit, the second number is the number of nucleotides in the gap region, and the third number is the number of modified nucleotides in the wing region, preferably at least one being an LNA unit, preferably all being an LNA unit.

As indicated, the oligomer of the invention may comprise or may be a gapmer. Alternatively expressed, a gapmer oligomer is an oligomer which comprises a contiguous stretch of nucleotides which is capable of recruiting an RNAse, such as RNAseH, such as a region of at least 6 or 7 DNA nucleotides, referred to herein in as region GH (GH), wherein region GH is flanked both 5' and 3' by regions of affinity enhancing nucleotide analogues, such as from 1-6 nucleotide analogues 5' and 3' to the contiguous stretch of nucleotides which is capable of recruiting RNAse—these regions are referred to as regions GX' (GX') and GZ' (GZ'). Regions GX, GH and GZ correspond to regions W, X and Y, respectively.

In some embodiments, the units which are capable of recruiting RNAse are selected from the group consisting of DNA units, alpha-L-LNA units, C4' alkylayted DNA units (see PCT/EP2009/050349 and Vester et al., Bioorg. Med. Chem. Lett. 18 (2008) 2296-2300, hereby incorporated by reference), and UNA (unlinked nucleic acid) nucleotides (see Fluiter et al., Mol. Biosyst., 2009, 10, 1039 hereby incorporated by reference). UNA is unlocked nucleic acid, typically where the C2-C3 C—C bond of the ribose has been removed, forming an unlocked "sugar" residue. Preferably the gapmer comprises a (poly)nucleotide sequence of formula (5' to 3'), GX'-GH-GZ', wherein; region GX' (GX') (5' region) consists or comprises of at least one nucleotide analogue, such as at least one BNA (e.g. LNA) unit, such as from 1-6 nucleotide analogues, such as BNA (e.g. LNA) units, and; region GH (H) consists or comprises of at least five consecutive nucleotides which are capable of recruiting RNAse (when formed in a duplex with a complementary RNA molecule, such as the mRNA target), such as DNA nucleotides, and; region GZ' (GZ') (3'region) consists or comprises of at least one nucleotide analogue, such as at least one BNA (e.g LNA unit), such as from 1-6 nucleotide analogues, such as BNA (e.g. LNA) units.

In some embodiments, region GX' consists of 1, 2, 3, 4, 5 or 6 nucleotide analogues, such as BNA (e.g. LNA) units, such as from 2-5 nucleotide analogues, such as 2-5 LNA units, such as 3 or 4 nucleotide analogues, such as 3 or 4 LNA units; and/or region GZ' consists of 1, 2, 3, 4, 5 or 6 nucleotide analogues, such as BNA (e.g. LNA) units, such as from 2-5 nucleotide analogues, such as 2-5 BNA (e.g. LNA units), such as 3 or 4 nucleotide analogues, such as 3 or 4 BNA (e.g. LNA) units.

In some embodiments GH consists or comprises of 5, 6, 7, 8, 9, 10, 11 or 12 consecutive nucleotides which are capable of recruiting RNAse, or from 6-10, or from 7-9, such as 8 consecutive nucleotides which are capable of recruiting RNAse. In some embodiments region GH consists or comprises at least one DNA nucleotide unit, such as 1-12 DNA units, preferably from 4-12 DNA units, more preferably from 6-10 DNA units, such as from 7-10 DNA units, most preferably 8, 9 or 10 DNA units.

In some embodiments region GX' consist of 3 or 4 nucleotide analogues, such as BNA (e.g. LNA), region X' consists of 7, 8, 9 or 10 DNA units, and region Z' consists of 3 or 4 nucleotide analogues, such as BNA (e.g. LNA). Such designs include (GX'-GH-GZ') 3-10-3, 3-10-4, 4-10-3, 3-9-3, 3-9-4, 4-9-3, 3-8-3, 3-8-4, 4-8-3, 3-7-3, 3-7-4, 4-7-3.

In some embodiments the oligomer, e.g. region GX', is consisting of a contiguous nucleotide sequence of a total of 10, 11, 12, 13 or 14 nucleotide units, wherein the contiguous nucleotide sequence comprises or is of formula (5'-3'), GX'-GH-GZ' wherein; GX' consists of 1, 2 or 3 nucleotide analogue units, such as BNA (e.g. LNA) units; GH consists of 7, 8 or 9 contiguous nucleotide units which are capable of recruiting RNAse when formed in a duplex with a complementary RNA molecule (such as a mRNA target); and GZ' consists of 1, 2 or 3 nucleotide analogue units, such as BNA (e.g. LNA) units.

In some embodiments GX' consists of 1 BNA (e.g. LNA) unit. In some embodiments GX' consists of 2 BNA (e.g. LNA) units. In some embodiments GX' consists of 3 BNA (e.g. LNA) units. In some embodiments GZ' consists of 1 BNA (e.g. LNA) units. In some embodiments GZ' consists of 2 BNA (e.g. LNA) units. In some embodiments GZ' consists of 3 BNA (e.g. LNA) units. In some embodiments GH consists of 7 nucleotide units. In some embodiments GH consists of 8 nucleotide units. In some embodiments GH consists of 9 nucleotide units. In certain embodiments, region GH consists of 10 nucleoside units. In certain embodiments, region GH consists or comprises 1-10 DNA units. In some embodiments GH comprises of from 1-9 DNA units, such as 2, 3, 4, 5, 6, 7, 8 or 9 DNA units. In some embodiments GH consists of DNA units. In some embodiments GH comprises of at least one BNA unit which is in the alpha-L configuration, such as 2, 3, 4, 5, 6, 7, 8 or 9 LNA units in the alpha-L-configuration.

In some embodiments GH comprises of at least one alpha-L-oxy BNA/LNA unit or wherein all the LNA units in the alpha-L-configuration are alpha-L-oxy LNA units. In some embodiments the number of nucleotides present in GX'-GH-GZ' are selected from the group consisting of (nucleotide analogue units—region GH—nucleotide analogue units): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, 3-10-1. In some embodiments the number of nucleotides in GX'-GH-GZ' are selected from the group consisting of: 2-7-1, 1-7-2, 2-7-2, 3-7-3, 2-7-3, 3-7-2, 3-7-4, and 4-7-3. In certain embodiments, each of regions GX' and GH consists of three BNA (e.g. LNA) units, and region GH consists of 8 or 9 or 10 nucleoside units, preferably DNA units. In some embodiments both GX' and GZ' consists of two BNA (e.g. LNA) units each, and GH consists of 8 or 9 nucleotide units, preferably DNA units. In various embodiments, other gapmer designs include those where regions GX' and/or GZ' consists of 3, 4, 5 or 6 nucleoside analogues, such as units containing a 2'-O-methoxyethyl-ribose sugar (2'-MOE) or units containing a 2'-fluoro-deoxyribose sugar, and region H consists of 8, 9, 10, 11 or 12 nucleosides, such as DNA units, where regions GX'-GH-GZ' have 3-9-3, 3-10-3, 5-10-5 or 4-12-4 units.

BNA and LNA Gapmers: The terms BNA and LNA are used interchangeably. A BNA gapmer is a gapmer oligomer (region GA) which comprises at least one BNA nucleotide. A LNA gapmer is a gapmer oligomer (region GA) which comprises at least one LNA nucleotide.

Internucleotide Linkages

The units of the oligomers and oligomer conjugates described herein are coupled together via linkage groups. Suitably, each unit is linked to the 3' adjacent unit via a linkage group.

The person having ordinary skill in the art would understand that, in the context of the present invention, the 5' unit at the end of an oligomer does not comprise a 5' linkage group, although it may or may not comprise a 5' terminal group.

The nucleotides of the oligomer of the invention or contiguous nucleotides sequence thereof are coupled together via linkage groups. Suitably each nucleotide is linked to the 3' adjacent nucleotide via a linkage group.

Optionally, the oligonucleotide of the invention or the oligonucleotide conjugate of the invention may comprise one or more linker groups and/or one or more brancher regions. In various embodiments, the linker groups are internucleoside or internucleotide linkages.

Suitable internucleotide linkages include those listed within WO2007/031091, for example the internucleotide linkages listed on the first paragraph of page 34 of WO2007/031091 (hereby incorporated by reference).

For some embodiments, it is preferred to modify the internucleotide linkage from its normal phosphodiester to one that is more resistant to nuclease attack, such as phosphorothioate or boranophosphate—these two, being cleavable by RNase H, also allow that route of antisense inhibition in reducing the expression of the target gene.

Suitable sulphur (S) containing internucleotide linkages as provided herein may be preferred. Phosphorothioate internucleotide linkages are also preferred, particularly for the gap region (X) of gapmers. Phosphorothioate linkages may also be used for the flanking regions (W and Y, and for linking W or Y to V or Z, and within region V or region Z, as appropriate).

Regions W, X and Y, may however comprise internucleotide linkages other than phosphorothioate, such as phosphodiester linkages, particularly, for instance when the use of nucleotide analogues protects the internucleotide linkages within regions W and Y from endonuclease degradation—such as when regions W and Y comprise LNA nucleotides.

The internucleotide linkages in the oligomer may be phosphodiester, phosphorothioate or boranophosphate so as to allow RNase H cleavage of targeted RNA. Phosphorothioate is preferred for improved nuclease resistance and other reasons, such as ease of manufacture.

In one aspect of the oligomer of the invention, the nucleotides and/or nucleotide analogues are linked to each other by means of phosphorothioate groups.

It is recognised that the inclusion of phosphodiester linkages, such as one or two linkages, into an otherwise phosphorothioate oligomer, particularly between or adjacent to nucleotide analogue units (typically in region W and or Y) can modify the bioavailability and/or bio-distribution of an oligomer—see WO2008/113832, hereby incorporated by reference.

In some embodiments, such as the embodiments referred to above, where suitable and not specifically indicated, all remaining linkage groups are either phosphodiester or phosphorothioate, or a mixture thereof.

In some embodiments all the internucleotide linkage groups are phosphorothioate.

When referring to specific gapmer oligonucleotide sequences, such as any of those specific sequences provided herein it will be understood that, in various embodiments, when the linkages are phosphorothioate linkages, alternative linkages, such as those disclosed herein may be used, for example phosphate (phosphodiester) linkages may be used, particularly for linkages between nucleotide analogues, such as LNA units. Likewise, when referring to specific gapmer oligonucleotide sequences, such as any of those specific sequences provided herein, when the C residues are annotated as 5'methyl modified cytosine, in various embodiments, one or more of the Cs present in the oligomer may be unmodified C residues.

WO09124238 refers to oligomeric compounds having at least one bicyclic nucleoside attached to the 3' or 5' termini by a neutral internucleoside linkage. The oligomers of the invention may therefore have at least one bicyclic nucleoside attached to the 3' or 5' termini by a neutral internucleoside linkage, such as one or more phosphotriester, methylphosphonate, MMI, amide-3, formacetal or thioformacetal. The remaining linkages may be phosphorothioate.

Carrier

In some embodiments, the oligomer of the present invention is linked to one or more carrier components, which may be the same or different.

In some embodiments, the oligomer conjugate has or comprises the structure:

Carrier component-L-First Oligomer Region wherein L is an optional linker or brancher region or tether molecule or bridging moiety.

Preferably L is selected from a physiologically labile linker (region PL) or an alternative linker (Region E), or a combination of both.

The first oligomer region can be linked to the linker or carrier via the 5'-end illustrated as follows:

Carrier component-L1-First Oligomer Region wherein L1 is an optional linker or brancher region or tether molecule or bridging moiety; or Alternatively the first oligomer region can be linked to the linker or carrier via the 3'-end illustrated as follows:

First Oligomer Region-L2-Carrier component wherein L2 is an optional linker or brancher region or tether molecule or bridging moiety.

For certain embodiments, preferably the oligomer conjugate has or comprises the structure:

Carrier component-L1-First Oligomer Region wherein L1 is an optional linker.

For certain embodiments, preferably Linker 1 is present.

For certain embodiments, preferably said carrier component is linked, preferably conjugated, to said first oligomer region.

For certain embodiments, preferably said carrier component is linked, preferably conjugated, to the 5' end of said oligomer.

For certain embodiments, preferably said carrier component is linked, preferably conjugated, to the 5' end of said oligomer by means of a linker group or a brancher region or tether molecule or bridging moiety.

For certain embodiments, preferably the linker group or the brancher region is a physiologically labile linker group or a physiologically labile brancher region or physiologically labile tether molecule or physiologically labile bridging moiety.

For certain embodiments, preferably the physiologically labile linker group is a nuclease susceptible linker, preferably a phosphodiester linker.

For certain empodiments the preferred L1 linker is composed of a physiologically labile linker and a C2-C36 amino alkyl group, including, for example C6 to C12 amino alkyl groups. In a preferred embodiment the L1 linker is composed a PO linker and a C6 amino linker.

In some embodiments, the carrier component is selected from a carbohydrate conjugate or a lipophilic conjugate, or the carrier component comprises both a carbohydrate and a lipophilic conjugate.

The carbohydrate conjugate moiety may for example be selected from the group consisting of galactose, galactosamine, N-formyl-galactosamine, Nacetylgalactosamine, N-propionyl-galactosamine, N-n-butanoyl-galactosamine, and N-isobutanoylgalactose-amine. Preferably the carbohydrate conjugate moiety is an asialoglycoprotein receptor targeting conjugate moiety. The lipophilic conjugate may be a hydrophobic group, such as a C16-20 hydrophobic group, a sterol, cholesterol. Other carbohydrate and lipophilic groups which may be used are, for example, disclosed herein.

For some embodiments, the oligomer may comprise an additional CA dinucleotide motif. Preferably, in the context of the oligomer conjugate, the CA motif is positioned between the carrier component and the oligomer. The CA motif preferably comprise a phosphidiester linkage and serves as a PO linker between the oligomer and the carrier component.

Hepatitis B Virus (Hbv)

It is intended that all oligomers and oligomer conjugates as described herein are capable of being used to treat a viral disorder, in particular a disorder associated with HBV. Such uses form part of the present invention.

It is intended that all oligomers and oligomer conjugates as described herein are capable of being used in the manufacture of a medicament to treat a viral disorder, in particular a disorder associated with HBV. Such uses form part of the present invention.

It is intended that all oligomers and oligomer conjugates as described herein are capable of being administered to a subject as part of a method for alleviating, curing or treating a viral disorder, in particular a disorder associated with HBV. Such methods form part of the present invention.

It is intended that all oligomers and oligomer conjugates as described herein are capable of comprising part of a pharmaceutical composition to treat a viral disorder, in particular a disorder associated with HBV. Such pharmaceutical compositions form part of the present invention.

Hepatitis B virus (HBV) is a species of the genus Orthohepadnavirus, which is a part of the Hepadnaviridae family. The virus causes the disease hepatitis B. In addition to causing hepatitis, infection with HBV can lead to cirrhosis and hepatocellular carcinoma. It has also been suggested that it may increase the risk of pancreatic cancer.

The virus is divided into four major serotypes (adr, adw, ayr, ayw) based on antigenic epitopes present on its envelope proteins, and into eight genotypes (A-H) according to overall nucleotide sequence variation of the genome. The genotypes have a distinct geographical distribution and differences between genotypes affect the disease severity, course and likelihood of complications, and response to treatment and possibly vaccination. The genotypes differ by at least 8%. Type F which diverges from the other genomes by 14% is the most divergent type known. Type A is prevalent in Europe, Africa and South-east Asia, including the Philippines. Type B and C are predominant in Asia; type D is common in the Mediterranean area, the Middle East and India; type E is localized in sub-Saharan Africa; type F (or H) is restricted to Central and South America. Type G has been found in France and Germany. Genotypes A, D and F are predominant in Brazil and all genotypes occur in the United States with frequencies dependent on ethnicity.

HBV has a circular DNA genome, however, the DNA is not fully double-stranded as one end of the full length strand is linked to the viral DNA polymerase. The genome is 3020-3320 nucleotides long (for the full length strand) and 1700-2800 nucleotides long (for the short length strand).

There are four known genes encoded by the HBV genome (C, P, S, and X). The core protein is coded for by gene C (HBcAg), and its start codon is preceded by an upstream in-frame AUG start codon from which the pre-core protein is produced. HBeAg is produced by proteolytic processing of the pre-core protein. The DNA polymerase is encoded by gene P.

HBx

The HBx polypeptide is a 154 residue protein which interferes with transcription, signal transduction, cell cycle progress, protein degradation, apoptosis and chromosomal stability in the host. It forms a heterodimeric complex with its cellular target protein (HBX interacting protein: HBXIP), and this interaction dysregulates centrosome dynamics and mitotic spindle formation. It interacts with DDB1 (Damaged DNA Binding Protein 1) redirecting the ubiquitin ligase activity of the CUL4-DDB1 E3 complexes, which are intimately involved in the intracellular regulation of DNA replication and repair, transcription and signal transduction.

Although it lacks significant sequence identity with any known vertebrate proteins, it is likely to have evolved from a DNA glycosylase. Transgenic mice expressing the X protein in liver are more likely than the wild type to develop hepatocellular carcinoma. This is because the X protein promotes cell cycle progression while binding to and inhibiting tumour suppressor protein p53 from performing their role. Experimental observations also suggest that HBx protein increases TERT and telomerase activity, prolonging the lifespan of hepatocytes and contributing to malignant transformation.

In a study purifying cancerous liver cells infected with HBV, the level of expression of protein arginine methyltransferase 1 (PRMT1) was found to be associated with changes in transcription due to the methyltransferase function of PRMT1. Overexpression causes a reduction in the number of HBV genes transcribed, while conversely, reduced expression causes an increase. PRMT1 was also found to be recruited by HBV DNA during the replication process to regulate the transcription process. Increased HBx expression in turn leads to an inhibition of PRMT1-mediated protein methylation, benefiting viral replication.

The HBx target sequence comprises sequences starting at the first reported transcription start site at position 1196 to the polyadenylation site at position 1941. The sequence from position 1196 to 1941 of the U95551 sequence is presented as SEQ ID No. 1. The U95551 sequence is presented as SEQ ID No. 3.

HBsAq

HBsAg (also known as Major surface antigen, HBV major surface antigen, HBV surface antigen and 'S') is the surface antigen of the HBV.

Gene S is the gene that codes for the surface antigen (HBsAg). The HBsAg gene is one long open reading frame but contains three in frame "start" (ATG) codons that divide the gene into three sections, pre-S1, pre-S2, and S. Because of the multiple start codons, polypeptides of three different sizes called large, middle, and small (pre-S1+pre-S2+S, pre-S2+S, or S) are produced.

The HBsAg is made up of three glycoproteins that are encoded by the same gene. The proteins are translated in the same reading frame but start at a different AUG start codon; thus, all have the same C-terminus. The largest protein is the L protein (42 kd) and contained within this is the M glycoprotein. The S glycoprotein (27 kD) is contained within the M protein. The HBsAg protein is also secreted into the patient's serum where it can be seen as spherical (mostly self-associated S protein) or filamentous particles (also mostly S protein but with some L and M). The former are smaller than the true virus but the filaments can be quite large (several hundred nanometers).

S-HBsAg is 226 amino acid residues in length. It is an integral membrane glycoprotein which is anchored in the ER lipid bilayer through an amino-terminal transmembrane domain (TMD-1) between residues 4 and 24. It comprises a downstream cytosolic loop (CYL-1) between residues 24 and 80, a second transmembrane domain (TMD-II) between residues 80 and 100, and an antigenic loop (AGL) encompassing residues 101 to 164, facing the ER lumen (or the surface of extracellular particles). The carboxyl terminus (residues 165 to 226) is predicted to contain two TMDs (TMD-III and -IV), located at positions 173 to 193 and 202 to 222, respectively, separated by a short sequence (residues 194 to 201) referred to here as cytosolic loop II (CYL-II) because it is predicted to reside at the cytosolic side of the ER membrane. The M-HBsAg protein sequence is longer than that of S-HBsAg by 55 residues (the pre-S2 domain) at its amino terminus; it is coassembled with the latter in the viral envelope but is dispensable for both morphogenesis and in vitro infectivity. L-HBsAg comprises the entire M polypeptide with an additional amino-terminal extension (pre-S1) of 108 to 119 residues depending on the HBV genotype. It has been described with two topologies, with the amino-terminal pre-S domain (pre-S1 plus pre-S2) being either cytosolic at the ER membrane (internal on secreted virions) or luminal (exposed at the virion surface). The internal conformation is involved in recruiting the nucleocapsid for virion assembly, whereas the external position corresponds to a receptor-binding function at viral entry.

All three envelope proteins are synthesized at the endoplasmic reticulum (ER) membrane, where they aggregate through protein-protein interactions leading primarily to the secretion of empty S-HBsAg-coated subviral particles (SVPs) It is only when L-HBsAg is present in the envelope protein aggregates at the ER membrane that the HBV nucleocapsid can be recruited in the budding complex and released as a mature virion. Owing to the overwhelming activity of S-HBsAg for self-assembly, in comparison to that of L-HBsAg, HBV virion formation occurs only on rare occasions.

The HBsAg target sequence comprises sequences starting of the circularized U95551 sequence from the transcription start site at position 3158 to 3182 and from position 1 to the polyadenylation site at position 1941. Thus, the HBsAg target sequence comprises sequences of the combined sequences from position 3158 to 3182 and position 1 to 1944 of the circularized U95551 sequence. This target sequence is presented as SEQ ID no. 2. The U95551 sequence is presented as SEQ ID No. 3.

Target

In a preferred aspect, suitably the oligomer or the oligomer conjugate of the invention is capable of modulating a target sequence in HBx or HBsAg of Hepatitis B Virus (HBV). In this regard, the oligomer of the invention can affect the inhibition of a target sequence, typically in a mammalian cell such as a human cell, such as a liver cell.

In some embodiments, the oligomer or the oligomer conjugate of the invention binds to the target nucleic acid and modulates expression by at least 10% or 20% compared to the normal expression level, more preferably at least a 30%, 40%, 50%, 60%, 70%, 80%, 90% or 95% compared to the normal expression level (such as the expression level in the absence of the oligomer(s) or oligomer conjugate(s)).

In one embodiment, the oligomer or the oligomer conjugate of the invention is capable of down-regulating (e.g. inhibiting, reducing or removing) expression of the HBx or HBsAg gene. In this regard, the oligomer of the invention can affect the inhibition of HBx or HBsAg. Such inhibition may typically occur in a mammalian cell such as a human cell, such as a liver cell. In some embodiments, the oligomers of the invention bind to the target nucleic acid and affect inhibition of expression of at least 10% or 20% compared to the normal expression level, more preferably at least a 30%, 40%, 50%, 60%, 70%, 80%, 90% or 95% inhibition compared to the normal expression level (such as the expression level in the absence of the oligomer(s) or oligomer conjugate (s)).

In some embodiments, such modulation is seen when using from 0.04 and 25 nM, such as from 0.8 and 20 nM concentration of the compound of the invention. In the same or a different embodiment, the modulation of expression is less than 100%, such as less than 98%, less than 95%, less than 90%, less than 80%, such as less than 70%. Modulation of expression level may be determined by measuring protein levels, e.g. by the methods such as SDS-PAGE followed by western blotting using suitable antibodies raised against the target protein. Alternatively, modulation of expression levels can be determined by measuring levels of mRNA, e.g. by northern blotting or quantitative RT-PCR. When measuring via mRNA levels, the level of down-regulation when using an appropriate dosage, such as from 0.04 and 25 nM, such as from 0.8 and 20 nM concentration, is, in some embodiments, typically to a level of from 10-20% the normal levels in the absence of the compound, conjugate or composition of the invention.

As illustrated herein the cells may be in vitro transfected cells. The concentration of the oligomer or the oligomer conjugate used may, in some embodiments, be 5 nM. The oligomer concentration used may, in some embodiments be 25 nM. The concentration of the oligomer or the oligomer conjugate used may, in some embodiments be 1 nM. It should be noted that the concentration of oligomer used to treat the cell is typically performed in an in vitro cell assay, using transfection (Lipofecton), as illustrated in the examples. In the absence of a transfection agent, the concentration of the oligomer or the oligomer conjugate required to obtain the down-regulation of the target is typically between 1 and 25 M, such as 5 M.

The invention therefore provides a method of down-regulating or inhibiting the expression of HBx or HBsAg protein and/or mRNA in a cell which is expressing HBx or HBsAg protein and/or mRNA, said method comprising administering the oligomer or conjugate according to the invention to said cell to down-regulate or inhibit the expression of HBx or HBsAg protein and/or mRNA in said cell. Suitably the cell is a mammalian cell such as a human cell. The administration may occur, in some embodiments, in vitro. The administration may occur, in some embodiments, in vivo.

For certain embodiments, the oligomer or the oligomer component of the oligomer conjugate that targets HBx also binds to HBsAg.

Target Sequence

The oligomers or oligomer conjugates comprise or consist of a contiguous nucleotide sequence which corresponds to the reverse complement of a nucleotide sequence present in the target sequence.

The target sequence may be a gene or a mRNA, such as a coding or a non-coding region of a gene or mRNA. For example, the target sequence may be a coding or non-coding exon. The target sequence may comprise at least part of an exon. The target sequence may be part of an exon, such as within an exon.

In the practice of the present invention, the target sequence may be single-stranded or double-stranded DNA or RNA; however, single-stranded DNA or RNA targets are preferred. It is understood that the target sequence to which the antisense oligonucleotides of the invention are directed include allelic forms of the targeted gene and the corresponding mRNAs including splice variants. There is substantial guidance in the literature for selecting particular sequences for antisense oligonucleotides given a knowledge of the sequence of the target polynucleotide, e.g., Cook S. T. *Antisense Drug Technology, Principles, Strategies, and Applications*, Marcel Dekker, Inc, 2001; Peyman and Ulmann, *Chemical Reviews,* 90:543-584, 1990; and Crooke, *Ann. Rev. Pharmacol. Toxicol.,* 32:329-376 (1992). mRNA targets may include the 5' cap site, tRNA primer binding site, the initiation codon site, the mRNA donor splice site, and the mRNA acceptor splice site.

Where the target polynucleotide sequence comprises a mRNA transcript, sequence complementary oligonucleotides can hybridize to any desired portion of the transcript. Such oligonucleotides are, in principle, effective for inhibiting translation, and capable of inducing the effects described herein. It is hypothesized that translation is most effectively inhibited by blocking the mRNA at a site at or near the initiation codon. Thus, oligonucleotides may be complementary to the 5'-region of mRNA transcript. Oligonucleotides may be complementary to the mRNA, including the initiation codon (the first codon at the 5' end of the translated portion of the transcript), or codons adjacent to the initiation codon.

In one embodiment, the target sequence may have identity between HBV genotypes A-H (described in detail below).

In one embodiment, the target sequence may have at least 80%, at least 85%, at least 90%, at least 95%, at least 98% or at least 99% identity with any one or more of the HBV genotypes A-H. For example, the target sequence may have at least 80%, at least 85%, at least 90%, at least 95%, at least 98% or at least 99% identity with HBV genotype A. For example, the target sequence may have at least 80%, at least 85%, at least 90%, at least 95%, at least 98% or at least 99% identity with HBV genotype B. For example, the target sequence may have at least 80%, at least 85%, at least 90%, at least 95%, at least 98% or at least 99% identity with HBV genotype C. For example, the target sequence may have at least 80%, at least 85%, at least 90%, at least 95%, at least 98% or at least 99% identity with HBV genotype D. For example, the target sequence may have at least 80%, at least 85%, at least 90%, at least 95%, at least 98% or at least 99% identity with HBV genotype E. For example, the target sequence may have at least 80%, at least 85%, at least 90%, at least 95%, at least 98% or at least 99% identity with HBV genotype F. For example, the target sequence may have at least 80%, at least 85%, at least 90%, at least 95%, at least 98% or at least 99% identity with HBV genotype G. For example, the target sequence may have at least 80%, at least 85%, at least 90%, at least 95%, at least 98% or at least 99% identity with HBV genotype H.

In one embodiment, the target sequence may have at least 80%, at least 85%, at least 90%, at least 95%, at least 98% identity between two or more of the HBV genotypes A-H.

In one embodiment, the target sequence may have identity between two or more of HBV genotypes A, B, C and D. The target sequence may have at least 80%, at least 85%, at least 90%, at least 95%, at least 98% between HBV genotypes A and B.

In one embodiment, the target sequence may have identity between two or more of HBV genotypes A, B, C and D. The target sequence may have at least 80%, at least 85%, at least 90%, at least 95%, at least 98% between HBV genotypes A and C.

In one embodiment, the target sequence may have identity between three or more of HBV genotypes A, B, C and D. The target sequence may have at least 80%, at least 85%, at least 90%, at least 95%, at least 98% identity between HBV genotypes A, B, C and D.

In one embodiment, the target sequence may have identity between three or more of HBV genotypes A, B, C and D. The target sequence may have at least 80%, at least 85%, at least 90%, at least 95%, at least 98% identity between HBV genotypes A, B and C.

In one embodiment, the target sequence may have identity between three or more of HBV genotypes A, B, C and D. The target sequence may have at least 80%, at least 85%, at least 90%, at least 95%, at least 98% identity between HBV genotypes A, B, and D.

In one embodiment, the target sequence may have identity between all of HBV genotypes A, B, C and D. The target sequence may have at least 80%, at least 85%, at least 90%, at least 95%, at least 98% or at least 99% identity between HBV genotypes A, B, C and D.

In various embodiments, the target sequence is within the sequence shown as SEQ ID No. 3.

In one embodiment, the target sequence comprises at least part of a gene or a mRNA encoding HBx or HBsAg or a naturally-occurring variant thereof.

In various embodiments, the target sequence is HBx or HBsAg or a naturally-occurring variant thereof.

In various embodiments, the target sequence is within the sequence shown as SEQ ID No. 1.

In various embodiments, the target sequence is within the sequence shown as SEQ ID No. 2. In various embodiments, the target sequence is selected from one or more of the following positions in SEQ ID NO 3: position 1 to 1944, position 157 to 1840, position 1196 to 1941, position 1376 to 1840 and position 3158-3182. Preferably, the target sequence is selected from position 1530 to 1598 of SEQ ID NO: 3, more preferable from position 1577 to 1598 of SEQ ID NO: 3 and most preferably from position 1530 to 1543 of SEQ ID NO: 3.

In various embodiments, the target sequence may be selected from the group consisting of any one or more of positions:
1264-1278;
1265-1277;
1530-1543;
1530-1544;
1531-1543;
1551-1565;
1551-1566;
1577-1589;
1577-1591;
1577-1592;
1577 to 1598;
1578-1590;
1578-1592;
1583-1598;
1584-1598;
1585-1598;
670-706

670-684
691-705;
691-706;
692-706;
693-706;
694-706;
of SEQ ID No. 3.

In an aspect, the oligomer or oligomer conjugate of the invention is capable of targeting from 8-30, 8-20, 8-18, 8-16, 8-14, 8-12 or 8-10 contiguous nucleotides within the sequence shown as position 1200 to 1900, preferably position 1530 to 1598, more preferable position 1577 to 1598, most preferably position 1530 to 1543 of SEQ ID NO: 3 of SEQ ID No. 3; preferably wherein said oligomer or oligomer conjugate is complementary to said contiguous nucleotides.

In an aspect, the oligomer or oligomer conjugate of the invention is capable of targeting at least 8, 9, 10, 11, 12, 13, 14, 15, 16, 17, 18, 19, 20, 21, 22, 23, 24, 25, 26, 27, 28, or 29 contiguous nucleotides within the sequence shown as position 1200 to 1900, preferably position 1530 to 1598, more preferable position 1577 to 1598, most preferably position 1530 to 1543 of SEQ ID NO: 3 of SEQ ID No. 3; preferably wherein said oligomer or oligomer conjugate is complementary to said contiguous nucleotides.

In an aspect the oligomer or oligomer conjugate of the invention is capable of targeting at least 8 contiguous nucleotides within the sequence shown as position 1200 to 1900, preferably position 1530 to 1598, more preferable position 1577 to 1598, most preferably position 1530 to 1543 of SEQ ID NO: 3 of SEQ ID NO: 3; preferably wherein said oligomer or oligomer conjugate is complementary to said contiguous nucleotides.

In an aspect the oligomer or oligomer conjugate of the invention is capable of targeting at least 9 contiguous nucleotides within the sequence shown as position 1200 to 1900, preferably position 1530 to 1598, more preferable position 1577 to 1598, most preferably position 1530 to 1543 of SEQ ID NO: 3 of SEQ ID NO: 3 preferably wherein said oligomer or oligomer conjugate is complementary to said contiguous nucleotides.

In an aspect the oligomer or oligomer conjugate of the invention is capable of targeting at least 10 contiguous nucleotides within the sequence shown as position 1200 to 1900, preferably position 1530 to 1598, more preferable position 1577 to 1598, most preferably position 1530 to 1543 of SEQ ID NO: 3 of SEQ ID NO: 3; preferably wherein said oligomer or oligomer conjugate is complementary to said contiguous nucleotides.

In an aspect the oligomer or oligomer conjugate of the invention is capable of targeting at least 11 contiguous nucleotides within the sequence shown as position 1200 to 1900, preferably position 1530 to 1598, more preferable position 1577 to 1598, most preferably position 1530 to 1543 of SEQ ID NO: 3 of SEQ ID NO: 3 preferably wherein said oligomer or oligomer conjugate is complementary to said contiguous nucleotides.

In an aspect the oligomer or oligomer conjugate of the invention is capable of targeting at least 12 contiguous nucleotides within the sequence shown as position 1200 to 1900, preferably position 1530 to 1598, more preferable position 1577 to 1598, most preferably position 1530 to 1543 of SEQ ID NO: 3 of SEQ ID NO: 3 preferably wherein said oligomer or oligomer conjugate is complementary to said contiguous nucleotides.

In an aspect the oligomer or oligomer conjugate of the invention is capable of targeting at least 13 contiguous nucleotides within the sequence shown as position 1200 to 1900, preferably position 1530 to 1598, more preferable position 1577 to 1598, most preferably position 1530 to 1543 of SEQ ID NO: 3 of SEQ ID NO: 3 preferably wherein said oligomer or oligomer conjugate is complementary to said contiguous nucleotides.

In an aspect the oligomer or oligomer conjugate of the invention is capable of targeting at least 14 contiguous nucleotides within the sequence shown as position 1200 to 1900, preferably position 1530 to 1598, more preferable position 1577 to 1598, most preferably position 1530 to 1543 of SEQ ID NO: 3 of SEQ ID NO: 3 preferably wherein said oligomer or oligomer conjugate is complementary to said contiguous nucleotides.

In an aspect the oligomer or oligomer conjugate of the invention is capable of targeting at least 15 contiguous nucleotides within the sequence shown as position 1200 to 1900, preferably position 1530 to 1598, more preferable position 1577 to 1598, most preferably position 1530 to 1543 of SEQ ID NO: 3 of SEQ ID NO: 3 preferably wherein said oligomer or oligomer conjugate is complementary to said contiguous nucleotides.

In an aspect the oligomer or oligomer conjugate of the invention is capable of targeting at least 16 contiguous nucleotides within the sequence shown as position 1200 to 1900, preferably position 1530 to 1598, more preferable position 1577 to 1598, most preferably position 1530 to 1543 of SEQ ID NO: 3 of SEQ ID NO: 3 preferably wherein said oligomer or oligomer conjugate is complementary to said contiguous nucleotides.

In one embodiment, the target sequence comprises a sequence within the sequence set forth in SEQ ID NO: 1 or SEQ ID No 2 or SEQ ID No 3 or a sequence having at least 80% identity thereto. Thus, the oligomer or oligomer conjugate can comprise or consist of a core motif selected from the group presented herein, wherein said oligomer or oligomer conjugate (or contiguous nucleotide portion thereof) may optionally have one, two, or three mismatches against said selected motif sequence:

```
                                    (SEQ ID NO: 13)
GCGTAAAGAGAGG;

(SEQ ID NO: 20)
AGCGAAGTGCACACG;

(SEQ ID NO: 11)
GCGTAAAGAGAGGT;

(SEQ ID NO: 26)
AGGTGAAGCGAAGTG;

(SEQ ID NO 18)
AGCGAAGTGCACACGG;

(SEQ ID NO: 7)
CGAACCACTGAACA;

(SEQ ID NO 4)
GAACCACTGAACAAA;

(SEQ ID NO 5)
CGAACCACTGAACAAA;

(SEQ ID NO 6)
CGAACCACTGAACAA;

(SEQ ID NO 8)
CGAACCACTGAAC (SEQ ID NO 9)
CCGCAGTATGGATCG
```

-continued

CGCAGTATGGATC; (SEQ ID NO: 10)

CGCGTAAAGAGAGGT; (SEQ ID NO 12)

AGAAGGCACAGACGG; (SEQ ID NO 14)

GAGAAGGCACAGACGG (SEQ ID NO 15)

GAAGTGCACACGG; (SEQ ID NO 16)

GCGAAGTGCACACGG; (SEQ ID NO 17)

CGAAGTGCACACG; (SEQ ID NO 19)

AGGTGAAGCGAAGT; and (SEQ ID NO 27)

TAGTAAACTGAGCCA (SEQ ID NO: 852)

In one embodiment, the target sequence comprises the sequence set forth below or a sequence having at least 80% identity to any thereto. Thus, the oligomer or oligomer conjugate can comprise or consist of a sequence hybridizing to a target sequence selected from the group presented below, wherein said oligomer or oligomer conjugate (or contiguous nucleotide portion thereof) may optionally have one, two, or three mismatches against said selected target sequence.

| Target Sequence |
| --- |
| acggggcgcacctctctttacgcg (SEQ ID NO: 827) |
| cgtgtgcacttcgcttcacctc (SEQ ID NO: 828) |
| ccgtctgtgccttctc (SEQ ID NO: 829) |
| cgatccatactgcgg (SEQ ID NO: 830) |
| tggctcagtttacta (SEQ ID NO: 831) |
| ctagtgccatttgtt (SEQ ID NO: 833) |

In some embodiments, the oligomer or oligomer conjugate may tolerate 1, 2, 3, or 4 (or more) mismatches, when hybridising to the target sequence and still sufficiently bind to the target to show the desired effect, i.e. down-regulation of the target. Mismatches may, for example, be compensated by increased length of the oligomer nucleotide sequence and/or an increased number of nucleotide analogues, such as LNA, present within the nucleotide sequence.

In some embodiments, the contiguous nucleotide sequence comprises no more than 3, such as no more than 2 mismatches when hybridizing to the target sequence, such as to the corresponding region of a nucleic acid which encodes HBx or HBsAg.

In some embodiments, the contiguous nucleotide sequence comprises no more than a single mismatch when hybridizing to the target sequence, such as the corresponding region of a nucleic acid which encodes HBx or HBsAg.

If the target is HBx, the nucleotide sequence of the oligomer or oligomer conjugate of the invention or the contiguous nucleotide sequence preferably has at least 80% identity (sometimes referred to as homology or homologous) to a corresponding sequence selected from the nucleotide sequences presented herein, such as at least 85%, at least 90%, at least 91%, at least 92%, at least 93%, at least 94%, at least 95%, at least 96% homologous, at least 97% homologous, at least 98% homologous, at least 99% homologous, such as 100% homologous (identical).

If the target is HBx, the nucleotide sequence of the oligomer or oligomer conjugate of the invention or the contiguous nucleotide sequence preferably has at least 80% identity (sometimes referred to as homology or homologous) to the reverse complement of a corresponding sequence within the sequence presented as SEQ ID No. 1, such as at least 85%, at least 90%, at least 91%, at least 92%, at least 93%, at least 94%, at least 95%, at least 96% homologous, at least 97% homologous, at least 98% homologous, at least 99% homologous, such as 100% homologous (identical).

If the target is HBx, the nucleotide sequence of the oligomer or oligomer conjugate of the invention or the contiguous nucleotide sequence is preferably at least 80% complementary to a sub-sequence present within the sequence presented as SEQ ID No. 1, such as at least 85%, at least 90%, at least 91%, at least 92%, at least 93%, at least 94%, at least 95%, at least 96% complementary, at least 97% complementary, at least 98% complementary, at least 99% complementary, such as 100% complementary (perfectly complementary).

In some embodiments if the target is HBx, the oligomer or oligomer conjugate (or contiguous nucleotide portion thereof) is selected from, or comprises, one of the sequences presented herein, or a sub-sequence of at least 10 contiguous nucleotides thereof, wherein said oligomer or oligomer conjugate (or contiguous nucleotide portion thereof) may optionally comprise one, two, or three mismatches when compared to the sequence.

If the target is HBsAg, the nucleotide sequence of the oligomer or oligomer conjugate of the invention or the contiguous nucleotide sequence preferably has at least 80% identity (sometimes referred to as homology or homologous) to a corresponding sequence selected from the group presented herein, such as at least 85%, at least 90%, at least 91%, at least 92%, at least 93%, at least 94%, at least 95%, at least 96% homologous, at least 97% homologous, at least 98% homologous, at least 99% homologous, such as 100% homologous (identical).

If the target is HBsAg, the nucleotide sequence of the oligomer or oligomer conjugate of the invention or the contiguous nucleotide sequence preferably has at least 80% identity (sometimes referred to as homology or homologous) to the reverse complement of a corresponding sequence present within the sequence presented as SEQ ID No. 2, such as at least 85%, at least 90%, at least 91%, at least 92% at least 93%, at least 94%, at least 95%, at least 96% homologous, at least 97% homologous, at least 98% homologous, at least 99% homologous, such as 100% homologous (identical).

If the target is HBsAg, the nucleotide sequence of the oligomer or oligomer conjugate of the invention or the contiguous nucleotide sequence is preferably at least 80% complementary to a sub-sequence present within the sequence presented as SEQ ID No. 2, such as at least 85%, at least 90%, at least 91%, at least 92%, at least 93%, at least 94%, at least 95%, at least 96% complementary, at least 97% complementary, at least 98% complementary, at least 99% complementary, such as 100% complementary (perfectly complementary).

In some embodiments if the target is HBsAg, the oligomer or oligomer conjugate (or contiguous nucleotide portion thereof) is selected from, or comprises, one of the sequences selected from the group presented herein, or a sub-sequence of at least 10 contiguous nucleotides thereof, wherein said oligomer or oligomer conjugate (or contiguous nucleotide portion thereof) may optionally comprise one, two, or three mismatches when compared to the sequence.

In some embodiments the sub-sequence may consist of 11, 12, 13, 14, 15, 16, 17, 18, 19, 20, 21, 22, 23, 24, 25, 26, 27, 28, or 29 contiguous nucleotides, such as from 12-22, such as from 12-18, such as from 12-16 nucleotides. Suitably, in some embodiments, the sub-sequence is of the same length as the contiguous nucleotide sequence of the oligomer of the invention.

However, it is recognised that, in some embodiments the nucleotide sequence of the oligomer or oligomer conjugate may comprise additional 5' or 3' nucleotides, such as, independently, 1, 2, 3, 4 or 5 additional nucleotides 5' and/or 3', which are non-complementary to the target sequence. In this respect the oligomer of the invention, may, in some embodiments, comprise a contiguous nucleotide sequence which is flanked 5' and or 3' by additional nucleotides. In some embodiments the additional 5' or 3' nucleotides are naturally occurring nucleotides, such as DNA or RNA. In some embodiments, the additional 5' or 3' nucleotides may represent region D as referred to in the context of gapmer oligomer or oligomer conjugate herein.

RNAse RECRUITMENT

It is recognised that an oligomeric molecule may function via non RNase mediated degradation of target mRNA, such as by steric hindrance of translation, or other methods.

For some embodiments, the oligomer or oligomer conjugate of the invention is capable of recruiting an endoribonuclease (RNase), such as RNase H.

It is preferable that the oligomer or oligomer conjugate of the invention comprises a region of at least 6, such as at least 7 consecutive nucleotide units, such as at least 8 or at least 9 consecutive nucleotide units (residues), including 7, 8, 9, 10, 11, 12, 13, 14, 15 or 16 consecutive nucleotides, which, when formed in a duplex with the complementary target RNA is capable of recruiting RNase. The contiguous sequence which is capable of recruiting RNAse may be region X as referred to in the context of a gapmer as described herein. In some embodiments the size of the contiguous sequence which is capable of recruiting RNAse, such as region X, may be higher, such as 10, 11, 12, 13, 14, 15, 16, 17, 18, 19 or 20 nucleotide units.

EP 1 222 309 provides in vitro methods for determining RNaseH activity, which may be used to determine the ability to recruit RNase. An oligomer is deemed capable of recruiting RNase H if, when provided with the complementary RNA target, it has an initial rate, as measured in pmol/l/min, of at least 1%, such as at least 5%, such as at least 10% or, more than 20% of the of the initial rate determined using DNA only oligonucleotide, having the same base sequence but containing only DNA units, with no 2' substitutions, with phosphorothioate linkage groups between all units in the oligonucleotide, using the methodology provided by Examples 91-95 of EP 1 222 309.

In some embodiments, an oligomer is deemed essentially incapable of recruiting RNaseH if, when provided with the complementary RNA target, and RNaseH, the RNaseH initial rate, as measured in pmol/1/min, is less than 1%, such as less than 5%, such as less than 10% or less than 20% of the initial rate determined using the equivalent DNA only oligonucleotide, with no 2' substitutions, with phosphorothioate linkage groups between all nucleotides in the oligonucleotide, using the methodology provided by Examples 91-95 of EP 1 222 309.

In other embodiments, an oligomer is deemed capable of recruiting RNaseH if, when provided with the complementary RNA target, and RNaseH, the RNaseH initial rate, as measured in pmol/1/min, is at least 20%, such as at least 40%, such as at least 60%, such as at least 80% of the initial rate determined using the equivalent DNA only oligonucleotide, with no 2' substitutions, with phosphorothioate linkage groups between all nucleotides in the oligonucleotide, using the methodology provided by Examples 91-95 of EP 1 222 309.

Typically the region of the oligomer or oligomer conjugate of the invention which forms the consecutive nucleotide units which, when formed in a duplex with the complementary target RNA is capable of recruiting RNase consists of nucleotide units which form a DNA/RNA like duplex with the RNA target—and include both DNA units and LNA units which are in the alpha-L configuration, particularly preferred being alpha-L-oxy LNA.

The oligomer or oligomer conjugate of the invention may comprise a nucleotide sequence which comprises both nucleotides and nucleotide analogues, and may be in the form of a gapmer, a headmer or a mixmer.

In some embodiments, in addition to enhancing affinity of the oligomer for the target region, some nucleoside analogues also mediate RNase (e.g., RNaseH) binding and cleavage. Since α-L-LNA units recruit RNaseH activity to a certain extent, in some embodiments, gap regions (e.g., region X as referred to herein) of oligomers containing α-L-LNA units consist of fewer units recognizable and cleavable by the RNaseH, and more flexibility in the mixmer construction is introduced.

Synthesis

The present invention provides a method of manufacturing an oligomer conjugate, comprising conjugating at least one oligomer to a carrier component, wherein said oligomer conjugate is suitable for treating a viral disorder.

The present invention also provides a method of manufacturing a polyoligomer conjugate as described herein, comprising attaching one or more oligomers to a linker group (E or L) or a symmetrical brancher region F which is then attached to a carrier component as described herein, wherein said oligomer conjugate is suitable for treating a viral disorder.

In some embodiments the symmetrical brancher region is either 1,3-pentylamidopropyl (from 1,3-bis-[5-(4,4'-dimethoxytrityloxy)pentylamido]propyl-2-[(2-cyanoethyl)-(N, N-diisopropyl)]-phosphoramidite), tris-2,2,2-(propyloxymethyl)ethyl (from tris-2,2,2-[3-(4,4'-dimethoxytrityloxy)propyloxymethyl]ethyl-[(2-cyanoethyl)-(N,N-diisopropyl)]-phosphoramidite) or tris-2,2,2-(propyloxymethyl)methyleneoxypropyl (from tris-2,2,2-[3-(4,4'-dimethoxytrityloxy) propyloxymethyl]methyleneoxypropyl-[(2-cyanoethyl)-(N, N-diisopropyl)]-phosphoramidite). In some embodiments the asymmetrical brancher region is 1,3-pentylamidopropyl (from 1-[5-(4,4'-dimethoxytrityloxy)pentylamido]-3-[5-fluorenomethoxycarbonyloxypentylamido]-propyl-2-[(2-cyanoethyl)-(N,N-diisopropyl)]-phosphoramidite), Glen Reseach, USA provides such suitable branchers (e.g. catalog number 0-1920, 10-1922 and 10-1925).

Linker groups and brancher regions as described herein may be cleavable or non-cleavable.

In a further aspect a method is provided for manufacturing the composition of the invention, comprising mixing the oligomer conjugate of the invention with a pharmaceutically acceptable diluent, solvent, carrier, salt and/or adjuvant.

Activated Oligomers

The term "activated oligomer," as used herein, refers to an oligomer of the invention that is covalently linked (i.e., functionalized) to at least one functional moiety that permits covalent linkage of the oligomer to one or more conjugated moieties, i.e., moieties that are not themselves nucleic acids or units, to form the conjugates herein described. Typically, a functional moiety will comprise a chemical group that is capable of covalently bonding to the oligomer via, e.g., a 3'-hydroxyl group or the exocyclic $NH_2$ group of the adenine base, a spacer that is preferably hydrophilic and a terminal group that is capable of binding to a conjugated moiety (e.g., an amino, sulfhydryl or hydroxyl group). In some embodiments, this terminal group is not protected, e.g., is an $NH_2$ group. In other embodiments, the terminal group is protected, for example, by any suitable protecting group such as those described in "Protective Groups in Organic Synthesis" by Theodora W Greene and Peter G M Wuts, 3rd edition (John Wiley & Sons, 1999). Examples of suitable hydroxyl protecting groups include esters such as acetate ester, aralkyl groups such as benzyl, diphenylmethyl, or triphenylmethyl, and tetrahydropyranyl. Examples of suitable amino protecting groups include benzyl, alpha-methylbenzyl, diphenylmethyl, triphenylmethyl, benzyloxycarbonyl, tert-butoxycarbonyl, and acyl groups such as trichloroacetyl or trifluoroacetyl. In some embodiments, the functional moiety is self-cleaving. In other embodiments, the functional moiety is biodegradable. See e.g., U.S. Pat. No. 7,087,229, which is incorporated by reference herein in its entirety.

In some embodiments, oligomers of the invention are functionalized at the 5' end in order to allow covalent attachment of the conjugated moiety to the 5' end of the oligomer. In other embodiments, oligomers of the invention can be functionalized at the 3' end. In still other embodiments, oligomers of the invention can be functionalized along the backbone or on the heterocyclic base moiety. In yet other embodiments, oligomers of the invention can be functionalized at more than one position independently selected from the 5' end, the 3' end, the backbone and the base.

In some embodiments, activated oligomers of the invention are synthesized by incorporating during the synthesis one or more units that is covalently attached to a functional moiety. In other embodiments, activated oligomers of the invention are synthesized with units that have not been functionalized, and the oligomer is functionalized upon completion of synthesis. In some embodiments, the oligomers are functionalized with a hindered ester containing an aminoalkyl linker, wherein the alkyl portion has the formula $(CH_2)w$, wherein w is an integer ranging from 1 to 10, preferably about 6, wherein the alkyl portion of the alkylamino group can be straight chain or branched chain, and wherein the functional group is attached to the oligomer via an ester group (—O—C(O)—$(CH_2)$wNH).

In other embodiments, the oligomers are functionalized with a hindered ester containing a $(CH_2)_w$-sulfhydryl (SH) linker, wherein w is an integer ranging from 1 to 10, preferably about 6, wherein the alkyl portion of the alkylamino group can be straight chain or branched chain, and wherein the functional group attached to the oligomer via an ester group (—O—C(O)—$(CH_2)$wSH). In some embodiments, sulfhydryl-activated oligonucleotides are conjugated with polymer moieties such as polyethylene glycol or peptides (via formation of a disulfide bond).

Activated oligomers containing hindered esters as described above can be synthesized by any method known in the art, and in particular by methods disclosed in PCT Publication No. WO 2008/034122 and the examples therein, which is incorporated herein by reference in its entirety.

In still other embodiments, the oligomers of the invention are functionalized by introducing sulfhydryl, amino or hydroxyl groups into the oligomer by means of a functionalizing reagent substantially as described in U.S. Pat. Nos. 4,962,029 and 4,914,210, i.e., a substantially linear reagent having a phosphoramidite at one end linked through a hydrophilic spacer chain to the opposing end which comprises a protected or unprotected sulfhydryl, amino or hydroxyl group. Such reagents primarily react with hydroxyl groups of the oligomer. In some embodiments, such activated oligomers have a functionalizing reagent coupled to a 5'-hydroxyl group of the oligomer. In other embodiments, the activated oligomers have a functionalizing reagent coupled to a 3'-hydroxyl group. In still other embodiments, the activated oligomers of the invention have a functionalizing reagent coupled to a hydroxyl group on the backbone of the oligomer. In yet further embodiments, the oligomer of the invention is functionalized with more than one of the functionalizing reagents as described in U.S. Pat. Nos. 4,962,029 and 4,914,210, incorporated herein by reference in their entirety. Methods of synthesizing such functionalizing reagents and incorporating them into units or oligomers are disclosed in U.S. Pat. Nos. 4,962,029 and 4,914,210.

In some embodiments, the 5'-terminus of a solid-phase bound oligomer is functionalized with a dienyl phosphoramidite derivative, followed by conjugation of the deprotected oligomer with, e.g., an amino acid or peptide via a Diels-Alder cycloaddition reaction.

In various embodiments, the incorporation of units containing 2'-sugar modifications, such as a 2'-carbamate substituted sugar or a 2'-(O-pentyl-N-phthalimido)-deoxyribose sugar into the oligomer facilitates covalent attachment of conjugated moieties to the sugars of the oligomer. In other embodiments, an oligomer with an amino-containing linker at the 2'-position of one or more units is prepared using a reagent such as, for example, 5'-dimethoxytrityl-2'-O-(e-phthalimidylaminopentyl)-2'-deoxyadenosine-3'-N,N-diisopropyl-cyanoethoxy phosphoramidite (see, e.g., Manoharan, et al., Tetrahedron Letters, 1991, 34, 7171.)

In still further embodiments, the oligomers of the invention may have amine-containing functional moieties on the nucleobase, including on the N6 purine amino groups, on the exocyclic N2 of guanine, or on the N4 or 5 positions of cytosine. In various embodiments, such functionalization may be achieved by using a commercial reagent that is already functionalized in the oligomer synthesis.

Some functional moieties are commercially available, for example, heterobifunctional and homobifunctional linking moieties are available from the Pierce Co. (Rockford, Ill.). Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, and 3'-Amino-Modifier is also available from Clontech Laboratories Inc. (Palo Alto, Calif.).

Polyoligomers

As indicated above, in some embodiments of the present invention, the oligomer or the oligomer component of the oligomer conjugate may comprise or be part of a molecule that has two targeting sequences. In some instances, these molecules are called polyoligomers.

In some embodiments, the oligomer conjugate has or comprises the structure:

Carrier component-L1-First Oligomer Region-L2-Second Oligomer Region
  wherein L1 is an optional linker or brancher region or tether molecule or bridging moiety
  wherein L2 is an optional linker or brancher region or tether molecule or bridging moiety
  wherein L1 and L2 can be the same or different; or wherein said oligomer conjugate has or comprises the structure:

First Oligomer Region-L2-Second Oligomer Region-L3-Carrier component
  wherein L2 is an optional linker or brancher region or tether molecule or bridging moiety
  wherein L3 is an optional linker or brancher region or tether molecule or bridging moiety
  wherein L2 and L3 can be the same or different different; or wherein said oligomer conjugate has or comprises the structure:

Carrier component 1-L1-First Oligomer Region-L2-Second Oligomer Region-L3-Carrier component 2
  wherein L1 is an optional linker or brancher region or tether molecule or bridging moiety
  wherein L2 is an optional linker or brancher region or tether molecule or bridging moiety
  wherein L3 is an optional linker or brancher region or tether molecule or bridging moiety
  wherein L1, L2 and L3 can be the same or different
  wherein Carrier component 1 and Carrier component 2 can be the same or different; or wherein said oligomer conjugate has or comprises the structure:

First Oligomer Region-L1-Carrier component 1-L2-Second Oligomer Region wherein L1 is an optional linker or brancher region or tether molecule or bridging moiety
  wherein L2 is an optional linker or brancher region or tether molecule or bridging moiety
  wherein L1 and L2 and L3 can be the same or different; or wherein said oligomer conjugate has or comprises the structure:

First Oligomer Region-L1-Carrier component 1-L2-Second Oligomer Region-L3-Carrier component 2
  wherein L1 is an optional linker or brancher region or tether molecule or bridging moiety
  wherein L2 is an optional linker or brancher region or tether molecule or bridging moiety
  wherein L3 is an optional linker or brancher region or tether molecule or bridging moiety
  wherein L1 and L2 can be the same or different
  wherein Carrier component 1 and Carrier component 2 can be the same or different; or wherein said oligomer conjugate has or comprises the structure:

Carrier component 1-L1-First Oligomer Region-L2-Carrier component 2-L3-Second Oligomer Region-L4-Carrier component 3
  wherein L1 is an optional linker or brancher region or tether molecule or bridging moiety
  wherein L2 is an optional linker or brancher region or tether molecule or bridging moiety
  wherein L3 is an optional linker or brancher region or tether molecule or bridging moiety
  wherein L1, L2 and L3 can be the same or different
  wherein Carrier component 1, Carrier Component 2 and Carrier component 3 can be the same or different.

In some embodiments, preferably the oligomer conjugate for the use according to the present invention wherein said oligomer conjugate has or comprises the structure:

Carrier component-L1-First Oligomer Region-L2-Second Oligomer Region
  wherein L1 is an optional linker or brancher region or tether molecule or bridging moiety
  wherein L2 is an optional linker or brancher region or tether molecule or bridging moiety
  wherein L1 and L2 can be the same or different.

In some embodiments, the Linker 1 is present.
In some embodiments, the Linker 2 is present.
In some embodiments, the Linker 3 is present.
In some embodiments, the carrier component is linked, preferably conjugated, to said first oligomer region.
In some embodiments, the carrier component is linked, preferably conjugated, to the 5' end of said oligomer.
In some embodiments, each of the first oligomer region and the second oligomer regions is linked, preferably conjugated, by means of a linker or brancher region.
In some embodiments, each of the first oligomer region and the second oligomer regions is linked, preferably conjugated, by means of a physiologically labile linker group or a physiologically labile brancher region.

In some embodiments, the invention provides for a poly-oligomeric compound which may comprise a first region (region PA), a second region (region PB) and a third region (region PC), wherein the first region is covalently linked to at least one further oligomeric compound (region PA'), wherein the first region (region PA) and region PA' are covalently linked via a biocleavable linker (region PB'), which may be, by way of example, as according to the second region as disclosed here, for example a region of at least one phosphodiester linked DNA or RNA (such as DNA), such as two, three, four or five phosphodiester linked DNA or RNA nucleosides (such as DNA nucleosides). Regions PB and PB' may, in some embodiments have the same structure, e.g. the same number of DNA/RNA nucleosides and phosphodiester linkages and/or the same nucleobase sequence. In other embodiments Regions PB and PB' may be different. By way of example such poly oligomeric compounds may have a structure such as: (5'-3' or 3' 5') Conjugate/Carrier Compound-PO—ON—PO'—ON', wherein conjugate/carrier compound is region PC, PO is region PB, PO' is region PB', and ON is region PA, and ON' is region PA'.

It should be understood that region PA' may, in some embodiments, comprise multiple further oligomeric compounds (such as a further 2 or 3 oligomeric compounds) linked in series (or in parallel) via biocleavable linkers, for example: Conjugate/Carrier Compound-PO—ON—PO—ON'-PO"-ON", or Conjugate/Carrier Compound-PO—ON—[PO—ON']n, wherein n may, for example be 1, 2 or 3, and each ON' may be the same or different, and if different may have the same or different targets.

In an aspect, the present invention employs poly-oligomeric compounds (also referred herein as oligomer compounds) for use in modulating, such as inhibiting a target nucleic acid in a cell, for example HBV HBx or HBsAg. The oligomer compound comprises at least two oligomer regions, e.g. (PA and PA') and may comprise further oligomer regions (e.g. PA"). At least one oligomer region is an oligomer which is capable of modulating a target sequence in HBx or HBsAg of HBV, for example an oligomer as provided by the present invention. In certain embodiments, each of PA, PA' (and PA" if present) may be an oligomer which is capable of modulating a target sequence in HBx or HBsAg of HBV, for example an oligomer as provided by the present invention. PA and PA' may be complements to different positions in the target sequence.

In some embodiments, PA may be an oligomer which is capable of modulating a target sequence in HBx and PA' (and/or PA" if present) may be oligomers which are capable of modulating a different target sequence. In certain embodiments, PA' (and/or PA" if present) may be capable of modulating a target sequence in HBsAg of HBV. For example PA' (and/or PA" if present) may be an oligomer capable of modulating a target sequence in HBsAg of HBV, as described herein.

In some embodiments, PA' may be an oligomer which is capable of modulating a target sequence in HBx and PA (and/or PA" if present) may be oligomers which are capable of modulating a different target sequence from HBV. In certain embodiments, PA (and/or PA" if present) may be capable of modulating a target sequence in HBsAg of HBV. For example PA (and/or PA" if present) may be an oligomer capable of modulating a target sequence in HBsAg of HBV, as described herein.

Each oligomer region may be flanked by a bio-cleavabe region (region PB), which may, for example, be a further region of 1-10 contiguous nucleotides (region PB), which comprise at least one phosphodiester linkage. Other physiological labile nucleoside regions may be used.

In some embodiments, the oligomer compounds of the invention are covalently linked to a conjugate group, a targeting group, a reactive group, an activation group, or a blocking group, optionally, via a short region comprising (e.g. 1-10) of phosphodiester linked DNA or RNA nucleoside(s). Examples of such groups are the carrier components and conjugate components mentioned herein.

In some embodiments, the compound of the invention does not comprise RNA (units). In some embodiments, the compound according to the invention forms a single contiguous sequence), optionally linked to a function group, such as a conjugate group, and is such a linear molecule or is synthesized as a linear molecule. The oligomeric compound may therefore be single stranded molecule. In some embodiments, the oligomer does not comprise short regions of, for example, at least 3, 4 or 5 contiguous nucleotides, which are complementary to equivalent regions within the same oligomeric compound (i.e. duplexes). The oligomer, in some embodiments, may be not (essentially) double stranded. In some embodiments, the oligomer is essentially not double stranded, such as is not a siRNA.

Oligomer regions PA, PA' and if present PA" are phosphorothioate oligomers, i.e. at least 70% of the internucleoside linkages within each oligomer region PA, PA' and if present PA", are phosphorothioate linkages, such as at least 80% or at least 90% or all of the internucleoside linkages if present oligomer regions PA, PA' and PA" (if present), are phosphorothioate.

In some embodiments, oligomer regions PA, PA' and if present PA" may form a single contiguous oligonucleotide sequence. Regions PA, PA' and PA" are interspaced by regions PB, for example regions of 1, 2, 3, 4, or 5 phosphodiester linked DNA nucleosides.

When region PB comprises only 1 nucleoside, at least one, or both of the internucleoside linkages between the region PB nucleoside (e.g. a DNA nucleoside) may be phosphodiester linkages. When region PB comprises only 2 or more nucleosides, the internucleoside linkages between the region PB nucleoside (e.g. the DNA nucleosides) may be phosphodiester linkages and/or may be another internucleoside linkage, such as phosphorothioate linkages.

The oligomers of the invention, such as PA, PA' and if present PA", do not form part of a siRNA complex. The oligomers of the invention, such as PA, PA' and if present PA", are non-complementary, e.g. they do not hybridize to one another to form a region of more than 8 or in some embodiments more than 6 contiguous base pairs. In some embodiments, regions PA and PA" do not hybridize to one another to form a region of more than 4 contiguous base pairs. Exemplary base pairs may be between A-T, G-C or A-U. In the case there are three oligomer regions, PA, PA' and PA", the non-complementarity is between PA and PA', and PA' and PA", as well as PA and PA".

The oligomer regions PA, PA' and if present PA" are not in the form of a duplex with a (substantially) complementary oligonucleotide—e.g. is not an siRNA.

In some embodiments, oligomer regions PA, PA' and PA" share the same contiguous nucleotide sequence. In some embodiments, oligomer regions PA and PA' share the same contiguous nucleotide sequence. In this respect the invention provides for a single compound which can be used to deliver multiple copies of an oligomer (i.e. with the same contiguous nucleobase sequence and optionally the same chemical modifications) to the target tissue.

The oligomer regions (PA, PA' and if present PA") are linked via at least one biocleavable region, referred to as region PB herein (and where there is more than one region PB, region PB' and region PB"). In some embodiments, region PB comprises 1-10 nucleosides which form a physiologically labile region between oligomer regions, or between an (or each) oligomer region and a linking group. Regions of DNA phosphodiester nucleosides may be used, but other nucleotide regions may be used if they are suitably physiologically labile.

In some embodiments, the internucleoside linkage between the oligomer region (PA, PA' or if present PA") and (each) second region PB, is a phosphodiester linked to the first (or only) DNA or RNA nucleoside of region PB comprises at least one phosphodiester linked DNA or RNA nucleoside.

The region PB may, in some embodiments, comprise further DNA or RNA nucleosides which may be phosphodiester linked.

As explained herein, region PB may also be used to join a functional group to the oligomeric region(s), optionally via a further linkage group (PY). The use of region PB as a cleavable linker to join functional groups to oligomer is described in detail in PCT/EP2013/073858, which is hereby incorporated by reference.

In some embodiments a region PB is further covalently linked to a third region which may, for example, be a conjugate, a targeting group a reactive group, and/or a blocking group (PC).

Group (PC) may be a carrier component as described herein.

In some aspects, the present invention is based upon the provision of a physiologically labile region, the second region, linking the first region, e.g. an antisense oligonucleotide, and a conjugate or functional group, e.g. carrier component. The physiologically labile region may comprises at least one phosphodiester linked nucleoside, such as a DNA or RNA nucleoside, such as 1, 2, 3, 4, 5, 6, 7, 8, 9 or 10 phosphodiester linked nucleosides, such as DNA or RNA.

In some embodiments, the oligomeric compound comprises a cleavable (physiologically labile) linker. In this respect the cleavable linker is preferably present in region PB (or in some embodiments, between region PA and PB).

In some embodiments, one (or more or all) region PB may comprise or consists of at least one DNA or RNA nucleosides linked to the first region via a phosphodiester linkage. In some aspects, the internucleoside linkage between an oligomer region and second region is considered as part of region PB.

In some embodiments, a (or more or each) region PB comprises or consists of at least between 1 and 10 linked nucleosides, such as 1, 2, 3, 4, 5, 6, 7, 8, 9 or 10 linked DNA or RNA nucleotides. Whilst a region of DNA/RNA phosphodiester is considered important in the provision of a cleavable linker, it is possible that region PB also comprises sugar-modified nucleoside analogues, such as those referred to under the first region above. However in some embodiments, the nucleosides of region PB are (optionally independently) selected from the group consisting of DNA and RNA. In some embodiments, the nucleosides of region PB are (optionally independently) DNA. It will be recognized that the nucleosides of region PB may comprise naturally occurring or non-naturally occurring nucleobases. Typically, region PB comprises at least one phosphodiester linked DNA or RNA nucleoside (which may, in some embodiments. be the first nucleoside adjacent to an oligomer). If region PB comprises other nucleosides, region PB may also comprise of other nucleoside linkages other than phosphodiester, such as (optionally independently) phosphorothioate, phosphodithioate, boranophosphate or methyl phosphonate. However, in other exemplified embodiments, all the internucleoside linkages in region PB are phosphorothioate. In some embodiments, all the nucleosides of region PB comprise (optionally independently) either a 2'-OH ribose sugar (RNA) or a 2'-H sugar—i.e. RNA or DNA. Between 1-5, or 1-4, such as 2, 3, 4 phosphate (phosphodiester) linked DNA nucleosides have been shown to be particularly useful in the compounds of the invention.

In some embodiments, the second region comprises or consists of at least between 1 and 10 (e.g. phosphodiester) linked DNA or RNA nucleosides, such as 1, 2, 3, 4, 5, 6, 7, 8, 9 or 10 (e.g. phosphodiester) linked DNA or RNA nucleotides.

In some embodiments, region PB comprises no more than 3 or no more than 4 consecutive DNA or RNA nucleosides (such as DNA nucleosides). As such region PB may be so short as it does not recruit RNAseH, an aspect which may be important in embodiments when region PB does not form a part of a single contiguous nucleobase sequence which is complementary to the target. Shorter region PBs, e.g. of 1-4 nts in length may also be preferable in some embodiments, as they are unlikely to be the target of sequence specific restriction enzymes. As such it is possible to vary the susceptibility of the region PB to endonuclease cleavage, and thereby fine-tune the rate of activation of the active oligomer in vivo, or even intra-cellular. Suitably, if very rapid activation is required, longer region PBs may be employed and/or region Bs which comprise the recognition sites of (e.g. cell or tissue specific or differentially expressed) restriction enzymes.

In some embodiments, a region PB may be conjugated to a functional group (PC), such as a conjugate, targeting reactive group, an activation group, or blocking group, optionally via a linker group (PY such as those provided herein). Functional groups may also be joined to an oligomer region, or the compound of the invention via other means, e.g. via phosphate nucleoside linkage (e.g. phosphodiester, phosphorothioate, phosphodithioate, boranophosphate or methylphosphonate) or a triazol group. In some aspects, the linkage group is the same as the region PB between at least two of the oligomer regions, and as such may be a phosphodiester linkage.

In some embodiments the DNA or RNA nucleotides of an (or more or each) region PB are independently selected from DNA and RNA nucleotides. In some embodiments the DNA or RNA nucleotides of an (or more or each) region PB are DNA nucleotides. In some embodiments the DNA or RNA nucleotides of an (or more or each) region PB are RNA nucleotides.

In the context of the second region, the term DNA and RNA nucleoside may comprise a naturally occurring or non-naturally occurring base (also referred to as a base analogue or modified base).

It will be recognized that, in some embodiments, an (or more or each) region PB may further comprise other nucleotides or nucleotide analogues. In some embodiments, (or more or each) region PB comprises only DNA or RNA nucleosides. In some embodiments, an (or more or each) region PB comprises more than one nucleoside, the internucleoside linkages in an or each region PB comprise phosphodiester linkages. In some embodiments, when an (or more or each) region PB comprises more than one nucleoside, all the internucleoside linkages in the second region comprise phosphodiester linkages.

In some embodiments, at least two consecutive nucleosides of an (or more or each) region PB are DNA nucleosides (such as at least 3 or 4 or 5 consecutive DNA nucleotides). In some embodiments the at least two consecutive nucleosides an (or more or each) region PB are RNA nucleosides (such as at least 3 or 4 or 5 consecutive RNA nucleotides). In some embodiments the at least two consecutive nucleosides of the (or more or each) region PB are at least one DNA and at least one RNA nucleoside. The internucleoside linkage between a region PA and region PB may be a phosphodiester linkage. In some embodiments, when region PB comprises more than one nucleoside, at least one further internucleoside linkage is phosphodiester—such as the linkage group(s) between the 2 (or 3 or 4 or 5) nucleosides adjacent to a region PA.

A region PB may be flanked on at least one side (either 5' or 3') by the first region, e.g. an antisense oligonucleotide, and on the other side (either 3' or 5' respectfully, via a further oligomer region (PA'), or a conjugate moiety or similar group (e.g. a blocking moiety/group, a targeting moiety/group or therapeutic small molecule moiety), optionally via a linker group (i.e. between the second region and the conjugate/blocking group etc. moiety).

In some embodiments, region PB does not form a complementary sequence when the oligomer region (e.g. PA, PA' and/or PA") and PB is aligned to the complementary target sequence.

In some embodiments, region PB does form a complementary sequence when the oligomer region (e.g. PA, PA' and/or PA") and PB is aligned to the complementary target sequence. In this respect region PA and PB together may form a single contiguous sequence which is complementary to the target sequence.

In some embodiments, the sequence of bases in region PB is selected to provide an optimal endonuclease cleavage site, based upon the predominant endonuclease cleavage enzymes present in the target tissue or cell or sub-cellular compartment. In this respect, by isolating cell extracts from target tissues and non-target tissues, endonuclease cleavage sequences for use in region PB may be selected based upon a preferential cleavage activity in the desired target cell (e.g. liver/hepatocytes) as compared to a non-target cell (e.g. kidney). In this respect, the potency of the compound for target down-regulation may be optimized for the desired tissue/cell.

In some embodiments region PB comprises a dinucleotide of sequence AA, AT, AC, AG, TA, TT, TC, TG, CA, CT, CC, CG, GA, GT, GC, or GG, wherein C may be 5-mthylcytosine, and/or T may be replaced with U.

In some embodiments region PB comprises a trinucleotide of sequence AAA, AAT, AAC, AAG, ATA, ATT, ATC, ATG, ACA, ACT, ACC, ACG, AGA, AGT, AGC, AGG, TAA, TAT, TAC, TAG, TTA, TTT, TTC, TAG, TCA, TCT, TCC, TCG, TGA, TGT, TGC, TGG, CAA, CAT, CAC, CAG, CTA, CTG, CTC, CTT, CCA, CCT, CCC, CCG, CGA, CGT, CGC, CGG, GAA, GAT, GAC, CAG, GTA, GTT, GTC, GTG, GCA, GCT, GCC, GCG, GGA, GGT, GGC, and GGG wherein C may be 5-mthylcytosine and/or T may be replaced with U.

In some embodiments region PB comprises a trinucleotide of sequence AAAX, AATX, AACX, AAGX, ATAX, ATTX, ATCX, ATGX, ACAX, ACTX, ACCX, ACGX, AGAX, AGTX, AGCX, AGGX, TAAX, TATX, TACX, TAGX, TTAX, TTTX, TTCX, TAGX, TCAX, TCTX, TCCX, TCGX, TGAX, TGTX, TGCX, TGGX, CAAX, CATX, CACX, CAGX, CTAX, CTGX, CTCX, CTTX, CCAX, CCTX, CCCX, CCGX, CGAX, CGTX, CGCX, CGGX, GAAX, GATX, GACX, CAGX, GTAX, GTTX, GTCX, GTGX, GCAX, GCTX, GCCX, GCGX, GGAX, GGTX, GGCX, and GGGX, wherein X may be selected from the group consisting of A, T, U, G, C and analogues thereof, wherein C may be 5-mthylcytosine and/or T may be replaced with U. It will be recognized that when referring to (naturally occurring) nucleobases A, T, U, G, C, these may be substituted with nucleobase analogues which function as the equivalent natural nucleobase (e.g. base pair with the complementary nucleoside).

In some embodiments, the compound of the invention may comprise more than one conjugate group (or more than one functional group PX—such as a conjugate, targeting, blocking or activated group or a reactive or activation group), such as 2 or 3 such groups. In some embodiments, region PB is covalently linked, optionally via a [e.g. non-nucleotide] linker group), to at least one functional group, such as two or three functional groups. In some embodiments, the first region (PA) may be covalently linked (e.g. via internucleoside linkages, such as phosphodiester linkages), to two region PBs, for example, one 5' and one 3' to the first region PA, wherein each region PB may be (optionally independently) selected from the region PB described herein.

Composition

Oligomers of the invention and oligomer conjugates of the invention may be used in pharmaceutical formulations and compositions. Suitably, such compositions comprise a pharmaceutically acceptable diluent, carrier, salt or adjuvant. WO 2007/03109 provides suitable and preferred pharmaceutically acceptable diluent, carrier and adjuvants—which are hereby incorporated by reference. Suitable dosages, formulations, administration routes, compositions, dosage forms, combinations with other therapeutic agents, pro-drug formulations are also provided in WO 2007/03109—which are also hereby incorporated by reference.

Pharmaceutical compositions of the invention may include a pharmaceutically acceptable carrier that may contain a variety of components that provide a variety of functions, including regulation of drug concentration, regulation of solubility, chemical stabilization, regulation of viscosity, absorption enhancement, regulation of pH, and the like.

The pharmaceutical carrier may comprise a suitable liquid vehicle or excipient and an optional auxiliary additive or additives. The liquid vehicles and excipients are conventional and commercially available. Illustrative thereof are distilled water, physiological saline, aqueous solutions of dextrose, and the like. For water soluble formulations, the pharmaceutical composition preferably includes a buffer such as a phosphate buffer, or other organic acid salt, preferably at a pH in the range of 6.5 to 8. For formulations containing weakly soluble antisense compounds, microemulsions may be employed, for example by using a non-ionic surfactant such as polysorbate 80 in an amount of 0.04-0.05% (w/v), to increase solubility. Other components may include antioxidants, such as ascorbic acid, hydrophilic polymers, such as, monosaccharides, disaccharides, and other carbohydrates including cellulose or its derivatives, dextrins, chelating agents, such as EDTA, and like components well known to those in the pharmaceutical sciences, e.g., *Remington's Pharmaceutical Science*, latest edition (Mack Publishing Company, Easton, Pa.).

Oligonucleotides of the invention include the pharmaceutically acceptable salts thereof, including those of alkaline earth salts, e.g., sodium or magnesium, ammonium or $NX_4^+$, wherein X is $C_1$-$C_4$ alkyl. Other pharmaceutically acceptable salts include organic carboxylic acids such as formic, acetic, lactic, tartaric, malic, isethionic, lactobionic, and succinic acids; organic sulfonic acids such as methanesulfonic, ethanesulfonic, toluenesulfonic acid and benzenesulfonic; and inorganic acids such as hydrochloric, sulfuric, phosphoric, and sulfamic acids. Pharmaceutically acceptable salts of a compound having a hydroxyl group include the anion of such compound with a suitable cation such as $Na^+$, $NH_4^+$, or the like.

The patient should receive a sufficient daily dosage of oligonucleotide to achieve an effective yet safe intercellular concentrations of combined oligonucleotides. Those skilled in the art should be readily able to derive appropriate dosages and schedules of administration to suit the specific circumstance and needs of the patient.

The effectiveness of the treatment may be assessed by routine methods, which are used for determining whether or not remission has occurred. Such methods generally depend upon morphological, cytochemical, cytogenetic, immunologic and molecular analyses. In addition, remission can be assessed genetically by probing the level of expression of one or more relevant genes. The reverse transcriptase polymerase chain reaction (RT-PCR) methodology can be used to detect even very low numbers of mRNA transcript.

Oligonucleotide Delivery Techniques

Oligonucleotides and conjugates of the invention may be preferably administered to a subject orally or topically but may also be administered intravenously by injection. The vehicle is designed accordingly. Alternatively, the oligonucleotide may be administered subcutaneously via controlled release dosage forms or conventional formulation for intravenous injection. A preferred method of administration of oligonucleotides comprises either topical, systemic or regional perfusion, as is appropriate. According to a method of regional perfusion, the afferent and efferent vessels supplying the extremity containing the lesion are isolated and connected to a low-flow perfusion pump in continuity with an oxygenator and a heat exchanger. The iliac vessels may be used for perfusion of the lower extremity. The axillary vessels are cannulated high in the axilla for upper extremity lesions. Oligonucleotide is added to the perfusion circuit, and the perfusion is continued for an appropriate time period, e.g., one hour. Perfusion rates of from about 100 to about 150 ml/minute may be employed for lower extremity lesions, while half that rate should be employed for upper extremity lesions. Systemic heparinization may be used throughout the perfusion, and reversed after the perfusion is complete. This isolation perfusion technique permits administration of higher doses of chemotherapeutic agent than would otherwise be tolerated upon infusion into the arterial or venous systemic circulation.

In a particular embodiment, oligomers and conjugates of the invention are administered systemically or formulated for systemic administration.

For systemic infusion, the oligonucleotides are preferably delivered via a central venous catheter, which is connected to an appropriate continuous infusion device. Indwelling catheters provide long term access to the intravenous circulation for frequent administration of drugs over extended time periods. They are generally surgically inserted into the external cephalic or internal jugular vein under general or local anesthesia. The subclavian vein is another common site of catheterization. The infuser pump may be external, or may form part of an entirely implantable central venous system such as the INFUSAPORT system available from Infusaid Corp., Norwood, Mass. and the PORT-A-CATH system available from Pharmacia Laboratories, Piscataway, N.J. These devices are implanted into a subcutaneous pocket under local anesthesia. A catheter, connected to the pump injection port, is threaded through the subclavian vein to the superior vena cava. The implant contains a supply of oligonucleotide in a reservoir which may be replenished as needed by injection of additional drug from a hypodermic needle through a self-sealing diaphragm in the reservoir. Completely implantable infusers are preferred, as they are generally well accepted by patients because of the convenience, ease of maintenance and cosmetic advantage of such devices.

Oligonucleotides and conjugates of the invention may be introduced by any of the methods described in U.S. Pat. No. 4,740,463, incorporated herein by reference. One technique is in vitro transfection, which can be done by several different methods. One method of transfection involves the addition of DEAE-dextran to increase the uptake of the naked DNA molecules by a recipient cell. See McCutchin, J. H. and Pagano, J. S., *J. Natl. Cancer Inst.* 41, 351-7 (1968). Another method of transfection is the calcium phosphate precipitation technique which depends upon the addition of $Ca^{2+}$ to a phosphate-containing DNA solution. The resulting precipitate apparently includes DNA in association with calcium phosphate crystals. These crystals settle onto a cell monolayer; the resulting apposition of crystals and cell surface appears to lead to uptake of the DNA. A small proportion of the DNA taken up becomes expressed in a transfectant, as well as in its clonal descendants. See Graham, F. L. and van der Eb, A. J., Virology 52, 456-467 (1973) and Virology 54, 536-539 (1973).

Transfection may also be carried out by cationic phospholipid-mediated delivery. In particular, polycationic liposomes can be formed from N-[1-(2,3-di-oleyloxy)propyl]-N,N,N-trimethylammonium chloride (DOT-MA). See Felgner et al., *Proc. Natl. Acad. Sci.*, 84, 7413-7417 (1987) (DNA-transfection); Malone et al., *Proc. Natl. Acad. Sci.*, 86, 6077-6081 (1989) (RNA-transfection).

For systemic or regional in vivo administration, the amount of oligonucleotides may vary depending on the nature and extent of the disease, the particular oligonucleotides utilized, and other factors. The actual dosage administered may take into account the size and weight of the patient, whether the nature of the treatment is prophylactic or therapeutic in nature, the age, health and sex of the patient, the route of administration, whether the treatment is regional or systemic, and other factors.

In addition to administration with conventional pharmaceutical carriers, the antisense oligonucleotides may be administered by a variety of specialized oligonucleotide delivery techniques. Sustained release systems suitable for use with the pharmaceutical compositions of the invention include semi-permeable polymer matrices in the form of films, microcapsules, or the like, which may comprise polylactides; copolymers of L-glutamic acid and gamma-ethyl-L-glutamate, poly(2-hydroxyethyl methacrylate), and like materials, e.g., Rosenberg et al., International application PCT/US92/05305.

The oligonucleotides and conjugates may be encapsulated in liposomes for therapeutic delivery, as described for example in Liposome Technology, Vol. II, Incorporation of Drugs, Proteins, and Genetic Material, CRC Press. The oligonucleotide, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, ionic surfactants such as diacetylphosphate, stearylamine, or phosphatidic acid, and/or other materials of a hydrophobic nature. Also comprised are the novel cationic amphiphiles, termed "molecular umbrellas", that are described in (DeLong et al, *Nucl. Acid. Res.*, 1999, 27(16), 3334-3341).

The embodiments of the present invention may be delivered by means of particulate systems and/or polymers. Particulate systems and polymers for in vitro and in vivo delivery of polynucleotides have been extensively reviewed by Felgner in *Advanced Drug Delivery Reviews* 5, 163-187 (1990). Techniques for direct delivery are also described in Cook S. T. *Antisense Drug Technology, Principles, Strategies, and Applications*, Marcel Dekker, Inc, 2001.

Pro-Drugs

The oligonucleotides may be synthesized as pro-drugs carrying lipophilic groups, such as for example methyl-SATE (S-acetylthioethyl) or t-Bu-SATE (S-pivaloylthioethyl) protecting groups, that confers nuclease resistance to the oligo, improve cellular uptake and selectively deprotects after entry into the cell as described in Vives et al. *Nucl. Acids Res.* 1999, Vol. 27, 4071-4076.

Circular Molecules

The oligonucleotides may be synthesized as circular molecules in which the 5' and 3' ends of the oligonucleotides are covalently linked or held together by an affinity pair one member of which is attached covalently to the 5' end and the other attached covalently to the 3'end. Such circularization protects the oligonucleotide against degradation by exonucleases and may also improve cellular uptake and distribution. In one aspect of the invention the moiety linking the 5' and 3' end of a circular oligonucleotide is cleaved automatically upon entry into any type of human or vertebrate cell thereby linearising the oligonucleotide and enabling it to efficiently hybridize to its target sequence. In another aspect, the moiety linking the 5' and 3'ends of the oligonucleotide is so designed that cleavage preferably occurs only in the particular type of cells that expresses the mRNA that is the target for the antisense oligonucleotide. For instance, a circular antisense oligonucleotide directed against a gene involved in a viral disorder may be brought into action by linearisation only in the subset of cells expressing the gene in question, for example HBV HBx or HBsAg.

Additional Pharmaceutical Entity

Oligomers and oligomer conjugates of the invention may be used as the primary therapeutic for the treatment of the disease state, or may be used in combination with non-oligonucleotide drugs.

Accordingly, the present invention provides a pharmaceutical system comprising a pharmaceutical composition as described herein and an additional pharmaceutical entity. The additional pharmaceutical entity may be any therapeutic agent known in the art. For example, the additional pharmaceutical entity may be an antibody, a small molecule therapeutic, a polynucleotide or gene therapy vector (e.g. a vector capable of expressing therapeutic polypeptides or RNAi agents).

Hence, the oligomer or the oligomer conjugate of the present invention may be used in combination with other actives, such as other anti-viral actives.

By way of example, the oligomer or the oligomer conjugate of the present invention may be used in combination with other actives, such as oligonucleotide-based antivirals—such as sequence specific oligonucleotide-based antivirals—acting either through antisense (including other LNA oligomers), siRNAs (such as ARC520), aptamers, morpholinos or any other antiviral, nucleotide sequence-dependent mode of action.

By way of further example, the oligomer or the oligomer conjugate of the present invention may be used in combination with other actives, such as immune stimulatory antiviral compounds, such as interferon (e.g. pegylated interferon alpha), TLR7 agonists (e.g. GS-9620), or therapeutic vaccines.

By way of further example, the oligomer or the oligomer conjugate of the present invention may be used in combination with other actives, such as small molecules, with antiviral activity. These other actives could be, for example, nucleoside/nucleotide inhibitors (eg entecavir or tenofovir disoproxil fumarate), encapsidation inhibitors, entry inhibitors (eg Myrcludex B).

In certain embodiments, the additional therapeutic agent may be an HBV agent, an Hepatitis C virus (HCV) agent, a chemotherapeutic agent, an antibiotic, an analgesic, a non-steroidal anti-inflammatory (NSAID) agent, an antifungal agent, an antiparasitic agent, an anti-nausea agent, an anti-diarrheal agent, or an immunosuppressant agent.

In particular related embodiments, the additional HBV agent may be interferon alpha-2b, interferon alpha-2a, and interferon alphacon-1 (pegylated and unpegylated), ribavirin; an HBV RNA replication inhibitor; a second antisense oligomer; an HBV therapeutic vaccine; an HBV prophylactic vaccine; lamivudine (3TC); entecavir (ETV); tenofovir diisoproxil fumarate (TDF); telbivudine (LdT); adefovir; or an HBV antibody therapy (monoclonal or polyclonal).

In other particular related embodiments, the additional HCV agent may be interferon alpha-2b, interferon alpha-2a, and interferon alphacon-1 (pegylated and unpegylated); ribavirin; an HCV RNA replication inhibitor (e.g., ViroPharma's VP50406 series); an HCV antisense agent; an HCV therapeutic vaccine; an HCV protease inhibitor; an HCV helicase inhibitor; or an HCV monoclonal or polyclonal antibody therapy.

The additional pharmaceutical entity may be an oligomer or oligomer conjugate as defined herein.

In certain embodiments the pharmaceutical system may comprise at least one, at least two, at least three, up to a plurality of oligomers or oligomer conjugates provided by the present invention.

In certain embodiments the additional pharmaceutical entity may an oligomer or oligomer conjugate capable of modulating a target sequence in HBV. The oligomers or conjugates may each be capable of modulating a target sequence in HBV HBx or HBsAg. The oligomers or conjugates may be capable of modulating a target sequence in HBV which is not within HBx or HBsAg. For example, at least one oligomer or conjugate may be capable of modulating a target sequence within the HBV gene or mRNA for HBcAg, HBeAg, or DNA polymerase.

In certain embodiments, the oligomer, or additional oligomer, or conjugate, or additional conjugate, may be capable of modulating a target sequence in the HBV gene or mRNA for HBsAg.

When a combination of oligonucleotides targeting different target sequences are employed, the ratio of the amounts of the different types of oligonucleotide may vary over a broad range.

According to one preferred embodiment of the invention, the oligonucleotides of all types are present in approximately equal amounts, by molarity.

Administration and Dosage

The present invention also relates pharmaceutical compositions that contain a therapeutically effective amount of a conjugate of the invention. The composition can be formulated for use in a variety of drug delivery systems. One or more physiologically acceptable excipients or carriers can also be included in the composition for proper formulation. Suitable formulations for use in the present invention are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

The pharmaceutical compositions of the present invention are intended for parenteral, intranasal, topical, oral, or local administration, such as by a transdermal means, for prophylactic and/or therapeutic treatment. The pharmaceutical compositions can be administered parenterally (e.g., by intravenous, intramuscular, or subcutaneous injection), or by oral ingestion, or by topical application or intraarticular injection. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Sustained release administration is also specifically included in the invention, by such means as depot injections or erodible implants or components. Thus, the invention provides compositions for parenteral administration that comprise the above mention agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Furthermore, this invention provides compositions for local administration, which may contain inert ingredients such as solvents or emulsifiers for the formulation of a cream, an ointment, and the like.

In a particular embodiment, oligomers and conjugates of the invention are administered subcutaneously or formulated for subcutaneous administration.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration.

The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

The compositions containing an effective amount can be administered for prophylactic or therapeutic treatments. In prophylactic applications, compositions can be administered to a subject with a clinically determined predisposition or increased susceptibility to development of a tumor or cancer, neurodegenerative disease, or lysosomal disorder. Compositions of the invention can be administered to the patient (e.g., a human) in an amount sufficient to delay, reduce, or preferably prevent the onset of clinical disease or tumorigenesis. In therapeutic applications, compositions are administered to a subject (e.g., a human) already suffering from disease (e.g., a cancer, neurodegenerative disease, or lysosomal storage disorder) in an amount sufficient to cure or at least partially arrest the symptoms of the condition and its complications. An amount adequate to accomplish this purpose is defined as a "therapeutically effective dose," an amount of a compound sufficient to substantially improve some symptom associated with a disease or a medical condition. For example, in the treatment of cancer, neurodegenerative disease, or lysosomal storage disease, an agent or compound which decreases, prevents, delays, suppresses, or arrests any symptom of the disease or condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual. Amounts effective for this use may depend on the severity of the disease or condition and the weight and general state of the patient, but generally range from about 0.5 mg to about 3000 mg of the agent or agents per dose per patient. Suitable regimes for initial administration and booster administrations are typified by an initial administration followed by repeated doses at one or more hourly, daily, weekly, or monthly intervals by a subsequent administration. The total effective amount of an agent present in the compositions of the invention can be administered to a mammal as a single dose, either as a bolus or by infusion over a relatively short period of time, or can be administered using a fractionated treatment protocol, in which multiple doses are administered over a more prolonged period of time (e.g., a dose every 4-6, 8-12, 14-16, or 18-24 hours, or every 2-4 days, 1-2 weeks, once a month). Alternatively, continuous intravenous infusion sufficient to maintain therapeutically effective concentrations in the blood are contemplated.

The therapeutically effective amount of one or more agents present within the compositions of the invention and used in the methods of this invention applied to mammals (e.g., humans) can be determined by the ordinarily-skilled artisan with consideration of individual differences in age, weight, and the condition of the mammal. The agents of the invention are administered to a subject (e.g. a mammal, such as a human) in an effective amount, which is an amount that produces a desirable result in a treated subject (e.g. the slowing or remission of a cancer or neurodegenerative disorder). Therapeutically effective amounts can be determined empirically by those of skill in the art.

The patient may also receive an agent in the range of about 0.1 to 3,000 mg per dose one or more times per week (e.g., 2, 3, 4, 5, 6, or 7 or more times per week), 0.1 to 2,500 (e.g., 2,000, 1,500, 1,000, 500, 100, 10, 1, 0.5, or 0.1) mg dose per week. A patient may also receive an agent of the composition in the range of 0.1 to 3,000 mg per dose once every two or three weeks. Single or multiple administrations of the compositions of the invention comprising an effective amount can be carried out with dose levels and pattern being selected by the treating physician. The dose and administration schedule can be determined and adjusted based on the severity of the disease or condition in the patient, which may be monitored throughout the course of treatment according to the methods commonly practiced by clinicians or those described herein.

The carrier and conjugates of the present invention may be used in combination with either conventional methods of treatment or therapy or may be used separately from conventional methods of treatment or therapy.

When the conjugates of this invention are administered in combination therapies with other agents, they may be administered sequentially or concurrently to an individual. Alternatively, pharmaceutical compositions according to the present invention may be comprised of a combination of a carrier-agent conjugate of the present invention in association with a pharmaceutically acceptable excipient, as described herein, and another therapeutic or prophylactic agent known in the art.

Further Applications

The oligomers of the invention may be utilized as research reagents for, for example, diagnostics, therapeutics and prophylaxis.

In research, such oligomers may be used to specifically inhibit the synthesis of the expression product of a target sequence (typically by degrading or inhibiting the mRNA and thereby prevent protein formation) in cells and experimental animals thereby facilitating functional analysis of the target or an appraisal of its usefulness as a target for therapeutic intervention.

In diagnostics the oligomers may be used to detect and quantitate expression of the expression product of a target sequence in cell and tissues by northern blotting, in-situ hybridisation or similar techniques.

For therapeutics, an animal or a human, suspected of having a disease or disorder, which can be treated by modulating the expression of a target sequence is treated by administering oligomeric compounds in accordance with this invention. Further provided are methods of treating a mammal, such as treating a human, suspected of having or being prone to a disease or condition, associated with expression of a target sequence by administering a therapeutically or prophylactically effective amount of one or more of the oligomers or compositions of the invention. The oligomer, a conjugate or a pharmaceutical composition according to the invention is typically administered in an effective amount.

The invention also provides for the use of the compound or conjugate of the invention as described for the manufacture of a medicament for the treatment of a disorder as referred to herein, or for a method of the treatment of as a disorder as referred to herein.

The invention also provides for a method for treating a disorder as referred to herein said method comprising administering a compound according to the invention as herein described, and/or a conjugate according to the invention, and/or a pharmaceutical composition according to the invention to a patient in need thereof.

Viral Disorders

The oligomers, oligomer conjugates and other compositions according to the invention can be used for the treatment of conditions associated with the target sequence, such as over-expression or expression of a mutated version of the target sequence.

The invention further provides use of a compound of the invention in the manufacture of a medicament for the treatment of a disease, disorder or condition as referred to herein.

In the context of the present invention, said disease, disorder or condition may be a viral disorder.

In one embodiment, the viral disorder is associated with expression or over-expression of HBx or HBsAg. The viral disorder may be a disorder associated with HBV. Examples of such viral disorders include, but are not limited to, hepatitis B, cirrhosis, liver cancer (e.g. hepatocellular carcinoma), cholangiocarcinoma.

In one embodiment, the viral disorder is hepatitis B. As one of ordinary skill would recognise, the term "hepatitis B" in the context of the present invention refers to an infectious disorder of the liver caused by HBV. Hepatitis B may be acute or chronic. Acute disease causes liver inflammation, vomiting, jaundice and occasionally death. Chronic hepatitis B may cause cirrhosis and liver cancer.

In one embodiment, the viral disorder is cirrhosis. As one of ordinary skill would recognise, the term "cirrhosis" in the context of the present invention refers to an advanced liver disease characterised by the presence of fibrosis and regenerative nodules in the liver. These changes can lead to a loss a liver function.

In one embodiment, the viral disorder in liver cancer. As one of ordinary skill would recognise, "liver cancer" in the context of the present invention refers to a malignancy which originates in the liver.

In one embodiment, the viral disorder is hepatocellular carcinoma (HCC). As one of ordinary skill would recognise, "HCC" in the context of the present invention refers to a type of liver cancer which commonly occurs secondary to a viral hepatitis infection, for example hepatitis B. Macroscopically, HCC appears as a nodular or infiltrative tumour. The nodular type may be solitary (large mass) or multiple (when developed as a complication of cirrhosis). Tumour nodules are round to oval, grey or green (if the tumour produces bile), well circumscribed but not encapsulated. The diffuse type is poorly circumscribed and infiltrates the portal veins, or the hepatic veins (rarely). Microscopically, there are four architectural and cytological types (patterns) of HCC: fibrolamellar, pseudoglandular (adenoid), pleomorphic (giant cell) and clear cell. In well differentiated forms, tumour cells resemble hepatocytes, form trabeculae, cords and nests, and may contain bile pigment in cytoplasm. In poorly differentiated forms, malignant epithelial cells are discohesive, pleomorphic, anaplastic, giant. The tumour has a scant stroma and central necrosis because of the poor vascularization.

In one embodiment, the viral disorder is cholangiocarcinoma. As one of ordinary skill would recognise, "cholangiocarcinoma" in the context of the present invention refers to a form of cancer that is composed of mutated epithelial cells (or cells showing characteristics of epithelial differentiation) that originate in the bile ducts which drain bile from the liver into the small intestine.

Whilst various embodiments disclosed herein are related to a viral disorder associated with HBV infection, the present invention is not limited by these exemplary embodiments. Rather the present invention is applicable to any disorder associated with a viral infection.

Generally stated, one aspect of the invention is directed to a method of treating a mammal suffering from or susceptible to conditions associated with abnormal levels of the expression product of the target sequence, comprising administering to the mammal a therapeutically effective amount of an oligomer targeted to the target sequence. The oligomer of the invention may comprise one or more LNA units. The oligomer, a conjugate or a pharmaceutical composition according to the invention is typically administered in an effective amount.

An interesting aspect of the invention is directed to the use of an oligomer (compound) as defined herein or a oligomer conjugate as defined herein for the preparation of a medicament for the treatment of a disease, disorder or condition as referred to herein.

The methods of the invention are preferably employed for treatment or prophylaxis against diseases caused by abnormal levels of HBx or HBsAg.

Alternatively stated, in some embodiments, the invention is furthermore directed to a method for treating abnormal levels of HBx or HBsAg, said method comprising administering a oligomer of the invention, or a conjugate of the invention or a pharmaceutical composition of the invention to a patient in need thereof.

The invention also relates to an oligomer, a composition or an oligomer conjugate as defined herein for use as a medicament.

The invention further relates to use of a compound, composition, or a conjugate as defined herein for the manufacture of a medicament for the treatment of abnormal levels of HBx or HBsAg or expression of mutant forms of HBx or HBsAg (such as allelic variants, such as those associated with one of the diseases referred to herein).

Moreover, the invention relates to a method of treating a subject suffering from a disease or condition such as those referred to herein.

A patient who is in need of treatment is a patient suffering from or likely to suffer from the disease or disorder.

Example Oligomers

Examples of oligomers for use in the present invention are presented in the following Tables.

TABLE 1 oligonucleotide sequence motifs used to design LNA modified oligomers. The table indicates the fraction of conservation within all published full length genotype sequences of genotype A, B, C and D (GenBank), meaning that a given oligomer motif will be 100% complementary to the given fraction of target sequences within a genotype. All oligomer motifs were selected such that they will essentially target almost all sequences within genotypes A, B, C and D, thereby allowing for treatment of individual infected with any of these four genotypes.

| SEQ ID No. | Target HBx | Target HBsAg | Start position on U95551 | Oligosequence motif | Fraction of conservation within all sequences of genotype | | | |
|---|---|---|---|---|---|---|---|---|
| | | | | | A | B | C | D |
| SeqID 29 | X | | 201 | AAAACCCCGCCTGT | 0.97 | 0.98 | 0.95 | 0.99 |
| SeqID 30 | X | | 202 | AAAACCCCGCCTG | 0.96 | 0.97 | 0.97 | 0.97 |
| SeqID 31 | X | | 245 | ACGAGTCTAGACTCT | 0.96 | 0.97 | 0.97 | 0.97 |
| SeqID 32 | X | | 245 | CACGAGTCTAGACTCT | 0.96 | 0.97 | 0.97 | 0.97 |
| SeqID 33 | X | | 246 | ACGAGTCTAGACTC | 0.96 | 0.97 | 0.97 | 0.97 |
| SeqID 34 | X | | 246 | CACGAGTCTAGACTC | 0.96 | 0.97 | 0.97 | 0.97 |
| SeqID 35 | X | | 246 | CCACGAGTCTAGACTC | 0.96 | 0.97 | 0.97 | 0.97 |
| SeqID 36 | X | | 247 | ACGAGTCTAGACT | 0.96 | 0.97 | 0.97 | 0.97 |
| SeqID 37 | X | | 247 | CACGAGTCTAGACT | 0.96 | 0.97 | 0.97 | 0.97 |
| SeqID 38 | X | | 247 | CCACGAGTCTAGACT | 0.96 | 0.97 | 0.97 | 0.97 |
| SeqID 39 | X | | 247 | ACCACGAGTCTAGACT | 0.96 | 0.98 | 0.97 | 0.98 |
| SeqID 40 | X | | 248 | ACGAGTCTAGAC | 0.96 | 0.97 | 0.97 | 0.98 |
| SeqID 41 | X | | 248 | CACGAGTCTAGAC | 0.96 | 0.97 | 0.97 | 0.98 |
| SeqID 42 | X | | 248 | CCACGAGTCTAGAC | 0.96 | 0.97 | 0.97 | 0.97 |
| SeqID 43 | X | | 248 | ACCACGAGTCTAGAC | 0.96 | 0.97 | 0.96 | 0.97 |
| SeqID 44 | X | | 248 | CACCACGAGTCTAGAC | 0.99 | 0.97 | 0.97 | 0.98 |
| SeqID 45 | X | | 249 | ACCACGAGTCTAGA | 0.99 | 0.97 | 0.97 | 0.98 |
| SeqID 46 | X | | 249 | CACCACGAGTCTAGA | 0.99 | 0.97 | 0.97 | 0.98 |
| SeqID 47 | X | | 249 | CCACCACGAGTCTAGA | 0.99 | 0.98 | 0.97 | 0.98 |
| SeqID 48 | X | | 250 | CCACCACGAGTCTAG | 0.99 | 0.98 | 0.97 | 0.98 |
| SeqID 49 | X | | 250 | TCCACCACGAGTCTAG | 0.99 | 0.98 | 0.97 | 0.98 |
| SeqID 50 | X | | 251 | CCACCACGAGTCTA | 0.99 | 0.98 | 0.97 | 0.98 |
| SeqID 51 | X | | 251 | TCCACCACGAGTCTA | 0.98 | 0.97 | 0.97 | 0.98 |
| SeqID 52 | X | | 251 | GTCCACCACGAGTCTA | 0.99 | 0.98 | 0.97 | 0.98 |
| SeqID 53 | X | | 252 | TCCACCACGAGTCT | 0.98 | 0.97 | 0.97 | 0.98 |
| SeqID 54 | X | | 252 | GTCCACCACGAGTCT | 0.98 | 0.97 | 0.97 | 0.98 |
| SeqID 55 | X | | 252 | AGTCCACCACGAGTCT | 0.98 | 0.97 | 0.97 | 0.98 |
| SeqID 56 | X | | 253 | GTCCACCACGAGTC | 0.98 | 0.97 | 0.97 | 0.98 |
| SeqID 57 | X | | 253 | AGTCCACCACGAGTC | 0.98 | 0.97 | 0.97 | 0.98 |
| SeqID 58 | X | | 253 | AAGTCCACCACGAGTC | 0.98 | 0.97 | 0.98 | 0.99 |

TABLE 1-continued oligonucleotide sequence motifs used to design LNA modified oligomers.
The table indicates the fraction of conservation within all published full length genotype
sequences of genotype A, B, C and D (GenBank), meaning that a given oligomer motif will be
100% complementary to the given fraction of target sequences within a genotype. All oligomer
motifs were selected such that they will essentially target almost all sequences within
genotypes A, B, C and D, thereby allowing for treatment of individual infected with any
of these four genotypes.

| SEQ ID No. | Target HBx | Target HBsAg | Start position on U95551 | Oligosequence motif | Fraction of conservation within all sequences of genotype | | | |
|---|---|---|---|---|---|---|---|---|
| | | | | | A | B | C | D |
| SeqID 59 | X | | 254 | AGTCCACCACGAGT | 0.98 | 0.97 | 0.98 | 0.99 |
| SeqID 60 | X | | 254 | AAGTCCACCACGAGT | 0.98 | 0.97 | 0.97 | 0.99 |
| SeqID 61 | X | | 254 | GAAGTCCACCACGAGT | 0.98 | 0.97 | 0.98 | 0.99 |
| SeqID 62 | X | | 255 | AAGTCCACCACGAG | 0.98 | 0.97 | 0.98 | 0.99 |
| SeqID 63 | X | | 255 | GAAGTCCACCACGAG | 0.97 | 0.97 | 0.98 | 0.99 |
| SeqID 64 | X | | 255 | AGAAGTCCACCACGAG | 0.97 | 0.97 | 0.98 | 0.99 |
| SeqID 65 | X | | 256 | AGAAGTCCACCACGA | 0.97 | 0.97 | 0.98 | 0.99 |
| SeqID 66 | X | | 256 | GAGAAGTCCACCACGA | 0.97 | 0.97 | 0.98 | 0.99 |
| SeqID 67 | X | | 257 | GAGAAGTCCACCACG | 0.97 | 0.97 | 0.97 | 0.98 |
| SeqID 68 | X | | 257 | AGAGAAGTCCACCACG | 0.98 | 0.99 | 0.98 | 0.99 |
| SeqID 69 | X | | 258 | GAGAGAAGTCCACCAC | 0.98 | 0.99 | 0.98 | 0.99 |
| SeqID 70 | X | | 259 | GAGAGAAGTCCACCA | 0.98 | 0.99 | 0.98 | 0.99 |
| SeqID 71 | X | | 259 | TGAGAGAAGTCCACCA | 0.98 | 0.99 | 0.98 | 0.99 |
| SeqID 72 | X | | 260 | GAGAGAAGTCCACC | 0.98 | 0.99 | 0.98 | 0.99 |
| SeqID 73 | X | | 260 | TGAGAGAAGTCCACC | 0.98 | 0.99 | 0.98 | 0.99 |
| SeqID 74 | X | | 261 | TGAGAGAAGTCCAC | 0.99 | 0.96 | 0.95 | 0.98 |
| SeqID 75 | X | | 384 | AAAACGCCGCAGA | 0.98 | 0.96 | 0.95 | 0.98 |
| SeqID 76 | X | | 384 | TAAAACGCCGCAGA | 0.98 | 0.96 | 0.95 | 0.97 |
| SeqID 77 | X | | 384 | ATAAAACGCCGCAGA | 0.98 | 0.96 | 0.95 | 0.97 |
| SeqID 78 | X | | 384 | GATAAAACGCCGCAGA | 0.98 | 0.97 | 0.96 | 0.97 |
| SeqID 79 | X | | 385 | ATAAAACGCCGCAG | 0.98 | 0.97 | 0.96 | 0.97 |
| SeqID 80 | X | | 385 | GATAAAACGCCGCAG | 0.98 | 0.97 | 0.96 | 0.97 |
| SeqID 81 | X | | 385 | TGATAAAACGCCGCAG | 0.98 | 0.97 | 0.96 | 0.98 |
| SeqID 82 | X | | 386 | ATAAAACGCCGCA | 0.98 | 0.97 | 0.96 | 0.98 |
| SeqID 83 | X | | 386 | GATAAAACGCCGCA | 0.98 | 0.97 | 0.96 | 0.98 |
| SeqID 84 | X | | 386 | TGATAAAACGCCGCA | 0.98 | 0.97 | 0.96 | 0.98 |
| SeqID 85 | X | | 386 | ATGATAAAACGCCGCA | 0.98 | 0.98 | 0.97 | 0.98 |
| SeqID 86 | X | | 387 | ATAAAACGCCGC | 0.98 | 0.98 | 0.97 | 0.98 |
| SeqID 87 | X | | 387 | GATAAAACGCCGC | 0.98 | 0.97 | 0.97 | 0.98 |
| SeqID 88 | X | | 387 | TGATAAAACGCCGC | 0.98 | 0.97 | 0.97 | 0.98 |
| SeqID 89 | X | | 387 | ATGATAAAACGCCGC | 0.98 | 0.98 | 0.97 | 0.98 |
| SeqID 90 | X | | 388 | GATAAAACGCCG | 0.98 | 0.97 | 0.97 | 0.98 |
| SeqID 91 | X | | 388 | TGATAAAACGCCG | 0.98 | 0.97 | 0.97 | 0.98 |

TABLE 1-continued oligonucleotide sequence motifs used to design LNA modified oligomers.
The table indicates the fraction of conservation within all published full length genotype
sequences of genotype A, B, C and D (GenBank), meaning that a given oligomer motif will be
100% complementary to the given fraction of target sequences within a genotype. All oligomer
motifs were selected such that they will essentially target almost all sequences within
genotypes A, B, C and D, thereby allowing for treatment of individual infected with any
of these four genotypes.

| SEQ ID No. | Target HBx | Target HBsAg | Start position on U95551 | Oligosequence motif | Fraction of conservation within all sequences of genotype | | | |
|---|---|---|---|---|---|---|---|---|
| | | | | | A | B | C | D |
| SeqID 92 | X | | 388 | ATGATAAAACGCCG | 0.98 | 0.97 | 0.97 | 0.98 |
| SeqID 93 | X | | 389 | TGATAAAACGCC | 0.98 | 0.97 | 0.97 | 0.98 |
| SeqID 94 | X | | 389 | ATGATAAAACGCC | 0.98 | 0.97 | 0.97 | 0.98 |
| SeqID 95 | X | | 390 | ATGATAAAACGC | 1.00 | 0.99 | 0.98 | 0.97 |
| SeqID 96 | X | | 411 | TAGCAGCAGGATG | 1.00 | 0.99 | 0.98 | 0.97 |
| SeqID 97 | X | | 411 | ATAGCAGCAGGATG | 1.00 | 0.99 | 0.98 | 0.97 |
| SeqID 98 | X | | 411 | CATAGCAGCAGGATG | 1.00 | 0.98 | 0.98 | 0.97 |
| SeqID 99 | X | | 411 | GCATAGCAGCAGGATG | 1.00 | 0.99 | 0.98 | 0.97 |
| SeqID 100 | X | | 412 | GCATAGCAGCAGGAT | 1.00 | 0.99 | 0.98 | 0.97 |
| SeqID 101 | X | | 412 | GGCATAGCAGCAGGAT | 0.99 | 0.98 | 0.98 | 0.97 |
| SeqID 102 | X | | 414 | GAGGCATAGCAGCAGG | 0.99 | 0.98 | 0.98 | 0.97 |
| SeqID 103 | X | | 415 | TGAGGCATAGCAGCAG | 0.99 | 0.98 | 0.98 | 0.97 |
| SeqID 104 | X | | 416 | TGAGGCATAGCAGCA | 0.99 | 0.97 | 0.96 | 0.96 |
| SeqID 105 | X | | 416 | ATGAGGCATAGCAGCA | 0.99 | 0.98 | 0.98 | 0.97 |
| SeqID 106 | X | | 417 | TGAGGCATAGCAGC | 0.99 | 0.97 | 0.96 | 0.96 |
| SeqID 107 | X | | 417 | ATGAGGCATAGCAGC | 0.99 | 0.97 | 0.96 | 0.96 |
| SeqID 108 | X | | 417 | GATGAGGCATAGCAGC | 1.00 | 0.97 | 0.96 | 0.96 |
| SeqID 109 | X | | 418 | GATGAGGCATAGCAG | 1.00 | 0.97 | 0.96 | 0.96 |
| SeqID 110 | X | | 418 | AGATGAGGCATAGCAG | 1.00 | 0.97 | 0.97 | 0.96 |
| SeqID 111 | X | | 419 | GATGAGGCATAGCA | 1.00 | 0.97 | 0.97 | 0.96 |
| SeqID 112 | X | | 419 | AGATGAGGCATAGCA | 1.00 | 0.97 | 0.97 | 0.96 |
| SeqID 113 | X | | 419 | AAGATGAGGCATAGCA | 1.00 | 0.96 | 0.97 | 0.98 |
| SeqID 114 | X | | 422 | AAGAAGATGAGGCATA | 1.00 | 0.96 | 0.97 | 0.98 |
| SeqID 115 | X | | 423 | AAGAAGATGAGGCAT | 0.98 | 0.99 | 1.00 | 0.99 |
| SeqID 116 | X | | 601 | TGGGATGGGAATACA | 0.98 | 0.99 | 0.99 | 0.99 |
| SeqID 117 | X | | 601 | ATGGGATGGGAATACA | 0.98 | 0.99 | 1.00 | 0.99 |
| SeqID 118 | X | | 602 | TGGGATGGGAATAC | 0.98 | 0.99 | 1.00 | 0.99 |
| SeqID 119 | X | | 602 | ATGGGATGGGAATAC | 0.97 | 0.99 | 0.99 | 0.99 |
| SeqID 120 | X | | 602 | GATGGGATGGGAATAC | 0.98 | 0.99 | 1.00 | 0.99 |
| SeqID 121 | X | | 603 | ATGGGATGGGAATA | 0.97 | 0.99 | 0.99 | 0.99 |
| SeqID 122 | X | | 603 | GATGGGATGGGAATA | 0.97 | 0.99 | 0.99 | 0.99 |
| SeqID 123 | X | | 604 | GATGGGATGGGAAT | 0.99 | 0.97 | 0.96 | 0.98 |
| SeqID 834 | | | 670 | TAGTAAACTGAGCCA | | | | |

TABLE 1-continued oligonucleotide sequence motifs used to design LNA modified oligomers.
The table indicates the fraction of conservation within all published full length genotype sequences of genotype A, B, C and D (GenBank), meaning that a given oligomer motif will be 100% complementary to the given fraction of target sequences within a genotype. All oligomer motifs were selected such that they will essentially target almost all sequences within genotypes A, B, C and D, thereby allowing for treatment of individual infected with any of these four genotypes.

| SEQ ID No. | Target HBx | Target HBsAg | Start position on U95551 | Oligosequence motif | Fraction of conservation within all sequences of genotype | | | |
|---|---|---|---|---|---|---|---|---|
| | | | | | A | B | C | D |
| SeqID835 | | | 670 | CTAGTAAACTGAGCCA | | | | |
| SeqID836 | | | 671 | CTAGTAAACTGAGCC | | | | |
| SeqID837 | | | 674 | GCACTAGTAAACTGA | | | | |
| SeqID838 | | | 674 | GGCACTAGTAAACTGA | | | | |
| SeqID 124 | | X | 691 | AACCACTGAACAAA | 0.99 | 0.97 | 0.96 | 0.98 |
| SeqID 4 | | X | 691 | GAACCACTGAACAAA | 0.99 | 0.97 | 0.96 | 0.98 |
| SeqID 5 | | X | 691 | CGAACCACTGAACAAA | 0.99 | 0.97 | 0.96 | 0.98 |
| SeqID 6 | | X | 692 | CGAACCACTGAACAA | 0.99 | 0.97 | 0.96 | 0.98 |
| SeqID 7 | | X | 693 | CGAACCACTGAACA | 0.99 | 0.98 | 0.96 | 0.98 |
| SeqID 8 | | X | 694 | CGAACCACTGAAC | 0.99 | 0.98 | 0.96 | 0.98 |
| SeqID 125 | | X | 695 | CGAACCACTGAA | 0.98 | 0.97 | 0.98 | 0.98 |
| SeqID 126 | | X | 708 | GGGGGAAAGCCCT | 0.97 | 0.97 | 0.98 | 0.98 |
| SeqID 127 | | X | 708 | TGGGGGAAAGCCCT | 0.99 | 0.97 | 0.97 | 0.99 |
| SeqID839 | | | 1141 | CAACGGGGTAAAGGT | | | | |
| SeqID 128 | | X | 1142 | GCAACGGGGTAAAGG | 0.99 | 0.97 | 0.97 | 0.99 |
| SeqID 129 | | X | 1143 | GCAACGGGGTAAAG | 0.99 | 0.97 | 0.97 | 0.99 |
| SeqID 130 | | X | 1144 | GCAACGGGGTAAA | 0.99 | 0.98 | 0.97 | 0.99 |
| SeqID 131 | | X | 1176 | AGCAAACACTTGGCA | 0.99 | 0.98 | 0.97 | 0.99 |
| SeqID 132 | | X | 1176 | CAGCAAACACTTGGCA | 0.99 | 0.98 | 0.97 | 0.99 |
| SeqID 133 | | X | 1177 | CAGCAAACACTTGGC | 0.99 | 0.98 | 0.97 | 0.99 |
| SeqID 134 | | X | 1177 | TCAGCAAACACTTGGC | 0.99 | 0.98 | 0.97 | 0.99 |
| SeqID 135 | | X | 1178 | TCAGCAAACACTTGG | 0.98 | 0.96 | 0.96 | 0.97 |
| SeqID840 | | | 1261 | CAGTATGGATCGGCA | | | | |
| SeqID 136 | X | | 1264 | GCAGTATGGATCG | 0.98 | 0.95 | 0.96 | 0.97 |
| SeqID 137 | X | | 1264 | CGCAGTATGGATCG | 0.98 | 0.95 | 0.96 | 0.97 |
| SeqID 9 | X | | 1264 | CCGCAGTATGGATCG | 0.98 | 0.95 | 0.96 | 0.97 |
| SeqID 138 | X | | 1264 | TCCGCAGTATGGATCG | 0.98 | 0.95 | 0.96 | 0.97 |
| SeqID832 | | | 1264 | CCGCAGTATGGATCG | | | | |
| SeqID 10 | X | | 1265 | CGCAGTATGGATC | 0.98 | 0.95 | 0.96 | 0.97 |
| SeqID 139 | X | | 1265 | CCGCAGTATGGATC | 0.98 | 0.95 | 0.96 | 0.97 |
| SeqID 140 | X | | 1265 | TCCGCAGTATGGATC | 0.99 | 0.96 | 0.97 | 0.97 |
| SeqID841 | | | 1265 | TTCCGCAGTATGGATC | | | | |
| SeqID842 | | | 1266 | TTCCGCAGTATGGAT | | | | |

TABLE 1-continued oligonucleotide sequence motifs used to design LNA modified oligomers. The table indicates the fraction of conservation within all published full length genotype sequences of genotype A, B, C and D (GenBank), meaning that a given oligomer motif will be 100% complementary to the given fraction of target sequences within a genotype. All oligomer motifs were selected such that they will essentially target almost all sequences within genotypes A, B, C and D, thereby allowing for treatment of individual infected with any of these four genotypes.

| SEQ ID | Target | Target | Start position on | Oligosequence | Fraction of conservation within all sequences of genotype | | | |
|---|---|---|---|---|---|---|---|---|
| No. | HBx | HBsAg | U95551 | motif | A | B | C | D |
| SeqID843 | | | 1266 | GTTCCGCAGTATGGAT | | | | |
| SeqID 141 | X | | 1266 | CGCAGTATGGAT | 0.99 | 0.96 | 0.97 | 0.97 |
| SeqID 142 | X | | 1266 | CCGCAGTATGGAT | 0.99 | 0.96 | 0.97 | 0.97 |
| SeqID 143 | X | | 1266 | TCCGCAGTATGGAT | 0.99 | 0.96 | 0.97 | 0.97 |
| SeqID 144 | X | | 1267 | TCCGCAGTATGGA | 0.99 | 0.95 | 0.97 | 0.97 |
| SeqID844 | | | 1267 | GTTCCGCAGTATGGA | | | | |
| SeqID845 | | | 1267 | AGTTCCGCAGTATGGA | | | | |
| SeqID846 | | | 1268 | AGTTCCGCAGTATGG | | | | |
| SeqID847 | | | 1268 | GAGTTCCGCAGTATGG | | | | |
| SeqID848 | | | 1269 | GAGTTCCGCAGTATG | | | | |
| SeqID849 | | | 1269 | GGAGTTCCGCAGTATG | | | | |
| SeqID 145 | X | | 1269 | TTCCGCAGTATG | 0.99 | 0.99 | 0.99 | 0.99 |
| SeqID850 | | | 1525 | TAAAGAGAGGTGCGCC | | | | |
| SeqID851 | | | 1526 | TAAAGAGAGGTGCGC | | | | |
| SeqID852 | | | 1526 | GTAAAGAGAGGTGCGC | | | | |
| SeqID853 | | | 1527 | GTAAAGAGAGGTGCG | | | | |
| SeqID854 | | | 1527 | CGTAAAGAGAGGTGCG | | | | |
| SeqID855 | | | 1528 | CGTAAAGAGAGGTGC | | | | |
| SeqID856 | | | 1528 | GCGTAAAGAGAGGTGC | | | | |
| SeqID857 | | | 1529 | GCGTAAAGAGAGGTG | | | | |
| SeqID858 | | | 1529 | CGCGTAAAGAGAGGTG | | | | |
| SeqID 146 | X | | 1530 | CGTAAAGAGAGGT | 0.99 | 0.98 | 0.99 | 0.99 |
| SeqID 11 | X | | 1530 | GCGTAAAGAGAGGT | 0.99 | 0.98 | 0.99 | 0.99 |
| SeqID 12 | X | | 1530 | CGCGTAAAGAGAGGT | 0.99 | 0.98 | 0.99 | 0.99 |
| SeqID 147 | X | | 1530 | CCGCGTAAAGAGAGGT | 0.99 | 0.98 | 0.99 | 0.99 |
| SeqID 148 | X | | 1531 | CGTAAAGAGAGG | 0.99 | 0.98 | 0.99 | 0.99 |
| SeqID 13 | X | | 1531 | GCGTAAAGAGAGG | 0.99 | 0.98 | 0.99 | 0.99 |
| SeqID 149 | X | | 1531 | CGCGTAAAGAGAGG | 0.99 | 0.98 | 0.99 | 0.99 |
| SeqID 150 | X | | 1531 | CCGCGTAAAGAGAGG | 0.99 | 0.98 | 0.99 | 1.00 |
| SeqID 151 | X | | 1532 | CGCGTAAAGAGAG | 0.99 | 0.98 | 0.99 | 1.00 |
| SeqID 152 | X | | 1532 | CCGCGTAAAGAGAG | 0.99 | 0.98 | 0.99 | 1.00 |
| SeqID 153 | X | | 1533 | CGCGTAAAGAGA | 0.99 | 0.98 | 0.99 | 1.00 |
| SeqID 154 | X | | 1533 | CCGCGTAAAGAGA | 0.99 | 0.99 | 0.99 | 1.00 |

TABLE 1-continued oligonucleotide sequence motifs used to design LNA modified oligomers.
The table indicates the fraction of conservation within all published full length genotype
sequences of genotype A, B, C and D (GenBank), meaning that a given oligomer motif will be
100% complementary to the given fraction of target sequences within a genotype. All oligomer
motifs were selected such that they will essentially target almost all sequences within
genotypes A, B, C and D, thereby allowing for treatment of individual infected with any
of these four genotypes.

| SEQ ID No. | Target HBx | Target HBsAg | Start position on U95551 | Oligosequence motif | Fraction of conservation within all sequences of genotype | | | |
|---|---|---|---|---|---|---|---|---|
| | | | | | A | B | C | D |
| SeqID 155 | X | | 1534 | CCGCGTAAAGAG | 0.98 | 0.98 | 0.99 | 1.00 |
| SeqID 156 | X | | 1547 | GGCACAGACGGGAG | 0.98 | 0.98 | 0.99 | 1.00 |
| SeqID 157 | X | | 1547 | AGGCACAGACGGGAG | 0.98 | 0.99 | 0.99 | 1.00 |
| SeqID 158 | X | | 1548 | GGCACAGACGGGA | 0.98 | 0.98 | 0.99 | 1.00 |
| SeqID 159 | X | | 1548 | AGGCACAGACGGGA | 0.98 | 0.98 | 0.99 | 1.00 |
| SeqID 160 | X | | 1548 | AAGGCACAGACGGGA | 0.98 | 0.98 | 0.99 | 1.00 |
| SeqID 161 | X | | 1549 | AGGCACAGACGGGG | 0.98 | 0.98 | 0.99 | 1.00 |
| SeqID 162 | X | | 1549 | AAGGCACAGACGGGG | 0.98 | 0.97 | 0.99 | 0.99 |
| SeqID 163 | X | | 1549 | GAAGGCACAGACGGGG | 0.97 | 0.98 | 0.98 | 0.98 |
| SeqID 164 | X | | 1550 | AGAAGGCACAGACGGG | 0.97 | 0.98 | 0.98 | 0.98 |
| SeqID 14 | X | | 1551 | AGAAGGCACAGACGG | 0.97 | 0.98 | 0.98 | 0.98 |
| SeqID 15 | X | | 1551 | GAGAAGGCACAGACGG | 0.97 | 0.98 | 0.98 | 0.98 |
| SeqID 165 | X | | 1552 | GAGAAGGCACAGACG | 0.99 | 0.99 | 0.99 | 0.98 |
| SeqID859 | | | 1552 | TGAGAAGGCACAGACG | | | | |
| SeqID 16 | X | | 1577 | GAAGTGCACACGG | 0.99 | 0.99 | 0.99 | 0.98 |
| SeqID 166 | X | | 1577 | CGAAGTGCACACGG | 0.98 | 0.99 | 0.99 | 0.98 |
| SeqID 17 | X | | 1577 | GCGAAGTGCACACGG | 0.98 | 0.99 | 0.99 | 0.96 |
| SeqID 18 | X | | 1577 | AGCGAAGTGCACACGG | 0.99 | 0.99 | 0.99 | 0.98 |
| SeqID 19 | X | | 1578 | CGAAGTGCACACG | 0.98 | 0.99 | 0.99 | 0.98 |
| SeqID 167 | X | | 1578 | GCGAAGTGCACACG | 0.98 | 0.99 | 0.99 | 0.96 |
| SeqID 20 | X | | 1578 | AGCGAAGTGCACACG | 0.98 | 0.99 | 0.99 | 0.96 |
| SeqID 21 | X | | 1578 | AAGCGAAGTGCACACG | 0.98 | 0.99 | 0.99 | 0.98 |
| SeqID 168 | X | | 1579 | GCGAAGTGCACAC | 0.98 | 0.99 | 0.99 | 0.96 |
| SeqID 169 | X | | 1579 | AGCGAAGTGCACAC | 0.98 | 0.99 | 0.99 | 0.96 |
| SeqID 170 | X | | 1579 | AAGCGAAGTGCACAC | 0.98 | 0.99 | 0.99 | 0.96 |
| SeqID 171 | X | | 1579 | GAAGCGAAGTGCACAC | 0.98 | 0.99 | 0.99 | 0.96 |
| SeqID 172 | X | | 1580 | AGCGAAGTGCACA | 0.98 | 0.99 | 0.99 | 0.96 |
| SeqID 173 | X | | 1580 | AAGCGAAGTGCACA | 0.98 | 0.99 | 0.99 | 0.96 |
| SeqID 22 | X | | 1580 | GAAGCGAAGTGCACA | 0.98 | 0.99 | 0.99 | 0.96 |
| SeqID 174 | X | | 1580 | TGAAGCGAAGTGCACA | 0.98 | 0.99 | 0.99 | 0.96 |
| SeqID 175 | X | | 1581 | AAGCGAAGTGCAC | 0.98 | 0.99 | 0.99 | 0.96 |
| SeqID 176 | X | | 1581 | GAAGCGAAGTGCAC | 0.98 | 0.99 | 0.99 | 0.96 |
| SeqID 177 | X | | 1581 | TGAAGCGAAGTGCAC | 0.98 | 0.99 | 0.99 | 0.96 |

TABLE 1-continued oligonucleotide sequence motifs used to design LNA modified oligomers.
The table indicates the fraction of conservation within all published full length genotype
sequences of genotype A, B, C and D (GenBank), meaning that a given oligomer motif will be
100% complementary to the given fraction of target sequences within a genotype. All oligomer
motifs were selected such that they will essentially target almost all sequences within
genotypes A, B, C and D, thereby allowing for treatment of individual infected with any
of these four genotypes.

| SEQ ID No. | Target HBx | Target HBsAg | Start position on U95551 | Oligosequence motif | Fraction of conservation within all sequences of genotype | | | |
|---|---|---|---|---|---|---|---|---|
| | | | | | A | B | C | D |
| SeqID 178 | X | | 1581 | GTGAAGCGAAGTGCAC | 0.98 | 0.99 | 0.99 | 0.96 |
| SeqID 179 | X | | 1582 | AAGCGAAGTGCA | 0.98 | 0.99 | 0.99 | 0.96 |
| SeqID 180 | X | | 1582 | GAAGCGAAGTGCA | 0.98 | 0.99 | 0.99 | 0.96 |
| SeqID 181 | X | | 1582 | TGAAGCGAAGTGCA | 0.98 | 0.99 | 0.99 | 0.96 |
| SeqID 182 | X | | 1582 | GTGAAGCGAAGTGCA | 0.98 | 0.99 | 0.99 | 0.96 |
| SeqID 23 | X | | 1582 | GGTGAAGCGAAGTGCA | 0.98 | 0.99 | 0.99 | 0.96 |
| SeqID 183 | X | | 1583 | TGAAGCGAAGTGC | 0.98 | 0.99 | 0.99 | 0.96 |
| SeqID 184 | X | | 1583 | GTGAAGCGAAGTGC | 0.98 | 0.99 | 0.99 | 0.96 |
| SeqID 24 | X | | 1583 | GGTGAAGCGAAGTGC | 0.98 | 0.99 | 0.99 | 0.96 |
| SeqID 25 | X | | 1583 | AGGTGAAGCGAAGTGC | 0.98 | 0.99 | 0.99 | 0.96 |
| SeqID 185 | X | | 1584 | GTGAAGCGAAGTG | 0.98 | 0.99 | 0.99 | 0.96 |
| SeqID 186 | X | | 1584 | GGTGAAGCGAAGTG | 0.98 | 0.99 | 0.99 | 0.96 |
| SeqID 26 | X | | 1584 | AGGTGAAGCGAAGTG | 0.98 | 0.99 | 0.99 | 0.96 |
| SeqID 187 | X | | 1584 | GAGGTGAAGCGAAGTG | 0.98 | 0.99 | 0.99 | 0.96 |
| SeqID 188 | X | | 1585 | GTGAAGCGAAGT | 0.98 | 0.99 | 0.99 | 0.96 |
| SeqID 189 | X | | 1585 | GGTGAAGCGAAGT | 0.98 | 0.99 | 0.99 | 0.96 |
| SeqID 27 | X | | 1585 | AGGTGAAGCGAAGT | 0.98 | 0.99 | 0.99 | 0.96 |
| SeqID 190 | X | | 1585 | GAGGTGAAGCGAAGT | 0.98 | 0.99 | 0.99 | 0.96 |
| SeqID 191 | X | | 1585 | AGAGGTGAAGCGAAGT | 0.98 | 0.99 | 0.99 | 0.96 |
| SeqID 192 | X | | 1586 | AGAGGTGAAGCGAAG | 0.98 | 0.99 | 0.99 | 0.96 |
| SeqID 193 | X | | 1586 | CAGAGGTGAAGCGAAG | 0.99 | 0.99 | 0.99 | 0.96 |
| SeqID 194 | X | | 1587 | AGAGGTGAAGCGAA | 0.99 | 0.99 | 0.99 | 0.96 |
| SeqID 195 | X | | 1587 | CAGAGGTGAAGCGAA | 0.99 | 0.99 | 0.98 | 0.96 |
| SeqID 196 | X | | 1587 | GCAGAGGTGAAGCGAA | 0.99 | 0.99 | 0.99 | 0.97 |
| SeqID 28 | X | | 1588 | CAGAGGTGAAGCGA | 0.99 | 0.99 | 0.98 | 0.96 |
| SeqID 197 | X | | 1588 | GCAGAGGTGAAGCGA | 0.99 | 0.99 | 0.98 | 0.96 |
| SeqID 198 | X | | 1588 | TGCAGAGGTGAAGCGA | 0.99 | 0.99 | 0.98 | 0.96 |
| SeqID 199 | X | | 1589 | TGCAGAGGTGAAGCG | 0.99 | 0.99 | 0.98 | 0.96 |
| SeqID 200 | X | | 1589 | GTGCAGAGGTGAAGCG | 0.99 | 0.99 | 0.98 | 0.96 |
| SeqID 201 | X | | 1590 | CGTGCAGAGGTGAAGC | 0.99 | 0.99 | 0.98 | 0.96 |
| SeqID 202 | X | | 1591 | CGTGCAGAGGTGAAG | 0.99 | 0.99 | 0.98 | 0.96 |
| SeqID 203 | X | | 1591 | ACGTGCAGAGGTGAAG | 1.00 | 0.99 | 0.98 | 0.96 |
| SeqID 204 | X | | 1592 | CGTGCAGAGGTGAA | 1.00 | 0.99 | 0.98 | 0.96 |

TABLE 1-continued oligonucleotide sequence motifs used to design LNA modified oligomers.
The table indicates the fraction of conservation within all published full length genotype
sequences of genotype A, B, C and D (GenBank), meaning that a given oligomer motif will be
100% complementary to the given fraction of target sequences within a genotype. All oligomer
motifs were selected such that they will essentially target almost all sequences within
genotypes A, B, C and D, thereby allowing for treatment of individual infected with any
of these four genotypes.

| SEQ ID No. | Target HBx | Target HBsAg | Start position on U95551 | Oligosequence motif | Fraction of conservation within all sequences of genotype | | | |
|---|---|---|---|---|---|---|---|---|
| | | | | | A | B | C | D |
| SeqID 205 | X | | 1592 | ACGTGCAGAGGTGAA | 1.00 | 0.99 | 0.98 | 0.99 |
| SeqID 206 | X | | 1593 | CGTGCAGAGGTGA | 1.00 | 0.99 | 0.98 | 0.99 |
| SeqID 207 | X | | 1593 | ACGTGCAGAGGTGA | 0.98 | 0.97 | 0.96 | 0.97 |
| SeqID 208 | X | | 1616 | CGTTCACGGTGGT | 0.98 | 0.96 | 0.96 | 0.95 |
| SeqID 209 | X | | 1690 | CTCAAGGTCGGTC | 0.99 | 0.97 | 0.98 | 0.96 |
| SeqID860 | | | 1690 | GCCTCAAGGTCGGTC | | | | |
| SeqID 210 | X | | 1691 | CCTCAAGGTCGGT | 0.99 | 0.97 | 0.98 | 0.95 |
| SeqID 211 | X | | 1691 | GCCTCAAGGTCGGT | 0.98 | 0.97 | 0.98 | 0.99 |
| SeqID 212 | X | | 1706 | ACAGTCTTTGAAGTA | 0.99 | 0.95 | 0.95 | 0.99 |
| SeqID861 | | | 1778 | ATGCCTACAGCCTCC | | | | |
| SeqID 213 | X | | 1783 | TTTATGCCTACAG | 0.99 | 0.96 | 0.95 | 0.99 |
| SeqID 214 | X | | 1784 | AATTTATGCCTACA | 0.99 | 0.96 | 0.95 | 0.99 |
| SeqID 215 | X | | 1785 | AATTTATGCCTAC | 0.99 | 0.95 | 0.96 | 0.99 |
| SeqID862 | | | 1785 | ACCAATTTATGCCTAC | | | | |
| SeqID 216 | X | | 1787 | CCAATTTATGCCT | 0.97 | 0.99 | 0.99 | 0.98 |
| SeqID 217 | X | | 1865 | GCTTGGAGGCTTGAA | 0.97 | 0.99 | 0.98 | 0.98 |
| SeqID 218 | X | | 1865 | AGCTTGGAGGCTTGAA | 0.97 | 0.99 | 0.99 | 0.98 |
| SeqID 219 | X | | 1866 | GCTTGGAGGCTTGA | 0.97 | 0.99 | 0.99 | 0.98 |
| SeqID 220 | X | | 1866 | AGCTTGGAGGCTTGA | 0.97 | 0.98 | 0.98 | 0.98 |
| SeqID 221 | X | | 1866 | CAGCTTGGAGGCTTGA | 0.97 | 0.99 | 0.99 | 0.98 |
| SeqID 222 | X | | 1867 | GCTTGGAGGCTTG | 0.97 | 0.99 | 0.99 | 0.98 |
| SeqID 223 | X | | 1867 | AGCTTGGAGGCTTG | 0.97 | 0.98 | 0.98 | 0.98 |
| SeqID 224 | X | | 1867 | CAGCTTGGAGGCTTG | 0.97 | 0.98 | 0.98 | 0.98 |
| SeqID 225 | X | | 1867 | ACAGCTTGGAGGCTTG | 0.97 | 0.98 | 0.98 | 0.98 |
| SeqID 226 | X | | 1868 | CACAGCTTGGAGGCTT | 0.97 | 0.98 | 0.98 | 0.98 |
| SeqID 227 | X | | 1869 | CACAGCTTGGAGGCT | 0.97 | 0.98 | 0.98 | 0.98 |
| SeqID 228 | X | | 1869 | GCACAGCTTGGAGGCT | 0.97 | 0.98 | 0.98 | 0.98 |
| SeqID 229 | X | | 1870 | GCACAGCTTGGAGGC | 0.97 | 0.98 | 0.98 | 0.98 |
| SeqID 230 | X | | 1870 | GGCACAGCTTGGAGGC | 0.96 | 0.98 | 0.98 | 0.98 |
| SeqID 231 | X | | 1871 | AGGCACAGCTTGGAGG | 0.96 | 0.98 | 0.98 | 0.99 |
| SeqID 232 | X | | 1872 | AGGCACAGCTTGGAG | 0.96 | 0.97 | 0.98 | 0.99 |
| SeqID 233 | X | | 1872 | AAGGCACAGCTTGGAG | 0.96 | 0.97 | 0.98 | 0.99 |
| SeqID 234 | X | | 1873 | AAGGCACAGCTTGGA | 0.96 | 0.97 | 0.98 | 0.98 |

TABLE 1-continued oligonucleotide sequence motifs used to design LNA modified oligomers.
The table indicates the fraction of conservation within all published full length genotype
sequences of genotype A, B, C and D (GenBank), meaning that a given oligomer motif will be
100% complementary to the given fraction of target sequences within a genotype. All oligomer
motifs were selected such that they will essentially target almost all sequences within
genotypes A, B, C and D, thereby allowing for treatment of individual infected with any
of these four genotypes.

| SEQ ID No. | Target HBx | Target HBsAg | Start position on U95551 | Oligosequence motif | Fraction of conservation within all sequences of genotype | | | |
|---|---|---|---|---|---|---|---|---|
| | | | | | A | B | C | D |
| SeqID 235 | X | | 1873 | CAAGGCACAGCTTGGA | 0.96 | 0.97 | 0.98 | 0.99 |
| SeqID 236 | X | | 1874 | AAGGCACAGCTTGG | 0.96 | 0.97 | 0.98 | 0.99 |
| SeqID 237 | X | | 1874 | CAAGGCACAGCTTGG | 0.96 | 0.97 | 0.97 | 0.98 |
| SeqID 238 | X | | 1874 | CCAAGGCACAGCTTGG | 0.96 | 0.97 | 0.98 | 0.99 |
| SeqID 239 | X | | 1875 | CAAGGCACAGCTTG | 0.96 | 0.97 | 0.97 | 0.98 |
| SeqID 240 | X | | 1875 | CCAAGGCACAGCTTG | 0.96 | 0.97 | 0.97 | 0.99 |
| SeqID 241 | X | | 1876 | CCAAGGCACAGCTT | 0.96 | 0.97 | 0.96 | 0.97 |
| SeqID 242 | | | 2272 | TGCGAATCCACAC | 0.96 | 0.97 | 0.96 | 0.97 |
| SeqID 243 | | | 2272 | GTGCGAATCCACAC | 0.96 | 0.96 | 0.98 | 0.97 |
| SeqID 244 | | | 2370 | GGAGTTCTTCTTCTA | 0.96 | 0.96 | 0.98 | 0.97 |
| SeqID 245 | | | 2370 | GGGAGTTCTTCTTCTA | 0.96 | 0.96 | 0.98 | 0.97 |
| SeqID 246 | | | 2371 | GGGAGTTCTTCTTCT | 0.96 | 0.96 | 0.98 | 0.97 |
| SeqID 247 | | | 2371 | AGGGAGTTCTTCTTCT | 0.96 | 0.98 | 0.98 | 0.97 |
| SeqID 248 | | | 2372 | AGGGAGTTCTTCTTC | 0.96 | 0.98 | 0.97 | 0.97 |
| SeqID 249 | | | 2372 | GAGGGAGTTCTTCTTC | 0.97 | 0.98 | 0.98 | 0.97 |
| SeqID 250 | | | 2373 | AGGGAGTTCTTCTT | 0.97 | 0.98 | 0.98 | 0.97 |
| SeqID 251 | | | 2373 | GAGGGAGTTCTTCTT | 0.97 | 0.95 | 0.97 | 0.95 |
| SeqID 252 | | | 2373 | CGAGGGAGTTCTTCTT | 0.97 | 0.95 | 0.97 | 0.96 |
| SeqID 253 | | | 2374 | CGAGGGAGTTCTTCT | 0.97 | 0.95 | 0.97 | 0.96 |
| SeqID 254 | | | 2374 | GCGAGGGAGTTCTTCT | 0.97 | 0.96 | 0.97 | 0.96 |
| SeqID 255 | | | 2375 | GCGAGGGAGTTCTTC | 0.97 | 0.96 | 0.97 | 0.96 |
| SeqID 256 | | | 2375 | GGCGAGGGAGTTCTTC | 0.97 | 0.96 | 0.97 | 0.96 |
| SeqID 257 | | | 2376 | GCGAGGGAGTTCTT | 0.97 | 0.96 | 0.97 | 0.96 |
| SeqID 258 | | | 2376 | GGCGAGGGAGTTCTT | 0.97 | 0.96 | 0.97 | 0.96 |
| SeqID 259 | | | 2376 | AGGCGAGGGAGTTCTT | 0.98 | 0.96 | 0.97 | 0.96 |
| SeqID 260 | | | 2377 | GCGAGGGAGTTCT | 0.98 | 0.96 | 0.97 | 0.96 |
| SeqID 261 | | | 2377 | GGCGAGGGAGTTCT | 0.98 | 0.96 | 0.97 | 0.96 |
| SeqID 262 | | | 2377 | AGGCGAGGGAGTTCT | 0.98 | 0.96 | 0.97 | 0.96 |
| SeqID 263 | | | 2377 | GAGGCGAGGGAGTTCT | 0.99 | 0.96 | 0.98 | 0.97 |
| SeqID 264 | | | 2378 | GGCGAGGGAGTTC | 0.99 | 0.96 | 0.98 | 0.97 |
| SeqID 265 | | | 2378 | AGGCGAGGGAGTTC | 0.99 | 0.96 | 0.98 | 0.97 |
| SeqID 266 | | | 2378 | GAGGCGAGGGAGTTC | 0.99 | 0.96 | 0.97 | 0.97 |
| SeqID 267 | | | 2378 | CGAGGCGAGGGAGTTC | 0.99 | 0.96 | 0.98 | 0.97 |

TABLE 1-continued oligonucleotide sequence motifs used to design LNA modified oligomers.
The table indicates the fraction of conservation within all published full length genotype
sequences of genotype A, B, C and D (GenBank), meaning that a given oligomer motif will be
100% complementary to the given fraction of target sequences within a genotype. All oligomer
motifs were selected such that they will essentially target almost all sequences within
genotypes A, B, C and D, thereby allowing for treatment of individual infected with any
of these four genotypes.

| SEQ ID No. | Target HBx | Target HBsAg | Start position on U95551 | Oligosequence motif | Fraction of conservation within all sequences of genotype | | | |
|---|---|---|---|---|---|---|---|---|
| | | | | | A | B | C | D |
| SeqID 268 | | | 2379 | AGGCGAGGGAGTT | 0.99 | 0.96 | 0.98 | 0.97 |
| SeqID 269 | | | 2379 | GAGGCGAGGGAGTT | 0.99 | 0.96 | 0.98 | 0.97 |
| SeqID 270 | | | 2379 | CGAGGCGAGGGAGTT | 0.99 | 0.96 | 0.98 | 0.97 |
| SeqID 271 | | | 2379 | GCGAGGCGAGGGAGTT | 0.99 | 0.96 | 0.98 | 0.97 |
| SeqID 272 | | | 2380 | GAGGCGAGGGAGT | 0.99 | 0.96 | 0.98 | 0.97 |
| SeqID 273 | | | 2380 | CGAGGCGAGGGAGT | 0.99 | 0.96 | 0.98 | 0.97 |
| SeqID 274 | | | 2380 | GCGAGGCGAGGGAGT | 0.99 | 0.96 | 0.97 | 0.96 |
| SeqID 275 | | | 2380 | TGCGAGGCGAGGGAGT | 0.99 | 0.96 | 0.98 | 0.97 |
| SeqID 276 | | | 2381 | CGAGGCGAGGGAG | 0.99 | 0.96 | 0.98 | 0.97 |
| SeqID 277 | | | 2381 | GCGAGGCGAGGGAG | 0.99 | 0.96 | 0.97 | 0.97 |
| SeqID 278 | | | 2381 | TGCGAGGCGAGGGAG | 0.97 | 0.96 | 0.96 | 0.96 |
| SeqID 279 | | | 2381 | CTGCGAGGCGAGGGAG | 0.99 | 0.96 | 0.98 | 0.97 |
| SeqID 280 | | | 2382 | CGAGGCGAGGGA | 0.99 | 0.96 | 0.98 | 0.97 |
| SeqID 281 | | | 2382 | GCGAGGCGAGGGA | 0.99 | 0.96 | 0.97 | 0.97 |
| SeqID 282 | | | 2382 | TGCGAGGCGAGGGA | 0.97 | 0.96 | 0.96 | 0.96 |
| SeqID 283 | | | 2382 | CTGCGAGGCGAGGGA | 0.97 | 0.96 | 0.96 | 0.96 |
| SeqID 284 | | | 2382 | TCTGCGAGGCGAGGGA | 0.97 | 0.96 | 0.96 | 0.96 |
| SeqID 285 | | | 2383 | TCTGCGAGGCGAGGG | 0.97 | 0.96 | 0.96 | 0.96 |
| SeqID 286 | | | 2383 | GTCTGCGAGGCGAGGG | 0.98 | 0.97 | 0.96 | 0.95 |
| SeqID 287 | | | 2824 | GTTCCCAAGAATAT | 0.98 | 0.97 | 0.96 | 0.95 |
| SeqID 288 | | | 2824 | TGTTCCCAAGAATAT | 0.98 | 0.98 | 0.97 | 0.96 |
| SeqID 289 | | | 2825 | GTTCCCAAGAATA | 0.98 | 0.98 | 0.97 | 0.96 |
| SeqID 290 | | | 2825 | TGTTCCCAAGAATA | 0.97 | 0.97 | 0.96 | 0.96 |
| SeqID 291 | | | 2825 | TTGTTCCCAAGAATA | 0.98 | 0.98 | 0.97 | 0.96 |
| SeqID 292 | | | 2826 | TGTTCCCAAGAAT | 0.97 | 0.97 | 0.96 | 0.96 |
| SeqID 293 | | | 2826 | TTGTTCCCAAGAAT | | | | |

TABLE 2

A subset of oligomer motifs from table 1

| SEQ ID No. | Target HBx | Target HBsAg | Start position on U95551 | Oligo_seq |
|---|---|---|---|---|
| SeqID 4 | X | | 691 | GAACCACTGAACAAA |
| SeqID 5 | X | | 691 | CGAACCACTGAACAAA |

TABLE 2-continued

A subset of oligomer motifs from table 1

| SEQ ID No. | Target HBx | Target HBsAg | Start position on U95551 | Oligo_seq |
|---|---|---|---|---|
| SeqID 6 | | X | 692 | CGAACCACTGAACAA |
| SeqID 7 | | X | 693 | CGAACCACTGAACA |
| SeqID 8 | | X | 694 | CGAACCACTGAAC |
| SeqID 9 | X | | 1264 | CCGCAGTATGGATCG |
| SeqID 10 | X | | 1265 | CGCAGTATGGATC |
| SeqID 11 | X | | 1530 | GCGTAAAGAGAGGT |
| SeqID 12 | X | | 1530 | CGCGTAAAGAGAGGT |
| SeqID 13 | X | | 1531 | GCGTAAAGAGAGG |
| SeqID 14 | X | | 1551 | AGAAGGCACAGACGG |
| SeqID 15 | X | | 1551 | GAGAAGGCACAGACGG |
| SeqID 16 | X | | 1577 | GAAGTGCACACGG |
| SeqID 17 | X | | 1577 | GCGAAGTGCACACGG |
| SeqID 18 | X | | 1577 | AGCGAAGTGCACACGG |
| SeqID 19 | X | | 1578 | CGAAGTGCACACG |
| SeqID 20 | X | | 1578 | AGCGAAGTGCACACG |
| SeqID 21 | X | | 1578 | AAGCGAAGTGCACACG |
| SeqID 22 | X | | 1580 | GAAGCGAAGTGCACA |
| SeqID 23 | X | | 1582 | GGTGAAGCGAAGTGCA |
| SeqID 24 | X | | 1583 | GGTGAAGCGAAGTGC |
| SeqID 25 | X | | 1583 | AGGTGAAGCGAAGTGC |
| SeqID 26 | X | | 1584 | AGGTGAAGCGAAGTG |
| SeqID 27 | X | | 1585 | AGGTGAAGCGAAGT |
| SeqID 28 | X | | 1588 | CAGAGGTGAAGCGA |

TABLE 3

LNA oligomers
Upper case letters denote beta-D-oxy LNA, C LNA is 5-methyl C LNA, lower case letters denote DNA, $^m$c denotes a 5-methylcytosine DNA, all internucleoside linkages are phosphorothiate internucleoside linkages.

| SEQ ID No. | Target HBx | Target HBsAg | Start position on U95551 | Oligo_seq |
|---|---|---|---|---|
| SeqID 294 | | X | 691 | GAAccactgaacAAA |
| SeqID 295 | | X | 691 | CGAaccactgaacAAA |
| SeqID 296 | | X | 692 | CGAaccactgaaCAA |
| SeqID 297 | | X | 693 | CGAaccactgaACA |
| SeqID 298 | | X | 694 | CGAaccactgaAC |
| SeqID 299 | X | | 1264 | CCGcagtatggaTCG |
| SeqID 300 | X | | 1265 | CGCagtatggaTC |

TABLE 3-continued

LNA oligomers
Upper case letters denote beta-D-oxy LNA, C LNA is 5-methyl C LNA, lower
case letters denote DNA, $^m$c denotes a 5-methylcytosine DNA, all
internucleoside linkages are phosphorothiate internucleoside linkages.

| SEQ ID No. | Target HBx | Target HBsAg | Start position on U95551 | Oligo_seq |
|---|---|---|---|---|
| SeqID 301 | X | | 1530 | GCGtaaagagaGGT |
| SeqID 302 | X | | 1530 | CGCgtaaagagaGGT |
| SeqID 303 | X | | 1531 | GCGtaaagagaGG |
| SeqID 304 | X | | 1551 | AGAaggcacagaCGG |
| SeqID 305 | X | | 1551 | GAGaaggcacagaCGG |
| SeqID 306 | X | | 1577 | GAAgtgcaca$^m$cGG |
| SeqID 307 | X | | 1577 | GCGaagtgcacaCGG |
| SeqID 308 | X | | 1577 | AGCgaagtgcacaCGG |
| SeqID 309 | X | | 1578 | CGAagtgcacaCG |
| SeqID 310 | X | | 1578 | AGCgaagtgcacACG |
| SeqID 311 | X | | 1578 | AAG$^m$cgaagtgcacACG |
| SeqID 312 | X | | 1580 | GAAg$^m$cgaagtgcACA |
| SeqID 313 | X | | 1582 | GGTgaag$^m$cgaagtGCA |
| SeqID 314 | X | | 1583 | GGTgaag$^m$cgaagTGC |
| SeqID 315 | X | | 1583 | AGGtgaag$^m$cgaagTGC |
| SeqID 316 | X | | 1584 | AGGtgaag$^m$cgaaGTG |
| SeqID 317 | X | | 1585 | AGGtgaag$^m$cgaAGT |
| SeqID 318 | X | | 1588 | CAGaggtgaagCGA |
| SeqID 319 | | X | 201 | AAAaccc$^m$cgccTGT |
| SeqID 320 | | X | 202 | AAAaccc$^m$cgccTG |
| SeqID 321 | | X | 245 | ACGagtctagacTCT |
| SeqID 322 | | X | 245 | CACgagtctagacTCT |
| SeqID 323 | | X | 246 | ACGagtctagaCTC |
| SeqID 324 | | X | 246 | CACgagtctagaCTC |
| SeqID 325 | | X | 246 | CCA$^m$cgagtctagaCTC |
| SeqID 326 | | X | 247 | ACGagtctagaCT |
| SeqID 327 | | X | 247 | CACgagtctagACT |
| SeqID 328 | | X | 247 | CCA$^m$cgagtctagACT |
| SeqID 329 | | X | 247 | ACCa$^m$cgagtctagACT |
| SeqID 330 | | X | 248 | ACgagtctagAC |
| SeqID 331 | | X | 248 | CACgagtctagAC |
| SeqID 332 | | X | 248 | CCA$^m$cgagtctaGAC |
| SeqID 333 | | X | 248 | ACCa$^m$cgagtctaGAC |
| SeqID 334 | | X | 248 | CACca$^m$cgagtctaGAC |
| SeqID 335 | | X | 249 | ACCa$^m$cgagtctAGA |
| SeqID 336 | | X | 249 | CACca$^m$cgagtctAGA |

TABLE 3-continued

LNA oligomers
Upper case letters denote beta-D-oxy LNA, C LNA is 5-methyl C LNA, lower case letters denote DNA, $^m$c denotes a 5-methylcytosine DNA, all internucleoside linkages are phosphorothiate internucleoside linkages.

| SEQ ID No. | Target HBx | Target HBsAg | Start position on U95551 | Oligo_seq |
|---|---|---|---|---|
| SeqID 337 | X | | 249 | CCAcca$^m$cgagtctAGA |
| SeqID 338 | X | | 250 | CCAcca$^m$cgagtcTAG |
| SeqID 339 | X | | 250 | TCCacca$^m$cgagtcTAG |
| SeqID 340 | X | | 251 | CCAcca$^m$cgagtCTA |
| SeqID 341 | X | | 251 | TCCacca$^m$cgagtCTA |
| SeqID 342 | X | | 251 | GTCcacca$^m$cgagtCTA |
| SeqID 343 | X | | 252 | TCCacca$^m$cgagTCT |
| SeqID 344 | X | | 252 | GTCcacca$^m$cgagTCT |
| SeqID 345 | X | | 252 | AGTccacca$^m$cgagTCT |
| SeqID 346 | X | | 253 | GTCcacca$^m$cgaGTC |
| SeqID 347 | X | | 253 | AGTccacca$^m$cgaGTC |
| SeqID 348 | X | | 253 | AAGtccacca$^m$cgaGTC |
| SeqID 349 | X | | 254 | AGTccacca$^m$cgAGT |
| SeqID 350 | X | | 254 | AAGtccacca$^m$cgAGT |
| SeqID 351 | X | | 254 | GAAgtccacca$^m$cgAGT |
| SeqID 352 | X | | 255 | AAGtccacca$^m$cgAG |
| SeqID 353 | X | | 255 | GAAgtccacca$^m$cgAG |
| SeqID 354 | X | | 255 | AGAagtccacca$^m$cgAG |
| SeqID 355 | X | | 256 | AGAagtccaccaCGA |
| SeqID 356 | X | | 256 | GAGaagtccaccaCGA |
| SeqID 357 | X | | 257 | GAGaagtccaccACG |
| SeqID 358 | X | | 257 | AGAgaagtccaccACG |
| SeqID 359 | X | | 258 | GAGagaagtccacCAC |
| SeqID 360 | X | | 259 | GAGagaagtccaCCA |
| SeqID 361 | X | | 259 | TGAgagaagtccaCCA |
| SeqID 362 | X | | 260 | GAGagaagtccACC |
| SeqID 363 | X | | 260 | TGAgagaagtccACC |
| SeqID 364 | X | | 261 | TGAgagaagtcCAC |
| SeqID 365 | X | | 384 | AAAa$^m$cgc$^m$cgcaGA |
| SeqID 366 | X | | 384 | TAAaa$^m$cgc$^m$cgcAGA |
| SeqID 367 | X | | 384 | ATAaaa$^m$cgc$^m$cgcAGA |
| SeqID 368 | X | | 384 | GATaaaa$^m$cgc$^m$cgcAGA |
| SeqID 369 | X | | 385 | ATAaaa$^m$cgc$^m$cgCAG |
| SeqID 370 | X | | 385 | GATaaaa$^m$cgc$^m$cgCAG |
| SeqID 371 | X | | 385 | TGAtaaaa$^m$cgc$^m$cgCAG |
| SeqID 372 | X | | 386 | ATAaaa$^m$cgc$^m$cgCA |

TABLE 3-continued

LNA oligomers
Upper case letters denote beta-D-oxy LNA, C LNA is 5-methyl C LNA, lower case letters denote DNA, ᵐc denotes a 5-methylcytosine DNA, all internucleoside linkages are phosphorothiate internucleoside linkages.

| SEQ ID No. | Target HBx | Target HBsAg | Start position on U95551 | Oligo_seq |
|---|---|---|---|---|
| SeqID 373 | X | | 386 | GATaaaaᵐcgcᵐcGCA |
| SeqID 374 | X | | 386 | TGAtaaaaᵐcgcᵐcGCA |
| SeqID 375 | X | | 386 | ATGataaaaᵐcgcᵐcGCA |
| SeqID 376 | X | | 387 | ATaaaaᵐcgcᵐcGC |
| SeqID 377 | X | | 387 | GATaaaaᵐcgcᵐcGC |
| SeqID 378 | X | | 387 | TGAtaaaaᵐcgcCGC |
| SeqID 379 | X | | 387 | ATGataaaaᵐcgcCGC |
| SeqID 380 | X | | 388 | GAtaaaaᵐcgcCG |
| SeqID 381 | X | | 388 | TGAtaaaaᵐcgcCG |
| SeqID 382 | X | | 388 | ATGataaaaᵐcgCCG |
| SeqID 383 | X | | 389 | TGataaaaᵐcgCC |
| SeqID 384 | X | | 389 | ATGataaaaᵐcgCC |
| SeqID 385 | X | | 390 | ATgataaaaᵐcGC |
| SeqID 386 | X | | 411 | TAGcagcaggaTG |
| SeqID 387 | X | | 411 | ATAgcagcaggATG |
| SeqID 388 | X | | 411 | CATagcagcaggATG |
| SeqID 389 | X | | 411 | GCAtagcagcaggATG |
| SeqID 390 | X | | 412 | GCAtagcagcagGAT |
| SeqID 391 | X | | 412 | GGCatagcagcagGAT |
| SeqID 392 | X | | 414 | GAGgcatagcagcAGG |
| SeqID 393 | X | | 415 | TGAggcatagcagCAG |
| SeqID 394 | X | | 416 | TGAggcatagcaGCA |
| SeqID 395 | X | | 416 | ATGaggcatagcaGCA |
| SeqID 396 | X | | 417 | TGAggcatagcAGC |
| SeqID 397 | X | | 417 | ATGaggcatagcAGC |
| SeqID 398 | X | | 417 | GATgaggcatagcAGC |
| SeqID 399 | X | | 418 | GATgaggcatagCAG |
| SeqID 400 | X | | 418 | AGAtgaggcatagCAG |
| SeqID 401 | X | | 419 | GATgaggcataGCA |
| SeqID 402 | X | | 419 | AGAtgaggcataGCA |
| SeqID 403 | X | | 419 | AAGatgaggcataGCA |
| SeqID 404 | X | | 422 | AAGaagatgaggcATA |
| SeqID 405 | X | | 423 | AAGaagatgaggCAT |
| SeqID 406 | X | | 601 | TGGgatgggaatACA |
| SeqID 407 | X | | 601 | ATGggatgggaatACA |
| SeqID 408 | X | | 602 | TGGgatgggaaTAC |

TABLE 3-continued

LNA oligomers
Upper case letters denote beta-D-oxy LNA, C LNA is 5-methyl C LNA, lower case letters denote DNA, $^m$c denotes a 5-methylcytosine DNA, all internucleoside linkages are phosphorothiate internucleoside linkages.

| SEQ ID No. | Target HBx | Target HBsAg | Start position on U95551 | Oligo_seq |
|---|---|---|---|---|
| SeqID 409 | | X | 602 | ATGggatgggaaTAC |
| SeqID 410 | | X | 602 | GATggatgggaaTAC |
| SeqID 411 | | X | 603 | ATGggatgggaATA |
| SeqID 412 | | X | 603 | GATgggatgggaATA |
| SeqID 413 | | X | 604 | GATgggatgggAAT |
| SeqID 414 | | X | 691 | AACcactgaacAAA |
| SeqID 415 | | X | 695 | CGaaccactgAA |
| SeqID 416 | | X | 708 | GGGggaaagccCT |
| SeqID 417 | | X | 708 | TGGgggaaagcCCT |
| SeqID 418 | | X | 1142 | GCAa$^m$cggggtaaAGG |
| SeqID 419 | | X | 1143 | GCAa$^m$cggggtaAAG |
| SeqID 420 | | X | 1144 | GCAa$^m$cggggtaAA |
| SeqID 421 | | X | 1176 | AGCaaacacttgGCA |
| SeqID 422 | | X | 1176 | CAGcaaacacttgGCA |
| SeqID 423 | | X | 1177 | CAGcaaacacttGGC |
| SeqID 424 | | X | 1177 | TCAgcaaacacttGGC |
| SeqID 425 | | X | 1178 | TCAgcaaacactTGG |
| SeqID 426 | X | | 1264 | GCAgtatggatCG |
| SeqID 427 | X | | 1264 | CGCagtatggaTCG |
| SeqID 428 | X | | 1264 | TCCgcagtatggaTCG |
| SeqID 429 | X | | 1265 | CCGcagtatggATC |
| SeqID 430 | X | | 1265 | TCCgcagtatggATC |
| SeqID 431 | X | | 1266 | CGcagtatggAT |
| SeqID 432 | X | | 1266 | CCGcagtatggAT |
| SeqID 433 | X | | 1266 | TCCgcagtatgGAT |
| SeqID 434 | X | | 1267 | TCCgcagtatgGA |
| SeqID 435 | X | | 1269 | TTc$^m$cgcagtaTG |
| SeqID 436 | X | | 1530 | CGTaaagagagGT |
| SeqID 437 | X | | 1530 | CCG$^m$cgtaaagagaGGT |
| SeqID 438 | X | | 1531 | CGtaaagagaGG |
| SeqID 439 | X | | 1531 | CGCgtaaagagaAGG |
| SeqID 440 | X | | 1531 | CCG$^m$cgtaaagagAGG |
| SeqID 441 | X | | 1532 | CGCgtaaagaGAG |
| SeqID 442 | X | | 1532 | CCG$^m$cgtaaagaGAG |
| SeqID 443 | X | | 1533 | CG$^m$cgtaaagaGA |
| SeqID 444 | X | | 1533 | CCG$^m$cgtaaagaGA |

TABLE 3-continued

LNA oligomers
Upper case letters denote beta-D-oxy LNA, C LNA is 5-methyl C LNA, lower case letters denote DNA, $^m$c denotes a 5-methylcytosine DNA, all internucleoside linkages are phosphorothiate internucleoside linkages.

| SEQ ID No. | Target HBx | Target HBsAg | Start position on U95551 | Oligo_seq |
|---|---|---|---|---|
| SeqID 445 | X | | 1534 | CCg$^m$cgtaaagAG |
| SeqID 446 | X | | 1547 | GGCacaga$^m$cgggGAG |
| SeqID 447 | X | | 1547 | AGGcacaga$^m$cgggGAG |
| SeqID 448 | X | | 1548 | GGCacaga$^m$cggGGA |
| SeqID 449 | X | | 1548 | AGGcacaga$^m$cggGGA |
| SeqID 450 | X | | 1548 | AAGgcacaga$^m$cggGGA |
| SeqID 451 | X | | 1549 | AGGcacaga$^m$cgGGG |
| SeqID 452 | X | | 1549 | AAGgcacaga$^m$cgGGG |
| SeqID 453 | X | | 1549 | GAAggcacaga$^m$cgGGG |
| SeqID 454 | X | | 1550 | AGAaggcacaga$^m$cGGG |
| SeqID 455 | X | | 1552 | GAGaaggcacagACG |
| SeqID 456 | X | | 1577 | CGAagtgcacaCGG |
| SeqID 457 | X | | 1578 | GCGaagtgcacACG |
| SeqID 458 | X | | 1579 | GCGaagtgcacAC |
| SeqID 459 | X | | 1579 | AGCgaagtgcaCAC |
| SeqID 460 | X | | 1579 | AAG$^m$cgaagtgcaCAC |
| SeqID 461 | X | | 1579 | GAAg$^m$cgaagtgcaCAC |
| SeqID 462 | X | | 1580 | AGCgaagtgcaCA |
| SeqID 463 | X | | 1580 | AAG$^m$cgaagtgcACA |
| SeqID 464 | X | | 1580 | TGAag$^m$cgaagtgcACA |
| SeqID 465 | X | | 1581 | AAG$^m$cgaagtgcAC |
| SeqID 466 | X | | 1581 | GAAg$^m$cgaagtgCAC |
| SeqID 467 | X | | 1581 | TGAag$^m$cgaagtgCAC |
| SeqID 468 | X | | 1581 | GTGaag$^m$cgaagtgCAC |
| SeqID 469 | X | | 1582 | AAg$^m$cgaagtgCA |
| SeqID 470 | X | | 1582 | GAAg$^m$cgaagtgCA |
| SeqID 471 | X | | 1582 | TGAag$^m$cgaagtGCA |
| SeqID 472 | X | | 1582 | GTGaag$^m$cgaagtGCA |
| SeqID 473 | X | | 1583 | TGAag$^m$cgaagtGC |
| SeqID 474 | X | | 1583 | GTGaag$^m$cgaagTGC |
| SeqID 475 | X | | 1584 | GTGaag$^m$cgaagTG |
| SeqID 476 | X | | 1584 | GGTgaag$^m$cgaaGTG |
| SeqID 477 | X | | 1584 | GAGgtgaag$^m$cgaaGTG |
| SeqID 478 | X | | 1585 | GTgaag$^m$cgaaGT |
| SeqID 479 | X | | 1585 | GGTgaag$^m$cgaaGT |
| SeqID 480 | X | | 1585 | GAGgtgaag$^m$cgaAGT |

TABLE 3-continued

LNA oligomers
Upper case letters denote beta-D-oxy LNA, C LNA is 5-methyl C LNA, lower case letters denote DNA, $^m$c denotes a 5-methylcytosine DNA, all internucleoside linkages are phosphorothiate internucleoside linkages.

| SEQ ID No. | Target HBx | Target HBsAg | Start position on U95551 | Oligo_seq |
|---|---|---|---|---|
| SeqID 481 | X | | 1585 | AGAggtgaag$^m$cgaAGT |
| SeqID 482 | X | | 1586 | AGAggtgaag$^m$cgAAG |
| SeqID 483 | X | | 1586 | CAGaggtgaag$^m$cgAAG |
| SeqID 484 | X | | 1587 | AGAggtgaag$^m$cGAA |
| SeqID 485 | X | | 1587 | CAGaggtgaag$^m$cGAA |
| SeqID 486 | X | | 1587 | GCAgaggtgaag$^m$cGAA |
| SeqID 487 | X | | 1588 | GCAgaggtgaagCGA |
| SeqID 488 | X | | 1588 | TGCagaggtgaagCGA |
| SeqID 489 | X | | 1589 | TGCagaggtgaaGCG |
| SeqID 490 | X | | 1589 | GTGcagaggtgaaGCG |
| SeqID 491 | X | | 1590 | CGTgcagaggtgaAGC |
| SeqID 492 | X | | 1591 | CGTgcagaggtgAAG |
| SeqID 493 | X | | 1591 | ACGtgcagaggtgAAG |
| SeqID 494 | X | | 1592 | CGTgcagaggtGAA |
| SeqID 495 | X | | 1592 | ACGtgcagaggtGAA |
| SeqID 496 | X | | 1593 | CGTgcagaggtGA |
| SeqID 497 | X | | 1593 | ACGtgcagaggTGA |
| SeqID 498 | X | | 1616 | CGTtca$^m$cggtgGT |
| SeqID 499 | X | | 1690 | CTCaaggt$^m$cggTC |
| SeqID 500 | X | | 1691 | CCTcaaggt$^m$cgGT |
| SeqID 501 | X | | 1691 | GCCtcaaggt$^m$cGGT |
| SeqID 502 | X | | 1706 | ACAgtctttgaaGTA |
| SeqID 503 | X | | 1783 | TTTatgcctacAG |
| SeqID 504 | X | | 1784 | AATttatgcctACA |
| SeqID 505 | X | | 1785 | AATttatgcctAC |
| SeqID 506 | X | | 1787 | CCAatttatgcCT |
| SeqID 507 | X | | 1865 | GCTtggaggcttGAA |
| SeqID 508 | X | | 1865 | AGCttggaggcttGAA |
| SeqID 509 | X | | 1866 | GCTtggaggctTGA |
| SeqID 510 | X | | 1866 | AGCttggaggctTGA |
| SeqID 511 | X | | 1866 | CAGcttggaggctTGA |
| SeqID 512 | X | | 1867 | GCTtggaggctTG |
| SeqID 513 | X | | 1867 | AGCttggaggcTTG |
| SeqID 514 | X | | 1867 | CAGcttggaggcTTG |
| SeqID 515 | X | | 1867 | ACAgcttggaggcTTG |
| SeqID 516 | X | | 1868 | CACagcttggaggCTT |

TABLE 3-continued

LNA oligomers
Upper case letters denote beta-D-oxy LNA, C LNA is 5-methyl C LNA, lower case letters denote DNA, ᵐc denotes a 5-methylcytosine DNA, all internucleoside linkages are phosphorothiate internucleoside linkages.

| SEQ ID No. | Target HBx | Target HBsAg | Start position on U95551 | Oligo_seq |
|---|---|---|---|---|
| SeqID 517 | X | | 1869 | CACagcttggagGCT |
| SeqID 518 | X | | 1869 | GCAcagcttggagGCT |
| SeqID 519 | X | | 1870 | GCAcagcttggaGGC |
| SeqID 520 | X | | 1870 | GGCacagcttggaGGC |
| SeqID 521 | X | | 1871 | AGGcacagcttggAGG |
| SeqID 522 | X | | 1872 | AGGcacagcttgGAG |
| SeqID 523 | X | | 1872 | AAGgcacagcttgGAG |
| SeqID 524 | X | | 1873 | AAGgcacagcttGGA |
| SeqID 525 | X | | 1873 | CAAggcacagcttGGA |
| SeqID 526 | X | | 1874 | AAGgcacagctTGG |
| SeqID 527 | X | | 1874 | CAAggcacagctTGG |
| SeqID 528 | X | | 1874 | CCAaggcacagctTGG |
| SeqID 529 | X | | 1875 | CAAggcacagcTTG |
| SeqID 530 | X | | 1875 | CCAaggcacagcTTG |
| SeqID 531 | X | | 1876 | CCAaggcacagCTT |
| SeqID 532 | | | 2272 | TGCgaatccacAC |
| SeqID 533 | | | 2272 | GTGᵐcgaatccaCAC |
| SeqID 534 | | | 2370 | GGAgttcttcttCTA |
| SeqID 535 | | | 2370 | GGGagttcttcttCTA |
| SeqID 536 | | | 2371 | GGGagttcttctTCT |
| SeqID 537 | | | 2371 | AGGgagttcttctTCT |
| SeqID 538 | | | 2372 | AGGgagttcttcTTC |
| SeqID 539 | | | 2372 | GAGggagttcttTTC |
| SeqID 540 | | | 2373 | AGGgagttcttCTT |
| SeqID 541 | | | 2373 | GAGggagttcttCTT |
| SeqID 542 | | | 2373 | CGAgggagttcttCTT |
| SeqID 543 | | | 2374 | CGAgggagttctTCT |
| SeqID 544 | | | 2374 | GCGagggagttctTCT |
| SeqID 545 | | | 2375 | GCGagggagttcTTC |
| SeqID 546 | | | 2375 | GGCgagggagttcTTC |
| SeqID 547 | | | 2376 | GCGagggagttCTT |
| SeqID 548 | | | 2376 | GGCgagggagttCTT |
| SeqID 549 | | | 2376 | AGGᵐcgagggagttCTT |
| SeqID 550 | | | 2377 | GCGagggagttCT |
| SeqID 551 | | | 2377 | GGCgagggagtTCT |
| SeqID 552 | | | 2377 | AGGᵐcgagggagtTCT |

TABLE 3-continued

LNA oligomers
Upper case letters denote beta-D-oxy LNA, C LNA is 5-methyl C LNA, lower case letters denote DNA, $^m$c denotes a 5-methylcytosine DNA, all internucleoside linkages are phosphorothiate internucleoside linkages.

| SEQ ID No. | Target HBx | Target HBsAg | Start position on U95551 | Oligo_seq |
|---|---|---|---|---|
| SeqID 553 | | | 2377 | GAGg$^m$cgagggagtTCT |
| SeqID 554 | | | 2378 | GGCgagggagtTC |
| SeqID 555 | | | 2378 | AGG$^m$cgagggagTTC |
| SeqID 556 | | | 2378 | GAGg$^m$cgagggagTTC |
| SeqID 557 | | | 2378 | CGAgg$^m$cgagggagTTC |
| SeqID 558 | | | 2379 | AGG$^m$cgagggagTT |
| SeqID 559 | | | 2379 | GAGg$^m$cgagggaGTT |
| SeqID 560 | | | 2379 | CGAgg$^m$cgagggaGTT |
| SeqID 561 | | | 2379 | GCGagg$^m$cgagggaGTT |
| SeqID 562 | | | 2380 | GAGg$^m$cgagggaGT |
| SeqID 563 | | | 2380 | CGAgg$^m$cgagggAGT |
| SeqID 564 | | | 2380 | GCGagg$^m$cgagggAGT |
| SeqID 565 | | | 2380 | TGCgagg$^m$cgagggAGT |
| SeqID 566 | | | 2381 | CGAgg$^m$cgagggAG |
| SeqID 567 | | | 2381 | GCGagg$^m$cgaggGAG |
| SeqID 568 | | | 2381 | TGCgagg$^m$cgaggGAG |
| SeqID 569 | | | 2381 | CTG$^m$cgagg$^m$cgaggGAG |
| SeqID 570 | | | 2382 | CGagg$^m$cgaggGA |
| SeqID 571 | | | 2382 | GCGagg$^m$cgaggGA |
| SeqID 572 | | | 2382 | TGCgagg$^m$cgagGGA |
| SeqID 573 | | | 2382 | CTG$^m$cgagg$^m$cgagGGA |
| SeqID 574 | | | 2382 | TCTg$^m$cgagg$^m$cgagGGA |
| SeqID 575 | | | 2383 | TCTg$^m$cgagg$^m$cgaGGG |
| SeqID 576 | | | 2383 | GTCtg$^m$cgagg$^m$cgaGGG |
| SeqID 577 | | | 2824 | GTTcccaagaaTAT |
| SeqID 578 | | | 2824 | TGTtcccaagaaTAT |
| SeqID 579 | | | 2825 | GTTcccaagaaTA |
| SeqID 580 | | | 2825 | TGTtcccaagaATA |
| SeqID 581 | | | 2825 | TTGttcccaagaATA |
| SeqID 582 | | | 2826 | TGTtcccaagaAT |
| SeqID 583 | | | 2826 | TTGttcccaagAAT |
| SeqID 584 | X | | 414 | GAGGcatagcagCAGG |
| SeqID 585 | | | 691 | GAAccactgaaCAAA |
| SeqID 586 | | | 691 | GAACcactgaacAAA |
| SeqID 587 | | | 691 | CGaaccactgaaCAAA |
| SeqID 588 | | | 691 | CGAAccactgaacAAA |

TABLE 3-continued

LNA oligomers
Upper case letters denote beta-D-oxy LNA, C LNA is 5-methyl C LNA, lower case letters denote DNA, ᵐc denotes a 5-methylcytosine DNA, all internucleoside linkages are phosphorothiate internucleoside linkages.

| SEQ ID No. | Target HBx | Target HBsAg | Start position on U95551 | Oligo_seq |
|---|---|---|---|---|
| SeqID 589 | | | 691 | CGAaccactgaaCAAA |
| SeqID 590 | | | 691 | CGAAccactgaacaAA |
| SeqID 591 | | | 691 | CGAAccactgaaCAAA |
| SeqID 592 | | | 692 | CGAAccactgaacAA |
| SeqID 593 | | | 692 | CGAAccactgaaCAA |
| SeqID 594 | | | 692 | CGAaccactgaACAA |
| SeqID 595 | | | 693 | CGaaccactgAACA |
| SeqID 596 | | | 693 | CGAAccactgaaCA |
| SeqID 597 | | | 693 | CGAaccactgAACA |
| SeqID 598 | | | 693 | CGAAccactgaACA |
| SeqID 599 | | | 694 | CGaaccactgAAC |
| SeqID 600 | | | 694 | CGAaccactgAAC |
| SeqID 601 | | | 1264 | CCgcagtatggATCG |
| SeqID 602 | | | 1264 | CCGCagtatggatCG |
| SeqID 603 | | | 1264 | CCGCagtatggaTCG |
| SeqID 604 | | | 1264 | CCGcagtatggATCG |
| SeqID 605 | | | 1265 | CGCAgtatggaTC |
| SeqID 606 | | | 1265 | CGcagtatggATC |
| SeqID 607 | | | 1265 | CGCagtatggATC |
| SeqID 608 | | | 1265 | CGcagtatgGATC |
| SeqID 609 | | | 1530 | GCGTaaagagagGT |
| SeqID 610 | | | 1530 | GCgtaaagagAGGT |
| SeqID 611 | | | 1530 | GCGtaaagagAGGT |
| SeqID 612 | | | 1530 | GCGTaaagagaGGT |
| SeqID 613 | | | 1530 | CGCGtaaagagagGT |
| SeqID 614 | | | 1530 | CGCgtaaagagAGGT |
| SeqID 615 | | | 1530 | CGCGtaaagagaGGT |
| SeqID 616 | | | 1530 | CGCgtaaagagAGGT |
| SeqID 617 | | | 1531 | GCgtaaagagAGG |
| SeqID 618 | | | 1531 | GCGtaaagagAGG |
| SeqID 619 | | | 1531 | GCgtaaagaGAGG |
| SeqID 620 | | | 1531 | GCGTaaagagaGG |
| SeqID 621 | | | 1551 | AGaaggcacagACGG |
| SeqID 622 | | | 1551 | AGAaggcacagACGG |
| SeqID 623 | | | 1551 | AGAAggcacagaCGG |
| SeqID 624 | | | 1551 | GAGAaggcacagaCGG |

TABLE 3-continued

LNA oligomers
Upper case letters denote beta-D-oxy LNA, C LNA is 5-methyl C LNA, lower case letters denote DNA, ᵐc denotes a 5-methylcytosine DNA, all internucleoside linkages are phosphorothiate internucleoside linkages.

| SEQ ID No. | Target HBx | Target HBsAg | Start position on U95551 | Oligo_seq |
|---|---|---|---|---|
| SeqID 625 | | | 1551 | GAGaaggcacagACGG |
| SeqID 626 | | | 1551 | GAGAaggcacagACGG |
| SeqID 627 | | | 1577 | GAagtgcacaCGG |
| SeqID 628 | | | 1577 | GAAgtgcacaCGG |
| SeqID 629 | | | 1577 | GAAGtgcacaCGG |
| SeqID 630 | | | 1577 | GAAgtgcacACGG |
| SeqID 631 | | | 1577 | GCgaagtgcacaCGG |
| SeqID 632 | | | 1577 | GCGaagtgcacacGG |
| SeqID 633 | | | 1577 | GCGAagtgcacacGG |
| SeqID 634 | | | 1577 | GCgaagtgcacACGG |
| SeqID 635 | | | 1577 | AGCGaagtgcacacGG |
| SeqID 636 | | | 1577 | AGᵐcgaagtgcacACGG |
| SeqID 637 | | | 1577 | AGᵐcgaagtgcacaCGG |
| SeqID 638 | | | 1577 | AGCgaagtgcacacGG |
| SeqID 639 | | | 1578 | CGaagtgcaCACG |
| SeqID 640 | | | 1578 | CGAagtgcacACG |
| SeqID 641 | | | 1578 | CGaagtgcacACG |
| SeqID 642 | | | 1578 | AGCgaagtgcaCACG |
| SeqID 643 | | | 1578 | AGCGaagtgcacACG |
| SeqID 644 | | | 1578 | AGCGaagtgcacaCG |
| SeqID 645 | | | 1578 | AGᵐcgaagtgcaCACG |
| SeqID 646 | | | 1578 | AAgᵐcgaagtgcaCACG |
| SeqID 647 | | | 1578 | AAGCgaagtgcacaCG |
| SeqID 648 | | | 1578 | AAGᵐcgaagtgcaCACG |
| SeqID 649 | | | 1578 | AAGCgaagtgcacACG |
| SeqID 650 | | | 1578 | AAGCgaagtgcaCACG |
| SeqID 651 | | | 1580 | GAagᵐcgaagtgCACA |
| SeqID 652 | | | 1580 | GAAGᵐcgaagtgcaCA |
| SeqID 653 | | | 1580 | GAAgᵐcgaagtgCACA |
| SeqID 654 | | | 1580 | GAAGᵐcgaagtgCACA |
| SeqID 655 | | | 1582 | GGtgaagᵐcgaagtGCA |
| SeqID 656 | | | 1582 | GGTgaagᵐcgaagtgCA |
| SeqID 657 | | | 1582 | GGTGaagᵐcgaagtgCA |
| SeqID 658 | | | 1582 | GGtgaagᵐcgaagTGCA |
| SeqID 659 | | | 1583 | GGtgaagᵐcgaagTGC |
| SeqID 660 | | | 1583 | GGTgaagᵐcgaagtGC |

TABLE 3-continued

LNA oligomers
Upper case letters denote beta-D-oxy LNA, C LNA is 5-methyl C LNA, lower case letters denote DNA, $^m$c denotes a 5-methylcytosine DNA, all internucleoside linkages are phosphorothiate internucleoside linkages.

| SEQ ID No. | Target HBx | Target HBsAg | Start position on U95551 | Oligo_seq |
|---|---|---|---|---|
| SeqID 661 | | | 1583 | GGTGaag$^m$cgaagtGC |
| SeqID 662 | | | 1583 | GGtgaag$^m$cgaaGTGC |
| SeqID 663 | | | 1583 | AGgtgaag$^m$cgaagTGC |
| SeqID 664 | | | 1583 | AGGtgaag$^m$cgaagtGC |
| SeqID 665 | | | 1583 | AGGTgaag$^m$cgaagtGC |
| SeqID 666 | | | 1583 | AGgtgaag$^m$cgaaGTGC |
| SeqID 667 | | | 1584 | AGGTgaag$^m$cgaagTG |
| SeqID 668 | | | 1584 | AGgtgaag$^m$cgaAGTG |
| SeqID 669 | | | 1584 | AGGtgaag$^m$cgaAGTG |
| SeqID 670 | | | 1584 | AGGTgaag$^m$cgaaGTG |
| SeqID 671 | | | 1585 | AGGTgaag$^m$cgaaGT |
| SeqID 672 | | | 1585 | AGgtgaag$^m$cgAAGT |
| SeqID 673 | | | 1585 | AGGtgaag$^m$cgAAGT |
| SeqID 674 | | | 1585 | AGGTgaag$^m$cgaAGT |
| SeqID 675 | | | 1588 | CAGAggtgaagcGA |
| SeqID 676 | | | 1588 | CAgaggtgaaGCGA |
| SeqID 677 | | | 1588 | CAGaggtgaaGCGA |
| SeqID 678 | | | 670 | TAGtaaactgagCCA |
| SeqID 679 | | | 670 | TAgtaaactgaGCCA |
| SeqID 680 | | | 670 | TAGTaaactgagcCA |
| SeqID 681 | | | 670 | TAGtaaactgaGCCA |
| SeqID 682 | | | 670 | TAGTaaactgagCCA |
| SeqID 683 | | | 670 | CTAgtaaactgagCCA |
| SeqID 684 | | | 670 | CTagtaaactgaGCCA |
| SeqID 685 | | | 670 | CTAGtaaactgagcCA |
| SeqID 686 | | | 671 | CTAgtaaactgaGCC |
| SeqID 687 | | | 671 | CTagtaaactgAGCC |
| SeqID 688 | | | 671 | CTAGtaaactgagCC |
| SeqID 689 | | | 671 | CTagtaaactgaGCC |
| SeqID 690 | | | 671 | CTAgtaaactgagCC |
| SeqID 691 | | | 674 | GCActagtaaacTGA |
| SeqID 692 | | | 674 | GCactagtaaaCTGA |
| SeqID 693 | | | 674 | GCACtagtaaactGA |
| SeqID 694 | | | 674 | GCActagtaaaCTGA |
| SeqID 695 | | | 674 | GCACtagtaaacTGA |
| SeqID 696 | | | 674 | GGCactagtaaacTGA |

TABLE 3-continued

LNA oligomers
Upper case letters denote beta-D-oxy LNA, C LNA is 5-methyl C LNA, lower case letters denote DNA, $^m$c denotes a 5-methylcytosine DNA, all internucleoside linkages are phosphorothiate internucleoside linkages.

| SEQ ID No. | Target HBx | Target HBsAg | Start position on U95551 | Oligo_seq |
|---|---|---|---|---|
| SeqID 697 | | | 674 | GGcactagtaaaCTGA |
| SeqID 698 | | | 674 | GGCActagtaaactGA |
| SeqID 699 | | | 1141 | CAA$^m$cggggtaaaGGT |
| SeqID 700 | | | 1141 | CAa$^m$cggggtaaAGGT |
| SeqID 701 | | | 1141 | CAACggggtaaagGT |
| SeqID 702 | | | 1141 | CAA$^m$cggggtaaAGGT |
| SeqID 703 | | | 1141 | CAACggggtaaaGGT |
| SeqID 704 | | | 1261 | CAGtatggat$^m$cgGCA |
| SeqID 705 | | | 1261 | CAgtatggat$^m$cGGCA |
| SeqID 706 | | | 1261 | CAgtatggat$^m$cgGCA |
| SeqID 707 | | | 1261 | CAGtatggat$^m$cggCA |
| SeqID 708 | | | 1265 | TTC$^m$cgcagtatggATC |
| SeqID 709 | | | 1265 | TTc$^m$cgcagtatgGATC |
| SeqID 710 | | | 1265 | TTCCgcagtatggaTC |
| SeqID 711 | | | 1265 | TTC$^m$cgcagtatgGATC |
| SeqID 712 | | | 1265 | TTCCgcagtatggATC |
| SeqID 713 | | | 1266 | TTC$^m$cgcagtatgGAT |
| SeqID 714 | | | 1266 | TTc$^m$cgcagtatGGAT |
| SeqID 715 | | | 1266 | TTCCgcagtatggAT |
| SeqID 716 | | | 1266 | TTC$^m$cgcagtatGGAT |
| SeqID 717 | | | 1266 | TTCCgcagtatgGAT |
| SeqID 718 | | | 1266 | GTTc$^m$cgcagtatgGAT |
| SeqID 719 | | | 1266 | GTtc$^m$cgcagtatGGAT |
| SeqID 720 | | | 1266 | GTTC$^m$cgcagtatggAT |
| SeqID 721 | | | 1267 | GTtc$^m$cgcagtaTGGA |
| SeqID 722 | | | 1267 | GTTC$^m$cgcagtatgGA |
| SeqID 723 | | | 1267 | GTtc$^m$cgcagtatGGA |
| SeqID 724 | | | 1267 | GTTc$^m$cgcagtatgGA |
| SeqID 725 | | | 1267 | AGTtc$^m$cgcagtatGGA |
| SeqID 726 | | | 1267 | AGTTc$^m$cgcagtatgGA |
| SeqID 727 | | | 1267 | AGttc$^m$cgcagtatGGA |
| SeqID 728 | | | 1267 | AGTtc$^m$cgcagtatgGA |
| SeqID 729 | | | 1267 | AGttc$^m$cgcagtatgGA |
| SeqID 730 | | | 1268 | AGTtc$^m$cgcagtaTGG |
| SeqID 731 | | | 1268 | AGttc$^m$cgcagtaTGG |
| SeqID 732 | | | 1268 | AGTtc$^m$cgcagtatGG |

TABLE 3-continued

LNA oligomers
Upper case letters denote beta-D-oxy LNA, C LNA is 5-methyl C LNA, lower case letters denote DNA, ᵐc denotes a 5-methylcytosine DNA, all internucleoside linkages are phosphorothiate internucleoside linkages.

| SEQ ID No. | Target HBx | Target HBsAg | Start position on U95551 | Oligo_seq |
|---|---|---|---|---|
| SeqID 733 | | | 1268 | AGttcᵐcgcagtatGG |
| SeqID 734 | | | 1268 | GAgttcᵐcgcagtaTGG |
| SeqID 735 | | | 1268 | GAGttcᵐcgcagtatGG |
| SeqID 736 | | | 1268 | GAgttcᵐcgcagtatGG |
| SeqID 737 | | | 1269 | GAGTtcᵐcgcagtaTG |
| SeqID 738 | | | 1269 | GAgttcᵐcgcagtATG |
| SeqID 739 | | | 1269 | GAGttcᵐcgcagtaTG |
| SeqID 740 | | | 1269 | GAgttcᵐcgcagtaTG |
| SeqID 741 | | | 1269 | GGAGttcᵐcgcagtaTG |
| SeqID 742 | | | 1269 | GGagttcᵐcgcagtATG |
| SeqID 743 | | | 1269 | GGAgttcᵐcgcagtaTG |
| SeqID 744 | | | 1269 | GGagttcᵐcgcagtaTG |
| SeqID 745 | | | 1525 | TAAagagaggtgᵐcGCC |
| SeqID 746 | | | 1525 | TAaagagaggtgCGCC |
| SeqID 747 | | | 1525 | TAAAgagaggtgᵐcgCC |
| SeqID 748 | | | 1525 | TAAagagaggtgCGCC |
| SeqID 749 | | | 1525 | TAAagagaggtgᵐcGCC |
| SeqID 750 | | | 1526 | TAAagagaggtgCGC |
| SeqID 751 | | | 1526 | TAaagagaggtGCGC |
| SeqID 752 | | | 1526 | TAAagagaggtGCGC |
| SeqID 753 | | | 1526 | TAAAgagaggtgCGC |
| SeqID 754 | | | 1526 | GTAaagagaggtgCGC |
| SeqID 755 | | | 1526 | GTaaagagaggtGCGC |
| SeqID 756 | | | 1527 | GTAaagagaggtGCG |
| SeqID 757 | | | 1527 | GTaaagagaggTGCG |
| SeqID 758 | | | 1527 | GTAaagagaggTGCG |
| SeqID 759 | | | 1527 | GTAAagagaggtGCG |
| SeqID 760 | | | 1527 | CGtaaagagaggTGCG |
| SeqID 761 | | | 1527 | CGTAaagagaggtgCG |
| SeqID 762 | | | 1527 | CGTaaagagaggTGCG |
| SeqID 763 | | | 1527 | CGTAaagagaggtGCG |
| SeqID 764 | | | 1528 | CGTaaagagaggTGC |
| SeqID 765 | | | 1528 | CGtaaagagaGTGC |
| SeqID 766 | | | 1528 | CGTAaagagaggtGC |
| SeqID 767 | | | 1528 | CGTaaagagaGTGC |
| SeqID 768 | | | 1528 | CGTAaagagaggTGC |

TABLE 3-continued

LNA oligomers
Upper case letters denote beta-D-oxy LNA, C LNA is 5-methyl C LNA, lower case letters denote DNA, ᵐc denotes a 5-methylcytosine DNA, all internucleoside linkages are phosphorothiate internucleoside linkages.

| SEQ ID No. | Target HBx | Target HBsAg | Start position on U95551 | Oligo_seq |
|---|---|---|---|---|
| SeqID 769 | | | 1528 | GCGtaaagagaggTGC |
| SeqID 770 | | | 1528 | GCgtaaagagagGTGC |
| SeqID 771 | | | 1528 | GCGtaaagagaggTGC |
| SeqID 772 | | | 1528 | GCGtaaagagaggtGC |
| SeqID 773 | | | 1529 | GCGtaaagagagGTG |
| SeqID 774 | | | 1529 | GCgtaaagagaGGTG |
| SeqID 775 | | | 1529 | GCGTaaagagaggTG |
| SeqID 776 | | | 1529 | GCgtaaagagaGGTG |
| SeqID 777 | | | 1529 | GCGTaaagagagGTG |
| SeqID 778 | | | 1529 | CGCgtaaagagagGTG |
| SeqID 779 | | | 1529 | ᵐcgᵐcgtaaagagaGGTG |
| SeqID 780 | | | 1529 | CGCGtaaagagggTG |
| SeqID 781 | | | 1529 | CGCgtaaagagaGGTG |
| SeqID 782 | | | 1529 | CGCGtaaagagagGTG |
| SeqID 783 | | | 1552 | TGAgaaggcacagACG |
| SeqID 784 | | | 1552 | TGagaaggcacaGACG |
| SeqID 785 | | | 1552 | TGAGaaggcacagaCG |
| SeqID 786 | | | 1552 | TGAgaaggcacaGACG |
| SeqID 787 | | | 1552 | TGAGaaggcacagACG |
| SeqID 788 | | | 1690 | GCctcaaggtᵐcgGTC |
| SeqID 789 | | | 1690 | GCCtcaaggtᵐcggTC |
| SeqID 790 | | | 1690 | GCctcaaggtᵐcggTC |
| SeqID 791 | | | 1778 | ATgcctacagccTCC |
| SeqID 792 | | | 1778 | ATGcctacagcctCC |
| SeqID 793 | | | 1778 | ATgcctacagcctCC |
| SeqID 794 | | | 1785 | ACCAatttatgcCTAC |
| SeqID 795 | | | 1785 | ACCaatttatgcCTAC |
| SeqID 796 | | | 1785 | ACCAatttatgccTAC |
| SeqID 797 | | | 1785 | ACCaatttatgccTAC |
| SeqID 798 | | | 1785 | ACCaatttatgcCTAC |

TABLE 4

LNA oligomers with a GalNAc2 conjugate moiety linked via a C6 amino linker and a cleavable ca phosphodiester linkage to the oligomer. The GalNAc2 conjugate moiety can also be substituted with other GalNAc conjugate moieties or sterol moieties. The oligomer sequence motif which these oligomers are based on is a subset from Table 2 and 3. Upper case letters denote beta-D-oxy LNA, lower case letters denote DNA, $^mc/^mc$ denotes a 5-methylcytosine DNA/LNA, s denotes phosphorothiate internucleoside linkages. Where nothing is specified the linkage is a phosphodiester internucleoside linkage

| SEQ ID No | Design |
|---|---|
| SeqID 799 | 5'-GN2-C6 caG$_s$A$_s$A$_s$c$_s$c$_s$a$_s$c$_s$t$_s$g$_s$a$_s$a$_s$c$_s$A$_s$A$_s$A$_s$-3' |
| SeqID 800 | 5'-GN2-C6 ca$^m$C$_s$G$_s$A$_s$a$_s$c$_s$c$_s$a$_s$c$_s$t$_s$g$_s$a$_s$a$_s$c$_s$A$_s$A$_s$A-3' |
| SeqID 801 | 5'-GN2-C6 ca$^m$C$_s$G$_s$A$_s$a$_s$c$_s$c$_s$a$_s$c$_s$t$_s$g$_s$a$_s$a$_s$$^m$C$_s$A$_s$A-3' |
| SeqID 802 | 5'-GN2-C6 ca$^m$C$_s$$^m$C$_s$G$_s$c$_s$a$_s$g$_s$t$_s$a$_s$t$_s$g$_s$g$_s$a$_s$T$_s$$^m$C$_s$G-3' |
| SeqID 803 | 5'-GN2-C6 ca$^m$C$_s$G$_s$C$_s$g$_s$t$_s$a$_s$a$_s$a$_s$g$_s$a$_s$g$_s$a$_s$G$_s$G$_s$T-3' |
| SeqID 804 | 5'-GN2-C6 caA$_s$G$_s$A$_s$a$_s$g$_s$g$_s$c$_s$a$_s$c$_s$a$_s$g$_s$a$_s$$^m$C$_s$G$_s$G-3' |
| SeqID 805 | 5'-GN2-C6 caG$_s$A$_s$G$_s$a$_s$a$_s$g$_s$g$_s$c$_s$a$_s$c$_s$a$_s$g$_s$a$_s$$^m$C$_s$G$_s$G-3' |
| SeqID 806 | 5'-GN2-C6 caG$_s$$^m$C$_s$G$_s$a$_s$a$_s$g$_s$t$_s$g$_s$c$_s$a$_s$c$_s$a$_s$$^m$C$_s$G$_s$G-3' |
| SeqID 807 | 5'-GN2-C6 caA$_s$G$_s$$^m$C$_s$g$_s$a$_s$a$_s$g$_s$t$_s$g$_s$c$_s$a$_s$c$_s$a$_s$$^m$C$_s$G$_s$G-3' |
| SeqID 808 | 5'-GN2-C6 caA$_s$G$_s$$^m$C$_s$g$_s$a$_s$a$_s$g$_s$t$_s$g$_s$c$_s$a$_s$c$_s$A$_s$$^m$C$_s$G-3' |
| SeqID 809 | 5'-GN2-C6 caA$_s$G$_s$G$_s$t$_s$g$_s$a$_s$a$_s$g$_s$$^m$c$_s$g$_s$a$_s$a$_s$g$_s$T$_s$G$_s$$^m$C-3' |
| SeqID 810 | 5'-GN2-C6 caA$_s$G$_s$G$_s$t$_s$g$_s$a$_s$a$_s$g$_s$$^m$c$_s$g$_s$a$_s$a$_s$G$_s$T$_s$G-3' |
| SeqID 811 | 5'-GN2-C6 ca$^m$C$_s$G$_s$A$_s$a$_s$c$_s$c$_s$a$_s$c$_s$t$_s$g$_s$a$_s$A$_s$$^m$C$_s$A-3' |
| SeqID 812 | 5'-GN2-C6 ca$^m$C$_s$G$_s$A$_s$a$_s$c$_s$c$_s$a$_s$c$_s$t$_s$g$_s$a$_s$A$_s$$^m$C-3' |
| SeqID 813 | 5'-GN2-C6 ca$^m$C$_s$G$_s$$^m$C$_s$a$_s$g$_s$t$_s$a$_s$t$_s$g$_s$g$_s$a$_s$T$_s$$^m$C-3' |
| SeqID 814 | 5'-GN2-C6 caG$_s$$^m$C$_s$G$_s$t$_s$a$_s$a$_s$a$_s$g$_s$a$_s$g$_s$a$_s$G$_s$G$_s$T-3' |
| SeqID 815 | 5'-GN2-C6 caG$_s$$^m$C$_s$G$_s$t$_s$a$_s$a$_s$a$_s$g$_s$a$_s$g$_s$a$_s$G$_s$G-3' |
| SeqID 816 | 5'-GN2-C6 caG$_s$A$_s$A$_s$g$_s$t$_s$g$_s$c$_s$a$_s$c$_s$a$_s$$^m$c$_s$G$_s$G-3' |
| SeqID 817 | 5'-GN2-C6 ca$^m$C$_s$G$_s$A$_s$a$_s$g$_s$t$_s$g$_s$c$_s$a$_s$c$_s$a$_s$$^m$C$_s$G-3' |
| SeqID 818 | 5'-GN2-C6 caA$_s$G$_s$G$_s$t$_s$g$_s$a$_s$a$_s$g$_s$$^m$c$_s$g$_s$a$_s$A$_s$G$_s$T-3' |
| SeqID 819 | 5'-GN2-C6 caG$_s$A$_s$A$_s$c$_s$c$_s$a$_s$c$_s$t$_s$g$_s$a$_s$a$_s$$^m$C$_s$A$_s$A$_s$A-3' |
| SeqID 820 | 5'-GN2-C6 ca$^m$C$_s$G$_s$A$_s$A$_s$c$_s$c$_s$a$_s$c$_s$t$_s$g$_s$a$_s$a$_s$c$_s$A$_s$A$_s$A-3' |
| SeqID 821 | 5'-GN2-C6 caG$_s$A$_s$A$_s$g$_s$t$_s$g$_s$c$_s$a$_s$c$_s$a$_s$$^m$C$_s$G$_s$G-3' |
| SeqID 822 | 5'-GN2-C6 caT$_s$A$_s$G$_s$t$_s$a$_s$a$_s$a$_s$c$_s$t$_s$g$_s$a$_s$g$_s$$^m$C$_s$$^m$C$_s$A$_s$3' |
| SeqID 823 | 5'-GN2-C6 ca$^m$C$_s$G$_s$A$_s$a$_s$c$_s$c$_s$a$_s$c$_s$t$_s$g$_s$A$_s$A$_s$$^m$C-3' |
| SeqID 824 | 5'-GN2-C6 ca$^m$C$_s$G$_s$A$_s$a$_s$c$_s$c$_s$a$_s$c$_s$t$_s$g$_s$A$_s$A$_s$$^m$C$_s$A-3' |
| SeqID 825 | 5'-GN2-C6 caG$_s$$^m$C$_s$G$_s$t$_s$a$_s$a$_s$a$_s$g$_s$a$_s$g$_s$A$_s$G$_s$G-3' |
| SeqID 826 | 5'-GN2-C6 caA$_s$G$_s$g$_s$t$_s$g$_s$a$_s$a$_s$g$_s$$^m$c$_s$g$_s$a$_s$A$_s$G$_s$T$_s$G-3' |

Prior to conjugation with GalNAc, the LNA oligomers of table 4 are represented as AM-C6 ca-oligomer, where AM-C6 represents an amino linker ready for conjugation and ca is a cleavable phosphodiester linkage. These oligomers are incorporated by reference from table 4 in the priority application GB1408623.5.

Embodiments

The following embodiments of the present invention, presented as numbered paragraphs, may be used in combination with the other embodiments described herein:

1. An oligomer conjugate for use in the treatment of a viral disorder, wherein said oligomer conjugate comprises:

a) at least one first oligomer region capable of modulating a target sequence of Hepatitis B Virus (HBV), preferably HBx or HBsAg of HBV, to treat said viral disorder; and
b) a carrier component for delivering said first oligomer to the liver.

2. The oligomer conjugate for the use according to paragraph 1 wherein said carrier component is capable of delivering said oligomer to the liver of a subject to be treated by administration of said oligomer conjugate.

3. The oligomer conjugate for the use according to paragraph 1 or paragraph 2 wherein said carrier component is capable of delivering said oligomer to a hepatocyte of a subject to be treated by administration of said oligomer conjugate.

4. The oligomer conjugate for the use according to any of paragraphs 1 to 3 wherein said carrier component is a carbohydrate conjugate moiety.

5. The oligomer conjugate for the use according to any of paragraphs 1 to 4 wherein said carrier component is an asialoglycoprotein receptor (ASGP-R) targeting moiety.

6. The oligomer conjugate for the use according to paragraphs 4 or 5 wherein said carbohydrate conjugate moiety or ASGP-R targeting moiety is selected from the group consisting of galactose, galactosamine, N-formyl-galactosamine, N-acetylgalactosamine (GalNAc), N-propionyl-galactosamine, N-n-butanoyl-galactosamine, N-isobutanoylgalactose-amine or a cluster of any one or more thereof.

7. The oligomer conjugate for the use according to any of paragraphs 1 to 6 wherein said carrier component is a GalNAc cluster comprising two to four terminal galactose derivatives, a hydrophilic spacer linking each galactose derivative to a branch point group.

8. The oligomer conjugate for the use according to paragraph 7, wherein the galactose derivatives are GalNAc, the spacer is a PEG spacer and the branch point group is a comprising a peptide, with two or more amino groups, such as a di-lysine or tri-lysine.

9. The oligomer conjugate for the use according to any of paragraphs 1 to 8 wherein said carrier component is GalNAc2.

10. The oligomer conjugate for the use according to any of paragraphs 1 to 9 wherein said first oligomer region has at least 80% complementarity to the target sequence.

11. The oligomer conjugate for the use according to any of paragraphs 1 to 10 wherein said first oligomer region comprises one or more LNA units.

12. The oligomer conjugate for the use according to any of paragraphs 1 to 11 wherein said first oligomer region is a gapmer.

13. The oligomer conjugate for the use according to any of paragraphs 1 to 12 wherein said first oligomer region comprises a 2'-deoxyribonucleotide gap region flanked on each side by a wing, wherein each wing independently comprises one or more LNA units.

14. The oligomer conjugate for the use according to any of paragraphs 1 to 13 wherein said first oligomer region comprises any one of the motifs: 2-8-2, 3-8-3, 2-8-3, 3-8-2, 2-9-2, 3-9-3, 2-9-3, 3-9-2, 2-10-2, 3-10-3, 3-10-2, 2-10-3 wherein the first number is the number of LNA units in the 5' LNA wing region, the second number is the number of nucleotides in the gap region, and the third number is the number of LNA units in the 3' LNA wing region.

15. The oligomer conjugate for the use according to any of paragraph 1 to 14 wherein said first oligomer region is 8-30 nucleotides in length.

16. The oligomer conjugate for the use according to any of paragraphs 1 to 15 wherein said first oligomer region is 10-20 nucleotides in length.

17. The oligomer conjugate for the use according to any of paragraphs 1 to 16 wherein said first oligomer region is 10 to 16 nucleotides in length.

18. The oligomer conjugate for the use according to any of paragraphs 1 to 17 wherein said first oligomer region is 10 to 14 nucleotides in length.

19. The oligomer conjugate for the use according to any of paragraphs 1 to 18 wherein said first oligomer region binds to the target sequence.

20. The oligomer conjugate for the use according to any of paragraphs 1 to 19 wherein said first oligomer region is capable of inhibiting any one or more of the expression, replication or translation of the target sequence.

21. The oligomer conjugate for the use according to any of paragraphs 1 to 20 wherein said first oligomer region is capable of inhibiting the expression of the target sequence.

22. The oligomer conjugate for the use according to any of paragraphs 1 to 21 wherein said target sequence is a gene or a mRNA.

23. The oligomer conjugate for the use according to any of paragraphs 1 to 22 wherein said target sequence comprises at least part of a gene or a mRNA encoding HBx or HBsAg or a naturally-occurring variant thereof.

24. The oligomer conjugate for the use according to any of paragraphs 1 to 23 wherein said target sequence is a gene or a mRNA encoding HBx or HBsAg or a naturally-occurring variant thereof.

25. The oligomer conjugate for the use according to any of paragraphs 1 to 24 wherein said target sequence is within the sequence shown as SEQ ID No. 1 and/or SEQ ID No. 2, or a sequence that has at least 80% identity thereto, preferably at least 85% identity thereto, preferably at least 90% identity thereto, preferably at least 95% identity thereto.

26. The oligomer conjugate for the use according to any of paragraphs 1 to 24 wherein said target sequence is within the sequence shown as SEQ ID No. 1 and SEQ ID No. 2.

27. The oligomer conjugate for the use according to any of paragraphs 1 to 26 wherein said target sequence has at least 80%, at least 85%, at least 90%, at least 95%, at least 98% or at least 99% identity with any one or more of the HBV genotypes A-H.

28. The oligomer conjugate for the use according to any of paragraphs 1 to 27 wherein said target sequence is selected from the group consisting of any one or more of positions:
1264-1278;
1530-1544;
1551-1566;
1577 to 1598;
691-706;
670-684
of SEQ ID NO: 3.

29. The oligomer conjugate for the use according to any of paragraphs 1 to 28 wherein said first oligomer region is based on a core motif selected from the group consisting of any one or more of:

GCGTAAAGAGAGG; (SEQ ID NO: 13)

GCGTAAAGAGAGGT; (SEQ ID NO: 11)

AGCGAAGTGCACACG; (SEQ ID NO: 20)

AGGTGAAGCGAAGTG; (SEQ ID NO: 26)

AGCGAAGTGCACACGG; (SEQ ID NO 18)

CGAACCACTGAACA; (SEQ ID NO: 7)

GAACCACTGAACAAA; (SEQ ID NO 4)

CGAACCACTGAACAAA; (SEQ ID NO 5)

CGAACCACTGAACAA; (SEQ ID NO 6)

CGAACCACTGAAC (SEQ ID NO 8)

CCGCAGTATGGATCG (SEQ ID NO 9)

CGCAGTATGGATC; (SEQ ID NO: 10)

CGCGTAAAGAGAGGT; (SEQ ID NO 12)

AGAAGGCACAGACGG; (SEQ ID NO 14)

GAGAAGGCACAGACGG (SEQ ID NO 15)

GAAGTGCACACGG; (SEQ ID NO 16)

GCGAAGTGCACACGG; (SEQ ID NO 17)

CGAAGTGCACACG; (SEQ ID NO 19)

AGGTGAAGCGAAGT; and (SEQ ID NO 27)

TAGTAAACTGAGCCA. (SEQ ID NO: 852)

30. The oligomer conjugate for the use according any of paragraphs 1 to 29 wherein said first oligomer region is based on a sequence selected from the group consisting of any one or more of:

GCGtaaagagaGG; (SEQ ID NO: 303)

GCGtaaagagaGGT; (SEQ ID NO: 301)

GCGtaaagagAGG; (SEQ ID NO: 618)

AGCgaagtgcacACG (SEQ ID NO: 310)

AGgtgaagcgaAGTG; (SEQ ID NO: 668)

AGCgaagtgcacaCGG; (SEQ ID NO: 308)

CGAaccactgaACA; (SEQ ID NO: 297)

CGCagtatggaTC; (SEQ ID NO: 300)

AGGtgaagcgaagTGC; (SEQ ID NO: 315)

AGGtgaagcgaaGTG; (SEQ ID NO: 316)

GAAccactgaacAAA; (SEQ ID NO: 294)

CGAaccactgaacAAA; (SEQ ID NO: 295)

CGAaccactgaaCAA; (SEQ ID NO: 296)

CGAaccactgaAC; (SEQ ID NO: 298)

CCGcagtatggaTCG; (SEQ ID NO: 299)

CGCgtaaagagaGGT; (SEQ ID NO: 302)

AGAaggcacagaCGG; (SEQ ID NO: 304)

GAGaaggcacagaCGG; (SEQ ID NO: 305)

GAAgtgcacacGG; (SEQ ID NO: 306)

GCGaagtgcacaCGG; (SEQ ID NO: 307)

CGAagtgcacaCG; (SEQ ID NO: 309)

GAAccactgaaCAAA; (SEQ ID NO: 585)

CGAAccactgaacAAA (SEQ ID NO: 588)

GAAgtgcacaCGG; (SEQ ID NO: 628)

TAGtaaactgagCCA; (SEQ ID NO: 678)

CGAaccactgAAC; (SEQ ID NO: 600)

AGGtgaagcgaAGT; and (SEQ ID NO: 317)

CGAaccactgAACA. (SEQ ID NO: 597)

wherein uppercase letters denote LNA units and lower case letters denote DNA units.

31. The oligomer conjugate for the use according to any of paragraphs 1 to 30 wherein said oligomer conjugate is selected from the group consisting of any one or more of:

5'-GN2-C6 caG$_s$$^m$C$_s$G$_s$t$_s$a$_s$a$_s$a$_s$g$_s$a$_s$g$_s$a$_s$G$_s$G-3' (SEQ ID NO: 815)

5'-GN2-C6 caG$_s$$^m$C$_s$G$_s$t$_s$a$_s$a$_s$a$_s$g$_s$a$_s$g$_s$a$_s$G$_s$G$_s$T-3' (SEQ ID NO: 814)

5'-GN2-C6 caG$_s$$^m$C$_s$G$_s$t$_s$a$_s$a$_s$a$_s$g$_s$a$_s$g$_s$a$_s$A$_s$G$_s$G-3' (SEQ ID NO: 825)

5'-GN2-C6 caA$_s$G$_s$$^m$C$_s$g$_s$a$_s$a$_s$g$_s$t$_s$g$_s$c$_s$a$_s$c$_s$A$_s$$^m$C$_s$G-3' (SEQ ID NO: 808)

5'-GN2-C6 caA$_s$G$_s$g$_s$t$_s$g$_s$a$_s$a$_s$g$_s$$^m$c$_s$g$_s$a$_s$A$_s$G$_s$T$_s$G-3' (SEQ ID NO: 826)

5'-GN2-C6 caA$_s$G$_s$$^m$C$_s$g$_s$a$_s$a$_s$g$_s$t$_s$g$_s$c$_s$a$_s$c$_s$a$_s$$^m$C$_s$G-3' (SEQ ID NO: 807)

5'-GN2-C6 caG$_s$A$_s$A$_s$c$_s$c$_s$a$_s$c$_s$t$_s$g$_s$a$_s$a$_s$c$_s$A$_s$A$_s$A-3' (SEQ ID NO: 799)

5'-GN2-C6 ca$^m$C$_s$G$_s$A$_s$a$_s$c$_s$c$_s$a$_s$c$_s$t$_s$g$_s$a$_s$a$_s$c$_s$A$_s$A$_s$A-3' (SEQ ID NO: 800)

5'-GN2-C6 ca$^m$C$_s$G$_s$A$_s$a$_s$c$_s$c$_s$a$_s$c$_s$t$_s$g$_s$a$_s$a$_s$$^m$C$_s$A$_s$A-3' (SEQ ID NO: 801)

5'-GN2-C6 ca$^m$C$_s$$^m$C$_s$G$_s$c$_s$a$_s$g$_s$t$_s$a$_s$t$_s$g$_s$g$_s$a$_s$T$_s$$^m$C$_s$G-3' (SEQ ID NO: 802)

5'-GN2-C6 ca$^m$C$_s$G$_s$$^m$c$_s$g$_s$t$_s$a$_s$a$_s$a$_s$g$_s$a$_s$g$_s$a$_s$G$_s$G$_s$T-3' (SEQ ID NO: 803)

5'-GN2-C6 caA$_s$G$_s$A$_s$a$_s$g$_s$g$_s$c$_s$a$_s$c$_s$a$_s$g$_s$a$_s$$^m$C$_s$G-3' (SEQ ID NO: 804)

5'-GN2-C6 caG$_s$A$_s$G$_s$a$_s$a$_s$g$_s$g$_s$c$_s$a$_s$c$_s$a$_s$g$_s$a$_s$$^m$C$_s$G-3' (SEQ ID NO: 805)

5'-GN2-C6 caG$_s$$^m$C$_s$G$_s$a$_s$a$_s$g$_s$t$_s$g$_s$c$_s$a$_s$c$_s$a$_s$$^m$C$_s$G-3' (SEQ ID NO: 806)

5'-GN2-C6 caA$_s$G$_s$G$_s$t$_s$g$_s$a$_s$a$_s$g$_s$$^m$c$_s$g$_s$a$_s$a$_s$g$_s$T$_s$G$_s$$^m$C-3' (SEQ ID NO: 809)

5'-GN2-C6 caA$_s$G$_s$G$_s$t$_s$g$_s$a$_s$a$_s$g$_s$$^m$c$_s$g$_s$a$_s$a$_s$G$_s$T$_s$G-3' (SEQ ID NO: 810)

5'-GN2-C6 ca$^m$C$_s$G$_s$A$_s$a$_s$c$_s$c$_s$a$_s$c$_s$t$_s$g$_s$a$_s$a$_s$A$_s$$^m$C$_s$A-3' (SEQ ID NO: 811)

5'-GN2-C6 ca$^m$C$_s$G$_s$A$_s$a$_s$c$_s$c$_s$a$_s$c$_s$t$_s$g$_s$a$_s$a$_s$A$_s$$^m$C-3' (SEQ ID NO: 812)

5'-GN2-C6 ca$^m$C$_s$G$_s$$^m$C$_s$a$_s$g$_s$t$_s$a$_s$t$_s$g$_s$g$_s$a$_s$T$_s$$^m$C-3' (SEQ ID NO: 813)

5'-GN2-C6 caG$_s$A$_s$A$_s$g$_s$t$_s$g$_s$c$_s$a$_s$c$_s$a$_s$$^m$c$_s$G$_s$G-3' (SEQ ID NO: 816)

5'-GN2-C6 ca$^m$C$_s$G$_s$A$_s$a$_s$g$_s$t$_s$g$_s$c$_s$a$_s$c$_s$a$_s$$^m$C$_s$G-3' (SEQ ID NO: 817)

5'-GN2-C6 caA$_s$G$_s$G$_s$t$_s$g$_s$a$_s$a$_s$g$_s$$^m$c$_s$g$_s$a$_s$A$_s$G$_s$T-3' (SEQ ID NO: 818)

5'-GN2-C6 caG$_s$A$_s$A$_s$c$_s$c$_s$a$_s$t$_s$t$_s$g$_s$a$_s$a$_s$$^m$C$_s$A$_s$A$_s$A-3' (SEQ ID NO: 819)

5'-GN2-C6 ca$^m$C$_s$G$_s$A$_s$A$_s$c$_s$c$_s$a$_s$c$_s$t$_s$g$_s$a$_s$a$_s$c$_s$A$_s$A$_s$A-3' (SEQ ID NO: 820)

5'-GN2-C6 caG$_s$A$_s$A$_s$g$_s$t$_s$g$_s$c$_s$a$_s$c$_s$a$_s$$^m$C$_s$G$_s$G-3' (SEQ ID NO: 821)

5'-GN2-C6 caT$_s$A$_s$G$_s$t$_s$a$_s$a$_s$a$_s$c$_s$t$_s$g$_s$a$_s$g$_s$$^m$C$_s$$^m$C$_s$A$_s$3' (SEQ ID NO: 822)

5'-GN2-C6 ca$^m$C$_s$G$_s$A$_s$a$_s$c$_s$c$_s$a$_s$c$_s$t$_s$g$_s$A$_s$A$_s$$^m$C-3' (SEQ ID NO: 823)

5'-GN2-C6 ca$^m$C$_s$G$_s$A$_s$a$_s$c$_s$c$_s$a$_s$c$_s$t$_s$g$_s$A$_s$A$_s$$^m$C$_s$A-3' (SEQ ID NO: 824)

wherein uppercase letters denote beta-D-oxy-LNA units; lowercase letters denote DNA units; the subscript "s" denotes a phosphorothioate linkage; superscript m denotes a DNA or beta-D-oxy-LNA unit containing a 5-methylcytosine base; GN2-C6 denotes a GalNAc2 carrier component with a C6 linker.

32. The oligomer conjugate for the use according to any of paragraphs 1 to 29 wherein said first oligomer region is based on a core motif selected from the group consisting of any one or more of:

GCGTAAAGAGAGG (SEQ ID NO: 13)

GCGTAAAGAGAGGT (SEQ ID NO: 11)
and

CGCGTAAAGAGAGGT. (SEQ ID NO 12)

33. The oligomer conjugate for the use according to any of paragraphs 1 to 29 wherein said first oligomer region is based on a core motif selected from the group consisting of any one or more of:

AGCGAAGTGCACACG; (SEQ ID NO: 20)

AGGTGAAGCGAAGTG; (SEQ ID NO: 26)

AGCGAAGTGCACACGG; (SEQ ID NO 18)

GAAGTGCACACGG; (SEQ ID NO 16)

GCGAAGTGCACACGG; (SEQ ID NO 17)

CGAAGTGCACACG (SEQ ID NO 19)
and

AGGTGAAGCGAAGT. (SEQ ID NO 27)

34. The oligomer conjugate for the use according to any one of paragraphs 1 to 33 wherein said oligomer conjugate has or comprises the structure:
Carrier component-L1-First Oligomer Region
  wherein L1 is an optional linker or brancher region or tether molecule or bridging moiety; or
  wherein said oligomer conjugate has or comprises the structure:
First Oligomer Region-L2-Carrier component
  wherein L2 is an optional linker or brancher region or tether molecule or bridging moiety.

35. The oligomer conjugate for the use according to any one of paragraphs 1 to 34 wherein said oligomer conjugate has or comprises the structure:
Carrier component-L1-First Oligomer Region
  wherein L1 is an optional linker.

36. The oligomer conjugate for the use according to paragraph 34 or paragraph 35 wherein said Linker 1 is present.
37. The oligomer conjugate for the use according to any of paragraphs 1 to 36 wherein said carrier component is linked, preferably conjugated, to the 5' end of said oligomer.
38. The oligomer conjugate for the use according to paragraph 34 to 37 wherein the linker group or the brancher region is a physiologically labile linker group or a physiologically labile brancher region or physiologically labile tether molecule or physiologically labile bridging moiety.
39. The oligomer conjugate for the use according to paragraph 38 wherein the physiologically labile linker group is a nuclease susceptible linker.
40. The oligomer conjugate for the use according to paragraph 38 or 39 wherein the physiologically labile linker further is conjugated with a C6 to C12 amino alkyl group.
41. The oligomer conjugate for the use according to any of paragraphs 1 to 40 which further comprises a second oligomer region which is capable of modulating a target sequence.
42. The oligomer conjugate for the use according to paragraph 41 wherein each of the first oligomer region and the second oligomer regions is capable of modulating a target sequence in HBx or HBsAg of HBV.
43. The oligomer conjugate for the use according to any one of paragraphs 31 or 42 wherein each of the first oligomer region and the second oligomer regions is capable of modulating a target sequence in HBx or HBsAg of HBV; wherein said target regions are different.
44. The oligomer conjugate for the use according to any one of paragraphs 41 to 43 wherein said oligomer conjugate has or comprises the structure:
    Carrier component-L1-First Oligomer Region-L2-Second Oligomer Region
    wherein L1 is an optional linker or brancher region or tether molecule or bridging moiety
    wherein L2 is an optional linker or brancher region or tether molecule or bridging moiety
    wherein L1 and L2 can be the same or different; or
    wherein said oligomer conjugate has or comprises the structure:
    First Oligomer Region-L2-Second Oligomer Region-L3-Carrier component
    wherein L2 is an optional linker or brancher region or tether molecule or bridging moiety
    wherein L3 is an optional linker or brancher region or tether molecule or bridging moiety
    wherein L2 and L3 can be the same or different; or
    wherein said oligomer conjugate has or comprises the structure:
    Carrier component 1-L1-First Oligomer Region-L2-Second Oligomer Region-L3-Carrier component 2
    wherein L1 is an optional linker or brancher region or tether molecule or bridging moiety
    wherein L2 is an optional linker or brancher region or tether molecule or bridging moiety
    wherein L3 is an optional linker or brancher region or tether molecule or bridging moiety
    wherein L1, L2 and L3 can be the same or different
    wherein Carrier component 1 and Carrier component 2 can be the same or different; or
    wherein said oligomer conjugate has or comprises the structure:
    First Oligomer Region-L1-Carrier component 1-L2-Second Oligomer Region
    wherein L1 is an optional linker or brancher region or tether molecule or bridging moiety
    wherein L2 is an optional linker or brancher region or tether molecule or bridging moiety
    wherein L1 and L2 and L3 can be the same or different; or
    wherein said oligomer conjugate has or comprises the structure:
    First Oligomer Region-L1-Carrier component 1-L2-Second Oligomer Region-L3-Carrier component 2
    wherein L1 is an optional linker or brancher region or tether molecule or bridging moiety
    wherein L2 is an optional linker or brancher region or tether molecule or bridging moiety
    wherein L3 is an optional linker or brancher region or tether molecule or bridging moiety
    wherein L1 and L2 can be the same or different
    wherein Carrier component 1 and Carrier component 2 can be the same or different; or.
    wherein said oligomer conjugate has or comprises the structure:
    Carrier component 1-L1-First Oligomer Region-L2-Carrier component 2-L3-Second
    Oligomer Region-L4-Carrier component 3
    wherein L1 is an optional linker or brancher region or tether molecule or bridging moiety
    wherein L2 is an optional linker or brancher region or tether molecule or bridging moiety
    wherein L3 is an optional linker or brancher region or tether molecule or bridging moiety
    wherein L1, L2 and L3 can be the same or different
    wherein Carrier component 1, Carrier Component 2 and Carrier component 3 can be the same or different.
45. The oligomer conjugate for the use according to any one of paragraphs 39 to 43 wherein said oligomer conjugate has or comprises the structure:
    Carrier component-L1-First Oligomer Region-L2-Second Oligomer Region
    wherein L1 is an optional linker or brancher region or tether molecule or bridging moiety
    wherein L2 is an optional linker or brancher region or tether molecule or bridging moiety
    wherein L1 and L2 can be the same or different.
46. The oligomer conjugate for the use according to paragraph 45 wherein said Linker 1 is present.
47. The oligomer conjugate for the use according to paragraph 45 or paragraph 46 wherein said Linker 2 is present.
48. The oligomer conjugate for the use according to any of paragraphs 41 to 46 wherein said carrier component is linked, preferably conjugated, to the 5' end of said oligomer.
49. The oligomer conjugate for the use according to any of paragraphs 41 to 48 wherein each of the first oligomer region and the second oligomer regions is linked, preferably conjugated, by means of a linker or brancher region.
50. The oligomer conjugate for the use according to any of paragraphs 41 to 49 wherein each of the first oligomer region and the second oligomer regions is linked, preferably conjugated, by means of a physiologically labile linker group or a physiologically labile brancher region.

51. The oligomer conjugate for the use according to any of paragraphs 1 to 50 wherein said viral disorder is hepatitis B or a disorder associated with HBV 52. The oligomer conjugate for the use according to any of paragraphs 1 to 51 wherein said viral disorder is associated with expression or overexpression of HBx or HBsAg.

53. The oligomer conjugate for the use according to any of paragraphs 1 to 52, wherein said oligomer conjugate is administered subcutaneously.

54. A composition for use in the treatment of a viral disorder, wherein said composition comprises an oligomer conjugate as defined in any one of paragraphs 1 to 53 and at least one additional different oligonucleotide.

55. The composition for the use according to paragraph 54 wherein at least one of said additional different oligonucleotide is an oligomer conjugate.

56. The composition for the use according to paragraph 54 or paragraph 55 wherein each of said additional different oligonucleotide is an oligomer conjugate.

57. The composition for the use according to any one of paragraphs 54 to 56 wherein each of said additional different oligonucleotide is capable of modulating a target sequence in HBV.

58. The composition for the use according to any one of paragraphs 54 to 57 wherein at least one of said additional different oligonucleotide is capable of modulating a target sequence in HBx or HBsAg of HBV.

59. The composition for the use according to any one of paragraphs 54 to 58 wherein at least one of said additional different oligonucleotide is capable of modulating a target sequence in HBx or HBsAg of HBV; and wherein said at least one of said additional different oligonucleotide is capable of modulating a target sequence in HBx or HBsAg of HBV different to that targeted by an oligomer conjugate as defined in any one of paragraphs 1 to 53.

60. The composition for the use according to any one of paragraphs 54 to 59 wherein each of said additional different oligonucleotide is capable of modulating a target sequence in HBx or HBsAg of HBV.

61. The composition for the use according to any one of paragraphs 54 to 60 wherein each of said additional different oligonucleotide is capable of modulating a target sequence in HBx or HBsAg of HBV; and wherein each of said additional different oligonucleotide is capable of modulating a target sequence in HBx or HBsAg of HBV different to that targeted by an oligomer conjugate as defined in any one of paragraphs 1 to 53.

62. An oligomer conjugate suitable for the treatment of a viral disorder, wherein said oligomer conjugate comprises:
   a) at least one first oligomer region capable of modulating a target sequence of Hepatitis B Virus (HBV), preferably HBx or HBsAg of HBV, to treat said viral disorder; and
   b) a carrier component for delivering said first oligomer to the liver.

63. An oligomer conjugate according to paragraph 62 wherein said oligomer is as defined in any one of paragraphs 1 to 53.

64. A composition suitable for the treatment of a viral disorder, wherein said composition comprises an oligomer conjugate and at least one additional different oligonucleotide; wherein said oligomer conjugate comprises:
   a) at least one first oligomer region capable of modulating a target sequence of Hepatitis B Virus (HBV), preferably HBx or HBsAg of HBV, to treat said viral disorder; and
   b) a carrier component for delivering said first oligomer to the liver.

65. A composition according to paragraph 64 wherein said oligomer conjugate is an oligomer conjugate as defined in any one of paragraphs 1 to 53 or any one of paragraphs 62 to 63.

66. A composition according to paragraph 64 or paragraph 65 wherein said additional different oligonucleotide is an additional different oligonucleotide as defined in any one of paragraphs 62 to 63.

67. An oligomer based on a core motif selected from the group consisting of any one or more of:

```
GCGTAAAGAGAGG;          (SEQ ID NO: 13)

GCGTAAAGAGAGGT;         (SEQ ID NO: 11)

AGCGAAGTGCACACG;        (SEQ ID NO: 20)

AGGTGAAGCGAAGTG;        (SEQ ID NO: 26)

CGAACCACTGAACA;         (SEQ ID NO: 7)

GAACCACTGAACAAA;        (SEQ ID NO 4)

CGAACCACTGAACAAA;       (SEQ ID NO 5)

CGAACCACTGAACAA;        (SEQ ID NO 6)

CGAACCACTGAAC           (SEQ ID NO 8)

CCGCAGTATGGATCG         (SEQ ID NO 9)

CGCAGTATGGATC;          (SEQ ID NO: 10)

CGCGTAAAGAGAGGT;        (SEQ ID NO 12)

AGAAGGCACAGACGG;        (SEQ ID NO 14)

GAGAAGGCACAGACGG        (SEQ ID NO 15)

GAAGTGCACACGG;          (SEQ ID NO 16)

GCGAAGTGCACACGG;        (SEQ ID NO 17)

CGAAGTGCACACG;          (SEQ ID NO 19)
```

-continued

AGGTGAAGCGAAGT; (SEQ ID NO 27)
and

TAGTAAACTGAGCCA (SEQ ID NO: 852)

which is capable of modulating a target sequence in HBx or HBsAg of HBV to treat a viral disorder.

68. The oligomer of paragraph 67 wherein said oligomer region is based on a core motif selected from the group consisting of any one or more of:

GCGTAAAGAGAGG (SEQ ID NO: 13)

GCGTAAAGAGAGGT (SEQ ID NO: 11)
and

CGCGTAAAGAGAGGT. (SEQ ID NO 12)

69. The oligomer of paragraph 67 wherein said oligomer region is based on a core motif selected from the group consisting of any one or more of:

AGCGAAGTGCACACG; (SEQ ID NO: 20)

AGGTGAAGCGAAGTG; (SEQ ID NO: 26)

AGCGAAGTGCACACGG; (SEQ ID NO 18)

GAAGTGCACACGG; (SEQ ID NO 16)

GCGAAGTGCACACGG; (SEQ ID NO 17)

CGAAGTGCACACG (SEQ ID NO 19)
and

AGGTGAAGCGAAGT. (SEQ ID NO 27)

70. The oligomer according to any one of paragraphs 67 to 69, wherein said oligomer comprises one or more LNA units.
71. The oligomer according to any of paragraphs 67 to 70 wherein said oligomer is a gapmer.
72. The oligomer according to any of paragraphs 67 to 71 wherein said oligomer comprises a 2'-deoxyribonucleotide gap region flanked on each side by a wing, wherein each wing independently comprises one or more LNA units.
73. The oligomer according to any of paragraphs 67 to 72 wherein said oligomer any one of the motifs: 2-8-2, 3-8-3, 2-8-3, 3-8-2, 2-9-2, 3-9-3, 2-9-3, 3-9-2, 2-10-2, 3-10-3, 3-10-2, 2-10-3 wherein the first number is the number of LNA units in an LNA wing region, the second number is the number of nucleotides in the gap region, and the third number is the number of LNA units in an LNA wing region.
74. The oligomer according to any of paragraphs 67 to 73 wherein said first oligomer region is 10-18 nucleotides in length.
75. The oligomer according to any of paragraphs 67 to 74 wherein said first oligomer region is 10 to 16 nucleotides in length.
76. The oligomer according to any of paragraphs 67 to 75 wherein said first oligomer region is 10 to 14 nucleotides in length.
77. The oligomer according to any one of paragraphs 67 to 76 which is based on a sequence selected from the group consisting of any one or more of:

GCGtaaagagaGG; (SEQ ID NO: 303)

GCGtaaagagaGGT; (SEQ ID NO: 301)

GCGtaaagagAGG; (SEQ ID NO: 618)

AGCgaagtgcacACG (SEQ ID NO: 310)

AGgtgaagcgaAGTG; (SEQ ID NO: 668)

AGCgaagtgcacaCGG; (SEQ ID NO: 308)

CGAaccactgaACA; (SEQ ID NO: 297)

CGCagtatggaTC; (SEQ ID NO: 300)

AGGtgaagcgaagTGC; (SEQ ID NO: 315)

AGGtgaagcgaaGTG; (SEQ ID NO: 316)

GAAccactgaacAAA; (SEQ ID NO: 294)

CGAaccactgaacAAA; (SEQ ID NO: 295)

CGAaccactgaaCAA; (SEQ ID NO: 296)

CGAaccactgaAC; (SEQ ID NO: 298)

CCGcagtatggaTCG; (SEQ ID NO: 299)

CGCgtaaagagaGGT; (SEQ ID NO: 302)

AGAaggcacagaCGG; (SEQ ID NO: 304)

GAGaaggcacagaCGG; (SEQ ID NO: 305)

GAAgtgcacacGG; (SEQ ID NO: 306)

GCGaagtgcacaCGG; (SEQ ID NO: 307)

CGAagtgcacaCG; (SEQ ID NO: 309)

GAAccactgaaCAAA; (SEQ ID NO: 585)

CGAAccactgaacAAA (SEQ ID NO: 588)

GAAgtgcacaCGG; (SEQ ID NO: 628)

```
                                              (SEQ ID NO: 678)
TAGtaaactgagCCA;

(SEQ ID NO: 600)
CGAaccactgAAC;

(SEQ ID NO: 317)
AGGtgaagcgaAGT;
and (SEQ ID NO: 597)
CGAaccactgAACA,
``` wherein uppercase letters denote affinity enhancing nucleotide analogues and lower case letters denote DNA units.

78. The oligomer according to any of paragraphs 67 to 77 which is based on a selected from a sequence selected from the group consisting of any one or more of:

```
                                              (SEQ ID NO: 303)
5'-AM-C6 caG_s^mC_sG_st_sa_sa_sa_sg_sa_sg_sa_sG_sG-3'

(SEQ ID NO: 301)
5'-AM-C6 caG_s^mC_sG_st_sa_sa_sa_sg_sa_sg_sa_sG_sG_sT-3'

(SEQ ID NO: 618)
5'-AM-C6 caG_s^mC_sG_st_sa_sa_sa_sg_sa_sg_sA_sG_sG-3'

(SEQ ID NO: 310)
5'-AM-C6 caA_sG_s^mC_sg_sa_sa_sg_st_sg_sc_sa_sc_sA_s^mC_sG-3'

(SEQ ID NO: 668)
5'-AM-C6 caA_sG_sg_st_sg_sa_sa_sg_s^mc_sg_sa_sA_sG_sT_sG-3'

(SEQ ID NO: 308)
5'-AM-C6 caA_sG_s^mC_sg_sa_sa_sg_st_sg_sc_sa_sc_sa_s^mC_sG_sG-3'

(SEQ ID NO: 294)
5'-AM-C6 caG_sA_sA_sc_sc_sa_sc_st_sg_sa_sa_sc_sA_sA_sA-3'

(SEQ ID NO: 295)
5'-AM-C6 ca^mC_sG_sA_sa_sc_sc_sa_sc_st_sg_sa_sa_sc_sA_sA_sA-3'

(SEQ ID NO: 296)
5'-AM-C6 ca^mC_sG_sA_sa_sc_sc_sa_sc_st_sg_sa_sa_s^mC_sA_sA-3'

(SEQ ID NO: 299)
5'-AM-C6 ca^mC_s^mC_sG_sc_sa_sg_st_sa_st_sg_sg_sa_sT_s^mC_sG-3'

(SEQ ID NO: 302)
5'-AM-C6 ca^mC_sG_s^mC_sg_st_sa_sa_sa_sg_sa_sg_sa_sG_sG_sT-3'

(SEQ ID NO: 304)
5'-AM-C6 caA_sG_sA_sa_sg_sg_sc_sa_sc_sa_sg_sa_s^mC_sG_sG-3'

(SEQ ID NO: 305)
5'-AM-C6 caG_sA_sG_sa_sa_sg_sg_sc_sa_sc_sa_sg_sa_s^mC_sG_sG-3'

(SEQ ID NO: 307)
5'-AM-C6 caG_s^mC_sG_sa_sa_sg_st_sg_sc_sa_sc_sa_s^mC_sG_sG-3'

(SEQ ID NO: 315)
5'-AM-C6 caA_sG_sG_st_sg_sa_sa_sg_s^mc_sg_sa_sa_sg_sT_sG_s^mC-3'

(SEQ ID NO: 316)
5'-AM-C6 caA_sG_sG_st_sg_sa_sa_sg_s^mc_sg_sa_sa_sG_sT_sG-3'

(SEQ ID NO: 297)
5'-AM-C6 ca^mC_sG_sA_sa_sc_sc_sa_sc_st_sg_sa_sA_s^mC_sA-3'

(SEQ ID NO: 298)
5'-AM-C6 ca^mC_sG_sA_sa_sc_sc_sa_sc_st_sg_sa_sA_s^mC-3'

(SEQ ID NO: 300)
5'-AM-C6 ca^mC_sG_s^mC_sa_sg_st_sa_st_sg_sg_sa_sT_s^mC-3'

(SEQ ID NO: 306)
5'-AM-C6 caG_sA_sA_sg_st_sg_sc_sa_sc_sa_s^mc_sG_sG-3'

(SEQ ID NO: 309)
5'-AM-C6 ca^mC_sG_sA_sa_sg_st_sg_sc_sa_sc_sa_s^mC_sG-3'

(SEQ ID NO: 317)
5'-AM-C6 caA_sG_sG_st_sg_sa_sa_sg_s^mc_sg_sa_sA_sG_sT-3'

(SEQ ID NO: 585)
5'-AM-C6 caG_sA_sA_sc_sc_sa_sc_st_sg_sa_sa_s^mC_sA_sA_sA-3'

(SEQ ID NO: 588)
5'-AM-C6 ca^mC_sG_sA_sA_sc_sc_sa_sc_st_sg_sa_sa_sc_sA_sA_sA-3'

(SEQ ID NO: 628)
5'-AM-C6 caG_sA_sA_sg_st_sg_sc_sa_sc_sa_s^mC_sG_sG-3'

(SEQ ID NO: 678)
5'-AM-C6 caT_sA_sG_st_sa_sa_sa_sc_st_sg_sa_sg_s^mC_s^mC_sA_s3'

(SEQ ID NO: 600)
5'-AM-C6 ca^mC_sG_sA_sa_sc_sc_sa_sc_st_sg_sA_sA_s^mC-3'

(SEQ ID NO: 597)
5'-AM-C6 ca^mC_sG_sA_sa_sc_sc_sa_sc_st_sg_sA_sA_s^mC_sA-3'
``` wherein uppercase letters denote beta-D-oxy-LNA units; lowercase letters denote DNA units; the subscript "s" denotes a phosphorothioate linkage; superscript m denotes a DNA or beta-D-oxy-LNA unit containing a 5-methylcytosine base; AM-C6 is an amino-C6 linker; wherein the 5' terminal group "AM-C6 c a" is optional.

79. The oligomer as defined in any of paragraphs 67 to 78 for use in a medical treatment.

80. The oligomer as defined in any of paragraphs 67 to 79 for use in the treatment of a viral disorder.

81. The oligomer as defined in paragraph 79 or paragraph 80 wherein said oligomer is as defined in any one of paragraphs 1 to 53.

82. The oligomer as defined in paragraph 79 or paragraph 81 wherein said disorder is as defined in any one of paragraphs 1 to 53.

83. A composition suitable for the treatment of a viral disorder, wherein said composition comprises an oligomer and at least one additional different oligonucleotide; wherein said oligomer comprises at least one first oligomer region capable of modulating a target sequence of Hepatitis B Virus (HBV), preferably HBx or HBsAg of HBV, to treat said viral disorder.

84. A composition according to paragraph 83 wherein said oligomer is an oligomer as defined in any one of paragraphs 67 to 82.

85. A composition according to paragraph 83 or paragraph 84 wherein said at least one additional different oligonucleotide is an additional different oligonucleotide as defined in any one of paragraphs 54 to 61.

86. A method for treating a viral disorder, said method comprising administering to a subject in need of treatment an effective amount of an oligomer conjugate according to paragraph 62 or paragraph 63 or an oligomer conjugate as defined in any one of paragraphs 1 to 52.

87. A method for treating a viral disorder, said method comprising administering to a subject in need of treatment an effective amount of a composition according to any one of paragraphs 64 to 66 or a composition as defined in any one of paragraphs 54 to 61 or a composition as defined in any one of paragraphs 83 to 85.

88. A method for treating a viral disorder, said method comprising administering to a subject in need of treatment an effective amount of an oligomer according to any one of paragraphs 67 to 82.

89. A pharmaceutical composition comprising an oligomer conjugate according to paragraph 62 or paragraph 63 or an oligomer conjugate as defined in any one of paragraphs 1 to 53; and one or more pharmaceutically acceptable diluents, carriers, salts or adjuvants.
90. A pharmaceutical composition comprising a composition according to any one of paragraphs 64 to 66 or a composition as defined in any one of paragraphs 54 to 61 or a composition as defined in any one of paragraphs 83 to 85; and one or more pharmaceutically acceptable diluents, carriers, salts or adjuvants.
91. A pharmaceutical composition comprising an oligomer according to any one of paragraphs 67 to 82; and one or more pharmaceutically acceptable diluents, carriers, salts or adjuvants. A pharmaceutical system comprising a pharmaceutical composition according to any one of paragraphs 89 to 91 and an additional pharmaceutical entity.
92. A method of manufacturing an oligomer conjugate according to any one of paragraphs 1 to 52, comprising conjugating one or more oligomers as defined in any one of paragraphs 1 to 53 with a carrier component as defined in any one of paragraphs 1 to 53.
93. A method of manufacturing a composition according to any one of paragraphs 64 to 66, comprising admixing an oligomer conjugate as defined in any one of paragraphs 1 to 53 with a pharmaceutically acceptable diluent, carrier, salt or adjuvant.
94. A method of manufacturing a composition according to paragraph 91, comprising admixing an oligomer as defined in any one of paragraphs 67 to 82 with a pharmaceutically acceptable diluent, carrier, salt or adjuvant.
95. The invention according to any one of the preceding paragraphs wherein the oligomer or oligomer component of the oligomer conjugate comprises any one of the motifs: 3-10-3, 3-10-2, 3-9-3, 3-9-2, 3-8-3, 3-8-2 wherein the first number is the number of modified nucleotides in the wing region, preferably at least one being an LNA unit, preferably all being an LNA unit, the second number is the number of nucleotides in the gap region, and the third number is the number of modified nucleotides in the wing region, preferably at least one being an LNA unit, preferably all being an LNA unit.
96. An oligomer conjugate substantially as described herein and with reference to the Examples.
97. A composition substantially as described herein and with reference to the Examples.
98. An oligomer substantially as described herein and with reference to the Examples.
99. A method substantially as described herein and with reference to the Examples.

Particular Embodiments

The present invention relates to an oligomer conjugate for use in the treatment of a viral disorder. The oligomer conjugate comprises: a) an oligomer capable of modulating a target sequence in HBx or HBsAg of Hepatitis B Virus (HBV) to treat said viral disorder; and b) a carrier component conjugated to said oligomer. Preferably the carrier component is for delivering said first oligomer to the liver.
Preferred aspects for certain embodiments of the present invention are now provided.

In one aspect, the present invention provides an oligomer conjugate for use in the treatment of a viral disorder, wherein said oligomer conjugate comprises:
a) at least one first oligomer region capable of modulating a target sequence of Hepatitis B Virus (HBV), preferably HBx or HBsAg of HBV, to treat said viral disorder; and
b) a carrier component;
wherein said first oligomer region is 8-16 nucleotides in length;
wherein said first oligomer region is a gapmer, preferably wherein said first oligomer region comprises a 2'-deoxyribonucleotide gap region flanked on each side by a wing, preferably wherein each wing independently comprises one or more LNA units;
wherein said carrier component is a carbohydrate conjugate moiety, preferably said carrier component is selected from the group consisting of galactose, galactosamine, N-formyl-galactosamine, N-acetylgalactosamine (GalNAc), N-propionyl-galactosamine, N-n-butanoyl-galactosamine, N-isobutanoylgalactoseamine or a cluster of any one or more thereof; preferably said carrier component comprises GalNAc or a GalNAc cluster; preferably said carrier component is GalNAc2;
wherein said target sequence comprises at least part of a gene or a mRNA encoding HBx or HBsAg or a naturally-occurring variant thereof.

In one aspect, the present invention provides an oligomer conjugate suitable for the treatment of a viral disorder, wherein said oligomer conjugate comprises:
a) at least one first oligomer region capable of modulating a target sequence of Hepatitis B Virus (HBV), preferably HBx or HBsAg of HBV, to treat said viral disorder; and
b) a carrier component
wherein said first oligomer region is 8-16 nucleotides in length;
wherein said first oligomer region is a gapmer, preferably wherein said first oligomer region comprises a 2'-deoxyribonucleotide gap region flanked on each side by a wing, preferably wherein each wing independently comprises one or more LNA units;
wherein said carrier component is a carbohydrate conjugate moiety, preferably said carrier component is selected from the group consisting of galactose, galactosamine, N-formyl-galactosamine, N-acetylgalactosamine (GalNAc), N-propionyl-galactosamine, N-n-butanoyl-galactosamine, N-isobutanoylgalactoseamine or a cluster of any one or more thereof; preferably said carrier component comprises GalNAc or a GalNAc cluster; preferably said carrier component is GalNAc2;
wherein said target sequence comprises at least part of a gene or a mRNA encoding HBx or HBsAg or a naturally-occurring variant thereof.

In one aspect, the present invention provides a composition suitable for the treatment of a viral disorder, wherein said composition comprises an oligomer conjugate and at least one additional different oligonucleotide; wherein said oligomer conjugate comprises:
a) at least one first oligomer region capable of modulating a target sequence of Hepatitis B Virus (HBV), preferably HBx or HBsAg of HBV, to treat said viral disorder; and
b) a carrier component
wherein said first oligomer region is 8-16 nucleotides in length;

wherein said first oligomer region is a gapmer, preferably wherein said first oligomer region comprises a 2'-deoxyribonucleotide gap region flanked on each side by a wing, preferably wherein each wing independently comprises one or more LNA units;

wherein said carrier component is a carbohydrate conjugate moiety, preferably said carrier component is selected from the group consisting of galactose, galactosamine, N-formyl-galactosamine, N-acetylgalactosamine (GalNAc), N-propionyl-galactosamine, N-n-butanoyl-galactosamine, N-isobutanoylgalactoseamine or a cluster of any one or more thereof; preferably said carrier component comprises GalNAc or a GalNAc cluster; preferably said carrier component is GalNAc2;

wherein said target sequence comprises at least part of a gene or a mRNA encoding HBx or HBsAg or a naturally-occurring variant thereof.

In one aspect, the present invention provides an oligomer conjugate for use in the treatment of a viral disorder, wherein said oligomer conjugate comprises:

a) at least one first oligomer region capable of modulating a target sequence of Hepatitis B Virus (HBV), preferably HBx or HBsAg of HBV, to treat said viral disorder; and b) a carrier component;

wherein said first oligomer region is 8-16 nucleotides in length;

wherein said first oligomer region is a gapmer, preferably wherein said first oligomer region comprises a 2'-deoxyribonucleotide gap region flanked on each side by a wing, preferably wherein each wing independently comprises one or more LNA units;

wherein said carrier component is a carbohydrate conjugate moiety, preferably said carrier component is selected from the group consisting of galactose, galactosamine, N-formyl-galactosamine, N-acetylgalactosamine (GalNAc), N-propionyl-galactosamine, N-n-butanoyl-galactosamine, N-isobutanoylgalactoseamine or a cluster of any one or more thereof; preferably said carrier component comprises GalNAc or a GalNAc cluster; preferably said carrier component is GalNAc2;

wherein said target sequence comprises at least part of a gene or a mRNA encoding HBx or HBsAg or a naturally-occurring variant thereof;

wherein said first oligomer region is based on a core motif selected from the group consisting of any one or more of:

GCGTAAAGAGAGG; (SEQ ID NO: 13)

GCGTAAAGAGAGGT; (SEQ ID NO: 11)

AGCGAAGTGCACACG; (SEQ ID NO: 20)

AGGTGAAGCGAAGTG; (SEQ ID NO: 26)

AGCGAAGTGCACACGG; (SEQ ID NO 18)

CGAACCACTGAACA; (SEQ ID NO: 7)

GAACCACTGAACAAA; (SEQ ID NO 4)

CGAACCACTGAACAAA; (SEQ ID NO 5)

CGAACCACTGAACAA; (SEQ ID NO 6)

CGAACCACTGAAC (SEQ ID NO 8)

CCGCAGTATGGATCG (SEQ ID NO 9)

CGCAGTATGGATC; (SEQ ID NO: 10)

CGCGTAAAGAGAGGT; (SEQ ID NO 12)

AGAAGGCACAGACGG; (SEQ ID NO 14)

GAGAAGGCACAGACGG (SEQ ID NO 15)

GAAGTGCACACGG; (SEQ ID NO 16)

GCGAAGTGCACACGG; (SEQ ID NO 17)

CGAAGTGCACACG; (SEQ ID NO 19)

AGGTGAAGCGAAGT; (SEQ ID NO 27)
and

TAGTAAACTGAGCCA. (SEQ ID NO: 852)

In one aspect, the present invention provides an oligomer conjugate suitable for the treatment of a viral disorder, wherein said oligomer conjugate comprises:

a) at least one first oligomer region capable of modulating a target sequence of Hepatitis B Virus (HBV), preferably HBx or HBsAg of HBV, to treat said viral disorder; and b) a carrier component wherein said first oligomer region is 8-16 nucleotides in length;

wherein said first oligomer region is a gapmer, preferably wherein said first oligomer region comprises a 2'-deoxyribonucleotide gap region flanked on each side by a wing, preferably wherein each wing independently comprises one or more LNA units;

wherein said carrier component is a carbohydrate conjugate moiety, preferably said carrier component is selected from the group consisting of galactose, galactosamine, N-formyl-galactosamine, N-acetylgalactosamine (GalNAc), N-propionyl-galactosamine, N-n-butanoyl-galactosamine, N-isobutanoylgalactoseamine or a cluster of any one or more thereof; preferably said carrier component comprises GalNAc or a GalNAc cluster; preferably said carrier component is GalNAc2;

wherein said target sequence comprises at least part of a gene or a mRNA encoding HBx or HBsAg or a naturally-occurring variant thereof;

wherein said first oligomer region is based on a core motif selected from the group consisting of any one or more of:

| | |
|---|---|
| GCGTAAAGAGAGG; | (SEQ ID NO: 13) |
| AGCGAAGTGCACACG; | (SEQ ID NO: 20) |
| GCGTAAAGAGAGGT; | (SEQ ID NO: 11) |
| AGGTGAAGCGAAGTG; | (SEQ ID NO: 26) |
| AGCGAAGTGCACACGG; | (SEQ ID NO 18) |
| CGAACCACTGAACA; | (SEQ ID NO: 7) |
| GAACCACTGAACAAA; | (SEQ ID NO 4) |
| CGAACCACTGAACAAA; | (SEQ ID NO 5) |
| CGAACCACTGAACAA; | (SEQ ID NO 6) |
| CGAACCACTGAAC | (SEQ ID NO 8) |
| CCGCAGTATGGATCG | (SEQ ID NO 9) |
| CGCAGTATGGATC; | (SEQ ID NO: 10) |
| CGCGTAAAGAGAGGT; | (SEQ ID NO 12) |
| AGAAGGCACAGACGG; | (SEQ ID NO 14) |
| GAGAAGGCACAGACGG | (SEQ ID NO 15) |
| GAAGTGCACACGG; | (SEQ ID NO 16) |
| GCGAAGTGCACACGG; | (SEQ ID NO 17) |
| CGAAGTGCACACG; | (SEQ ID NO 19) |
| AGGTGAAGCGAAGT; and | (SEQ ID NO 27) |
| TAGTAAACTGAGCCA. | (SEQ ID NO: 852 |

In one aspect, the present invention provides a composition suitable for the treatment of a viral disorder, wherein said composition comprises an oligomer conjugate and at least one additional different oligonucleotide; wherein said oligomer conjugate comprises:
  a) at least one first oligomer region capable of modulating a target sequence of Hepatitis B Virus (HBV), preferably HBx or HBsAg of HBV, to treat said viral disorder; and
  b) a carrier component
wherein said first oligomer region is 8-16 nucleotides in length;
wherein said first oligomer region is a gapmer, preferably wherein said first oligomer region comprises a 2'-deoxyribonucleotide gap region flanked on each side by a wing, preferably wherein each wing independently comprises one or more LNA units;
wherein said carrier component is a carbohydrate conjugate moiety, preferably said carrier component is selected from the group consisting of galactose, galactosamine, N-formyl-galactosamine, N-acetylgalactosamine (GalNAc), N-propionyl-galactosamine, N-n-butanoyl-galactosamine, N-isobutanoylgalactoseamine or a cluster of any one or more thereof; preferably said carrier component comprises GalNAc or a GalNAc cluster; preferably said carrier component is GalNAc2;
wherein said target sequence comprises at least part of a gene or a mRNA encoding HBx or HBsAg or a naturally-occurring variant thereof;
wherein said first oligomer region is based on a core motif selected from the group consisting of any one or more of:

| | |
|---|---|
| GCGTAAAGAGAGG; | (SEQ ID NO: 13) |
| GCGTAAAGAGAGGT; | (SEQ ID NO: 11) |
| AGCGAAGTGCACACG; | (SEQ ID NO: 20) |
| AGGTGAAGCGAAGTG; | (SEQ ID NO: 26) |
| AGCGAAGTGCACACGG; | (SEQ ID NO 18) |
| CGAACCACTGAACA; | (SEQ ID NO: 7) |
| GAACCACTGAACAAA; | (SEQ ID NO 4) |
| CGAACCACTGAACAAA; | (SEQ ID NO 5) |
| CGAACCACTGAACAA; | (SEQ ID NO 6) |
| CGAACCACTGAAC | (SEQ ID NO 8) |
| CCGCAGTATGGATCG | (SEQ ID NO 9) |
| CGCAGTATGGATC; | (SEQ ID NO: 10) |
| CGCGTAAAGAGAGGT; | (SEQ ID NO 12) |
| AGAAGGCACAGACGG; | (SEQ ID NO 14) |
| GAGAAGGCACAGACGG | (SEQ ID NO 15) |
| GAAGTGCACACGG; | (SEQ ID NO 16) |
| GCGAAGTGCACACGG; | (SEQ ID NO 17) |
| CGAAGTGCACACG; | (SEQ ID NO 19) |
| AGGTGAAGCGAAGT; and | (SEQ ID NO 27) |
| TAGTAAACTGAGCCA. | (SEQ ID NO 852 |

In one aspect, the present invention provides an oligomer conjugate for use in the treatment of a viral disorder, wherein said oligomer conjugate comprises:
- a) at least one first oligomer region capable of modulating a target sequence of Hepatitis B Virus (HBV), preferably HBx or HBsAg of HBV, to treat said viral disorder; and
- b) a carrier component;

wherein said first oligomer region is 12-16 nucleotides in length;

wherein said first oligomer region is a gapmer, preferably wherein said first oligomer region comprises a 2'-deoxyribonucleotide gap region flanked on each side by a wing, preferably wherein each wing independently comprises one or more LNA units;

wherein said carrier component is a carbohydrate conjugate moiety, preferably said carrier component is selected from the group consisting of galactose, galactosamine, N-formyl-galactosamine, N-acetylgalactosamine (GalNAc), N-propionyl-galactosamine, N-n-butanoyl-galactosamine, N-isobutanoylgalactoseamine or a cluster of any one or more thereof; preferably said carrier component comprises GalNAc or a GalNAc cluster; preferably said carrier component is GalNAc2;

wherein said target sequence comprises at least part of a gene or a mRNA encoding HBx or HBsAg or a naturally-occurring variant thereof;

wherein the oligomer component of the oligomer conjugate comprises any one of the motifs: 3-10-3, 3-10-2, 3-9-3, 3-9-2, 3-8-3, 3-8-2 wherein the first number is the number of LNA units in the wing region, the second number is the number of nucleotides in the gap region, and the third number is the number of LNA units in the wing region.

In one aspect, the present invention provides an oligomer conjugate suitable for the treatment of a viral disorder, wherein said oligomer conjugate comprises:
- a) at least one first oligomer region capable of modulating a target sequence of Hepatitis B Virus (HBV), preferably HBx or HBsAg of HBV, to treat said viral disorder; and
- b) a carrier component wherein said first oligomer region is 12-16 nucleotides in length;

wherein said first oligomer region is a gapmer, preferably wherein said first oligomer region comprises a 2'-deoxyribonucleotide gap region flanked on each side by a wing, preferably wherein each wing independently comprises one or more LNA units;

wherein said carrier component is a carbohydrate conjugate moiety, preferably said carrier component is selected from the group consisting of galactose, galactosamine, N-formyl-galactosamine, N-acetylgalactosamine (GalNAc), N-propionyl-galactosamine, N-n-butanoyl-galactosamine, N-isobutanoylgalactoseamine or a cluster of any one or more thereof; preferably said carrier component comprises GalNAc or a GalNAc cluster; preferably said carrier component is GalNAc2;

wherein said target sequence comprises at least part of a gene or a mRNA encoding HBx or HBsAg or a naturally-occurring variant thereof;

wherein the oligomer component of the oligomer conjugate comprises any one of the motifs: 3-10-3, 3-10-2, 3-9-3, 3-9-2, 3-8-3, 3-8-2 wherein the first number is the number of LNA units in the wing region, the second number is the number of nucleotides in the gap region, and the third number is the number of LNA units in the wing region.

In one aspect, the present invention provides a composition suitable for the treatment of a viral disorder, wherein said composition comprises an oligomer conjugate and at least one additional different oligonucleotide; wherein said oligomer conjugate comprises:
- a) at least one first oligomer region capable of modulating a target sequence of Hepatitis B Virus (HBV), preferably HBx or HBsAg of HBV, to treat said viral disorder; and
- b) a carrier component wherein said first oligomer region is 12-16 nucleotides in length;

wherein said first oligomer region is a gapmer, preferably wherein said first oligomer region comprises a 2'-deoxyribonucleotide gap region flanked on each side by a wing, preferably wherein each wing independently comprises one or more LNA units;

wherein said carrier component is a carbohydrate conjugate moiety, preferably said carrier component is selected from the group consisting of galactose, galactosamine, N-formyl-galactosamine, N-acetylgalactosamine (GalNAc), N-propionyl-galactosamine, N-n-butanoyl-galactosamine, N-isobutanoylgalactoseamine or a cluster of any one or more thereof; preferably said carrier component comprises GalNAc or a GalNAc cluster; preferably said carrier component is GalNAc2;

wherein said target sequence comprises at least part of a gene or a mRNA encoding HBx or HBsAg or a naturally-occurring variant thereof;

wherein the oligomer component of the oligomer conjugate comprises any one of the motifs: 3-10-3, 3-10-2, 3-9-3, 3-9-2, 3-8-3, 3-8-2 wherein the first number is the number of LNA units in the wing region, the second number is the number of nucleotides in the gap region, and the third number is the number of LNA units in the wing region.

In one aspect, the present invention provides an oligomer conjugate for use in the treatment of a viral disorder, wherein said oligomer conjugate comprises:
- a) at least one first oligomer region capable of modulating a target sequence of Hepatitis B Virus (HBV), preferably HBx or HBsAg of HBV, to treat said viral disorder; and
- b) a carrier component;

wherein said first oligomer region is 12-16 nucleotides in length;

wherein said first oligomer region is a gapmer, preferably wherein said first oligomer region comprises a 2'-deoxyribonucleotide gap region flanked on each side by a wing, preferably wherein each wing independently comprises one or more LNA units;

wherein said carrier component is a carbohydrate conjugate moiety, preferably said carrier component is selected from the group consisting of galactose, galactosamine, N-formyl-galactosamine, N-acetylgalactosamine (GalNAc), N-propionyl-galactosamine, N-n-butanoyl-galactosamine, N-isobutanoylgalactoseamine or a cluster of any one or more thereof; preferably said carrier component comprises GalNAc or a GalNAc cluster; preferably said carrier component is GalNAc2;

wherein said target sequence comprises at least part of a gene or a mRNA encoding HBx or HBsAg or a naturally-occurring variant thereof;

wherein said first oligomer region is based on a core motif selected from the group consisting of any one or more of:

GCGTAAAGAGAGG; (SEQ ID NO: 13)

GCGTAAAGAGAGGT; (SEQ ID NO: 11)

AGCGAAGTGCACACG; (SEQ ID NO: 20)

AGGTGAAGCGAAGTG; (SEQ ID NO: 26)

AGCGAAGTGCACACGG; (SEQ ID NO 18)

CGAACCACTGAACA; (SEQ ID NO: 7)

GAACCACTGAACAAA; (SEQ ID NO 4)

CGAACCACTGAACAAA; (SEQ ID NO 5)

CGAACCACTGAACAA; (SEQ ID NO 6)

CGAACCACTGAAC (SEQ ID NO 8)

CCGCAGTATGGATCG (SEQ ID NO 9)

CGCAGTATGGATC; (SEQ ID NO: 10)

CGCGTAAAGAGAGGT; (SEQ ID NO 12)

AGAAGGCACAGACGG; (SEQ ID NO 14)

GAGAAGGCACAGACGG (SEQ ID NO 15)

GAAGTGCACACGG; (SEQ ID NO 16)

GCGAAGTGCACACGG; (SEQ ID NO 17)

CGAAGTGCACACG; (SEQ ID NO 19)

AGGTGAAGCGAAGT; and (SEQ ID NO 27)

TAGTAAACTGAGCCA; (SEQ ID NO: 852)

wherein the oligomer component of the oligomer conjugate comprises any one of the motifs: 3-10-3, 3-10-2, 3-9-3, 3-9-2, 3-8-3, 3-8-2 wherein the first number is the number of LNA units in the wing region, the second number is the number of nucleotides in the gap region, and the third number is the number of LNA units in the wing region.

In one aspect, the present invention provides an oligomer conjugate suitable for the treatment of a viral disorder, wherein said oligomer conjugate comprises:
a) at least one first oligomer region capable of modulating a target sequence of Hepatitis B Virus (HBV), preferably HBx or HBsAg of HBV, to treat said viral disorder; and b) a carrier component wherein said first oligomer region is 12-16 nucleotides in length;
wherein said first oligomer region is a gapmer, preferably wherein said first oligomer region comprises a 2'-deoxyribonucleotide gap region flanked on each side by a wing, preferably wherein each wing independently comprises one or more LNA units;
wherein said carrier component is a carbohydrate conjugate moiety, preferably said carrier component is selected from the group consisting of galactose, galactosamine, N-formyl-galactosamine, N-acetylgalactosamine (GalNAc), N-propionyl-galactosamine, N-n-butanoyl-galactosamine, N-isobutanoylgalactose-amine or a cluster of any one or more thereof; preferably said carrier component comprises GalNAc or a GalNAc cluster; preferably said carrier component is GalNAc2;

wherein said target sequence comprises at least part of a gene or a mRNA encoding HBx or HBsAg or a naturally-occurring variant thereof;

wherein said first oligomer region is based on a core motif selected from the group consisting of any one or more of:

```
GCGTAAAGAGAGG;        (SEQ ID NO: 13)

GCGTAAAGAGAGGT;       (SEQ ID NO: 11)

AGCGAAGTGCACACG;      (SEQ ID NO: 20)

AGGTGAAGCGAAGTG;      (SEQ ID NO: 26)

AGCGAAGTGCACACGG;     (SEQ ID NO 18)

CGAACCACTGAACA;       (SEQ ID NO: 7)

GAACCACTGAACAAA;      (SEQ ID NO 4)

CGAACCACTGAACAAA;     (SEQ ID NO 5)

CGAACCACTGAACAA;      (SEQ ID NO 6)

CGAACCACTGAAC         (SEQ ID NO 8)

CCGCAGTATGGATCG       (SEQ ID NO 9)

CGCAGTATGGATC;        (SEQ ID NO: 10)

CGCGTAAAGAGAGGT;      (SEQ ID NO 12)

AGAAGGCACAGACGG;      (SEQ ID NO 14)

GAGAAGGCACAGACGG      (SEQ ID NO 15)

GAAGTGCACACGG;        (SEQ ID NO 16)

GCGAAGTGCACACGG;      (SEQ ID NO 17)
```

-continued

CGAAGTGCACACG; (SEQ ID NO 19)

AGGTGAAGCGAAGT; (SEQ ID NO 27)
and

TAGTAAACTGAGCCA; (SEQ ID NO: 852)

wherein the oligomer component of the oligomer conjugate comprises any one of the motifs: 3-10-3, 3-10-2, 3-9-3, 3-9-2, 3-8-3, 3-8-2 wherein the first number is the number of LNA units in the wing region, the second number is the number of nucleotides in the gap region, and the third number is the number of LNA units in the wing region.

In one aspect, the present invention provides a composition suitable for the treatment of a viral disorder, wherein said composition comprises an oligomer conjugate and at least one additional different oligonucleotide; wherein said oligomer conjugate comprises:
  a) at least one first oligomer region capable of modulating a target sequence of Hepatitis B Virus (HBV), preferably HBx or HBsAg of HBV, to treat said viral disorder; and
  b) a carrier component, wherein said first oligomer region is 12-16 nucleotides in length;
wherein said first oligomer region is a gapmer, preferably wherein said first oligomer region comprises a 2'-deoxyribonucleotide gap region flanked on each side by a wing, preferably wherein each wing independently comprises one or more LNA units;
wherein said carrier component is a carbohydrate conjugate moiety, preferably said carrier component is selected from the group consisting of galactose, galactosamine, N-formyl-galactosamine, N-acetylgalactosamine (GalNAc), N-propionyl-galactosamine, N-n-butanoyl-galactosamine, N-isobutanoylgalactoseamine or a cluster of any one or more thereof; preferably said carrier component comprises GalNAc or a GalNAc cluster; preferably said carrier component is GalNAc2;
wherein said target sequence comprises at least part of a gene or a mRNA encoding HBx or HBsAg or a naturally-occurring variant thereof;
wherein said first oligomer region is based on a core motif selected from the group consisting of an one or more of:

GCGTAAAGAGAGG; (SEQ ID NO: 13)

GCGTAAAGAGAGGT; (SEQ ID NO: 11)

AGCGAAGTGCACACG; (SEQ ID NO: 20)

AGGTGAAGCGAAGTG; (SEQ ID NO: 26)

AGCGAAGTGCACACGG; (SEQ ID NO 18)

CGAACCACTGAACA; (SEQ ID NO: 7)

GAACCACTGAACAAA; (SEQ ID NO 4)

-continued

CGAACCACTGAACAAA; (SEQ ID NO 5)

CGAACCACTGAACAA; (SEQ ID NO 6)

CGAACCACTGAAC (SEQ ID NO 8)

CCGCAGTATGGATCG (SEQ ID NO 9)

CGCAGTATGGATC; (SEQ ID NO: 10)

CGCGTAAAGAGAGGT; (SEQ ID NO 12)

AGAAGGCACAGACGG; (SEQ ID NO 14)

GAGAAGGCACAGACGG (SEQ ID NO 15)

GAAGTGCACACGG; (SEQ ID NO 16)

GCGAAGTGCACACGG; (SEQ ID NO 17)

CGAAGTGCACACG; (SEQ ID NO 19)

AGGTGAAGCGAAGT; (SEQ ID NO 27)
and

TAGTAAACTGAGCCA; (SEQ ID NO: 852)

wherein the oligomer component of the oligomer conjugate comprises any one of the motifs: 3-10-3, 3-10-2, 3-9-3, 3-9-2, 3-8-3, 3-8-2 wherein the first number is the number of LNA units in the wing region, the second number is the number of nucleotides in the gap region, and the third number is the number of LNA units in the wing region.

In one aspect, the present invention provides an oligomer for the treatment of a viral disorder, wherein said oligomer comprises at least one first oligomer region capable of modulating a target sequence of Hepatitis B Virus (HBV), preferably HBx or HBsAg of HBV, to treat said viral disorder; and wherein said first oligomer region is 12-16 nucleotides in length;
  wherein said first oligomer region is a gapmer, preferably wherein said first oligomer region comprises a 2'-deoxyribonucleotide gap region flanked on each side by a wing, preferably wherein each wing independently comprises one or more LNA units;
  wherein said first oligomer region is based on a core motif selected from the group consisting of any one or more of:

GCGTAAAGAGAGG; (SEQ ID NO: 13)

GCGTAAAGAGAGGT; (SEQ ID NO: 11)

AGCGAAGTGCACACG; (SEQ ID NO: 20)

AGGTGAAGCGAAGTG; (SEQ ID NO: 26)

-continued

AGCGAAGTGCACACGG;
(SEQ ID NO 18)

CGAACCACTGAACA;
(SEQ ID NO: 7)

GAACCACTGAACAAA;
(SEQ ID NO 4)

CGAACCACTGAACAAA;
(SEQ ID NO 5)

CGAACCACTGAACAA;
(SEQ ID NO 6)

CGAACCACTGAAC
(SEQ ID NO 8)

CCGCAGTATGGATCG
(SEQ ID NO 9)

CGCAGTATGGATC;
(SEQ ID NO: 10)

CGCGTAAAGAGAGGT;
(SEQ ID NO 12)

AGAAGGCACAGACGG;
(SEQ ID NO 14)

GAGAAGGCACAGACGG
(SEQ ID NO 15)

GAAGTGCACACGG;
(SEQ ID NO 16)

GCGAAGTGCACACGG;
(SEQ ID NO 17)

CGAAGTGCACACG;
(SEQ ID NO 19)

AGGTGAAGCGAAGT;
and
(SEQ ID NO 27)

TAGTAAACTGAGCCA;
(SEQ ID NO: 852)

wherein the oligomer comprises any one of the motifs: 3-10-3, 3-10-2, 3-9-3, 3-9-2, 3-8-3, 3-8-2 wherein the first number is the number of LNA units in the wing region, the second number is the number of nucleotides in the gap region, and the third number is the number of LNA units in the wing region.

In one aspect, the present invention provides an oligomer suitable for the treatment of a viral disorder, wherein said oligomer comprises at least one first oligomer region capable of modulating a target sequence of Hepatitis B Virus (HBV), preferably HBx or HBsAg of HBV, to treat said viral disorder; and wherein said first oligomer region is 12-16 nucleotides in length;

wherein said first oligomer region is a gapmer, preferably wherein said first oligomer region comprises a 2'-deoxyribonucleotide gap region flanked on each side by a wing, preferably wherein each wing independently comprises one or more LNA units;

wherein said first oligomer region is based on a core motif selected from the group consisting of any one or more of:

GCGTAAAGAGAGG;
(SEQ ID NO: 13)

GCGTAAAGAGAGGT;
(SEQ ID NO: 11)

AGCGAAGTGCACACG;
(SEQ ID NO: 20)

AGGTGAAGCGAAGTG;
(SEQ ID NO: 26)

AGCGAAGTGCACACGG;
(SEQ ID NO 18)

CGAACCACTGAACA;
(SEQ ID NO: 7)

GAACCACTGAACAAA;
(SEQ ID NO 4)

CGAACCACTGAACAAA;
(SEQ ID NO 5)

CGAACCACTGAACAA;
(SEQ ID NO 6)

CGAACCACTGAAC
(SEQ ID NO 8)

CCGCAGTATGGATCG
(SEQ ID NO 9)

CGCAGTATGGATC;
(SEQ ID NO: 10)

CGCGTAAAGAGAGGT;
(SEQ ID NO 12)

AGAAGGCACAGACGG;
(SEQ ID NO 14)

GAGAAGGCACAGACGG
(SEQ ID NO 15)

GAAGTGCACACGG;
(SEQ ID NO 16)

GCGAAGTGCACACGG;
(SEQ ID NO 17)

CGAAGTGCACACG;
(SEQ ID NO 19)

AGGTGAAGCGAAGT;
and
(SEQ ID NO 27)

TAGTAAACTGAGCCA;
(SEQ ID NO: 852)

wherein the oligomer comprises any one of the motifs: 3-10-3, 3-10-2, 3-9-3, 3-9-2, 3-8-3, 3-8-2 wherein the first number is the number of LNA units in the wing region, the second number is the number of nucleotides in the gap region, and the third number is the number of LNA units in the wing region.

EXAMPLES

Materials and Methods

HBsAg and HBeAg Detection

Serum HBsAg and HBeAg level were determined in the serum of infected AAV-HBV mouse using the HBsAg chemoluminescence immunoassay (CLIA) and the HBeAg CLIA kit (Autobio diagnostics Co. Ltd., Zhengzhou, China, Cat. no. CLO310-2 and CL0312-2 respectively), according to the manufacturer's protocol. Briefly, 50 µl of serum was transferred to the respective antibody coated microtiter plate and 50 µl of enzyme conjugate reagent was added. The plate was incubated for 60 min on a shaker at room temperature before all wells were washed six times with washing buffer using an automatic washer. 25 µl of substrate A and then 25 µl of substrate B was added to each well. The plate was incubated for 10 min at RT before luminescence was measured using an Envision luminescence reader. HBsAg is given in the unit IU/ml; where 1 ng HBsAg=1.14 IU. HBeAg is given in the unit NCU/ml serum.

HBV DNA Extraction and qPCR

Initially mice serum was diluted by a factor of 10 (1:10) with Phosphate buffered saline (PBS). DNA was extracted using the MagNA Pure 96 (Roche) robot. 50 µl of the diluted serum was mixed in a processing cartridge with 200 ul MagNA Pure 96 external lysis buffer (Roche, Cat. no. 06374913001) and incubated for 10 minutes. DNA was then extracted using the "MagNA Pure 96 DNA and Viral Nucleic Acid Small Volume Kit" (Roche, Cat. no. 0654358001) and the "Viral NA Plasma SV external lysis 2.0" protocol. DNA elution volume was 50 µl.

Quantification of extracted HBV DNA was performed using a Taqman qPCR machine (ViiA7, life technologies). Each DNA sample was tested in duplicate in the PCR. 5 µl of DNA sample was added to 15 µl of PCR mastermix containing 10 µl TaqMan Gene Expression Master Mix (Applied Biosystems, Cat. no. 4369016), 0.5 µl PrimeTime XL qPCR Primer/Probe (IDT) and 4.5 µl distilled water in a 384 well plate and the PCR was performed using the following settings: UDG Incubation (2 min, 50° C.), Enzyme Activation (10 min, 95° C.) and PCR (40 cycles with 15 sec, 95° for Denaturing and 1 min, 60° C. for annealing and extension). DNA copy numbers were calculated from $C_t$ values based on a HBV plasmid DNA standard curve by the ViiA7 software.

Sequences for TaqMan primers and probes (IDT):

```
Forward core primer (F3_core):
CTG TGC CTT GGG TGG CTT T

Reverse primer (R3_core):
AAG GAA AGA AGT CAG AAG GCA AAA

Taqman probe (P3_core):
56-FAM/AGC TCC AAA /ZEN/TTC TTT ATA AGG GTC GAT
GTC CAT G/3IABKFQ
```

Tissue Specific In Vitro Linker Cleavage Assay

FAM-labeled oligomers with the physiologically labile linker to be tested (e.g. a DNA phosphodiester linker (PO linker)) are subjected to in vitro cleavage using homogenates of the relevant tissues (e.g. liver or kidney) and Serum.

The tissue and serum samples are collected from a suitable animal (e.g. mice, monkey, pig or rat) and homogenized in a homogenisation buffer (0.5% Igepal CA-630, 25 mM Tris pH 8.0, 100 mM NaCl, pH 8.0 (adjusted with 1 N NaOH). The tissue homogenates and Serum are spiked with oligomer to concentrations of 200 µg/g tissue. The samples are incubated for 24 hours at 37° C. and thereafter the samples are extracted with phenol—chloroform. The solutions are subjected to AIE HPLC analyses on a Dionex Ultimate 3000 using an Dionex DNApac p-100 column and a gradient ranging from 10 mM-1 M sodium perchlorate at pH 7.5. The content of cleaved and non-cleaved oligomer is determined against a standard using both a fluoresense detector at 615 nm and a uv detector at 260 nm.

S1 Nuclease Cleavage Assay

FAM-labelled oligomers with S1 nuclease susceptible linkers (e.g. a DNA phosphodiester linker (PO linker)) are subjected to in vitro cleavage in S1 nuclease extract or Serum.

100 µM of the oligomer are subjected to in vitro cleavage by S1 nuclease in nuclease buffer (60 U pr. 100 µL) for 20 and 120 minutes. The enzymatic activity is stopped by adding EDTA to the buffer solution. The solutions are subjected to AIE HPLC analyses on a Dionex Ultimate 3000 using an Dionex DNApac p-100 column and a gradient ranging from 10 mM-1 M sodium perchlorate at pH 7.5. The content of cleaved and non-cleaved oligomer is determined against a standard using both a fluoresense detector at 615 nm and a uv detector at 260 nm.

Example 1 Construction of Conjugates

Oligonucleotides were synthesized on uridine universal supports or UnyLinker support from Kinovate using the phosphoramidite approach on a MerMade12 or an Oligo-Maker DNA/RNA synthesizerat 4 µmol scale. At the end of the synthesis, the oligonucleotides were cleaved from the solid support using aqueous ammonia for 1-2 hours at room temperature, and further deprotected for 16 hours at 65° C. The oligonucleotides were purified by reverse phase HPLC (RP-HPLC) and characterized by UPLC, and the molecular mass was further confirmed by ESI-MS. See below for more details.

Elongation of the Oligonucleotide

The coupling of β-cyanoethyl-phosphoramidites (DNA-A(Bz), DNA-G(ibu), DNA-C(Bz), DNA-T, LNA-5-methyl-C(Bz), LNA-A(Bz), LNA-G(dmf), LNA-T or Amino-C6 linker) was performed by using a solution of 0.1 M of the 5'-O-DMT-protected phosphoramidite in acetonitrile and DCI (4,5-dicyanoimidazole) in acetonitrile (0.25 M) as activator. Thiolation for introduction of phosphorthioate linkages was carried out using xanthane hydride (0.01 M in acetonitrile/pyridine 9:1). Phosphordiester linkages were introduced using 0.02 M iodine in THF/Pyridine/water 7:2:1. The rest of the reagents were the ones typically used for oligonucleotide synthesis. For post solid phase synthesis conjugation a commercially available C6 aminolinker phorphoramidite was used in the last cycle of the solid phase synthesis and after deprotection and cleavage from the solid support the aminolinked deprotected oligonucleotide was isolated. The conjugate was introduced via activation of the carboxylic acid and subsequent reaction with the amine on the 5'-end of the oligonucleotide using standard synthesis methods.

Purification by RP-HPLC:

The crude compound was purified by preparative RP-HPLC on a Phenomenex Jupiter C18 10µ 150×10 mm column. 0.1 M ammonium acetate pH 8 and acetonitrile was used as buffers at a flow rate of 5 mL/min. The collected fractions were lyophilized to give the purified compound typically as a white solid.

Abbreviations:
  DCI: 4,5-Dicyanoimidazole
  DCM: Dichloromethane
  DMF: Dimethylformamide
  DMT: 4,4'-Dimethoxytrityl
  THF: Tetrahydrofurane
  Bz: Benzoyl
  Ibu: Isobutyryl
  RP-HPLC: Reverse phase high performance liquid chromatography

Example 2 Testing In Vitro Efficacy

Introduction

The HbsAg assay used in the following studies is a standard method. It measures the amount of virus produced. It therefore measures a reduction in virus due to oligomers or oligomer conjugates targeting HBx or HBsAg. In addition, oligomers or oligomer conjugates that target the HBx transcriptet will also target the HbsAg transcript (see also column 3 and 4 in the results table).

Cell Lines

HepG2.2.15 cells were cultured in DMEM+Glutamax-I medium (Invitrogen, Carlsbad, CA, USA), supplemented with 10% fetal bovine serum (Invitrogen) and G418 (Invitrogen) at a final concentration of 200 mg/L and maintained in 5% $CO_2$ at 37° C.

HBsAg Assay

HepG2.2.15 cells (a constitutively HBV-expressing cell line) were seeded in duplicate into white, 96-well plates at $1.5\times10^4$ cells/well. The cells were treated with single concentrations of oligomers or with a three-fold serial dilution series of the compounds in DMSO. The final DMSO concentration in all wells was 1% and DMSO was used as control.

The HBsAg chemiluminescence immunoassay (CLIA) kit (Autobio Diagnostics Co., Zhengzhou, China) was used to measure the levels of secreted HBV antigens semi-quantitatively. For the detection 50 uL/well culture supernatant was used and the procedure conducted as directed by manufacturer's instructions. The cytotoxicity was measured using CellTiter-Glo (Promega, Madison, WI, USA, Cat #G7571). Using the E-WorkBook Suite (ID Business Solutions Ltd., Guildford, UK) dose-response curves were generated and the $IC_{50}$ and $CC_{50}$ values extrapolated. The $IC_{50}$ and $CC_{50}$ are defined as the compound concentration (or conditioned media log dilution) at which HBsAg secretion (IC50) and cytotoxicity (CC50), respectively, are reduced by 50% compared to the control. Data may be presented as the EC50 value for an oligomer, when testing at a range of concentrations, or as the absolute level of HBsAg in the supernatant as a percent of the HBsAg levels in the no drug control samples, when testing at a single concentration.

Results from Single Concentration Treatments

Figure 5:
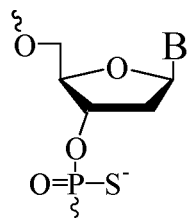
FIG. 5: Presents structures for a series of nucleoside analogues.
Figure 5:
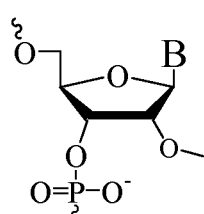
Figure 5:
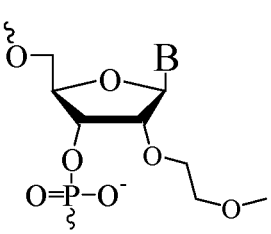
Figure 5:
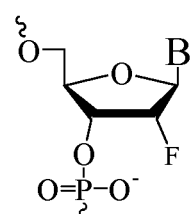
Figure 5:
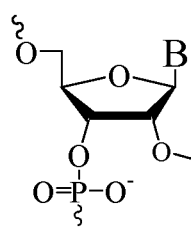
Figure 5:
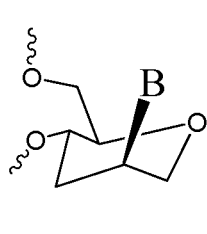
Figure 5:
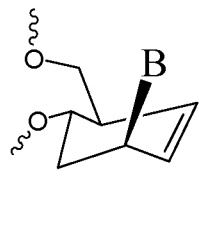
Figure 5:
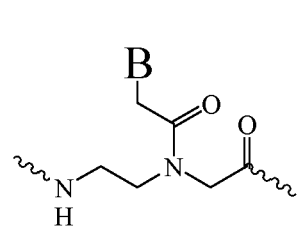
Figure 5:
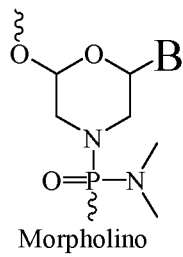
Figure 5:
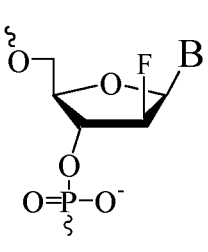
Figure 5:
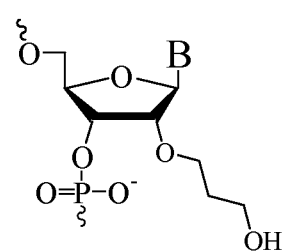
Figure 5:
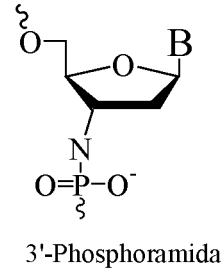
Figure 5:
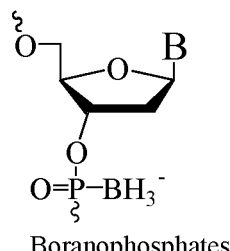
Figure 6:
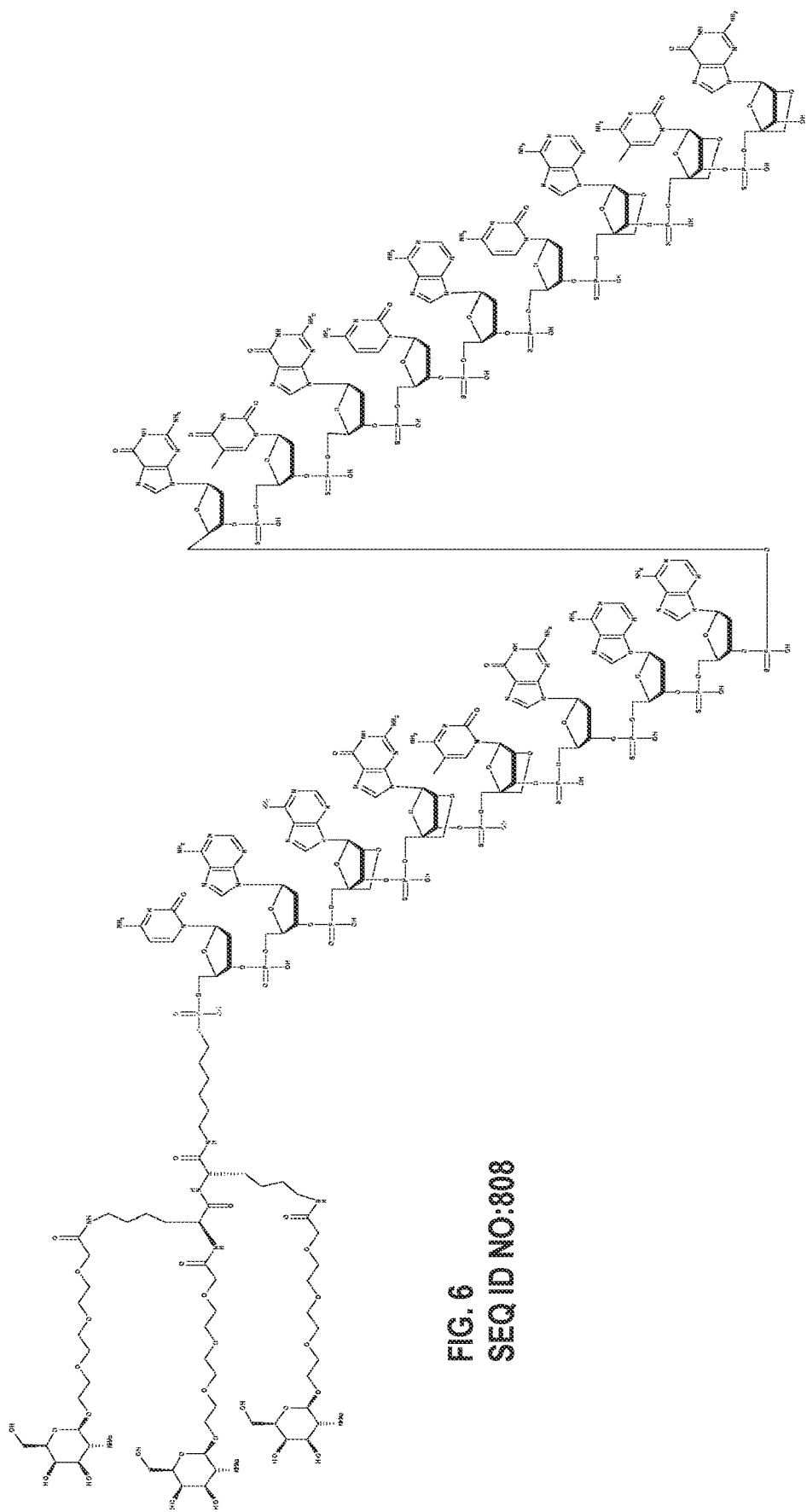
FIG. 6: present the structure of SEQ ID NO: 808
Figure 7:
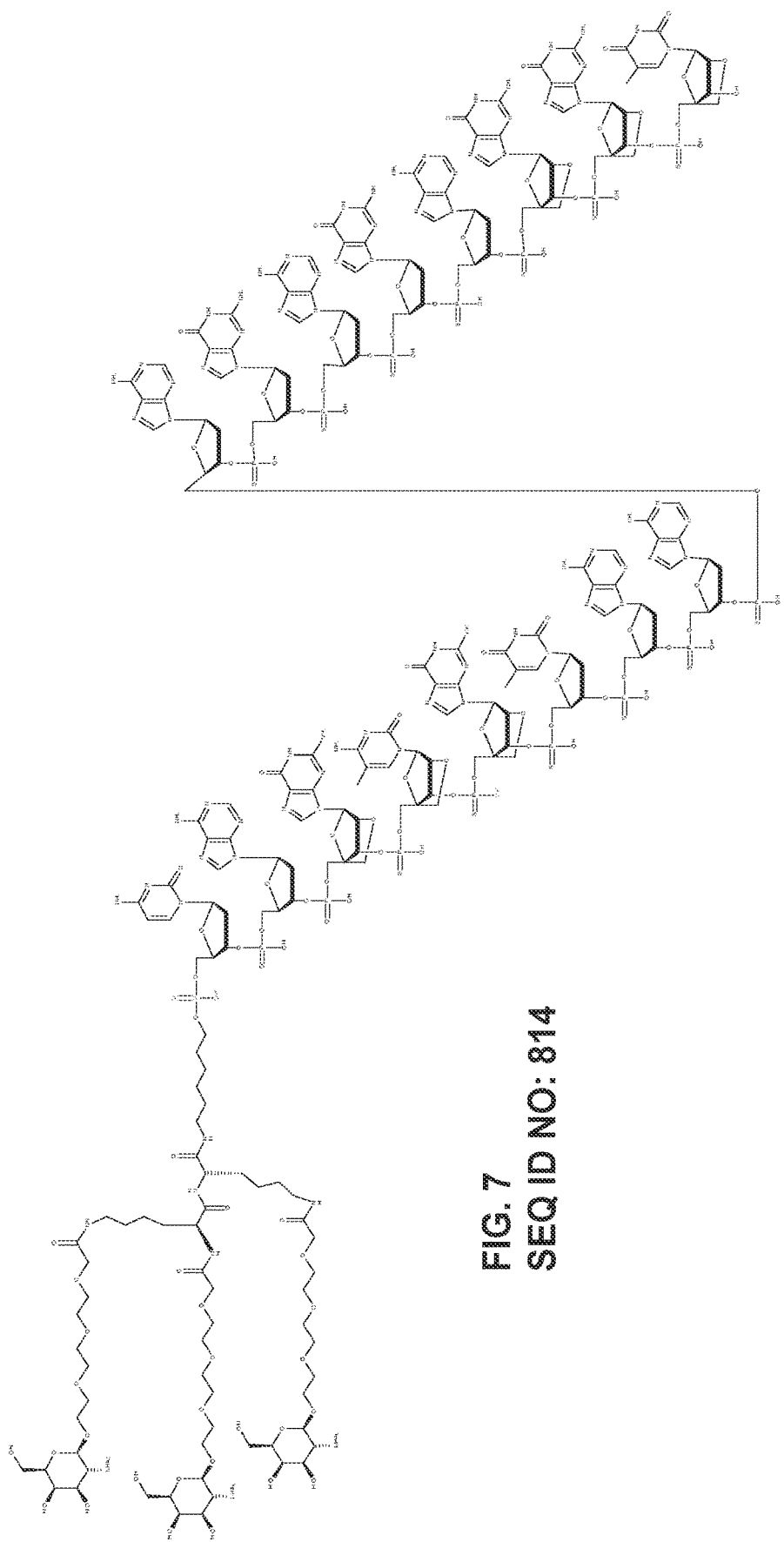
FIG. 7: present the structure of SEQ ID NO: 814
Figure 8:
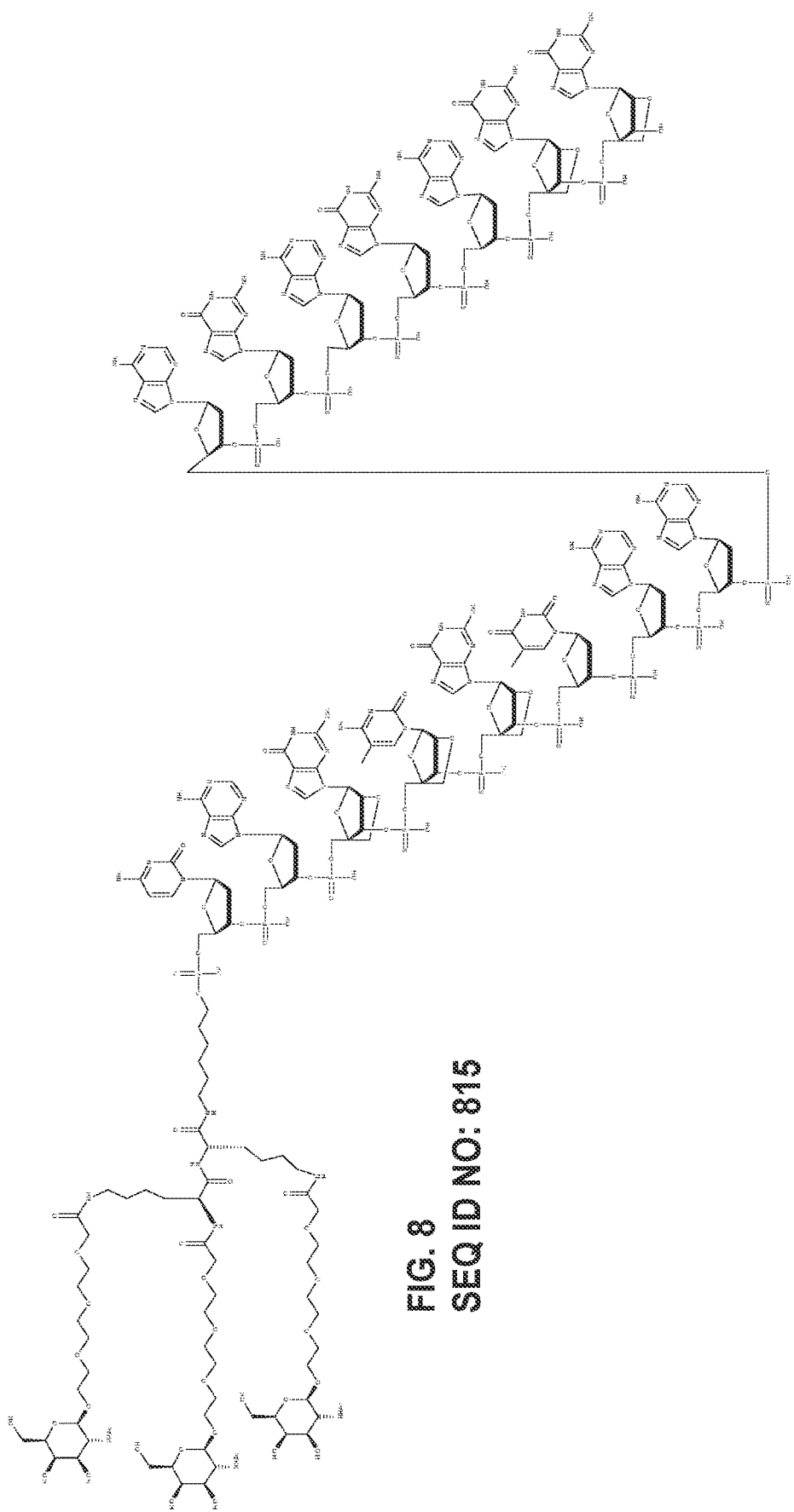
FIG. 8: present the structure of SEQ ID NO: 815
Figure 9:
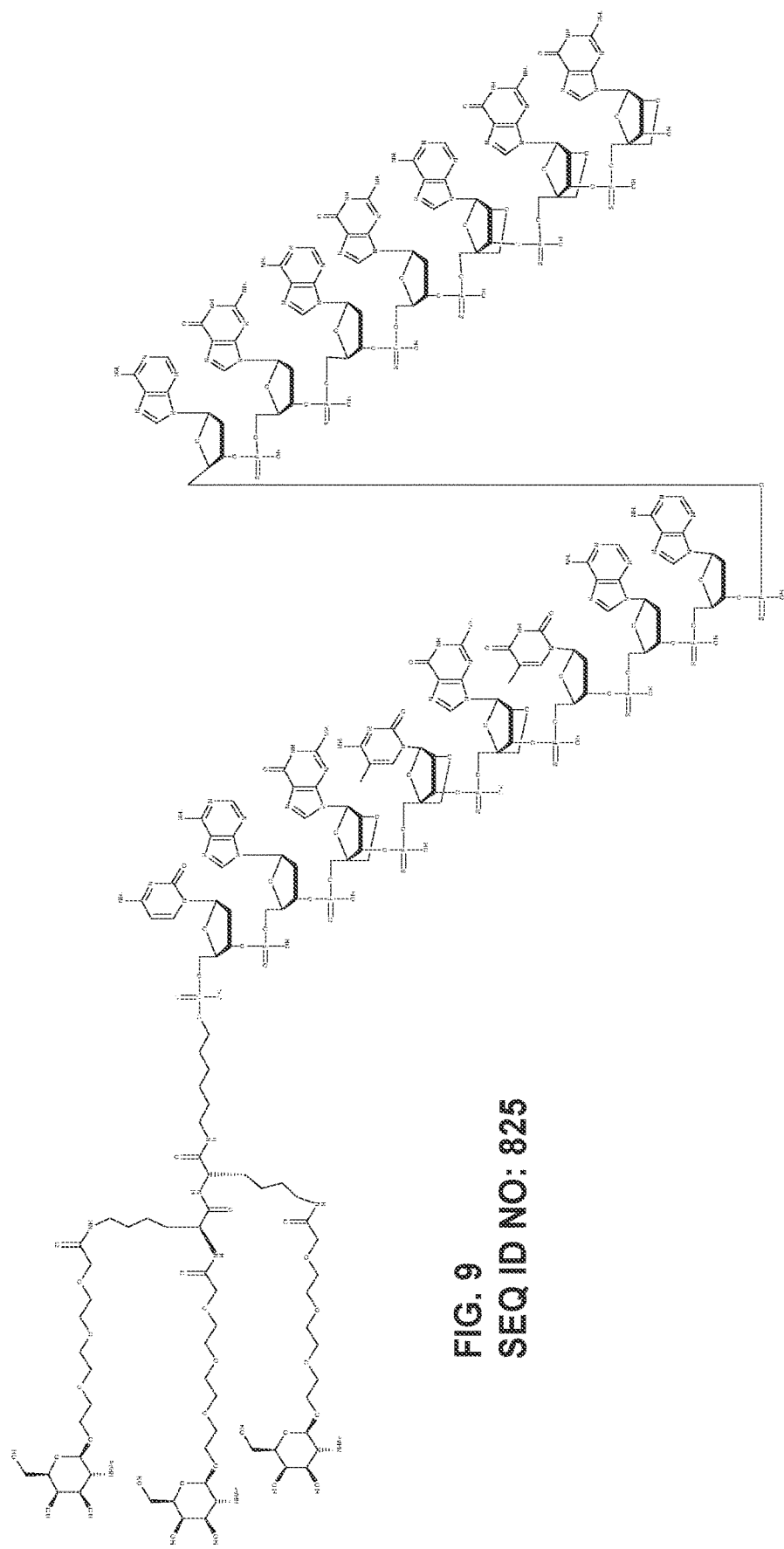
FIG. 9: present the structure of SEQ ID NO: 825
Figure 10:
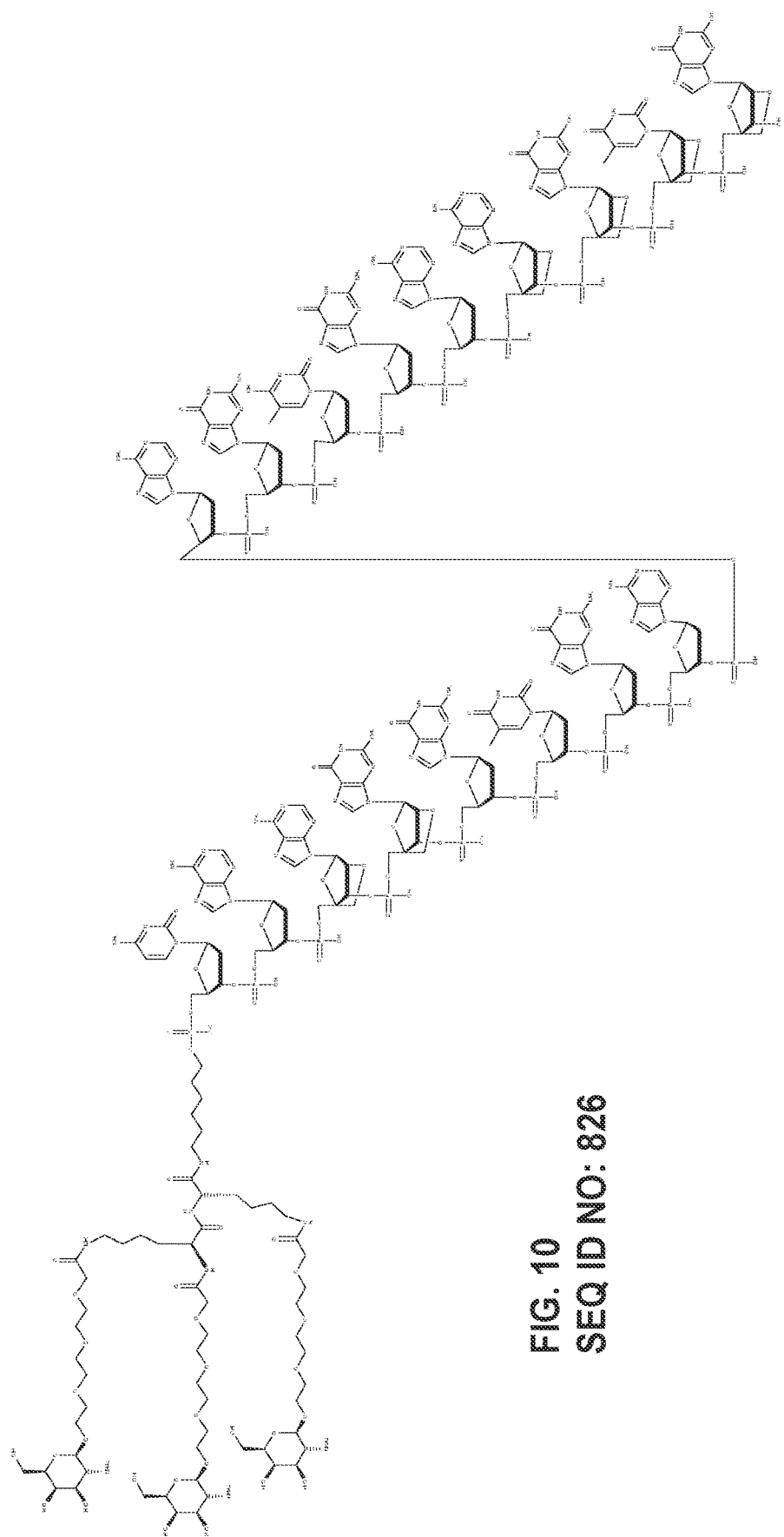
FIG. 10: present the structure of SEQ ID NO: 826

A total of 290 oligomers without conjugate were screened in the in vitro efficacy assay using a single dose of 25 μM oligomer. HBV antigen (HBsAg) secretion was measured after 13 days. Table 5 below show the results of the screening. The oligomers of SEQ ID NO 294 to SEQ ID NO 318 all reduced the HBsAg activity to less than 40% of the control. The oligomer of SEQ ID NO 584 corresponds to the oligomer disclosed as SEQ ID NO 16 in U.S. Pat. No. 8,598,334. An additional 213 oligomers were screened in the in vitro efficacy assay using a single dose of 25 μM oligomer. The results are shown in FIG. 5a.

TABLE 5

HBsAg activity of 25 μM oligomer as % of control.

| SeqID | Oligomers that bind both the HBsAg and the HBx transcript (SEQ ID NO 2) | Oligomers that bind HBsAg transcripts (SEQ ID NO 3), but not HBx transcript | Oligomer start position U95551 (SEQ ID NO 1) | LNA oligomer sequnces (Upper case letters = beta-D-oxy LNA, C LNA is 5-methyl C LNA, lower case letters = DNA, $^m$c = 5-methylcytosine DNA, all internucleoside linkages are phosphorothioate internucleoside linkages) | Activity (HBsAg levels in culture supernatant as percent of DMSO treated cells) | standard dev |
|---|---|---|---|---|---|---|
| SeqID 294 |   | X | 691 | GAAccactgaacAAA | 22.07 | 2.28 |
| SeqID 295 |   | X | 691 | CGAaccactgaacAAA | 18.38 | 2.08 |
| SeqID 296 |   | X | 692 | CGAaccactgaaCAA | 10.28 | 0.83 |
| SeqID 297 |   | X | 693 | CGAaccactgaACA | 14.74 | 1.99 |
| SeqID 298 |   | X | 694 | CGAaccactgaAC | 15.68 | 1.09 |
| SeqID 299 | X |   | 1264 | CCGcagtatggaTCG | 38.83 | 4.40 |
| SeqID 300 | X |   | 1265 | CGCagtatggaTC | 26.86 | 2.15 |
| SeqID 301 | X |   | 1530 | GCGtaaagagaGGT | 34.38 | 1.52 |
| SeqID 302 | X |   | 1530 | CGCgtaaagagaGGT | 38.30 | 6.35 |
| SeqID 303 | X |   | 1531 | GCGtaaagagaGG | 37.42 | 3.29 |
| SeqID 304 | X |   | 1551 | AGAaggcacagaCGG | 25.28 | 1.62 |
| SeqID 305 | X |   | 1551 | GAGaaggcacagaCGG | 25.02 | 1.51 |
| SeqID 306 | X |   | 1577 | GAAgtgcaca$^m$cGG | 14.81 | 3.11 |
| SeqID 307 | X |   | 1577 | GCGaagtgcacaCGG | 21.88 | 2.55 |
| SeqID 308 | X |   | 1577 | AGCgaagtgcacaCGG | 16.33 | 2.31 |

TABLE 5-continued

HBsAg activity of 25 µM oligomer as % of control.

| SeqID | Oligomers that bind both the HBsAg and the HBx transcript (S

TABLE 5-continued

HBsAg activity of 25 µM oligomer as % of control.

| SeqID | Oligomers that bind both the HBsAg and the HBx transcript (S

TABLE 5-continued

HBsAg activity of 25 μM oligomer as % of control.

| SeqID | Oligomers that bind both the HBsAg and the HBx transcript (SE

TABLE 5-continued

HBsAg activity of 25 µM oligomer as % of control.

| SeqID | Oligomers that bind both the HBsAg and the HBx transcript (S

TABLE 5-continued

HBsAg activity of 25 µM oligomer as % of control.

| SeqID | Oligomers that bind both the HBsAg and the HBx transcript (S

TABLE 5-continued

HBsAg activity of 25 µM oligomer as % of control.

| SeqID | Oligomers that bind both the HBsAg and the HBx transcript (

TABLE 5-continued

HBsAg activity of 25 µM oligomer as % of control.

| SeqID | Oligomers that bind both the HBsAg and the HBx transcript (S

TABLE 5-continued

HBsAg activity of 25 µM oligomer as % of control.

| SeqID | Oligomers that bind both the HBsAg and the HBx transcript (SEQ ID NO 2) | Oligomers that bind HBsAg transcripts (SEQ ID NO 3), but not HBx transcript | Oligomer start position U95551 (SEQ ID NO 1) | LNA oligomer sequnces (Upper case letters = beta-D-oxy LNA, C LNA is 5-methyl C LNA, lower case letters = DNA, $^m$c = 5-methylcytosine DNA, all internucleoside linkages are phosphorothiate internucleoside linkages) | Activity (HBsAg levels in culture supernatant as percent of DMSO treated cells) | standard dev |
|---|---|---|---|---|---|---|
| SeqID 537 | | X | 2371 | AGGgagttcttctTCT | 115.73 | 2.39 |
| SeqID 538 | | X | 2372 | AGGgagttcttcTTC | 115.60 | 13.69 |
| SeqID 539 | | X | 2372 | GAGggagttcttcTTC | 160.52 | 12.84 |
| SeqID 540 | | X | 2373 | AGGgagttcttCTT | 187.99 | 14.17 |
| SeqID 541 | | X | 2373 | GAGggagttcttCTT | 152.23 | 3.57 |
| SeqID 542 | | X | 2373 | CGAgggagttcttCTT | 125.29 | 10.56 |
| SeqID 543 | | X | 2374 | CGAgggagttctTCT | 125.58 | 12.12 |
| SeqID 544 | | X | 2374 | GCGagggagttctTCT | 127.13 | 7.13 |
| SeqID 545 | | X | 2375 | GCGagggagttcTTC | 140.39 | 2.94 |
| SeqID 546 | | X | 2375 | GGCgagggagttcTTC | 103.21 | 15.13 |
| SeqID 547 | | X | 2376 | GCGagggagttCTT | 104.72 | 31.01 |
| SeqID 548 | | X | 2376 | GGCgagggagttCTT | 120.43 | 4.29 |
| SeqID 549 | | X | 2376 | AGG$^m$cgagggagttCTT | 126.12 | 8.49 |
| SeqID 550 | | X | 2377 | GCGagggagttCT | 99.63 | 21.49 |
| SeqID 551 | | X | 2377 | GGCgagggagtTCT | 126.46 | 5.07 |
| SeqID 552 | | X | 2377 | AGG$^m$cgagggagtTCT | 124.41 | 7.46 |
| SeqID 553 | | X | 2377 | GAGg$^m$cgagggagtTCT | 122.05 | 4.13 |
| SeqID 554 | | X | 2378 | GGCgagggagtTC | 93.75 | 32.13 |
| SeqID 555 | | X | 2378 | AGG$^m$cgagggagTTC | 97.91 | 10.99 |
| SeqID 556 | | X | 2378 | GAGg$^m$cgagggagTTC | 125.97 | 14.10 |
| SeqID 557 | | X | 2378 | CGAgg$^m$cgagggagTTC | 114.85 | 11.32 |
| SeqID 558 | | X | 2379 | AGG$^m$cgagggagTT | 161.79 | 17.40 |
| SeqID 559 | | X | 2379 | GAGg$^m$cgagggaGTT | 112.49 | 14.53 |
| SeqID 560 | | X | 2379 | CGAgg$^m$cgagggaGTT | 99.73 | 6.03 |
| SeqID 561 | | X | 2379 | GCGagg$^m$cgagggaGTT | 26.82 | 16.61 |
| SeqID 562 | | X | 2380 | GAGg$^m$cgagggaGT | 126.11 | 10.60 |
| SeqID 563 | | X | 2380 | CGAgg$^m$cgagggAGT | 113.92 | 2.48 |
| SeqID 564 | | X | 2380 | GCGagg$^m$cgagggAGT | 114.21 | 22.83 |
| SeqID 565 | | X | 2380 | TGCgagg$^m$cgagggAGT | 120.75 | 7.83 |
| SeqID 566 | | X | 2381 | CGAgg$^m$cgagggAG | 96.48 | 7.91 |
| SeqID 567 | | X | 2381 | GCGagg$^m$cgaggGAG | 111.38 | 23.08 |
| SeqID 568 | | X | 2381 | TGCgagg$^m$cgaggGAG | 150.61 | 9.91 |

TABLE 5-continued

HBsAg activity of 25 µM oligomer as % of control.

| SeqID | Oligomers that bind both the HBsAg and the HBx transcript (SEQ ID NO 2) | Oligomers that bind HBsAg transcripts (SEQ ID NO 3), but not HBx transcript | Oligomer start position U95551 (SEQ ID NO 1) | LNA oligomer sequnces (Upper case letters = beta-D-oxy LNA, C LNA is 5-methyl C LNA, lower case letters = DNA, ᵐc = 5-methylcytosine DNA, all internucleoside linkages are phosphorothiate internucleoside linkages) | Activity (HBsAg levels in culture supernatant as percent of DMSO treated cells) | standard dev |
|---|---|---|---|---|---|---|
| SeqID 569 | | X | 2381 | CTGᵐcgaggᵐcgaggGAG | 115.39 | 3.45 |
| SeqID 570 | | X | 2382 | CGaggᵐcgaggGA | 94.94 | 9.74 |
| SeqID 571 | | X | 2382 | GCGaggᵐcgaggGA | 107.97 | 15.32 |
| SeqID 572 | | X | 2382 | TGCgaggᵐcgagGGA | 90.20 | 10.52 |
| SeqID 573 | | X | 2382 | CTGᵐcgaggᵐcgagGGA | 117.46 | 22.79 |
| SeqID 574 | | X | 2382 | TCTgᵐcgaggᵐcgagGGA | 119.40 | 1.22 |
| SeqID 575 | | X | 2383 | TCTgᵐcgaggᵐcgaGGG | 139.98 | 6.20 |
| SeqID 576 | | X | 2383 | GTCtgᵐcgaggᵐcgaGGG | 17.32 | 7.04 |
| SeqID 577 | | X | 2824 | GTTcccaagaaTAT | 121.37 | 5.20 |
| SeqID 578 | | X | 2824 | TGTtcccaagaaTAT | 119.62 | 5.98 |
| SeqID 579 | | X | 2825 | GTTcccaagaaTA | 118.81 | 12.04 |
| SeqID 580 | | X | 2825 | TGTtcccaagaATA | 119.14 | 20.21 |
| SeqID 581 | | X | 2825 | TTGttcccaagaATA | 109.70 | 3.36 |
| SeqID 582 | | X | 2826 | TGTtcccaagaAT | 110.02 | 17.04 |
| SeqID 583 | | X | 2826 | TTGttcccaagAAT | 132.22 | 4.26 |
| SeqID 584 | | X | 414 | GAGGcatagcagCAGG | 79.64 | 10.52 |

TABLE 5a

HBsAg activity of 25 μM oligomer as % of control.

| SeqID | Oligomer start position U95551 (SEQ ID NO 1) | LNA oligomer sequnces (Upper case letters = beta-D-oxy LNA, C LNA is 5-methyl C LNA, lower case letters = DNA, $^m$c = 5-methylcytosine DNA, all internucleoside linkages are phosphorothiate internucleoside linkages) | Activity (HBsAg levels in culture supernatant as percent of DMSO treated cells) | standard dev |
|---|---|---|---|---|
| 585 | 691 | GAAccactgaaCAAA | 31.9 | 2.6 |
| 586 | 691 | GAACcactgaacAAA | 35.1 | 1.3 |
| 587 | 691 | CGaaccactgaaCAAA | 45.5 | 2.4 |
| 588 | 691 | CGAAccactgaacAAA | 18.3 | 2.2 |
| 589 | 691 | CGAaccactgaaCAAA | 36.2 | 9.1 |
| 590 | 691 | CGAAccactgaacaAA | 22.4 | 1.6 |
| 591 | 691 | CGAAccactgaaCAAA | 26.3 | 2.3 |
| 592 | 692 | CGAAccactgaacAA | 11.8 | 1.2 |
| 593 | 692 | CGAAccactgaaCAA | 21.9 | 8.5 |

TABLE 5a-continued

HBsAg activity of 25 µM oligomer as % of control.

| SeqID | Oligomer start position U95551 (SEQ ID NO 1) | LNA oligomer sequnces (Upper case letters = beta-D-oxy LNA, C LNA is 5-methyl C LNA, lower case letters = DNA, $^m$c = 5-methylcytosine DNA, all internucleoside linkages are phosphorothiate internucleoside linkages) | Activity (HBsAg levels in culture supernatant as percent of DMSO treated cells) | standard dev |
|---|---|---|---|---|
| 594 | 692 | CGAaccactgaACAA | 18.3 | 0.6 |
| 595 | 693 | CGaaccactgAACA | 25.8 | 1.6 |
| 596 | 693 | CGAAccactgaaCA | 9.5 | 1.5 |
| 597 | 693 | CGAaccactgAACA | 23.6 | 2.0 |
| 598 | 693 | CGAAccactgaACA | 14.6 | 0.9 |
| 599 | 694 | CGaaccactgAAC | 42.1 | 3.8 |
| 600 | 694 | CGAaccactgAAC | 25.0 | 1.7 |
| 601 | 1264 | CCgcagtatggATCG | 98.7 | 16.4 |
| 602 | 1264 | CCGCagtatggatCG | 62.0 | 2.0 |
| 603 | 1264 | CCGCagtatggaTCG | 79.6 | 21.3 |
| 604 | 1264 | CCGcagtatggATCG | 113.3 | 12.3 |
| 605 | 1265 | CGCAgtatggaTC | 43.0 | 5.9 |
| 606 | 1265 | CGcagtatggATC | 97.7 | 22.6 |
| 607 | 1265 | CGCagtatggATC | 80.1 | 21.3 |
| 608 | 1265 | CGcagtatgGATC | 110.0 | 11.2 |
| 609 | 1530 | GCGTaaagagagGT | 65.2 | 6.6 |
| 610 | 1530 | GCgtaaagagAGGT | 43.4 | 6.1 |
| 611 | 1530 | GCGtaaagagAGGT | 59.9 | 5.8 |
| 612 | 1530 | GCGTaaagagaGGT | 52.7 | 1.9 |
| 613 | 1530 | CGCGtaaagagagGT | 96.7 | 9.7 |
| 614 | 1530 | CG$^m$cgtaaagagAGGT | 35.9 | 1.1 |
| 615 | 1530 | CGCGtaaagagaGGT | 63.1 | 3.9 |
| 616 | 1530 | CGCgtaaagagAGGT | 65.0 | 4.6 |
| 617 | 1531 | GCgtaaagagAGG | 24.6 | 1.5 |
| 618 | 1531 | GCGtaaagagAGG | 32.2 | 1.3 |
| 619 | 1531 | GCgtaaagaGAGG | 54.7 | 4.7 |
| 620 | 1531 | GCGTaaagagaGG | 59.0 | 0.4 |
| 621 | 1551 | AGaaggcacagACGG | 41.2 | 4.2 |
| 622 | 1551 | AGAaggcacagACGG | 45.4 | 10.9 |
| 623 | 1551 | AGAAggcacagaCGG | 38.3 | 4.0 |
| 624 | 1551 | GAGAaggcacagaCGG | 35.0 | 11.1 |
| 625 | 1551 | GAGaaggcacagACGG | 50.3 | 10.2 |
| 626 | 1551 | GAGAaggcacagACGG | 48.1 | 2.1 |
| 627 | 1577 | GAagtgcacaCGG | 21.5 | 2.1 |

TABLE 5a-continued

HBsAg activity of 25 μM oligomer as % of control.

| SeqID | Oligomer start position U95551 (SEQ ID NO 1) | LNA oligomer sequnces (Upper case letters = beta-D-oxy LNA, C LNA is 5-methyl C LNA, lower case letters = DNA, ᵐc = 5-methylcytosine DNA, all internucleoside linkages are phosphorothiate internucleoside linkages) | Activity (HBsAg levels in culture supernatant as percent of DMSO treated cells) | standard dev |
|---|---|---|---|---|
| 628 | 1577 | GAAgtgcacaCGG | 23.7 | 1.4 |
| 629 | 1577 | GAAGtgcacaCGG | 41.2 | 1.3 |
| 630 | 1577 | GAAgtgcacACGG | 29.3 | 1.3 |
| 631 | 1577 | GCgaagtgcacaCGG | 54.0 | 19.6 |
| 632 | 1577 | GCGaagtgcacaᵐcGG | 49.7 | 10.7 |
| 633 | 1577 | GCGAagtgcacaᵐcGG | 30.3 | 5.2 |
| 634 | 1577 | GCgaagtgcacACGG | 46.9 | 7.3 |
| 635 | 1577 | AGCGaagtgcacaᵐcGG | 47.5 | 10.3 |
| 636 | 1577 | AGᵐcgaagtgcacACGG | 38.1 | 4.2 |
| 637 | 1577 | AGᵐcgaagtgcacaCGG | 83.2 | 37.3 |
| 638 | 1577 | AGCgaagtgcacaᵐcGG | 43.1 | 17.7 |
| 639 | 1578 | CGaagtgcaCACG | 58.3 | 6.9 |
| 640 | 1578 | CGAagtgcacACG | 30.9 | 2.7 |
| 641 | 1578 | CGaagtgcacACG | 45.4 | 2.1 |
| 642 | 1578 | AGCgaagtgcaCACG | 128.1 | 7.6 |
| 643 | 1578 | AGCGaagtgcacACG | 49.6 | 5.3 |
| 644 | 1578 | AGCGaagtgcacaCG | 47.4 | 5.3 |
| 645 | 1578 | AGᵐcgaagtgcaCACG | 59.1 | 3.5 |
| 646 | 1578 | AAgᵐcgaagtgcaCACG | 91.7 | 20.2 |
| 647 | 1578 | AAGCgaagtgcacaCG | 49.5 | 3.0 |
| 648 | 1578 | AAGᵐcgaagtgcaCACG | 63.2 | 1.9 |
| 649 | 1578 | AAGCgaagtgcacACG | 41.9 | 2.1 |
| 650 | 1578 | AAGCgaagtgcaCACG | 64.7 | 4.5 |
| 651 | 1580 | GAagᵐcgaagtgCACA | 142.9 | 18.3 |
| 652 | 1580 | GAAGᵐcgaagtgcaCA | 61.5 | 4.1 |
| 653 | 1580 | GAAgᵐcgaagtgCACA | 152.1 | 21.8 |
| 654 | 1580 | GAAGᵐcgaagtgCACA | 167.2 | 17.5 |
| 655 | 1582 | GGtgaagᵐcgaagtGCA | 117.8 | 18.0 |
| 656 | 1582 | GGTgaagᵐcgaagtgCA | 108.0 | 10.4 |
| 657 | 1582 | GGTGaagᵐcgaagtgCA | 93.5 | 24.7 |
| 658 | 1582 | GGtgaagᵐcgaaGTGCA | 125.1 | 18.6 |
| 659 | 1583 | GGtgaagᵐcgaaGTGC | 109.4 | 18.5 |
| 660 | 1583 | GGTgaagᵐcgaagtGC | 104.1 | 14.0 |
| 661 | 1583 | GGTGaagᵐcgaagtGC | 84.4 | 23.1 |
| 662 | 1583 | GGtgaagᵐcgaaGTGC | 60.1 | 9.7 |

TABLE 5a-continued

HBsAg activity of 25 µM oligomer as % of control.

| SeqID | Oligomer start position U95551 (SEQ ID NO 1) | LNA oligomer sequnces (Upper case letters = beta-D-oxy LNA, C LNA is 5-methyl C LNA, lower case letters = DNA, ᵐc = 5-methylcytosine DNA, all internucleoside linkages are phosphorothiate internucleoside linkages) | Activity (HBsAg levels in culture supernatant as percent of DMSO treated cells) | standard dev |
|---|---|---|---|---|
| 663 | 1583 | AGgtgaagᵐcgaagTGC | 48.4 | 5.5 |
| 664 | 1583 | AGGtgaagᵐcgaagtGC | 42.3 | 3.7 |
| 665 | 1583 | AGGTgaagᵐcgaagtGC | 71.6 | 12.3 |
| 666 | 1583 | AGgtgaagᵐcgaaGTGC | 50.7 | 10.7 |
| 667 | 1584 | AGGTgaagᵐcgaagTG | 47.7 | 44.6 |
| 668 | 1584 | AGgtgaagᵐcgaAGTG | 27.7 | 2.1 |
| 669 | 1584 | AGgtgaagᵐcgaAGTG | 15.7 | 2.1 |
| 670 | 1584 | AGGTgaagᵐcgaAGTG | 58.8 | 49.5 |
| 671 | 1585 | AGGTgaagᵐcgaaGT | 118.2 | 14.8 |
| 672 | 1585 | AGgtgaagᵐcgAAGT | 31.5 | 38.6 |
| 673 | 1585 | AGgtgaagᵐcgAAGT | 25.8 | 4.4 |
| 674 | 1585 | AGGTgaagᵐcgaAGT | 48.2 | 37.8 |
| 675 | 1588 | CAGAggtgaagᵐcGA | 52.4 | 4.6 |
| 676 | 1588 | CAgaggtgaaGCGA | 67.4 | 0.1 |
| 677 | 1588 | CAGAggtgaaGCGA | 79.0 | 9.4 |
| 678 | 670 | TAGtaaactgagCCA | 31.3 | 2.7 |
| 679 | 670 | TAgtaaactgaGCCA | 93.0 | 12.1 |
| 680 | 670 | TAGTaaactgagcCA | 15.8 | 2.4 |
| 681 | 670 | TAGtaaactgaGCCA | 66.9 | 6.6 |
| 682 | 670 | TAGTaaactgagCCA | 26.6 | 4.9 |
| 683 | 670 | CTAgtaaactgagCCA | 101.6 | 6.7 |
| 684 | 670 | CTagtaaactgaGCCA | 158.0 | 11.6 |
| 685 | 670 | CTAGtaaactgagcCA | 102.4 | 34.7 |
| 686 | 671 | CTAgtaaactgaGCC | 76.3 | 32.9 |
| 687 | 671 | CTagtaaactgAGCC | 53.0 | 13.8 |
| 688 | 671 | CTAGtaaactgagCC | 41.9 | 5.1 |
| 689 | 671 | CTagtaaactgaGCC | 31.8 | 2.2 |
| 690 | 671 | CTAgtaaactgagCC | 102.9 | 10.2 |
| 691 | 674 | GCActagtaaacTGA | 53.6 | 4.8 |
| 692 | 674 | GCactagtaaaCTGA | 74.4 | 1.5 |
| 693 | 674 | GCACtagtaaactGA | 81.9 | 10.6 |
| 694 | 674 | GCActagtaaaCTGA | 54.5 | 1.5 |
| 695 | 674 | GCACtagtaaacTGA | 74.9 | 4.5 |
| 696 | 674 | GGCactagtaaacTGA | 42.8 | 60.5 |

TABLE 5a-continued

HBsAg activity of 25 μM oligomer as % of control.

| SeqID | Oligomer start position U95551 (SEQ ID NO 1) | LNA oligomer sequnces (Upper case letters = beta-D-oxy LNA, C LNA is 5-methyl C LNA, lower case letters = DNA, ᵐc = 5-methylcytosine DNA, all internucleoside linkages are phosphorothiate internucleoside linkages) | Activity (HBsAg levels in culture supernatant as percent of DMSO treated cells) | standard dev |
|---|---|---|---|---|
| 697 | 674 | GGcactagtaaaCTGA | 47.1 | 38.9 |
| 698 | 674 | GGCActagtaaactGA | 147.7 | 7.1 |
| 699 | 1141 | CAAᵐcggggtaaaGGT | 187.2 | 5.6 |
| 700 | 1141 | CAaᵐcggggtaaAGGT | 176.2 | 18.0 |
| 701 | 1141 | CAACggggtaaagGT | 187.9 | 3.8 |
| 702 | 1141 | CAAᵐcggggtaaAGGT | 142.7 | 19.7 |
| 703 | 1141 | CAACggggtaaaGGT | 144.8 | 31.8 |
| 704 | 1261 | CAGtatggatᵐcgGCA | 59.6 | 19.9 |
| 705 | 1261 | CAgtatggatᵐcGGCA | 54.3 | 4.1 |
| 706 | 1261 | CAgtatggatᵐcgGCA | 70.0 | 8.6 |
| 707 | 1261 | CAGtatggatᵐcggCA | 60.3 | 8.0 |
| 708 | 1265 | TTCᵐcgcagtatggATC | 110.7 | 2.0 |
| 709 | 1265 | TTcᵐcgcagtatgGATC | 105.5 | 4.2 |
| 710 | 1265 | TTCCgcagtatggaTC | 104.1 | 6.7 |
| 711 | 1265 | TTCᵐcgcagtatgGATC | 107.1 | 8.8 |
| 712 | 1265 | TTCCgcagtatggATC | 119.0 | 9.6 |
| 713 | 1266 | TTCᵐcgcagtatgGAT | 99.8 | 6.8 |
| 714 | 1266 | TTcᵐcgcagtatGGAT | 92.3 | 5.1 |
| 715 | 1266 | TTCCgcagtatggAT | 104.7 | 3.6 |
| 716 | 1266 | TTCᵐcgcagtatGGAT | 108.7 | 3.8 |
| 717 | 1266 | TTCCgcagtatgGAT | 112.0 | 2.1 |
| 718 | 1266 | GTTcᵐcgcagtatgGAT | 85.5 | 4.5 |
| 719 | 1266 | GTtcᵐcgcagtatGGAT | 80.0 | 6.7 |
| 720 | 1266 | GTTCᵐcgcagtatggAT | 127.9 | 16.9 |
| 721 | 1267 | GTtcᵐcgcagtaTGGA | 67.2 | 5.0 |
| 722 | 1267 | GTTCᵐcgcagtatgGA | 150.8 | 5.9 |
| 723 | 1267 | GTtcᵐcgcagtatGGA | 78.6 | 8.0 |
| 724 | 1267 | GTTcᵐcgcagtatgGA | 76.5 | 7.9 |
| 725 | 1267 | AGTtcᵐcgcagtatGGA | 72.6 | 5.2 |
| 726 | 1267 | AGTTcᵐcgcagtatgGA | 87.1 | 5.6 |
| 727 | 1267 | AGttcᵐcgcagtatGGA | 83.1 | 4.3 |
| 728 | 1267 | AGtcᵐcgcagtatgGA | 79.4 | 5.6 |
| 729 | 1267 | AGttcᵐcgcagtatgGA | 89.9 | 2.0 |
| 730 | 1268 | AGTtcᵐcgcagtaTGG | 51.2 | 4.0 |
| 731 | 1268 | AGttcᵐcgcagtaTGG | 63.6 | 0.5 |

TABLE 5a-continued

HBsAg activity of 25 µM oligomer as % of control.

| SeqID | Oligomer start position U95551 (SEQ ID NO 1) | LNA oligomer sequnces (Upper case letters = beta-D-oxy LNA, C LNA is 5-methyl C LNA, lower case letters = DNA, ᵐc = 5-methylcytosine DNA, all internucleoside linkages are phosphorothiate internucleoside linkages) | Activity (HBsAg levels in culture supernatant as percent of DMSO treated cells) | standard dev |
|---|---|---|---|---|
| 732 | 1268 | AGTtcᵐcgcagtatGG | 65.9 | 1.6 |
| 733 | 1268 | AGttcᵐcgcagtatGG | 80.9 | 2.5 |
| 734 | 1268 | GAgttcᵐcgcagtaTGG | 49.2 | 4.7 |
| 735 | 1268 | GAGttcᵐcgcagtatGG | 60.1 | 6.1 |
| 736 | 1268 | GAgttcᵐcgcagtatGG | 73.9 | 1.1 |
| 737 | 1269 | GAGTtcᵐcgcagtaTG | 58.6 | 6.6 |
| 738 | 1269 | GAgttcᵐcgcagtATG | 57.1 | 8.1 |
| 739 | 1269 | GAGttcᵐcgcagtaTG | 49.8 | 6.8 |
| 740 | 1269 | GAgttcᵐcgcagtaTG | 60.8 | 1.6 |
| 741 | 1269 | GGAGttcᵐcgcagtaTG | 137.3 | 2.6 |
| 742 | 1269 | GGagttcᵐcgcagtATG | 90.5 | 22.8 |
| 743 | 1269 | GGAgttcᵐcgcagtaTG | 117.5 | 2.4 |
| 744 | 1269 | GGagttcᵐcgcagtaTG | 124.7 | 6.4 |
| 745 | 1525 | TAAagagaggtgᵐcGCC | 71.3 | 60.7 |
| 746 | 1525 | TAaagagaggtgCGCC | 73.9 | 59.0 |
| 747 | 1525 | TAAAgagaggtgᵐcgCC | 79.5 | 45.6 |
| 748 | 1525 | TAAagagaggtgCGCC | 93.6 | 4.6 |
| 749 | 1525 | TAAAgagaggtgᵐcGCC | 28.0 | 22.3 |
| 750 | 1526 | TAAagagaggtgCGC | 96.3 | 22.2 |
| 751 | 1526 | TAaagagaggtGCGC | 101.9 | 73.2 |
| 752 | 1526 | TAAagagaggtGCGC | 44.3 | 72.6 |
| 753 | 1526 | TAAAgagaggtgCGC | 64.1 | 50.8 |
| 754 | 1526 | GTAaagagaggtgCGC | 27.0 | 47.8 |
| 755 | 1526 | GTaaagagaggtGCGC | 65.6 | 58.8 |
| 756 | 1527 | GTAaagagaggtGCG | 23.6 | 42.9 |
| 757 | 1527 | GTaaagagaggTGCG | 80.5 | 2.4 |
| 758 | 1527 | GTaaagagaggTGCG | 81.8 | 61.8 |
| 759 | 1527 | GTAAagagaggtGCG | 31.5 | 35.2 |
| 760 | 1527 | CGtaaagagaggTGCG | 91.5 | 62.5 |
| 761 | 1527 | CGTAaagagaggtgCG | 70.5 | 60.0 |
| 762 | 1527 | CGTaaagagaggTGCG | 79.6 | 60.1 |
| 763 | 1527 | CGTAaagagaggtGCG | 4.5 | 4.1 |
| 764 | 1528 | CGTaaagagaggTGC | 37.0 | 55.1 |
| 765 | 1528 | CGtaaagagagGTGC | 89.4 | 17.7 |

TABLE 5a-continued

HBsAg activity of 25 µM oligomer as % of control.

| SeqID | Oligomer start position U95551 (SEQ ID NO 1) | LNA oligomer sequnces (Upper case letters = beta-D-oxy LNA, C LNA is 5-methyl C LNA, lower case letters = DNA, ᵐc = 5-methylcytosine DNA, all internucleoside linkages are phosphorothiate internucleoside linkages) | Activity (HBsAg levels in culture supernatant as percent of DMSO treated cells) | standard dev |
|---|---|---|---|---|
| 766 | 1528 | CGTAaagagaggtGC | 93.3 | 17.1 |
| 767 | 1528 | CGTaaagagagGTGC | 63.4 | 4.2 |
| 768 | 1528 | CGTAaagagaggTGC | 34.1 | 51.7 |
| 769 | 1528 | GCGtaaagagaggTGC | 50.5 | 83.8 |
| 770 | 1528 | GCgtaaagagagGTGC | 43.6 | 73.2 |
| 771 | 1528 | GCgtaaagagaggTGC | 31.3 | 53.0 |
| 772 | 1528 | GCGtaaagagaggtGC | 43.9 | 69.9 |
| 773 | 1529 | GCGtaaagagagGTG | 53.2 | 67.4 |
| 774 | 1529 | GCgtaaagagaGGTG | 2.9 | 3.1 |
| 775 | 1529 | GCGTaaagagaggTG | 44.0 | 32.8 |
| 776 | 1529 | GCGtaaagagaGGTG | 8.8 | 4.3 |
| 777 | 1529 | GCGTaaagagagGTG | −0.6 | 0.6 |
| 778 | 1529 | CGCgtaaagagagGTG | 43.2 | 40.7 |
| 779 | 1529 | ᵐcgᵐcgtaaagagaGGTG | 8.3 | 5.3 |
| 780 | 1529 | CGCGtaaagagaggTG | 37.6 | 40.0 |
| 781 | 1529 | CGCgtaaagagaGGTG | 33.5 | 40.4 |
| 782 | 1529 | CGCGtaaagagagGTG | 33.5 | 54.0 |
| 783 | 1552 | TGAgaaggcacagACG | 95.2 | 5.5 |
| 784 | 1552 | TGagaaggcacaGACG | 54.4 | 48.4 |
| 785 | 1552 | TGAGaaggcacagaCG | 67.2 | 6.3 |
| 786 | 1552 | TGAgaaggcacaGACG | 49.4 | 43.8 |
| 787 | 1552 | TGAGaaggcacagACG | 56.1 | 9.5 |
| 788 | 1690 | GCctcaaggtᵐcgGTC | 78.8 | 70.1 |
| 789 | 1690 | GCCtcaaggtᵐcggTC | 21.6 | 40.1 |
| 790 | 1690 | GCctcaaggtᵐcggTC | 46.7 | 74.2 |
| 791 | 1778 | ATgcctacagccTCC | 51.8 | 1.4 |
| 792 | 1778 | ATGcctacagcctCC | 51.1 | 2.2 |
| 793 | 1778 | ATgcctacagcctCC | 59.4 | 7.0 |
| 794 | 1785 | ACCAatttatgcCTAC | 145.3 | 4.8 |
| 795 | 1785 | ACCaatttatgcCTAC | 138.6 | 10.2 |
| 796 | 1785 | ACCAatttatgccTAC | 137.4 | 0.4 |
| 797 | 1785 | ACCaatttatgccTAC | 131.3 | 9.2 |
| 798 | 1785 | ACcaatttatgcCTAC | 126.0 | 8.7 |

Results from Multiple Concentration Treatments

A selection of oligomers from Table 5 were tested using three-fold serial dilutions (25.000, 8.3333, 2.7778, 0.9259, 0.0343, 0.0114, 0.0038, 0.0013 µM oligomer) in the in vitro efficacy assay to assess IC 50 and CC50 values for the oligomers. HBV antigen (HBsAg) secretion was measured after 13 days. Table 6 below show the results of the analysis. The oligomer of SEQ ID NO 585 corresponds to the oligomer disclosed as SEQ ID NO 16 in U.S. Pat. No. 8,598,334.

TABLE 6

| Seq ID | IC$_{50}$ (µM) | CC$_{50}$ (µM) |
|---|---|---|
| SeqID 294 | 2.07 | >25 |
| SeqID 295 | 2.05 | >25 |
| SeqID 296 | 1.72 | <0.0013 |
| SeqID 297 | 0.45 | >25 |
| SeqID 298 | 0.44 | >25 |
| SeqID 300 | 0.54 | >25 |
| SeqID 301 | 0.96 | >25 |
| SeqID 303 | 2.57 | >25 |
| SeqID 304 | 1.70 | <0.0013 |
| SeqID 305 | 2.05 | >25 |
| SeqID 306 | 1.18 | >25 |
| SeqID 307 | 0.68 | >25 |
| SeqID 308 | 2.62 | >25 |
| SeqID 309 | 2.15 | >25 |
| SeqID 310 | 2.04 | >25 |
| SeqID 311 | 9.75 | >25 |
| SeqID 315 | 1.12 | >25 |
| SeqID 316 | 1.13 | >25 |
| SeqID 317 | 0.80 | >25 |
| SeqID 318 | 5.27 | >25 |
| SeqID 368 | >25 | <0.0013 |
| SeqID 386 | 12.32 | >25 |
| SeqID 389 | 23.43 | >25 |
| SeqID 390 | 2.57 | >25 |
| SeqID 391 | 5.91 | >25 |
| SeqID 393 | 3.08 | >25 |
| SeqID 398 | 19.84 | >25 |
| SeqID 400 | 3.07 | >25 |
| SeqID 402 | 2.00 | >25 |
| SeqID 424 | 2.43 | >25 |
| SeqID 427 | 0.61 | >25 |
| SeqID 442 | 2.24 | >25 |
| SeqID 456 | 0.78 | >25 |
| SeqID 457 | 6.05 | >25 |
| SeqID 473 | 3.91 | >25 |
| SeqID 474 | 4.67 | >25 |
| SeqID 475 | 6.15 | >25 |
| SeqID 476 | 3.82 | >25 |
| SeqID 479 | 5.88 | >25 |
| SeqID 481 | 6.63 | >25 |
| SeqID 482 | 10.10 | >25 |
| SeqID 484 | 17.04 | >25 |
| SeqID 485 | 4.34 | >25 |
| SeqID 584 | >25 | >25 |

Example 3 In Vivo AAV/HBV Mouse Model

Anti-HBV LNAs can be evaluated in AAV/HBV mouse model. In this model, mice infected with a recombinant adeno-associated virus (AAV) carrying the HBV genome (AAV/HBV) maintains stable viremia and antigenimia for more than 30 weeks (Dan Yang, et al. 2014 Cellular & Molecular Immunology 11, 71-78).

Male C57BL/6 mice (4-6 weeks old), specific pathogen free, are purchased from SLAC (Shanghai Laboratory Animal Center of Chinese Academy of Sciences) and housed in an animal care facility in individually ventilated cages. Guidelines are followed for the care and use of animals as indicated by WuXi IACUC (Institutional Animal Care and Use Committee, WUXI IACUC protocol number R20131126-Mouse). Mice are allowed to acclimate to the new environment for 3 days and are grouped according to the experimental design.

Recombinant AAV-HBV was diluted in PBS, 200 µL per injection. This recombinant virus carries 1.3 copies of the HBV genome (genotype D, serotype ayw).

On day 0, all mice are injected through tail vein with 200 µL AAV-HBV. On days 6, 13 and 20 after AAV injection, all mice in are submandibularly bled (0.1 ml blood/mouse) for serum collection. On day 22 post injection, mice with stable viremia are treated with vehicle or anti-HBV LNAs dosed intravenously at 5 mg/kg. The LNA oligomers can be unconjugated or GalNAc conjugated.

Mice are dosed biweekly for two weeks. On days 3, 7, 10 and 14 days after first LNA dosing, all mice are submandibularly bled (0.1 ml blood/mouse) for serum collection to monitor HBV surface antigen (HBsAg), HBV e antigen (HBeAg), and HBV genomic DNA in serum.

Example 4 In Vivo Study of Bi-Weekly Injections at Single Dose

The AAV/HBV Mouse Model as prepared in Example 3 was used in this study. Ten GalNAc conjugated Anti-HBV LNA oligomers were tested with saline as control in C57BL/6 mice with stable viremia. Some of the oligomers were compared with the standard of care nucleoside analog, Entecavir (ETV), administered as prescribed with 0.03 mg per kilo as a daily oral dosis. Mice were dosed subcutaneously twice weekly for two weeks on days 0, 3, 7 and 10 or day 0, 3, 6 and 9 with a dose of 2 mg/kg pr injection. HBV surface antigen (HBsAg), HBV e antigen (HBeAg), and HBV genomic DNA in serum was measured at the indicated days using the methods described in the "Materials and methods" section. The mice were followed for 23-24 days. The results are shown in the tables below.

TABLE 7A-C

Serum level of HBsAg ($\log_{10}$(IU/ml)) following twice-weekly dosages of 2 mg/kg Data are from three independent studies.

A

| Day | Saline HBsAg | Stdev | SEQID806 HBsAg | Stdev | SEQID807 HBsAg | StDev | SEQID815 HBsAg | StDev | SEQID800 HBsAg | StDev | SEQID802 HBsAg | Stdev | ETV HBsAg | Stdev |
|---|---|---|---|---|---|---|---|---|---|---|---|---|---|---|
| 0 | 4.23 | 0.53 | 4.79 | 0.04 | 4.68 | 0.04 | 4.06 | 0.76 | 4.73 | 0.01 | 4.07 | 0.37 | 4.49 | 0.24 |
| 3 | 4.05 | 0.40 | 4.48 | 0.16 | 4.00 | 0.12 | 3.48 | 0.83 | 4.08 | 0.14 | 3.89 | 0.24 | 4.37 | 0.30 |
| 7 | 4.26 | 0.22 | 4.17 | 0.13 | 3.37 | 0.20 | 2.68 | 0.71 | 3.23 | 0.23 | 3.57 | 0.52 | 4.33 | 0.33 |
| 10 | 4.38 | 0.17 | 4.09 | 0.14 | 3.12 | 0.17 | 2.60 | 0.61 | 2.90 | 0.30 | 3.66 | 0.53 | 4.43 | 0.25 |
| 14 | 4.37 | 0.20 | 3.86 | 0.33 | 2.82 | 0.21 | 2.69 | 0.45 | 2.67 | 0.38 | 3.52 | 0.52 | 4.53 | 0.22 |

TABLE 7A-C-continued

Serum level of HBsAg ($\log_{10}$(IU/ml)) following twice-weekly dosages of 2 mg/kg Data are from three independent studies.

| 17 | 4.47 | 0.12 | 4.10 | 0.23 | 3.03 | 0.20 | 2.91 | 0.36 | 2.20 | 0.84 | 3.62 | 0.49 | 3.71 | 1.52 |
|---|---|---|---|---|---|---|---|---|---|---|---|---|---|---|
| 21 | 4.55 | 0.12 | 4.21 | 0.22 | 3.37 | 0.20 | 3.36 | 0.44 | 2.92 | 0.24 | 3.72 | 0.50 | 4.64 | 0.11 |
| 24 | 4.57 | 0.11 | 4.36 | 0.20 | 3.67 | 0.08 | 3.91 | 0.34 | 3.21 | 0.25 | 4.06 | 0.32 | 4.72 | 0.15 |

B

| | Saline HBsAg | | SEQID808 HBsAg | | SEQID814 HBsAg | | SEQID826 HBsAg | | SEQID825 HBsAg | |
|---|---|---|---|---|---|---|---|---|---|---|
| Day | | stdev | | stdev | | stdev | | stdev | | stdev |
| 0 | 4.68 | 0.10 | 4.64 | 0.05 | 4.67 | 0.07 | 4.00 | 0.43 | 4.50 | 0.09 |
| 3 | 4.40 | 0.12 | 3.99 | 0.09 | 3.64 | 0.16 | 3.21 | 0.90 | 3.44 | 0.05 |
| 6 | 4.49 | 0.09 | 3.56 | 0.07 | 2.78 | 0.20 | 2.62 | 1.03 | 2.59 | 0.13 |
| 9 | 4.50 | 0.07 | 3.24 | 0.07 | 2.36 | 0.16 | 2.32 | 1.00 | 2.16 | 0.20 |
| 13 | 4.71 | 0.07 | 3.16 | 0.14 | 2.29 | 0.15 | 2.21 | 1.03 | 2.03 | 0.22 |
| 16 | 4.58 | 0.05 | 3.10 | 0.15 | 2.64 | 0.08 | 2.37 | 1.05 | 2.27 | 0.21 |
| 20 | 4.71 | 0.03 | 3.37 | 0.21 | 3.05 | 0.14 | 2.45 | 1.18 | 2.47 | 0.33 |
| 23 | 4.62 | 0.08 | 3.47 | 0.23 | 3.36 | 0.12 | 2.68 | 1.24 | 2.54 | 0.62 |

C

| | Saline HBsAg | | SEQID824 HBsAg | |
|---|---|---|---|---|
| day | | stdev | | stdev |
| 0 | 4.49 | 0.13 | 4.67 | 0.03 |
| 3 | 4.62 | 0.13 | 4.14 | 0.06 |
| 6 | 4.50 | 0.14 | 3.00 | 0.13 |
| 9 | 4.45 | 0.21 | 2.35 | 0.15 |
| 13 | 4.36 | 0.38 | 2.19 | 0.25 |
| 16 | 4.20 | 0.66 | 2.45 | 0.20 |
| 20 | 4.46 | 0.09 | 3.45 | 0.22 |
| 23 | 3.97 | 1.05 | 2.42 | 0.18 |

From these data it can be concluded that in vivo all GalNAc conjugated anti-HBV antisense oligomers are capable of reducing serum levels of HBV s antigen (HBsAg) to a level that is lower than saline and standard of care. In particular SEQ ID NO 807, SEQ ID NO: 808, SEQ ID NO: 814, SEQ ID NO: 815, SEQ ID NO: 825, SEQ ID NO: 826 can be demonstrated to greatly reduce the serum levels of HBsAg.

TABLE 8A-C

Serum level of HBeAg ($\log_{10}$(NCU/ml)) following twice-weekly dosages of 2 mg/kg

A

| | Saline HBeAg | | SEQID806 HBeAg | | SEQID807 HBeAg | | SEQID815 HBeAg | | SEQID800 HBeAg | | SEQID802 HBeAg | | ETV HBeAg | |
|---|---|---|---|---|---|---|---|---|---|---|---|---|---|---|
| Day | | Stdev | | Stdev | | Stdev | | Stdev | | Stdev | | Stdev | | Stdev |
| 0 | 3.63 | 0.05 | 3.66 | 0.05 | 3.62 | 0.03 | 3.65 | 0.04 | 3.63 | 0.03 | 3.63 | 0.03 | 3.59 | 0.05 |
| 3 | 3.54 | 0.04 | 3.21 | 0.06 | 2.91 | 0.05 | 3.04 | 0.05 | 2.65 | 0.03 | 3.43 | 0.04 | 3.62 | 0.03 |
| 7 | 3.61 | 0.08 | 3.00 | 0.05 | 2.41 | 0.14 | 2.54 | 0.13 | 2.19 | 0.05 | 3.37 | 0.03 | 3.64 | 0.02 |
| 10 | 3.63 | 0.05 | 2.21 | 1.05 | 2.21 | 0.11 | 2.35 | 0.93 | 1.96 | 0.05 | 2.29 | 0.91 | 3.67 | 0.02 |
| 14 | 3.63 | 0.04 | 2.69 | 0.34 | 2.09 | 0.10 | 2.95 | 0.29 | 1.98 | 0.10 | 2.96 | 0.33 | 3.67 | 0.03 |
| 17 | 3.66 | 0.06 | 2.90 | 0.24 | 2.27 | 0.10 | 2.84 | 0.30 | 1.73 | 0.54 | 2.83 | 0.25 | 2.96 | 1.20 |
| 21 | 3.67 | 0.04 | 3.05 | 0.08 | 2.45 | 0.09 | 2.82 | 0.10 | 2.07 | 0.20 | 3.33 | 0.03 | 3.68 | 0.01 |
| 24 | 3.70 | 0.07 | 3.27 | 0.03 | 2.66 | 0.06 | 3.12 | 0.06 | 2.29 | 0.03 | 3.40 | 0.02 | 3.74 | 0.04 |

B

| | Saline HBeAg | | SEQID808 HBeAg | | SEQID814 HBeAg | | SEQID826 HBeAg | | SEQID825 HBeAg | |
|---|---|---|---|---|---|---|---|---|---|---|
| Day | | stdev | | stdev | | stdev | | stdev | | Stdev |
| 0 | 3.72 | 0.08 | 3.63 | 0.03 | 3.56 | 0.03 | 3.32 | 0.17 | 3.51 | 0.12 |
| 3 | 3.43 | 0.06 | 2.74 | 0.03 | 2.48 | 0.08 | 2.82 | 0.18 | 2.31 | 0.07 |
| 6 | 3.44 | 0.02 | 2.35 | 0.06 | 1.98 | 0.07 | 2.43 | 0.16 | 1.94 | 0.06 |
| 9 | 3.36 | 0.02 | 2.03 | 0.11 | 1.84 | 0.07 | 2.22 | 0.11 | 1.76 | 0.05 |
| 13 | 3.72 | 0.05 | 2.25 | 0.08 | 1.96 | 0.03 | 2.23 | 0.09 | 1.95 | 0.08 |

TABLE 8A-C-continued

Serum level of HBeAg ($\log_{10}$(NCU/ml)) following twice-weekly dosages of 2 mg/kg

| 16 | 3.66 | 0.10 | 2.32 | 0.06 | 2.08 | 0.04 | 2.45 | 0.15 | 1.98 | 0.08 |
| 20 | 3.74 | 0.01 | 2.58 | 0.04 | 2.36 | 0.05 | 2.67 | 0.18 | 2.21 | 0.11 |
| 23 | 3.65 | 0.05 | 2.60 | 0.07 | 2.52 | 0.08 | 2.82 | 0.10 | 2.33 | 0.11 |

C

| | Saline HBeAg | | SEQID824 HBeAg | |
|---|---|---|---|---|
| day | | stdev | | stdev |
| 0 | 3.75 | 0.02 | 3.74 | 0.02 |
| 3 | 3.52 | 0.09 | 2.35 | 0.07 |
| 6 | 3.45 | 0.06 | 1.89 | 0.03 |
| 9 | 3.60 | 0.06 | 1.94 | 0.04 |
| 13 | 3.58 | 0.10 | 1.58 | 0.04 |
| 16 | 3.58 | 0.15 | 1.64 | 0.04 |
| 20 | 3.48 | 0.13 | 2.69 | 0.05 |
| 23 | 3.59 | 0.12 | 1.75 | 0.02 |

From these data it can be concluded that in vivo all GalNAc conjugated anti-HBV antisense oligomers are capable of reducing serum levels of HBeAg to a level that is lower than saline and standard of care. In particular SEQ ID NO: 807, SEQ ID NO: 808, SEQ ID NO: 814, SEQ ID NO: 815, SEQ ID NO: 825, SEQ ID NO: 826 can be demonstrated to greatly reduce the serum levels of HBeAg.

TABLE 9A-C

Serum level of HBV DNA (by $\log_{10}$ copy number) following biweekly dosages of 2 mg/kg

A

| | Saline DNA | | SEQID806 DNA | | SEQID807 DNA | | SEQID815 DNA | | SEQID800 DNA | | SEQID802 DNA | | ETV DNA | |
|---|---|---|---|---|---|---|---|---|---|---|---|---|---|---|
| Day | | StDev | | StDev | | StDev | | StDev | | StDev | | StDev | | StDev |
| 0 | 7.08 | 0.54 | 7.78 | 0.08 | 7.27 | 0.38 | 7.06 | 0.39 | 7.26 | 0.35 | 6.92 | 0.31 | 7.30 | 0.37 |
| 3 | 7.21 | 0.36 | 7.28 | 0.20 | 6.45 | 0.54 | 6.11 | 0.41 | 5.99 | 0.45 | 6.78 | 0.33 | 5.73 | 0.83 |
| 7 | 6.81 | 0.54 | 6.53 | 0.15 | 5.16 | 0.86 | 4.52 | 0.38 | 5.16 | 0.50 | 6.43 | 0.58 | 5.15 | 0.50 |
| 10 | 7.64 | 0.14 | 6.38 | 0.37 | 4.72 | 0.52 | 4.23 | LLOQ | 4.23 | LLOQ | 6.39 | 0.60 | 4.23 | LLOQ |
| 14 | 7.71 | 0.09 | 5.97 | 0.70 | 4.23 | LLOQ | 4.23 | LLOQ | 4.23 | LLOQ | 6.12 | 0.46 | 4.23 | LLOQ |
| 17 | 7.76 | 0.04 | 6.13 | 0.57 | 4.23 | LLOQ | 4.56 | 0.57 | 4.23 | LLOQ | 6.07 | 0.58 | 4.23 | LLOQ |
| 21 | 7.80 | 0.08 | 6.62 | 0.43 | 4.29 | 0.11 | 4.65 | 0.49 | 4.44 | 0.35 | 6.54 | 0.42 | 4.89 | 0.41 |
| 24 | 8.01 | 0.03 | 6.91 | 0.34 | 4.65 | 0.41 | 5.60 | 0.68 | 4.23 | LLOQ | 7.01 | 0.33 | 5.22 | 0.57 |

B

| | Saline DNA | | SEQID808 DNA | | SEQID814 DNA | | SEQID826 DNA | | SEQID825 DNA | |
|---|---|---|---|---|---|---|---|---|---|---|
| Day | | StDev | | StDev | | StDev | | StDev | | StDev |
| 0 | 6.95 | 0.35 | 6.79 | 0.30 | 7.13 | 0.24 | 6.94 | 0.40 | 7.02 | 0.18 |
| 3 | 7.15 | 0.26 | 5.92 | 0.27 | 5.88 | 0.15 | 6.25 | 0.50 | 5.90 | 0.35 |
| 6 | 7.26 | 0.22 | 4.80 | 0.64 | 4.44 | 0.48 | 5.34 | 0.70 | 4.56 | 0.68 |
| 9 | 7.44 | 0.23 | 4.16 | LLOQ | 4.16 | LLOQ | 4.78 | 0.62 | 4.16 | LLOQ |
| 13 | 7.13 | 0.26 | 4.16 | LLOQ | 4.16 | LLOQ | 4.35 | 0.33 | 4.16 | LLOQ |
| 16 | 7.04 | 0.44 | 4.16 | LLOQ | 4.16 | LLOQ | 4.27 | 0.20 | 4.16 | LLOQ |
| 20 | 7.04 | 0.36 | 4.16 | LLOQ | 4.16 | LLOQ | 4.40 | 0.41 | 4.16 | LLOQ |
| 23 | 7.24 | 0.14 | 4.16 | LLOQ | 4.16 | LLOQ | 4.77 | 0.63 | 4.34 | 0.30 |

C

| | Saline DNA | | SEQID824 DNA | |
|---|---|---|---|---|
| day | | StDev | | StDev |
| 0 | 7.47 | 0.23 | 7.33 | 0.16 |
| 3 | 7.55 | 0.21 | 5.99 | 0.25 |
| 6 | 7.74 | 0.19 | 4.89 | 0.48 |

TABLE 9A-C-continued

Serum level of HBV DNA (by $\log_{10}$ copy number) following biweekly dosages of 2 mg/kg

| 9  | 7.76 | 0.21 | 4.51 | 0.40 |
| 13 | 7.82 | 0.27 | 4.32 | LLOQ |
| 16 | 7.60 | 0.42 | 4.32 | LLOQ |
| 20 | 7.42 | 0.16 | 5.03 | 0.53 |
| 23 | 7.58 | 0.57 | 4.32 | LLOQ |

LLOQ = less than lower level of quantification

From these data it can be concluded that all GalNAc conjugated anti-HBV antisense oligomers are capable of reducing serum levels of HBV genomic DNA to a level that is lower than saline and or equal to the ETV (the clinical standard of care). In particular SEQ ID NO: 807, SEQ ID NO: 808, SEQ ID NO: 814, SEQ ID NO: 815, SEQ ID NO: 825, SEQ ID NO: 826 can be demonstrated to greatly reduce the serum levels of HBV genomic DNA.

The overall conclusion from these data is that in vivo the GalNAc-conjugated, HBV-targeting LNAs can target and reduce expression of HBsAg and HBeAg better than ETV (the clinical standard of care) and the HBV serum DNA with equal or better efficacy as compared to ETV. Given the broader effect on the viral transcriptional program than the nucleoside analog ETV, these data suggest that the use of GalNAc conjugated HBV-targeting LNAs in the clinic is likely to lead to a much improved outcome, including significantly increasing the cure rate for chronically infected HBV patients. Particularly the reduction of the immune suppressor HBsAg will lead to a recovery of the HBV-directed host immune response.

Example 5 In Vivo Study of Bi-Weekly Injections at Several Doses

The AAV/HBV Mouse Model as prepared in Example 3 was used in this study. Seven GalNAc conjugated Anti-HBV LNA oligomers were tested at different doses with saline as control in C57BL/6 mice with stable viremia.

Mice were dosed subcutaneously twice weekly for two weeks on days 0, 3, 7 and 10 or day 0, 3, 6 and 9 with the dose in mg/kg (mpk) pr injection indicated in the tables below. HBV surface antigen (HBsAg), HBV e antigen (HBeAg), and HBV genomic DNA in serum was measured at the indicated days using the methods described in the "Materials and methods" section. The mice were followed for 23-24 days.

The results are shown in the tables below.

TABLE 10A-G

Serum level of HBsAg ($\log_{10}$(IU/ml)) following biweekly dosages at the concentration indicated

A

| | SEQID 807 ||||||||
|---|---|---|---|---|---|---|---|---|
| | Saline HBsAg || 7.1 mpk HBsAg || 1.4 mpk HBsAg || 0.28 mpk HBsAg ||
| Day | Serum level | stdev | Serum level | stdev | Serum level | stdev | Serum level | stdev |
| 0  | 4.63 | 0.12 | 4.74 | 0.06 | 4.71 | 0.05 | 4.51 | 0.24 |
| 3  | 4.67 | 0.09 | 3.79 | 0.19 | 4.23 | 0.08 | 4.23 | 0.45 |
| 6  | 4.63 | 0.11 | 2.68 | 0.15 | 3.50 | 0.08 | 3.83 | 0.52 |
| 9  | 4.62 | 0.10 | 2.09 | 0.09 | 2.95 | 0.05 | 3.62 | 0.42 |
| 13 | 4.64 | 0.06 | 1.84 | 0.09 | 2.50 | 0.04 | 3.54 | 0.28 |
| 16 | 4.56 | 0.05 | 1.72 | 0.05 | 2.53 | 0.13 | 3.63 | 0.35 |
| 20 | 4.69 | 0.03 | 1.97 | 0.29 | 2.92 | 0.17 | 3.91 | 0.25 |
| 23 | 4.67 | 0.10 | 1.78 | 0.11 | 3.18 | 0.15 | 4.08 | 0.20 |

B

| | SEQID815 ||||||||
|---|---|---|---|---|---|---|---|---|
| | Saline HBsAg || 7.5 mpk HBsAg || 1.5 mpk HBsAg || 0.3 mpk HBsAg ||
| Day | Serum level | stdev | Serum level | stdev | Serum level | stdev | Serum level | stdev |
| 0  | 4.63 | 0.12 | 4.74 | 0.05 | 4.67 | 0.18 | 4.14 | 0.61 |
| 3  | 4.67 | 0.09 | 3.47 | 0.10 | 3.55 | 0.38 | 3.46 | 0.99 |
| 7  | 4.63 | 0.11 | 2.25 | 0.20 | 2.70 | 0.32 | 3.02 | 0.99 |
| 10 | 4.62 | 0.10 | 1.89 | 0.17 | 2.07 | 0.27 | 2.68 | 1.14 |
| 14 | 4.64 | 0.06 | 1.48 | 0.19 | 1.81 | 0.24 | 2.60 | 1.07 |
| 17 | 4.56 | 0.05 | 1.59 | 0.19 | 2.22 | 0.21 | 2.79 | 1.13 |
| 21 | 4.69 | 0.03 | 1.68 | 0.16 | 2.99 | 0.16 | 3.24 | 1.15 |
| 24 | 4.67 | 0.10 | 2.17 | 0.29 | 3.54 | 0.16 | 3.53 | 1.11 |

C

| | SEQID814 ||||||||
|---|---|---|---|---|---|---|---|---|
| | Saline HBsAg || 6.15 mg/kg HBsAg || 1.26 mg/kg HBsAg || 0.252 mg/kg HBsAg ||
| Day | Serum level | stdev | Serum level | stdev | Serum level | stdev | Serum level | stdev |
| 0  | 4.49 | 0.13 | 4.59 | 0.07 | 4.55 | 0.17 | 4.48 | 0.18 |
| 3  | 4.62 | 0.13 | 3.56 | 0.21 | 4.02 | 0.29 | 4.51 | 0.18 |
| 7  | 4.5  | 0.14 | 2.22 | 0.23 | 3.26 | 0.23 | 4.25 | 0.23 |
| 10 | 4.45 | 0.21 | 1.89 | 0.24 | 2.9  | 0.2  | 4.21 | 0.22 |
| 14 | 4.36 | 0.38 | 1.69 | 0.27 | 2.77 | 0.24 | 4.33 | 0.16 |
| 17 | 4.2  | 0.66 | 1.75 | 0.2  | 3.02 | 0.19 | 4.4  | 0.09 |
| 21 | 4.46 | 0.09 | 2.13 | 0.21 | 3.5  | 0.29 | 4.31 | 0.17 |
| 24 | 3.97 | 1.05 | 2.45 | 0.17 | 3.54 | 0.36 | 4.51 | 0.09 |

D

| | SEQID825 ||||||||
|---|---|---|---|---|---|---|---|---|
| | Saline HBsAg || 7.5 mg/kg HBsAg || 1.5 mg/kg HBsAg || 0.3 mg/kg HBsAg ||
| Day | Serum level | stdev | Serum level | stdev | Serum level | stdev | Serum level | stdev |
| 0  | 4.49 | 0.13 | 4.62 | 0.06 | 4.51 | 0.04 | 4.48 | 0.25 |
| 3  | 4.62 | 0.13 | 3.56 | 0.18 | 3.73 | 0.15 | 4.47 | 0.31 |
| 7  | 4.5  | 0.14 | 2.36 | 0.12 | 2.84 | 0.16 | 4.15 | 0.32 |
| 10 | 4.45 | 0.21 | 1.99 | 0.08 | 2.43 | 0.15 | 3.95 | 0.35 |
| 14 | 4.36 | 0.38 | 1.87 | 0.09 | 2.2  | 0.12 | 4.01 | 0.25 |
| 17 | 4.2  | 0.66 | 1.93 | 0.06 | 2.51 | 0.12 | 4.1  | 0.22 |
| 21 | 4.46 | 0.09 | 2.2  | 0.11 | 3.04 | 0.14 | 4.42 | 0.13 |
| 24 | 3.97 | 1.05 | 2.45 | 0.19 | 3.32 | 0.17 | 4.49 | 0.08 |

TABLE 10A-G-continued

Serum level of HBsAg ($\log_{10}$(IU/ml)) following biweekly dosages at the concentration indicated

E

| | Saline HBsAg | | SEQID808 7.1 mg/kg SC HBsAg | | 1.42 mg/kg SC HBsAg | | 0.29 mg/kg SC HBsAg | |
|---|---|---|---|---|---|---|---|---|
| Day | Serum level | stdev | Serum level | stdev | Serum level | stdev | Serum level | stdev |
| 0 | 4.78 | 0.11 | 4.58 | 0.29 | 4.86 | 0.08 | 4.55 | 0.34 |
| 3 | 4.75 | 0.1 | 3.38 | 0.72 | 4.27 | 0.24 | 4.36 | 0.43 |
| 7 | 4.85 | 0.05 | 2.8 | 0.55 | 3.7 | 0.45 | 4.25 | 0.37 |
| 10 | 4.81 | 0.08 | 2.31 | 0.43 | 3.42 | 0.35 | 4.06 | 0.5 |
| 14 | 4.99 | 0.02 | 2.36 | 0.31 | 3.51 | 0.4 | 4.18 | 0.68 |
| 17 | 4.91 | 0.04 | 2.36 | 0.31 | 3.52 | 0.3 | 4.11 | 0.68 |
| 21 | 4.89 | 0.04 | 2.26 | 0.34 | 3.66 | 0.35 | 4.32 | 0.64 |
| 24 | 4.8 | 0.06 | 2.4 | 0.28 | 3.87 | 0.3 | 4.45 | 0.47 |

F

| | Saline HBsAg | | SEQID824 7.4 mg/kg SC HBsAg | | 1.5 mg/kg SC HBsAg | | 0.3 mg/kg SC HBsAg | |
|---|---|---|---|---|---|---|---|---|
| Day | Serum level | stdev | Serum level | stdev | Serum level | stdev | Serum level | stdev |
| 0 | 4.78 | 0.11 | 4.78 | 0.05 | 4.57 | 0.34 | 4.7 | 0.11 |
| 3 | 4.75 | 0.1 | 3.86 | 0.23 | 4 | 0.51 | 4.6 | 0.15 |
| 7 | 4.85 | 0.05 | 2.44 | 0.32 | 2.87 | 0.54 | 4.15 | 0.16 |
| 10 | 4.81 | 0.08 | 2.38 | 0.25 | 2.18 | 0.58 | 3.86 | 0.17 |
| 14 | 4.99 | 0.02 | 2.85 | 0.4 | 2.21 | 0.82 | 3.84 | 0.28 |
| 17 | 4.91 | 0.04 | 2.85 | 0.41 | 2.28 | 0.82 | 3.49 | 0.54 |
| 21 | 4.89 | 0.04 | | | 2.25 | 0.91 | 3.63 | 0.74 |
| 24 | 4.8 | 0.06 | | | 2.2 | 0.76 | 3.7 | 0.66 |

G

| | Saline HBsAg | | SEQID826 7.1 mg/kg HBsAg | | 1.42 mg/kg HBsAg | | 0.29 mg/kg HBsAg | |
|---|---|---|---|---|---|---|---|---|
| Day | Serum level | stdev | Serum level | stdev | Serum level | stdev | Serum level | stdev |
| 0 | 4.78 | 0.11 | 4.61 | 0.26 | 4.67 | 0.06 | 4.57 | 0.14 |
| 3 | 4.75 | 0.1 | 3.78 | 0.45 | 4.42 | 0.03 | 4.66 | 0.2 |
| 7 | 4.85 | 0.05 | 2.46 | 0.51 | 3.84 | 0.13 | 4.52 | 0.2 |
| 10 | 4.81 | 0.08 | 2.02 | 0.57 | 3.61 | 0.11 | 4.42 | 0.24 |
| 14 | 4.99 | 0.02 | 2.08 | 0.63 | 3.65 | 0.27 | 4.63 | 0.21 |
| 17 | 4.91 | 0.04 | 1.94 | 0.55 | 3.73 | 0.18 | 4.57 | 0.21 |
| 21 | 4.89 | 0.04 | 2.54 | 0.25 | 4.09 | 0.13 | 4.73 | 0.2 |
| 24 | 4.8 | 0.06 | 3.04 | 0.21 | 4.23 | 0.17 | 4.79 | 0.24 |

Figure 11:
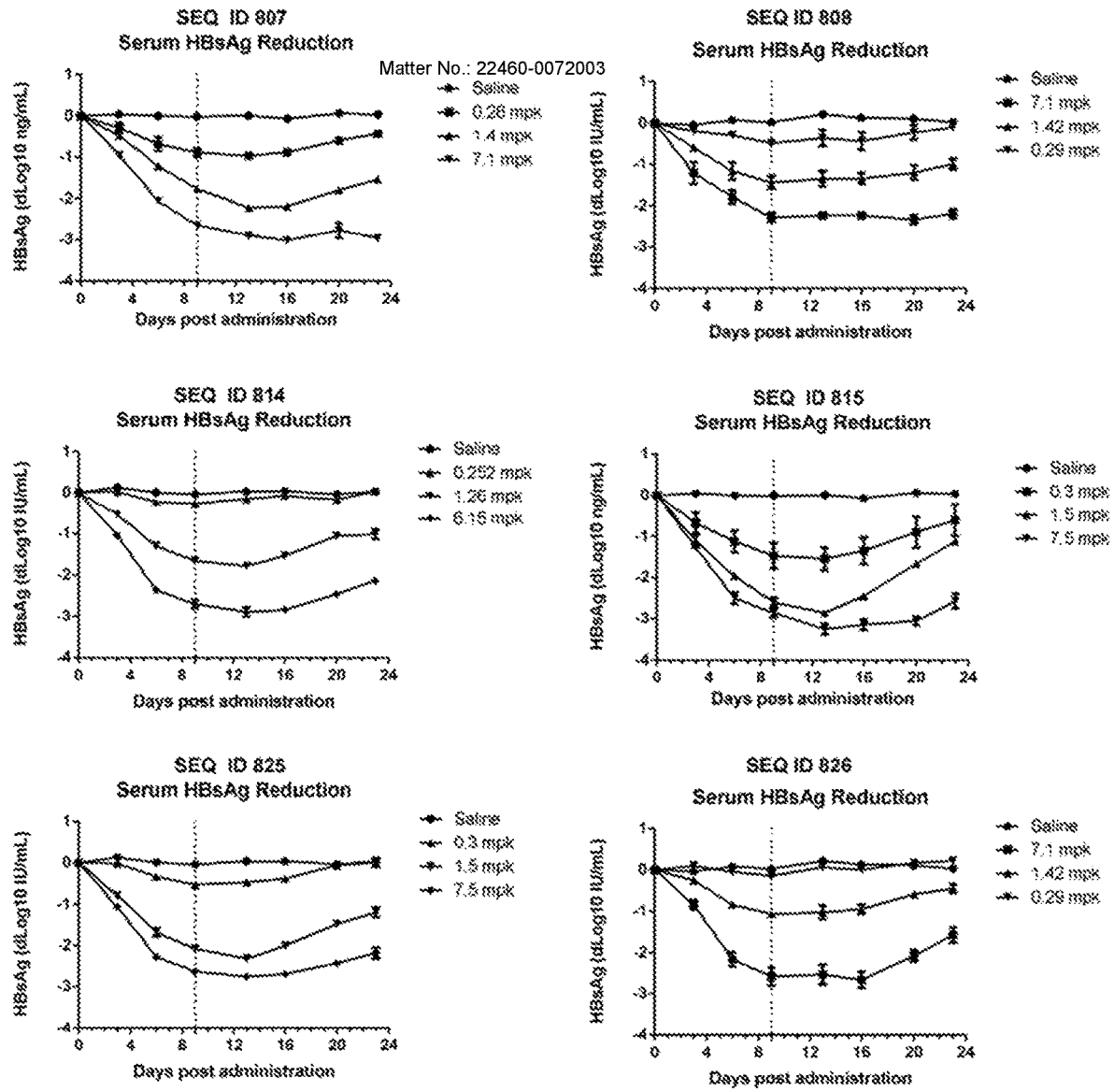
FIG. 11: HBsAG reduction of SEQ ID NO: 807 at dose 0.28 mpk (■), 1.4 mg/kg (▲) and 7.1 mpk (▼); SEQ ID NO: 808 at dose 7.1 mg/kg (■), 1.42 mg/kg (▲) and 0.29 mg/kg (▼); SEQ ID NO: 814 at dose 0.252 mg/kg (▲) and 1.26 mg/kg (▼), 6.15 mg/kg (♦); SEQ ID NO: 815 at dose 0.3 mg/kg (■), 1.5 mg/kg (▲) and 7.5 mg/kg (▼); SEQ ID NO: 825 at dose 0.3 mg/kg (▲), 1.5 mg/kg (▼), and 7.5 mg/kg (♦); SEQ ID NO: 826 at dose 7.1 mg/kg (■), 1.42 mg/kg (▲) and 0.29 mg/kg (▼).

The above data are also presented in FIG. 11.

TABLE 11A-G

Serum level of HBeAg ($\log_{10}$(NCU/ml)) following biweekly dosages at the concentrations indicated.

A

| | Saline HBeAg | | SEQID 807 7.1 mpk HBeAg | | 1.4 mpk HBeAg | | 0.28 mpk HBeAg | |
|---|---|---|---|---|---|---|---|---|
| Day | Serum level | stdev | Serum level | stdev | Serum level | stdev | Serum level | stdev |
| 0 | 3.83 | 0.04 | 3.82 | 0.02 | 3.78 | 0.02 | 3.75 | 0.03 |
| 3 | 3.74 | 0.02 | 2.24 | 0.04 | 2.83 | 0.07 | 3.39 | 0.05 |
| 6 | 3.69 | 0.02 | 1.67 | 0.04 | 2.32 | 0.06 | 3.16 | 0.03 |
| 9 | 3.68 | 0.03 | 1.48 | 0.05 | 2.04 | 0.03 | 3.01 | 0.02 |
| 13 | 3.66 | 0.03 | 1.53 | 0.02 | 1.75 | 0.03 | 2.83 | 0.14 |
| 16 | 3.69 | 0.03 | 1.21 | 0.07 | 1.85 | 0.03 | 2.98 | 0.04 |
| 20 | 3.66 | 0.04 | 1.48 | 0.07 | 1.98 | 0.05 | 3.12 | 0.04 |
| 23 | 3.63 | 0.04 | 1.34 | 0.09 | 2.19 | 0.06 | 3.24 | 0.07 |

B

| | Saline HBeAg | | SEQID815 7.5 mpk HBeAg | | 1.5 mpk HBeAg | | 0.3 mpk HBeAg | |
|---|---|---|---|---|---|---|---|---|
| Day | Serum level | stdev | Serum level | stdev | Serum level | stdev | Serum level | stdev |
| 0 | 3.83 | 0.04 | 3.80 | 0.07 | 3.77 | 0.03 | 3.67 | 0.15 |
| 3 | 3.74 | 0.02 | 2.00 | 0.08 | 2.56 | 0.12 | 3.37 | 0.15 |
| 7 | 3.69 | 0.02 | 1.60 | 0.05 | 2.02 | 0.08 | 3.04 | 0.11 |
| 10 | 3.68 | 0.03 | 1.47 | 0.03 | 1.85 | 0.10 | 2.75 | 0.38 |
| 14 | 3.66 | 0.03 | 1.40 | 0.39 | 1.64 | 0.09 | 2.81 | 0.10 |
| 17 | 3.69 | 0.03 | 1.29 | 0.12 | 1.85 | 0.09 | 2.78 | 0.29 |
| 21 | 3.66 | 0.04 | 1.74 | 0.14 | 2.27 | 0.09 | 3.10 | 0.23 |
| 24 | 3.63 | 0.04 | 1.88 | 0.07 | 2.50 | 0.09 | 3.19 | 0.18 |

C

| | Saline HBeAg | | SEQID814 6.15 mg/kg HBeAg | | 1.26 mg/kg HBeAg | | 0.252 mg/kg HBeAg | |
|---|---|---|---|---|---|---|---|---|
| Day | Serum level | stdev | Serum level | stdev | Serum level | stdev | Serum level | stdev |
| 0 | 3.75 | 0.02 | 3.8 | 0.08 | 3.8 | 0.05 | 3.75 | 0.08 |
| 3 | 3.52 | 0.09 | 2.15 | 0.06 | 2.97 | 0.05 | 3.46 | 0.09 |
| 7 | 3.45 | 0.06 | 1.73 | 0.05 | 2.47 | 0.02 | 3.22 | 0.09 |
| 10 | 3.6 | 0.06 | 1.7 | 0.07 | 2.32 | 0.05 | 3.2 | 0.08 |
| 14 | 3.58 | 0.1 | 1.4 | 0.05 | 2.15 | 0.04 | 3.24 | 0.12 |
| 17 | 3.58 | 0.15 | 1.55 | 0.05 | 2.44 | 0.06 | 3.34 | 0.1 |
| 21 | 3.48 | 0.13 | 1.75 | 0.04 | 2.7 | 0.05 | 3.34 | 0.15 |
| 24 | 3.59 | 0.12 | 1.92 | 0.05 | 2.8 | 0.04 | 3.44 | 0.13 |

D

| | Saline HBeAg | | SEQID825 7.5 mg/kg HBeAg | | 1.5 mg/kg HBeAg | | 0.3 mg/kg HBeAg | |
|---|---|---|---|---|---|---|---|---|
| Day | Serum level | stdev | Serum level | stdev | Serum level | stdev | Serum level | stdev |
| 0 | 3.75 | 0.02 | 3.72 | 0.08 | 3.71 | 0.09 | 3.93 | 0.16 |
| 3 | 3.52 | 0.09 | 2.22 | 0.1 | 2.68 | 0.06 | 3.39 | 0.06 |
| 7 | 3.45 | 0.06 | 1.77 | 0.1 | 2.36 | 0.05 | 3.14 | 0.12 |
| 10 | 3.6 | 0.06 | 1.7 | 0.05 | 2.18 | 0.1 | 3.17 | 0.1 |
| 14 | 3.58 | 0.1 | 1.47 | 0.07 | 1.92 | 0.07 | 3.14 | 0.02 |
| 17 | 3.58 | 0.15 | 1.69 | 0.06 | 2.17 | 0.13 | 3.25 | 0.04 |
| 21 | 3.48 | 0.13 | 1.87 | 0.08 | 2.4 | 0.08 | 3.38 | 0.05 |
| 24 | 3.59 | 0.12 | 1.98 | 0.09 | 2.55 | 0.06 | 3.48 | 0.02 |

E

| | Saline HBeAg | | SEQID808 7.1 mg/kg SC HBeAg | | 1.42 mg/kg SC HBeAg | | 0.29 mg/kg SC HBeAg | |
|---|---|---|---|---|---|---|---|---|
| Day | Serum level | stdev | Serum level | stdev | Serum level | stdev | Serum level | stdev |
| 0 | 3.59 | 0.06 | 3.51 | 0.04 | 3.56 | 0.01 | 3.47 | 0.07 |
| 3 | 3.59 | 0.03 | 2.5 | 0.06 | 2.98 | 0.02 | 3.4 | 0.07 |
| 7 | 3.69 | 0.02 | 2.05 | 0.08 | 2.63 | 0.03 | 3.2 | 0.07 |

TABLE 11A-G-continued

Serum level of HBeAg ($\log_{10}$(NCU/ml)) following biweekly dosages at the concentrations indicated.

| Day | Serum level | stdev | Serum level | stdev | Serum level | stdev | Serum level | stdev |
|---|---|---|---|---|---|---|---|---|
| 10 | 3.67 | 0.04 | 1.84 | 0.11 | 2.46 | 0.04 | 3.19 | 0.06 |
| 14 | 3.81 | 0.03 | 1.72 | 0.07 | 2.45 | 0.02 | 3.27 | 0.07 |
| 17 | 3.74 | 0.03 | 1.68 | 0.14 | 2.5 | 0.02 | 3.27 | 0.07 |
| 21 | 3.72 | 0.03 | 1.58 | 0.18 | 2.64 | 0.04 | 3.35 | 0.08 |
| 24 | 3.73 | 0.06 | 1.77 | 0.19 | 2.8 | 0.04 | 3.55 | 0.05 |

F

| | Saline HBeAg | | SEQID824 7.4 mg/kg SC HBeAg | | 1.5 mg/kg SC HBeAg | | 0.3 mg/kg SC HBeAg | |
|---|---|---|---|---|---|---|---|---|
| Day | Serum level | stdev | Serum level | stdev | Serum level | stdev | Serum level | stdev |
| 0 | 3.59 | 0.06 | 3.5 | 0.03 | 3.51 | 0.02 | 3.49 | 0.03 |
| 3 | 3.59 | 0.03 | 2.09 | 0.08 | 2.47 | 0.13 | 3.28 | 0.03 |
| 7 | 3.69 | 0.02 | 1.81 | 0.05 | 1.95 | 0.05 | 2.88 | 0.04 |
| 10 | 3.67 | 0.04 | 1.88 | 0.07 | 1.88 | 0.03 | 2.65 | 0.06 |
| 14 | 3.81 | 0.03 | 1.71 | 0.06 | 1.72 | 0.1 | 2.48 | 0.05 |
| 17 | 3.74 | 0.03 | 1.68 | 0.06 | 1.68 | 0.05 | 2.56 | 0.05 |
| 21 | 3.72 | 0.03 | | | 1.8 | 0.04 | 2.63 | 0.08 |
| 24 | 3.73 | 0.06 | | | 2.02 | 0.06 | 2.81 | 0.05 |

G

| | Saline HBeAg | | SEQID826 7.1 mg/kg HBeAg | | 1.42 mg/kg HBeAg | | 0.29 mg/kg HBeAg | |
|---|---|---|---|---|---|---|---|---|
| Day | Serum level | stdev | Serum level | stdev | Serum level | stdev | Serum level | stdev |
| 0 | 3.59 | 0.06 | 3.44 | 0.09 | 3.45 | 0.06 | 3.5 | 0.02 |
| 3 | 3.59 | 0.03 | 2.58 | 0.08 | 3.17 | 0.07 | 3.52 | 0.02 |
| 7 | 3.69 | 0.02 | 1.81 | 0.08 | 2.8 | 0.1 | 3.4 | 0.03 |
| 10 | 3.67 | 0.04 | 1.45 | 0.06 | 2.67 | 0.09 | 3.37 | 0.05 |
| 14 | 3.81 | 0.03 | 1.27 | 0.05 | 2.54 | 0.12 | 3.39 | 0.07 |
| 17 | 3.74 | 0.03 | 1.51 | 0.05 | 2.76 | 0.08 | 3.45 | 0.04 |
| 21 | 3.72 | 0.03 | 1.83 | 0.11 | 2.9 | 0.08 | 3.54 | 0.03 |
| 24 | 3.73 | 0.06 | 2.23 | 0.18 | 3.18 | 0.1 | 3.66 | 0.03 |

Figure 12:
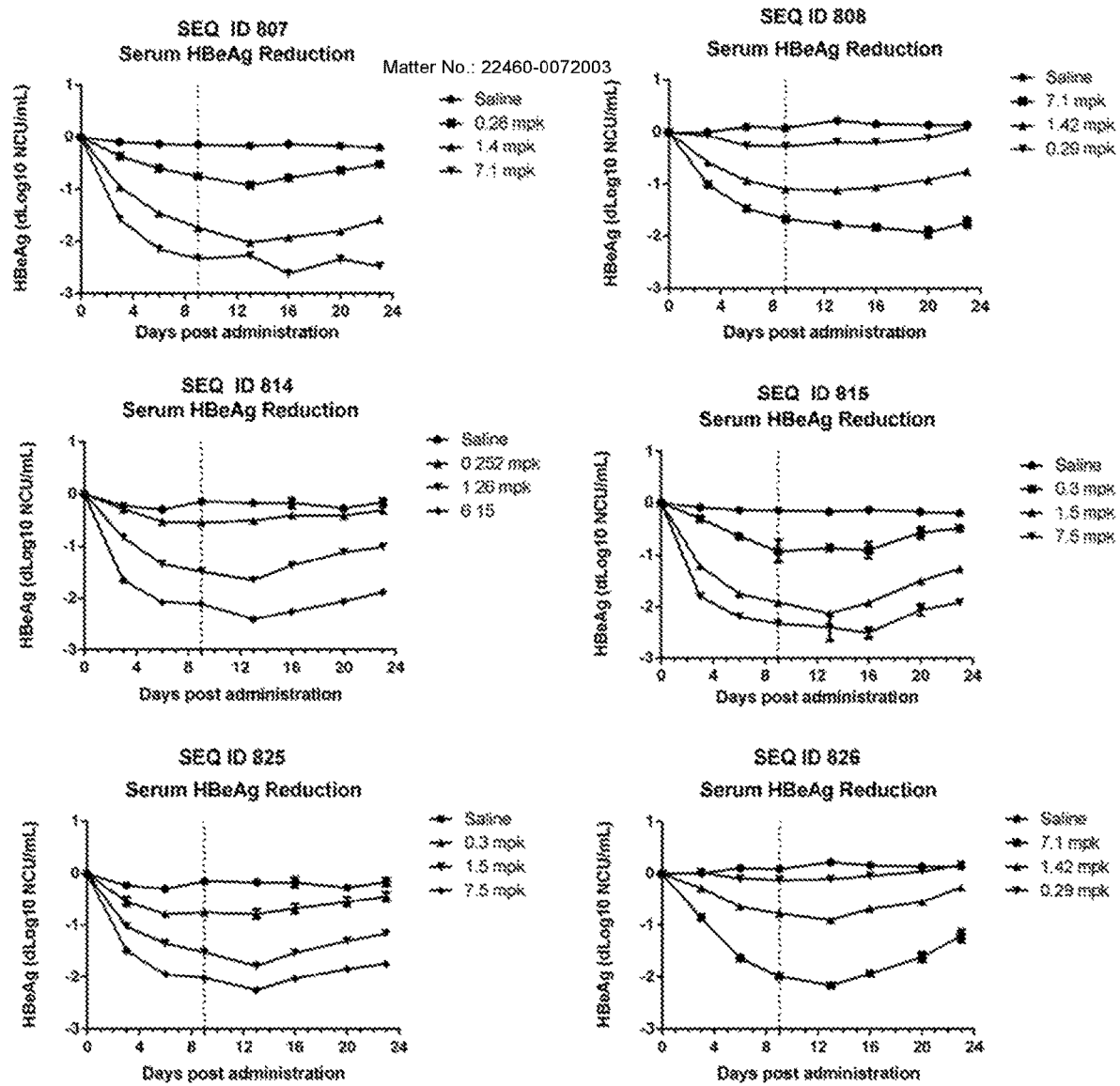
FIG. 12: HBeAG reduction of SEQ ID NO: 807 at dose 0.28 mg/kg (■), 1.4 mg/kg (▲) and 7.1 mg/kg (▼); SEQ ID NO: 808 at dose 7.1 mg/kg (■), 1.42 mg/kg (▲) and 0.29 mg/kg (▼); SEQ ID NO: 814 at dose 0.252 mg/kg (▲) and 1.26 mg/kg (▼), 6.15 mg/kg (♦); SEQ ID NO: 815 at dose 0.3 mg/kg (■), 1.5 mg/kg (▲) and 7.5 mg/kg (▼); SEQ ID NO: 825 at dose 0.3 mg/kg (▲), 1.5 mg/kg (▼), and 7.5 mg/kg (♦); SEQ ID NO: 826 at dose 7.1 mg/kg (♦), 1.42 mg/kg (▲) and 0.29 mg/kg (▼).

The above data are also presented in FIG. 12.

TABLE 12A-G

Serum level of $\log_{10}$(HBV DNA) (by copy number) following biweekly dosages at the concentrations indicated.

A

| | Saline DNA | | SEQID 807 7.1 mpk DNA | | 1.4 mpk DNA | | 0.28 mpk DNA | |
|---|---|---|---|---|---|---|---|---|
| Day | Serum level | StDev | Serum level | StDev | Serum level | StDev | Serum level | StDev |
| 0 | 6.64 | 0.31 | 6.77 | 0.57 | 6.46 | 0.22 | 6.80 | 0.38 |
| 3 | 6.58 | 0.42 | 4.86 | 0.58 | 4.61 | 0.49 | 6.10 | 0.11 |
| 6 | 7.25 | 0.49 | 4.43 | 0.18 | 4.32 | LLOQ | 5.87 | 0.31 |
| 9 | 7.14 | 0.23 | 4.32 | LLOQ | 4.32 | 0.01 | 5.19 | 0.58 |
| 13 | 7.32 | 0.33 | 4.30 | LLOQ | 4.30 | LLOQ | 5.23 | 0.54 |
| 16 | 7.28 | 0.27 | 4.30 | LLOQ | 4.30 | LLOQ | 5.60 | 0.27 |
| 20 | 7.23 | 0.31 | 4.30 | LLOQ | 4.40 | 0.17 | 6.05 | 0.19 |
| 23 | 7.43 | 0.28 | 4.30 | LLOQ | 4.30 | LLOQ | 6.41 | 0.20 |

B

| | Saline DNA | | SEQID815 7.5 mpk DNA | | 1.5 mpk DNA | | 0.3 mpk DNA | |
|---|---|---|---|---|---|---|---|---|
| Day | Serum level | StDev | Serum level | StDev | Serum level | StDev | Serum level | StDev |
| 0 | 6.64 | 0.31 | 6.64 | 0.32 | 6.48 | 0.31 | 6.54 | 0.42 |
| 3 | 6.58 | 0.42 | 4.44 | 0.21 | 4.59 | 0.46 | 4.95 | 0.67 |
| 7 | 7.25 | 0.49 | 4.32 | LLOQ | 4.32 | LLOQ | 4.56 | 0.41 |
| 10 | 7.14 | 0.23 | 4.31 | 0.01 | 4.32 | LLOQ | 4.38 | 0.11 |
| 14 | 7.32 | 0.33 | 4.30 | LLOQ | 4.30 | LLOQ | 4.30 | LLOQ |
| 17 | 7.28 | 0.27 | 4.30 | LLOQ | 4.30 | LLOQ | 4.64 | 0.58 |
| 21 | 7.23 | 0.31 | 4.30 | LLOQ | 4.30 | LLOQ | 5.12 | 0.87 |
| 24 | 7.43 | 0.28 | 4.30 | LLOQ | 4.30 | LLOQ | 5.37 | 1.08 |

TABLE 12A-G-continued

Serum level of $\log_{10}$(HBV DNA) (by copy number) following biweekly dosages at the concentrations indicated.

C

| | | SEQID814 | | | | | |
|---|---|---|---|---|---|---|---|
| | Saline DNA | | 6.15 mg/kg DNA | | 1.26 mg/kg DNA | | 0.252 mg/kg DNA |
| Day | Serum level | StDev | Serum level | StDev | Serum level | StDev | Serum level | StDev |
| 0 | 7.47 | 0.23 | 7.55 | 0.18 | 7.48 | 0.22 | 7.64 | 0.17 |
| 3 | 7.55 | 0.21 | 6.2 | 0.18 | 6.44 | 0.26 | 7.37 | 0.14 |
| 7 | 7.74 | 0.19 | 5.31 | 0.25 | 5.53 | 0.36 | 7.31 | 0.08 |
| 10 | 7.76 | 0.21 | 4.46 | 0.19 | 4.65 | 0.49 | 7.22 | 0.1 |
| 14 | 7.82 | 0.27 | 4.32 | 0 | 4.32 | 0 | 7.27 | 0.09 |
| 17 | 7.6 | 0.42 | 4.32 | 0.01 | 4.38 | 0.09 | 7.41 | 0.14 |
| 21 | 7.42 | 0.16 | 4.32 | 0 | 4.62 | 0.56 | 7.42 | 0.09 |
| 24 | 7.58 | 0.57 | 4.32 | 0 | 5.48 | 0.7 | 7.66 | 0.16 |

D

| | | SEQID825 | | | | | |
|---|---|---|---|---|---|---|---|
| | Saline DNA | | 7.5 mg/kg DNA | | 1.5 mg/kg DNA | | 0.3 mg/kg DNA |
| Day | Serum level | StDev | Serum level | StDev | Serum level | StDev | Serum level | StDev |
| 0 | 7.47 | 0.23 | 7.36 | 0.28 | 7.41 | 0.32 | 7.5 | 0.44 |
| 3 | 7.55 | 0.21 | 5.89 | 0.31 | 5.84 | 0.67 | 6.95 | 0.43 |
| 7 | 7.74 | 0.19 | 4.75 | 0.57 | 4.92 | 0.55 | 6.73 | 0.43 |
| 10 | 7.76 | 0.21 | 4.35 | 0.13 | 4.28 | 0 | 6.49 | 0.44 |
| 14 | 7.82 | 0.27 | 4.32 | 0 | 4.32 | 0 | 6.52 | 0.48 |
| 17 | 7.6 | 0.42 | 4.32 | 0.01 | 4.31 | 0.01 | 6.68 | 0.26 |
| 21 | 7.42 | 0.16 | 4.32 | 0 | 4.32 | 0 | 6.82 | 0.57 |
| 24 | 7.58 | 0.57 | 4.32 | 0.01 | 4.63 | 0.31 | 7.19 | 0.32 |

E

| | | SEQID808 | | | | | |
|---|---|---|---|---|---|---|---|
| | Saline DNA | | 7.1 mg/kg SC DNA | | 1.42 mg/kg SC DNA | | 0.29 mg/kg SC DNA |
| Day | Serum level | StDev | Serum level | StDev | Serum level | StDev | Serum level | StDev |
| 0 | 7.77 | 0.17 | 7.97 | 0.26 | 7.93 | 0.11 | 7.93 | 0.24 |
| 3 | 7.8 | 0.05 | 6.29 | 0.4 | 6.69 | 0.21 | 7.31 | 0.35 |
| 7 | 7.75 | 0.15 | 5.02 | 0.59 | 5.67 | 0.43 | 7.24 | 0.35 |
| 10 | 7.79 | 0.09 | 4.5 | 0.36 | 4.95 | 0.75 | 6.98 | 0.3 |
| 14 | 8.01 | 0.09 | 4.29 | 0 | 4.56 | 0.46 | 6.83 | 0.55 |
| 17 | 7.89 | 0.13 | 4.29 | 0 | 4.29 | 0 | 6.97 | 0.46 |
| 21 | 7.94 | 0.06 | 4.29 | 0 | 4.72 | 0.47 | 7.13 | 0.41 |
| 24 | 7.83 | 0.08 | 4.29 | 0 | 4.97 | 0.45 | 7.37 | 0.36 |

F

| | | SEQID824 | | | | | |
|---|---|---|---|---|---|---|---|
| | Saline DNA | | 7.4 mg/kg SC DNA | | 1.5 mg/kg SC DNA | | 0.3 mg/kg SC DNA |
| Day | Serum level | StDev | Serum level | StDev | Serum level | StDev | Serum level | StDev |
| 0 | 7.77 | 0.17 | 8 | 0.24 | 7.98 | 0.23 | 7.87 | 0.17 |
| 3 | 7.8 | 0.05 | 6.64 | 0.22 | 6.44 | 0.47 | 7.05 | 0.24 |
| 7 | 7.75 | 0.15 | 5.58 | 0.32 | 5.34 | 0.75 | 6.25 | 0.26 |
| 10 | 7.79 | 0.09 | 4.59 | 0.36 | 4.87 | 0.4 | 5.64 | 0.3 |

TABLE 12A-G-continued

Serum level of $\log_{10}$(HBV DNA) (by copy number) following biweekly dosages at the concentrations indicated.

| Day | Serum level | StDev | Serum level | StDev | Serum level | StDev | Serum level | StDev |
|---|---|---|---|---|---|---|---|---|
| 14 | 8.01 | 0.09 | 4.29 | 0 | 4.59 | 0.2 | 4.81 | 0.35 |
| 17 | 7.89 | 0.13 | 4.29 | 0 | 4.29 | 0 | 4.61 | 0.37 |
| 21 | 7.94 | 0.06 | | | 4.29 | 0 | 4.94 | 0.43 |
| 24 | 7.83 | 0.08 | | | 4.29 | 0 | 5.24 | 0.56 |

G

| | Saline DNA | | SEQID826 | | | | | |
|---|---|---|---|---|---|---|---|---|
| | | | 7.1 mg/kg DNA | | 1.42 mg/kg DNA | | 0.29 mg/kg DNA | |
| Day | Serum level | StDev | Serum level | StDev | Serum level | StDev | Serum level | StDev |
| 0 | 7.77 | 0.17 | 7.86 | 0.29 | 7.86 | 0.18 | 7.87 | 0.22 |
| 3 | 7.8 | 0.05 | 6.45 | 0.24 | 7.05 | 0.34 | 7.72 | 0.18 |
| 7 | 7.75 | 0.15 | 5.32 | 0.47 | 6.42 | 0.31 | 7.57 | 0.16 |
| 10 | 7.79 | 0.09 | 4.76 | 0.47 | 6.01 | 0.48 | 7.53 | 0.12 |
| 14 | 8.01 | 0.09 | 4.29 | 0 | 5.39 | 0.7 | 7.53 | 0.14 |
| 17 | 7.89 | 0.13 | 4.29 | 0 | 5.47 | 0.83 | 7.57 | 0.16 |
| 21 | 7.94 | 0.06 | 4.29 | 0 | 6.24 | 0.5 | 7.66 | 0.16 |
| 24 | 7.83 | 0.08 | 4.29 | 0 | 6.43 | 0.55 | 7.74 | 0.16 |

LLOQ = less than lower level of quantification

Figure 13:
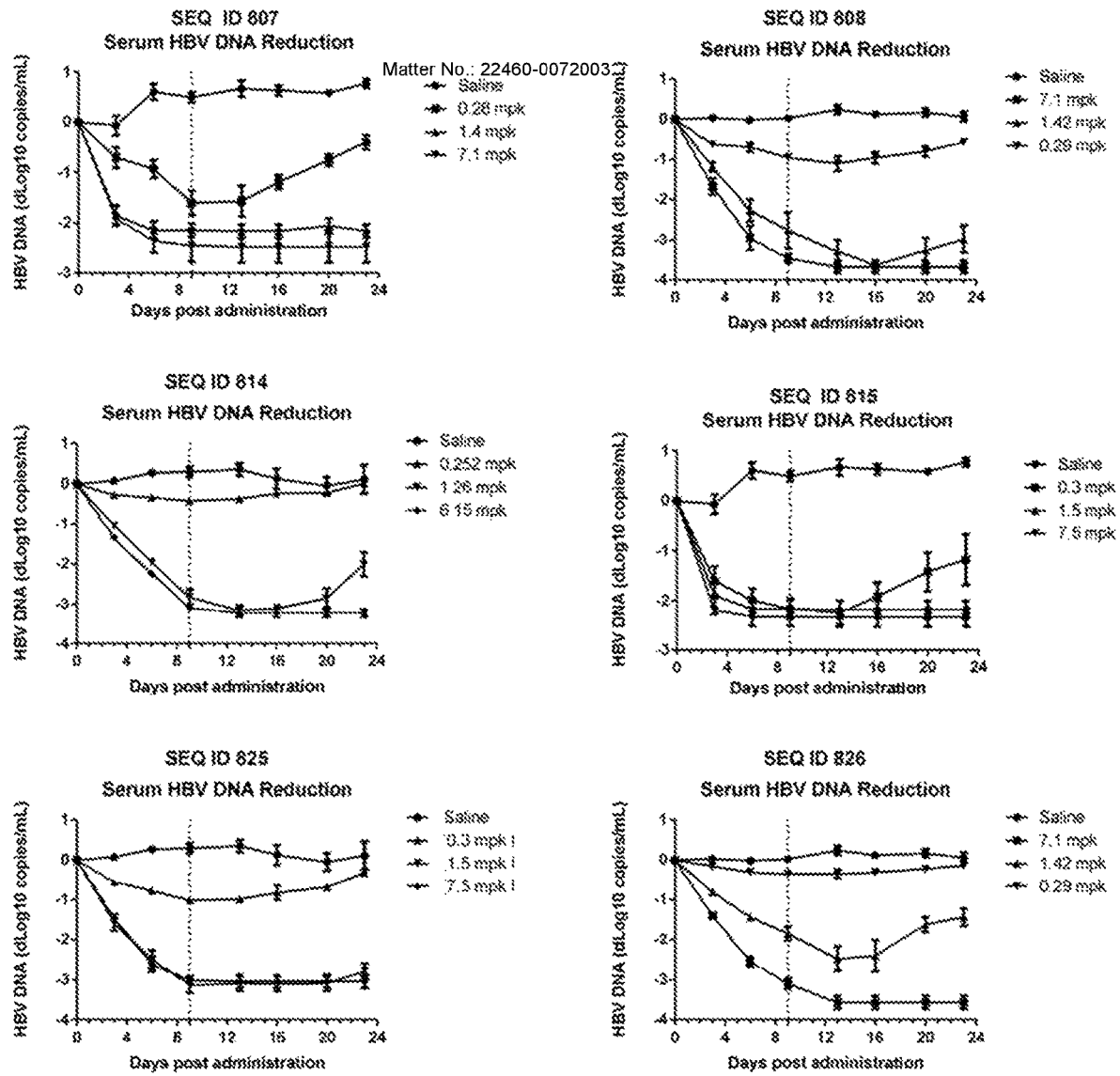
FIG. 13: HBV DNA reduction of SEQ ID NO: 807 at dose 0.28 mg/kg (■), 1.4 mg/kg (A) and 7.1 mg/kg (▼); SEQ ID NO: 808 at dose 7.1 mg/kg (■), 1.42 mg/kg (▲) and 0.29 mg/kg (▼); SEQ ID NO: 814 at dose 0.252 mg/kg (▲) and 1.26 mg/kg (▼), 6.15 mg/kg (♦); SEQ ID NO: 815 at dose 0.3 mg/kg (■), 1.5 mg/kg (▲) and 7.5 mg/kg (▼); SEQ ID NO: 825 at dose 0.3 mg/kg (▲), 1.5 mg/kg (▼), and 7.5 mg/kg (♦); SEQ ID NO: 826 at dose 7.1 mg/kg (♦), 1.42 mg/kg (▲) and 0.29 mg/kg (▼).
Figure 14A:
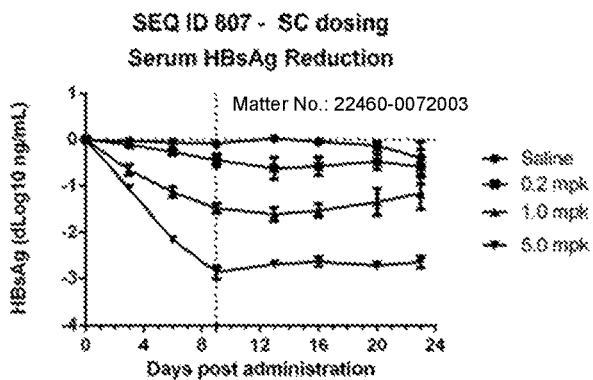
FIGS. 14A, 14B and 14C: Presents results from subcutaneous (SC) and intravenous (IV) administration routes of SEQ ID NO: 807 at dose 0.2 mg/kg, 1.0 mg/kg and 5.0 mg/kg.
Figure 14A:
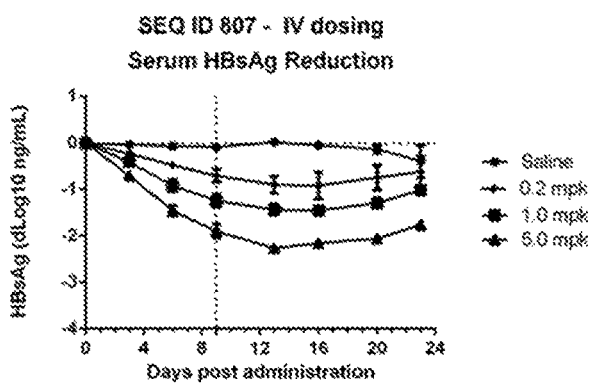
Figure 14B:
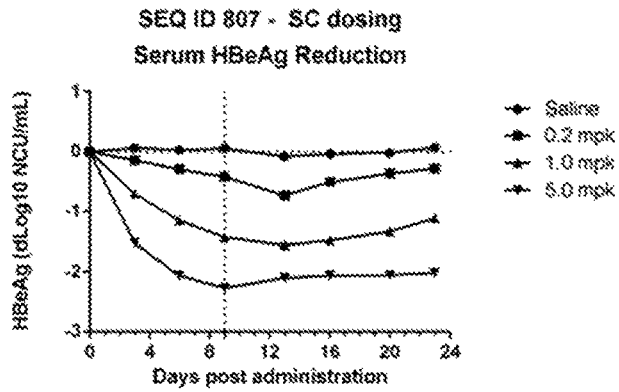
Figure 14B:
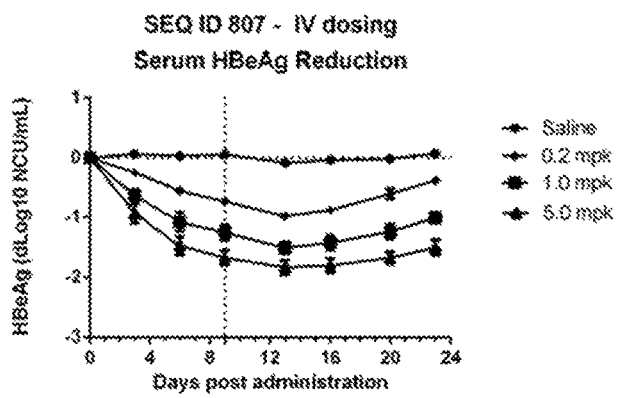
Figure 14C:
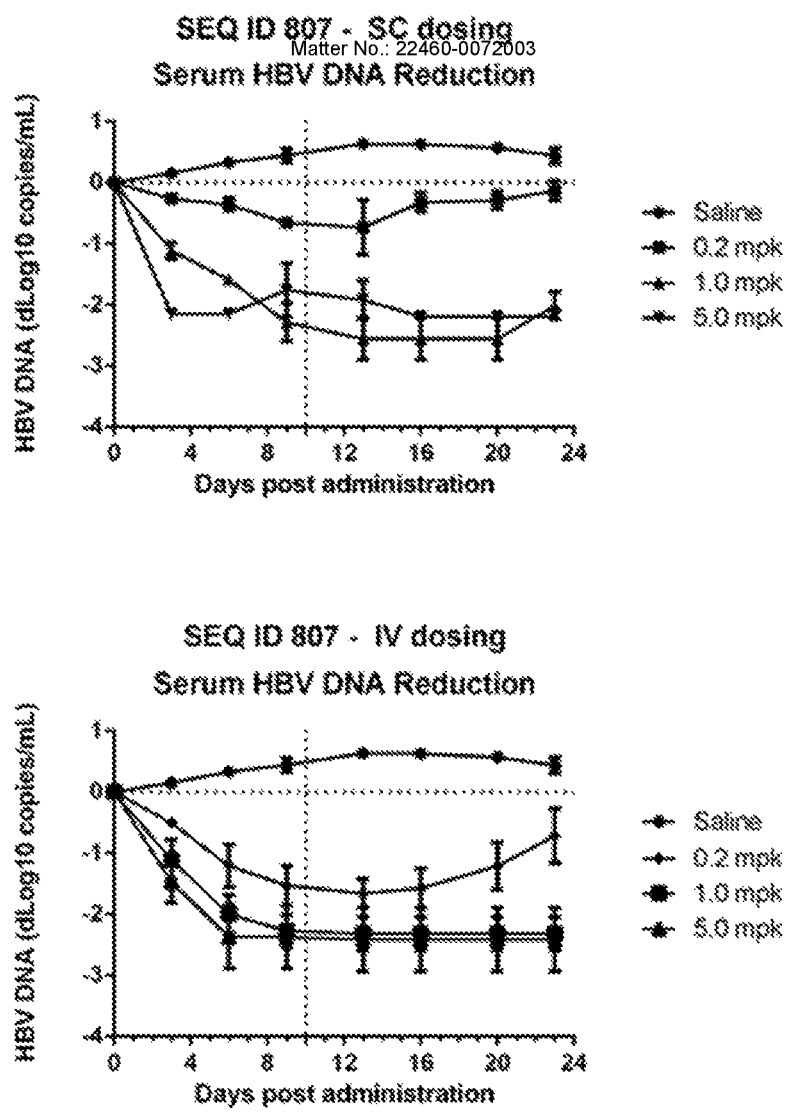

The above data are also presented in FIG. 13.

From these data it can be concluded that all GalNAc conjugated anti-HBV antisense oligomers are capable of reducing serum levels of HBsAG, HBeAG and HBV genomic DNA to a level that is lower than saline. In particular SEQ ID NO: 807, 814, 815 and 825 show very efficient HBsAG decrease even at the intermediate dose. At the highest dose the antigen reduction is maintained at least 11 days after treatment ended for SEQ ID NO: 807 and 815. SEQ ID0814, 815 and 825 demonstrate the most efficacious knock-down of viral serum DNA, demonstrating a particularly potent effect on the viral polymerase-expressing transcripts.

Example 6 Comparing Antiviral Efficacy by Different Route of Administrations

The AAV/HBV Mouse Model as prepared in Example 3 was used in this study. A GalNAc conjugated Anti-HBV LNA oligomer was tested at different doses using either subcutaneous (SC) or intravenous (IV) administration routes with saline as control in C57BL/6 mice with stable viremia.

Mice were dosed subcutaneously or intravenously twice weekly for two weeks on days 0, 3, 6 and 9 with the dose in mg/kg (mpk) pr injection indicated in the tables below. HBV surface antigen (HBsAg), HBV e antigen (HBeAg), and HBV genomic DNA in serum was measured at the indicated days using the methods described in the "Materials and methods" section. The mice were followed for 23 days after first dosing.

The results are shown in the tables below.

TABLE 13A

Serum level of HBsAg ($\log_{10}$(IU/ml)) following biweekly SC dosages at the concentration indicated

A

| | Saline HBsAg | | SEQID 807 | | | | | |
|---|---|---|---|---|---|---|---|---|
| | | | 0.2 mpk HBsAg | | 1.0 mpk HBsAg | | 5.0 mpk HBsAg | |
| Day | Serum level | StDev | Serum level | StDev | Serum level | StDev | Serum level | StDev |
| 0 | 4.64 | 0.11 | 4.55 | 0.08 | 4.46 | 0.13 | 4.69 | 0.07 |
| 3 | 4.61 | 0.11 | 4.44 | 0.06 | 3.80 | 0.22 | 3.64 | 0.10 |
| 6 | 4.58 | 0.07 | 4.29 | 0.08 | 3.33 | 0.19 | 2.54 | 0.12 |
| 9 | 4.57 | 0.10 | 4.11 | 0.05 | 2.98 | 0.20 | 1.83 | 0.14 |
| 13 | 4.67 | 0.08 | 3.93 | 0.18 | 2.85 | 0.23 | 2.00 | 0.08 |
| 16 | 4.61 | 0.08 | 3.98 | 0.15 | 2.93 | 0.19 | 2.05 | 0.09 |
| 20 | 4.52 | 0.08 | 4.08 | 0.11 | 3.11 | 0.31 | 1.98 | 0.11 |
| 23 | 4.25 | 0.52 | 3.97 | 0.26 | 3.30 | 0.33 | 2.05 | 0.16 |

TABLE 13B

Serum level of HBsAg (log$_{10}$(IU/ml)) following biweekly IV dosages at the concentration indicated

| | B | | | | | | | |
|---|---|---|---|---|---|---|---|---|
| | | | | SEQID 807 | | | | |
| | Saline HBsAg | | 0.2 mpk HBsAg | | 1.0 mpk HBsAg | | 5.0 mpk HBsAg | |
| Day | Serum level | StDev | Serum level | StDev | Serum level | StDev | Serum level | StDev |
| 0 | 4.64 | 0.11 | 4.61 | 0.09 | 4.60 | 0.11 | 4.63 | 0.12 |
| 3 | 4.61 | 0.11 | 4.39 | 0.06 | 4.19 | 0.12 | 3.93 | 0.11 |
| 6 | 4.58 | 0.07 | 4.13 | 0.05 | 3.69 | 0.13 | 3.17 | 0.13 |
| 9 | 4.57 | 0.10 | 3.91 | 0.12 | 3.36 | 0.15 | 2.73 | 0.20 |
| 13 | 4.67 | 0.08 | 3.72 | 0.21 | 3.16 | 0.02 | 2.36 | 0.14 |
| 16 | 4.61 | 0.08 | 3.70 | 0.30 | 3.14 | 0.14 | 2.47 | 0.16 |
| 20 | 4.52 | 0.08 | 3.86 | 0.28 | 3.31 | 0.14 | 2.57 | 0.12 |
| 23 | 4.25 | 0.52 | 3.99 | 0.34 | 3.59 | 0.13 | 2.86 | 0.11 |

TABLE 14A

Serum level of HBeAg (log$_{10}$(IU/ml)) following biweekly SC dosages at the concentration indicated.

| | A | | | | | | | |
|---|---|---|---|---|---|---|---|---|
| | | | | SEQID 807 | | | | |
| | Saline HBeAg | | 0.2 mpk HBeAg | | 1.0 mpk HBeAg | | 5.0 mpk HBeAg | |
| Day | Serum level | StDev | Serum level | StDev | Serum level | StDev | Serum level | StDev |
| 0 | 3.57 | 0.06 | 3.57 | 0.04 | 3.57 | 0.04 | 6.85 | 0.60 |
| 3 | 3.63 | 0.04 | 3.43 | 0.03 | 2.87 | 0.07 | 5.74 | 0.82 |
| 6 | 3.61 | 0.04 | 3.28 | 0.03 | 2.42 | 0.09 | 5.27 | 0.60 |
| 9 | 3.63 | 0.05 | 3.15 | 0.03 | 2.14 | 0.09 | 4.57 | 0.40 |
| 13 | 3.49 | 0.07 | 2.84 | 0.09 | 2.01 | 0.05 | 4.30 | LLOQ |
| 16 | 3.53 | 0.06 | 3.06 | 0.04 | 2.09 | 0.06 | 4.30 | LLOQ |
| 20 | 3.56 | 0.05 | 3.21 | 0.03 | 2.24 | 0.08 | 4.30 | LLOQ |
| 23 | 3.64 | 0.06 | 3.29 | 0.03 | 2.46 | 0.09 | 4.85 | 0.54 |

LLOQ = less than lower level of quantification

TABLE 14B

Serum level of HBeAg (log$_{10}$(IU/ml)) following biweekly IV dosages at the concentration indicated

| | B | | | | | | | |
|---|---|---|---|---|---|---|---|---|
| | | | | SEQID 807 | | | | |
| | Saline HBeAg | | 0.2 mpk HBeAg | | 1.0 mpk HBeAg | | 5.0 mpk HBeAg | |
| Day | Serum level | StDev | Serum level | StDev | Serum level | StDev | Serum level | StDev |
| 0 | 3.57 | 0.06 | 3.65 | 0.06 | 3.62 | 0.04 | 3.61 | 0.08 |
| 3 | 3.63 | 0.04 | 2.13 | 0.06 | 3.37 | 0.05 | 2.96 | 0.03 |
| 6 | 3.61 | 0.04 | 1.59 | 0.05 | 3.05 | 0.04 | 2.52 | 0.07 |
| 9 | 3.63 | 0.05 | 1.39 | 0.07 | 2.88 | 0.06 | 2.35 | 0.03 |
| 13 | 3.49 | 0.07 | 1.55 | 0.03 | 2.63 | 0.04 | 2.10 | 0.04 |
| 16 | 3.53 | 0.06 | 1.59 | 0.04 | 2.73 | 0.06 | 2.18 | 0.08 |
| 20 | 3.56 | 0.05 | 1.60 | 0.03 | 3.01 | 0.06 | 2.37 | 0.11 |
| 23 | 3.64 | 0.06 | 1.64 | 0.08 | 3.22 | 0.05 | 2.60 | 0.07 |

TABLE 15A

Serum level of HBV DNA (by log₁₀ (copy number)) following biweekly SC dosages at the concentrations indicated

A

| | Saline DNA | | SEQID 807 | | | | | |
|---|---|---|---|---|---|---|---|---|
| | | | 0.2 mpk DNA | | 1.0 mpk DNA | | 5.0 mpk DNA | |
| Day | Serum level | StDev | Serum level | StDev | Serum level | StDev | Serum level | StDev |
| 0 | 6.50 | 0.21 | 6.56 | 0.19 | 6.85 | 0.60 | 6.48 | 0.14 |
| 3 | 6.65 | 0.31 | 6.30 | 0.33 | 5.74 | 0.82 | 4.34 | LLOQ |
| 6 | 6.83 | 0.31 | 6.20 | 0.33 | 5.27 | 0.60 | 4.34 | LLOQ |
| 9 | 6.94 | 0.37 | 5.90 | 0.32 | 4.57 | 0.40 | 4.73 | 0.67 |
| 13 | 7.13 | 0.21 | 5.82 | 0.88 | 4.30 | LLOQ | 4.56 | 0.46 |
| 16 | 7.12 | 0.31 | 6.23 | 0.38 | 4.30 | LLOQ | 4.30 | LLOQ |
| 20 | 7.06 | 0.17 | 6.27 | 0.35 | 4.30 | LLOQ | 4.30 | LLOQ |
| 23 | 6.94 | 0.32 | 6.42 | 0.32 | 4.85 | 0.54 | 4.30 | LLOQ |

LLOQ = less than lower level of quantification

TABLE 15B

Serum level of HBV DNA (by log₁₀ (copy number)) following biweekly IV dosages at the concentrations indicated

A

| | Saline DNA | | SEQID 807 | | | | | |
|---|---|---|---|---|---|---|---|---|
| | | | 0.2 mpk DNA | | 1.0 mpk DNA | | 5.0 mpk DNA | |
| Day | Serum level | StDev | Serum level | StDev | Serum level | StDev | Serum level | StDev |
| 0 | 6.50 | 0.21 | 6.71 | 0.59 | 6.62 | 0.23 | 6.71 | 0.45 |
| 3 | 6.65 | 0.31 | 6.20 | 0.59 | 5.50 | 0.43 | 5.24 | 0.69 |
| 6 | 6.83 | 0.31 | 5.50 | 0.90 | 4.62 | 0.48 | 4.34 | LLOQ |
| 9 | 6.94 | 0.37 | 5.18 | 0.85 | 4.34 | LLOQ | 4.34 | LLOQ |
| 13 | 7.13 | 0.21 | 5.05 | 0.76 | 4.30 | LLOQ | 4.30 | LLOQ |
| 16 | 7.12 | 0.31 | 5.13 | 0.84 | 4.30 | LLOQ | 4.30 | LLOQ |
| 20 | 7.06 | 0.17 | 5.50 | 0.80 | 4.30 | LLOQ | 4.30 | LLOQ |
| 23 | 6.94 | 0.32 | 5.99 | 0.41 | 4.30 | LLOQ | 4.30 | LLOQ |

LLOQ = less than lower level of quantification

The data are also presented in FIG. 14.

From these data it can be concluded that administration of GalNAc conjugated anti-HBV antisense oligomers more efficiently reduces serum levels of HBsAG, HBeAG and HBV genomic DNA to a level that is lower than saline, when dosed by subcutaneous administration, as compared to intravenous administration.

Example 7: Comparison of Conjugated and Unconjugated Oligonucleotides

The AAV/HBV Mouse Model as prepared in Example 3 was used in this study. Unconjugated (SEQ ID NO 308 and 303) and GalNAc conjugated (SEQ ID NO: 807 and 815) Anti-HBV LNA oligomers were tested at equimolar oligomer doses with saline as control in C57BL/6 mice with stable viremia.

Mice were dosed subcutaneously twice weekly for two weeks on days 0, 3, 6 and 9 with the dose in mg/kg (mpk) pr injection indicated in the tables below. HBV surface antigen (HBsAg), HBV e antigen (HBeAg), and HBV genomic DNA in serum was measured at the indicated days using the methods described in the "Materials and methods" section. The mice were followed for 23.

The results are shown in the tables below.

TABLE 16A-B

Serum level of HBsAg (log₁₀(IU/ml)) following biweekly dosages at equimolarconcentrations

A

| | Saline HBsAg | | SEQ ID 308 5 mpk HBsAg | | SEQ ID 807 7.1 mpk HBsAg | |
|---|---|---|---|---|---|---|
| Day | Serum level | StDev | Serum level | StDev | Serum level | StDev |
| 0 | 4.63 | 0.12 | 4.70 | 0.05 | 4.74 | 0.06 |
| 3 | 4.67 | 0.09 | 4.44 | 0.14 | 3.79 | 0.19 |
| 6 | 4.63 | 0.11 | 3.91 | 0.44 | 2.68 | 0.15 |
| 9 | 4.62 | 0.10 | 3.50 | 0.44 | 2.09 | 0.09 |
| 13 | 4.64 | 0.06 | 3.27 | 0.43 | 1.84 | 0.09 |
| 16 | 4.56 | 0.05 | 3.20 | 0.53 | 1.72 | 0.05 |

TABLE 16A-B-continued

Serum level of HBsAg (log₁₀(IU/ml)) following biweekly dosages at equimolarconcentrations

| 20 | 4.69 | 0.03 | 3.61 | 0.54 | 1.97 | 0.29 |
| 23 | 4.67 | 0.10 | 3.96 | 0.34 | 1.78 | 0.11 |

B

| | Saline HBsAg | | SEQ ID 303 1 mpk HBsAg | | SEQ ID 815 1.5 mpk HBsAg | |
|---|---|---|---|---|---|---|
| Day | Serum level | StDev | Serum level | StDev | Serum level | StDev |
| 0 | 4.63 | 0.28 | 4.49 | 0.54 | 4.62 | 0.25 |
| 3 | 4.70 | 0.17 | 4.58 | 0.38 | 3.31 | 0.09 |
| 6 | 4.84 | 0.12 | 4.78 | 0.17 | 3.21 | 0.14 |
| 9 | 4.81 | 0.13 | 4.81 | 0.13 | 2.64 | 0.22 |
| 13 | 4.86 | 0.12 | 4.91 | 0.06 | 2.63 | 0.58 |
| 16 | 4.83 | 0.13 | 4.85 | 0.10 | 2.04 | 0.57 |
| 20 | 4.73 | 0.18 | 4.68 | 0.14 | 2.26 | 0.58 |
| 23 | 4.66 | 0.20 | 4.48 | 0.40 | 2.74 | 0.64 |

TABLE 17A-B

Serum level of HBeAg (log₁₀(IU/ml)) following biweekly dosages at equimolar concentrations

A

| | Saline HBeAg | | SEQ ID 308 5 mpk HBeAg | | SEQ ID 807 7.1 mpk HBeAg | |
|---|---|---|---|---|---|---|
| Day | Serum level | StDev | Serum level | StDev | Serum level | StDev |
| 0 | 3.83 | 0.04 | 3.79 | 0.05 | 3.82 | 0.02 |
| 3 | 3.74 | 0.02 | 3.39 | 0.08 | 2.24 | 0.04 |
| 6 | 3.69 | 0.02 | 3.07 | 0.02 | 1.67 | 0.04 |
| 9 | 3.68 | 0.03 | 2.82 | 0.04 | 1.48 | 0.05 |
| 13 | 3.66 | 0.03 | 2.66 | 0.03 | 1.53 | 0.02 |
| 16 | 3.69 | 0.03 | 2.75 | 0.03 | 1.21 | 0.07 |
| 20 | 3.66 | 0.04 | 3.01 | 0.02 | 1.48 | 0.07 |
| 23 | 3.63 | 0.04 | 3.10 | 0.05 | 1.34 | 0.09 |

B

| | Saline HBeAg | | SEQ ID 303 1 mpk HBeAg | | SEQ ID 815 1.5 mpk HBeAg | |
|---|---|---|---|---|---|---|
| Day | Serum level | StDev | Serum level | StDev | Serum level | StDev |
| 0 | 3.82 | 0.03 | 3.74 | 0.04 | 3.80 | 0.06 |
| 3 | 3.82 | 0.03 | 3.78 | 0.02 | 2.48 | 0.10 |
| 6 | 3.85 | 0.02 | 3.83 | 0.06 | 2.70 | 0.05 |
| 9 | 3.81 | 0.03 | 3.75 | 0.02 | 2.29 | 0.07 |
| 13 | 3.84 | 0.02 | 3.84 | 0.03 | 2.45 | 0.08 |
| 16 | 3.84 | 0.04 | 3.80 | 0.02 | 2.19 | 0.02 |
| 20 | 3.78 | 0.04 | 3.73 | 0.04 | 2.27 | 0.06 |
| 23 | 3.79 | 0.03 | 3.79 | 0.01 | 2.60 | 0.04 |

TABLE 18A-B

Serum level of HBV DNA (by log₁₀ (copy number)) following biweekly dosages at equimolar concentrations

A

| | Saline DNA | | SEQ ID 308 DNA 5 mpk | | SEQ ID 807 DNA 7.1 mpk | |
|---|---|---|---|---|---|---|
| Day | Serum level | StDev | Serum level | StDev | Serum level | StDev |
| 0 | 6.64 | 0.31 | 6.53 | 0.26 | 6.77 | 0.57 |
| 3 | 6.58 | 0.42 | 5.18 | 0.88 | 4.86 | 0.58 |
| 6 | 7.25 | 0.49 | 5.05 | 0.73 | 4.43 | 0.18 |
| 9 | 7.14 | 0.23 | 4.54 | 0.37 | 4.32 | LLOQ |
| 13 | 7.32 | 0.33 | 4.30 | LLOQ | 4.30 | LLOQ |
| 16 | 7.28 | 0.27 | 4.41 | 0.19 | 4.30 | LLOQ |
| 20 | 7.23 | 0.31 | 4.63 | 0.57 | 4.30 | LLOQ |
| 23 | 7.43 | 0.28 | 5.23 | 0.93 | 4.30 | LLOQ |

B

| | Saline DNA | | SEQ ID 303 DNA 1 mpk | | SEQ ID 815 DNA 1.5 mpk | |
|---|---|---|---|---|---|---|
| Day | Serum level | StDev | Serum level | StDev | Serum level | StDev |
| 0 | 7.89 | 0.16 | 7.91 | 0.42 | 7.91 | 0.23 |
| 3 | 8.28 | 0.13 | 8.06 | 0.41 | 6.54 | 0.25 |
| 6 | 8.03 | 0.13 | 7.94 | 0.20 | 5.38 | 0.63 |
| 9 | 8.19 | 0.13 | 8.07 | 0.14 | 4.30 | LLOQ |
| 13 | 8.37 | 0.16 | 8.31 | 0.13 | 4.30 | LLOQ |
| 16 | 8.41 | 0.19 | 8.16 | 0.18 | 4.30 | LLOQ |
| 20 | 8.23 | 0.09 | 7.94 | 0.19 | 4.30 | LLOQ |
| 23 | 8.20 | 0.06 | 7.89 | 0.28 | 4.30 | LLOQ |

LLOQ = less than lower level of quantification

Figure 15C:
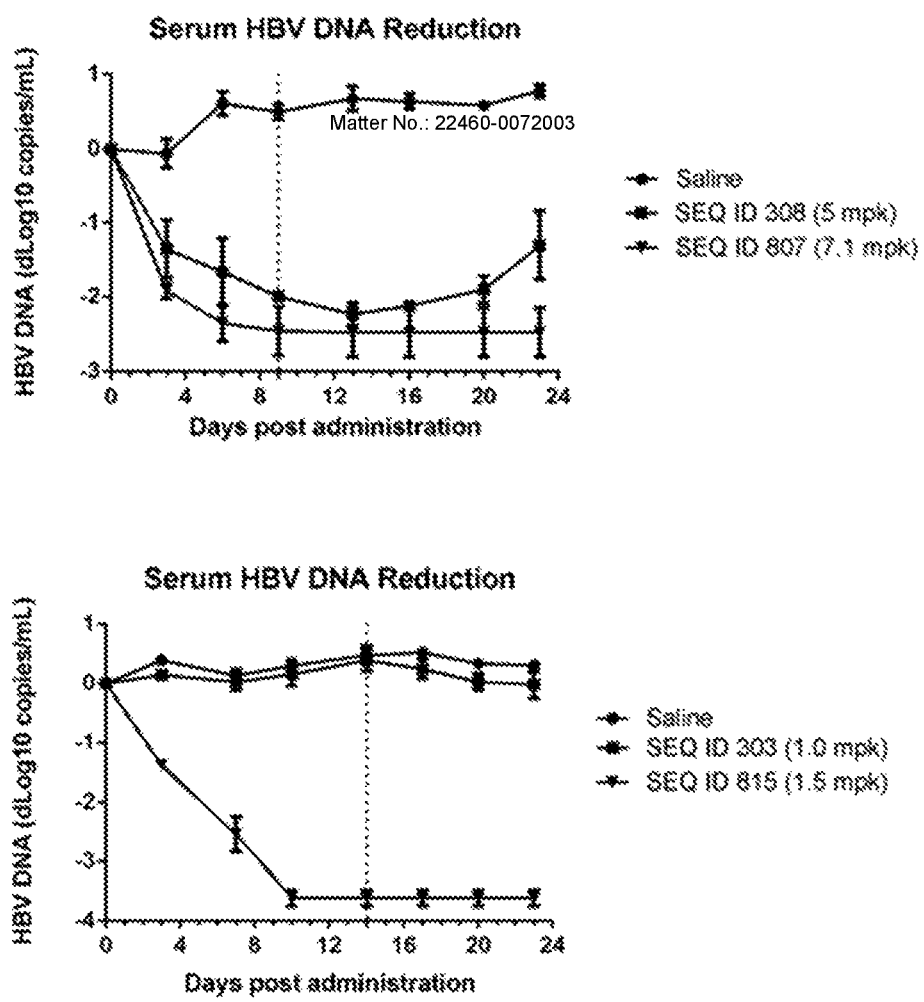

The data are also presented in FIG. 15.

From these data it can be concluded that administration of GalNAc conjugated anti-HBV antisense oligomers more efficiently reduces serum levels of HBsAG and HBeAG to a level that is lower than saline, when dosed by subcutaneous administration, as compared to intravenous administration. Serum HBV DNA is reduced with equal efficacy by the two methods of delivery, although the limitation of the assay precludes discrimination at high doses.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law). All headings and sub-headings are used herein for convenience only and should not be construed as limiting the invention in any way. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents. This invention includes all modifications and equivalents of the subject matter recited in the claims appended hereto as permitted by applicable law.

The invention claimed is:

1. An oligomer conjugate suitable for use in the treatment of a viral disorder, wherein said oligomer conjugate comprises:
   a) at least one first oligomer region capable of modulating a target sequence of Hepatitis B Virus (HBV) to treat said viral disorder; and
   b) a carrier component;
   wherein said first oligomer region is 10-20 nucleotides in length;
   wherein said carrier component is a asialoglycoprotein receptor (ASGP-R) targeting moiety or a cholesterol conjugate moiety; and
   wherein said target sequence comprises at least part of a gene or a mRNA encoding HBx (SEQ ID NO: 1) or HBsAg (SEQ ID NO: 2) or a naturally-occurring variant thereof.

* * * * *

SEQUENCE LISTING

```
Sequence total quantity: 862
SEQ ID NO: 1              moltype = DNA   length = 746
FEATURE                   Location/Qualifiers
source                    1..746
                          mol_type = other DNA
                          organism = Hepatitis B virus
SEQUENCE: 1
aacccccact ggctggggct tggtcatggg ccatcagcgc gtgcgtggaa ccttttcggc   60
tcctctgccg atccatactg cggaactcct agccgcttgt tttgctcgca gcaggtctgg  120
agcaaacatt atcgggactg ataactctgt tgtcctctcc cgcaaatata catcgtatcc  180
atggctgcta ggctgtgctg ccaactggat cctgcgcggg acgtcctttg tttacgtccc  240
gtcggcgctg aatcctgcgg acgaccttc tcggggtcgc ttgggactct ctcgtccct   300
tctccgtctg ccgttccgac cgaccacggg gcgcacctct ctttacgcgg actcccgtc   360
tgtgccttct catctgccgg accgtgtgca cttcgcttca cctctgcacg tcgcatggag  420
accaccgtga acgcccaccg aatgttgccc aaggtcttac ataagaggac tcttggactc  480
tctgcaatgt caacgaccga ccttgaggca tacttcaaag actgtttgtt taaagactgg  540
gaggagttgg gggaggagat tagattaaag gtctttgtac taggaggctg taggcataaa  600
ttggtctgcg caccagcacc atgcaacttt ttcacctctg cctaatcatc tcttgttcat  660
gtcctactgt tcaagcctcc aagctgtgcc ttgggtggct ttggggcatg gacatcgacc  720
cttataaaga atttggagct actgtg                                       746

SEQ ID NO: 2              moltype = DNA   length = 1969
FEATURE                   Location/Qualifiers
source                    1..1969
                          mol_type = other DNA
                          organism = Hepatitis B virus
SEQUENCE: 2
cactcatcct caggccatgc agtggaattc cacaaccttt caccaaactc tgcaagatcc   60
cagagtgaga ggcctgtatt tccctgctgg tggctccagt tcaggagcag taaaccctgt  120
tccgactact gcctctccct tatcgtcaat cttctcgagg attggggacc ctgcgctgaa  180
catggagaac atcacatcag gattcctagg acccctctc gtgttacagg cggggttttt  240
cttgttgaca agaatcctca caataccgca gagtctagac tcgtggtggg acttctctcaa  300
ttttctaggg ggaactaccg tgtgtcttgg ccaaaattcg cagtcccaa cctccaatca  360
ctcaccaacc tcctgtcctc caacttgtcc tggttatcgc tggatgtgtc tgcggcgttt  420
tatcatcttc ctcttcatcc tgctgctatg cctcatcttc ttgttggttc ttctggacta  480
tcaaggtatg ttgcccgttt gtcctctaat tccaggatcc tcaaccacca gcacgggacc  540
atgccgaacc tgcatgacta ctgctcaagg aacctctatg tatccctcct gttgctgtac  600
caaaccttcg gacggaaatt gcacctgtat tcccatccca tcatcctggg ctttcggaaa  660
attcctatgg gagtgggcct cagcccgttt ctcctggctc agtttactag tgccatttgt  720
tcagtggttc gtagggcttt cccccactgt ttggctttca gttatatgga tgatgtggta  780
ttgggggcca agtctgtaca gcatcttgag tccctttta ccgctgttac caattttctt  840
ttgtctttgg gtatacattt aaaccctaac aaaacaaaga gatggggtta ctctctgaat  900
tttatgggtt atgtcattgg aagttatggg tccttgccac aagaacacat catacaaaaa  960
atcaaagaat gttttagaaa acttcctatt aacaggcctat tggattggaa agtatgtcaa 1020
cgaattgtgg gtcttttggg ttttgctgcc ccatttacac aatgtggtta tcctgcgtta 1080
atgcccttgt atgcatgtat tcaatctaag caggctttca ctttctcgcc aacttacaag 1140
gcctttctgt gtaaacaata cctgaacctt taccccgttg cccggcaacg gccaggtctg 1200
tgccaagtgt ttgctgacgc aacccccact ggctggggct tggtcatggg ccatcagcgc 1260
gtgcgtggaa ccttttcggc tcctctgccg atccatactg cggaactcct agccgcttgt 1320
tttgctcgca gcaggtctgg agcaaacatt atcgggactg ataactctgt tgtcctctcc 1380
cgcaaatata catcgtatcc atggctgcta ggctgtgctg ccaactggat cctgcgcggg 1440
acgtcctttg tttacgtccc gtcggcgctg aatcctgcgg acgaccttc tcggggtcgc 1500
ttgggactct ctcgtccct tctccgtctg ccgttccgac cgaccacggg gcgcacctct 1560
ctttacgcgg actcccgtc tgtgccttct catctgccgg accgtgtgca cttcgcttca 1620
cctctgcacg tcgcatggag accaccgtga acgcccaccg aatgttgccc aaggtcttac 1680
ataagaggac tcttggactc tctgcaatgt caacgaccga ccttgaggca tacttcaaag 1740
actgtttgtt taaagactgg gaggagttgg gggaggagat tagattaaag gtctttgtac 1800
taggaggctg taggcataaa ttggtctgcg caccagcacc atgcaacttt ttcacctctg 1860
cctaatcatc tcttgttcat gtcctactgt tcaagcctcc aagctgtgcc ttgggtggct 1920
ttggggcatg gacatcgacc cttataaaga atttggagct actgtggag               1969

SEQ ID NO: 3              moltype = DNA   length = 3182
FEATURE                   Location/Qualifiers
source                    1..3182
                          mol_type = other DNA
                          organism = Hepatitis B virus
SEQUENCE: 3
aattccacaa cctttcacca aactctgcaa gatcccagag tgagaggcct gtatttccct   60
gctggtggct ccagttcagg agcagtaaac cctgttccga ctactgcctc tcccttatcg  120
tcaatcttct cgaggattgg ggaccctgcg ctgaacatgg agaacatcac atcaggattc  180
ctaggacccc ttctcgtgtt acaggcgggg ttttcttgt tgacaagaat cctcacaata  240
ccgcagagtc tagactcgtg gtggacttct ctcaattttc tagggggaac taccgtgtgt  300
cttggccaaa attcgcagtc cccaacctcc aatcactcac caacctcctg tcctccaact  360
tgtcctggtt atcgctggat gtgtctgcgg cgttttatca tcttcctctt catcctgctg  420
ctatgcctca tcttcttgtt ggttcttctg gactatcaag gtatgttgcc cgtttgtcct  480
ctaattccag gatcctcaac caccagcacg ggaccatgcc gaacctgcat gactactgct  540
caaggaacct ctatgtatcc ctcctgttgc tgtaccaaac cttcggacgg aaattgcacc  600
tgtattccca tcccatcatc ctgggctttc ggaaaattcc tatgggagtg ggcctcagcc  660
```

-continued

```
cgtttctcct ggctcagttt actagtgcca tttgttcagt ggttcgtagg gctttccccc    720
actgtttggc tttcagttat atggatgatg tggtattggg ggccaagtct gtacagcatc    780
ttgagtccct ttttaccgct gttaccaatt ttcttttgtc tttgggtata catttaaacc    840
ctaacaaaac aaagagatgg ggttactctc tgaattttat gggttatgtc attggaagtt    900
atgggtcctt gccacaagaa cacatcatac aaaaaatcaa agaatgtttt agaaaacttc    960
ctattaacag gccattgat tggaaagtat gtcaacgaat tgtgggtctt ttgggttttg    1020
ctgccccatt tacacaatgt ggttatcctg cgttaatgcc cttgtatgca tgtattcaat   1080
ctaagcaggc tttcactttc tcgccaactt acaaggcctt tctgtgtaaa caatacctga   1140
acctttaccc cgttgcccgg caacggccag gtctgtgcca agtgtttgct gacgcaaccc   1200
ccactggctg gggcttggtc atgggccatc agcgcgtgcg tggaaccttt tcggctcctc   1260
tgccgatcca tactgcggaa ctcctagccg cttgttttgc tcgcagcagg tctggagcaa   1320
acattatcgg gactgataac tctgttgtcc tctcccgcaa atatacatcg tatccatggc   1380
tgctaggctg tgctgccaac tggatcctgc gcgggacgtc ctttgtttac gtcccgtcgg   1440
cgctgaatcc tgcggacgac cctctcgggg tcgcttggg actctctcgt cccctttctc   1500
gtctgccgtt ccgaccgacc acggggcgca cctctcttta cgcggactcc ccgtctgtgc   1560
cttctcatct gccggaccgt gtgcacttcg cttcacctct gcacgtcgca tggagaccac   1620
cgtgaacgcc caccgaatgt tgcccaaggt cttacataag aggactcttg gactctctgc   1680
aatgtcaacg accgaccttg aggcatactt caaagacttg ttgtttaaag actgggagga   1740
gttgggggag gagattagat taaaggtctt tgtactagga ggctgtaggc ataaattggt   1800
ctgcgcacca gcaccatgca actttttcac ctctgcctaa tcatctcttg ttcatgtcct   1860
actgttcaag cctccaagct gtgccttggg tggctttggg gcatggacat cgacccttat   1920
aaagaatttg gagctactgt ggagttactc tcgttttgtc ttctgactt cttccttca    1980
gtacgagatc ttctagatac cgcctcagct ctgtatcggg aagcttaga gtctcctgag   2040
cattgttcac ctcaccatac tgcactcagg caagcaattc tttgctgggg ggaactaatg   2100
actctagcta cctgggtggg tgttaatttg gaagatccag catctagaga cctagtagtc   2160
agttatgtca acactaatat gggcctaaag ttcaggcaac tctgtggtt tcacatttct   2220
tgtctcactt ttggaagaga aaccgttata gagtatttgg tgtctttcgg agtgtggatt   2280
cgcactcctc cagcttatag accaccaaat gccccatcc tatcaacact tccggaaact   2340
actgttgtta gacgacgagg caggtcccct agaagaagaa ctcctcgcc tcgcagacga    2400
aggtctcaat cgccgcgtcg cagaagatct caatctcggg aacctcaatg ttagtattcc   2460
ttggactcat aaggtgggga acttactgg tctttattct tctactgtac ctgtctttaa    2520
tcctcattgg aaaacaccat cttttcctaa tatacattta caccaagaca ttatcaaaaa   2580
atgtgaacag tttgtaggcc cacttacagt taatgagaaa agaagattgc aattgattat   2640
gcctgctagg ttttatccaa aggttaccaa atatttacca ttggataagg gtattaaacc   2700
ttattatcca gaacatctag ttaatcatta cttccaaact agacactatt tacacactgt   2760
atggaaggcg ggtatattat ataagagaga acaacacat agcgcctcat tttgtgggtc   2820
accatattct tgggaacaag atctacagca tggggcagaa tctttccacc agcaatcctc   2880
tgggattctt tcccgaccac cagttggatc cagccttcag agcaaacaca gcaaatccag   2940
attgggactt caatcccaac aaggacacct ggccagacgc caacaaggta gggagctgga   3000
cattcgggct gggtttcacc ccaccgcacg gaggcctttt gggtggagc cctcaggctc    3060
agggcatact acaaactttg ccagcaaatc cgcctcctgc ctccaccaat cgccagacag   3120
gaaggcagcc taccccgctg tctccacctt tgagaaacac tcatcctcag gccatgcagt   3180
gg                                                                  3182

SEQ ID NO: 4              moltype = DNA  length = 15
FEATURE                   Location/Qualifiers
misc_feature              1..15
                          note = oligonucleotide sequence motif
source                    1..15
                          mol_type = other DNA
                          organism = synthetic construct
SEQUENCE: 4
gaaccactga acaaa                                                     15

SEQ ID NO: 5              moltype = DNA  length = 16
FEATURE                   Location/Qualifiers
misc_feature              1..16
                          note = oligonucleotide sequence motif
source                    1..16
                          mol_type = other DNA
                          organism = synthetic construct
SEQUENCE: 5
cgaaccactg aacaaa                                                    16

SEQ ID NO: 6              moltype = DNA  length = 15
FEATURE                   Location/Qualifiers
misc_feature              1..15
                          note = oligonucleotide sequence motif
source                    1..15
                          mol_type = other DNA
                          organism = synthetic construct
SEQUENCE: 6
cgaaccactg aacaa                                                     15

SEQ ID NO: 7              moltype = DNA  length = 14
FEATURE                   Location/Qualifiers
misc_feature              1..14
                          note = oligonucleotide sequence motif
source                    1..14
```

```
                        mol_type = other DNA
                        organism = synthetic construct
SEQUENCE: 7
cgaaccactg aaca                                                    14

SEQ ID NO: 8           moltype = DNA   length = 13
FEATURE                Location/Qualifiers
misc_feature           1..13
                       note = oligonucleotide sequence motif
source                 1..13
                       mol_type = other DNA
                       organism = synthetic construct
SEQUENCE: 8
cgaaccactg aac                                                     13

SEQ ID NO: 9           moltype = DNA   length = 15
FEATURE                Location/Qualifiers
misc_feature           1..15
                       note = oligonucleotide sequence motif
source                 1..15
                       mol_type = other DNA
                       organism = synthetic construct
SEQUENCE: 9
ccgcagtatg gatcg                                                   15

SEQ ID NO: 10          moltype = DNA   length = 13
FEATURE                Location/Qualifiers
misc_feature           1..13
                       note = oligonucleotide sequence motif
source                 1..13
                       mol_type = other DNA
                       organism = synthetic construct
SEQUENCE: 10
cgcagtatgg atc                                                     13

SEQ ID NO: 11          moltype = DNA   length = 14
FEATURE                Location/Qualifiers
misc_feature           1..14
                       note = oligonucleotide sequence motif
source                 1..14
                       mol_type = other DNA
                       organism = synthetic construct
SEQUENCE: 11
gcgtaaagag aggt                                                    14

SEQ ID NO: 12          moltype = DNA   length = 15
FEATURE                Location/Qualifiers
misc_feature           1..15
                       note = oligonucleotide sequence motif
source                 1..15
                       mol_type = other DNA
                       organism = synthetic construct
SEQUENCE: 12
cgcgtaaaga gaggt                                                   15

SEQ ID NO: 13          moltype = DNA   length = 13
FEATURE                Location/Qualifiers
misc_feature           1..13
                       note = oligonucleotide sequence motif
source                 1..13
                       mol_type = other DNA
                       organism = synthetic construct
SEQUENCE: 13
gcgtaaagag agg                                                     13

SEQ ID NO: 14          moltype = DNA   length = 15
FEATURE                Location/Qualifiers
misc_feature           1..15
                       note = oligonucleotide sequence motif
source                 1..15
                       mol_type = other DNA
                       organism = synthetic construct
SEQUENCE: 14
agaaggcaca gacgg                                                   15

SEQ ID NO: 15          moltype = DNA   length = 16
FEATURE                Location/Qualifiers
misc_feature           1..16
                       note = oligonucleotide sequence motif
```

```
source                     1..16
                           mol_type = other DNA
                           organism = synthetic construct
SEQUENCE: 15
gagaaggcac agacgg                                                            16

SEQ ID NO: 16              moltype = DNA   length = 13
FEATURE                    Location/Qualifiers
misc_feature               1..13
                           note = oligonucleotide sequence motif
source                     1..13
                           mol_type = other DNA
                           organism = synthetic construct
SEQUENCE: 16
gaagtgcaca cgg                                                               13

SEQ ID NO: 17              moltype = DNA   length = 15
FEATURE                    Location/Qualifiers
misc_feature               1..15
                           note = oligonucleotide sequence motif
source                     1..15
                           mol_type = other DNA
                           organism = synthetic construct
SEQUENCE: 17
gcgaagtgca cacgg                                                             15

SEQ ID NO: 18              moltype = DNA   length = 16
FEATURE                    Location/Qualifiers
misc_feature               1..16
                           note = oligonucleotide sequence motif
source                     1..16
                           mol_type = other DNA
                           organism = synthetic construct
SEQUENCE: 18
agcgaagtgc acacgg                                                            16

SEQ ID NO: 19              moltype = DNA   length = 13
FEATURE                    Location/Qualifiers
misc_feature               1..13
                           note = oligonucleotide sequence motif
source                     1..13
                           mol_type = other DNA
                           organism = synthetic construct
SEQUENCE: 19
cgaagtgcac acg                                                               13

SEQ ID NO: 20              moltype = DNA   length = 15
FEATURE                    Location/Qualifiers
misc_feature               1..15
                           note = oligonucleotide sequence motif
source                     1..15
                           mol_type = other DNA
                           organism = synthetic construct
SEQUENCE: 20
agcgaagtgc acacg                                                             15

SEQ ID NO: 21              moltype = DNA   length = 16
FEATURE                    Location/Qualifiers
misc_feature               1..16
                           note = oligonucleotide sequence motif
source                     1..16
                           mol_type = other DNA
                           organism = synthetic construct
SEQUENCE: 21
aagcgaagtg cacacg                                                            16

SEQ ID NO: 22              moltype = DNA   length = 15
FEATURE                    Location/Qualifiers
misc_feature               1..15
                           note = oligonucleotide sequence motif
source                     1..15
                           mol_type = other DNA
                           organism = synthetic construct
SEQUENCE: 22
gaagcgaagt gcaca                                                             15

SEQ ID NO: 23              moltype = DNA   length = 16
FEATURE                    Location/Qualifiers
misc_feature               1..16
```

```
                          note = oligonucleotide sequence motif
source                    1..16
                          mol_type = other DNA
                          organism = synthetic construct
SEQUENCE: 23
ggtgaagcga agtgca                                                           16

SEQ ID NO: 24             moltype = DNA   length = 15
FEATURE                   Location/Qualifiers
misc_feature              1..15
                          note = oligonucleotide sequence motif
source                    1..15
                          mol_type = other DNA
                          organism = synthetic construct
SEQUENCE: 24
ggtgaagcga agtgc                                                            15

SEQ ID NO: 25             moltype = DNA   length = 16
FEATURE                   Location/Qualifiers
misc_feature              1..16
                          note = oligonucleotide sequence motif
source                    1..16
                          mol_type = other DNA
                          organism = synthetic construct
SEQUENCE: 25
aggtgaagcg aagtgc                                                           16

SEQ ID NO: 26             moltype = DNA   length = 15
FEATURE                   Location/Qualifiers
misc_feature              1..15
                          note = oligonucleotide sequence motif
source                    1..15
                          mol_type = other DNA
                          organism = synthetic construct
SEQUENCE: 26
aggtgaagcg aagtg                                                            15

SEQ ID NO: 27             moltype = DNA   length = 14
FEATURE                   Location/Qualifiers
misc_feature              1..14
                          note = oligonucleotide sequence motif
source                    1..14
                          mol_type = other DNA
                          organism = synthetic construct
SEQUENCE: 27
aggtgaagcg aagt                                                             14

SEQ ID NO: 28             moltype = DNA   length = 14
FEATURE                   Location/Qualifiers
misc_feature              1..14
                          note = oligonucleotide sequence motif
source                    1..14
                          mol_type = other DNA
                          organism = synthetic construct
SEQUENCE: 28
cagaggtgaa gcga                                                             14

SEQ ID NO: 29             moltype = DNA   length = 14
FEATURE                   Location/Qualifiers
misc_feature              1..14
                          note = oligonucleotide sequence motif
source                    1..14
                          mol_type = other DNA
                          organism = synthetic construct
SEQUENCE: 29
aaaacccgc ctgt                                                              14

SEQ ID NO: 30             moltype = DNA   length = 13
FEATURE                   Location/Qualifiers
misc_feature              1..13
                          note = oligonucleotide sequence motif
source                    1..13
                          mol_type = other DNA
                          organism = synthetic construct
SEQUENCE: 30
aaaacccgc ctg                                                               13

SEQ ID NO: 31             moltype = DNA   length = 15
FEATURE                   Location/Qualifiers
```

```
                    misc_feature     1..15
                                     note = oligonucleotide sequence motif
                    source           1..15
                                     mol_type = other DNA
                                     organism = synthetic construct
SEQUENCE: 31
acgagtctag actct                                                            15

SEQ ID NO: 32       moltype = DNA  length = 16
FEATURE             Location/Qualifiers
misc_feature        1..16
                    note = oligonucleotide sequence motif
source              1..16
                    mol_type = other DNA
                    organism = synthetic construct
SEQUENCE: 32
cacgagtcta gactct                                                           16

SEQ ID NO: 33       moltype = DNA  length = 14
FEATURE             Location/Qualifiers
misc_feature        1..14
                    note = oligonucleotide sequence motif
source              1..14
                    mol_type = other DNA
                    organism = synthetic construct
SEQUENCE: 33
acgagtctag actc                                                             14

SEQ ID NO: 34       moltype = DNA  length = 15
FEATURE             Location/Qualifiers
misc_feature        1..15
                    note = oligonucleotide sequence motif
source              1..15
                    mol_type = other DNA
                    organism = synthetic construct
SEQUENCE: 34
cacgagtcta gactc                                                            15

SEQ ID NO: 35       moltype = DNA  length = 16
FEATURE             Location/Qualifiers
misc_feature        1..16
                    note = oligonucleotide sequence motif
source              1..16
                    mol_type = other DNA
                    organism = synthetic construct
SEQUENCE: 35
ccacgagtct agactc                                                           16

SEQ ID NO: 36       moltype = DNA  length = 13
FEATURE             Location/Qualifiers
misc_feature        1..13
                    note = oligonucleotide sequence motif
source              1..13
                    mol_type = other DNA
                    organism = synthetic construct
SEQUENCE: 36
acgagtctag act                                                              13

SEQ ID NO: 37       moltype = DNA  length = 14
FEATURE             Location/Qualifiers
misc_feature        1..14
                    note = oligonucleotide sequence motif
source              1..14
                    mol_type = other DNA
                    organism = synthetic construct
SEQUENCE: 37
cacgagtcta gact                                                             14

SEQ ID NO: 38       moltype = DNA  length = 15
FEATURE             Location/Qualifiers
misc_feature        1..15
                    note = oligonucleotide sequence motif
source              1..15
                    mol_type = other DNA
                    organism = synthetic construct
SEQUENCE: 38
ccacgagtct agact                                                            15

SEQ ID NO: 39       moltype = DNA  length = 16
```

-continued

```
FEATURE                 Location/Qualifiers
misc_feature            1..16
                        note = oligonucleotide sequence motif
source                  1..16
                        mol_type = other DNA
                        organism = synthetic construct SEQUENCE: 39
accacgagtc tagact                                                       16

SEQ ID NO: 40           moltype = DNA   length = 12
FEATURE                 Location/Qualifiers
misc_feature            1..12
                        note = oligonucleotide sequence motif
source                  1..12
                        mol_type = other DNA
                        organism = synthetic construct SEQUENCE: 40
acgagtctag ac                                                           12

SEQ ID NO: 41           moltype = DNA   length = 13
FEATURE                 Location/Qualifiers
misc_feature            1..13
                        note = oligonucleotide sequence motif
source                  1..13
                        mol_type = other DNA
                        organism = synthetic construct SEQUENCE: 41
cacgagtcta gac                                                          13

SEQ ID NO: 42           moltype = DNA   length = 14
FEATURE                 Location/Qualifiers
misc_feature            1..14
                        note = oligonucleotide sequence motif
source                  1..14
                        mol_type = other DNA
                        organism = synthetic construct SEQUENCE: 42
ccacgagtct agac                                                         14

SEQ ID NO: 43           moltype = DNA   length = 15
FEATURE                 Location/Qualifiers
misc_feature            1..15
                        note = oligonucleotide sequence motif
source                  1..15
                        mol_type = other DNA
                        organism = synthetic construct SEQUENCE: 43
accacgagtc tagac                                                        15

SEQ ID NO: 44           moltype = DNA   length = 16
FEATURE                 Location/Qualifiers
misc_feature            1..16
                        note = oligonucleotide sequence motif
source                  1..16
                        mol_type = other DNA
                        organism = synthetic construct SEQUENCE: 44
caccacgagt ctagac                                                       16

SEQ ID NO: 45           moltype = DNA   length = 14
FEATURE                 Location/Qualifiers
misc_feature            1..14
                        note = oligonucleotide sequence motif
source                  1..14
                        mol_type = other DNA
                        organism = synthetic construct SEQUENCE: 45
accacgagtc taga                                                         14

SEQ ID NO: 46           moltype = DNA   length = 15
FEATURE                 Location/Qualifiers
misc_feature            1..15
                        note = oligonucleotide sequence motif
source                  1..15
                        mol_type = other DNA
                        organism = synthetic construct SEQUENCE: 46
caccacgagt ctaga                                                        15
```

```
SEQ ID NO: 47            moltype = DNA  length = 16
FEATURE                  Location/Qualifiers
misc_feature             1..16
                         note = oligonucleotide sequence motif
source                   1..16
                         mol_type = other DNA
                         organism = synthetic construct
SEQUENCE: 47
ccaccacgag tctaga                                                          16

SEQ ID NO: 48            moltype = DNA  length = 15
FEATURE                  Location/Qualifiers
misc_feature             1..15
                         note = oligonucleotide sequence motif
source                   1..15
                         mol_type = other DNA
                         organism = synthetic construct
SEQUENCE: 48
ccaccacgag tctag                                                           15

SEQ ID NO: 49            moltype = DNA  length = 16
FEATURE                  Location/Qualifiers
misc_feature             1..16
                         note = oligonucleotide sequence motif
source                   1..16
                         mol_type = other DNA
                         organism = synthetic construct
SEQUENCE: 49
tccaccacga gtctag                                                          16

SEQ ID NO: 50            moltype = DNA  length = 14
FEATURE                  Location/Qualifiers
misc_feature             1..14
                         note = oligonucleotide sequence motif
source                   1..14
                         mol_type = other DNA
                         organism = synthetic construct
SEQUENCE: 50
ccaccacgag tcta                                                            14

SEQ ID NO: 51            moltype = DNA  length = 15
FEATURE                  Location/Qualifiers
misc_feature             1..15
                         note = oligonucleotide sequence motif
source                   1..15
                         mol_type = other DNA
                         organism = synthetic construct
SEQUENCE: 51
tccaccacga gtcta                                                           15

SEQ ID NO: 52            moltype = DNA  length = 16
FEATURE                  Location/Qualifiers
misc_feature             1..16
                         note = oligonucleotide sequence motif
source                   1..16
                         mol_type = other DNA
                         organism = synthetic construct
SEQUENCE: 52
gtccaccacg agtcta                                                          16

SEQ ID NO: 53            moltype = DNA  length = 14
FEATURE                  Location/Qualifiers
misc_feature             1..14
                         note = oligonucleotide sequence motif
source                   1..14
                         mol_type = other DNA
                         organism = synthetic construct
SEQUENCE: 53
tccaccacga gtct                                                            14

SEQ ID NO: 54            moltype = DNA  length = 15
FEATURE                  Location/Qualifiers
misc_feature             1..15
                         note = oligonucleotide sequence motif
source                   1..15
                         mol_type = other DNA
                         organism = synthetic construct
SEQUENCE: 54
gtccaccacg agtct                                                           15
```

```
SEQ ID NO: 55              moltype = DNA  length = 16
FEATURE                    Location/Qualifiers
misc_feature               1..16
                           note = oligonucleotide sequence motif
source                     1..16
                           mol_type = other DNA
                           organism = synthetic construct
SEQUENCE: 55
agtccaccac gagtct                                                         16

SEQ ID NO: 56              moltype = DNA  length = 14
FEATURE                    Location/Qualifiers
misc_feature               1..14
                           note = oligonucleotide sequence motif
source                     1..14
                           mol_type = other DNA
                           organism = synthetic construct
SEQUENCE: 56
gtccaccacg agtc                                                           14

SEQ ID NO: 57              moltype = DNA  length = 15
FEATURE                    Location/Qualifiers
misc_feature               1..15
                           note = oligonucleotide sequence motif
source                     1..15
                           mol_type = other DNA
                           organism = synthetic construct
SEQUENCE: 57
agtccaccac gagtc                                                          15

SEQ ID NO: 58              moltype = DNA  length = 16
FEATURE                    Location/Qualifiers
misc_feature               1..16
                           note = oligonucleotide sequence motif
source                     1..16
                           mol_type = other DNA
                           organism = synthetic construct
SEQUENCE: 58
aagtccacca cgagtc                                                         16

SEQ ID NO: 59              moltype = DNA  length = 14
FEATURE                    Location/Qualifiers
misc_feature               1..14
                           note = oligonucleotide sequence motif
source                     1..14
                           mol_type = other DNA
                           organism = synthetic construct
SEQUENCE: 59
agtccaccac gagt                                                           14

SEQ ID NO: 60              moltype = DNA  length = 15
FEATURE                    Location/Qualifiers
misc_feature               1..15
                           note = oligonucleotide sequence motif
source                     1..15
                           mol_type = other DNA
                           organism = synthetic construct
SEQUENCE: 60
aagtccacca cgagt                                                          15

SEQ ID NO: 61              moltype = DNA  length = 16
FEATURE                    Location/Qualifiers
misc_feature               1..16
                           note = oligonucleotide sequence motif
source                     1..16
                           mol_type = other DNA
                           organism = synthetic construct
SEQUENCE: 61
gaagtccacc acgagt                                                         16

SEQ ID NO: 62              moltype = DNA  length = 14
FEATURE                    Location/Qualifiers
misc_feature               1..14
                           note = oligonucleotide sequence motif
source                     1..14
                           mol_type = other DNA
                           organism = synthetic construct
SEQUENCE: 62
```

```
aagtccacca cgag                                                          14

SEQ ID NO: 63          moltype = DNA  length = 15
FEATURE                Location/Qualifiers
misc_feature           1..15
                       note = oligonucleotide sequence motif
source                 1..15
                       mol_type = other DNA
                       organism = synthetic construct
SEQUENCE: 63
gaagtccacc acgag                                                         15

SEQ ID NO: 64          moltype = DNA  length = 16
FEATURE                Location/Qualifiers
misc_feature           1..16
                       note = oligonucleotide sequence motif
source                 1..16
                       mol_type = other DNA
                       organism = synthetic construct
SEQUENCE: 64
agaagtccac cacgag                                                        16

SEQ ID NO: 65          moltype = DNA  length = 15
FEATURE                Location/Qualifiers
misc_feature           1..15
                       note = oligonucleotide sequence motif
source                 1..15
                       mol_type = other DNA
                       organism = synthetic construct
SEQUENCE: 65
agaagtccac cacga                                                         15

SEQ ID NO: 66          moltype = DNA  length = 16
FEATURE                Location/Qualifiers
misc_feature           1..16
                       note = oligonucleotide sequence motif
source                 1..16
                       mol_type = other DNA
                       organism = synthetic construct
SEQUENCE: 66
gagaagtcca ccacga                                                        16

SEQ ID NO: 67          moltype = DNA  length = 15
FEATURE                Location/Qualifiers
misc_feature           1..15
                       note = oligonucleotide sequence motif
source                 1..15
                       mol_type = other DNA
                       organism = synthetic construct
SEQUENCE: 67
gagaagtcca ccacg                                                         15

SEQ ID NO: 68          moltype = DNA  length = 16
FEATURE                Location/Qualifiers
misc_feature           1..16
                       note = oligonucleotide sequence motif
source                 1..16
                       mol_type = other DNA
                       organism = synthetic construct
SEQUENCE: 68
agagaagtcc accacg                                                        16

SEQ ID NO: 69          moltype = DNA  length = 16
FEATURE                Location/Qualifiers
misc_feature           1..16
                       note = oligonucleotide sequence motif
source                 1..16
                       mol_type = other DNA
                       organism = synthetic construct
SEQUENCE: 69
gagagaagtc caccac                                                        16

SEQ ID NO: 70          moltype = DNA  length = 15
FEATURE                Location/Qualifiers
misc_feature           1..15
                       note = oligonucleotide sequence motif
source                 1..15
                       mol_type = other DNA
                       organism = synthetic construct
```

```
SEQUENCE: 70
gagagaagtc cacca                                                          15

SEQ ID NO: 71           moltype = DNA  length = 16
FEATURE                 Location/Qualifiers
misc_feature            1..16
                        note = oligonucleotide sequence motif
source                  1..16
                        mol_type = other DNA
                        organism = synthetic construct
SEQUENCE: 71
tgagagaagt ccacca                                                         16

SEQ ID NO: 72           moltype = DNA  length = 14
FEATURE                 Location/Qualifiers
misc_feature            1..14
                        note = oligonucleotide sequence motif
source                  1..14
                        mol_type = other DNA
                        organism = synthetic construct
SEQUENCE: 72
gagagaagtc cacc                                                           14

SEQ ID NO: 73           moltype = DNA  length = 15
FEATURE                 Location/Qualifiers
misc_feature            1..15
                        note = oligonucleotide sequence motif
source                  1..15
                        mol_type = other DNA
                        organism = synthetic construct
SEQUENCE: 73
tgagagaagt ccacc                                                          15

SEQ ID NO: 74           moltype = DNA  length = 14
FEATURE                 Location/Qualifiers
misc_feature            1..14
                        note = oligonucleotide sequence motif
source                  1..14
                        mol_type = other DNA
                        organism = synthetic construct
SEQUENCE: 74
tgagagaagt ccac                                                           14

SEQ ID NO: 75           moltype = DNA  length = 13
FEATURE                 Location/Qualifiers
misc_feature            1..13
                        note = oligonucleotide sequence motif
source                  1..13
                        mol_type = other DNA
                        organism = synthetic construct
SEQUENCE: 75
aaaacgccgc aga                                                            13

SEQ ID NO: 76           moltype = DNA  length = 14
FEATURE                 Location/Qualifiers
misc_feature            1..14
                        note = oligonucleotide sequence motif
source                  1..14
                        mol_type = other DNA
                        organism = synthetic construct
SEQUENCE: 76
taaaacgccg caga                                                           14

SEQ ID NO: 77           moltype = DNA  length = 15
FEATURE                 Location/Qualifiers
misc_feature            1..15
                        note = oligonucleotide sequence motif
source                  1..15
                        mol_type = other DNA
                        organism = synthetic construct
SEQUENCE: 77
ataaaacgcc gcaga                                                          15

SEQ ID NO: 78           moltype = DNA  length = 16
FEATURE                 Location/Qualifiers
misc_feature            1..16
                        note = oligonucleotide sequence motif
source                  1..16
                        mol_type = other DNA
```

```
                            organism = synthetic construct
SEQUENCE: 78
gataaaacgc cgcaga                                                           16

SEQ ID NO: 79           moltype = DNA   length = 14
FEATURE                 Location/Qualifiers
misc_feature            1..14
                        note = oligonucleotide sequence motif
source                  1..14
                        mol_type = other DNA
                        organism = synthetic construct
SEQUENCE: 79
ataaaacgcc gcag                                                             14

SEQ ID NO: 80           moltype = DNA   length = 15
FEATURE                 Location/Qualifiers
misc_feature            1..15
                        note = oligonucleotide sequence motif
source                  1..15
                        mol_type = other DNA
                        organism = synthetic construct
SEQUENCE: 80
gataaaacgc cgcag                                                            15

SEQ ID NO: 81           moltype = DNA   length = 16
FEATURE                 Location/Qualifiers
misc_feature            1..16
                        note = oligonucleotide sequence motif
source                  1..16
                        mol_type = other DNA
                        organism = synthetic construct
SEQUENCE: 81
tgataaaacg ccgcag                                                           16

SEQ ID NO: 82           moltype = DNA   length = 13
FEATURE                 Location/Qualifiers
misc_feature            1..13
                        note = oligonucleotide sequence motif
source                  1..13
                        mol_type = other DNA
                        organism = synthetic construct
SEQUENCE: 82
ataaaacgcc gca                                                              13

SEQ ID NO: 83           moltype = DNA   length = 14
FEATURE                 Location/Qualifiers
misc_feature            1..14
                        note = oligonucleotide sequence motif
source                  1..14
                        mol_type = other DNA
                        organism = synthetic construct
SEQUENCE: 83
gataaaacgc cgca                                                             14

SEQ ID NO: 84           moltype = DNA   length = 15
FEATURE                 Location/Qualifiers
misc_feature            1..15
                        note = oligonucleotide sequence motif
source                  1..15
                        mol_type = other DNA
                        organism = synthetic construct
SEQUENCE: 84
tgataaaacg ccgca                                                            15

SEQ ID NO: 85           moltype = DNA   length = 16
FEATURE                 Location/Qualifiers
misc_feature            1..16
                        note = oligonucleotide sequence motif
source                  1..16
                        mol_type = other DNA
                        organism = synthetic construct
SEQUENCE: 85
atgataaaac gccgca                                                           16

SEQ ID NO: 86           moltype = DNA   length = 12
FEATURE                 Location/Qualifiers
misc_feature            1..12
                        note = oligonucleotide sequence motif
source                  1..12
```

```
                        mol_type = other DNA
                        organism = synthetic construct
SEQUENCE: 86
ataaaacgcc gc                                                          12

SEQ ID NO: 87           moltype = DNA   length = 13
FEATURE                 Location/Qualifiers
misc_feature            1..13
                        note = oligonucleotide sequence motif
source                  1..13
                        mol_type = other DNA
                        organism = synthetic construct
SEQUENCE: 87
gataaaacgc cgc                                                         13

SEQ ID NO: 88           moltype = DNA   length = 14
FEATURE                 Location/Qualifiers
misc_feature            1..14
                        note = oligonucleotide sequence motif
source                  1..14
                        mol_type = other DNA
                        organism = synthetic construct
SEQUENCE: 88
tgataaaacg ccgc                                                        14

SEQ ID NO: 89           moltype = DNA   length = 15
FEATURE                 Location/Qualifiers
misc_feature            1..15
                        note = oligonucleotide sequence motif
source                  1..15
                        mol_type = other DNA
                        organism = synthetic construct
SEQUENCE: 89
atgataaaac gccgc                                                       15

SEQ ID NO: 90           moltype = DNA   length = 12
FEATURE                 Location/Qualifiers
misc_feature            1..12
                        note = oligonucleotide sequence motif
source                  1..12
                        mol_type = other DNA
                        organism = synthetic construct
SEQUENCE: 90
gataaaacgc cg                                                          12

SEQ ID NO: 91           moltype = DNA   length = 13
FEATURE                 Location/Qualifiers
misc_feature            1..13
                        note = oligonucleotide sequence motif
source                  1..13
                        mol_type = other DNA
                        organism = synthetic construct
SEQUENCE: 91
tgataaaacg ccg                                                         13

SEQ ID NO: 92           moltype = DNA   length = 14
FEATURE                 Location/Qualifiers
misc_feature            1..14
                        note = oligonucleotide sequence motif
source                  1..14
                        mol_type = other DNA
                        organism = synthetic construct
SEQUENCE: 92
atgataaaac gccg                                                        14

SEQ ID NO: 93           moltype = DNA   length = 12
FEATURE                 Location/Qualifiers
misc_feature            1..12
                        note = oligonucleotide sequence motif
source                  1..12
                        mol_type = other DNA
                        organism = synthetic construct
SEQUENCE: 93
tgataaaacg cc                                                          12

SEQ ID NO: 94           moltype = DNA   length = 13
FEATURE                 Location/Qualifiers
misc_feature            1..13
                        note = oligonucleotide sequence motif
```

```
source                    1..13
                          mol_type = other DNA
                          organism = synthetic construct
SEQUENCE: 94
atgataaaac gcc                                                              13

SEQ ID NO: 95             moltype = DNA   length = 12
FEATURE                   Location/Qualifiers
misc_feature              1..12
                          note = oligonucleotide sequence motif
source                    1..12
                          mol_type = other DNA
                          organism = synthetic construct
SEQUENCE: 95
atgataaaac gc                                                               12

SEQ ID NO: 96             moltype = DNA   length = 13
FEATURE                   Location/Qualifiers
misc_feature              1..13
                          note = oligonucleotide sequence motif
source                    1..13
                          mol_type = other DNA
                          organism = synthetic construct
SEQUENCE: 96
tagcagcagg atg                                                              13

SEQ ID NO: 97             moltype = DNA   length = 14
FEATURE                   Location/Qualifiers
misc_feature              1..14
                          note = oligonucleotide sequence motif
source                    1..14
                          mol_type = other DNA
                          organism = synthetic construct
SEQUENCE: 97
atagcagcag gatg                                                             14

SEQ ID NO: 98             moltype = DNA   length = 15
FEATURE                   Location/Qualifiers
misc_feature              1..15
                          note = oligonucleotide sequence motif
source                    1..15
                          mol_type = other DNA
                          organism = synthetic construct
SEQUENCE: 98
catagcagca ggatg                                                            15

SEQ ID NO: 99             moltype = DNA   length = 16
FEATURE                   Location/Qualifiers
misc_feature              1..16
                          note = oligonucleotide sequence motif
source                    1..16
                          mol_type = other DNA
                          organism = synthetic construct
SEQUENCE: 99
gcatagcagc aggatg                                                           16

SEQ ID NO: 100            moltype = DNA   length = 15
FEATURE                   Location/Qualifiers
misc_feature              1..15
                          note = oligonucleotide sequence motif
source                    1..15
                          mol_type = other DNA
                          organism = synthetic construct
SEQUENCE: 100
gcatagcagc aggat                                                            15

SEQ ID NO: 101            moltype = DNA   length = 16
FEATURE                   Location/Qualifiers
misc_feature              1..16
                          note = oligonucleotide sequence motif
source                    1..16
                          mol_type = other DNA
                          organism = synthetic construct
SEQUENCE: 101
ggcatagcag caggat                                                           16

SEQ ID NO: 102            moltype = DNA   length = 16
FEATURE                   Location/Qualifiers
misc_feature              1..16
```

```
                        note = oligonucleotide sequence motif
source                  1..16
                        mol_type = other DNA
                        organism = synthetic construct
SEQUENCE: 102
gaggcatagc agcagg                                                       16

SEQ ID NO: 103          moltype = DNA  length = 16
FEATURE                 Location/Qualifiers
misc_feature            1..16
                        note = oligonucleotide sequence motif
source                  1..16
                        mol_type = other DNA
                        organism = synthetic construct
SEQUENCE: 103
tgaggcatag cagcag                                                       16

SEQ ID NO: 104          moltype = DNA  length = 15
FEATURE                 Location/Qualifiers
misc_feature            1..15
                        note = oligonucleotide sequence motif
source                  1..15
                        mol_type = other DNA
                        organism = synthetic construct
SEQUENCE: 104
tgaggcatag cagca                                                        15

SEQ ID NO: 105          moltype = DNA  length = 16
FEATURE                 Location/Qualifiers
misc_feature            1..16
                        note = oligonucleotide sequence motif
source                  1..16
                        mol_type = other DNA
                        organism = synthetic construct
SEQUENCE: 105
atgaggcata gcagca                                                       16

SEQ ID NO: 106          moltype = DNA  length = 14
FEATURE                 Location/Qualifiers
misc_feature            1..14
                        note = oligonucleotide sequence motif
source                  1..14
                        mol_type = other DNA
                        organism = synthetic construct
SEQUENCE: 106
tgaggcatag cagc                                                         14

SEQ ID NO: 107          moltype = DNA  length = 15
FEATURE                 Location/Qualifiers
misc_feature            1..15
                        note = oligonucleotide sequence motif
source                  1..15
                        mol_type = other DNA
                        organism = synthetic construct
SEQUENCE: 107
atgaggcata gcagc                                                        15

SEQ ID NO: 108          moltype = DNA  length = 16
FEATURE                 Location/Qualifiers
misc_feature            1..16
                        note = oligonucleotide sequence motif
source                  1..16
                        mol_type = other DNA
                        organism = synthetic construct
SEQUENCE: 108
gatgaggcat agcagc                                                       16

SEQ ID NO: 109          moltype = DNA  length = 15
FEATURE                 Location/Qualifiers
misc_feature            1..15
                        note = oligonucleotide sequence motif
source                  1..15
                        mol_type = other DNA
                        organism = synthetic construct
SEQUENCE: 109
gatgaggcat agcag                                                        15

SEQ ID NO: 110          moltype = DNA  length = 16
FEATURE                 Location/Qualifiers
```

```
misc_feature          1..16
                      note = oligonucleotide sequence motif
source                1..16
                      mol_type = other DNA
                      organism = synthetic construct
SEQUENCE: 110
agatgaggca tagcag                                                      16

SEQ ID NO: 111        moltype = DNA  length = 14
FEATURE               Location/Qualifiers
misc_feature          1..14
                      note = oligonucleotide sequence motif
source                1..14
                      mol_type = other DNA
                      organism = synthetic construct
SEQUENCE: 111
gatgaggcat agca                                                        14

SEQ ID NO: 112        moltype = DNA  length = 15
FEATURE               Location/Qualifiers
misc_feature          1..15
                      note = oligonucleotide sequence motif
source                1..15
                      mol_type = other DNA
                      organism = synthetic construct
SEQUENCE: 112
agatgaggca tagca                                                       15

SEQ ID NO: 113        moltype = DNA  length = 16
FEATURE               Location/Qualifiers
misc_feature          1..16
                      note = oligonucleotide sequence motif
source                1..16
                      mol_type = other DNA
                      organism = synthetic construct
SEQUENCE: 113
aagatgaggc atagca                                                      16

SEQ ID NO: 114        moltype = DNA  length = 16
FEATURE               Location/Qualifiers
misc_feature          1..16
                      note = oligonucleotide sequence motif
source                1..16
                      mol_type = other DNA
                      organism = synthetic construct
SEQUENCE: 114
aagaagatga ggcata                                                      16

SEQ ID NO: 115        moltype = DNA  length = 15
FEATURE               Location/Qualifiers
misc_feature          1..15
                      note = oligonucleotide sequence motif
source                1..15
                      mol_type = other DNA
                      organism = synthetic construct
SEQUENCE: 115
aagaagatga ggcat                                                       15

SEQ ID NO: 116        moltype = DNA  length = 15
FEATURE               Location/Qualifiers
misc_feature          1..15
                      note = oligonucleotide sequence motif
source                1..15
                      mol_type = other DNA
                      organism = synthetic construct
SEQUENCE: 116
tgggatggga ataca                                                       15

SEQ ID NO: 117        moltype = DNA  length = 16
FEATURE               Location/Qualifiers
misc_feature          1..16
                      note = oligonucleotide sequence motif
source                1..16
                      mol_type = other DNA
                      organism = synthetic construct
SEQUENCE: 117
atgggatggg aataca                                                      16

SEQ ID NO: 118        moltype = DNA  length = 14
```

```
                           -continued

FEATURE              Location/Qualifiers
misc_feature         1..14
                     note = oligonucleotide sequence motif
source               1..14
                     mol_type = other DNA
                     organism = synthetic construct
SEQUENCE: 118
tgggatggga atac                                                     14

SEQ ID NO: 119       moltype = DNA   length = 15
FEATURE              Location/Qualifiers
misc_feature         1..15
                     note = oligonucleotide sequence motif
source               1..15
                     mol_type = other DNA
                     organism = synthetic construct
SEQUENCE: 119
atgggatggg aatac                                                    15

SEQ ID NO: 120       moltype = DNA   length = 16
FEATURE              Location/Qualifiers
misc_feature         1..16
                     note = oligonucleotide sequence motif
source               1..16
                     mol_type = other DNA
                     organism = synthetic construct
SEQUENCE: 120
gatgggatgg gaatac                                                   16

SEQ ID NO: 121       moltype = DNA   length = 14
FEATURE              Location/Qualifiers
misc_feature         1..14
                     note = oligonucleotide sequence motif
source               1..14
                     mol_type = other DNA
                     organism = synthetic construct
SEQUENCE: 121
atgggatggg aata                                                     14

SEQ ID NO: 122       moltype = DNA   length = 15
FEATURE              Location/Qualifiers
misc_feature         1..15
                     note = oligonucleotide sequence motif
source               1..15
                     mol_type = other DNA
                     organism = synthetic construct
SEQUENCE: 122
gatgggatgg gaata                                                    15

SEQ ID NO: 123       moltype = DNA   length = 14
FEATURE              Location/Qualifiers
misc_feature         1..14
                     note = oligonucleotide sequence motif
source               1..14
                     mol_type = other DNA
                     organism = synthetic construct
SEQUENCE: 123
gatgggatgg gaat                                                     14

SEQ ID NO: 124       moltype = DNA   length = 14
FEATURE              Location/Qualifiers
misc_feature         1..14
                     note = oligonucleotide sequence motif
source               1..14
                     mol_type = other DNA
                     organism = synthetic construct
SEQUENCE: 124
aaccactgaa caaa                                                     14

SEQ ID NO: 125       moltype = DNA   length = 12
FEATURE              Location/Qualifiers
misc_feature         1..12
                     note = oligonucleotide sequence motif
source               1..12
                     mol_type = other DNA
                     organism = synthetic construct
SEQUENCE: 125
cgaaccactg aa                                                       12
```

```
SEQ ID NO: 126         moltype = DNA   length = 13
FEATURE                Location/Qualifiers
misc_feature           1..13
                       note = oligonucleotide sequence motif
source                 1..13
                       mol_type = other DNA
                       organism = synthetic construct
SEQUENCE: 126
gggggaaagc cct                                                         13

SEQ ID NO: 127         moltype = DNA   length = 14
FEATURE                Location/Qualifiers
misc_feature           1..14
                       note = oligonucleotide sequence motif
source                 1..14
                       mol_type = other DNA
                       organism = synthetic construct
SEQUENCE: 127
tgggggaaag ccct                                                        14

SEQ ID NO: 128         moltype = DNA   length = 15
FEATURE                Location/Qualifiers
misc_feature           1..15
                       note = oligonucleotide sequence motif
source                 1..15
                       mol_type = other DNA
                       organism = synthetic construct
SEQUENCE: 128
gcaacggggt aaagg                                                       15

SEQ ID NO: 129         moltype = DNA   length = 14
FEATURE                Location/Qualifiers
misc_feature           1..14
                       note = oligonucleotide sequence motif
source                 1..14
                       mol_type = other DNA
                       organism = synthetic construct
SEQUENCE: 129
gcaacggggt aaag                                                        14

SEQ ID NO: 130         moltype = DNA   length = 13
FEATURE                Location/Qualifiers
misc_feature           1..13
                       note = oligonucleotide sequence motif
source                 1..13
                       mol_type = other DNA
                       organism = synthetic construct
SEQUENCE: 130
gcaacggggt aaa                                                         13

SEQ ID NO: 131         moltype = DNA   length = 15
FEATURE                Location/Qualifiers
misc_feature           1..15
                       note = oligonucleotide sequence motif
source                 1..15
                       mol_type = other DNA
                       organism = synthetic construct
SEQUENCE: 131
agcaaacact tggca                                                       15

SEQ ID NO: 132         moltype = DNA   length = 16
FEATURE                Location/Qualifiers
misc_feature           1..16
                       note = oligonucleotide sequence motif
source                 1..16
                       mol_type = other DNA
                       organism = synthetic construct
SEQUENCE: 132
cagcaaacac ttggca                                                      16

SEQ ID NO: 133         moltype = DNA   length = 15
FEATURE                Location/Qualifiers
misc_feature           1..15
                       note = oligonucleotide sequence motif
source                 1..15
                       mol_type = other DNA
                       organism = synthetic construct
SEQUENCE: 133
cagcaaacac ttggc                                                       15
```

| | | |
|---|---|---|
| SEQ ID NO: 134<br>FEATURE<br>misc_feature<br>source | moltype = DNA  length = 16<br>Location/Qualifiers<br>1..16<br>note = oligonucleotide sequence motif<br>1..16<br>mol_type = other DNA<br>organism = synthetic construct | |
| SEQUENCE: 134<br>tcagcaaaca cttggc | | 16 |
| SEQ ID NO: 135<br>FEATURE<br>misc_feature<br>source | moltype = DNA  length = 15<br>Location/Qualifiers<br>1..15<br>note = oligonucleotide sequence motif<br>1..15<br>mol_type = other DNA<br>organism = synthetic construct | |
| SEQUENCE: 135<br>tcagcaaaca cttgg | | 15 |
| SEQ ID NO: 136<br>FEATURE<br>misc_feature<br>source | moltype = DNA  length = 13<br>Location/Qualifiers<br>1..13<br>note = oligonucleotide sequence motif<br>1..13<br>mol_type = other DNA<br>organism = synthetic construct | |
| SEQUENCE: 136<br>gcagtatgga tcg | | 13 |
| SEQ ID NO: 137<br>FEATURE<br>misc_feature<br>source | moltype = DNA  length = 14<br>Location/Qualifiers<br>1..14<br>note = oligonucleotide sequence motif<br>1..14<br>mol_type = other DNA<br>organism = synthetic construct | |
| SEQUENCE: 137<br>cgcagtatgg atcg | | 14 |
| SEQ ID NO: 138<br>FEATURE<br>misc_feature<br>source | moltype = DNA  length = 16<br>Location/Qualifiers<br>1..16<br>note = oligonucleotide sequence motif<br>1..16<br>mol_type = other DNA<br>organism = synthetic construct | |
| SEQUENCE: 138<br>tccgcagtat ggatcg | | 16 |
| SEQ ID NO: 139<br>FEATURE<br>misc_feature<br>source | moltype = DNA  length = 14<br>Location/Qualifiers<br>1..14<br>note = oligonucleotide sequence motif<br>1..14<br>mol_type = other DNA<br>organism = synthetic construct | |
| SEQUENCE: 139<br>ccgcagtatg gatc | | 14 |
| SEQ ID NO: 140<br>FEATURE<br>misc_feature<br>source | moltype = DNA  length = 15<br>Location/Qualifiers<br>1..15<br>note = oligonucleotide sequence motif<br>1..15<br>mol_type = other DNA<br>organism = synthetic construct | |
| SEQUENCE: 140<br>tccgcagtat ggatc | | 15 |
| SEQ ID NO: 141<br>FEATURE<br>misc_feature<br>source | moltype = DNA  length = 12<br>Location/Qualifiers<br>1..12<br>note = oligonucleotide sequence motif<br>1..12<br>mol_type = other DNA<br>organism = synthetic construct | |
| SEQUENCE: 141 | | |

```
cgcagtatgg at                                                                           12

SEQ ID NO: 142          moltype = DNA   length = 13
FEATURE                 Location/Qualifiers
misc_feature            1..13
                        note = oligonucleotide sequence motif
source                  1..13
                        mol_type = other DNA
                        organism = synthetic construct SEQUENCE: 142
ccgcagtatg gat                                                                          13

SEQ ID NO: 143          moltype = DNA   length = 14
FEATURE                 Location/Qualifiers
misc_feature            1..14
                        note = oligonucleotide sequence motif
source                  1..14
                        mol_type = other DNA
                        organism = synthetic construct SEQUENCE: 143
tccgcagtat ggat                                                                         14

SEQ ID NO: 144          moltype = DNA   length = 13
FEATURE                 Location/Qualifiers
misc_feature            1..13
                        note = oligonucleotide sequence motif
source                  1..13
                        mol_type = other DNA
                        organism = synthetic construct SEQUENCE: 144
tccgcagtat gga                                                                          13

SEQ ID NO: 145          moltype = DNA   length = 12
FEATURE                 Location/Qualifiers
misc_feature            1..12
                        note = oligonucleotide sequence motif
source                  1..12
                        mol_type = other DNA
                        organism = synthetic construct SEQUENCE: 145
ttccgcagta tg                                                                           12

SEQ ID NO: 146          moltype = DNA   length = 13
FEATURE                 Location/Qualifiers
misc_feature            1..13
                        note = oligonucleotide sequence motif
source                  1..13
                        mol_type = other DNA
                        organism = synthetic construct SEQUENCE: 146
cgtaaagaga ggt                                                                          13

SEQ ID NO: 147          moltype = DNA   length = 16
FEATURE                 Location/Qualifiers
misc_feature            1..16
                        note = oligonucleotide sequence motif
source                  1..16
                        mol_type = other DNA
                        organism = synthetic construct SEQUENCE: 147
ccgcgtaaag agaggt                                                                       16

SEQ ID NO: 148          moltype = DNA   length = 12
FEATURE                 Location/Qualifiers
misc_feature            1..12
                        note = oligonucleotide sequence motif
source                  1..12
                        mol_type = other DNA
                        organism = synthetic construct SEQUENCE: 148
cgtaaagaga gg                                                                           12

SEQ ID NO: 149          moltype = DNA   length = 14
FEATURE                 Location/Qualifiers
misc_feature            1..14
                        note = oligonucleotide sequence motif
source                  1..14
                        mol_type = other DNA
                        organism = synthetic construct
```

```
SEQUENCE: 149
cgcgtaaaga gagg                                                                       14

SEQ ID NO: 150          moltype = DNA  length = 15
FEATURE                 Location/Qualifiers
misc_feature            1..15
                        note = oligonucleotide sequence motif
source                  1..15
                        mol_type = other DNA
                        organism = synthetic construct
SEQUENCE: 150
ccgcgtaaag agagg                                                                      15

SEQ ID NO: 151          moltype = DNA  length = 13
FEATURE                 Location/Qualifiers
misc_feature            1..13
                        note = oligonucleotide sequence motif
source                  1..13
                        mol_type = other DNA
                        organism = synthetic construct
SEQUENCE: 151
cgcgtaaaga gag                                                                        13

SEQ ID NO: 152          moltype = DNA  length = 14
FEATURE                 Location/Qualifiers
misc_feature            1..14
                        note = oligonucleotide sequence motif
source                  1..14
                        mol_type = other DNA
                        organism = synthetic construct
SEQUENCE: 152
ccgcgtaaag agag                                                                       14

SEQ ID NO: 153          moltype = DNA  length = 12
FEATURE                 Location/Qualifiers
misc_feature            1..12
                        note = oligonucleotide sequence motif
source                  1..12
                        mol_type = other DNA
                        organism = synthetic construct
SEQUENCE: 153
cgcgtaaaga ga                                                                         12

SEQ ID NO: 154          moltype = DNA  length = 13
FEATURE                 Location/Qualifiers
misc_feature            1..13
                        note = oligonucleotide sequence motif
source                  1..13
                        mol_type = other DNA
                        organism = synthetic construct
SEQUENCE: 154
ccgcgtaaag aga                                                                        13

SEQ ID NO: 155          moltype = DNA  length = 12
FEATURE                 Location/Qualifiers
misc_feature            1..12
                        note = oligonucleotide sequence motif
source                  1..12
                        mol_type = other DNA
                        organism = synthetic construct
SEQUENCE: 155
ccgcgtaaag ag                                                                         12

SEQ ID NO: 156          moltype = DNA  length = 15
FEATURE                 Location/Qualifiers
misc_feature            1..15
                        note = oligonucleotide sequence motif
source                  1..15
                        mol_type = other DNA
                        organism = synthetic construct
SEQUENCE: 156
ggcacagacg gggag                                                                      15

SEQ ID NO: 157          moltype = DNA  length = 16
FEATURE                 Location/Qualifiers
misc_feature            1..16
                        note = oligonucleotide sequence motif
source                  1..16
                        mol_type = other DNA
```

-continued

```
                        organism = synthetic construct
SEQUENCE: 157
aggcacagac ggggag                                                        16

SEQ ID NO: 158          moltype = DNA   length = 14
FEATURE                 Location/Qualifiers
misc_feature            1..14
                        note = oligonucleotide sequence motif
source                  1..14
                        mol_type = other DNA
                        organism = synthetic construct
SEQUENCE: 158
ggcacagacg ggga                                                          14

SEQ ID NO: 159          moltype = DNA   length = 15
FEATURE                 Location/Qualifiers
misc_feature            1..15
                        note = oligonucleotide sequence motif
source                  1..15
                        mol_type = other DNA
                        organism = synthetic construct
SEQUENCE: 159
aggcacagac ggga                                                          15

SEQ ID NO: 160          moltype = DNA   length = 16
FEATURE                 Location/Qualifiers
misc_feature            1..16
                        note = oligonucleotide sequence motif
source                  1..16
                        mol_type = other DNA
                        organism = synthetic construct
SEQUENCE: 160
aaggcacaga cgggga                                                        16

SEQ ID NO: 161          moltype = DNA   length = 14
FEATURE                 Location/Qualifiers
misc_feature            1..14
                        note = oligonucleotide sequence motif
source                  1..14
                        mol_type = other DNA
                        organism = synthetic construct
SEQUENCE: 161
aggcacagac gggg                                                          14

SEQ ID NO: 162          moltype = DNA   length = 15
FEATURE                 Location/Qualifiers
misc_feature            1..15
                        note = oligonucleotide sequence motif
source                  1..15
                        mol_type = other DNA
                        organism = synthetic construct
SEQUENCE: 162
aaggcacaga cgggg                                                         15

SEQ ID NO: 163          moltype = DNA   length = 16
FEATURE                 Location/Qualifiers
misc_feature            1..16
                        note = oligonucleotide sequence motif
source                  1..16
                        mol_type = other DNA
                        organism = synthetic construct
SEQUENCE: 163
gaaggcacag acggg                                                         16

SEQ ID NO: 164          moltype = DNA   length = 16
FEATURE                 Location/Qualifiers
misc_feature            1..16
                        note = oligonucleotide sequence motif
source                  1..16
                        mol_type = other DNA
                        organism = synthetic construct
SEQUENCE: 164
agaaggcaca gacggg                                                        16

SEQ ID NO: 165          moltype = DNA   length = 15
FEATURE                 Location/Qualifiers
misc_feature            1..15
                        note = oligonucleotide sequence motif
source                  1..15
```

```
                    mol_type = other DNA
                    organism = synthetic construct
SEQUENCE: 165
gagaaggcac agacg                                                       15

SEQ ID NO: 166      moltype = DNA   length = 14
FEATURE             Location/Qualifiers
misc_feature        1..14
                    note = oligonucleotide sequence motif
source              1..14
                    mol_type = other DNA
                    organism = synthetic construct
SEQUENCE: 166
cgaagtgcac acgg                                                        14

SEQ ID NO: 167      moltype = DNA   length = 14
FEATURE             Location/Qualifiers
misc_feature        1..14
                    note = oligonucleotide sequence motif
source              1..14
                    mol_type = other DNA
                    organism = synthetic construct
SEQUENCE: 167
gcgaagtgca cacg                                                        14

SEQ ID NO: 168      moltype = DNA   length = 13
FEATURE             Location/Qualifiers
misc_feature        1..13
                    note = oligonucleotide sequence motif
source              1..13
                    mol_type = other DNA
                    organism = synthetic construct
SEQUENCE: 168
gcgaagtgca cac                                                         13

SEQ ID NO: 169      moltype = DNA   length = 14
FEATURE             Location/Qualifiers
misc_feature        1..14
                    note = oligonucleotide sequence motif
source              1..14
                    mol_type = other DNA
                    organism = synthetic construct
SEQUENCE: 169
agcgaagtgc acac                                                        14

SEQ ID NO: 170      moltype = DNA   length = 15
FEATURE             Location/Qualifiers
misc_feature        1..15
                    note = oligonucleotide sequence motif
source              1..15
                    mol_type = other DNA
                    organism = synthetic construct
SEQUENCE: 170
aagcgaagtg cacac                                                       15

SEQ ID NO: 171      moltype = DNA   length = 16
FEATURE             Location/Qualifiers
misc_feature        1..16
                    note = oligonucleotide sequence motif
source              1..16
                    mol_type = other DNA
                    organism = synthetic construct
SEQUENCE: 171
gaagcgaagt gcacac                                                      16

SEQ ID NO: 172      moltype = DNA   length = 13
FEATURE             Location/Qualifiers
misc_feature        1..13
                    note = oligonucleotide sequence motif
source              1..13
                    mol_type = other DNA
                    organism = synthetic construct
SEQUENCE: 172
agcgaagtgc aca                                                         13

SEQ ID NO: 173      moltype = DNA   length = 14
FEATURE             Location/Qualifiers
misc_feature        1..14
                    note = oligonucleotide sequence motif
```

```
source                          1..14
                                mol_type = other DNA
                                organism = synthetic construct
SEQUENCE: 173
aagcgaagtg caca                                                         14

SEQ ID NO: 174                  moltype = DNA   length = 16
FEATURE                         Location/Qualifiers
misc_feature                    1..16
                                note = oligonucleotide sequence motif
source                          1..16
                                mol_type = other DNA
                                organism = synthetic construct
SEQUENCE: 174
tgaagcgaag tgcaca                                                       16

SEQ ID NO: 175                  moltype = DNA   length = 13
FEATURE                         Location/Qualifiers
misc_feature                    1..13
                                note = oligonucleotide sequence motif
source                          1..13
                                mol_type = other DNA
                                organism = synthetic construct
SEQUENCE: 175
aagcgaagtg cac                                                          13

SEQ ID NO: 176                  moltype = DNA   length = 14
FEATURE                         Location/Qualifiers
misc_feature                    1..14
                                note = oligonucleotide sequence motif
source                          1..14
                                mol_type = other DNA
                                organism = synthetic construct
SEQUENCE: 176
gaagcgaagt gcac                                                         14

SEQ ID NO: 177                  moltype = DNA   length = 15
FEATURE                         Location/Qualifiers
misc_feature                    1..15
                                note = oligonucleotide sequence motif
source                          1..15
                                mol_type = other DNA
                                organism = synthetic construct
SEQUENCE: 177
tgaagcgaag tgcac                                                        15

SEQ ID NO: 178                  moltype = DNA   length = 16
FEATURE                         Location/Qualifiers
misc_feature                    1..16
                                note = oligonucleotide sequence motif
source                          1..16
                                mol_type = other DNA
                                organism = synthetic construct
SEQUENCE: 178
gtgaagcgaa gtgcac                                                       16

SEQ ID NO: 179                  moltype = DNA   length = 12
FEATURE                         Location/Qualifiers
misc_feature                    1..12
                                note = oligonucleotide sequence motif
source                          1..12
                                mol_type = other DNA
                                organism = synthetic construct
SEQUENCE: 179
aagcgaagtg ca                                                           12

SEQ ID NO: 180                  moltype = DNA   length = 13
FEATURE                         Location/Qualifiers
misc_feature                    1..13
                                note = oligonucleotide sequence motif
source                          1..13
                                mol_type = other DNA
                                organism = synthetic construct
SEQUENCE: 180
gaagcgaagt gca                                                          13

SEQ ID NO: 181                  moltype = DNA   length = 14
FEATURE                         Location/Qualifiers
misc_feature                    1..14
```

```
                        note = oligonucleotide sequence motif
source                  1..14
                        mol_type = other DNA
                        organism = synthetic construct
SEQUENCE: 181
tgaagcgaag tgca                                                              14

SEQ ID NO: 182          moltype = DNA   length = 15
FEATURE                 Location/Qualifiers
misc_feature            1..15
                        note = oligonucleotide sequence motif
source                  1..15
                        mol_type = other DNA
                        organism = synthetic construct
SEQUENCE: 182
gtgaagcgaa gtgca                                                             15

SEQ ID NO: 183          moltype = DNA   length = 13
FEATURE                 Location/Qualifiers
misc_feature            1..13
                        note = oligonucleotide sequence motif
source                  1..13
                        mol_type = other DNA
                        organism = synthetic construct
SEQUENCE: 183
tgaagcgaag tgc                                                               13

SEQ ID NO: 184          moltype = DNA   length = 14
FEATURE                 Location/Qualifiers
misc_feature            1..14
                        note = oligonucleotide sequence motif
source                  1..14
                        mol_type = other DNA
                        organism = synthetic construct
SEQUENCE: 184
gtgaagcgaa gtgc                                                              14

SEQ ID NO: 185          moltype = DNA   length = 13
FEATURE                 Location/Qualifiers
misc_feature            1..13
                        note = oligonucleotide sequence motif
source                  1..13
                        mol_type = other DNA
                        organism = synthetic construct
SEQUENCE: 185
gtgaagcgaa gtg                                                               13

SEQ ID NO: 186          moltype = DNA   length = 14
FEATURE                 Location/Qualifiers
misc_feature            1..14
                        note = oligonucleotide sequence motif
source                  1..14
                        mol_type = other DNA
                        organism = synthetic construct
SEQUENCE: 186
ggtgaagcga agtg                                                              14

SEQ ID NO: 187          moltype = DNA   length = 16
FEATURE                 Location/Qualifiers
misc_feature            1..16
                        note = oligonucleotide sequence motif
source                  1..16
                        mol_type = other DNA
                        organism = synthetic construct
SEQUENCE: 187
gaggtgaagc gaagtg                                                            16

SEQ ID NO: 188          moltype = DNA   length = 12
FEATURE                 Location/Qualifiers
misc_feature            1..12
                        note = oligonucleotide sequence motif
source                  1..12
                        mol_type = other DNA
                        organism = synthetic construct
SEQUENCE: 188
gtgaagcgaa gt                                                                12

SEQ ID NO: 189          moltype = DNA   length = 13
FEATURE                 Location/Qualifiers
```

```
misc_feature            1..13
                        note = oligonucleotide sequence motif
source                  1..13
                        mol_type = other DNA
                        organism = synthetic construct
SEQUENCE: 189
ggtgaagcga agt                                                          13

SEQ ID NO: 190          moltype = DNA  length = 15
FEATURE                 Location/Qualifiers
misc_feature            1..15
                        note = oligonucleotide sequence motif
source                  1..15
                        mol_type = other DNA
                        organism = synthetic construct
SEQUENCE: 190
gaggtgaagc gaagt                                                        15

SEQ ID NO: 191          moltype = DNA  length = 16
FEATURE                 Location/Qualifiers
misc_feature            1..16
                        note = oligonucleotide sequence motif
source                  1..16
                        mol_type = other DNA
                        organism = synthetic construct
SEQUENCE: 191
agaggtgaag cgaagt                                                       16

SEQ ID NO: 192          moltype = DNA  length = 15
FEATURE                 Location/Qualifiers
misc_feature            1..15
                        note = oligonucleotide sequence motif
source                  1..15
                        mol_type = other DNA
                        organism = synthetic construct
SEQUENCE: 192
agaggtgaag cgaag                                                        15

SEQ ID NO: 193          moltype = DNA  length = 16
FEATURE                 Location/Qualifiers
misc_feature            1..16
                        note = oligonucleotide sequence motif
source                  1..16
                        mol_type = other DNA
                        organism = synthetic construct
SEQUENCE: 193
cagaggtgaa gcgaag                                                       16

SEQ ID NO: 194          moltype = DNA  length = 14
FEATURE                 Location/Qualifiers
misc_feature            1..14
                        note = oligonucleotide sequence motif
source                  1..14
                        mol_type = other DNA
                        organism = synthetic construct
SEQUENCE: 194
agaggtgaag cgaa                                                         14

SEQ ID NO: 195          moltype = DNA  length = 15
FEATURE                 Location/Qualifiers
misc_feature            1..15
                        note = oligonucleotide sequence motif
source                  1..15
                        mol_type = other DNA
                        organism = synthetic construct
SEQUENCE: 195
cagaggtgaa gcgaa                                                        15

SEQ ID NO: 196          moltype = DNA  length = 16
FEATURE                 Location/Qualifiers
misc_feature            1..16
                        note = oligonucleotide sequence motif
source                  1..16
                        mol_type = other DNA
                        organism = synthetic construct
SEQUENCE: 196
gcagaggtga agcgaa                                                       16

SEQ ID NO: 197          moltype = DNA  length = 15
```

```
                           -continued

FEATURE                 Location/Qualifiers
misc_feature            1..15
                        note = oligonucleotide sequence motif
source                  1..15
                        mol_type = other DNA
                        organism = synthetic construct SEQUENCE: 197
gcagaggtga agcga                                                        15

SEQ ID NO: 198          moltype = DNA   length = 16
FEATURE                 Location/Qualifiers
misc_feature            1..16
                        note = oligonucleotide sequence motif
source                  1..16
                        mol_type = other DNA
                        organism = synthetic construct SEQUENCE: 198
tgcagaggtg aagcga                                                       16

SEQ ID NO: 199          moltype = DNA   length = 15
FEATURE                 Location/Qualifiers
misc_feature            1..15
                        note = oligonucleotide sequence motif
source                  1..15
                        mol_type = other DNA
                        organism = synthetic construct SEQUENCE: 199
tgcagaggtg aagcg                                                        15

SEQ ID NO: 200          moltype = DNA   length = 16
FEATURE                 Location/Qualifiers
misc_feature            1..16
                        note = oligonucleotide sequence motif
source                  1..16
                        mol_type = other DNA
                        organism = synthetic construct SEQUENCE: 200
gtgcagaggt gaagcg                                                       16

SEQ ID NO: 201          moltype = DNA   length = 16
FEATURE                 Location/Qualifiers
misc_feature            1..16
                        note = oligonucleotide sequence motif
source                  1..16
                        mol_type = other DNA
                        organism = synthetic construct SEQUENCE: 201
cgtgcagagg tgaagc                                                       16

SEQ ID NO: 202          moltype = DNA   length = 15
FEATURE                 Location/Qualifiers
misc_feature            1..15
                        note = oligonucleotide sequence motif
source                  1..15
                        mol_type = other DNA
                        organism = synthetic construct SEQUENCE: 202
cgtgcagagg tgaag                                                        15

SEQ ID NO: 203          moltype = DNA   length = 16
FEATURE                 Location/Qualifiers
misc_feature            1..16
                        note = oligonucleotide sequence motif
source                  1..16
                        mol_type = other DNA
                        organism = synthetic construct SEQUENCE: 203
acgtgcagag gtgaag                                                       16

SEQ ID NO: 204          moltype = DNA   length = 14
FEATURE                 Location/Qualifiers
misc_feature            1..14
                        note = oligonucleotide sequence motif
source                  1..14
                        mol_type = other DNA
                        organism = synthetic construct SEQUENCE: 204
cgtgcagagg tgaa                                                         14
```

```
SEQ ID NO: 205           moltype = DNA  length = 15
FEATURE                  Location/Qualifiers
misc_feature             1..15
                         note = oligonucleotide sequence motif
source                   1..15
                         mol_type = other DNA
                         organism = synthetic construct
SEQUENCE: 205
acgtgcagag gtgaa                                                           15

SEQ ID NO: 206           moltype = DNA  length = 13
FEATURE                  Location/Qualifiers
misc_feature             1..13
                         note = oligonucleotide sequence motif
source                   1..13
                         mol_type = other DNA
                         organism = synthetic construct
SEQUENCE: 206
cgtgcagagg tga                                                             13

SEQ ID NO: 207           moltype = DNA  length = 14
FEATURE                  Location/Qualifiers
misc_feature             1..14
                         note = oligonucleotide sequence motif
source                   1..14
                         mol_type = other DNA
                         organism = synthetic construct
SEQUENCE: 207
acgtgcagag gtga                                                            14

SEQ ID NO: 208           moltype = DNA  length = 13
FEATURE                  Location/Qualifiers
misc_feature             1..13
                         note = oligonucleotide sequence motif
source                   1..13
                         mol_type = other DNA
                         organism = synthetic construct
SEQUENCE: 208
cgttcacggt ggt                                                             13

SEQ ID NO: 209           moltype = DNA  length = 13
FEATURE                  Location/Qualifiers
misc_feature             1..13
                         note = oligonucleotide sequence motif
source                   1..13
                         mol_type = other DNA
                         organism = synthetic construct
SEQUENCE: 209
ctcaaggtcg gtc                                                             13

SEQ ID NO: 210           moltype = DNA  length = 13
FEATURE                  Location/Qualifiers
misc_feature             1..13
                         note = oligonucleotide sequence motif
source                   1..13
                         mol_type = other DNA
                         organism = synthetic construct
SEQUENCE: 210
cctcaaggtc ggt                                                             13

SEQ ID NO: 211           moltype = DNA  length = 14
FEATURE                  Location/Qualifiers
misc_feature             1..14
                         note = oligonucleotide sequence motif
source                   1..14
                         mol_type = other DNA
                         organism = synthetic construct
SEQUENCE: 211
gcctcaaggt cggt                                                            14

SEQ ID NO: 212           moltype = DNA  length = 15
FEATURE                  Location/Qualifiers
misc_feature             1..15
                         note = oligonucleotide sequence motif
source                   1..15
                         mol_type = other DNA
                         organism = synthetic construct
SEQUENCE: 212
acagtctttg aagta                                                           15
```

```
SEQ ID NO: 213           moltype = DNA  length = 13
FEATURE                  Location/Qualifiers
misc_feature             1..13
                         note = oligonucleotide sequence motif
source                   1..13
                         mol_type = other DNA
                         organism = synthetic construct
SEQUENCE: 213
tttatgccta cag                                                              13

SEQ ID NO: 214           moltype = DNA  length = 14
FEATURE                  Location/Qualifiers
misc_feature             1..14
                         note = oligonucleotide sequence motif
source                   1..14
                         mol_type = other DNA
                         organism = synthetic construct
SEQUENCE: 214
aatttatgcc taca                                                             14

SEQ ID NO: 215           moltype = DNA  length = 13
FEATURE                  Location/Qualifiers
misc_feature             1..13
                         note = oligonucleotide sequence motif
source                   1..13
                         mol_type = other DNA
                         organism = synthetic construct
SEQUENCE: 215
aatttatgcc tac                                                              13

SEQ ID NO: 216           moltype = DNA  length = 13
FEATURE                  Location/Qualifiers
misc_feature             1..13
                         note = oligonucleotide sequence motif
source                   1..13
                         mol_type = other DNA
                         organism = synthetic construct
SEQUENCE: 216
ccaatttatg cct                                                              13

SEQ ID NO: 217           moltype = DNA  length = 15
FEATURE                  Location/Qualifiers
misc_feature             1..15
                         note = oligonucleotide sequence motif
source                   1..15
                         mol_type = other DNA
                         organism = synthetic construct
SEQUENCE: 217
gcttggaggc ttgaa                                                            15

SEQ ID NO: 218           moltype = DNA  length = 16
FEATURE                  Location/Qualifiers
misc_feature             1..16
                         note = oligonucleotide sequence motif
source                   1..16
                         mol_type = other DNA
                         organism = synthetic construct
SEQUENCE: 218
agcttggagg cttgaa                                                           16

SEQ ID NO: 219           moltype = DNA  length = 14
FEATURE                  Location/Qualifiers
misc_feature             1..14
                         note = oligonucleotide sequence motif
source                   1..14
                         mol_type = other DNA
                         organism = synthetic construct
SEQUENCE: 219
gcttggaggc ttga                                                             14

SEQ ID NO: 220           moltype = DNA  length = 15
FEATURE                  Location/Qualifiers
misc_feature             1..15
                         note = oligonucleotide sequence motif
source                   1..15
                         mol_type = other DNA
                         organism = synthetic construct
SEQUENCE: 220
```

```
agcttggagg cttga                                                          15

SEQ ID NO: 221         moltype = DNA  length = 16
FEATURE                Location/Qualifiers
misc_feature           1..16
                       note = oligonucleotide sequence motif
source                 1..16
                       mol_type = other DNA
                       organism = synthetic construct
SEQUENCE: 221
cagcttggag gcttga                                                         16

SEQ ID NO: 222         moltype = DNA  length = 13
FEATURE                Location/Qualifiers
misc_feature           1..13
                       note = oligonucleotide sequence motif
source                 1..13
                       mol_type = other DNA
                       organism = synthetic construct
SEQUENCE: 222
gcttggaggc ttg                                                            13

SEQ ID NO: 223         moltype = DNA  length = 14
FEATURE                Location/Qualifiers
misc_feature           1..14
                       note = oligonucleotide sequence motif
source                 1..14
                       mol_type = other DNA
                       organism = synthetic construct
SEQUENCE: 223
agcttggagg cttg                                                           14

SEQ ID NO: 224         moltype = DNA  length = 15
FEATURE                Location/Qualifiers
misc_feature           1..15
                       note = oligonucleotide sequence motif
source                 1..15
                       mol_type = other DNA
                       organism = synthetic construct
SEQUENCE: 224
cagcttggag gcttg                                                          15

SEQ ID NO: 225         moltype = DNA  length = 16
FEATURE                Location/Qualifiers
misc_feature           1..16
                       note = oligonucleotide sequence motif
source                 1..16
                       mol_type = other DNA
                       organism = synthetic construct
SEQUENCE: 225
acagcttgga ggcttg                                                         16

SEQ ID NO: 226         moltype = DNA  length = 16
FEATURE                Location/Qualifiers
misc_feature           1..16
                       note = oligonucleotide sequence motif
source                 1..16
                       mol_type = other DNA
                       organism = synthetic construct
SEQUENCE: 226
cacagcttgg aggctt                                                         16

SEQ ID NO: 227         moltype = DNA  length = 15
FEATURE                Location/Qualifiers
misc_feature           1..15
                       note = oligonucleotide sequence motif
source                 1..15
                       mol_type = other DNA
                       organism = synthetic construct
SEQUENCE: 227
cacagcttgg aggct                                                          15

SEQ ID NO: 228         moltype = DNA  length = 16
FEATURE                Location/Qualifiers
misc_feature           1..16
                       note = oligonucleotide sequence motif
source                 1..16
                       mol_type = other DNA
                       organism = synthetic construct
```

```
SEQUENCE: 228
gcacagcttg gaggct                                                          16

SEQ ID NO: 229          moltype = DNA  length = 15
FEATURE                 Location/Qualifiers
misc_feature            1..15
                        note = oligonucleotide sequence motif
source                  1..15
                        mol_type = other DNA
                        organism = synthetic construct
SEQUENCE: 229
gcacagcttg gaggc                                                           15

SEQ ID NO: 230          moltype = DNA  length = 16
FEATURE                 Location/Qualifiers
misc_feature            1..16
                        note = oligonucleotide sequence motif
source                  1..16
                        mol_type = other DNA
                        organism = synthetic construct
SEQUENCE: 230
ggcacagctt ggaggc                                                          16

SEQ ID NO: 231          moltype = DNA  length = 16
FEATURE                 Location/Qualifiers
misc_feature            1..16
                        note = oligonucleotide sequence motif
source                  1..16
                        mol_type = other DNA
                        organism = synthetic construct
SEQUENCE: 231
aggcacagct tggagg                                                          16

SEQ ID NO: 232          moltype = DNA  length = 15
FEATURE                 Location/Qualifiers
misc_feature            1..15
                        note = oligonucleotide sequence motif
source                  1..15
                        mol_type = other DNA
                        organism = synthetic construct
SEQUENCE: 232
aggcacagct tggag                                                           15

SEQ ID NO: 233          moltype = DNA  length = 16
FEATURE                 Location/Qualifiers
misc_feature            1..16
                        note = oligonucleotide sequence motif
source                  1..16
                        mol_type = other DNA
                        organism = synthetic construct
SEQUENCE: 233
aaggcacagc ttggag                                                          16

SEQ ID NO: 234          moltype = DNA  length = 15
FEATURE                 Location/Qualifiers
misc_feature            1..15
                        note = oligonucleotide sequence motif
source                  1..15
                        mol_type = other DNA
                        organism = synthetic construct
SEQUENCE: 234
aaggcacagc ttgga                                                           15

SEQ ID NO: 235          moltype = DNA  length = 16
FEATURE                 Location/Qualifiers
misc_feature            1..16
                        note = oligonucleotide sequence motif
source                  1..16
                        mol_type = other DNA
                        organism = synthetic construct
SEQUENCE: 235
caaggcacag cttgga                                                          16

SEQ ID NO: 236          moltype = DNA  length = 14
FEATURE                 Location/Qualifiers
misc_feature            1..14
                        note = oligonucleotide sequence motif
source                  1..14
                        mol_type = other DNA
```

```
                         organism = synthetic construct
SEQUENCE: 236
aaggcacagc ttgg                                                           14

SEQ ID NO: 237           moltype = DNA   length = 15
FEATURE                  Location/Qualifiers
misc_feature             1..15
                         note = oligonucleotide sequence motif
source                   1..15
                         mol_type = other DNA
                         organism = synthetic construct
SEQUENCE: 237
caaggcacag cttgg                                                          15

SEQ ID NO: 238           moltype = DNA   length = 16
FEATURE                  Location/Qualifiers
misc_feature             1..16
                         note = oligonucleotide sequence motif
source                   1..16
                         mol_type = other DNA
                         organism = synthetic construct
SEQUENCE: 238
ccaaggcaca gcttgg                                                         16

SEQ ID NO: 239           moltype = DNA   length = 14
FEATURE                  Location/Qualifiers
misc_feature             1..14
                         note = oligonucleotide sequence motif
source                   1..14
                         mol_type = other DNA
                         organism = synthetic construct
SEQUENCE: 239
caaggcacag cttg                                                           14

SEQ ID NO: 240           moltype = DNA   length = 15
FEATURE                  Location/Qualifiers
misc_feature             1..15
                         note = oligonucleotide sequence motif
source                   1..15
                         mol_type = other DNA
                         organism = synthetic construct
SEQUENCE: 240
ccaaggcaca gcttg                                                          15

SEQ ID NO: 241           moltype = DNA   length = 14
FEATURE                  Location/Qualifiers
misc_feature             1..14
                         note = oligonucleotide sequence motif
source                   1..14
                         mol_type = other DNA
                         organism = synthetic construct
SEQUENCE: 241
ccaaggcaca gctt                                                           14

SEQ ID NO: 242           moltype = DNA   length = 13
FEATURE                  Location/Qualifiers
misc_feature             1..13
                         note = oligonucleotide sequence motif
source                   1..13
                         mol_type = other DNA
                         organism = synthetic construct
SEQUENCE: 242
tgcgaatcca cac                                                            13

SEQ ID NO: 243           moltype = DNA   length = 14
FEATURE                  Location/Qualifiers
misc_feature             1..14
                         note = oligonucleotide sequence motif
source                   1..14
                         mol_type = other DNA
                         organism = synthetic construct
SEQUENCE: 243
gtgcgaatcc acac                                                           14

SEQ ID NO: 244           moltype = DNA   length = 15
FEATURE                  Location/Qualifiers
misc_feature             1..15
                         note = oligonucleotide sequence motif
source                   1..15
```

```
                        mol_type = other DNA
                        organism = synthetic construct
SEQUENCE: 244
ggagttcttc ttcta                                                         15

SEQ ID NO: 245          moltype = DNA   length = 16
FEATURE                 Location/Qualifiers
misc_feature            1..16
                        note = oligonucleotide sequence motif
source                  1..16
                        mol_type = other DNA
                        organism = synthetic construct
SEQUENCE: 245
gggagttctt cttcta                                                        16

SEQ ID NO: 246          moltype = DNA   length = 15
FEATURE                 Location/Qualifiers
misc_feature            1..15
                        note = oligonucleotide sequence motif
source                  1..15
                        mol_type = other DNA
                        organism = synthetic construct
SEQUENCE: 246
gggagttctt cttct                                                         15

SEQ ID NO: 247          moltype = DNA   length = 16
FEATURE                 Location/Qualifiers
misc_feature            1..16
                        note = oligonucleotide sequence motif
source                  1..16
                        mol_type = other DNA
                        organism = synthetic construct
SEQUENCE: 247
agggagttct tcttct                                                        16

SEQ ID NO: 248          moltype = DNA   length = 15
FEATURE                 Location/Qualifiers
misc_feature            1..15
                        note = oligonucleotide sequence motif
source                  1..15
                        mol_type = other DNA
                        organism = synthetic construct
SEQUENCE: 248
agggagttct tcttc                                                         15

SEQ ID NO: 249          moltype = DNA   length = 16
FEATURE                 Location/Qualifiers
misc_feature            1..16
                        note = oligonucleotide sequence motif
source                  1..16
                        mol_type = other DNA
                        organism = synthetic construct
SEQUENCE: 249
gagggagttc ttcttc                                                        16

SEQ ID NO: 250          moltype = DNA   length = 14
FEATURE                 Location/Qualifiers
misc_feature            1..14
                        note = oligonucleotide sequence motif
source                  1..14
                        mol_type = other DNA
                        organism = synthetic construct
SEQUENCE: 250
agggagttct tctt                                                          14

SEQ ID NO: 251          moltype = DNA   length = 15
FEATURE                 Location/Qualifiers
misc_feature            1..15
                        note = oligonucleotide sequence motif
source                  1..15
                        mol_type = other DNA
                        organism = synthetic construct
SEQUENCE: 251
gagggagttc ttctt                                                         15

SEQ ID NO: 252          moltype = DNA   length = 16
FEATURE                 Location/Qualifiers
misc_feature            1..16
                        note = oligonucleotide sequence motif
```

```
source                   1..16
                         mol_type = other DNA
                         organism = synthetic construct
SEQUENCE: 252
cgagggagtt cttctt                                                  16

SEQ ID NO: 253           moltype = DNA   length = 15
FEATURE                  Location/Qualifiers
misc_feature             1..15
                         note = oligonucleotide sequence motif
source                   1..15
                         mol_type = other DNA
                         organism = synthetic construct
SEQUENCE: 253
cgagggagtt cttct                                                   15

SEQ ID NO: 254           moltype = DNA   length = 16
FEATURE                  Location/Qualifiers
misc_feature             1..16
                         note = oligonucleotide sequence motif
source                   1..16
                         mol_type = other DNA
                         organism = synthetic construct
SEQUENCE: 254
gcgagggagt tcttct                                                  16

SEQ ID NO: 255           moltype = DNA   length = 15
FEATURE                  Location/Qualifiers
misc_feature             1..15
                         note = oligonucleotide sequence motif
source                   1..15
                         mol_type = other DNA
                         organism = synthetic construct
SEQUENCE: 255
gcgagggagt tcttc                                                   15

SEQ ID NO: 256           moltype = DNA   length = 16
FEATURE                  Location/Qualifiers
misc_feature             1..16
                         note = oligonucleotide sequence motif
source                   1..16
                         mol_type = other DNA
                         organism = synthetic construct
SEQUENCE: 256
ggcgagggag ttcttc                                                  16

SEQ ID NO: 257           moltype = DNA   length = 14
FEATURE                  Location/Qualifiers
misc_feature             1..14
                         note = oligonucleotide sequence motif
source                   1..14
                         mol_type = other DNA
                         organism = synthetic construct
SEQUENCE: 257
gcgagggagt tctt                                                    14

SEQ ID NO: 258           moltype = DNA   length = 15
FEATURE                  Location/Qualifiers
misc_feature             1..15
                         note = oligonucleotide sequence motif
source                   1..15
                         mol_type = other DNA
                         organism = synthetic construct
SEQUENCE: 258
ggcgagggag ttctt                                                   15

SEQ ID NO: 259           moltype = DNA   length = 16
FEATURE                  Location/Qualifiers
misc_feature             1..16
                         note = oligonucleotide sequence motif
source                   1..16
                         mol_type = other DNA
                         organism = synthetic construct
SEQUENCE: 259
aggcgaggga gttctt                                                  16

SEQ ID NO: 260           moltype = DNA   length = 13
FEATURE                  Location/Qualifiers
misc_feature             1..13
```

```
                        note = oligonucleotide sequence motif
source                  1..13
                        mol_type = other DNA
                        organism = synthetic construct
SEQUENCE: 260
gcgagggagt tct                                                         13

SEQ ID NO: 261          moltype = DNA   length = 14
FEATURE                 Location/Qualifiers
misc_feature            1..14
                        note = oligonucleotide sequence motif
source                  1..14
                        mol_type = other DNA
                        organism = synthetic construct
SEQUENCE: 261
ggcgagggag ttct                                                        14

SEQ ID NO: 262          moltype = DNA   length = 15
FEATURE                 Location/Qualifiers
misc_feature            1..15
                        note = oligonucleotide sequence motif
source                  1..15
                        mol_type = other DNA
                        organism = synthetic construct
SEQUENCE: 262
aggcgaggga gttct                                                       15

SEQ ID NO: 263          moltype = DNA   length = 16
FEATURE                 Location/Qualifiers
misc_feature            1..16
                        note = oligonucleotide sequence motif
source                  1..16
                        mol_type = other DNA
                        organism = synthetic construct
SEQUENCE: 263
gaggcgaggg agttct                                                      16

SEQ ID NO: 264          moltype = DNA   length = 13
FEATURE                 Location/Qualifiers
misc_feature            1..13
                        note = oligonucleotide sequence motif
source                  1..13
                        mol_type = other DNA
                        organism = synthetic construct
SEQUENCE: 264
ggcgagggag ttc                                                         13

SEQ ID NO: 265          moltype = DNA   length = 14
FEATURE                 Location/Qualifiers
misc_feature            1..14
                        note = oligonucleotide sequence motif
source                  1..14
                        mol_type = other DNA
                        organism = synthetic construct
SEQUENCE: 265
aggcgaggga gttc                                                        14

SEQ ID NO: 266          moltype = DNA   length = 15
FEATURE                 Location/Qualifiers
misc_feature            1..15
                        note = oligonucleotide sequence motif
source                  1..15
                        mol_type = other DNA
                        organism = synthetic construct
SEQUENCE: 266
gaggcgaggg agttc                                                       15

SEQ ID NO: 267          moltype = DNA   length = 16
FEATURE                 Location/Qualifiers
misc_feature            1..16
                        note = oligonucleotide sequence motif
source                  1..16
                        mol_type = other DNA
                        organism = synthetic construct
SEQUENCE: 267
cgaggcgagg gagttc                                                      16

SEQ ID NO: 268          moltype = DNA   length = 13
FEATURE                 Location/Qualifiers
```

|  |  |  |
|---|---|---|
| misc_feature | 1..13<br>note = oligonucleotide sequence motif | |
| source | 1..13<br>mol_type = other DNA<br>organism = synthetic construct | |
| SEQUENCE: 268<br>aggcgaggga gtt | | 13 |
| SEQ ID NO: 269<br>FEATURE<br>misc_feature | moltype = DNA   length = 14<br>Location/Qualifiers<br>1..14<br>note = oligonucleotide sequence motif | |
| source | 1..14<br>mol_type = other DNA<br>organism = synthetic construct | |
| SEQUENCE: 269<br>gaggcgaggg agtt | | 14 |
| SEQ ID NO: 270<br>FEATURE<br>misc_feature | moltype = DNA   length = 15<br>Location/Qualifiers<br>1..15<br>note = oligonucleotide sequence motif | |
| source | 1..15<br>mol_type = other DNA<br>organism = synthetic construct | |
| SEQUENCE: 270<br>cgaggcgagg gagtt | | 15 |
| SEQ ID NO: 271<br>FEATURE<br>misc_feature | moltype = DNA   length = 16<br>Location/Qualifiers<br>1..16<br>note = oligonucleotide sequence motif | |
| source | 1..16<br>mol_type = other DNA<br>organism = synthetic construct | |
| SEQUENCE: 271<br>gcgaggcgag ggagtt | | 16 |
| SEQ ID NO: 272<br>FEATURE<br>misc_feature | moltype = DNA   length = 13<br>Location/Qualifiers<br>1..13<br>note = oligonucleotide sequence motif | |
| source | 1..13<br>mol_type = other DNA<br>organism = synthetic construct | |
| SEQUENCE: 272<br>gaggcgaggg agt | | 13 |
| SEQ ID NO: 273<br>FEATURE<br>misc_feature | moltype = DNA   length = 14<br>Location/Qualifiers<br>1..14<br>note = oligonucleotide sequence motif | |
| source | 1..14<br>mol_type = other DNA<br>organism = synthetic construct | |
| SEQUENCE: 273<br>cgaggcgagg gagt | | 14 |
| SEQ ID NO: 274<br>FEATURE<br>misc_feature | moltype = DNA   length = 15<br>Location/Qualifiers<br>1..15<br>note = oligonucleotide sequence motif | |
| source | 1..15<br>mol_type = other DNA<br>organism = synthetic construct | |
| SEQUENCE: 274<br>gcgaggcgag ggagt | | 15 |
| SEQ ID NO: 275<br>FEATURE<br>misc_feature | moltype = DNA   length = 16<br>Location/Qualifiers<br>1..16<br>note = oligonucleotide sequence motif | |
| source | 1..16<br>mol_type = other DNA<br>organism = synthetic construct | |
| SEQUENCE: 275<br>tgcgaggcga gggagt | | 16 |
| SEQ ID NO: 276 | moltype = DNA   length = 13 | |

```
FEATURE                 Location/Qualifiers
misc_feature            1..13
                        note = oligonucleotide sequence motif
source                  1..13
                        mol_type = other DNA
                        organism = synthetic construct SEQUENCE: 276
cgaggcgagg gag                                                              13

SEQ ID NO: 277          moltype = DNA   length = 14
FEATURE                 Location/Qualifiers
misc_feature            1..14
                        note = oligonucleotide sequence motif
source                  1..14
                        mol_type = other DNA
                        organism = synthetic construct SEQUENCE: 277
gcgaggcgag ggag                                                             14

SEQ ID NO: 278          moltype = DNA   length = 15
FEATURE                 Location/Qualifiers
misc_feature            1..15
                        note = oligonucleotide sequence motif
source                  1..15
                        mol_type = other DNA
                        organism = synthetic construct SEQUENCE: 278
tgcgaggcga gggag                                                            15

SEQ ID NO: 279          moltype = DNA   length = 16
FEATURE                 Location/Qualifiers
misc_feature            1..16
                        note = oligonucleotide sequence motif
source                  1..16
                        mol_type = other DNA
                        organism = synthetic construct SEQUENCE: 279
ctgcgaggcg agggag                                                           16

SEQ ID NO: 280          moltype = DNA   length = 12
FEATURE                 Location/Qualifiers
misc_feature            1..12
                        note = oligonucleotide sequence motif
source                  1..12
                        mol_type = other DNA
                        organism = synthetic construct SEQUENCE: 280
cgaggcgagg ga                                                               12

SEQ ID NO: 281          moltype = DNA   length = 13
FEATURE                 Location/Qualifiers
misc_feature            1..13
                        note = oligonucleotide sequence motif
source                  1..13
                        mol_type = other DNA
                        organism = synthetic construct SEQUENCE: 281
gcgaggcgag gga                                                              13

SEQ ID NO: 282          moltype = DNA   length = 14
FEATURE                 Location/Qualifiers
misc_feature            1..14
                        note = oligonucleotide sequence motif
source                  1..14
                        mol_type = other DNA
                        organism = synthetic construct SEQUENCE: 282
tgcgaggcga ggga                                                             14

SEQ ID NO: 283          moltype = DNA   length = 15
FEATURE                 Location/Qualifiers
misc_feature            1..15
                        note = oligonucleotide sequence motif
source                  1..15
                        mol_type = other DNA
                        organism = synthetic construct SEQUENCE: 283
ctgcgaggcg aggga                                                            15
```

```
SEQ ID NO: 284           moltype = DNA   length = 16
FEATURE                  Location/Qualifiers
misc_feature             1..16
                         note = oligonucleotide sequence motif
source                   1..16
                         mol_type = other DNA
                         organism = synthetic construct
SEQUENCE: 284
tctgcgaggc gaggga                                                          16

SEQ ID NO: 285           moltype = DNA   length = 15
FEATURE                  Location/Qualifiers
misc_feature             1..15
                         note = oligonucleotide sequence motif
source                   1..15
                         mol_type = other DNA
                         organism = synthetic construct
SEQUENCE: 285
tctgcgaggc gaggg                                                           15

SEQ ID NO: 286           moltype = DNA   length = 16
FEATURE                  Location/Qualifiers
misc_feature             1..16
                         note = oligonucleotide sequence motif
source                   1..16
                         mol_type = other DNA
                         organism = synthetic construct
SEQUENCE: 286
gtctgcgagg cgaggg                                                          16

SEQ ID NO: 287           moltype = DNA   length = 14
FEATURE                  Location/Qualifiers
misc_feature             1..14
                         note = oligonucleotide sequence motif
source                   1..14
                         mol_type = other DNA
                         organism = synthetic construct
SEQUENCE: 287
gttcccaaga atat                                                            14

SEQ ID NO: 288           moltype = DNA   length = 15
FEATURE                  Location/Qualifiers
misc_feature             1..15
                         note = oligonucleotide sequence motif
source                   1..15
                         mol_type = other DNA
                         organism = synthetic construct
SEQUENCE: 288
tgttcccaag aatat                                                           15

SEQ ID NO: 289           moltype = DNA   length = 13
FEATURE                  Location/Qualifiers
misc_feature             1..13
                         note = oligonucleotide sequence motif
source                   1..13
                         mol_type = other DNA
                         organism = synthetic construct
SEQUENCE: 289
gttcccaaga ata                                                             13

SEQ ID NO: 290           moltype = DNA   length = 14
FEATURE                  Location/Qualifiers
misc_feature             1..14
                         note = oligonucleotide sequence motif
source                   1..14
                         mol_type = other DNA
                         organism = synthetic construct
SEQUENCE: 290
tgttcccaag aata                                                            14

SEQ ID NO: 291           moltype = DNA   length = 15
FEATURE                  Location/Qualifiers
misc_feature             1..15
                         note = oligonucleotide sequence motif
source                   1..15
                         mol_type = other DNA
                         organism = synthetic construct
SEQUENCE: 291
ttgttcccaa gaata                                                           15
```

```
SEQ ID NO: 292          moltype = DNA  length = 13
FEATURE                 Location/Qualifiers
misc_feature            1..13
                        note = oligonucleotide sequence motif
source                  1..13
                        mol_type = other DNA
                        organism = synthetic construct
SEQUENCE: 292
tgttcccaag aat                                                              13

SEQ ID NO: 293          moltype = DNA  length = 14
FEATURE                 Location/Qualifiers
misc_feature            1..14
                        note = oligonucleotide sequence motif
source                  1..14
                        mol_type = other DNA
                        organism = synthetic construct
SEQUENCE: 293
ttgttcccaa gaat                                                             14

SEQ ID NO: 294          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 294
gaaccactga acaaa                                                            15

SEQ ID NO: 295          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct
SEQUENCE: 295
cgaaccactg aacaaa                                                           16

SEQ ID NO: 296          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 296
cgaaccactg aacaa                                                            15

SEQ ID NO: 297          moltype = DNA  length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
```

```
source                  1..14
                        mol_type = other DNA
                        organism = synthetic construct
SEQUENCE: 297
cgaaccactg aaca                                                         14

SEQ ID NO: 298          moltype = DNA   length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
                        mod_base = OTHER
                        note = LNA nucleosides
source                  1..13
                        mol_type = other DNA
                        organism = synthetic construct
SEQUENCE: 298
cgaaccactg aac                                                          13

SEQ ID NO: 299          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 299
ccgcagtatg gatcg                                                        15

SEQ ID NO: 300          moltype = DNA   length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
                        mod_base = OTHER
                        note = LNA nucleosides
source                  1..13
                        mol_type = other DNA
                        organism = synthetic construct
SEQUENCE: 300
cgcagtatgg atc                                                          13

SEQ ID NO: 301          moltype = DNA   length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
source                  1..14
                        mol_type = other DNA
                        organism = synthetic construct
SEQUENCE: 301
gcgtaaagag aggt                                                         14

SEQ ID NO: 302          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
```

-continued

```
                          note = LNA nucleosides
source                    1..15
                          mol_type = other DNA
                          organism = synthetic construct
SEQUENCE: 302
cgcgtaaaga gaggt                                                            15

SEQ ID NO: 303            moltype = DNA  length = 13
FEATURE                   Location/Qualifiers
misc_feature              1..13
                          note = LNA antisense gapmer oligonucleotide
modified_base             1..13
                          mod_base = OTHER
                          note = Phosphorothiate Internucleoside linkages
modified_base             order(1..3,12,13)
                          mod_base = OTHER
                          note = LNA nucleosides
source                    1..13
                          mol_type = other DNA
                          organism = synthetic construct
SEQUENCE: 303
gcgtaaagag agg                                                              13

SEQ ID NO: 304            moltype = DNA  length = 15
FEATURE                   Location/Qualifiers
misc_feature              1..15
                          note = LNA antisense gapmer oligonucleotide
modified_base             1..15
                          mod_base = OTHER
                          note = Phosphorothiate Internucleoside linkages
modified_base             order(1..3,13..15)
                          mod_base = OTHER
                          note = LNA nucleosides
source                    1..15
                          mol_type = other DNA
                          organism = synthetic construct
SEQUENCE: 304
agaaggcaca gacgg                                                            15

SEQ ID NO: 305            moltype = DNA  length = 16
FEATURE                   Location/Qualifiers
misc_feature              1..16
                          note = LNA antisense gapmer oligonucleotide
modified_base             1..16
                          mod_base = OTHER
                          note = Phosphorothiate Internucleoside linkages
modified_base             order(1..3,14..16)
                          mod_base = OTHER
                          note = LNA nucleosides
source                    1..16
                          mol_type = other DNA
                          organism = synthetic construct
SEQUENCE: 305
gagaaggcac agacgg                                                           16

SEQ ID NO: 306            moltype = DNA  length = 13
FEATURE                   Location/Qualifiers
misc_feature              1..13
                          note = LNA antisense gapmer oligonucleotide
modified_base             1..13
                          mod_base = OTHER
                          note = Phosphorothiate Internucleoside linkages
modified_base             order(1..3,12,13)
                          mod_base = OTHER
                          note = LNA nucleosides
modified_base             11
                          mod_base = OTHER
                          note = 5-methyl c
source                    1..13
                          mol_type = other DNA
                          organism = synthetic construct
SEQUENCE: 306
gaagtgcaca cgg                                                              13

SEQ ID NO: 307            moltype = DNA  length = 15
FEATURE                   Location/Qualifiers
misc_feature              1..15
                          note = LNA antisense gapmer oligonucleotide
modified_base             1..15
```

| | | |
|---|---|---|
| modified_base | | mod_base = OTHER<br>note = Phosphorothiate Internucleoside linkages<br>order(1..3,13..15)<br>mod_base = OTHER<br>note = LNA nucleosides |
| source | | 1..15<br>mol_type = other DNA<br>organism = synthetic construct |
| SEQUENCE: 307 | | |
| gcgaagtgca cacgg | | 15 |

| | | |
|---|---|---|
| SEQ ID NO: 308<br>FEATURE<br>misc_feature | | moltype = DNA length = 16<br>Location/Qualifiers<br>1..16<br>note = LNA antisense gapmer oligonucleotide |
| modified_base | | 1..16<br>mod_base = OTHER<br>note = Phosphorothiate Internucleoside linkages |
| modified_base | | order(1..3,14..16)<br>mod_base = OTHER<br>note = LNA nucleosides |
| source | | 1..16<br>mol_type = other DNA<br>organism = synthetic construct |
| SEQUENCE: 308 | | |
| agcgaagtgc acacgg | | 16 |

| | | |
|---|---|---|
| SEQ ID NO: 309<br>FEATURE<br>misc_feature | | moltype = DNA length = 13<br>Location/Qualifiers<br>1..13<br>note = LNA antisense gapmer oligonucleotide |
| modified_base | | 1..13<br>mod_base = OTHER<br>note = Phosphorothiate Internucleoside linkages |
| modified_base | | order(1..3,12,13)<br>mod_base = OTHER<br>note = LNA nucleosides |
| source | | 1..13<br>mol_type = other DNA<br>organism = synthetic construct |
| SEQUENCE: 309 | | |
| cgaagtgcac acg | | 13 |

| | | |
|---|---|---|
| SEQ ID NO: 310<br>FEATURE<br>misc_feature | | moltype = DNA length = 15<br>Location/Qualifiers<br>1..15<br>note = LNA antisense gapmer oligonucleotide |
| modified_base | | 1..15<br>mod_base = OTHER<br>note = Phosphorothiate Internucleoside linkages |
| modified_base | | order(1..3,13..15)<br>mod_base = OTHER<br>note = LNA nucleosides |
| source | | 1..15<br>mol_type = other DNA<br>organism = synthetic construct |
| SEQUENCE: 310 | | |
| agcgaagtgc acacg | | 15 |

| | | |
|---|---|---|
| SEQ ID NO: 311<br>FEATURE<br>misc_feature | | moltype = DNA length = 16<br>Location/Qualifiers<br>1..16<br>note = LNA antisense gapmer oligonucleotide |
| modified_base | | 1..16<br>mod_base = OTHER<br>note = Phosphorothiate Internucleoside linkages |
| modified_base | | order(1..3,14..16)<br>mod_base = OTHER<br>note = LNA nucleosides |
| modified_base | | 4<br>mod_base = OTHER<br>note = 5-methyl c |
| source | | 1..16<br>mol_type = other DNA<br>organism = synthetic construct |
| SEQUENCE: 311 | | |
| aagcgaagtg cacacg | | 16 |

| | | |
|---|---|---|
| SEQ ID NO: 312 | | moltype = DNA length = 15 |

```
FEATURE              Location/Qualifiers
misc_feature         1..15
                     note = LNA antisense gapmer oligonucleotide
modified_base        1..15
                     mod_base = OTHER
                     note = Phosphorothiate Internucleoside linkages
modified_base        order(1..3,13..15)
                     mod_base = OTHER
                     note = LNA nucleosides
modified_base        5
                     mod_base = OTHER
                     note = 5-methyl c
source               1..15
                     mol_type = other DNA
                     organism = synthetic construct
SEQUENCE: 312
gaagcgaagt gcaca                                                      15

SEQ ID NO: 313       moltype = DNA  length = 16
FEATURE              Location/Qualifiers
misc_feature         1..16
                     note = LNA antisense gapmer oligonucleotide
modified_base        1..16
                     mod_base = OTHER
                     note = Phosphorothiate Internucleoside linkages
modified_base        order(1..3,14..16)
                     mod_base = OTHER
                     note = LNA nucleosides
modified_base        8
                     mod_base = OTHER
                     note = 5-methyl c
source               1..16
                     mol_type = other DNA
                     organism = synthetic construct
SEQUENCE: 313
ggtgaagcga agtgca                                                     16

SEQ ID NO: 314       moltype = DNA  length = 15
FEATURE              Location/Qualifiers
misc_feature         1..15
                     note = LNA antisense gapmer oligonucleotide
modified_base        1..15
                     mod_base = OTHER
                     note = Phosphorothiate Internucleoside linkages
modified_base        order(1..3,13..15)
                     mod_base = OTHER
                     note = LNA nucleosides
modified_base        8
                     mod_base = OTHER
                     note = 5-methyl c
source               1..15
                     mol_type = other DNA
                     organism = synthetic construct
SEQUENCE: 314
ggtgaagcga agtgc                                                      15

SEQ ID NO: 315       moltype = DNA  length = 16
FEATURE              Location/Qualifiers
misc_feature         1..16
                     note = LNA antisense gapmer oligonucleotide
modified_base        1..16
                     mod_base = OTHER
                     note = Phosphorothiate Internucleoside linkages
modified_base        order(1..3,14..16)
                     mod_base = OTHER
                     note = LNA nucleosides
modified_base        9
                     mod_base = OTHER
                     note = 5-methyl c
source               1..16
                     mol_type = other DNA
                     organism = synthetic construct
SEQUENCE: 315
aggtgaagcg aagtgc                                                     16

SEQ ID NO: 316       moltype = DNA  length = 15
FEATURE              Location/Qualifiers
misc_feature         1..15
                     note = LNA antisense gapmer oligonucleotide
```

-continued

```
modified_base         1..15
                      mod_base = OTHER
                      note = Phosphorothiate Internucleoside linkages
modified_base         order(1..3,13..15)
                      mod_base = OTHER
                      note = LNA nucleosides
modified_base         9
                      mod_base = OTHER
                      note = 5-methyl c
source                1..15
                      mol_type = other DNA
                      organism = synthetic construct SEQUENCE: 316
aggtgaagcg aagtg                                                              15

SEQ ID NO: 317        moltype = DNA   length = 14
FEATURE               Location/Qualifiers
misc_feature          1..14
                      note = LNA antisense gapmer oligonucleotide
modified_base         1..14
                      mod_base = OTHER
                      note = Phosphorothiate Internucleoside linkages
modified_base         order(1..3,12..14)
                      mod_base = OTHER
                      note = LNA nucleosides
modified_base         9
                      mod_base = OTHER
                      note = 5-methyl c
source                1..14
                      mol_type = other DNA
                      organism = synthetic construct SEQUENCE: 317
aggtgaagcg aagt                                                               14

SEQ ID NO: 318        moltype = DNA   length = 14
FEATURE               Location/Qualifiers
misc_feature          1..14
                      note = LNA antisense gapmer oligonucleotide
modified_base         1..14
                      mod_base = OTHER
                      note = Phosphorothiate Internucleoside linkages
modified_base         order(1..3,12..14)
                      mod_base = OTHER
                      note = LNA nucleosides
source                1..14
                      mol_type = other DNA
                      organism = synthetic construct SEQUENCE: 318
cagaggtgaa gcga                                                               14

SEQ ID NO: 319        moltype = DNA   length = 14
FEATURE               Location/Qualifiers
misc_feature          1..14
                      note = LNA antisense gapmer oligonucleotide
modified_base         1..14
                      mod_base = OTHER
                      note = Phosphorothiate Internucleoside linkages
modified_base         order(1..3,12..14)
                      mod_base = OTHER
                      note = LNA nucleosides
modified_base         8
                      mod_base = OTHER
                      note = 5-methyl c
source                1..14
                      mol_type = other DNA
                      organism = synthetic construct SEQUENCE: 319
aaaaccccgc ctgt                                                               14

SEQ ID NO: 320        moltype = DNA   length = 13
FEATURE               Location/Qualifiers
misc_feature          1..13
                      note = LNA antisense gapmer oligonucleotide
modified_base         1..13
                      mod_base = OTHER
                      note = Phosphorothiate Internucleoside linkages
modified_base         order(1..3,12,13)
                      mod_base = OTHER
                      note = LNA nucleosides
```

```
                        modified_base      8
                                           mod_base = OTHER
                                           note = 5-methyl c
                        source             1..13
                                           mol_type = other DNA
                                           organism = synthetic construct
SEQUENCE: 320
aaaacccgc ctg                                                                          13

SEQ ID NO: 321     moltype = DNA  length = 15
                        FEATURE            Location/Qualifiers
                        misc_feature       1..15
                                           note = LNA antisense gapmer oligonucleotide
                        modified_base      1..15
                                           mod_base = OTHER
                                           note = Phosphorothiate Internucleoside linkages
                        modified_base      order(1..3,13..15)
                                           mod_base = OTHER
                                           note = LNA nucleosides
                        source             1..15
                                           mol_type = other DNA
                                           organism = synthetic construct
SEQUENCE: 321
acgagtctag actct                                                                       15

SEQ ID NO: 322     moltype = DNA  length = 16
                        FEATURE            Location/Qualifiers
                        misc_feature       1..16
                                           note = LNA antisense gapmer oligonucleotide
                        modified_base      1..16
                                           mod_base = OTHER
                                           note = Phosphorothiate Internucleoside linkages
                        modified_base      order(1..3,14..16)
                                           mod_base = OTHER
                                           note = LNA nucleosides
                        source             1..16
                                           mol_type = other DNA
                                           organism = synthetic construct
SEQUENCE: 322
cacgagtcta gactct                                                                      16

SEQ ID NO: 323     moltype = DNA  length = 14
                        FEATURE            Location/Qualifiers
                        misc_feature       1..14
                                           note = LNA antisense gapmer oligonucleotide
                        modified_base      1..14
                                           mod_base = OTHER
                                           note = Phosphorothiate Internucleoside linkages
                        modified_base      order(1..3,12..14)
                                           mod_base = OTHER
                                           note = LNA nucleosides
                        source             1..14
                                           mol_type = other DNA
                                           organism = synthetic construct
SEQUENCE: 323
acgagtctag actc                                                                        14

SEQ ID NO: 324     moltype = DNA  length = 15
                        FEATURE            Location/Qualifiers
                        misc_feature       1..15
                                           note = LNA antisense gapmer oligonucleotide
                        modified_base      1..15
                                           mod_base = OTHER
                                           note = Phosphorothiate Internucleoside linkages
                        modified_base      order(1..3,13..15)
                                           mod_base = OTHER
                                           note = LNA nucleosides
                        source             1..15
                                           mol_type = other DNA
                                           organism = synthetic construct
SEQUENCE: 324
cacgagtcta gactc                                                                       15

SEQ ID NO: 325     moltype = DNA  length = 16
                        FEATURE            Location/Qualifiers
                        misc_feature       1..16
                                           note = LNA antisense gapmer oligonucleotide
                        modified_base      1..16
                                           mod_base = OTHER
```

```
                    note = Phosphorothiate Internucleoside linkages
modified_base       order(1..3,14..16)
                    mod_base = OTHER
                    note = LNA nucleosides
modified_base       4
                    mod_base = OTHER
                    note = 5-methyl c
source              1..16
                    mol_type = other DNA
                    organism = synthetic construct
SEQUENCE: 325
ccacgagtct agactc                                                    16

SEQ ID NO: 326      moltype = DNA  length = 13
FEATURE             Location/Qualifiers
misc_feature        1..13
                    note = LNA antisense gapmer oligonucleotide
modified_base       1..13
                    mod_base = OTHER
                    note = Phosphorothiate Internucleoside linkages
modified_base       order(1..3,12,13)
                    mod_base = OTHER
                    note = LNA nucleosides
source              1..13
                    mol_type = other DNA
                    organism = synthetic construct
SEQUENCE: 326
acgagtctag act                                                       13

SEQ ID NO: 327      moltype = DNA  length = 14
FEATURE             Location/Qualifiers
misc_feature        1..14
                    note = LNA antisense gapmer oligonucleotide
modified_base       1..14
                    mod_base = OTHER
                    note = Phosphorothiate Internucleoside linkages
modified_base       order(1..3,12..14)
                    mod_base = OTHER
                    note = LNA nucleosides
source              1..14
                    mol_type = other DNA
                    organism = synthetic construct
SEQUENCE: 327
cacgagtcta gact                                                      14

SEQ ID NO: 328      moltype = DNA  length = 15
FEATURE             Location/Qualifiers
misc_feature        1..15
                    note = LNA antisense gapmer oligonucleotide
modified_base       1..15
                    mod_base = OTHER
                    note = Phosphorothiate Internucleoside linkages
modified_base       order(1..3,13..15)
                    mod_base = OTHER
                    note = LNA nucleosides
modified_base       4
                    mod_base = OTHER
                    note = 5-methyl c
source              1..15
                    mol_type = other DNA
                    organism = synthetic construct
SEQUENCE: 328
ccacgagtct agact                                                     15

SEQ ID NO: 329      moltype = DNA  length = 16
FEATURE             Location/Qualifiers
misc_feature        1..16
                    note = LNA antisense gapmer oligonucleotide
modified_base       1..16
                    mod_base = OTHER
                    note = Phosphorothiate Internucleoside linkages
modified_base       order(1..3,14..16)
                    mod_base = OTHER
                    note = LNA nucleosides
modified_base       5
                    mod_base = OTHER
                    note = 5-methyl c
source              1..16
                    mol_type = other DNA
```

```
                       organism = synthetic construct
SEQUENCE: 329
accacgagtc tagact                                                          16

SEQ ID NO: 330         moltype = DNA  length = 12
FEATURE                Location/Qualifiers
misc_feature           1..12
                       note = LNA antisense gapmer oligonucleotide
modified_base          1..12
                       mod_base = OTHER
                       note = Phosphorothiate Internucleoside linkages
modified_base          order(1,2,11,12)
                       mod_base = OTHER
                       note = LNA nucleosides
source                 1..12
                       mol_type = other DNA
                       organism = synthetic construct
SEQUENCE: 330
acgagtctag ac                                                              12

SEQ ID NO: 331         moltype = DNA  length = 13
FEATURE                Location/Qualifiers
misc_feature           1..13
                       note = LNA antisense gapmer oligonucleotide
modified_base          1..13
                       mod_base = OTHER
                       note = Phosphorothiate Internucleoside linkages
modified_base          order(1..3,12,13)
                       mod_base = OTHER
                       note = LNA nucleosides
source                 1..13
                       mol_type = other DNA
                       organism = synthetic construct
SEQUENCE: 331
cacgagtcta gac                                                             13

SEQ ID NO: 332         moltype = DNA  length = 14
FEATURE                Location/Qualifiers
misc_feature           1..14
                       note = LNA antisense gapmer oligonucleotide
modified_base          1..14
                       mod_base = OTHER
                       note = Phosphorothiate Internucleoside linkages
modified_base          order(1..3,12..14)
                       mod_base = OTHER
                       note = LNA nucleosides
modified_base          4
                       mod_base = OTHER
                       note = 5-methyl c
source                 1..14
                       mol_type = other DNA
                       organism = synthetic construct
SEQUENCE: 332
ccacgagtct agac                                                            14

SEQ ID NO: 333         moltype = DNA  length = 15
FEATURE                Location/Qualifiers
misc_feature           1..15
                       note = LNA antisense gapmer oligonucleotide
modified_base          1..15
                       mod_base = OTHER
                       note = Phosphorothiate Internucleoside linkages
modified_base          order(1..3,13..15)
                       mod_base = OTHER
                       note = LNA nucleosides
modified_base          5
                       mod_base = OTHER
                       note = 5-methyl c
source                 1..15
                       mol_type = other DNA
                       organism = synthetic construct
SEQUENCE: 333
accacgagtc tagac                                                           15

SEQ ID NO: 334         moltype = DNA  length = 16
FEATURE                Location/Qualifiers
misc_feature           1..16
                       note = LNA antisense gapmer oligonucleotide
modified_base          1..16
```

```
                        mod_base = OTHER
                        note = Phosphorothiate Internucleoside linkages
modified_base           order(1..3,14..16)
                        mod_base = OTHER
                        note = LNA nucleosides
modified_base           6
                        mod_base = OTHER
                        note = 5-methyl c
source                  1..16
                        mol_type = other DNA
                        organism = synthetic construct
SEQUENCE: 334
caccacgagt ctagac                                                         16

SEQ ID NO: 335          moltype = DNA  length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
modified_base           5
                        mod_base = OTHER
                        note = 5-methyl c
source                  1..14
                        mol_type = other DNA
                        organism = synthetic construct
SEQUENCE: 335
accacgagtc taga                                                           14

SEQ ID NO: 336          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
modified_base           6
                        mod_base = OTHER
                        note = 5-methyl c
source                  1..15
                        mol_type = other DNA
                        organism = synthetic construct
SEQUENCE: 336
caccacgagt ctaga                                                          15

SEQ ID NO: 337          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           7
                        mod_base = OTHER
                        note = 5-methyl c
source                  1..16
                        mol_type = other DNA
                        organism = synthetic construct
SEQUENCE: 337
ccaccacgag tctaga                                                         16

SEQ ID NO: 338          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
```

```
                        mod_base = OTHER
                        note = LNA nucleosides
modified_base           7
                        mod_base = OTHER
                        note = 5-methyl c
source                  1..15
                        mol_type = other DNA
                        organism = synthetic construct
SEQUENCE: 338
ccaccacgag tctag                                                         15

SEQ ID NO: 339          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           8
                        mod_base = OTHER
                        note = 5-methyl c
source                  1..16
                        mol_type = other DNA
                        organism = synthetic construct
SEQUENCE: 339
tccaccacga gtctag                                                        16

SEQ ID NO: 340          moltype = DNA  length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
modified_base           7
                        mod_base = OTHER
                        note = 5-methyl c
source                  1..14
                        mol_type = other DNA
                        organism = synthetic construct
SEQUENCE: 340
ccaccacgag tcta                                                          14

SEQ ID NO: 341          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
modified_base           8
                        mod_base = OTHER
                        note = 5-methyl c
source                  1..15
                        mol_type = other DNA
                        organism = synthetic construct
SEQUENCE: 341
tccaccacga gtcta                                                         15

SEQ ID NO: 342          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           9
```

```
                         mod_base = OTHER
                         note = 5-methyl c
source                   1..16
                         mol_type = other DNA
                         organism = synthetic construct
SEQUENCE: 342
gtccaccacg agtcta                                                          16

SEQ ID NO: 343           moltype = DNA  length = 14
FEATURE                  Location/Qualifiers
misc_feature             1..14
                         note = LNA antisense gapmer oligonucleotide
modified_base            1..14
                         mod_base = OTHER
                         note = Phosphorothiate Internucleoside linkages
modified_base            order(1..3,12..14)
                         mod_base = OTHER
                         note = LNA nucleosides
modified_base            8
                         mod_base = OTHER
                         note = 5-methyl c
source                   1..14
                         mol_type = other DNA
                         organism = synthetic construct
SEQUENCE: 343
tccaccacga gtct                                                            14

SEQ ID NO: 344           moltype = DNA  length = 15
FEATURE                  Location/Qualifiers
misc_feature             1..15
                         note = LNA antisense gapmer oligonucleotide
modified_base            1..15
                         mod_base = OTHER
                         note = Phosphorothiate Internucleoside linkages
modified_base            order(1..3,13..15)
                         mod_base = OTHER
                         note = LNA nucleosides
modified_base            9
                         mod_base = OTHER
                         note = 5-methyl c
source                   1..15
                         mol_type = other DNA
                         organism = synthetic construct
SEQUENCE: 344
gtccaccacg agtct                                                           15

SEQ ID NO: 345           moltype = DNA  length = 16
FEATURE                  Location/Qualifiers
misc_feature             1..16
                         note = LNA antisense gapmer oligonucleotide
modified_base            1..16
                         mod_base = OTHER
                         note = Phosphorothiate Internucleoside linkages
modified_base            order(1..3,14..16)
                         mod_base = OTHER
                         note = LNA nucleosides
modified_base            10
                         mod_base = OTHER
                         note = 5-methyl c
source                   1..16
                         mol_type = other DNA
                         organism = synthetic construct
SEQUENCE: 345
agtccaccac gagtct                                                          16

SEQ ID NO: 346           moltype = DNA  length = 14
FEATURE                  Location/Qualifiers
misc_feature             1..14
                         note = LNA antisense gapmer oligonucleotide
modified_base            1..14
                         mod_base = OTHER
                         note = Phosphorothiate Internucleoside linkages
modified_base            order(1..3,12..14)
                         mod_base = OTHER
                         note = LNA nucleosides
modified_base            9
                         mod_base = OTHER
                         note = 5-methyl c
source                   1..14
```

```
                        mol_type = other DNA
                        organism = synthetic construct
SEQUENCE: 346
gtccaccacg agtc                                                      14

SEQ ID NO: 347          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
modified_base           10
                        mod_base = OTHER
                        note = 5-methyl c
source                  1..15
                        mol_type = other DNA
                        organism = synthetic construct
SEQUENCE: 347
agtccaccac gagtc                                                     15

SEQ ID NO: 348          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           11
                        mod_base = OTHER
                        note = 5-methyl c
source                  1..16
                        mol_type = other DNA
                        organism = synthetic construct
SEQUENCE: 348
aagtccacca cgagtc                                                    16

SEQ ID NO: 349          moltype = DNA  length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
modified_base           10
                        mod_base = OTHER
                        note = 5-methyl c
source                  1..14
                        mol_type = other DNA
                        organism = synthetic construct
SEQUENCE: 349
agtccaccac gagt                                                      14

SEQ ID NO: 350          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
modified_base           11
                        mod_base = OTHER
                        note = 5-methyl c
source                  1..15
                        mol_type = other DNA
                        organism = synthetic construct
SEQUENCE: 350
```

```
aagtccacca cgagt                                                        15

SEQ ID NO: 351          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           12
                        mod_base = OTHER
                        note = 5-methyl c
source                  1..16
                        mol_type = other DNA
                        organism = synthetic construct
SEQUENCE: 351
gaagtccacc acgagt                                                       16

SEQ ID NO: 352          moltype = DNA   length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,13,14)
                        mod_base = OTHER
                        note = LNA nucleosides
modified_base           11
                        mod_base = OTHER
                        note = 5-methyl c
source                  1..14
                        mol_type = other DNA
                        organism = synthetic construct
SEQUENCE: 352
aagtccacca cgag                                                         14

SEQ ID NO: 353          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,14,15)
                        mod_base = OTHER
                        note = LNA nucleosides
modified_base           12
                        mod_base = OTHER
                        note = 5-methyl c
source                  1..15
                        mol_type = other DNA
                        organism = synthetic construct
SEQUENCE: 353
gaagtccacc acgag                                                        15

SEQ ID NO: 354          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,15,16)
                        mod_base = OTHER
                        note = LNA nucleosides
modified_base           13
                        mod_base = OTHER
                        note = 5-methyl c
source                  1..16
                        mol_type = other DNA
                        organism = synthetic construct
SEQUENCE: 354
agaagtccac cacgag                                                       16

SEQ ID NO: 355          moltype = DNA   length = 15
```

```
FEATURE              Location/Qualifiers
misc_feature         1..15
                     note = LNA antisense gapmer oligonucleotide
modified_base        1..15
                     mod_base = OTHER
                     note = Phosphorothiate Internucleoside linkages
modified_base        order(1..3,13..15)
                     mod_base = OTHER
                     note = LNA nucleosides
source               1..15
                     mol_type = other DNA
                     organism = synthetic construct
SEQUENCE: 355
agaagtccac cacga                                                    15

SEQ ID NO: 356       moltype = DNA  length = 16
FEATURE              Location/Qualifiers
misc_feature         1..16
                     note = LNA antisense gapmer oligonucleotide
modified_base        1..16
                     mod_base = OTHER
                     note = Phosphorothiate Internucleoside linkages
modified_base        order(1..3,14..16)
                     mod_base = OTHER
                     note = LNA nucleosides
source               1..16
                     mol_type = other DNA
                     organism = synthetic construct
SEQUENCE: 356
gagaagtcca ccacga                                                   16

SEQ ID NO: 357       moltype = DNA  length = 15
FEATURE              Location/Qualifiers
misc_feature         1..15
                     note = LNA antisense gapmer oligonucleotide
modified_base        1..15
                     mod_base = OTHER
                     note = Phosphorothiate Internucleoside linkages
modified_base        order(1..3,13..15)
                     mod_base = OTHER
                     note = LNA nucleosides
source               1..15
                     mol_type = other DNA
                     organism = synthetic construct
SEQUENCE: 357
gagaagtcca ccacg                                                    15

SEQ ID NO: 358       moltype = DNA  length = 16
FEATURE              Location/Qualifiers
misc_feature         1..16
                     note = LNA antisense gapmer oligonucleotide
modified_base        1..16
                     mod_base = OTHER
                     note = Phosphorothiate Internucleoside linkages
modified_base        order(1..3,14..16)
                     mod_base = OTHER
                     note = LNA nucleosides
source               1..16
                     mol_type = other DNA
                     organism = synthetic construct
SEQUENCE: 358
agagaagtcc accacg                                                   16

SEQ ID NO: 359       moltype = DNA  length = 16
FEATURE              Location/Qualifiers
misc_feature         1..16
                     note = LNA antisense gapmer oligonucleotide
modified_base        1..16
                     mod_base = OTHER
                     note = Phosphorothiate Internucleoside linkages
modified_base        order(1..3,14..16)
                     mod_base = OTHER
                     note = LNA nucleosides
source               1..16
                     mol_type = other DNA
                     organism = synthetic construct
SEQUENCE: 359
gagagaagtc caccac                                                   16
```

-continued

```
SEQ ID NO: 360            moltype = DNA  length = 15
FEATURE                   Location/Qualifiers
misc_feature              1..15
                          note = LNA antisense gapmer oligonucleotide
modified_base             1..15
                          mod_base = OTHER
                          note = Phosphorothiate Internucleoside linkages
modified_base             order(1..3,13..15)
                          mod_base = OTHER
                          note = LNA nucleosides
source                    1..15
                          mol_type = other DNA
                          organism = synthetic construct
SEQUENCE: 360
gagagaagtc cacca                                                          15

SEQ ID NO: 361            moltype = DNA  length = 16
FEATURE                   Location/Qualifiers
misc_feature              1..16
                          note = LNA antisense gapmer oligonucleotide
modified_base             1..16
                          mod_base = OTHER
                          note = Phosphorothiate Internucleoside linkages
modified_base             order(1..3,14..16)
                          mod_base = OTHER
                          note = LNA nucleosides
source                    1..16
                          mol_type = other DNA
                          organism = synthetic construct
SEQUENCE: 361
tgagagaagt ccacca                                                         16

SEQ ID NO: 362            moltype = DNA  length = 14
FEATURE                   Location/Qualifiers
misc_feature              1..14
                          note = LNA antisense gapmer oligonucleotide
modified_base             1..14
                          mod_base = OTHER
                          note = Phosphorothiate Internucleoside linkages
modified_base             order(1..3,12..14)
                          mod_base = OTHER
                          note = LNA nucleosides
source                    1..14
                          mol_type = other DNA
                          organism = synthetic construct
SEQUENCE: 362
gagagaagtc cacc                                                           14

SEQ ID NO: 363            moltype = DNA  length = 15
FEATURE                   Location/Qualifiers
misc_feature              1..15
                          note = LNA antisense gapmer oligonucleotide
modified_base             1..15
                          mod_base = OTHER
                          note = Phosphorothiate Internucleoside linkages
modified_base             order(1..3,13..15)
                          mod_base = OTHER
                          note = LNA nucleosides
source                    1..15
                          mol_type = other DNA
                          organism = synthetic construct
SEQUENCE: 363
tgagagaagt ccacc                                                          15

SEQ ID NO: 364            moltype = DNA  length = 14
FEATURE                   Location/Qualifiers
misc_feature              1..14
                          note = LNA antisense gapmer oligonucleotide
modified_base             1..14
                          mod_base = OTHER
                          note = Phosphorothiate Internucleoside linkages
modified_base             order(1..3,12..14)
                          mod_base = OTHER
                          note = LNA nucleosides
source                    1..14
                          mol_type = other DNA
                          organism = synthetic construct
SEQUENCE: 364
tgagagaagt ccac                                                           14
```

| SEQ ID NO: 365 | moltype = DNA  length = 13 |
| --- | --- |
| FEATURE | Location/Qualifiers |
| misc_feature | 1..13 |
| | note = LNA antisense gapmer oligonucleotide |
| modified_base | 1..13 |
| | mod_base = OTHER |
| | note = Phosphorothiate Internucleoside linkages |
| modified_base | order(1..3,12,13) |
| | mod_base = OTHER |
| | note = LNA nucleosides |
| modified_base | order(5,8) |
| | mod_base = OTHER |
| | note = 5-methyl c |
| source | 1..13 |
| | mol_type = other DNA |
| | organism = synthetic construct |

SEQUENCE: 365
aaaacgccgc aga                                                              13

| SEQ ID NO: 366 | moltype = DNA  length = 14 |
| --- | --- |
| FEATURE | Location/Qualifiers |
| misc_feature | 1..14 |
| | note = LNA antisense gapmer oligonucleotide |
| modified_base | 1..14 |
| | mod_base = OTHER |
| | note = Phosphorothiate Internucleoside linkages |
| modified_base | order(1..3,12..14) |
| | mod_base = OTHER |
| | note = LNA nucleosides |
| modified_base | order(6,9) |
| | mod_base = OTHER |
| | note = 5-methyl c |
| source | 1..14 |
| | mol_type = other DNA |
| | organism = synthetic construct |

SEQUENCE: 366
taaaacgccg caga                                                             14

| SEQ ID NO: 367 | moltype = DNA  length = 15 |
| --- | --- |
| FEATURE | Location/Qualifiers |
| misc_feature | 1..15 |
| | note = LNA antisense gapmer oligonucleotide |
| modified_base | 1..15 |
| | mod_base = OTHER |
| | note = Phosphorothiate Internucleoside linkages |
| modified_base | order(1..3,13..15) |
| | mod_base = OTHER |
| | note = LNA nucleosides |
| modified_base | order(7,10) |
| | mod_base = OTHER |
| | note = 5-methyl c |
| source | 1..15 |
| | mol_type = other DNA |
| | organism = synthetic construct |

SEQUENCE: 367
ataaaacgcc gcaga                                                            15

| SEQ ID NO: 368 | moltype = DNA  length = 16 |
| --- | --- |
| FEATURE | Location/Qualifiers |
| misc_feature | 1..16 |
| | note = LNA antisense gapmer oligonucleotide |
| modified_base | 1..16 |
| | mod_base = OTHER |
| | note = Phosphorothiate Internucleoside linkages |
| modified_base | order(1..3,14..16) |
| | mod_base = OTHER |
| | note = LNA nucleosides |
| modified_base | order(8,11) |
| | mod_base = OTHER |
| | note = 5-methyl c |
| source | 1..16 |
| | mol_type = other DNA |
| | organism = synthetic construct |

SEQUENCE: 368
gataaaacgc cgcaga                                                           16

| SEQ ID NO: 369 | moltype = DNA  length = 14 |
| --- | --- |
| FEATURE | Location/Qualifiers |

-continued

```
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
modified_base           order(7,10)
                        mod_base = OTHER
                        note = 5-methyl c
source                  1..14
                        mol_type = other DNA
                        organism = synthetic construct
SEQUENCE: 369
ataaaacgcc gcag                                                          14

SEQ ID NO: 370          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
modified_base           order(8,11)
                        mod_base = OTHER
                        note = 5-methyl c
source                  1..15
                        mol_type = other DNA
                        organism = synthetic construct
SEQUENCE: 370
gataaaacgc cgcag                                                         15

SEQ ID NO: 371          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           order(9,12)
                        mod_base = OTHER
                        note = 5-methyl c
source                  1..16
                        mol_type = other DNA
                        organism = synthetic construct
SEQUENCE: 371
tgataaaacg ccgcag                                                        16

SEQ ID NO: 372          moltype = DNA  length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
                        mod_base = OTHER
                        note = LNA nucleosides
modified_base           order(7,10)
                        mod_base = OTHER
                        note = 5-methyl c
source                  1..13
                        mol_type = other DNA
                        organism = synthetic construct
SEQUENCE: 372
ataaaacgcc gca                                                           13

SEQ ID NO: 373          moltype = DNA  length = 14
FEATURE                 Location/Qualifiers
misc_feature            1..14
                        note = LNA antisense gapmer oligonucleotide
modified_base           1..14
```

```
                        mod_base = OTHER
                        note = Phosphorothiate Internucleoside linkages
modified_base           order(1..3,12..14)
                        mod_base = OTHER
                        note = LNA nucleosides
modified_base           order(8,11)
                        mod_base = OTHER
                        note = 5-methyl c
source                  1..14
                        mol_type = other DNA
                        organism = synthetic construct
SEQUENCE: 373
gataaaacgc cgca                                                                 14

SEQ ID NO: 374          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
modified_base           order(9,12)
                        mod_base = OTHER
                        note = 5-methyl c
source                  1..15
                        mol_type = other DNA
                        organism = synthetic construct
SEQUENCE: 374
tgataaaacg ccgca                                                                15

SEQ ID NO: 375          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           order(10,13)
                        mod_base = OTHER
                        note = 5-methyl c
source                  1..16
                        mol_type = other DNA
                        organism = synthetic construct
SEQUENCE: 375
atgataaaac gccgca                                                               16

SEQ ID NO: 376          moltype = DNA  length = 12
FEATURE                 Location/Qualifiers
misc_feature            1..12
                        note = LNA antisense gapmer oligonucleotide
modified_base           1..12
                        mod_base = OTHER
                        note = Phosphorothiate Internucleoside linkages
modified_base           order(1,2,11,12)
                        mod_base = OTHER
                        note = LNA nucleosides
modified_base           order(7,10)
                        mod_base = OTHER
                        note = 5-methyl c
source                  1..12
                        mol_type = other DNA
                        organism = synthetic construct
SEQUENCE: 376
ataaacgcc gc                                                                    12

SEQ ID NO: 377          moltype = DNA  length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
```

```
                              mod_base = OTHER
                              note = LNA nucleosides
modified_base                 order(8,11)
                              mod_base = OTHER
                              note = 5-methyl c
source                        1..13
                              mol_type = other DNA
                              organism = synthetic construct
SEQUENCE: 377
gataaaacgc cgc                                                         13

SEQ ID NO: 378                moltype = DNA  length = 14
FEATURE                       Location/Qualifiers
misc_feature                  1..14
                              note = LNA antisense gapmer oligonucleotide
modified_base                 1..14
                              mod_base = OTHER
                              note = Phosphorothiate Internucleoside linkages
modified_base                 order(1..3,12..14)
                              mod_base = OTHER
                              note = LNA nucleosides
modified_base                 9
                              mod_base = OTHER
                              note = 5-methyl c
source                        1..14
                              mol_type = other DNA
                              organism = synthetic construct
SEQUENCE: 378
tgataaaacg ccgc                                                        14

SEQ ID NO: 379                moltype = DNA  length = 15
FEATURE                       Location/Qualifiers
misc_feature                  1..15
                              note = LNA antisense gapmer oligonucleotide
modified_base                 1..15
                              mod_base = OTHER
                              note = Phosphorothiate Internucleoside linkages
modified_base                 order(1..3,13..15)
                              mod_base = OTHER
                              note = LNA nucleosides
modified_base                 10
                              mod_base = OTHER
                              note = 5-methyl c
source                        1..15
                              mol_type = other DNA
                              organism = synthetic construct
SEQUENCE: 379
atgataaaac gccgc                                                       15

SEQ ID NO: 380                moltype = DNA  length = 12
FEATURE                       Location/Qualifiers
misc_feature                  1..12
                              note = LNA antisense gapmer oligonucleotide
modified_base                 1..12
                              mod_base = OTHER
                              note = Phosphorothiate Internucleoside linkages
modified_base                 order(1,2,11,12)
                              mod_base = OTHER
                              note = LNA nucleosides
modified_base                 8
                              mod_base = OTHER
                              note = 5-methyl c
source                        1..12
                              mol_type = other DNA
                              organism = synthetic construct
SEQUENCE: 380
gataaaacgc cg                                                          12

SEQ ID NO: 381                moltype = DNA  length = 13
FEATURE                       Location/Qualifiers
misc_feature                  1..13
                              note = LNA antisense gapmer oligonucleotide
modified_base                 1..13
                              mod_base = OTHER
                              note = Phosphorothiate Internucleoside linkages
modified_base                 order(1..3,12,13)
                              mod_base = OTHER
                              note = LNA nucleosides
modified_base                 9
```

-continued

```
                        mod_base = OTHER
                        note = 5-methyl c
source                  1..13
                        mol_type = other DNA
                        organism = synthetic construct
SEQUENCE: 381
tgataaaacg ccg                                                         13

SEQ ID NO: 382          moltype = DNA  length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
modified_base           10
                        mod_base = OTHER
                        note = 5-methyl c
source                  1..14
                        mol_type = other DNA
                        organism = synthetic construct
SEQUENCE: 382
atgataaaac gccg                                                        14

SEQ ID NO: 383          moltype = DNA  length = 12
FEATURE                 Location/Qualifiers
misc_feature            1..12
                        note = LNA antisense gapmer oligonucleotide
modified_base           1..12
                        mod_base = OTHER
                        note = Phosphorothiate Internucleoside linkages
modified_base           order(1,2,11,12)
                        mod_base = OTHER
                        note = LNA nucleosides
modified_base           9
                        mod_base = OTHER
                        note = 5-methyl c
source                  1..12
                        mol_type = other DNA
                        organism = synthetic construct
SEQUENCE: 383
tgataaaacg cc                                                          12

SEQ ID NO: 384          moltype = DNA  length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
                        mod_base = OTHER
                        note = LNA nucleosides
modified_base           10
                        mod_base = OTHER
                        note = 5-methyl c
source                  1..13
                        mol_type = other DNA
                        organism = synthetic construct
SEQUENCE: 384
atgataaaac gcc                                                         13

SEQ ID NO: 385          moltype = DNA  length = 12
FEATURE                 Location/Qualifiers
misc_feature            1..12
                        note = LNA antisense gapmer oligonucleotide
modified_base           1..12
                        mod_base = OTHER
                        note = Phosphorothiate Internucleoside linkages
modified_base           order(1,2,11,12)
                        mod_base = OTHER
                        note = LNA nucleosides
modified_base           10
                        mod_base = OTHER
                        note = 5-methyl c
source                  1..12
```

```
                        mol_type = other DNA
                        organism = synthetic construct
SEQUENCE: 385
atgataaaac gc                                                          12

SEQ ID NO: 386          moltype = DNA   length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
                        mod_base = OTHER
                        note = LNA nucleosides
source                  1..13
                        mol_type = other DNA
                        organism = synthetic construct
SEQUENCE: 386
tagcagcagg atg                                                         13

SEQ ID NO: 387          moltype = DNA   length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
source                  1..14
                        mol_type = other DNA
                        organism = synthetic construct
SEQUENCE: 387
atagcagcag gatg                                                        14

SEQ ID NO: 388          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 388
catagcagca ggatg                                                       15

SEQ ID NO: 389          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct
SEQUENCE: 389
gcatagcagc aggatg                                                      16

SEQ ID NO: 390          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
```

```
source                          1..15
                                mol_type = other DNA
                                organism = synthetic construct
SEQUENCE: 390
gcatagcagc aggat                                                              15

SEQ ID NO: 391                  moltype = DNA   length = 16
FEATURE                         Location/Qualifiers
misc_feature                    1..16
                                note = LNA antisense gapmer oligonucleotide
modified_base                   1..16
                                mod_base = OTHER
                                note = Phosphorothiate Internucleoside linkages
modified_base                   order(1..3,14..16)
                                mod_base = OTHER
                                note = LNA nucleosides
source                          1..16
                                mol_type = other DNA
                                organism = synthetic construct
SEQUENCE: 391
ggcatagcag caggat                                                             16

SEQ ID NO: 392                  moltype = DNA   length = 16
FEATURE                         Location/Qualifiers
misc_feature                    1..16
                                note = LNA antisense gapmer oligonucleotide
modified_base                   1..16
                                mod_base = OTHER
                                note = Phosphorothiate Internucleoside linkages
modified_base                   order(1..3,14..16)
                                mod_base = OTHER
                                note = LNA nucleosides
source                          1..16
                                mol_type = other DNA
                                organism = synthetic construct
SEQUENCE: 392
gaggcatagc agcagg                                                             16

SEQ ID NO: 393                  moltype = DNA   length = 16
FEATURE                         Location/Qualifiers
misc_feature                    1..16
                                note = LNA antisense gapmer oligonucleotide
modified_base                   1..16
                                mod_base = OTHER
                                note = Phosphorothiate Internucleoside linkages
modified_base                   order(1..3,14..16)
                                mod_base = OTHER
                                note = LNA nucleosides
source                          1..16
                                mol_type = other DNA
                                organism = synthetic construct
SEQUENCE: 393
tgaggcatag cagcag                                                             16

SEQ ID NO: 394                  moltype = DNA   length = 15
FEATURE                         Location/Qualifiers
misc_feature                    1..15
                                note = LNA antisense gapmer oligonucleotide
modified_base                   1..15
                                mod_base = OTHER
                                note = Phosphorothiate Internucleoside linkages
modified_base                   order(1..3,13..15)
                                mod_base = OTHER
                                note = LNA nucleosides
source                          1..15
                                mol_type = other DNA
                                organism = synthetic construct
SEQUENCE: 394
tgaggcatag cagca                                                              15

SEQ ID NO: 395                  moltype = DNA   length = 16
FEATURE                         Location/Qualifiers
misc_feature                    1..16
                                note = LNA antisense gapmer oligonucleotide
modified_base                   1..16
                                mod_base = OTHER
                                note = Phosphorothiate Internucleoside linkages
modified_base                   order(1..3,14..16)
                                mod_base = OTHER
```

```
                        note = LNA nucleosides
source                  1..16
                        mol_type = other DNA
                        organism = synthetic construct
SEQUENCE: 395
atgaggcata gcagca                                                  16

SEQ ID NO: 396          moltype = DNA   length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
source                  1..14
                        mol_type = other DNA
                        organism = synthetic construct
SEQUENCE: 396
tgaggcatag cagc                                                    14

SEQ ID NO: 397          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 397
atgaggcata gcagc                                                   15

SEQ ID NO: 398          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct
SEQUENCE: 398
gatgaggcat agcagc                                                  16

SEQ ID NO: 399          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 399
gatgaggcat agcag                                                   15

SEQ ID NO: 400          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
```

```
                        mod_base = OTHER
                        note = LNA nucleosides
source                  1..16
                        mol_type = other DNA
                        organism = synthetic construct
SEQUENCE: 400
agatgaggca tagcag                                                   16

SEQ ID NO: 401          moltype = DNA  length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
source                  1..14
                        mol_type = other DNA
                        organism = synthetic construct
SEQUENCE: 401
gatgaggcat agca                                                     14

SEQ ID NO: 402          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 402
agatgaggca tagca                                                    15

SEQ ID NO: 403          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct
SEQUENCE: 403
aagatgaggc atagca                                                   16

SEQ ID NO: 404          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct
SEQUENCE: 404
aagaagatga ggcata                                                   16

SEQ ID NO: 405          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
```

|  |  |  |
|---|---|---|
| modified_base | order(1..3,13..15)<br>mod_base = OTHER<br>note = LNA nucleosides | |
| source | 1..15<br>mol_type = other DNA<br>organism = synthetic construct | |
| SEQUENCE: 405<br>aagaagatga ggcat | | 15 |
| SEQ ID NO: 406<br>FEATURE<br>misc_feature | moltype = DNA  length = 15<br>Location/Qualifiers<br>1..15<br>note = LNA antisense gapmer oligonucleotide | |
| modified_base | 1..15<br>mod_base = OTHER<br>note = Phosphorothiate Internucleoside linkages | |
| modified_base | order(1..3,13..15)<br>mod_base = OTHER<br>note = LNA nucleosides | |
| source | 1..15<br>mol_type = other DNA<br>organism = synthetic construct | |
| SEQUENCE: 406<br>tgggatggga ataca | | 15 |
| SEQ ID NO: 407<br>FEATURE<br>misc_feature | moltype = DNA  length = 16<br>Location/Qualifiers<br>1..16<br>note = LNA antisense gapmer oligonucleotide | |
| modified_base | 1..16<br>mod_base = OTHER<br>note = Phosphorothiate Internucleoside linkages | |
| modified_base | order(1..3,14..16)<br>mod_base = OTHER<br>note = LNA nucleosides | |
| source | 1..16<br>mol_type = other DNA<br>organism = synthetic construct | |
| SEQUENCE: 407<br>atgggatggg aataca | | 16 |
| SEQ ID NO: 408<br>FEATURE<br>misc_feature | moltype = DNA  length = 14<br>Location/Qualifiers<br>1..14<br>note = LNA antisense gapmer oligonucleotide | |
| modified_base | 1..14<br>mod_base = OTHER<br>note = Phosphorothiate Internucleoside linkages | |
| modified_base | order(1..3,12..14)<br>mod_base = OTHER<br>note = LNA nucleosides | |
| source | 1..14<br>mol_type = other DNA<br>organism = synthetic construct | |
| SEQUENCE: 408<br>tgggatggga atac | | 14 |
| SEQ ID NO: 409<br>FEATURE<br>misc_feature | moltype = DNA  length = 15<br>Location/Qualifiers<br>1..15<br>note = LNA antisense gapmer oligonucleotide | |
| modified_base | 1..15<br>mod_base = OTHER<br>note = Phosphorothiate Internucleoside linkages | |
| modified_base | order(1..3,13..15)<br>mod_base = OTHER<br>note = LNA nucleosides | |
| source | 1..15<br>mol_type = other DNA<br>organism = synthetic construct | |
| SEQUENCE: 409<br>atgggatggg aatac | | 15 |
| SEQ ID NO: 410<br>FEATURE<br>misc_feature | moltype = DNA  length = 16<br>Location/Qualifiers<br>1..16<br>note = LNA antisense gapmer oligonucleotide | |
| modified_base | 1..16<br>mod_base = OTHER | |

```
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct
SEQUENCE: 410
gatgggatgg gaatac                                                        16

SEQ ID NO: 411          moltype = DNA   length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
source                  1..14
                        mol_type = other DNA
                        organism = synthetic construct
SEQUENCE: 411
atgggatggg aata                                                          14

SEQ ID NO: 412          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 412
gatgggatgg gaata                                                         15

SEQ ID NO: 413          moltype = DNA   length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
source                  1..14
                        mol_type = other DNA
                        organism = synthetic construct
SEQUENCE: 413
gatgggatgg gaat                                                          14

SEQ ID NO: 414          moltype = DNA   length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
source                  1..14
                        mol_type = other DNA
                        organism = synthetic construct
SEQUENCE: 414
aaccactgaa caaa                                                          14

SEQ ID NO: 415          moltype = DNA   length = 12
FEATURE                 Location/Qualifiers
misc_feature            1..12
                        note = LNA antisense gapmer oligonucleotide
misc_feature            1..12
```

|   |   |   |
|---|---|---|
| modified_base | note = Phosphorothiate Internucleoside linkages order(1,2,11,12) mod_base = OTHER note = LNA nucleosides | |
| source | 1..12 mol_type = other DNA organism = synthetic construct | |
| SEQUENCE: 415 cgaaccactg aa | | 12 |
| SEQ ID NO: 416 FEATURE misc_feature | moltype = DNA length = 13 Location/Qualifiers 1..13 note = LNA antisense gapmer oligonucleotide | |
| modified_base | 1..13 mod_base = OTHER note = Phosphorothiate Internucleoside linkages | |
| modified_base | order(1..3,12,13) mod_base = OTHER note = LNA nucleosides | |
| source | 1..13 mol_type = other DNA organism = synthetic construct | |
| SEQUENCE: 416 ggggaaagc cct | | 13 |
| SEQ ID NO: 417 FEATURE misc_feature | moltype = DNA length = 14 Location/Qualifiers 1..14 note = LNA antisense gapmer oligonucleotide | |
| modified_base | 1..14 mod_base = OTHER note = Phosphorothiate Internucleoside linkages | |
| modified_base | order(1..3,12..14) mod_base = OTHER note = LNA nucleosides | |
| source | 1..14 mol_type = other DNA organism = synthetic construct | |
| SEQUENCE: 417 tgggggaaag ccct | | 14 |
| SEQ ID NO: 418 FEATURE misc_feature | moltype = DNA length = 15 Location/Qualifiers 1..15 note = LNA antisense gapmer oligonucleotide | |
| modified_base | 1..15 mod_base = OTHER note = Phosphorothiate Internucleoside linkages | |
| modified_base | order(1..3,13..15) mod_base = OTHER note = LNA nucleosides | |
| modified_base | 5 mod_base = OTHER note = 5-methyl c | |
| source | 1..15 mol_type = other DNA organism = synthetic construct | |
| SEQUENCE: 418 gcaacggggt aaagg | | 15 |
| SEQ ID NO: 419 FEATURE misc_feature | moltype = DNA length = 14 Location/Qualifiers 1..14 note = LNA antisense gapmer oligonucleotide | |
| modified_base | 1..14 mod_base = OTHER note = Phosphorothiate Internucleoside linkages | |
| modified_base | order(1..3,12..14) mod_base = OTHER note = LNA nucleosides | |
| modified_base | 5 mod_base = OTHER note = 5-methyl c | |
| source | 1..14 mol_type = other DNA organism = synthetic construct | |
| SEQUENCE: 419 gcaacggggt aaag | | 14 |

```
SEQ ID NO: 420            moltype = DNA  length = 13
FEATURE                   Location/Qualifiers
misc_feature              1..13
                          note = LNA antisense gapmer oligonucleotide
modified_base             1..13
                          mod_base = OTHER
                          note = Phosphorothiate Internucleoside linkages
modified_base             order(1..3,12,13)
                          mod_base = OTHER
                          note = LNA nucleosides
modified_base             5
                          mod_base = OTHER
                          note = 5-methyl c
source                    1..13
                          mol_type = other DNA
                          organism = synthetic construct
SEQUENCE: 420
gcaacggggt aaa                                                             13

SEQ ID NO: 421            moltype = DNA  length = 15
FEATURE                   Location/Qualifiers
misc_feature              1..15
                          note = LNA antisense gapmer oligonucleotide
modified_base             1..15
                          mod_base = OTHER
                          note = Phosphorothiate Internucleoside linkages
modified_base             order(1..3,13..15)
                          mod_base = OTHER
                          note = LNA nucleosides
source                    1..15
                          mol_type = other DNA
                          organism = synthetic construct
SEQUENCE: 421
agcaaacact tggca                                                           15

SEQ ID NO: 422            moltype = DNA  length = 16
FEATURE                   Location/Qualifiers
misc_feature              1..16
                          note = LNA antisense gapmer oligonucleotide
modified_base             1..16
                          mod_base = OTHER
                          note = Phosphorothiate Internucleoside linkages
modified_base             order(1..3,14..16)
                          mod_base = OTHER
                          note = LNA nucleosides
source                    1..16
                          mol_type = other DNA
                          organism = synthetic construct
SEQUENCE: 422
cagcaaaacac ttggca                                                         16

SEQ ID NO: 423            moltype = DNA  length = 15
FEATURE                   Location/Qualifiers
misc_feature              1..15
                          note = LNA antisense gapmer oligonucleotide
modified_base             1..15
                          mod_base = OTHER
                          note = Phosphorothiate Internucleoside linkages
modified_base             order(1..3,13..15)
                          mod_base = OTHER
                          note = LNA nucleosides
source                    1..15
                          mol_type = other DNA
                          organism = synthetic construct
SEQUENCE: 423
cagcaaaacac ttggc                                                          15

SEQ ID NO: 424            moltype = DNA  length = 16
FEATURE                   Location/Qualifiers
modified_base             1..16
                          mod_base = OTHER
                          note = Phosphorothiate Internucleoside linkages
modified_base             order(1..3,14..16)
                          mod_base = OTHER
                          note = LNA nucleosides
source                    1..16
                          mol_type = other DNA
                          organism = synthetic construct
```

```
misc_feature              1..16
                          note = LNA antisense gapmer oligonucleotide
SEQUENCE: 424
tcagcaaaca cttggc                                                      16

SEQ ID NO: 425            moltype = DNA  length = 15
FEATURE                   Location/Qualifiers
misc_feature              1..15
                          note = LNA antisense gapmer oligonucleotide
modified_base             1..15
                          mod_base = OTHER
                          note = Phosphorothiate Internucleoside linkages
modified_base             order(1..3,13..15)
                          mod_base = OTHER
                          note = LNA nucleosides
source                    1..15
                          mol_type = other DNA
                          organism = synthetic construct
SEQUENCE: 425
tcagcaaaca cttgg                                                       15

SEQ ID NO: 426            moltype = DNA  length = 13
FEATURE                   Location/Qualifiers
misc_feature              1..13
                          note = LNA antisense gapmer oligonucleotide
modified_base             1..13
                          mod_base = OTHER
                          note = Phosphorothiate Internucleoside linkages
modified_base             order(1..3,12,13)
                          mod_base = OTHER
                          note = LNA nucleosides
source                    1..13
                          mol_type = other DNA
                          organism = synthetic construct
SEQUENCE: 426
gcagtatgga tcg                                                         13

SEQ ID NO: 427            moltype = DNA  length = 14
FEATURE                   Location/Qualifiers
misc_feature              1..14
                          note = LNA antisense gapmer oligonucleotide
modified_base             1..14
                          mod_base = OTHER
                          note = Phosphorothiate Internucleoside linkages
modified_base             order(1..3,12..14)
                          mod_base = OTHER
                          note = LNA nucleosides
source                    1..14
                          mol_type = other DNA
                          organism = synthetic construct
SEQUENCE: 427
cgcagtatgg atcg                                                        14

SEQ ID NO: 428            moltype = DNA  length = 16
FEATURE                   Location/Qualifiers
misc_feature              1..16
                          note = LNA antisense gapmer oligonucleotide
modified_base             1..16
                          mod_base = OTHER
                          note = Phosphorothiate Internucleoside linkages
modified_base             order(1..3,14..16)
                          mod_base = OTHER
                          note = LNA nucleosides
source                    1..16
                          mol_type = other DNA
                          organism = synthetic construct
SEQUENCE: 428
tccgcagtat ggatcg                                                      16

SEQ ID NO: 429            moltype = DNA  length = 14
FEATURE                   Location/Qualifiers
misc_feature              1..14
                          note = LNA antisense gapmer oligonucleotide
modified_base             1..14
                          mod_base = OTHER
                          note = Phosphorothiate Internucleoside linkages
modified_base             order(1..3,12..14)
                          mod_base = OTHER
                          note = LNA nucleosides
```

```
source                  1..14
                        mol_type = other DNA
                        organism = synthetic construct
SEQUENCE: 429
ccgcagtatg gatc                                                              14

SEQ ID NO: 430          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 430
tccgcagtat ggatc                                                             15

SEQ ID NO: 431          moltype = DNA   length = 12
FEATURE                 Location/Qualifiers
misc_feature            1..12
                        note = LNA antisense gapmer oligonucleotide
modified_base           1..12
                        mod_base = OTHER
                        note = Phosphorothiate Internucleoside linkages
modified_base           order(1,2,11,12)
                        mod_base = OTHER
                        note = LNA nucleosides
source                  1..12
                        mol_type = other DNA
                        organism = synthetic construct
SEQUENCE: 431
cgcagtatgg at                                                                12

SEQ ID NO: 432          moltype = DNA   length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
                        mod_base = OTHER
                        note = LNA nucleosides
source                  1..13
                        mol_type = other DNA
                        organism = synthetic construct
SEQUENCE: 432
ccgcagtatg gat                                                               13

SEQ ID NO: 433          moltype = DNA   length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
source                  1..14
                        mol_type = other DNA
                        organism = synthetic construct
SEQUENCE: 433
tccgcagtat ggat                                                              14

SEQ ID NO: 434          moltype = DNA   length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
                        mod_base = OTHER
```

```
                        note = LNA nucleosides
source                  1..13
                        mol_type = other DNA
                        organism = synthetic construct
SEQUENCE: 434
tccgcagtat gga                                                          13

SEQ ID NO: 435          moltype = DNA  length = 12
FEATURE                 Location/Qualifiers
misc_feature            1..12
                        note = LNA antisense gapmer oligonucleotide
modified_base           1..12
                        mod_base = OTHER
                        note = Phosphorothiate Internucleoside linkages
modified_base           order(1,2,11,12)
                        mod_base = OTHER
                        note = LNA nucleosides
modified_base           4
                        mod_base = OTHER
                        note = 5-methyl c
source                  1..12
                        mol_type = other DNA
                        organism = synthetic construct
SEQUENCE: 435
ttccgcagta tg                                                           12

SEQ ID NO: 436          moltype = DNA  length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
                        mod_base = OTHER
                        note = LNA nucleosides
source                  1..13
                        mol_type = other DNA
                        organism = synthetic construct
SEQUENCE: 436
cgtaaagaga ggt                                                          13

SEQ ID NO: 437          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           4
                        mod_base = OTHER
                        note = 5-methyl c
source                  1..16
                        mol_type = other DNA
                        organism = synthetic construct
SEQUENCE: 437
ccgcgtaaag agaggt                                                       16

SEQ ID NO: 438          moltype = DNA  length = 12
FEATURE                 Location/Qualifiers
misc_feature            1..12
                        note = LNA antisense gapmer oligonucleotide
modified_base           1..12
                        mod_base = OTHER
                        note = Phosphorothiate Internucleoside linkages
modified_base           order(1,2,11,12)
                        mod_base = OTHER
                        note = LNA nucleosides
source                  1..12
                        mol_type = other DNA
                        organism = synthetic construct
SEQUENCE: 438
cgtaaagaga gg                                                           12

SEQ ID NO: 439          moltype = DNA  length = 14
FEATURE                 Location/Qualifiers
```

```
misc_feature             1..14
                         note = LNA antisense gapmer oligonucleotide
modified_base            1..14
                         mod_base = OTHER
                         note = Phosphorothiate Internucleoside linkages
modified_base            order(1..3,12..14)
                         mod_base = OTHER
                         note = LNA nucleosides
source                   1..14
                         mol_type = other DNA
                         organism = synthetic construct
SEQUENCE: 439
cgcgtaaaga gagg                                                              14

SEQ ID NO: 440           moltype = DNA  length = 15
FEATURE                  Location/Qualifiers
misc_feature             1..15
                         note = LNA antisense gapmer oligonucleotide
modified_base            1..15
                         mod_base = OTHER
                         note = Phosphorothiate Internucleoside linkages
modified_base            order(1..3,13..15)
                         mod_base = OTHER
                         note = LNA nucleosides
modified_base            4
                         mod_base = OTHER
                         note = 5-methyl c
source                   1..15
                         mol_type = other DNA
                         organism = synthetic construct
SEQUENCE: 440
ccgcgtaaag agagg                                                             15

SEQ ID NO: 441           moltype = DNA  length = 13
FEATURE                  Location/Qualifiers
misc_feature             1..13
                         note = LNA antisense gapmer oligonucleotide
modified_base            1..13
                         mod_base = OTHER
                         note = Phosphorothiate Internucleoside linkages
modified_base            order(1..3,12,13)
                         mod_base = OTHER
                         note = LNA nucleosides
source                   1..13
                         mol_type = other DNA
                         organism = synthetic construct
SEQUENCE: 441
cgcgtaaaga gag                                                               13

SEQ ID NO: 442           moltype = DNA  length = 14
FEATURE                  Location/Qualifiers
misc_feature             1..14
                         note = LNA antisense gapmer oligonucleotide
modified_base            1..14
                         mod_base = OTHER
                         note = Phosphorothiate Internucleoside linkages
modified_base            order(1..3,12..14)
                         mod_base = OTHER
                         note = LNA nucleosides
modified_base            4
                         mod_base = OTHER
                         note = 5-methyl c
source                   1..14
                         mol_type = other DNA
                         organism = synthetic construct
SEQUENCE: 442
ccgcgtaaag agag                                                              14

SEQ ID NO: 443           moltype = DNA  length = 12
FEATURE                  Location/Qualifiers
misc_feature             1..12
                         note = LNA antisense gapmer oligonucleotide
modified_base            1..12
                         mod_base = OTHER
                         note = Phosphorothiate Internucleoside linkages
modified_base            order(1,2,11,12)
                         mod_base = OTHER
                         note = LNA nucleosides
modified_base            3
```

```
                        mod_base = OTHER
                        note = 5-methyl c
source                  1..12
                        mol_type = other DNA
                        organism = synthetic construct
SEQUENCE: 443
cgcgtaaaga ga                                                              12

SEQ ID NO: 444          moltype = DNA   length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
                        mod_base = OTHER
                        note = LNA nucleosides
modified_base           4
                        mod_base = OTHER
                        note = 5-methyl c
source                  1..13
                        mol_type = other DNA
                        organism = synthetic construct
SEQUENCE: 444
ccgcgtaaag aga                                                             13

SEQ ID NO: 445          moltype = DNA   length = 12
FEATURE                 Location/Qualifiers
misc_feature            1..12
                        note = LNA antisense gapmer oligonucleotide
modified_base           1..12
                        mod_base = OTHER
                        note = Phosphorothiate Internucleoside linkages
modified_base           order(1,2,11,12)
                        mod_base = OTHER
                        note = LNA nucleosides
modified_base           4
                        mod_base = OTHER
                        note = 5-methyl c
source                  1..12
                        mol_type = other DNA
                        organism = synthetic construct
SEQUENCE: 445
ccgcgtaaag ag                                                              12

SEQ ID NO: 446          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
modified_base           9
                        mod_base = OTHER
                        note = 5-methyl c
source                  1..15
                        mol_type = other DNA
                        organism = synthetic construct
SEQUENCE: 446
ggcacagacg gggag                                                           15

SEQ ID NO: 447          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           10
                        mod_base = OTHER
                        note = 5-methyl c
source                  1..16
```

```
                        mol_type = other DNA
                        organism = synthetic construct
SEQUENCE: 447
aggcacagac ggggag                                                    16

SEQ ID NO: 448          moltype = DNA  length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
modified_base           9
                        mod_base = OTHER
                        note = 5-methyl c
source                  1..14
                        mol_type = other DNA
                        organism = synthetic construct
SEQUENCE: 448
ggcacagacg ggga                                                      14

SEQ ID NO: 449          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
modified_base           10
                        mod_base = OTHER
                        note = 5-methyl c
source                  1..15
                        mol_type = other DNA
                        organism = synthetic construct
SEQUENCE: 449
aggcacagac gggga                                                     15

SEQ ID NO: 450          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           11
                        mod_base = OTHER
                        note = 5-methyl c
source                  1..16
                        mol_type = other DNA
                        organism = synthetic construct
SEQUENCE: 450
aaggcacaga cgggga                                                    16

SEQ ID NO: 451          moltype = DNA  length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
modified_base           10
                        mod_base = OTHER
                        note = 5-methyl c
source                  1..14
                        mol_type = other DNA
                        organism = synthetic construct
SEQUENCE: 451
```
aggcacagac gggg                                                          14

SEQ ID NO: 452          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
modified_base           11
                        mod_base = OTHER
                        note = 5-methyl c
source                  1..15
                        mol_type = other DNA
                        organism = synthetic construct SEQUENCE: 452
aaggcacaga cgggg                                                         15

SEQ ID NO: 453          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           12
                        mod_base = OTHER
                        note = 5-methyl c
source                  1..16
                        mol_type = other DNA
                        organism = synthetic construct SEQUENCE: 453
gaaggcacag acgggg                                                        16

SEQ ID NO: 454          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           13
                        mod_base = OTHER
                        note = 5-methyl c
source                  1..16
                        mol_type = other DNA
                        organism = synthetic construct SEQUENCE: 454
agaaggcaca gacggg                                                        16

SEQ ID NO: 455          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct SEQUENCE: 455
gagaaggcac agacg                                                         15

SEQ ID NO: 456          moltype = DNA   length = 14
FEATURE                 Location/Qualifiers
misc_feature            1..14
                        note = LNA antisense gapmer oligonucleotide

```
modified_base            1..14
                         mod_base = OTHER
                         note = Phosphorothiate Internucleoside linkages
modified_base            order(1..3,12..14)
                         mod_base = OTHER
                         note = LNA nucleosides
source                   1..14
                         mol_type = other DNA
                         organism = synthetic construct
SEQUENCE: 456
cgaagtgcac acgg                                                              14

SEQ ID NO: 457           moltype = DNA   length = 14
FEATURE                  Location/Qualifiers
misc_feature             1..14
                         note = LNA antisense gapmer oligonucleotide
modified_base            1..14
                         mod_base = OTHER
                         note = Phosphorothiate Internucleoside linkages
modified_base            order(1..3,12..14)
                         mod_base = OTHER
                         note = LNA nucleosides
source                   1..14
                         mol_type = other DNA
                         organism = synthetic construct
SEQUENCE: 457
gcgaagtgca cacg                                                              14

SEQ ID NO: 458           moltype = DNA   length = 13
FEATURE                  Location/Qualifiers
misc_feature             1..13
                         note = LNA antisense gapmer oligonucleotide
modified_base            1..13
                         mod_base = OTHER
                         note = Phosphorothiate Internucleoside linkages
modified_base            order(1..3,12,13)
                         mod_base = OTHER
                         note = LNA nucleosides
source                   1..13
                         mol_type = other DNA
                         organism = synthetic construct
SEQUENCE: 458
gcgaagtgca cac                                                               13

SEQ ID NO: 459           moltype = DNA   length = 14
FEATURE                  Location/Qualifiers
misc_feature             1..14
                         note = LNA antisense gapmer oligonucleotide
modified_base            1..14
                         mod_base = OTHER
                         note = Phosphorothiate Internucleoside linkages
modified_base            order(1..3,12..14)
                         mod_base = OTHER
                         note = LNA nucleosides
source                   1..14
                         mol_type = other DNA
                         organism = synthetic construct
SEQUENCE: 459
agcgaagtgc acac                                                              14

SEQ ID NO: 460           moltype = DNA   length = 15
FEATURE                  Location/Qualifiers
misc_feature             1..15
                         note = LNA antisense gapmer oligonucleotide
modified_base            1..15
                         mod_base = OTHER
                         note = Phosphorothiate Internucleoside linkages
modified_base            order(1..3,13..15)
                         mod_base = OTHER
                         note = LNA nucleosides
modified_base            4
                         mod_base = OTHER
                         note = 5-methyl c
source                   1..15
                         mol_type = other DNA
                         organism = synthetic construct
SEQUENCE: 460
aagcgaagtg cacac                                                             15
```

-continued

| | |
|---|---|
| SEQ ID NO: 461 | moltype = DNA length = 16 |
| FEATURE | Location/Qualifiers |
| misc_feature | 1..16 |
| | note = LNA antisense gapmer oligonucleotide |
| modified_base | 1..16 |
| | mod_base = OTHER |
| | note = Phosphorothiate Internucleoside linkages |
| modified_base | order(1..3,14..16) |
| | mod_base = OTHER |
| | note = LNA nucleosides |
| modified_base | 5 |
| | mod_base = OTHER |
| | note = 5-methyl c |
| source | 1..16 |
| | mol_type = other DNA |
| | organism = synthetic construct |

SEQUENCE: 461
gaagcgaagt gcacac                                                          16

| | |
|---|---|
| SEQ ID NO: 462 | moltype = DNA length = 13 |
| FEATURE | Location/Qualifiers |
| misc_feature | 1..13 |
| | note = LNA antisense gapmer oligonucleotide |
| modified_base | 1..13 |
| | mod_base = OTHER |
| | note = Phosphorothiate Internucleoside linkages |
| modified_base | order(1..3,12,13) |
| | mod_base = OTHER |
| | note = LNA nucleosides |
| source | 1..13 |
| | mol_type = other DNA |
| | organism = synthetic construct |

SEQUENCE: 462
agcgaagtgc aca                                                             13

| | |
|---|---|
| SEQ ID NO: 463 | moltype = DNA length = 14 |
| FEATURE | Location/Qualifiers |
| misc_feature | 1..14 |
| | note = LNA antisense gapmer oligonucleotide |
| modified_base | 1..14 |
| | mod_base = OTHER |
| | note = Phosphorothiate Internucleoside linkages |
| modified_base | order(1..3,12..14) |
| | mod_base = OTHER |
| | note = LNA nucleosides |
| modified_base | 4 |
| | mod_base = OTHER |
| | note = 5-methyl c |
| source | 1..14 |
| | mol_type = other DNA |
| | organism = synthetic construct |

SEQUENCE: 463
aagcgaagtg caca                                                            14

| | |
|---|---|
| SEQ ID NO: 464 | moltype = DNA length = 16 |
| FEATURE | Location/Qualifiers |
| misc_feature | 1..16 |
| | note = LNA antisense gapmer oligonucleotide |
| modified_base | 1..16 |
| | mod_base = OTHER |
| | note = Phosphorothiate Internucleoside linkages |
| modified_base | order(1..3,14..16) |
| | mod_base = OTHER |
| | note = LNA nucleosides |
| modified_base | 6 |
| | mod_base = OTHER |
| | note = 5-methyl c |
| source | 1..16 |
| | mol_type = other DNA |
| | organism = synthetic construct |

SEQUENCE: 464
tgaagcgaag tgcaca                                                          16

| | |
|---|---|
| SEQ ID NO: 465 | moltype = DNA length = 13 |
| FEATURE | Location/Qualifiers |
| misc_feature | 1..13 |
| | note = LNA antisense gapmer oligonucleotide |
| modified_base | 1..13 |
| | mod_base = OTHER |

```
                          note = Phosphorothiate Internucleoside linkages
modified_base             order(1..3,12,13)
                          mod_base = OTHER
                          note = LNA nucleosides
modified_base             4
                          mod_base = OTHER
                          note = 5-methyl c
source                    1..13
                          mol_type = other DNA
                          organism = synthetic construct
SEQUENCE: 465
aagcgaagtg cac                                                                      13

SEQ ID NO: 466            moltype = DNA  length = 14
FEATURE                   Location/Qualifiers
misc_feature              1..14
                          note = LNA antisense gapmer oligonucleotide
modified_base             1..14
                          mod_base = OTHER
                          note = Phosphorothiate Internucleoside linkages
modified_base             order(1..3,12..14)
                          mod_base = OTHER
                          note = LNA nucleosides
modified_base             5
                          mod_base = OTHER
                          note = 5-methyl c
source                    1..14
                          mol_type = other DNA
                          organism = synthetic construct
SEQUENCE: 466
gaagcgaagt gcac                                                                     14

SEQ ID NO: 467            moltype = DNA  length = 15
FEATURE                   Location/Qualifiers
misc_feature              1..15
                          note = LNA antisense gapmer oligonucleotide
modified_base             1..15
                          mod_base = OTHER
                          note = Phosphorothiate Internucleoside linkages
modified_base             order(1..3,13..15)
                          mod_base = OTHER
                          note = LNA nucleosides
modified_base             6
                          mod_base = OTHER
                          note = 5-methyl c
source                    1..15
                          mol_type = other DNA
                          organism = synthetic construct
SEQUENCE: 467
tgaagcgaag tgcac                                                                    15

SEQ ID NO: 468            moltype = DNA  length = 16
FEATURE                   Location/Qualifiers
misc_feature              1..16
                          note = LNA antisense gapmer oligonucleotide
modified_base             1..16
                          mod_base = OTHER
                          note = Phosphorothiate Internucleoside linkages
modified_base             order(1..3,14..16)
                          mod_base = OTHER
                          note = LNA nucleosides
modified_base             7
                          mod_base = OTHER
                          note = 5-methyl c
source                    1..16
                          mol_type = other DNA
                          organism = synthetic construct
SEQUENCE: 468
gtgaagcgaa gtgcac                                                                   16

SEQ ID NO: 469            moltype = DNA  length = 12
FEATURE                   Location/Qualifiers
misc_feature              1..12
                          note = LNA antisense gapmer oligonucleotide
modified_base             1..12
                          mod_base = OTHER
                          note = Phosphorothiate Internucleoside linkages
modified_base             order(1,2,11,12)
                          mod_base = OTHER
```

|                    |                                                      |    |
|--------------------|------------------------------------------------------|----|
|                    | note = LNA nucleosides                               |    |
| modified_base      | 4                                                    |    |
|                    | mod_base = OTHER                                     |    |
|                    | note = 5-methyl c                                    |    |
| source             | 1..12                                                |    |
|                    | mol_type = other DNA                                 |    |
|                    | organism = synthetic construct                       |    |
| SEQUENCE: 469      |                                                      |    |
| aagcgaagtg ca      |                                                      | 12 |
| SEQ ID NO: 470     | moltype = DNA   length = 13                          |    |
| FEATURE            | Location/Qualifiers                                  |    |
| misc_feature       | 1..13                                                |    |
|                    | note = LNA antisense gapmer oligonucleotide          |    |
| modified_base      | 1..13                                                |    |
|                    | mod_base = OTHER                                     |    |
|                    | note = Phosphorothiate Internucleoside linkages      |    |
| modified_base      | order(1..3,12,13)                                    |    |
|                    | mod_base = OTHER                                     |    |
|                    | note = LNA nucleosides                               |    |
| modified_base      | 5                                                    |    |
|                    | mod_base = OTHER                                     |    |
|                    | note = 5-methyl c                                    |    |
| source             | 1..13                                                |    |
|                    | mol_type = other DNA                                 |    |
|                    | organism = synthetic construct                       |    |
| SEQUENCE: 470      |                                                      |    |
| gaagcgaagt gca     |                                                      | 13 |
| SEQ ID NO: 471     | moltype = DNA   length = 14                          |    |
| FEATURE            | Location/Qualifiers                                  |    |
| misc_feature       | 1..14                                                |    |
|                    | note = LNA antisense gapmer oligonucleotide          |    |
| modified_base      | 1..14                                                |    |
|                    | mod_base = OTHER                                     |    |
|                    | note = Phosphorothiate Internucleoside linkages      |    |
| modified_base      | order(1..3,12..14)                                   |    |
|                    | mod_base = OTHER                                     |    |
|                    | note = LNA nucleosides                               |    |
| modified_base      | 6                                                    |    |
|                    | mod_base = OTHER                                     |    |
|                    | note = 5-methyl c                                    |    |
| source             | 1..14                                                |    |
|                    | mol_type = other DNA                                 |    |
|                    | organism = synthetic construct                       |    |
| SEQUENCE: 471      |                                                      |    |
| tgaagcgaag tgca    |                                                      | 14 |
| SEQ ID NO: 472     | moltype = DNA   length = 15                          |    |
| FEATURE            | Location/Qualifiers                                  |    |
| misc_feature       | 1..15                                                |    |
|                    | note = LNA antisense gapmer oligonucleotide          |    |
| modified_base      | 1..15                                                |    |
|                    | mod_base = OTHER                                     |    |
|                    | note = Phosphorothiate Internucleoside linkages      |    |
| modified_base      | order(1..3,13..15)                                   |    |
|                    | mod_base = OTHER                                     |    |
|                    | note = LNA nucleosides                               |    |
| modified_base      | 7                                                    |    |
|                    | mod_base = OTHER                                     |    |
|                    | note = 5-methyl c                                    |    |
| source             | 1..15                                                |    |
|                    | mol_type = other DNA                                 |    |
|                    | organism = synthetic construct                       |    |
| SEQUENCE: 472      |                                                      |    |
| gtgaagcgaa gtgca   |                                                      | 15 |
| SEQ ID NO: 473     | moltype = DNA   length = 13                          |    |
| FEATURE            | Location/Qualifiers                                  |    |
| misc_feature       | 1..13                                                |    |
|                    | note = LNA antisense gapmer oligonucleotide          |    |
| modified_base      | 1..13                                                |    |
|                    | mod_base = OTHER                                     |    |
|                    | note = Phosphorothiate Internucleoside linkages      |    |
| modified_base      | order(1..3,12,13)                                    |    |
|                    | mod_base = OTHER                                     |    |
|                    | note = LNA nucleosides                               |    |
| modified_base      | 6                                                    |    |
|                    | mod_base = OTHER                                     |    |

|  | note = 5-methyl c |  |
| --- | --- | --- |
| source | 1..13 |  |
|  | mol_type = other DNA |  |
|  | organism = synthetic construct |  |
| SEQUENCE: 473 |  |  |
| tgaagcgaag tgc |  | 13 |
|  |  |  |
| SEQ ID NO: 474 | moltype = DNA   length = 14 |  |
| FEATURE | Location/Qualifiers |  |
| misc_feature | 1..14 |  |
|  | note = LNA antisense gapmer oligonucleotide |  |
| modified_base | 1..14 |  |
|  | mod_base = OTHER |  |
|  | note = Phosphorothiate Internucleoside linkages |  |
| modified_base | order(1..3,12..14) |  |
|  | mod_base = OTHER |  |
|  | note = LNA nucleosides |  |
| modified_base | 7 |  |
|  | mod_base = OTHER |  |
|  | note = 5-methyl c |  |
| source | 1..14 |  |
|  | mol_type = other DNA |  |
|  | organism = synthetic construct |  |
| SEQUENCE: 474 |  |  |
| gtgaagcgaa gtgc |  | 14 |
|  |  |  |
| SEQ ID NO: 475 | moltype = DNA   length = 13 |  |
| FEATURE | Location/Qualifiers |  |
| misc_feature | 1..13 |  |
|  | note = LNA antisense gapmer oligonucleotide |  |
| modified_base | 1..13 |  |
|  | mod_base = OTHER |  |
|  | note = Phosphorothiate Internucleoside linkages |  |
| modified_base | order(1..3,12,13) |  |
|  | mod_base = OTHER |  |
|  | note = LNA nucleosides |  |
| modified_base | 7 |  |
|  | mod_base = OTHER |  |
|  | note = 5-methyl c |  |
| source | 1..13 |  |
|  | mol_type = other DNA |  |
|  | organism = synthetic construct |  |
| SEQUENCE: 475 |  |  |
| gtgaagcgaa gtg |  | 13 |
|  |  |  |
| SEQ ID NO: 476 | moltype = DNA   length = 14 |  |
| FEATURE | Location/Qualifiers |  |
| misc_feature | 1..14 |  |
|  | note = LNA antisense gapmer oligonucleotide |  |
| modified_base | 1..14 |  |
|  | mod_base = OTHER |  |
|  | note = Phosphorothiate Internucleoside linkages |  |
| modified_base | order(1..3,12..14) |  |
|  | mod_base = OTHER |  |
|  | note = LNA nucleosides |  |
| modified_base | 8 |  |
|  | mod_base = OTHER |  |
|  | note = 5-methyl c |  |
| source | 1..14 |  |
|  | mol_type = other DNA |  |
|  | organism = synthetic construct |  |
| SEQUENCE: 476 |  |  |
| ggtgaagcga agtg |  | 14 |
|  |  |  |
| SEQ ID NO: 477 | moltype = DNA   length = 16 |  |
| FEATURE | Location/Qualifiers |  |
| misc_feature | 1..16 |  |
|  | note = LNA antisense gapmer oligonucleotide |  |
| modified_base | 1..16 |  |
|  | mod_base = OTHER |  |
|  | note = Phosphorothiate Internucleoside linkages |  |
| modified_base | order(1..3,14..16) |  |
|  | mod_base = OTHER |  |
|  | note = LNA nucleosides |  |
| modified_base | 10 |  |
|  | mod_base = OTHER |  |
|  | note = 5-methyl c |  |
| source | 1..16 |  |
|  | mol_type = other DNA |  |

```
                         organism = synthetic construct
SEQUENCE: 477
gaggtgaagc gaagtg                                                             16

SEQ ID NO: 478           moltype = DNA  length = 12
FEATURE                  Location/Qualifiers
misc_feature             1..12
                         note = LNA antisense gapmer oligonucleotide
modified_base            1..12
                         mod_base = OTHER
                         note = Phosphorothiate Internucleoside linkages
modified_base            order(1,2,11,12)
                         mod_base = OTHER
                         note = LNA nucleosides
modified_base            7
                         mod_base = OTHER
                         note = 5-methyl c
source                   1..12
                         mol_type = other DNA
                         organism = synthetic construct
SEQUENCE: 478
gtgaagcgaa gt                                                                 12

SEQ ID NO: 479           moltype = DNA  length = 13
FEATURE                  Location/Qualifiers
misc_feature             1..13
                         note = LNA antisense gapmer oligonucleotide
modified_base            1..13
                         mod_base = OTHER
                         note = Phosphorothiate Internucleoside linkages
modified_base            order(1..3,12,13)
                         mod_base = OTHER
                         note = LNA nucleosides
modified_base            8
                         mod_base = OTHER
                         note = 5-methyl c
source                   1..13
                         mol_type = other DNA
                         organism = synthetic construct
SEQUENCE: 479
ggtgaagcga agt                                                                13

SEQ ID NO: 480           moltype = DNA  length = 15
FEATURE                  Location/Qualifiers
misc_feature             1..15
                         note = LNA antisense gapmer oligonucleotide
modified_base            1..15
                         mod_base = OTHER
                         note = Phosphorothiate Internucleoside linkages
modified_base            order(1..3,13..15)
                         mod_base = OTHER
                         note = LNA nucleosides
modified_base            10
                         mod_base = OTHER
                         note = 5-methyl c
source                   1..15
                         mol_type = other DNA
                         organism = synthetic construct
SEQUENCE: 480
gaggtgaagc gaagt                                                              15

SEQ ID NO: 481           moltype = DNA  length = 16
FEATURE                  Location/Qualifiers
misc_feature             1..16
                         note = LNA antisense gapmer oligonucleotide
modified_base            1..16
                         mod_base = OTHER
                         note = Phosphorothiate Internucleoside linkages
modified_base            order(1..3,14..16)
                         mod_base = OTHER
                         note = LNA nucleosides
modified_base            11
                         mod_base = OTHER
                         note = 5-methyl c
source                   1..16
                         mol_type = other DNA
                         organism = synthetic construct
SEQUENCE: 481
agaggtgaag cgaagt                                                             16
```

```
SEQ ID NO: 482          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
modified_base           11
                        mod_base = OTHER
                        note = 5-methyl c
source                  1..15
                        mol_type = other DNA
                        organism = synthetic construct
SEQUENCE: 482
agaggtgaag cgaag                                                          15

SEQ ID NO: 483          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           12
                        mod_base = OTHER
                        note = 5-methyl c
source                  1..16
                        mol_type = other DNA
                        organism = synthetic construct
SEQUENCE: 483
cagaggtgaa gcgaag                                                         16

SEQ ID NO: 484          moltype = DNA  length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
modified_base           11
                        mod_base = OTHER
                        note = 5-methyl c
source                  1..14
                        mol_type = other DNA
                        organism = synthetic construct
SEQUENCE: 484
agaggtgaag cgaa                                                           14

SEQ ID NO: 485          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
modified_base           12
                        mod_base = OTHER
                        note = 5-methyl c
source                  1..15
                        mol_type = other DNA
                        organism = synthetic construct
SEQUENCE: 485
cagaggtgaa gcgaa                                                          15

SEQ ID NO: 486          moltype = DNA  length = 16
FEATURE                 Location/Qualifiers
```

```
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           13
                        mod_base = OTHER
                        note = 5-methyl c
source                  1..16
                        mol_type = other DNA
                        organism = synthetic construct
SEQUENCE: 486
gcagaggtga agcgaa                                                           16

SEQ ID NO: 487          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 487
gcagaggtga agcga                                                            15

SEQ ID NO: 488          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct
SEQUENCE: 488
tgcagaggtg aagcga                                                           16

SEQ ID NO: 489          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 489
tgcagaggtg aagcg                                                            15

SEQ ID NO: 490          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct
SEQUENCE: 490
```

```
gtgcagaggt gaagcg                                                    16

SEQ ID NO: 491          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct SEQUENCE: 491
cgtgcagagg tgaagc                                                    16

SEQ ID NO: 492          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct SEQUENCE: 492
cgtgcagagg tgaag                                                     15

SEQ ID NO: 493          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct SEQUENCE: 493
acgtgcagag gtgaag                                                    16

SEQ ID NO: 494          moltype = DNA   length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
source                  1..14
                        mol_type = other DNA
                        organism = synthetic construct SEQUENCE: 494
cgtgcagagg tgaa                                                      14

SEQ ID NO: 495          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
```

```
SEQUENCE: 495
acgtgcagag gtgaa                                                      15

SEQ ID NO: 496          moltype = DNA  length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
                        mod_base = OTHER
                        note = LNA nucleosides
source                  1..13
                        mol_type = other DNA
                        organism = synthetic construct
SEQUENCE: 496
cgtgcagagg tga                                                        13

SEQ ID NO: 497          moltype = DNA  length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
source                  1..14
                        mol_type = other DNA
                        organism = synthetic construct
SEQUENCE: 497
acgtgcagag gtga                                                       14

SEQ ID NO: 498          moltype = DNA  length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
                        mod_base = OTHER
                        note = LNA nucleosides
modified_base           7
                        mod_base = OTHER
                        note = 5-methyl c
source                  1..13
                        mol_type = other DNA
                        organism = synthetic construct
SEQUENCE: 498
cgttcacggt ggt                                                        13

SEQ ID NO: 499          moltype = DNA  length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
                        mod_base = OTHER
                        note = LNA nucleosides
modified_base           9
                        mod_base = OTHER
                        note = 5-methyl c
source                  1..13
                        mol_type = other DNA
                        organism = synthetic construct
SEQUENCE: 499
ctcaaggtcg gtc                                                        13

SEQ ID NO: 500          moltype = DNA  length = 13
FEATURE                 Location/Qualifiers
misc_feature            1..13
                        note = LNA antisense gapmer oligonucleotide
modified_base           1..13
                        mod_base = OTHER
```

```
                        note = Phosphorothiate Internucleoside linkages
modified_base           order(1..3,12,13)
                        mod_base = OTHER
                        note = LNA nucleosides
modified_base           10
                        mod_base = OTHER
                        note = 5-methyl c
source                  1..13
                        mol_type = other DNA
                        organism = synthetic construct
SEQUENCE: 500
cctcaaggtc ggt                                                                       13

SEQ ID NO: 501          moltype = DNA  length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
modified_base           11
                        mod_base = OTHER
                        note = 5-methyl c
source                  1..14
                        mol_type = other DNA
                        organism = synthetic construct
SEQUENCE: 501
gcctcaaggt cggt                                                                      14

SEQ ID NO: 502          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 502
acagtctttg aagta                                                                     15

SEQ ID NO: 503          moltype = DNA  length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
                        mod_base = OTHER
                        note = LNA nucleosides
source                  1..13
                        mol_type = other DNA
                        organism = synthetic construct
SEQUENCE: 503
tttatgccta cag                                                                       13

SEQ ID NO: 504          moltype = DNA  length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
source                  1..14
                        mol_type = other DNA
                        organism = synthetic construct
SEQUENCE: 504
aatttatgcc taca                                                                      14
```

```
SEQ ID NO: 505              moltype = DNA  length = 13
FEATURE                     Location/Qualifiers
misc_feature                1..13
                            note = LNA antisense gapmer oligonucleotide
modified_base               1..13
                            mod_base = OTHER
                            note = Phosphorothiate Internucleoside linkages
modified_base               order(1..3,12,13)
                            mod_base = OTHER
                            note = LNA nucleosides
source                      1..13
                            mol_type = other DNA
                            organism = synthetic construct
SEQUENCE: 505
aatttatgcc tac                                                            13

SEQ ID NO: 506              moltype = DNA  length = 13
FEATURE                     Location/Qualifiers
misc_feature                1..13
                            note = LNA antisense gapmer oligonucleotide
modified_base               1..13
                            mod_base = OTHER
                            note = Phosphorothiate Internucleoside linkages
modified_base               order(1..3,12,13)
                            mod_base = OTHER
                            note = LNA nucleosides
source                      1..13
                            mol_type = other DNA
                            organism = synthetic construct
SEQUENCE: 506
ccaatttatg cct                                                            13

SEQ ID NO: 507              moltype = DNA  length = 15
FEATURE                     Location/Qualifiers
misc_feature                1..15
                            note = LNA antisense gapmer oligonucleotide
modified_base               1..15
                            mod_base = OTHER
                            note = Phosphorothiate Internucleoside linkages
modified_base               order(1..3,13..15)
                            mod_base = OTHER
                            note = LNA nucleosides
source                      1..15
                            mol_type = other DNA
                            organism = synthetic construct
SEQUENCE: 507
gcttggaggc ttgaa                                                          15

SEQ ID NO: 508              moltype = DNA  length = 16
FEATURE                     Location/Qualifiers
misc_feature                1..16
                            note = LNA antisense gapmer oligonucleotide
modified_base               1..16
                            mod_base = OTHER
                            note = Phosphorothiate Internucleoside linkages
modified_base               order(1..3,14..16)
                            mod_base = OTHER
                            note = LNA nucleosides
source                      1..16
                            mol_type = other DNA
                            organism = synthetic construct
SEQUENCE: 508
agcttggagg cttgaa                                                         16

SEQ ID NO: 509              moltype = DNA  length = 14
FEATURE                     Location/Qualifiers
misc_feature                1..14
                            note = LNA antisense gapmer oligonucleotide
modified_base               1..14
                            mod_base = OTHER
                            note = Phosphorothiate Internucleoside linkages
modified_base               order(1..3,12..14)
                            mod_base = OTHER
                            note = LNA nucleosides
source                      1..14
                            mol_type = other DNA
                            organism = synthetic construct
SEQUENCE: 509
```

```
gcttggaggc ttga                                                       14

SEQ ID NO: 510         moltype = DNA   length = 15
FEATURE                Location/Qualifiers
misc_feature           1..15
                       note = LNA antisense gapmer oligonucleotide
modified_base          1..15
                       mod_base = OTHER
                       note = Phosphorothiate Internucleoside linkages
modified_base          order(1..3,13..15)
                       mod_base = OTHER
                       note = LNA nucleosides
source                 1..15
                       mol_type = other DNA
                       organism = synthetic construct SEQUENCE: 510
agcttggagg cttga                                                      15

SEQ ID NO: 511         moltype = DNA   length = 16
FEATURE                Location/Qualifiers
misc_feature           1..16
                       note = LNA antisense gapmer oligonucleotide
modified_base          1..16
                       mod_base = OTHER
                       note = Phosphorothiate Internucleoside linkages
modified_base          order(1..3,14..16)
                       mod_base = OTHER
                       note = LNA nucleosides
source                 1..16
                       mol_type = other DNA
                       organism = synthetic construct SEQUENCE: 511
cagcttggag gcttga                                                     16

SEQ ID NO: 512         moltype = DNA   length = 13
FEATURE                Location/Qualifiers
misc_feature           1..13
                       note = LNA antisense gapmer oligonucleotide
modified_base          1..13
                       mod_base = OTHER
                       note = Phosphorothiate Internucleoside linkages
modified_base          order(1..3,12,13)
                       mod_base = OTHER
                       note = LNA nucleosides
source                 1..13
                       mol_type = other DNA
                       organism = synthetic construct SEQUENCE: 512
gcttggaggc ttg                                                        13

SEQ ID NO: 513         moltype = DNA   length = 14
FEATURE                Location/Qualifiers
misc_feature           1..14
                       note = LNA antisense gapmer oligonucleotide
modified_base          1..14
                       mod_base = OTHER
                       note = Phosphorothiate Internucleoside linkages
modified_base          order(1..3,12..14)
                       mod_base = OTHER
                       note = LNA nucleosides
source                 1..14
                       mol_type = other DNA
                       organism = synthetic construct SEQUENCE: 513
agcttggagg cttg                                                       14

SEQ ID NO: 514         moltype = DNA   length = 15
FEATURE                Location/Qualifiers
misc_feature           1..15
                       note = LNA antisense gapmer oligonucleotide
modified_base          1..15
                       mod_base = OTHER
                       note = Phosphorothiate Internucleoside linkages
modified_base          order(1..3,13..15)
                       mod_base = OTHER
                       note = LNA nucleosides
source                 1..15
                       mol_type = other DNA
                       organism = synthetic construct
```

```
SEQUENCE: 514
cagcttggag gcttg                                                    15

SEQ ID NO: 515          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct
SEQUENCE: 515
acagcttgga ggcttg                                                   16

SEQ ID NO: 516          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct
SEQUENCE: 516
cacagcttgg aggctt                                                   16

SEQ ID NO: 517          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 517
cacagcttgg aggct                                                    15

SEQ ID NO: 518          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct
SEQUENCE: 518
gcacagcttg gaggct                                                   16

SEQ ID NO: 519          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
```

-continued

```
                            organism = synthetic construct
SEQUENCE: 519
gcacagcttg gaggc                                                           15

SEQ ID NO: 520              moltype = DNA   length = 16
FEATURE                     Location/Qualifiers
misc_feature                1..16
                            note = LNA antisense gapmer oligonucleotide
modified_base               1..16
                            mod_base = OTHER
                            note = Phosphorothiate Internucleoside linkages
modified_base               order(1..3,14..16)
                            mod_base = OTHER
                            note = LNA nucleosides
source                      1..16
                            mol_type = other DNA
                            organism = synthetic construct
SEQUENCE: 520
ggcacagctt ggaggc                                                          16

SEQ ID NO: 521              moltype = DNA   length = 16
FEATURE                     Location/Qualifiers
misc_feature                1..16
                            note = LNA antisense gapmer oligonucleotide
modified_base               1..16
                            mod_base = OTHER
                            note = Phosphorothiate Internucleoside linkages
modified_base               order(1..3,14..16)
                            mod_base = OTHER
                            note = LNA nucleosides
source                      1..16
                            mol_type = other DNA
                            organism = synthetic construct
SEQUENCE: 521
aggcacagct tggagg                                                          16

SEQ ID NO: 522              moltype = DNA   length = 15
FEATURE                     Location/Qualifiers
misc_feature                1..15
                            note = LNA antisense gapmer oligonucleotide
modified_base               1..15
                            mod_base = OTHER
                            note = Phosphorothiate Internucleoside linkages
modified_base               order(1..3,13..15)
                            mod_base = OTHER
                            note = LNA nucleosides
source                      1..15
                            mol_type = other DNA
                            organism = synthetic construct
SEQUENCE: 522
aggcacagct tggag                                                           15

SEQ ID NO: 523              moltype = DNA   length = 16
FEATURE                     Location/Qualifiers
misc_feature                1..16
                            note = LNA antisense gapmer oligonucleotide
modified_base               1..16
                            mod_base = OTHER
                            note = Phosphorothiate Internucleoside linkages
modified_base               order(1..3,14..16)
                            mod_base = OTHER
                            note = LNA nucleosides
source                      1..16
                            mol_type = other DNA
                            organism = synthetic construct
SEQUENCE: 523
aaggcacagc ttggag                                                          16

SEQ ID NO: 524              moltype = DNA   length = 15
FEATURE                     Location/Qualifiers
misc_feature                1..15
                            note = LNA antisense gapmer oligonucleotide
modified_base               1..15
                            mod_base = OTHER
                            note = Phosphorothiate Internucleoside linkages
modified_base               order(1..3,13..15)
                            mod_base = OTHER
                            note = LNA nucleosides
source                      1..15
```

```
                              mol_type = other DNA
                              organism = synthetic construct
SEQUENCE: 524
aaggcacagc ttgga                                                           15

SEQ ID NO: 525                moltype = DNA  length = 16
FEATURE                       Location/Qualifiers
misc_feature                  1..16
                              note = LNA antisense gapmer oligonucleotide
modified_base                 1..16
                              mod_base = OTHER
                              note = Phosphorothiate Internucleoside linkages
modified_base                 order(1..3,14..16)
                              mod_base = OTHER
                              note = LNA nucleosides
source                        1..16
                              mol_type = other DNA
                              organism = synthetic construct
SEQUENCE: 525
caaggcacag cttgga                                                          16

SEQ ID NO: 526                moltype = DNA  length = 14
FEATURE                       Location/Qualifiers
misc_feature                  1..14
                              note = LNA antisense gapmer oligonucleotide
modified_base                 1..14
                              mod_base = OTHER
                              note = Phosphorothiate Internucleoside linkages
modified_base                 order(1..3,12..14)
                              mod_base = OTHER
                              note = LNA nucleosides
source                        1..14
                              mol_type = other DNA
                              organism = synthetic construct
SEQUENCE: 526
aaggcacagc ttgg                                                            14

SEQ ID NO: 527                moltype = DNA  length = 15
FEATURE                       Location/Qualifiers
misc_feature                  1..15
                              note = LNA antisense gapmer oligonucleotide
modified_base                 1..15
                              mod_base = OTHER
                              note = Phosphorothiate Internucleoside linkages
modified_base                 order(1..3,13..15)
                              mod_base = OTHER
                              note = LNA nucleosides
source                        1..15
                              mol_type = other DNA
                              organism = synthetic construct
SEQUENCE: 527
caaggcacag cttgg                                                           15

SEQ ID NO: 528                moltype = DNA  length = 16
FEATURE                       Location/Qualifiers
misc_feature                  1..16
                              note = LNA antisense gapmer oligonucleotide
modified_base                 1..16
                              mod_base = OTHER
                              note = Phosphorothiate Internucleoside linkages
modified_base                 order(1..3,14..16)
                              mod_base = OTHER
                              note = LNA nucleosides
source                        1..16
                              mol_type = other DNA
                              organism = synthetic construct
SEQUENCE: 528
ccaaggcaca gcttgg                                                          16

SEQ ID NO: 529                moltype = DNA  length = 14
FEATURE                       Location/Qualifiers
misc_feature                  1..14
                              note = LNA antisense gapmer oligonucleotide
modified_base                 1..14
                              mod_base = OTHER
                              note = Phosphorothiate Internucleoside linkages
modified_base                 order(1..3,12..14)
                              mod_base = OTHER
                              note = LNA nucleosides
```

```
source                  1..14
                        mol_type = other DNA
                        organism = synthetic construct
SEQUENCE: 529
caaggcacag cttg                                                              14

SEQ ID NO: 530          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 530
ccaaggcaca gcttg                                                             15

SEQ ID NO: 531          moltype = DNA   length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
source                  1..14
                        mol_type = other DNA
                        organism = synthetic construct
SEQUENCE: 531
ccaaggcaca gctt                                                              14

SEQ ID NO: 532          moltype = DNA   length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
                        mod_base = OTHER
                        note = LNA nucleosides
source                  1..13
                        mol_type = other DNA
                        organism = synthetic construct
SEQUENCE: 532
tgcgaatcca cac                                                               13

SEQ ID NO: 533          moltype = DNA   length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
modified_base           4
                        mod_base = OTHER
                        note = 5-methyl c
source                  1..14
                        mol_type = other DNA
                        organism = synthetic construct
SEQUENCE: 533
gtgcgaatcc acac                                                              14

SEQ ID NO: 534          moltype = DNA   length = 15
FEATURE                 Location/Qualifiers
misc_feature            1..15
                        note = LNA antisense gapmer oligonucleotide
modified_base           1..15
                        mod_base = OTHER
```

```
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 534
ggagttcttc ttcta                                                      15

SEQ ID NO: 535          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct
SEQUENCE: 535
gggagttctt cttcta                                                     16

SEQ ID NO: 536          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 536
gggagttctt cttct                                                      15

SEQ ID NO: 537          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct
SEQUENCE: 537
agggagttct tcttct                                                     16

SEQ ID NO: 538          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 538
agggagttct tcttc                                                      15

SEQ ID NO: 539          moltype = DNA   length = 16
FEATURE                 Location/Qualifiers
misc_feature            1..16
                        note = LNA antisense gapmer oligonucleotide
modified_base           1..16
```

|   |   |   |
|---|---|---|
| modified_base | mod_base = OTHER<br>note = Phosphorothiate Internucleoside linkages<br>order(1..3,14..16)<br>mod_base = OTHER<br>note = LNA nucleosides | |
| source | 1..16<br>mol_type = other DNA<br>organism = synthetic construct | |
| SEQUENCE: 539<br>gagggagttc ttcttc | | 16 |
| SEQ ID NO: 540<br>FEATURE | moltype = DNA  length = 14<br>Location/Qualifiers | |
| misc_feature | 1..14<br>note = LNA antisense gapmer oligonucleotide | |
| modified_base | 1..14<br>mod_base = OTHER<br>note = Phosphorothiate Internucleoside linkages | |
| modified_base | order(1..3,12..14)<br>mod_base = OTHER<br>note = LNA nucleosides | |
| source | 1..14<br>mol_type = other DNA<br>organism = synthetic construct | |
| SEQUENCE: 540<br>agggagttct tctt | | 14 |
| SEQ ID NO: 541<br>FEATURE | moltype = DNA  length = 15<br>Location/Qualifiers | |
| misc_feature | 1..15<br>note = LNA antisense gapmer oligonucleotide | |
| modified_base | 1..15<br>mod_base = OTHER<br>note = Phosphorothiate Internucleoside linkages | |
| modified_base | order(1..3,13..15)<br>mod_base = OTHER<br>note = LNA nucleosides | |
| source | 1..15<br>mol_type = other DNA<br>organism = synthetic construct | |
| SEQUENCE: 541<br>gagggagttc ttctt | | 15 |
| SEQ ID NO: 542<br>FEATURE | moltype = DNA  length = 16<br>Location/Qualifiers | |
| misc_feature | 1..16<br>note = LNA antisense gapmer oligonucleotide | |
| modified_base | 1..16<br>mod_base = OTHER<br>note = Phosphorothiate Internucleoside linkages | |
| modified_base | order(1..3,14..16)<br>mod_base = OTHER<br>note = LNA nucleosides | |
| source | 1..16<br>mol_type = other DNA<br>organism = synthetic construct | |
| SEQUENCE: 542<br>cgagggagtt cttctt | | 16 |
| SEQ ID NO: 543<br>FEATURE | moltype = DNA  length = 15<br>Location/Qualifiers | |
| misc_feature | 1..15<br>note = LNA antisense gapmer oligonucleotide | |
| modified_base | 1..15<br>mod_base = OTHER<br>note = Phosphorothiate Internucleoside linkages | |
| modified_base | order(1..3,13..15)<br>mod_base = OTHER<br>note = LNA nucleosides | |
| source | 1..15<br>mol_type = other DNA<br>organism = synthetic construct | |
| SEQUENCE: 543<br>cgagggagtt cttct | | 15 |
| SEQ ID NO: 544<br>FEATURE | moltype = DNA  length = 16<br>Location/Qualifiers | |
| misc_feature | 1..16<br>note = LNA antisense gapmer oligonucleotide | |

```
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct
SEQUENCE: 544
gcgagggagt tcttct                                                            16

SEQ ID NO: 545          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 545
gcgagggagt tcttc                                                             15

SEQ ID NO: 546          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct
SEQUENCE: 546
ggcgagggag ttcttc                                                            16

SEQ ID NO: 547          moltype = DNA  length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
source                  1..14
                        mol_type = other DNA
                        organism = synthetic construct
SEQUENCE: 547
gcgagggagt tctt                                                              14

SEQ ID NO: 548          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 548
ggcgagggag ttctt                                                             15

SEQ ID NO: 549          moltype = DNA  length = 16
FEATURE                 Location/Qualifiers
misc_feature            1..16
```

|   |   |   |
|---|---|---|
| | note = LNA antisense gapmer oligonucleotide | |
| modified_base | 1..16 | |
| | mod_base = OTHER | |
| | note = Phosphorothiate Internucleoside linkages | |
| modified_base | order(1..3,14..16) | |
| | mod_base = OTHER | |
| | note = LNA nucleosides | |
| modified_base | 4 | |
| | mod_base = OTHER | |
| | note = 5-methyl c | |
| source | 1..16 | |
| | mol_type = other DNA | |
| | organism = synthetic construct | |
| SEQUENCE: 549 | | |
| aggcgaggga gttctt | | 16 |
| | | |
| SEQ ID NO: 550 | moltype = DNA   length = 13 | |
| FEATURE | Location/Qualifiers | |
| misc_feature | 1..13 | |
| | note = LNA antisense gapmer oligonucleotide | |
| modified_base | 1..13 | |
| | mod_base = OTHER | |
| | note = Phosphorothiate Internucleoside linkages | |
| modified_base | order(1..3,12,13) | |
| | mod_base = OTHER | |
| | note = LNA nucleosides | |
| source | 1..13 | |
| | mol_type = other DNA | |
| | organism = synthetic construct | |
| SEQUENCE: 550 | | |
| gcgagggagt tct | | 13 |
| | | |
| SEQ ID NO: 551 | moltype = DNA   length = 14 | |
| FEATURE | Location/Qualifiers | |
| misc_feature | 1..14 | |
| | note = LNA antisense gapmer oligonucleotide | |
| modified_base | 1..14 | |
| | mod_base = OTHER | |
| | note = Phosphorothiate Internucleoside linkages | |
| modified_base | order(1..3,12..14) | |
| | mod_base = OTHER | |
| | note = LNA nucleosides | |
| source | 1..14 | |
| | mol_type = other DNA | |
| | organism = synthetic construct | |
| SEQUENCE: 551 | | |
| ggcgagggag ttct | | 14 |
| | | |
| SEQ ID NO: 552 | moltype = DNA   length = 15 | |
| FEATURE | Location/Qualifiers | |
| misc_feature | 1..15 | |
| | note = LNA antisense gapmer oligonucleotide | |
| modified_base | 1..15 | |
| | mod_base = OTHER | |
| | note = Phosphorothiate Internucleoside linkages | |
| modified_base | order(1..3,13..15) | |
| | mod_base = OTHER | |
| | note = LNA nucleosides | |
| modified_base | 4 | |
| | mod_base = OTHER | |
| | note = 5-methyl c | |
| source | 1..15 | |
| | mol_type = other DNA | |
| | organism = synthetic construct | |
| SEQUENCE: 552 | | |
| aggcgaggga gttct | | 15 |
| | | |
| SEQ ID NO: 553 | moltype = DNA   length = 16 | |
| FEATURE | Location/Qualifiers | |
| misc_feature | 1..16 | |
| | note = LNA antisense gapmer oligonucleotide | |
| modified_base | 1..16 | |
| | mod_base = OTHER | |
| | note = Phosphorothiate Internucleoside linkages | |
| modified_base | order(1..3,14..16) | |
| | mod_base = OTHER | |
| | note = LNA nucleosides | |
| modified_base | 5 | |
| | mod_base = OTHER | |

```
                        note = 5-methyl c
source                  1..16
                        mol_type = other DNA
                        organism = synthetic construct
SEQUENCE: 553
gaggcgaggg agttct                                                         16

SEQ ID NO: 554          moltype = DNA  length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
                        mod_base = OTHER
                        note = LNA nucleosides
source                  1..13
                        mol_type = other DNA
                        organism = synthetic construct
SEQUENCE: 554
ggcgagggag ttc                                                            13

SEQ ID NO: 555          moltype = DNA  length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
modified_base           4
                        mod_base = OTHER
                        note = 5-methyl c
source                  1..14
                        mol_type = other DNA
                        organism = synthetic construct
SEQUENCE: 555
aggcgaggga gttc                                                           14

SEQ ID NO: 556          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
modified_base           5
                        mod_base = OTHER
                        note = 5-methyl c
source                  1..15
                        mol_type = other DNA
                        organism = synthetic construct
SEQUENCE: 556
gaggcgaggg agttc                                                          15

SEQ ID NO: 557          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           6
                        mod_base = OTHER
                        note = 5-methyl c
source                  1..16
                        mol_type = other DNA
                        organism = synthetic construct
SEQUENCE: 557
cgaggcgagg gagttc                                                         16
```

| | | |
|---|---|---|
| SEQ ID NO: 558 | moltype = DNA  length = 13 | |
| FEATURE | Location/Qualifiers | |
| misc_feature | 1..13 | |
| | note = LNA antisense gapmer oligonucleotide | |
| modified_base | 1..13 | |
| | mod_base = OTHER | |
| | note = Phosphorothiate Internucleoside linkages | |
| modified_base | order(1..3,12,13) | |
| | mod_base = OTHER | |
| | note = LNA nucleosides | |
| modified_base | 4 | |
| | mod_base = OTHER | |
| | note = 5-methyl c | |
| source | 1..13 | |
| | mol_type = other DNA | |
| | organism = synthetic construct | |
| SEQUENCE: 558 | | |
| aggcgaggga gtt | | 13 |
| | | |
| SEQ ID NO: 559 | moltype = DNA  length = 14 | |
| FEATURE | Location/Qualifiers | |
| misc_feature | 1..14 | |
| | note = LNA antisense gapmer oligonucleotide | |
| modified_base | 1..14 | |
| | mod_base = OTHER | |
| | note = Phosphorothiate Internucleoside linkages | |
| modified_base | order(1..3,12..14) | |
| | mod_base = OTHER | |
| | note = LNA nucleosides | |
| modified_base | 5 | |
| | mod_base = OTHER | |
| | note = 5-methyl c | |
| source | 1..14 | |
| | mol_type = other DNA | |
| | organism = synthetic construct | |
| SEQUENCE: 559 | | |
| gaggcgaggg agtt | | 14 |
| | | |
| SEQ ID NO: 560 | moltype = DNA  length = 15 | |
| FEATURE | Location/Qualifiers | |
| misc_feature | 1..15 | |
| | note = LNA antisense gapmer oligonucleotide | |
| modified_base | 1..15 | |
| | mod_base = OTHER | |
| | note = Phosphorothiate Internucleoside linkages | |
| modified_base | order(1..3,13..15) | |
| | mod_base = OTHER | |
| | note = LNA nucleosides | |
| modified_base | 6 | |
| | mod_base = OTHER | |
| | note = 5-methyl c | |
| source | 1..15 | |
| | mol_type = other DNA | |
| | organism = synthetic construct | |
| SEQUENCE: 560 | | |
| cgaggcgagg gagtt | | 15 |
| | | |
| SEQ ID NO: 561 | moltype = DNA  length = 16 | |
| FEATURE | Location/Qualifiers | |
| misc_feature | 1..16 | |
| | note = LNA antisense gapmer oligonucleotide | |
| modified_base | 1..16 | |
| | mod_base = OTHER | |
| | note = Phosphorothiate Internucleoside linkages | |
| modified_base | order(1..3,14..16) | |
| | mod_base = OTHER | |
| | note = LNA nucleosides | |
| modified_base | 7 | |
| | mod_base = OTHER | |
| | note = 5-methyl c | |
| source | 1..16 | |
| | mol_type = other DNA | |
| | organism = synthetic construct | |
| SEQUENCE: 561 | | |
| gcgaggcgag ggagtt | | 16 |
| | | |
| SEQ ID NO: 562 | moltype = DNA  length = 13 | |
| FEATURE | Location/Qualifiers | |

```
misc_feature               1..13
                           note = LNA antisense gapmer oligonucleotide
modified_base              1..13
                           mod_base = OTHER
                           note = Phosphorothiate Internucleoside linkages
modified_base              order(1..3,12,13)
                           mod_base = OTHER
                           note = LNA nucleosides
modified_base              5
                           mod_base = OTHER
                           note = 5-methyl c
source                     1..13
                           mol_type = other DNA
                           organism = synthetic construct
SEQUENCE: 562
gaggcgaggg agt                                                              13

SEQ ID NO: 563             moltype = DNA  length = 14
FEATURE                    Location/Qualifiers
misc_feature               1..14
                           note = LNA antisense gapmer oligonucleotide
modified_base              1..14
                           mod_base = OTHER
                           note = Phosphorothiate Internucleoside linkages
modified_base              order(1..3,12..14)
                           mod_base = OTHER
                           note = LNA nucleosides
modified_base              6
                           mod_base = OTHER
                           note = 5-methyl c
source                     1..14
                           mol_type = other DNA
                           organism = synthetic construct
SEQUENCE: 563
cgaggcgagg gagt                                                             14

SEQ ID NO: 564             moltype = DNA  length = 15
FEATURE                    Location/Qualifiers
misc_feature               1..15
                           note = LNA antisense gapmer oligonucleotide
modified_base              1..15
                           mod_base = OTHER
                           note = Phosphorothiate Internucleoside linkages
modified_base              order(1..3,13..15)
                           mod_base = OTHER
                           note = LNA nucleosides
modified_base              7
                           mod_base = OTHER
                           note = 5-methyl c
source                     1..15
                           mol_type = other DNA
                           organism = synthetic construct
SEQUENCE: 564
gcgaggcgag ggagt                                                            15

SEQ ID NO: 565             moltype = DNA  length = 16
FEATURE                    Location/Qualifiers
misc_feature               1..16
                           note = LNA antisense gapmer oligonucleotide
modified_base              1..16
                           mod_base = OTHER
                           note = Phosphorothiate Internucleoside linkages
modified_base              order(1..3,14..16)
                           mod_base = OTHER
                           note = LNA nucleosides
modified_base              8
                           mod_base = OTHER
                           note = 5-methyl c
source                     1..16
                           mol_type = other DNA
                           organism = synthetic construct
SEQUENCE: 565
tgcgaggcga gggagt                                                           16

SEQ ID NO: 566             moltype = DNA  length = 13
FEATURE                    Location/Qualifiers
misc_feature               1..13
                           note = LNA antisense gapmer oligonucleotide
modified_base              1..13
```

-continued

```
                          mod_base = OTHER
                          note = Phosphorothiate Internucleoside linkages
modified_base             order(1..3,12,13)
                          mod_base = OTHER
                          note = LNA nucleosides
modified_base             6
                          mod_base = OTHER
                          note = 5-methyl c
source                    1..13
                          mol_type = other DNA
                          organism = synthetic construct
SEQUENCE: 566
cgaggcgagg gag                                                              13

SEQ ID NO: 567            moltype = DNA  length = 14
FEATURE                   Location/Qualifiers
misc_feature              1..14
                          note = LNA antisense gapmer oligonucleotide
modified_base             1..14
                          mod_base = OTHER
                          note = Phosphorothiate Internucleoside linkages
modified_base             order(1..3,12..14)
                          mod_base = OTHER
                          note = LNA nucleosides
modified_base             7
                          mod_base = OTHER
                          note = 5-methyl c
source                    1..14
                          mol_type = other DNA
                          organism = synthetic construct
SEQUENCE: 567
gcgaggcgag ggag                                                             14

SEQ ID NO: 568            moltype = DNA  length = 15
FEATURE                   Location/Qualifiers
misc_feature              1..15
                          note = LNA antisense gapmer oligonucleotide
modified_base             1..15
                          mod_base = OTHER
                          note = Phosphorothiate Internucleoside linkages
modified_base             order(1..3,13..15)
                          mod_base = OTHER
                          note = LNA nucleosides
modified_base             8
                          mod_base = OTHER
                          note = 5-methyl c
source                    1..15
                          mol_type = other DNA
                          organism = synthetic construct
SEQUENCE: 568
tgcgaggcga gggag                                                            15

SEQ ID NO: 569            moltype = DNA  length = 16
FEATURE                   Location/Qualifiers
misc_feature              1..16
                          note = LNA antisense gapmer oligonucleotide
modified_base             1..16
                          mod_base = OTHER
                          note = Phosphorothiate Internucleoside linkages
modified_base             order(1..3,14..16)
                          mod_base = OTHER
                          note = LNA nucleosides
modified_base             order(4,9)
                          mod_base = OTHER
                          note = 5-methyl c
source                    1..16
                          mol_type = other DNA
                          organism = synthetic construct
SEQUENCE: 569
ctgcgaggcg agggag                                                           16

SEQ ID NO: 570            moltype = DNA  length = 12
FEATURE                   Location/Qualifiers
misc_feature              1..12
                          note = LNA antisense gapmer oligonucleotide
modified_base             1..12
                          mod_base = OTHER
                          note = Phosphorothiate Internucleoside linkages
modified_base             order(1,2,11,12)
```

```
                        mod_base = OTHER
                        note = LNA nucleosides
modified_base           6
                        mod_base = OTHER
                        note = 5-methyl c
source                  1..12
                        mol_type = other DNA
                        organism = synthetic construct
SEQUENCE: 570
cgaggcgagg ga                                                           12

SEQ ID NO: 571          moltype = DNA  length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
                        mod_base = OTHER
                        note = LNA nucleosides
modified_base           7
                        mod_base = OTHER
                        note = 5-methyl c
source                  1..13
                        mol_type = other DNA
                        organism = synthetic construct
SEQUENCE: 571
gcgaggcgag gga                                                          13

SEQ ID NO: 572          moltype = DNA  length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
modified_base           8
                        mod_base = OTHER
                        note = 5-methyl c
source                  1..14
                        mol_type = other DNA
                        organism = synthetic construct
SEQUENCE: 572
tgcgaggcga ggga                                                         14

SEQ ID NO: 573          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
modified_base           order(4,9)
                        mod_base = OTHER
                        note = 5-methyl c
source                  1..15
                        mol_type = other DNA
                        organism = synthetic construct
SEQUENCE: 573
ctgcgaggcg aggga                                                        15

SEQ ID NO: 574          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           order(5,10)
```

```
                        mod_base = OTHER
                        note = 5-methyl c
source                  1..16
                        mol_type = other DNA
                        organism = synthetic construct
SEQUENCE: 574
tctgcgaggc gaggga                                                           16

SEQ ID NO: 575          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
modified_base           order(5,10)
                        mod_base = OTHER
                        note = 5-methyl c
source                  1..15
                        mol_type = other DNA
                        organism = synthetic construct
SEQUENCE: 575
tctgcgaggc gaggg                                                            15

SEQ ID NO: 576          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           order(6,11)
                        mod_base = OTHER
                        note = 5-methyl c
source                  1..16
                        mol_type = other DNA
                        organism = synthetic construct
SEQUENCE: 576
gtctgcgagg cgaggg                                                           16

SEQ ID NO: 577          moltype = DNA  length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
source                  1..14
                        mol_type = other DNA
                        organism = synthetic construct
SEQUENCE: 577
gttcccaaga atat                                                             14

SEQ ID NO: 578          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 578
tgttcccaag aatat                                                            15

SEQ ID NO: 579          moltype = DNA  length = 13
```

```
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
                        mod_base = OTHER
                        note = LNA nucleosides
source                  1..13
                        mol_type = other DNA
                        organism = synthetic construct
SEQUENCE: 579
gttcccaaga ata                                                             13

SEQ ID NO: 580          moltype = DNA   length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
source                  1..14
                        mol_type = other DNA
                        organism = synthetic construct
SEQUENCE: 580
tgttcccaag aata                                                            14

SEQ ID NO: 581          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 581
ttgttcccaa gaata                                                           15

SEQ ID NO: 582          moltype = DNA   length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,12,13)
                        mod_base = OTHER
                        note = LNA nucleosides
source                  1..13
                        mol_type = other DNA
                        organism = synthetic construct
SEQUENCE: 582
tgttcccaag aat                                                             13

SEQ ID NO: 583          moltype = DNA   length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,12..14)
                        mod_base = OTHER
                        note = LNA nucleosides
source                  1..14
                        mol_type = other DNA
                        organism = synthetic construct
SEQUENCE: 583
ttgttcccaa gaat                                                            14
```

| | | |
|---|---|---|
| SEQ ID NO: 584 | moltype = DNA   length = 16 | |
| FEATURE | Location/Qualifiers | |
| misc_feature | 1..16 | |
| | note = LNA antisense gapmer oligonucleotide | |
| modified_base | 1..16 | |
| | mod_base = OTHER | |
| | note = Phosphorothiate Internucleoside linkages | |
| modified_base | order(1..4,13..16) | |
| | mod_base = OTHER | |
| | note = LNA nucleosides | |
| source | 1..16 | |
| | mol_type = other DNA | |
| | organism = synthetic construct | |
| SEQUENCE: 584 | | |
| gaggcatagc agcagg | | 16 |
| | | |
| SEQ ID NO: 585 | moltype = DNA   length = 15 | |
| FEATURE | Location/Qualifiers | |
| misc_feature | 1..15 | |
| | note = LNA antisense gapmer oligonucleotide | |
| modified_base | 1..15 | |
| | mod_base = OTHER | |
| | note = Phosphorothiate Internucleoside linkages | |
| modified_base | order(1..3,12..15) | |
| | mod_base = OTHER | |
| | note = LNA nucleosides | |
| source | 1..15 | |
| | mol_type = other DNA | |
| | organism = synthetic construct | |
| SEQUENCE: 585 | | |
| gaaccactga acaaa | | 15 |
| | | |
| SEQ ID NO: 586 | moltype = DNA   length = 15 | |
| FEATURE | Location/Qualifiers | |
| misc_feature | 1..15 | |
| | note = LNA antisense gapmer oligonucleotide | |
| modified_base | 1..15 | |
| | mod_base = OTHER | |
| | note = Phosphorothiate Internucleoside linkages | |
| modified_base | order(1..4,13..15) | |
| | mod_base = OTHER | |
| | note = LNA nucleosides | |
| source | 1..15 | |
| | mol_type = other DNA | |
| | organism = synthetic construct | |
| SEQUENCE: 586 | | |
| gaaccactga acaaa | | 15 |
| | | |
| SEQ ID NO: 587 | moltype = DNA   length = 16 | |
| FEATURE | Location/Qualifiers | |
| misc_feature | 1..16 | |
| | note = LNA antisense gapmer oligonucleotide | |
| modified_base | 1..16 | |
| | mod_base = OTHER | |
| | note = Phosphorothiate Internucleoside linkages | |
| modified_base | order(1,2,13..16) | |
| | mod_base = OTHER | |
| | note = LNA nucleosides | |
| source | 1..16 | |
| | mol_type = other DNA | |
| | organism = synthetic construct | |
| SEQUENCE: 587 | | |
| cgaaccactg aacaaa | | 16 |
| | | |
| SEQ ID NO: 588 | moltype = DNA   length = 16 | |
| FEATURE | Location/Qualifiers | |
| misc_feature | 1..16 | |
| | note = LNA antisense gapmer oligonucleotide | |
| modified_base | 1..16 | |
| | mod_base = OTHER | |
| | note = Phosphorothiate Internucleoside linkages | |
| modified_base | order(1..4,14..16) | |
| | mod_base = OTHER | |
| | note = LNA nucleosides | |
| source | 1..16 | |
| | mol_type = other DNA | |
| | organism = synthetic construct | |
| SEQUENCE: 588 | | |
| cgaaccactg aacaaa | | 16 |

```
SEQ ID NO: 589           moltype = DNA  length = 16
FEATURE                  Location/Qualifiers
misc_feature             1..16
                         note = LNA antisense gapmer oligonucleotide
modified_base            1..16
                         mod_base = OTHER
                         note = Phosphorothiate Internucleoside linkages
modified_base            order(1..3,13..16)
                         mod_base = OTHER
                         note = LNA nucleosides
source                   1..16
                         mol_type = other DNA
                         organism = synthetic construct
SEQUENCE: 589
cgaaccactg aacaaa                                                         16

SEQ ID NO: 590           moltype = DNA  length = 16
FEATURE                  Location/Qualifiers
misc_feature             1..16
                         note = LNA antisense gapmer oligonucleotide
modified_base            1..16
                         mod_base = OTHER
                         note = Phosphorothiate Internucleoside linkages
modified_base            order(1..4,15,16)
                         mod_base = OTHER
                         note = LNA nucleosides
source                   1..16
                         mol_type = other DNA
                         organism = synthetic construct
SEQUENCE: 590
cgaaccactg aacaaa                                                         16

SEQ ID NO: 591           moltype = DNA  length = 16
FEATURE                  Location/Qualifiers
misc_feature             1..16
                         note = LNA antisense gapmer oligonucleotide
modified_base            1..16
                         mod_base = OTHER
                         note = Phosphorothiate Internucleoside linkages
modified_base            order(1..4,13..16)
                         mod_base = OTHER
                         note = LNA nucleosides
source                   1..16
                         mol_type = other DNA
                         organism = synthetic construct
SEQUENCE: 591
cgaaccactg aacaaa                                                         16

SEQ ID NO: 592           moltype = DNA  length = 15
FEATURE                  Location/Qualifiers
misc_feature             1..15
                         note = LNA antisense gapmer oligonucleotide
modified_base            1..15
                         mod_base = OTHER
                         note = Phosphorothiate Internucleoside linkages
modified_base            order(1..4,14,15)
                         mod_base = OTHER
                         note = LNA nucleosides
source                   1..15
                         mol_type = other DNA
                         organism = synthetic construct
SEQUENCE: 592
cgaaccactg aacaa                                                          15

SEQ ID NO: 593           moltype = DNA  length = 15
FEATURE                  Location/Qualifiers
misc_feature             1..15
                         note = LNA antisense gapmer oligonucleotide
modified_base            1..15
                         mod_base = OTHER
                         note = Phosphorothiate Internucleoside linkages
modified_base            order(1..4,13..15)
                         mod_base = OTHER
                         note = LNA nucleosides
source                   1..15
                         mol_type = other DNA
                         organism = synthetic construct
SEQUENCE: 593
```

```
cgaaccactg aacaa                                                      15

SEQ ID NO: 594          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,12..15)
                        mod_base = OTHER
                        note = LNA nucleosides
source                  1..15
                        mol_type = other DNA
                        organism = synthetic construct SEQUENCE: 594
cgaaccactg aacaa                                                      15

SEQ ID NO: 595          moltype = DNA   length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1,2,11..14)
                        mod_base = OTHER
                        note = LNA nucleosides
source                  1..14
                        mol_type = other DNA
                        organism = synthetic construct SEQUENCE: 595
cgaaccactg aaca                                                       14

SEQ ID NO: 596          moltype = DNA   length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..4,13,14)
                        mod_base = OTHER
                        note = LNA nucleosides
source                  1..14
                        mol_type = other DNA
                        organism = synthetic construct SEQUENCE: 596
cgaaccactg aaca                                                       14

SEQ ID NO: 597          moltype = DNA   length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..3,11..14)
                        mod_base = OTHER
                        note = LNA nucleosides
source                  1..14
                        mol_type = other DNA
                        organism = synthetic construct SEQUENCE: 597
cgaaccactg aaca                                                       14

SEQ ID NO: 598          moltype = DNA   length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..4,12..14)
                        mod_base = OTHER
                        note = LNA nucleosides
source                  1..14
                        mol_type = other DNA
                        organism = synthetic construct
```

```
SEQUENCE: 598
cgaaccactg aaca                                                         14

SEQ ID NO: 599          moltype = DNA   length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1,2,11..13)
                        mod_base = OTHER
                        note = LNA nucleosides
source                  1..13
                        mol_type = other DNA
                        organism = synthetic construct
SEQUENCE: 599
cgaaccactg aac                                                          13

SEQ ID NO: 600          moltype = DNA   length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..3,11..13)
                        mod_base = OTHER
                        note = LNA nucleosides
source                  1..13
                        mol_type = other DNA
                        organism = synthetic construct
SEQUENCE: 600
cgaaccactg aac                                                          13

SEQ ID NO: 601          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1,2,12..15)
                        mod_base = OTHER
                        note = LNA nucleosides
source                  1..15
                        mol_type = other DNA
                        organism = synthetic construct
SEQUENCE: 601
ccgcagtatg gatcg                                                        15

SEQ ID NO: 602          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..4,14,15)
                        mod_base = OTHER
                        note = LNA nucleosides
source                  1..15
                        mol_type = other DNA
                        organism = synthetic construct
SEQUENCE: 602
ccgcagtatg gatcg                                                        15

SEQ ID NO: 603          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..4,13..15)
                        mod_base = OTHER
                        note = LNA nucleosides
source                  1..15
                        mol_type = other DNA
```

```
                       organism = synthetic construct
SEQUENCE: 603
ccgcagtatg gatcg                                                              15

SEQ ID NO: 604         moltype = DNA   length = 15
FEATURE                Location/Qualifiers
misc_feature           1..15
                       note = LNA antisense gapmer oligonucleotide
modified_base          1..15
                       mod_base = OTHER
                       note = Phosphorothiate Internucleoside linkages
modified_base          order(1..3,12..15)
                       mod_base = OTHER
                       note = LNA nucleosides
source                 1..15
                       mol_type = other DNA
                       organism = synthetic construct
SEQUENCE: 604
ccgcagtatg gatcg                                                              15

SEQ ID NO: 605         moltype = DNA   length = 13
FEATURE                Location/Qualifiers
misc_feature           1..13
                       note = LNA antisense gapmer oligonucleotide
modified_base          1..13
                       mod_base = OTHER
                       note = Phosphorothiate Internucleoside linkages
modified_base          order(1..4,12,13)
                       mod_base = OTHER
                       note = LNA nucleosides
source                 1..13
                       mol_type = other DNA
                       organism = synthetic construct
SEQUENCE: 605
cgcagtatgg atc                                                                13

SEQ ID NO: 606         moltype = DNA   length = 13
FEATURE                Location/Qualifiers
misc_feature           1..13
                       note = LNA antisense gapmer oligonucleotide
modified_base          1..13
                       mod_base = OTHER
                       note = Phosphorothiate Internucleoside linkages
modified_base          order(1,2,11..13)
                       mod_base = OTHER
                       note = LNA nucleosides
source                 1..13
                       mol_type = other DNA
                       organism = synthetic construct
SEQUENCE: 606
cgcagtatgg atc                                                                13

SEQ ID NO: 607         moltype = DNA   length = 13
FEATURE                Location/Qualifiers
misc_feature           1..13
                       note = LNA antisense gapmer oligonucleotide
modified_base          1..13
                       mod_base = OTHER
                       note = Phosphorothiate Internucleoside linkages
modified_base          order(1..3,11..13)
                       mod_base = OTHER
                       note = LNA nucleosides
source                 1..13
                       mol_type = other DNA
                       organism = synthetic construct
SEQUENCE: 607
cgcagtatgg atc                                                                13

SEQ ID NO: 608         moltype = DNA   length = 13
FEATURE                Location/Qualifiers
misc_feature           1..13
                       note = LNA antisense gapmer oligonucleotide
modified_base          1..13
                       mod_base = OTHER
                       note = Phosphorothiate Internucleoside linkages
modified_base          order(1,2,10..13)
                       mod_base = OTHER
                       note = LNA nucleosides
source                 1..13
```

```
                         mol_type = other DNA
                         organism = synthetic construct
SEQUENCE: 608
cgcagtatgg atc                                                          13

SEQ ID NO: 609           moltype = DNA  length = 14
FEATURE                  Location/Qualifiers
misc_feature             1..14
                         note = LNA antisense gapmer oligonucleotide
modified_base            1..14
                         mod_base = OTHER
                         note = Phosphorothiate Internucleoside linkages
modified_base            order(1..4,13,14)
                         mod_base = OTHER
                         note = LNA nucleosides
source                   1..14
                         mol_type = other DNA
                         organism = synthetic construct
SEQUENCE: 609
gcgtaaagag aggt                                                         14

SEQ ID NO: 610           moltype = DNA  length = 14
FEATURE                  Location/Qualifiers
misc_feature             1..14
                         note = LNA antisense gapmer oligonucleotide
modified_base            1..14
                         mod_base = OTHER
                         note = Phosphorothiate Internucleoside linkages
modified_base            order(1,2,11..14)
                         mod_base = OTHER
                         note = LNA nucleosides
source                   1..14
                         mol_type = other DNA
                         organism = synthetic construct
SEQUENCE: 610
gcgtaaagag aggt                                                         14

SEQ ID NO: 611           moltype = DNA  length = 14
FEATURE                  Location/Qualifiers
misc_feature             1..14
                         note = LNA antisense gapmer oligonucleotide
modified_base            1..14
                         mod_base = OTHER
                         note = Phosphorothiate Internucleoside linkages
modified_base            order(1..3,11..14)
                         mod_base = OTHER
                         note = LNA nucleosides
source                   1..14
                         mol_type = other DNA
                         organism = synthetic construct
SEQUENCE: 611
gcgtaaagag aggt                                                         14

SEQ ID NO: 612           moltype = DNA  length = 14
FEATURE                  Location/Qualifiers
misc_feature             1..14
                         note = LNA antisense gapmer oligonucleotide
modified_base            1..14
                         mod_base = OTHER
                         note = Phosphorothiate Internucleoside linkages
modified_base            order(1..4,12..14)
                         mod_base = OTHER
                         note = LNA nucleosides
source                   1..14
                         mol_type = other DNA
                         organism = synthetic construct
SEQUENCE: 612
gcgtaaagag aggt                                                         14

SEQ ID NO: 613           moltype = DNA  length = 15
FEATURE                  Location/Qualifiers
misc_feature             1..15
                         note = LNA antisense gapmer oligonucleotide
modified_base            1..15
                         mod_base = OTHER
                         note = Phosphorothiate Internucleoside linkages
modified_base            order(1..4,14,15)
                         mod_base = OTHER
                         note = LNA nucleosides
```

```
source                   1..15
                         mol_type = other DNA
                         organism = synthetic construct
SEQUENCE: 613
cgcgtaaaga gaggt                                                              15

SEQ ID NO: 614           moltype = DNA   length = 15
FEATURE                  Location/Qualifiers
misc_feature             1..15
                         note = LNA antisense gapmer oligonucleotide
modified_base            1..15
                         mod_base = OTHER
                         note = Phosphorothiate Internucleoside linkages
modified_base            order(1,2,12..15)
                         mod_base = OTHER
                         note = LNA nucleosides
source                   1..15
                         mol_type = other DNA
                         organism = synthetic construct
SEQUENCE: 614
cgcgtaaaga gaggt                                                              15

SEQ ID NO: 615           moltype = DNA   length = 15
FEATURE                  Location/Qualifiers
misc_feature             1..15
                         note = LNA antisense gapmer oligonucleotide
modified_base            1..15
                         mod_base = OTHER
                         note = Phosphorothiate Internucleoside linkages
modified_base            order(1..4,13..15)
                         mod_base = OTHER
                         note = LNA nucleosides
source                   1..15
                         mol_type = other DNA
                         organism = synthetic construct
SEQUENCE: 615
cgcgtaaaga gaggt                                                              15

SEQ ID NO: 616           moltype = DNA   length = 15
FEATURE                  Location/Qualifiers
misc_feature             1..15
                         note = LNA antisense gapmer oligonucleotide
modified_base            1..15
                         mod_base = OTHER
                         note = Phosphorothiate Internucleoside linkages
modified_base            order(1..3,12..15)
                         mod_base = OTHER
                         note = LNA nucleosides
source                   1..15
                         mol_type = other DNA
                         organism = synthetic construct
SEQUENCE: 616
cgcgtaaaga gaggt                                                              15

SEQ ID NO: 617           moltype = DNA   length = 13
FEATURE                  Location/Qualifiers
misc_feature             1..13
                         note = LNA antisense gapmer oligonucleotide
modified_base            1..13
                         mod_base = OTHER
                         note = Phosphorothiate Internucleoside linkages
modified_base            order(1,2,11..13)
                         mod_base = OTHER
                         note = LNA nucleosides
source                   1..13
                         mol_type = other DNA
                         organism = synthetic construct
SEQUENCE: 617
gcgtaaagag agg                                                                13

SEQ ID NO: 618           moltype = DNA   length = 13
FEATURE                  Location/Qualifiers
misc_feature             1..13
                         note = LNA antisense gapmer oligonucleotide
modified_base            1..13
                         mod_base = OTHER
                         note = Phosphorothiate Internucleoside linkages
modified_base            order(1..3,11..13)
                         mod_base = OTHER
```

```
                        note = LNA nucleosides
source                  1..13
                        mol_type = other DNA
                        organism = synthetic construct
SEQUENCE: 618
gcgtaaagag agg                                                          13

SEQ ID NO: 619          moltype = DNA  length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1,2,10..13)
                        mod_base = OTHER
                        note = LNA nucleosides
source                  1..13
                        mol_type = other DNA
                        organism = synthetic construct
SEQUENCE: 619
gcgtaaagag agg                                                          13

SEQ ID NO: 620          moltype = DNA  length = 13
FEATURE                 Location/Qualifiers
misc_feature            1..13
                        note = LNA antisense gapmer oligonucleotide
modified_base           1..13
                        mod_base = OTHER
                        note = Phosphorothiate Internucleoside linkages
modified_base           order(1..4,12,13)
                        mod_base = OTHER
                        note = LNA nucleosides
source                  1..13
                        mol_type = other DNA
                        organism = synthetic construct
SEQUENCE: 620
gcgtaaagag agg                                                          13

SEQ ID NO: 621          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1,2,12..15)
                        mod_base = OTHER
                        note = LNA nucleosides
source                  1..15
                        mol_type = other DNA
                        organism = synthetic construct
SEQUENCE: 621
agaaggcaca gacgg                                                        15

SEQ ID NO: 622          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,12..15)
                        mod_base = OTHER
                        note = LNA nucleosides
source                  1..15
                        mol_type = other DNA
                        organism = synthetic construct
SEQUENCE: 622
agaaggcaca gacgg                                                        15

SEQ ID NO: 623          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..4,13..15)
```

-continued

```
                            mod_base = OTHER
                            note = LNA nucleosides
source                      1..15
                            mol_type = other DNA
                            organism = synthetic construct
SEQUENCE: 623
agaaggcaca gacgg                                                              15

SEQ ID NO: 624              moltype = DNA   length = 16
FEATURE                     Location/Qualifiers
misc_feature                1..16
                            note = LNA antisense gapmer oligonucleotide
modified_base               1..16
                            mod_base = OTHER
                            note = Phosphorothiate Internucleoside linkages
modified_base               order(1..4,14..16)
                            mod_base = OTHER
                            note = LNA nucleosides
source                      1..16
                            mol_type = other DNA
                            organism = synthetic construct
SEQUENCE: 624
gagaaggcac agacgg                                                             16

SEQ ID NO: 625              moltype = DNA   length = 16
FEATURE                     Location/Qualifiers
misc_feature                1..16
                            note = LNA antisense gapmer oligonucleotide
modified_base               1..16
                            mod_base = OTHER
                            note = Phosphorothiate Internucleoside linkages
modified_base               order(1..3,13..16)
                            mod_base = OTHER
                            note = LNA nucleosides
source                      1..16
                            mol_type = other DNA
                            organism = synthetic construct
SEQUENCE: 625
gagaaggcac agacgg                                                             16

SEQ ID NO: 626              moltype = DNA   length = 16
FEATURE                     Location/Qualifiers
misc_feature                1..16
                            note = LNA antisense gapmer oligonucleotide
modified_base               1..16
                            mod_base = OTHER
                            note = Phosphorothiate Internucleoside linkages
modified_base               order(1..4,13..16)
                            mod_base = OTHER
                            note = LNA nucleosides
source                      1..16
                            mol_type = other DNA
                            organism = synthetic construct
SEQUENCE: 626
gagaaggcac agacgg                                                             16

SEQ ID NO: 627              moltype = DNA   length = 13
FEATURE                     Location/Qualifiers
misc_feature                1..13
                            note = LNA antisense gapmer oligonucleotide
modified_base               1..13
                            mod_base = OTHER
                            note = Phosphorothiate Internucleoside linkages
modified_base               order(1,2,11..13)
                            mod_base = OTHER
                            note = LNA nucleosides
source                      1..13
                            mol_type = other DNA
                            organism = synthetic construct
SEQUENCE: 627
gaagtgcaca cgg                                                                13

SEQ ID NO: 628              moltype = DNA   length = 13
FEATURE                     Location/Qualifiers
misc_feature                1..13
                            note = LNA antisense gapmer oligonucleotide
modified_base               1..13
                            mod_base = OTHER
                            note = Phosphorothiate Internucleoside linkages
```

```
modified_base          order(1..3,11..13)
                       mod_base = OTHER
                       note = LNA nucleosides
source                 1..13
                       mol_type = other DNA
                       organism = synthetic construct
SEQUENCE: 628
gaagtgcaca cgg                                                       13

SEQ ID NO: 629         moltype = DNA  length = 13
FEATURE                Location/Qualifiers
misc_feature           1..13
                       note = LNA antisense gapmer oligonucleotide
modified_base          1..13
                       mod_base = OTHER
                       note = Phosphorothiate Internucleoside linkages
modified_base          order(1..4,11..13)
                       mod_base = OTHER
                       note = LNA nucleosides
source                 1..13
                       mol_type = other DNA
                       organism = synthetic construct
SEQUENCE: 629
gaagtgcaca cgg                                                       13

SEQ ID NO: 630         moltype = DNA  length = 13
FEATURE                Location/Qualifiers
misc_feature           1..13
                       note = LNA antisense gapmer oligonucleotide
modified_base          1..13
                       mod_base = OTHER
                       note = Phosphorothiate Internucleoside linkages
modified_base          order(1..3,10..13)
                       mod_base = OTHER
                       note = LNA nucleosides
source                 1..13
                       mol_type = other DNA
                       organism = synthetic construct
SEQUENCE: 630
gaagtgcaca cgg                                                       13

SEQ ID NO: 631         moltype = DNA  length = 15
FEATURE                Location/Qualifiers
misc_feature           1..15
                       note = LNA antisense gapmer oligonucleotide
modified_base          1..15
                       mod_base = OTHER
                       note = Phosphorothiate Internucleoside linkages
modified_base          order(1,2,13..15)
                       mod_base = OTHER
                       note = LNA nucleosides
source                 1..15
                       mol_type = other DNA
                       organism = synthetic construct
SEQUENCE: 631
gcgaagtgca cacgg                                                     15

SEQ ID NO: 632         moltype = DNA  length = 15
FEATURE                Location/Qualifiers
misc_feature           1..15
                       note = LNA antisense gapmer oligonucleotide
modified_base          1..15
                       mod_base = OTHER
                       note = Phosphorothiate Internucleoside linkages
modified_base          order(1..3,14,15)
                       mod_base = OTHER
                       note = LNA nucleosides
source                 1..15
                       mol_type = other DNA
                       organism = synthetic construct
SEQUENCE: 632
gcgaagtgca cacgg                                                     15

SEQ ID NO: 633         moltype = DNA  length = 15
FEATURE                Location/Qualifiers
misc_feature           1..15
                       note = LNA antisense gapmer oligonucleotide
modified_base          1..15
                       mod_base = OTHER
```

```
                            note = Phosphorothiate Internucleoside linkages
modified_base               order(1..4,14,15)
                            mod_base = OTHER
                            note = LNA nucleosides
source                      1..15
                            mol_type = other DNA
                            organism = synthetic construct
SEQUENCE: 633
gcgaagtgca cacgg                                                            15

SEQ ID NO: 634              moltype = DNA  length = 15
FEATURE                     Location/Qualifiers
misc_feature                1..15
                            note = LNA antisense gapmer oligonucleotide
modified_base               1..15
                            mod_base = OTHER
                            note = Phosphorothiate Internucleoside linkages
modified_base               order(1,2,12..15)
                            mod_base = OTHER
                            note = LNA nucleosides
source                      1..15
                            mol_type = other DNA
                            organism = synthetic construct
SEQUENCE: 634
gcgaagtgca cacgg                                                            15

SEQ ID NO: 635              moltype = DNA  length = 16
FEATURE                     Location/Qualifiers
misc_feature                1..16
                            note = LNA antisense gapmer oligonucleotide
modified_base               1..16
                            mod_base = OTHER
                            note = Phosphorothiate Internucleoside linkages
modified_base               order(1..4,15,16)
                            mod_base = OTHER
                            note = LNA nucleosides
source                      1..16
                            mol_type = other DNA
                            organism = synthetic construct
SEQUENCE: 635
agcgaagtgc acacgg                                                           16

SEQ ID NO: 636              moltype = DNA  length = 16
FEATURE                     Location/Qualifiers
misc_feature                1..16
                            note = LNA antisense gapmer oligonucleotide
modified_base               1..16
                            mod_base = OTHER
                            note = Phosphorothiate Internucleoside linkages
modified_base               order(1,2,13..16)
                            mod_base = OTHER
                            note = LNA nucleosides
modified_base               3
                            mod_base = OTHER
                            note = 5-methyl c
source                      1..16
                            mol_type = other DNA
                            organism = synthetic construct
SEQUENCE: 636
agcgaagtgc acacgg                                                           16

SEQ ID NO: 637              moltype = DNA  length = 16
FEATURE                     Location/Qualifiers
misc_feature                1..16
                            note = LNA antisense gapmer oligonucleotide
modified_base               1..16
                            mod_base = OTHER
                            note = Phosphorothiate Internucleoside linkages
modified_base               order(1,2,14..16)
                            mod_base = OTHER
                            note = LNA nucleosides
modified_base               3
                            mod_base = OTHER
                            note = 5-methyl c
source                      1..16
                            mol_type = other DNA
                            organism = synthetic construct
SEQUENCE: 637
agcgaagtgc acacgg                                                           16
```

```
SEQ ID NO: 638           moltype = DNA  length = 16
FEATURE                  Location/Qualifiers
misc_feature             1..16
                         note = LNA antisense gapmer oligonucleotide
modified_base            1..16
                         mod_base = OTHER
                         note = Phosphorothiate Internucleoside linkages
modified_base            order(1..3,15,16)
                         mod_base = OTHER
                         note = LNA nucleosides
source                   1..16
                         mol_type = other DNA
                         organism = synthetic construct
SEQUENCE: 638
agcgaagtgc acacgg                                                         16

SEQ ID NO: 639           moltype = DNA  length = 13
FEATURE                  Location/Qualifiers
misc_feature             1..13
                         note = LNA antisense gapmer oligonucleotide
modified_base            1..13
                         mod_base = OTHER
                         note = Phosphorothiate Internucleoside linkages
modified_base            order(1,2,10..13)
                         mod_base = OTHER
                         note = LNA nucleosides
source                   1..13
                         mol_type = other DNA
                         organism = synthetic construct
SEQUENCE: 639
cgaagtgcac acg                                                            13

SEQ ID NO: 640           moltype = DNA  length = 13
FEATURE                  Location/Qualifiers
misc_feature             1..13
                         note = LNA antisense gapmer oligonucleotide
modified_base            1..13
                         mod_base = OTHER
                         note = Phosphorothiate Internucleoside linkages
modified_base            order(1..3,11..13)
                         mod_base = OTHER
                         note = LNA nucleosides
source                   1..13
                         mol_type = other DNA
                         organism = synthetic construct
SEQUENCE: 640
cgaagtgcac acg                                                            13

SEQ ID NO: 641           moltype = DNA  length = 13
FEATURE                  Location/Qualifiers
misc_feature             1..13
                         note = LNA antisense gapmer oligonucleotide
modified_base            1..13
                         mod_base = OTHER
                         note = Phosphorothiate Internucleoside linkages
modified_base            order(1,2,11..13)
                         mod_base = OTHER
                         note = LNA nucleosides
source                   1..13
                         mol_type = other DNA
                         organism = synthetic construct
SEQUENCE: 641
cgaagtgcac acg                                                            13

SEQ ID NO: 642           moltype = DNA  length = 15
FEATURE                  Location/Qualifiers
misc_feature             1..15
                         note = LNA antisense gapmer oligonucleotide
modified_base            1..15
                         mod_base = OTHER
                         note = Phosphorothiate Internucleoside linkages
modified_base            order(1..3,12..15)
                         mod_base = OTHER
                         note = LNA nucleosides
source                   1..15
                         mol_type = other DNA
                         organism = synthetic construct
SEQUENCE: 642
```

```
agcgaagtgc acacg                                                              15

SEQ ID NO: 643          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..4,13..15)
                        mod_base = OTHER
                        note = LNA nucleosides
source                  1..15
                        mol_type = other DNA
                        organism = synthetic construct
SEQUENCE: 643
agcgaagtgc acacg                                                              15

SEQ ID NO: 644          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..4,14,15)
                        mod_base = OTHER
                        note = LNA nucleosides
source                  1..15
                        mol_type = other DNA
                        organism = synthetic construct
SEQUENCE: 644
agcgaagtgc acacg                                                              15

SEQ ID NO: 645          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1,2,12..15)
                        mod_base = OTHER
                        note = LNA nucleosides
modified_base           3
                        mod_base = OTHER
                        note = 5-methyl c
source                  1..15
                        mol_type = other DNA
                        organism = synthetic construct
SEQUENCE: 645
agcgaagtgc acacg                                                              15

SEQ ID NO: 646          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1,2,13..16)
                        mod_base = OTHER
                        note = LNA nucleosides
modified_base           4
                        mod_base = OTHER
                        note = 5-methyl c
source                  1..16
                        mol_type = other DNA
                        organism = synthetic construct
SEQUENCE: 646
aagcgaagtg cacacg                                                             16

SEQ ID NO: 647          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
```

```
                        -continued modified_base           order(1..4,15,16)
                        mod_base = OTHER
                        note = LNA nucleosides
source                  1..16
                        mol_type = other DNA
                        organism = synthetic construct
SEQUENCE: 647
aagcgaagtg cacacg                                                        16

SEQ ID NO: 648          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,13..16)
                        mod_base = OTHER
                        note = LNA nucleosides
modified_base           4
                        mod_base = OTHER
                        note = 5-methyl c
source                  1..16
                        mol_type = other DNA
                        organism = synthetic construct
SEQUENCE: 648
aagcgaagtg cacacg                                                        16

SEQ ID NO: 649          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..4,14..16)
                        mod_base = OTHER
                        note = LNA nucleosides
source                  1..16
                        mol_type = other DNA
                        organism = synthetic construct
SEQUENCE: 649
aagcgaagtg cacacg                                                        16

SEQ ID NO: 650          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..4,13..16)
                        mod_base = OTHER
                        note = LNA nucleosides
source                  1..16
                        mol_type = other DNA
                        organism = synthetic construct
SEQUENCE: 650
aagcgaagtg cacacg                                                        16

SEQ ID NO: 651          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1,2,12..15)
                        mod_base = OTHER
                        note = LNA nucleosides
modified_base           5
                        mod_base = OTHER
                        note = 5-methyl c
source                  1..15
                        mol_type = other DNA
                        organism = synthetic construct
SEQUENCE: 651
gaagcgaagt gcaca                                                         15
```

-continued

```
SEQ ID NO: 652           moltype = DNA   length = 15
FEATURE                  Location/Qualifiers
misc_feature             1..15
                         note = LNA antisense gapmer oligonucleotide
modified_base            1..15
                         mod_base = OTHER
                         note = Phosphorothiate Internucleoside linkages
modified_base            order(1..4,14,15)
                         mod_base = OTHER
                         note = LNA nucleosides
modified_base            5
                         mod_base = OTHER
                         note = 5-methyl c
source                   1..15
                         mol_type = other DNA
                         organism = synthetic construct
SEQUENCE: 652
gaagcgaagt gcaca                                                      15

SEQ ID NO: 653           moltype = DNA   length = 15
FEATURE                  Location/Qualifiers
misc_feature             1..15
                         note = LNA antisense gapmer oligonucleotide
modified_base            1..15
                         mod_base = OTHER
                         note = Phosphorothiate Internucleoside linkages
modified_base            order(1..3,12..15)
                         mod_base = OTHER
                         note = LNA nucleosides
modified_base            5
                         mod_base = OTHER
                         note = 5-methyl c
source                   1..15
                         mol_type = other DNA
                         organism = synthetic construct
SEQUENCE: 653
gaagcgaagt gcaca                                                      15

SEQ ID NO: 654           moltype = DNA   length = 15
FEATURE                  Location/Qualifiers
misc_feature             1..15
                         note = LNA antisense gapmer oligonucleotide
modified_base            1..15
                         mod_base = OTHER
                         note = Phosphorothiate Internucleoside linkages
modified_base            order(1..4,12..15)
                         mod_base = OTHER
                         note = LNA nucleosides
modified_base            5
                         mod_base = OTHER
                         note = 5-methyl c
source                   1..15
                         mol_type = other DNA
                         organism = synthetic construct
SEQUENCE: 654
gaagcgaagt gcaca                                                      15

SEQ ID NO: 655           moltype = DNA   length = 16
FEATURE                  Location/Qualifiers
misc_feature             1..16
                         note = LNA antisense gapmer oligonucleotide
modified_base            1..16
                         mod_base = OTHER
                         note = Phosphorothiate Internucleoside linkages
modified_base            order(1,2,14..16)
                         mod_base = OTHER
                         note = LNA nucleosides
modified_base            8
                         mod_base = OTHER
                         note = 5-methyl c
source                   1..16
                         mol_type = other DNA
                         organism = synthetic construct
SEQUENCE: 655
ggtgaagcga agtgca                                                     16

SEQ ID NO: 656           moltype = DNA   length = 16
FEATURE                  Location/Qualifiers
misc_feature             1..16
```

-continued

```
                          note = LNA antisense gapmer oligonucleotide
modified_base             1..16
                          mod_base = OTHER
                          note = Phosphorothiate Internucleoside linkages
modified_base             order(1..3,15,16)
                          mod_base = OTHER
                          note = LNA nucleosides
modified_base             8
                          mod_base = OTHER
                          note = 5-methyl c
source                    1..16
                          mol_type = other DNA
                          organism = synthetic construct
SEQUENCE: 656
ggtgaagcga agtgca                                                              16

SEQ ID NO: 657            moltype = DNA  length = 16
FEATURE                   Location/Qualifiers
misc_feature              1..16
                          note = LNA antisense gapmer oligonucleotide
modified_base             1..16
                          mod_base = OTHER
                          note = Phosphorothiate Internucleoside linkages
modified_base             order(1..4,15,16)
                          mod_base = OTHER
                          note = LNA nucleosides
modified_base             8
                          mod_base = OTHER
                          note = 5-methyl c
source                    1..16
                          mol_type = other DNA
                          organism = synthetic construct
SEQUENCE: 657
ggtgaagcga agtgca                                                              16

SEQ ID NO: 658            moltype = DNA  length = 16
FEATURE                   Location/Qualifiers
misc_feature              1..16
                          note = LNA antisense gapmer oligonucleotide
modified_base             1..16
                          mod_base = OTHER
                          note = Phosphorothiate Internucleoside linkages
modified_base             order(1,2,13..16)
                          mod_base = OTHER
                          note = LNA nucleosides
modified_base             8
                          mod_base = OTHER
                          note = 5-methyl c
source                    1..16
                          mol_type = other DNA
                          organism = synthetic construct
SEQUENCE: 658
ggtgaagcga agtgca                                                              16

SEQ ID NO: 659            moltype = DNA  length = 15
FEATURE                   Location/Qualifiers
misc_feature              1..15
                          note = LNA antisense gapmer oligonucleotide
modified_base             1..15
                          mod_base = OTHER
                          note = Phosphorothiate Internucleoside linkages
modified_base             order(1,2,13..15)
                          mod_base = OTHER
                          note = LNA nucleosides
modified_base             8
                          mod_base = OTHER
                          note = 5-methyl c
source                    1..15
                          mol_type = other DNA
                          organism = synthetic construct
SEQUENCE: 659
ggtgaagcga agtgc                                                               15

SEQ ID NO: 660            moltype = DNA  length = 15
FEATURE                   Location/Qualifiers
misc_feature              1..15
                          note = LNA antisense gapmer oligonucleotide
modified_base             1..15
                          mod_base = OTHER
```

```
                        note = Phosphorothiate Internucleoside linkages
modified_base           order(1..3,14,15)
                        mod_base = OTHER
                        note = LNA nucleosides
modified_base           8
                        mod_base = OTHER
                        note = 5-methyl c
source                  1..15
                        mol_type = other DNA
                        organism = synthetic construct
SEQUENCE: 660
ggtgaagcga agtgc                                                           15

SEQ ID NO: 661          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..4,14,15)
                        mod_base = OTHER
                        note = LNA nucleosides
modified_base           8
                        mod_base = OTHER
                        note = 5-methyl c
source                  1..15
                        mol_type = other DNA
                        organism = synthetic construct
SEQUENCE: 661
ggtgaagcga agtgc                                                           15

SEQ ID NO: 662          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1,2,12..15)
                        mod_base = OTHER
                        note = LNA nucleosides
modified_base           8
                        mod_base = OTHER
                        note = 5-methyl c
source                  1..15
                        mol_type = other DNA
                        organism = synthetic construct
SEQUENCE: 662
ggtgaagcga agtgc                                                           15

SEQ ID NO: 663          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1,2,14..16)
                        mod_base = OTHER
                        note = LNA nucleosides
modified_base           9
                        mod_base = OTHER
                        note = 5-methyl c
source                  1..16
                        mol_type = other DNA
                        organism = synthetic construct
SEQUENCE: 663
aggtgaagcg aagtgc                                                          16

SEQ ID NO: 664          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,15,16)
                        mod_base = OTHER
```

|                | | |
|---|---|---|
| modified_base  | note = LNA nucleosides<br>9<br>mod_base = OTHER<br>note = 5-methyl c | |
| source         | 1..16<br>mol_type = other DNA<br>organism = synthetic construct | |
| SEQUENCE: 664  | | |
| aggtgaagcg aagtgc | | 16 |
| SEQ ID NO: 665<br>FEATURE | moltype = DNA  length = 16<br>Location/Qualifiers | |
| misc_feature   | 1..16<br>note = LNA antisense gapmer oligonucleotide | |
| modified_base  | 1..16<br>mod_base = OTHER<br>note = Phosphorothiate Internucleoside linkages | |
| modified_base  | order(1..4,15,16)<br>mod_base = OTHER<br>note = LNA nucleosides | |
| modified_base  | 9<br>mod_base = OTHER<br>note = 5-methyl c | |
| source         | 1..16<br>mol_type = other DNA<br>organism = synthetic construct | |
| SEQUENCE: 665  | | |
| aggtgaagcg aagtgc | | 16 |
| SEQ ID NO: 666<br>FEATURE | moltype = DNA  length = 16<br>Location/Qualifiers | |
| misc_feature   | 1..16<br>note = LNA antisense gapmer oligonucleotide | |
| modified_base  | 1..16<br>mod_base = OTHER<br>note = Phosphorothiate Internucleoside linkages | |
| modified_base  | order(1,2,13..16)<br>mod_base = OTHER<br>note = LNA nucleosides | |
| modified_base  | 9<br>mod_base = OTHER<br>note = 5-methyl c | |
| source         | 1..16<br>mol_type = other DNA<br>organism = synthetic construct | |
| SEQUENCE: 666  | | |
| aggtgaagcg aagtgc | | 16 |
| SEQ ID NO: 667<br>FEATURE | moltype = DNA  length = 15<br>Location/Qualifiers | |
| misc_feature   | 1..15<br>note = LNA antisense gapmer oligonucleotide | |
| modified_base  | 1..15<br>mod_base = OTHER<br>note = Phosphorothiate Internucleoside linkages | |
| modified_base  | order(1..4,14,15)<br>mod_base = OTHER<br>note = LNA nucleosides | |
| modified_base  | 9<br>mod_base = OTHER<br>note = 5-methyl c | |
| source         | 1..15<br>mol_type = other DNA<br>organism = synthetic construct | |
| SEQUENCE: 667  | | |
| aggtgaagcg aagtg | | 15 |
| SEQ ID NO: 668<br>FEATURE | moltype = DNA  length = 15<br>Location/Qualifiers | |
| misc_feature   | 1..15<br>note = LNA antisense gapmer oligonucleotide | |
| modified_base  | 1..15<br>mod_base = OTHER<br>note = Phosphorothiate Internucleoside linkages | |
| modified_base  | order(1,2,12..15)<br>mod_base = OTHER<br>note = LNA nucleosides | |
| modified_base  | 9<br>mod_base = OTHER | |

```
                        note = 5-methyl c
source                  1..15
                        mol_type = other DNA
                        organism = synthetic construct
SEQUENCE: 668
aggtgaagcg aagtg                                                       15

SEQ ID NO: 669          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,12..15)
                        mod_base = OTHER
                        note = LNA nucleosides
modified_base           9
                        mod_base = OTHER
                        note = 5-methyl c
source                  1..15
                        mol_type = other DNA
                        organism = synthetic construct
SEQUENCE: 669
aggtgaagcg aagtg                                                       15

SEQ ID NO: 670          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..4,13..15)
                        mod_base = OTHER
                        note = LNA nucleosides
modified_base           9
                        mod_base = OTHER
                        note = 5-methyl c
source                  1..15
                        mol_type = other DNA
                        organism = synthetic construct
SEQUENCE: 670
aggtgaagcg aagtg                                                       15

SEQ ID NO: 671          moltype = DNA  length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1..4,13,14)
                        mod_base = OTHER
                        note = LNA nucleosides
modified_base           9
                        mod_base = OTHER
                        note = 5-methyl c
source                  1..14
                        mol_type = other DNA
                        organism = synthetic construct
SEQUENCE: 671
aggtgaagcg aagt                                                        14

SEQ ID NO: 672          moltype = DNA  length = 14
FEATURE                 Location/Qualifiers
misc_feature            1..14
                        note = LNA antisense gapmer oligonucleotide
modified_base           1..14
                        mod_base = OTHER
                        note = Phosphorothiate Internucleoside linkages
modified_base           order(1,2,11..14)
                        mod_base = OTHER
                        note = LNA nucleosides
modified_base           9
                        mod_base = OTHER
                        note = 5-methyl c
source                  1..14
                        mol_type = other DNA
```

```
                          organism = synthetic construct
SEQUENCE: 672
aggtgaagcg aagt                                                          14

SEQ ID NO: 673            moltype = DNA   length = 14
FEATURE                   Location/Qualifiers
misc_feature              1..14
                          note = LNA antisense gapmer oligonucleotide
modified_base             1..14
                          mod_base = OTHER
                          note = Phosphorothiate Internucleoside linkages
modified_base             order(1..3,11..14)
                          mod_base = OTHER
                          note = LNA nucleosides
modified_base             9
                          mod_base = OTHER
                          note = 5-methyl c
source                    1..14
                          mol_type = other DNA
                          organism = synthetic construct
SEQUENCE: 673
aggtgaagcg aagt                                                          14

SEQ ID NO: 674            moltype = DNA   length = 14
FEATURE                   Location/Qualifiers
misc_feature              1..14
                          note = LNA antisense gapmer oligonucleotide
modified_base             1..14
                          mod_base = OTHER
                          note = Phosphorothiate Internucleoside linkages
modified_base             order(1..4,12..14)
                          mod_base = OTHER
                          note = LNA nucleosides
modified_base             9
                          mod_base = OTHER
                          note = 5-methyl c
source                    1..14
                          mol_type = other DNA
                          organism = synthetic construct
SEQUENCE: 674
aggtgaagcg aagt                                                          14

SEQ ID NO: 675            moltype = DNA   length = 14
FEATURE                   Location/Qualifiers
misc_feature              1..14
                          note = LNA antisense gapmer oligonucleotide
modified_base             1..14
                          mod_base = OTHER
                          note = Phosphorothiate Internucleoside linkages
modified_base             order(1..4,13,14)
                          mod_base = OTHER
                          note = LNA nucleosides
source                    1..14
                          mol_type = other DNA
                          organism = synthetic construct
SEQUENCE: 675
cagaggtgaa gcga                                                          14

SEQ ID NO: 676            moltype = DNA   length = 14
FEATURE                   Location/Qualifiers
misc_feature              1..14
                          note = LNA antisense gapmer oligonucleotide
modified_base             1..14
                          mod_base = OTHER
                          note = Phosphorothiate Internucleoside linkages
modified_base             order(1,2,11..14)
                          mod_base = OTHER
                          note = LNA nucleosides
source                    1..14
                          mol_type = other DNA
                          organism = synthetic construct
SEQUENCE: 676
cagaggtgaa gcga                                                          14

SEQ ID NO: 677            moltype = DNA   length = 14
FEATURE                   Location/Qualifiers
misc_feature              1..14
                          note = LNA antisense gapmer oligonucleotide
modified_base             1..14
```

```
                        mod_base = OTHER
                        note = Phosphorothiate Internucleoside linkages
modified_base           order(1..3,11..14)
                        mod_base = OTHER
                        note = LNA nucleosides
source                  1..14
                        mol_type = other DNA
                        organism = synthetic construct
SEQUENCE: 677
cagaggtgaa gcga                                                            14

SEQ ID NO: 678          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 678
tagtaaactg agcca                                                           15

SEQ ID NO: 679          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1,2,12..15)
                        mod_base = OTHER
                        note = LNA nucleosides
source                  1..15
                        mol_type = other DNA
                        organism = synthetic construct
SEQUENCE: 679
tagtaaactg agcca                                                           15

SEQ ID NO: 680          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..4,14,15)
                        mod_base = OTHER
                        note = LNA nucleosides
source                  1..15
                        mol_type = other DNA
                        organism = synthetic construct
SEQUENCE: 680
tagtaaactg agcca                                                           15

SEQ ID NO: 681          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,12..15)
                        mod_base = OTHER
                        note = LNA nucleosides
source                  1..15
                        mol_type = other DNA
                        organism = synthetic construct
SEQUENCE: 681
tagtaaactg agcca                                                           15

SEQ ID NO: 682          moltype = DNA  length = 15
FEATURE                 Location/Qualifiers
misc_feature            1..15
                        note = LNA antisense gapmer oligonucleotide
```

```
modified_base            1..15
                         mod_base = OTHER
                         note = Phosphorothiate Internucleoside linkages
modified_base            order(1..4,13..15)
                         mod_base = OTHER
                         note = LNA nucleosides
source                   1..15
                         mol_type = other DNA
                         organism = synthetic construct
SEQUENCE: 682
tagtaaactg agcca                                                          15

SEQ ID NO: 683           moltype = DNA  length = 16
FEATURE                  Location/Qualifiers
misc_feature             1..16
                         note = LNA antisense gapmer oligonucleotide
modified_base            1..16
                         mod_base = OTHER
                         note = Phosphorothiate Internucleoside linkages
modified_base            order(1..3,14..16)
                         mod_base = OTHER
                         note = LNA nucleosides
source                   1..16
                         mol_type = other DNA
                         organism = synthetic construct
SEQUENCE: 683
ctagtaaact gagcca                                                         16

SEQ ID NO: 684           moltype = DNA  length = 16
FEATURE                  Location/Qualifiers
misc_feature             1..16
                         note = LNA antisense gapmer oligonucleotide
modified_base            1..16
                         mod_base = OTHER
                         note = Phosphorothiate Internucleoside linkages
modified_base            order(1,2,13..16)
                         mod_base = OTHER
                         note = LNA nucleosides
source                   1..16
                         mol_type = other DNA
                         organism = synthetic construct
SEQUENCE: 684
ctagtaaact gagcca                                                         16

SEQ ID NO: 685           moltype = DNA  length = 16
FEATURE                  Location/Qualifiers
misc_feature             1..16
                         note = LNA antisense gapmer oligonucleotide
modified_base            1..16
                         mod_base = OTHER
                         note = Phosphorothiate Internucleoside linkages
modified_base            order(1..4,15,16)
                         mod_base = OTHER
                         note = LNA nucleosides
source                   1..16
                         mol_type = other DNA
                         organism = synthetic construct
SEQUENCE: 685
ctagtaaact gagcca                                                         16

SEQ ID NO: 686           moltype = DNA  length = 15
FEATURE                  Location/Qualifiers
misc_feature             1..15
                         note = LNA antisense gapmer oligonucleotide
modified_base            1..15
                         mod_base = OTHER
                         note = Phosphorothiate Internucleoside linkages
modified_base            order(1..3,13..15)
                         mod_base = OTHER
                         note = LNA nucleosides
source                   1..15
                         mol_type = other DNA
                         organism = synthetic construct
SEQUENCE: 686
ctagtaaact gagcc                                                          15

SEQ ID NO: 687           moltype = DNA  length = 15
FEATURE                  Location/Qualifiers
misc_feature             1..15
```

```
                        note = LNA antisense gapmer oligonucleotide
modified_base           1..15
                        mod_base = OTHER
                        note = Phosphorothiate Internucleoside linkages
modified_base           order(1,2,12..15)
                        mod_base = OTHER
                        note = LNA nucleosides
source                  1..15
                        mol_type = other DNA
                        organism = synthetic construct
SEQUENCE: 687
ctagtaaact gagcc                                                         15

SEQ ID NO: 688          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..4,14,15)
                        mod_base = OTHER
                        note = LNA nucleosides
source                  1..15
                        mol_type = other DNA
                        organism = synthetic construct
SEQUENCE: 688
ctagtaaact gagcc                                                         15

SEQ ID NO: 689          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1,2,13..15)
                        mod_base = OTHER
                        note = LNA nucleosides
source                  1..15
                        mol_type = other DNA
                        organism = synthetic construct
SEQUENCE: 689
ctagtaaact gagcc                                                         15

SEQ ID NO: 690          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,14,15)
                        mod_base = OTHER
                        note = LNA nucleosides
source                  1..15
                        mol_type = other DNA
                        organism = synthetic construct
SEQUENCE: 690
ctagtaaact gagcc                                                         15

SEQ ID NO: 691          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 691
gcactagtaa actga                                                         15

SEQ ID NO: 692          moltype = DNA  length = 15
FEATURE                 Location/Qualifiers
```

| | |
|---|---|
| misc_feature | 1..15<br>note = LNA antisense gapmer oligonucleotide |
| modified_base | 1..15<br>mod_base = OTHER<br>note = Phosphorothiate Internucleoside linkages |
| modified_base | order(1,2,12..15)<br>mod_base = OTHER<br>note = LNA nucleosides |
| source | 1..15<br>mol_type = other DNA<br>organism = synthetic construct |

SEQUENCE: 692
gcactagtaa actga 15

| | |
|---|---|
| SEQ ID NO: 693 | moltype = DNA length = 15 |
| FEATURE | Location/Qualifiers |
| misc_feature | 1..15<br>note = LNA antisense gapmer oligonucleotide |
| modified_base | 1..15<br>mod_base = OTHER<br>note = Phosphorothiate Internucleoside linkages |
| modified_base | order(1..4,14,15)<br>mod_base = OTHER<br>note = LNA nucleosides |
| source | 1..15<br>mol_type = other DNA<br>organism = synthetic construct |

SEQUENCE: 693
gcactagtaa actga 15

| | |
|---|---|
| SEQ ID NO: 694 | moltype = DNA length = 15 |
| FEATURE | Location/Qualifiers |
| misc_feature | 1..15<br>note = LNA antisense gapmer oligonucleotide |
| modified_base | 1..15<br>mod_base = OTHER<br>note = Phosphorothiate Internucleoside linkages |
| modified_base | order(1..3,12..15)<br>mod_base = OTHER<br>note = LNA nucleosides |
| source | 1..15<br>mol_type = other DNA<br>organism = synthetic construct |

SEQUENCE: 694
gcactagtaa actga 15

| | |
|---|---|
| SEQ ID NO: 695 | moltype = DNA length = 15 |
| FEATURE | Location/Qualifiers |
| misc_feature | 1..15<br>note = LNA antisense gapmer oligonucleotide |
| modified_base | 1..15<br>mod_base = OTHER<br>note = Phosphorothiate Internucleoside linkages |
| modified_base | order(1..4,13..15)<br>mod_base = OTHER<br>note = LNA nucleosides |
| source | 1..15<br>mol_type = other DNA<br>organism = synthetic construct |

SEQUENCE: 695
gcactagtaa actga 15

| | |
|---|---|
| SEQ ID NO: 696 | moltype = DNA length = 16 |
| FEATURE | Location/Qualifiers |
| misc_feature | 1..16<br>note = LNA antisense gapmer oligonucleotide |
| modified_base | 1..16<br>mod_base = OTHER<br>note = Phosphorothiate Internucleoside linkages |
| modified_base | order(1..3,14..16)<br>mod_base = OTHER<br>note = LNA nucleosides |
| source | 1..16<br>mol_type = other DNA<br>organism = synthetic construct |

SEQUENCE: 696
ggcactagta aactga 16

| | |
|---|---|
| SEQ ID NO: 697 | moltype = DNA length = 16 |

```
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1,2,13..16)
                        mod_base = OTHER
                        note = LNA nucleosides
source                  1..16
                        mol_type = other DNA
                        organism = synthetic construct
SEQUENCE: 697
ggcactagta aactga                                                        16

SEQ ID NO: 698          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..4,15,16)
                        mod_base = OTHER
                        note = LNA nucleosides
source                  1..16
                        mol_type = other DNA
                        organism = synthetic construct
SEQUENCE: 698
ggcactagta aactga                                                        16

SEQ ID NO: 699          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
modified_base           4
                        mod_base = OTHER
                        note = 5-methyl c
source                  1..15
                        mol_type = other DNA
                        organism = synthetic construct
SEQUENCE: 699
caacggggta aaggt                                                         15

SEQ ID NO: 700          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1,2,12..15)
                        mod_base = OTHER
                        note = LNA nucleosides
modified_base           4
                        mod_base = OTHER
                        note = 5-methyl c
source                  1..15
                        mol_type = other DNA
                        organism = synthetic construct
SEQUENCE: 700
caacggggta aaggt                                                         15

SEQ ID NO: 701          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..4,14,15)
                        mod_base = OTHER
                        note = LNA nucleosides
```

```
source                    1..15
                          mol_type = other DNA
                          organism = synthetic construct
SEQUENCE: 701
caacggggta aaggt                                                          15

SEQ ID NO: 702            moltype = DNA  length = 15
FEATURE                   Location/Qualifiers
misc_feature              1..15
                          note = LNA antisense gapmer oligonucleotide
modified_base             1..15
                          mod_base = OTHER
                          note = Phosphorothiate Internucleoside linkages
modified_base             order(1..3,12..15)
                          mod_base = OTHER
                          note = LNA nucleosides
modified_base             4
                          mod_base = OTHER
                          note = 5-methyl c
source                    1..15
                          mol_type = other DNA
                          organism = synthetic construct
SEQUENCE: 702
caacggggta aaggt                                                          15

SEQ ID NO: 703            moltype = DNA  length = 15
FEATURE                   Location/Qualifiers
misc_feature              1..15
                          note = LNA antisense gapmer oligonucleotide
modified_base             1..15
                          mod_base = OTHER
                          note = Phosphorothiate Internucleoside linkages
modified_base             order(1..4,13..15)
                          mod_base = OTHER
                          note = LNA nucleosides
source                    1..15
                          mol_type = other DNA
                          organism = synthetic construct
SEQUENCE: 703
caacggggta aaggt                                                          15

SEQ ID NO: 704            moltype = DNA  length = 15
FEATURE                   Location/Qualifiers
misc_feature              1..15
                          note = LNA antisense gapmer oligonucleotide
modified_base             1..15
                          mod_base = OTHER
                          note = Phosphorothiate Internucleoside linkages
modified_base             order(1..3,13..15)
                          mod_base = OTHER
                          note = LNA nucleosides
modified_base             11
                          mod_base = OTHER
                          note = 5-methyl c
source                    1..15
                          mol_type = other DNA
                          organism = synthetic construct
SEQUENCE: 704
cagtatggat cggca                                                          15

SEQ ID NO: 705            moltype = DNA  length = 15
FEATURE                   Location/Qualifiers
misc_feature              1..15
                          note = LNA antisense gapmer oligonucleotide
modified_base             1..15
                          mod_base = OTHER
                          note = Phosphorothiate Internucleoside linkages
modified_base             order(1,2,12..15)
                          mod_base = OTHER
                          note = LNA nucleosides
modified_base             11
                          mod_base = OTHER
                          note = 5-methyl c
source                    1..15
                          mol_type = other DNA
                          organism = synthetic construct
SEQUENCE: 705
cagtatggat cggca                                                          15
```

-continued

| | |
|---|---|
| SEQ ID NO: 706 | moltype = DNA length = 15 |
| FEATURE | Location/Qualifiers |
| misc_feature | 1..15 |
| | note = LNA antisense gapmer oligonucleotide |
| modified_base | 1..15 |
| | mod_base = OTHER |
| | note = Phosphorothiate Internucleoside linkages |
| modified_base | order(1,2,13..15) |
| | mod_base = OTHER |
| | note = LNA nucleosides |
| modified_base | 11 |
| | mod_base = OTHER |
| | note = 5-methyl c |
| source | 1..15 |
| | mol_type = other DNA |
| | organism = synthetic construct |

SEQUENCE: 706
cagtatggat cggca 15

| | |
|---|---|
| SEQ ID NO: 707 | moltype = DNA length = 15 |
| FEATURE | Location/Qualifiers |
| misc_feature | 1..15 |
| | note = LNA antisense gapmer oligonucleotide |
| modified_base | 1..15 |
| | mod_base = OTHER |
| | note = Phosphorothiate Internucleoside linkages |
| modified_base | order(1..3,14,15) |
| | mod_base = OTHER |
| | note = LNA nucleosides |
| modified_base | 11 |
| | mod_base = OTHER |
| | note = 5-methyl c |
| source | 1..15 |
| | mol_type = other DNA |
| | organism = synthetic construct |

SEQUENCE: 707
cagtatggat cggca 15

| | |
|---|---|
| SEQ ID NO: 708 | moltype = DNA length = 16 |
| FEATURE | Location/Qualifiers |
| misc_feature | 1..16 |
| | note = LNA antisense gapmer oligonucleotide |
| modified_base | 1..16 |
| | mod_base = OTHER |
| | note = Phosphorothiate Internucleoside linkages |
| modified_base | order(1..3,14..16) |
| | mod_base = OTHER |
| | note = LNA nucleosides |
| modified_base | 4 |
| | mod_base = OTHER |
| | note = 5-methyl c |
| source | 1..16 |
| | mol_type = other DNA |
| | organism = synthetic construct |

SEQUENCE: 708
ttccgcagta tggatc 16

| | |
|---|---|
| SEQ ID NO: 709 | moltype = DNA length = 16 |
| FEATURE | Location/Qualifiers |
| misc_feature | 1..16 |
| | note = LNA antisense gapmer oligonucleotide |
| modified_base | 1..16 |
| | mod_base = OTHER |
| | note = Phosphorothiate Internucleoside linkages |
| modified_base | order(1,2,13..16) |
| | mod_base = OTHER |
| | note = LNA nucleosides |
| modified_base | 4 |
| | mod_base = OTHER |
| | note = 5-methyl c |
| source | 1..16 |
| | mol_type = other DNA |
| | organism = synthetic construct |

SEQUENCE: 709
ttccgcagta tggatc 16

| | |
|---|---|
| SEQ ID NO: 710 | moltype = DNA length = 16 |
| FEATURE | Location/Qualifiers |
| misc_feature | 1..16 |

```
                        note = LNA antisense gapmer oligonucleotide
modified_base           1..16
                        mod_base = OTHER
                        note = Phosphorothiate Internucleoside linkages
modified_base           order(1..4,15,16)
                        mod_base = OTHER
                        note = LNA nucleosides
source                  1..16
                        mol_type = other DNA
                        organism = synthetic construct
SEQUENCE: 710
ttccgcagta tggatc                                                            16

SEQ ID NO: 711          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,13..16)
                        mod_base = OTHER
                        note = LNA nucleosides
modified_base           4
                        mod_base = OTHER
                        note = 5-methyl c
source                  1..16
                        mol_type = other DNA
                        organism = synthetic construct
SEQUENCE: 711
ttccgcagta tggatc                                                            16

SEQ ID NO: 712          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..4,14..16)
                        mod_base = OTHER
                        note = LNA nucleosides
source                  1..16
                        mol_type = other DNA
                        organism = synthetic construct
SEQUENCE: 712
ttccgcagta tggatc                                                            16

SEQ ID NO: 713          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
modified_base           4
                        mod_base = OTHER
                        note = 5-methyl c
source                  1..15
                        mol_type = other DNA
                        organism = synthetic construct
SEQUENCE: 713
ttccgcagta tggat                                                             15

SEQ ID NO: 714          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1,2,12..15)
                        mod_base = OTHER
                        note = LNA nucleosides
modified_base           4
                        mod_base = OTHER
```

-continued

```
                        note = 5-methyl c
source                  1..15
                        mol_type = other DNA
                        organism = synthetic construct
SEQUENCE: 714
ttccgcagta tggat                                                         15

SEQ ID NO: 715          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..4,14,15)
                        mod_base = OTHER
                        note = LNA nucleosides
source                  1..15
                        mol_type = other DNA
                        organism = synthetic construct
SEQUENCE: 715
ttccgcagta tggat                                                         15

SEQ ID NO: 716          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,12..15)
                        mod_base = OTHER
                        note = LNA nucleosides
modified_base           4
                        mod_base = OTHER
                        note = 5-methyl c
source                  1..15
                        mol_type = other DNA
                        organism = synthetic construct
SEQUENCE: 716
ttccgcagta tggat                                                         15

SEQ ID NO: 717          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..4,13..15)
                        mod_base = OTHER
                        note = LNA nucleosides
source                  1..15
                        mol_type = other DNA
                        organism = synthetic construct
SEQUENCE: 717
ttccgcagta tggat                                                         15

SEQ ID NO: 718          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           5
                        mod_base = OTHER
                        note = 5-methyl c
source                  1..16
                        mol_type = other DNA
                        organism = synthetic construct
SEQUENCE: 718
gttccgcagt atggat                                                        16

SEQ ID NO: 719          moltype = DNA  length = 16
FEATURE                 Location/Qualifiers
```

```
misc_feature            1..16
                        note = LNA antisense gapmer oligonucleotide
modified_base           1..16
                        mod_base = OTHER
                        note = Phosphorothiate Internucleoside linkages
modified_base           order(1,2,13..16)
                        mod_base = OTHER
                        note = LNA nucleosides
modified_base           5
                        mod_base = OTHER
                        note = 5-methyl c
source                  1..16
                        mol_type = other DNA
                        organism = synthetic construct
SEQUENCE: 719
gttccgcagt atggat                                                          16

SEQ ID NO: 720          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..4,15,16)
                        mod_base = OTHER
                        note = LNA nucleosides
modified_base           5
                        mod_base = OTHER
                        note = 5-methyl c
source                  1..16
                        mol_type = other DNA
                        organism = synthetic construct
SEQUENCE: 720
gttccgcagt atggat                                                          16

SEQ ID NO: 721          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1,2,12..15)
                        mod_base = OTHER
                        note = LNA nucleosides
modified_base           5
                        mod_base = OTHER
                        note = 5-methyl c
source                  1..15
                        mol_type = other DNA
                        organism = synthetic construct
SEQUENCE: 721
gttccgcagt atgga                                                           15

SEQ ID NO: 722          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..4,14,15)
                        mod_base = OTHER
                        note = LNA nucleosides
modified_base           5
                        mod_base = OTHER
                        note = 5-methyl c
source                  1..15
                        mol_type = other DNA
                        organism = synthetic construct
SEQUENCE: 722
gttccgcagt atgga                                                           15

SEQ ID NO: 723          moltype = DNA  length = 15
FEATURE                 Location/Qualifiers
misc_feature            1..15
                        note = LNA antisense gapmer oligonucleotide
modified_base           1..15
```

```
                        mod_base = OTHER
                        note = Phosphorothiate Internucleoside linkages
modified_base           order(1,2,13..15)
                        mod_base = OTHER
                        note = LNA nucleosides
modified_base           5
                        mod_base = OTHER
                        note = 5-methyl c
source                  1..15
                        mol_type = other DNA
                        organism = synthetic construct
SEQUENCE: 723
gttccgcagt atgga                                                          15

SEQ ID NO: 724          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,14,15)
                        mod_base = OTHER
                        note = LNA nucleosides
modified_base           5
                        mod_base = OTHER
                        note = 5-methyl c
source                  1..15
                        mol_type = other DNA
                        organism = synthetic construct
SEQUENCE: 724
gttccgcagt atgga                                                          15

SEQ ID NO: 725          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
modified_base           6
                        mod_base = OTHER
                        note = 5-methyl c
source                  1..16
                        mol_type = other DNA
                        organism = synthetic construct
SEQUENCE: 725
agttccgcag tatgga                                                         16

SEQ ID NO: 726          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..4,15,16)
                        mod_base = OTHER
                        note = LNA nucleosides
modified_base           6
                        mod_base = OTHER
                        note = 5-methyl c
source                  1..16
                        mol_type = other DNA
                        organism = synthetic construct
SEQUENCE: 726
agttccgcag tatgga                                                         16

SEQ ID NO: 727          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1,2,14..16)
```

```
                       mod_base = OTHER
                       note = LNA nucleosides
modified_base          6
                       mod_base = OTHER
                       note = 5-methyl c
source                 1..16
                       mol_type = other DNA
                       organism = synthetic construct
SEQUENCE: 727
agttccgcag tatgga                                              16

SEQ ID NO: 728         moltype = DNA  length = 16
FEATURE                Location/Qualifiers
misc_feature           1..16
                       note = LNA antisense gapmer oligonucleotide
modified_base          1..16
                       mod_base = OTHER
                       note = Phosphorothiate Internucleoside linkages
modified_base          order(1..3,15,16)
                       mod_base = OTHER
                       note = LNA nucleosides
modified_base          6
                       mod_base = OTHER
                       note = 5-methyl c
source                 1..16
                       mol_type = other DNA
                       organism = synthetic construct
SEQUENCE: 728
agttccgcag tatgga                                              16

SEQ ID NO: 729         moltype = DNA  length = 16
FEATURE                Location/Qualifiers
misc_feature           1..16
                       note = LNA antisense gapmer oligonucleotide
modified_base          1..16
                       mod_base = OTHER
                       note = Phosphorothiate Internucleoside linkages
modified_base          order(1,2,15,16)
                       mod_base = OTHER
                       note = LNA nucleosides
modified_base          6
                       mod_base = OTHER
                       note = 5-methyl c
source                 1..16
                       mol_type = other DNA
                       organism = synthetic construct
SEQUENCE: 729
agttccgcag tatgga                                              16

SEQ ID NO: 730         moltype = DNA  length = 15
FEATURE                Location/Qualifiers
misc_feature           1..15
                       note = LNA antisense gapmer oligonucleotide
modified_base          1..15
                       mod_base = OTHER
                       note = Phosphorothiate Internucleoside linkages
modified_base          order(1..3,13..15)
                       mod_base = OTHER
                       note = LNA nucleosides
modified_base          6
                       mod_base = OTHER
                       note = 5-methyl c
source                 1..15
                       mol_type = other DNA
                       organism = synthetic construct
SEQUENCE: 730
agttccgcag tatgg                                               15

SEQ ID NO: 731         moltype = DNA  length = 15
FEATURE                Location/Qualifiers
misc_feature           1..15
                       note = LNA antisense gapmer oligonucleotide
modified_base          1..15
                       mod_base = OTHER
                       note = Phosphorothiate Internucleoside linkages
modified_base          order(1,2,13..15)
                       mod_base = OTHER
                       note = LNA nucleosides
modified_base          6
```

```
                        mod_base = OTHER
                        note = 5-methyl c
source                  1..15
                        mol_type = other DNA
                        organism = synthetic construct
SEQUENCE: 731
agttccgcag tatgg                                                          15

SEQ ID NO: 732          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,14,15)
                        mod_base = OTHER
                        note = LNA nucleosides
modified_base           6
                        mod_base = OTHER
                        note = 5-methyl c
source                  1..15
                        mol_type = other DNA
                        organism = synthetic construct
SEQUENCE: 732
agttccgcag tatgg                                                          15

SEQ ID NO: 733          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1,2,14,15)
                        mod_base = OTHER
                        note = LNA nucleosides
modified_base           6
                        mod_base = OTHER
                        note = 5-methyl c
source                  1..15
                        mol_type = other DNA
                        organism = synthetic construct
SEQUENCE: 733
agttccgcag tatgg                                                          15

SEQ ID NO: 734          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1,2,14..16)
                        mod_base = OTHER
                        note = LNA nucleosides
modified_base           7
                        mod_base = OTHER
                        note = 5-methyl c
source                  1..16
                        mol_type = other DNA
                        organism = synthetic construct
SEQUENCE: 734
gagttccgca gtatgg                                                         16

SEQ ID NO: 735          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,15,16)
                        mod_base = OTHER
                        note = LNA nucleosides
modified_base           7
                        mod_base = OTHER
                        note = 5-methyl c
source                  1..16
```

```
                        mol_type = other DNA
                        organism = synthetic construct
SEQUENCE: 735
gagttccgca gtatgg                                                    16

SEQ ID NO: 736          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1,2,15,16)
                        mod_base = OTHER
                        note = LNA nucleosides
modified_base           7
                        mod_base = OTHER
                        note = 5-methyl c
source                  1..16
                        mol_type = other DNA
                        organism = synthetic construct
SEQUENCE: 736
gagttccgca gtatgg                                                    16

SEQ ID NO: 737          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..4,14,15)
                        mod_base = OTHER
                        note = LNA nucleosides
modified_base           7
                        mod_base = OTHER
                        note = 5-methyl c
source                  1..15
                        mol_type = other DNA
                        organism = synthetic construct
SEQUENCE: 737
gagttccgca gtatg                                                     15

SEQ ID NO: 738          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1,2,13..15)
                        mod_base = OTHER
                        note = LNA nucleosides
modified_base           7
                        mod_base = OTHER
                        note = 5-methyl c
source                  1..15
                        mol_type = other DNA
                        organism = synthetic construct
SEQUENCE: 738
gagttccgca gtatg                                                     15

SEQ ID NO: 739          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,14,15)
                        mod_base = OTHER
                        note = LNA nucleosides
modified_base           7
                        mod_base = OTHER
                        note = 5-methyl c
source                  1..15
                        mol_type = other DNA
                        organism = synthetic construct
SEQUENCE: 739
```

```
gagttccgca gtatg                                                          15

SEQ ID NO: 740          moltype = DNA   length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1,2,14,15)
                        mod_base = OTHER
                        note = LNA nucleosides
modified_base           7
                        mod_base = OTHER
                        note = 5-methyl c
source                  1..15
                        mol_type = other DNA
                        organism = synthetic construct
SEQUENCE: 740
gagttccgca gtatg                                                          15

SEQ ID NO: 741          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..4,15,16)
                        mod_base = OTHER
                        note = LNA nucleosides
modified_base           8
                        mod_base = OTHER
                        note = 5-methyl c
source                  1..16
                        mol_type = other DNA
                        organism = synthetic construct
SEQUENCE: 741
ggagttccgc agtatg                                                         16

SEQ ID NO: 742          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1,2,14..16)
                        mod_base = OTHER
                        note = LNA nucleosides
modified_base           8
                        mod_base = OTHER
                        note = 5-methyl c
source                  1..16
                        mol_type = other DNA
                        organism = synthetic construct
SEQUENCE: 742
ggagttccgc agtatg                                                         16

SEQ ID NO: 743          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,15,16)
                        mod_base = OTHER
                        note = LNA nucleosides
modified_base           8
                        mod_base = OTHER
                        note = 5-methyl c
source                  1..16
                        mol_type = other DNA
                        organism = synthetic construct
SEQUENCE: 743
ggagttccgc agtatg                                                         16

SEQ ID NO: 744          moltype = DNA   length = 16
```

```
FEATURE                    Location/Qualifiers
misc_feature               1..16
                           note = LNA antisense gapmer oligonucleotide
modified_base              1..16
                           mod_base = OTHER
                           note = Phosphorothiate Internucleoside linkages
modified_base              order(1,2,15,16)
                           mod_base = OTHER
                           note = LNA nucleosides
modified_base              8
                           mod_base = OTHER
                           note = 5-methyl c
source                     1..16
                           mol_type = other DNA
                           organism = synthetic construct
SEQUENCE: 744
ggagttccgc agtatg                                                        16

SEQ ID NO: 745             moltype = DNA  length = 16
FEATURE                    Location/Qualifiers
misc_feature               1..16
                           note = LNA antisense gapmer oligonucleotide
modified_base              1..16
                           mod_base = OTHER
                           note = Phosphorothiate Internucleoside linkages
modified_base              order(1..3,14..16)
                           mod_base = OTHER
                           note = LNA nucleosides
modified_base              13
                           mod_base = OTHER
                           note = 5-methyl c
source                     1..16
                           mol_type = other DNA
                           organism = synthetic construct
SEQUENCE: 745
taaagagagg tgcgcc                                                        16

SEQ ID NO: 746             moltype = DNA  length = 16
FEATURE                    Location/Qualifiers
misc_feature               1..16
                           note = LNA antisense gapmer oligonucleotide
modified_base              1..16
                           mod_base = OTHER
                           note = Phosphorothiate Internucleoside linkages
modified_base              order(1,2,13..16)
                           mod_base = OTHER
                           note = LNA nucleosides
source                     1..16
                           mol_type = other DNA
                           organism = synthetic construct
SEQUENCE: 746
taaagagagg tgcgcc                                                        16

SEQ ID NO: 747             moltype = DNA  length = 16
FEATURE                    Location/Qualifiers
misc_feature               1..16
                           note = LNA antisense gapmer oligonucleotide
modified_base              1..16
                           mod_base = OTHER
                           note = Phosphorothiate Internucleoside linkages
modified_base              order(1..4,15,16)
                           mod_base = OTHER
                           note = LNA nucleosides
modified_base              13
                           mod_base = OTHER
                           note = 5-methyl c
source                     1..16
                           mol_type = other DNA
                           organism = synthetic construct
SEQUENCE: 747
taaagagagg tgcgcc                                                        16

SEQ ID NO: 748             moltype = DNA  length = 16
FEATURE                    Location/Qualifiers
misc_feature               1..16
                           note = LNA antisense gapmer oligonucleotide
modified_base              1..16
                           mod_base = OTHER
                           note = Phosphorothiate Internucleoside linkages
```

```
modified_base          order(1..3,13..16)
                       mod_base = OTHER
                       note = LNA nucleosides
source                 1..16
                       mol_type = other DNA
                       organism = synthetic construct
SEQUENCE: 748
taaagagagg tgcgcc                                                           16

SEQ ID NO: 749         moltype = DNA  length = 16
FEATURE                Location/Qualifiers
misc_feature           1..16
                       note = LNA antisense gapmer oligonucleotide
modified_base          1..16
                       mod_base = OTHER
                       note = Phosphorothiate Internucleoside linkages
modified_base          order(1..4,14..16)
                       mod_base = OTHER
                       note = LNA nucleosides
modified_base          13
                       mod_base = OTHER
                       note = 5-methyl c
source                 1..16
                       mol_type = other DNA
                       organism = synthetic construct
SEQUENCE: 749
taaagagagg tgcgcc                                                           16

SEQ ID NO: 750         moltype = DNA  length = 15
FEATURE                Location/Qualifiers
misc_feature           1..15
                       note = LNA antisense gapmer oligonucleotide
modified_base          1..15
                       mod_base = OTHER
                       note = Phosphorothiate Internucleoside linkages
modified_base          order(1..3,13..15)
                       mod_base = OTHER
                       note = LNA nucleosides
source                 1..15
                       mol_type = other DNA
                       organism = synthetic construct
SEQUENCE: 750
taaagagagg tgcgc                                                            15

SEQ ID NO: 751         moltype = DNA  length = 15
FEATURE                Location/Qualifiers
misc_feature           1..15
                       note = LNA antisense gapmer oligonucleotide
modified_base          1..15
                       mod_base = OTHER
                       note = Phosphorothiate Internucleoside linkages
modified_base          order(1,2,12..15)
                       mod_base = OTHER
                       note = LNA nucleosides
source                 1..15
                       mol_type = other DNA
                       organism = synthetic construct
SEQUENCE: 751
taaagagagg tgcgc                                                            15

SEQ ID NO: 752         moltype = DNA  length = 15
FEATURE                Location/Qualifiers
misc_feature           1..15
                       note = LNA antisense gapmer oligonucleotide
modified_base          1..15
                       mod_base = OTHER
                       note = Phosphorothiate Internucleoside linkages
modified_base          order(1..3,12..15)
                       mod_base = OTHER
                       note = LNA nucleosides
source                 1..15
                       mol_type = other DNA
                       organism = synthetic construct
SEQUENCE: 752
taaagagagg tgcgc                                                            15

SEQ ID NO: 753         moltype = DNA  length = 15
FEATURE                Location/Qualifiers
misc_feature           1..15
```

```
                        note = LNA antisense gapmer oligonucleotide
modified_base           1..15
                        mod_base = OTHER
                        note = Phosphorothiate Internucleoside linkages
modified_base           order(1..4,13..15)
                        mod_base = OTHER
                        note = LNA nucleosides
source                  1..15
                        mol_type = other DNA
                        organism = synthetic construct
SEQUENCE: 753
taaagagagg tgcgc                                                            15

SEQ ID NO: 754          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct
SEQUENCE: 754
gtaaagagag gtgcgc                                                           16

SEQ ID NO: 755          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1,2,13..16)
                        mod_base = OTHER
                        note = LNA nucleosides
source                  1..16
                        mol_type = other DNA
                        organism = synthetic construct
SEQUENCE: 755
gtaaagagag gtgcgc                                                           16

SEQ ID NO: 756          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,13..15)
                        mod_base = OTHER
                        note = LNA nucleosides
source                  1..15
                        mol_type = other DNA
                        organism = synthetic construct
SEQUENCE: 756
gtaaagagag gtgcg                                                            15

SEQ ID NO: 757          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1,2,12..15)
                        mod_base = OTHER
                        note = LNA nucleosides
source                  1..15
                        mol_type = other DNA
                        organism = synthetic construct
SEQUENCE: 757
gtaaagagag gtgcg                                                            15

SEQ ID NO: 758          moltype = DNA  length = 15
FEATURE                 Location/Qualifiers
```

```
                       -continued misc_feature           1..15
                       note = LNA antisense gapmer oligonucleotide
modified_base          1..15
                       mod_base = OTHER
                       note = Phosphorothiate Internucleoside linkages
modified_base          order(1..3,12..15)
                       mod_base = OTHER
                       note = LNA nucleosides
source                 1..15
                       mol_type = other DNA
                       organism = synthetic construct
SEQUENCE: 758
gtaaagagag gtgcg                                                          15

SEQ ID NO: 759         moltype = DNA  length = 15
FEATURE                Location/Qualifiers
misc_feature           1..15
                       note = LNA antisense gapmer oligonucleotide
modified_base          1..15
                       mod_base = OTHER
                       note = Phosphorothiate Internucleoside linkages
modified_base          order(1..4,13..15)
                       mod_base = OTHER
                       note = LNA nucleosides
source                 1..15
                       mol_type = other DNA
                       organism = synthetic construct
SEQUENCE: 759
gtaaagagag gtgcg                                                          15

SEQ ID NO: 760         moltype = DNA  length = 16
FEATURE                Location/Qualifiers
misc_feature           1..16
                       note = LNA antisense gapmer oligonucleotide
modified_base          1..16
                       mod_base = OTHER
                       note = Phosphorothiate Internucleoside linkages
modified_base          order(1,2,13..16)
                       mod_base = OTHER
                       note = LNA nucleosides
source                 1..16
                       mol_type = other DNA
                       organism = synthetic construct
SEQUENCE: 760
cgtaaagaga ggtgcg                                                         16

SEQ ID NO: 761         moltype = DNA  length = 16
FEATURE                Location/Qualifiers
misc_feature           1..16
                       note = LNA antisense gapmer oligonucleotide
modified_base          1..16
                       mod_base = OTHER
                       note = Phosphorothiate Internucleoside linkages
modified_base          order(1..4,15,16)
                       mod_base = OTHER
                       note = LNA nucleosides
source                 1..16
                       mol_type = other DNA
                       organism = synthetic construct
SEQUENCE: 761
cgtaaagaga ggtgcg                                                         16

SEQ ID NO: 762         moltype = DNA  length = 16
FEATURE                Location/Qualifiers
misc_feature           1..16
                       note = LNA antisense gapmer oligonucleotide
modified_base          1..16
                       mod_base = OTHER
                       note = Phosphorothiate Internucleoside linkages
modified_base          order(1..3,13..16)
                       mod_base = OTHER
                       note = LNA nucleosides
source                 1..16
                       mol_type = other DNA
                       organism = synthetic construct
SEQUENCE: 762
cgtaaagaga ggtgcg                                                         16

SEQ ID NO: 763         moltype = DNA  length = 16
```

```
FEATURE              Location/Qualifiers
misc_feature         1..16
                     note = LNA antisense gapmer oligonucleotide
modified_base        1..16
                     mod_base = OTHER
                     note = Phosphorothiate Internucleoside linkages
modified_base        order(1..4,14..16)
                     mod_base = OTHER
                     note = LNA nucleosides
source               1..16
                     mol_type = other DNA
                     organism = synthetic construct
SEQUENCE: 763
cgtaaagaga ggtgcg                                                         16

SEQ ID NO: 764       moltype = DNA   length = 15
FEATURE              Location/Qualifiers
misc_feature         1..15
                     note = LNA antisense gapmer oligonucleotide
modified_base        1..15
                     mod_base = OTHER
                     note = Phosphorothiate Internucleoside linkages
modified_base        order(1..3,13..15)
                     mod_base = OTHER
                     note = LNA nucleosides
source               1..15
                     mol_type = other DNA
                     organism = synthetic construct
SEQUENCE: 764
cgtaaagaga ggtgc                                                          15

SEQ ID NO: 765       moltype = DNA   length = 15
FEATURE              Location/Qualifiers
misc_feature         1..15
                     note = LNA antisense gapmer oligonucleotide
modified_base        1..15
                     mod_base = OTHER
                     note = Phosphorothiate Internucleoside linkages
modified_base        order(1,2,12..15)
                     mod_base = OTHER
                     note = LNA nucleosides
source               1..15
                     mol_type = other DNA
                     organism = synthetic construct
SEQUENCE: 765
cgtaaagaga ggtgc                                                          15

SEQ ID NO: 766       moltype = DNA   length = 15
FEATURE              Location/Qualifiers
misc_feature         1..15
                     note = LNA antisense gapmer oligonucleotide
modified_base        1..15
                     mod_base = OTHER
                     note = Phosphorothiate Internucleoside linkages
modified_base        order(1..4,14,15)
                     mod_base = OTHER
                     note = LNA nucleosides
source               1..15
                     mol_type = other DNA
                     organism = synthetic construct
SEQUENCE: 766
cgtaaagaga ggtgc                                                          15

SEQ ID NO: 767       moltype = DNA   length = 15
FEATURE              Location/Qualifiers
misc_feature         1..15
                     note = LNA antisense gapmer oligonucleotide
modified_base        1..15
                     mod_base = OTHER
                     note = Phosphorothiate Internucleoside linkages
modified_base        order(1..3,12..15)
                     mod_base = OTHER
                     note = LNA nucleosides
source               1..15
                     mol_type = other DNA
                     organism = synthetic construct
SEQUENCE: 767
cgtaaagaga ggtgc                                                          15
```

-continued

| | | |
|---|---|---|
| SEQ ID NO: 768 | moltype = DNA length = 15 | |
| FEATURE | Location/Qualifiers | |
| misc_feature | 1..15 | |
| | note = LNA antisense gapmer oligonucleotide | |
| modified_base | 1..15 | |
| | mod_base = OTHER | |
| | note = Phosphorothiate Internucleoside linkages | |
| modified_base | order(1..4,13..15) | |
| | mod_base = OTHER | |
| | note = LNA nucleosides | |
| source | 1..15 | |
| | mol_type = other DNA | |
| | organism = synthetic construct | |
| SEQUENCE: 768 | | |
| cgtaaagaga ggtgc | | 15 |
| | | |
| SEQ ID NO: 769 | moltype = DNA length = 16 | |
| FEATURE | Location/Qualifiers | |
| misc_feature | 1..16 | |
| | note = LNA antisense gapmer oligonucleotide | |
| modified_base | 1..16 | |
| | mod_base = OTHER | |
| | note = Phosphorothiate Internucleoside linkages | |
| modified_base | order(1..3,14..16) | |
| | mod_base = OTHER | |
| | note = LNA nucleosides | |
| source | 1..16 | |
| | mol_type = other DNA | |
| | organism = synthetic construct | |
| SEQUENCE: 769 | | |
| gcgtaaagag aggtgc | | 16 |
| | | |
| SEQ ID NO: 770 | moltype = DNA length = 16 | |
| FEATURE | Location/Qualifiers | |
| misc_feature | 1..16 | |
| | note = LNA antisense gapmer oligonucleotide | |
| modified_base | 1..16 | |
| | mod_base = OTHER | |
| | note = Phosphorothiate Internucleoside linkages | |
| modified_base | order(1,2,13..16) | |
| | mod_base = OTHER | |
| | note = LNA nucleosides | |
| source | 1..16 | |
| | mol_type = other DNA | |
| | organism = synthetic construct | |
| SEQUENCE: 770 | | |
| gcgtaaagag aggtgc | | 16 |
| | | |
| SEQ ID NO: 771 | moltype = DNA length = 16 | |
| FEATURE | Location/Qualifiers | |
| misc_feature | 1..16 | |
| | note = LNA antisense gapmer oligonucleotide | |
| modified_base | 1..16 | |
| | mod_base = OTHER | |
| | note = Phosphorothiate Internucleoside linkages | |
| modified_base | order(1,2,14..16) | |
| | mod_base = OTHER | |
| | note = LNA nucleosides | |
| source | 1..16 | |
| | mol_type = other DNA | |
| | organism = synthetic construct | |
| SEQUENCE: 771 | | |
| gcgtaaagag aggtgc | | 16 |
| | | |
| SEQ ID NO: 772 | moltype = DNA length = 16 | |
| FEATURE | Location/Qualifiers | |
| misc_feature | 1..16 | |
| | note = LNA antisense gapmer oligonucleotide | |
| modified_base | 1..16 | |
| | mod_base = OTHER | |
| | note = Phosphorothiate Internucleoside linkages | |
| modified_base | order(1..3,15,16) | |
| | mod_base = OTHER | |
| | note = LNA nucleosides | |
| source | 1..16 | |
| | mol_type = other DNA | |
| | organism = synthetic construct | |
| SEQUENCE: 772 | | |
| gcgtaaagag aggtgc | | 16 |

```
SEQ ID NO: 773              moltype = DNA  length = 15
FEATURE                     Location/Qualifiers
misc_feature                1..15
                            note = LNA antisense gapmer oligonucleotide
modified_base               1..15
                            mod_base = OTHER
                            note = Phosphorothiate Internucleoside linkages
modified_base               order(1..3,3..15)
                            mod_base = OTHER
                            note = LNA nucleosides
source                      1..15
                            mol_type = other DNA
                            organism = synthetic construct
SEQUENCE: 773
gcgtaaagag aggtg                                                        15

SEQ ID NO: 774              moltype = DNA  length = 15
FEATURE                     Location/Qualifiers
misc_feature                1..15
                            note = LNA antisense gapmer oligonucleotide
modified_base               1..15
                            mod_base = OTHER
                            note = Phosphorothiate Internucleoside linkages
modified_base               order(1,2,12..15)
                            mod_base = OTHER
                            note = LNA nucleosides
source                      1..15
                            mol_type = other DNA
                            organism = synthetic construct
SEQUENCE: 774
gcgtaaagag aggtg                                                        15

SEQ ID NO: 775              moltype = DNA  length = 15
FEATURE                     Location/Qualifiers
misc_feature                1..15
                            note = LNA antisense gapmer oligonucleotide
modified_base               1..15
                            mod_base = OTHER
                            note = Phosphorothiate Internucleoside linkages
modified_base               order(1..4,14,15)
                            mod_base = OTHER
                            note = LNA nucleosides
source                      1..15
                            mol_type = other DNA
                            organism = synthetic construct
SEQUENCE: 775
gcgtaaagag aggtg                                                        15

SEQ ID NO: 776              moltype = DNA  length = 15
FEATURE                     Location/Qualifiers
misc_feature                1..15
                            note = LNA antisense gapmer oligonucleotide
modified_base               1..15
                            mod_base = OTHER
                            note = Phosphorothiate Internucleoside linkages
modified_base               order(1..3,12..15)
                            mod_base = OTHER
                            note = LNA nucleosides
source                      1..15
                            mol_type = other DNA
                            organism = synthetic construct
SEQUENCE: 776
gcgtaaagag aggtg                                                        15

SEQ ID NO: 777              moltype = DNA  length = 15
FEATURE                     Location/Qualifiers
misc_feature                1..15
                            note = LNA antisense gapmer oligonucleotide
modified_base               1..15
                            mod_base = OTHER
                            note = Phosphorothiate Internucleoside linkages
modified_base               order(1..4,13..15)
                            mod_base = OTHER
                            note = LNA nucleosides
source                      1..15
                            mol_type = other DNA
                            organism = synthetic construct
SEQUENCE: 777
```

```
gcgtaaagag aggtg                                                      15

SEQ ID NO: 778         moltype = DNA   length = 16
FEATURE                Location/Qualifiers
misc_feature           1..16
                       note = LNA antisense gapmer oligonucleotide
modified_base          1..16
                       mod_base = OTHER
                       note = Phosphorothiate Internucleoside linkages
modified_base          order(1..3,14..16)
                       mod_base = OTHER
                       note = LNA nucleosides
source                 1..16
                       mol_type = other DNA
                       organism = synthetic construct
SEQUENCE: 778
cgcgtaaaga gaggtg                                                     16

SEQ ID NO: 779         moltype = DNA   length = 16
FEATURE                Location/Qualifiers
misc_feature           1..16
                       note = LNA antisense gapmer oligonucleotide
modified_base          1..16
                       mod_base = OTHER
                       note = Phosphorothiate Internucleoside linkages
modified_base          order(1,3)
                       mod_base = OTHER
                       note = 5-methyl c
modified_base          13..16
                       mod_base = OTHER
                       note = LNA nucleosides
source                 1..16
                       mol_type = other DNA
                       organism = synthetic construct
SEQUENCE: 779
cgcgtaaaga gaggtg                                                     16

SEQ ID NO: 780         moltype = DNA   length = 16
FEATURE                Location/Qualifiers
misc_feature           1..16
                       note = LNA antisense gapmer oligonucleotide
modified_base          1..16
                       mod_base = OTHER
                       note = Phosphorothiate Internucleoside linkages
modified_base          order(1..4,15,16)
                       mod_base = OTHER
                       note = LNA nucleosides
source                 1..16
                       mol_type = other DNA
                       organism = synthetic construct
SEQUENCE: 780
cgcgtaaaga gaggtg                                                     16

SEQ ID NO: 781         moltype = DNA   length = 16
FEATURE                Location/Qualifiers
misc_feature           1..16
                       note = LNA antisense gapmer oligonucleotide
modified_base          1..16
                       mod_base = OTHER
                       note = Phosphorothiate Internucleoside linkages
modified_base          order(1..3,13..16)
                       mod_base = OTHER
                       note = LNA nucleosides
source                 1..16
                       mol_type = other DNA
                       organism = synthetic construct
SEQUENCE: 781
cgcgtaaaga gaggtg                                                     16

SEQ ID NO: 782         moltype = DNA   length = 16
FEATURE                Location/Qualifiers
misc_feature           1..16
                       note = LNA antisense gapmer oligonucleotide
modified_base          1..16
                       mod_base = OTHER
                       note = Phosphorothiate Internucleoside linkages
modified_base          order(1..4,14..16)
                       mod_base = OTHER
                       note = LNA nucleosides
```

```
source                  1..16
                        mol_type = other DNA
                        organism = synthetic construct
SEQUENCE: 782
cgcgtaaaga gaggtg                                                               16

SEQ ID NO: 783          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct
SEQUENCE: 783
tgagaaggca cagacg                                                               16

SEQ ID NO: 784          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1,2,13..16)
                        mod_base = OTHER
                        note = LNA nucleosides
source                  1..16
                        mol_type = other DNA
                        organism = synthetic construct
SEQUENCE: 784
tgagaaggca cagacg                                                               16

SEQ ID NO: 785          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..4,15,16)
                        mod_base = OTHER
                        note = LNA nucleosides
source                  1..16
                        mol_type = other DNA
                        organism = synthetic construct
SEQUENCE: 785
tgagaaggca cagacg                                                               16

SEQ ID NO: 786          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,13..16)
                        mod_base = OTHER
                        note = LNA nucleosides
source                  1..16
                        mol_type = other DNA
                        organism = synthetic construct
SEQUENCE: 786
tgagaaggca cagacg                                                               16

SEQ ID NO: 787          moltype = DNA   length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..4,14..16)
                        mod_base = OTHER
```

```
                        note = LNA nucleosides
source                  1..16
                        mol_type = other DNA
                        organism = synthetic construct
SEQUENCE: 787
tgagaaggca cagacg                                                   16

SEQ ID NO: 788          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1,2,13..15)
                        mod_base = OTHER
                        note = LNA nucleosides
modified_base           11
                        mod_base = OTHER
                        note = 5-methyl c
source                  1..15
                        mol_type = other DNA
                        organism = synthetic construct
SEQUENCE: 788
gcctcaaggt cggtc                                                    15

SEQ ID NO: 789          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,14,15)
                        mod_base = OTHER
                        note = LNA nucleosides
modified_base           11
                        mod_base = OTHER
                        note = 5-methyl c
source                  1..15
                        mol_type = other DNA
                        organism = synthetic construct
SEQUENCE: 789
gcctcaaggt cggtc                                                    15

SEQ ID NO: 790          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1,2,14,15)
                        mod_base = OTHER
                        note = LNA nucleosides
modified_base           11
                        mod_base = OTHER
                        note = 5-methyl c
source                  1..15
                        mol_type = other DNA
                        organism = synthetic construct
SEQUENCE: 790
gcctcaaggt cggtc                                                    15

SEQ ID NO: 791          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1,2,13..15)
                        mod_base = OTHER
                        note = LNA nucleosides
source                  1..15
                        mol_type = other DNA
                        organism = synthetic construct
SEQUENCE: 791
atgcctacag cctcc                                                    15
```

```
SEQ ID NO: 792          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1..3,14,15)
                        mod_base = OTHER
                        note = LNA nucleosides
source                  1..15
                        mol_type = other DNA
                        organism = synthetic construct
SEQUENCE: 792
atgcctacag cctcc                                                            15

SEQ ID NO: 793          moltype = DNA  length = 15
FEATURE                 Location/Qualifiers
misc_feature            1..15
                        note = LNA antisense gapmer oligonucleotide
modified_base           1..15
                        mod_base = OTHER
                        note = Phosphorothiate Internucleoside linkages
modified_base           order(1,2,14,15)
                        mod_base = OTHER
                        note = LNA nucleosides
source                  1..15
                        mol_type = other DNA
                        organism = synthetic construct
SEQUENCE: 793
atgcctacag cctcc                                                            15

SEQ ID NO: 794          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..4,13..16)
                        mod_base = OTHER
                        note = LNA nucleosides
source                  1..16
                        mol_type = other DNA
                        organism = synthetic construct
SEQUENCE: 794
accaatttat gcctac                                                           16

SEQ ID NO: 795          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,13..16)
                        mod_base = OTHER
                        note = LNA nucleosides
source                  1..16
                        mol_type = other DNA
                        organism = synthetic construct
SEQUENCE: 795
accaatttat gcctac                                                           16

SEQ ID NO: 796          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..4,14..16)
                        mod_base = OTHER
                        note = LNA nucleosides
source                  1..16
                        mol_type = other DNA
                        organism = synthetic construct
SEQUENCE: 796
```

```
accaatttat gcctac                                                       16

SEQ ID NO: 797          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1..3,14..16)
                        mod_base = OTHER
                        note = LNA nucleosides
source                  1..16
                        mol_type = other DNA
                        organism = synthetic construct
SEQUENCE: 797
accaatttat gcctac                                                       16

SEQ ID NO: 798          moltype = DNA  length = 16
FEATURE                 Location/Qualifiers
misc_feature            1..16
                        note = LNA antisense gapmer oligonucleotide
modified_base           1..16
                        mod_base = OTHER
                        note = Phosphorothiate Internucleoside linkages
modified_base           order(1,2,13..16)
                        mod_base = OTHER
                        note = LNA nucleosides
source                  1..16
                        mol_type = other DNA
                        organism = synthetic construct
SEQUENCE: 798
accaatttat gcctac                                                       16

SEQ ID NO: 799          moltype = DNA  length = 17
FEATURE                 Location/Qualifiers
misc_feature            1..17
                        note = Antisense oligonucleotide GalNAc conjugate
misc_feature            1
                        note = GalNAc2-C6
modified_base           1..3
                        mod_base = OTHER
                        note = Phosphodiester Internucleoside linkages
modified_base           order(3..5,15..17)
                        mod_base = OTHER
                        note = LNA nucleosides
modified_base           4..17
                        mod_base = OTHER
                        note = Phosphorothiate Internucleoside linkages
source                  1..17
                        mol_type = other DNA
                        organism = synthetic construct
SEQUENCE: 799
cagaaccact gaacaaa                                                      17

SEQ ID NO: 800          moltype = DNA  length = 18
FEATURE                 Location/Qualifiers
misc_feature            1..18
                        note = Antisense oligonucleotide GalNAc conjugate
misc_feature            1
                        note = GalNAc2-C6
modified_base           1..3
                        mod_base = OTHER
                        note = Phosphodiester Internucleoside linkages
modified_base           order(3..5,16..18)
                        mod_base = OTHER
                        note = LNA nucleosides
modified_base           4..18
                        mod_base = OTHER
                        note = Phosphorothiate Internucleoside linkages
source                  1..18
                        mol_type = other DNA
                        organism = synthetic construct
modified_base           3
                        mod_base = OTHER
                        note = 5-methyl C
SEQUENCE: 800
cacgaaccac tgaacaaa                                                     18
```

```
SEQ ID NO: 801                moltype = DNA  length = 17
FEATURE                       Location/Qualifiers
misc_feature                  1..17
                              note = Antisense oligonucleotide GalNAc conjugate
misc_feature                  1
                              note = GalNAc2-C6
modified_base                 1..3
                              mod_base = OTHER
                              note = Phosphodiester lnternucleoside linkages
modified_base                 order(3..5,15..17)
                              mod_base = OTHER
                              note = LNA nucleosides
modified_base                 4..17
                              mod_base = OTHER
                              note = Phosphorothiate Internucleoside linkages
source                        1..17
                              mol_type = other DNA
                              organism = synthetic construct
modified_base                 order(3,15)
                              mod_base = OTHER
                              note = 5-methyl C
SEQUENCE: 801
cacgaaccac tgaacaa                                                        17

SEQ ID NO: 802                moltype = DNA  length = 17
FEATURE                       Location/Qualifiers
misc_feature                  1..17
                              note = Antisense oligonucleotide GalNAc conjugate
misc_feature                  1
                              note = GalNAc2-C6
modified_base                 1..3
                              mod_base = OTHER
                              note = Phosphodiester lnternucleoside linkages
modified_base                 order(3..5,15..17)
                              mod_base = OTHER
                              note = LNA nucleosides
modified_base                 4..17
                              mod_base = OTHER
                              note = Phosphorothiate Internucleoside linkages
source                        1..17
                              mol_type = other DNA
                              organism = synthetic construct
modified_base                 order(3,16)
                              mod_base = OTHER
                              note = 5-methyl C
SEQUENCE: 802
caccgcagta tggatcg                                                        17

SEQ ID NO: 803                moltype = DNA  length = 17
FEATURE                       Location/Qualifiers
misc_feature                  1..17
                              note = Antisense oligonucleotide GalNAc conjugate
modified_base                 1..3
                              mod_base = OTHER
                              note = Phosphodiester lnternucleoside linkages
modified_base                 order(3..5,15..17)
                              mod_base = OTHER
                              note = LNA nucleosides
modified_base                 4..17
                              mod_base = OTHER
                              note = Phosphorothiate Internucleoside linkages
source                        1..17
                              mol_type = other DNA
                              organism = synthetic construct
modified_base                 3
                              mod_base = OTHER
                              note = 5-methyl C
SEQUENCE: 803
cacgcgtaaa gagaggt                                                        17

SEQ ID NO: 804                moltype = DNA  length = 17
FEATURE                       Location/Qualifiers
misc_feature                  1..17
                              note = Antisense oligonucleotide GalNAc conjugate
misc_feature                  1
                              note = GalNAc2-C6
modified_base                 1..3
                              mod_base = OTHER
                              note = Phosphodiester lnternucleoside linkages
```

```
modified_base                   order(3..5,15..17)
                                mod_base = OTHER
                                note = LNA nucleosides
modified_base                   4..17
                                mod_base = OTHER
                                note = Phosphorothiate Internucleoside linkages
source                          1..17
                                mol_type = other DNA
                                organism = synthetic construct
modified_base                   15
                                mod_base = OTHER
                                note = 5-methyl C
SEQUENCE: 804
caagaaggca cagacgg                                                              17

SEQ ID NO: 805                  moltype = DNA   length = 18
FEATURE                         Location/Qualifiers
misc_feature                    1..18
                                note = Antisense oligonucleotide GalNAc conjugate
misc_feature                    1
                                note = GalNAc2-C6
modified_base                   1..3
                                mod_base = OTHER
                                note = Phosphodiester lnternucleoside linkages
modified_base                   order(3..5,16..18)
                                mod_base = OTHER
                                note = LNA nucleosides
modified_base                   4..18
                                mod_base = OTHER
                                note = Phosphorothiate Internucleoside linkages
source                          1..18
                                mol_type = other DNA
                                organism = synthetic construct
modified_base                   16
                                mod_base = OTHER
                                note = 5-methyl C
SEQUENCE: 805
cagagaaggc acagacgg                                                             18

SEQ ID NO: 806                  moltype = DNA   length = 17
FEATURE                         Location/Qualifiers
misc_feature                    1..17
                                note = Antisense oligonucleotide GalNAc conjugate
misc_feature                    1
                                note = GalNAc2-C6
modified_base                   1..3
                                mod_base = OTHER
                                note = Phosphodiester lnternucleoside linkages
modified_base                   order(3..5,15..17)
                                mod_base = OTHER
                                note = LNA nucleosides
modified_base                   4..17
                                mod_base = OTHER
                                note = Phosphorothiate Internucleoside linkages
source                          1..17
                                mol_type = other DNA
                                organism = synthetic construct
modified_base                   order(4,15)
                                mod_base = OTHER
                                note = 5-methyl C
SEQUENCE: 806
cagcgaagtg cacacgg                                                              17

SEQ ID NO: 807                  moltype = DNA   length = 18
FEATURE                         Location/Qualifiers
misc_feature                    1..18
                                note = Antisense oligonucleotide GalNAc conjugate
misc_feature                    1
                                note = GalNAc2-C6
modified_base                   1..3
                                mod_base = OTHER
                                note = Phosphodiester lnternucleoside linkages
modified_base                   order(3..5,16..18)
                                mod_base = OTHER
                                note = LNA nucleosides
modified_base                   4..18
                                mod_base = OTHER
                                note = Phosphorothiate Internucleoside linkages
source                          1..18
```

|  |  |
|---|---|
|  | mol_type = other DNA |
|  | organism = synthetic construct |
| modified_base | order(5,16) |
|  | mod_base = OTHER |
|  | note = 5-methyl C |
| SEQUENCE: 807 |  |
| caagcgaagt gcacacgg | 18 |
|  |  |
| SEQ ID NO: 808 | moltype = DNA  length = 17 |
| FEATURE | Location/Qualifiers |
| misc_feature | 1..17 |
|  | note = Antisense oligonucleotide GalNAc conjugate |
| misc_feature | 1 |
|  | note = GalNAc2-C6 |
| modified_base | 1..3 |
|  | mod_base = OTHER |
|  | note = Phosphodiester lnternucleoside linkages |
| modified_base | order(3..5,15..17) |
|  | mod_base = OTHER |
|  | note = LNA nucleosides |
| modified_base | 4..17 |
|  | mod_base = OTHER |
|  | note = Phosphorothiate Internucleoside linkages |
| source | 1..17 |
|  | mol_type = other DNA |
|  | organism = synthetic construct |
| modified_base | order(5,16) |
|  | mod_base = OTHER |
|  | note = 5-methyl C |
| SEQUENCE: 808 |  |
| caagcgaagt gcacacg | 17 |
|  |  |
| SEQ ID NO: 809 | moltype = DNA  length = 18 |
| FEATURE | Location/Qualifiers |
| misc_feature | 1..18 |
|  | note = Antisense oligonucleotide GalNAc conjugate |
| misc_feature | 1 |
|  | note = GalNAc2-C6 |
| modified_base | 1..3 |
|  | mod_base = OTHER |
|  | note = Phosphodiester lnternucleoside linkages |
| modified_base | order(3..5,16..18) |
|  | mod_base = OTHER |
|  | note = LNA nucleosides |
| modified_base | 4..18 |
|  | mod_base = OTHER |
|  | note = Phosphorothiate Internucleoside linkages |
| modified_base | order(11,18) |
|  | mod_base = OTHER |
|  | note = 5-methyl C |
| source | 1..18 |
|  | mol_type = other DNA |
|  | organism = synthetic construct |
| SEQUENCE: 809 |  |
| caaggtgaag cgaagtgc | 18 |
|  |  |
| SEQ ID NO: 810 | moltype = DNA  length = 17 |
| FEATURE | Location/Qualifiers |
| misc_feature | 1..17 |
|  | note = Antisense oligonucleotide GalNAc conjugate |
| misc_feature | 1 |
|  | note = GalNAc2-C6 |
| modified_base | 1..3 |
|  | mod_base = OTHER |
|  | note = Phosphodiester lnternucleoside linkages |
| modified_base | order(3..5,15..17) |
|  | mod_base = OTHER |
|  | note = LNA nucleosides |
| modified_base | 4..17 |
|  | mod_base = OTHER |
|  | note = Phosphorothiate Internucleoside linkages |
| modified_base | 11 |
|  | mod_base = OTHER |
|  | note = 5-methyl C |
| source | 1..17 |
|  | mol_type = other DNA |
|  | organism = synthetic construct |
| SEQUENCE: 810 |  |
| caaggtgaag cgaagtg | 17 |

```
SEQ ID NO: 811              moltype = DNA  length = 16
FEATURE                     Location/Qualifiers
misc_feature                1..16
                            note = Antisense oligonucleotide GalNAc conjugate
misc_feature                1
                            note = GalNAc2-C6
modified_base               1..3
                            mod_base = OTHER
                            note = Phosphodiester lnternucleoside linkages
modified_base               order(3..5,14..16)
                            mod_base = OTHER
                            note = LNA nucleosides
modified_base               4..16
                            mod_base = OTHER
                            note = Phosphorothiate Internucleoside linkages
source                      1..16
                            mol_type = other DNA
                            organism = synthetic construct
modified_base               order(3,15)
                            mod_base = OTHER
                            note = 5-methyl C
SEQUENCE: 811
cacgaaccac tgaaca                                                         16

SEQ ID NO: 812              moltype = DNA  length = 15
FEATURE                     Location/Qualifiers
misc_feature                1..15
                            note = Antisense oligonucleotide GalNAc conjugate
misc_feature                1
                            note = GalNAc2-C6
modified_base               1..3
                            mod_base = OTHER
                            note = Phosphodiester lnternucleoside linkages
modified_base               order(3..5,14,15)
                            mod_base = OTHER
                            note = LNA nucleosides
modified_base               4..15
                            mod_base = OTHER
                            note = Phosphorothiate Internucleoside linkages
source                      1..15
                            mol_type = other DNA
                            organism = synthetic construct
modified_base               order(3,15)
                            mod_base = OTHER
                            note = 5-methyl C
SEQUENCE: 812
cacgaaccac tgaac                                                          15

SEQ ID NO: 813              moltype = DNA  length = 15
FEATURE                     Location/Qualifiers
misc_feature                1..15
                            note = Antisense oligonucleotide GalNAc conjugate
misc_feature                1
                            note = GalNAc2-C6
modified_base               1..3
                            mod_base = OTHER
                            note = Phosphodiester lnternucleoside linkages
modified_base               order(3..5,14,15)
                            mod_base = OTHER
                            note = LNA nucleosides
modified_base               4..15
                            mod_base = OTHER
                            note = Phosphorothiate Internucleoside linkages
source                      1..15
                            mol_type = other DNA
                            organism = synthetic construct
modified_base               order(3,15)
                            mod_base = OTHER
                            note = 5-methyl C
SEQUENCE: 813
cacgcagtat ggatc                                                          15

SEQ ID NO: 814              moltype = DNA  length = 16
FEATURE                     Location/Qualifiers
misc_feature                1..16
                            note = Antisense oligonucleotide GalNAc conjugate
misc_feature                1
                            note = GalNAc2-C6
```

```
modified_base          1..3
                       mod_base = OTHER
                       note = Phosphodiester lnternucleoside linkages
modified_base          order(3..5,14..16)
                       mod_base = OTHER
                       note = LNA nucleosides
modified_base          4..16
                       mod_base = OTHER
                       note = Phosphorothiate Internucleoside linkages
source                 1..16
                       mol_type = other DNA
                       organism = synthetic construct
modified_base          4
                       mod_base = OTHER
                       note = 5-methyl C
SEQUENCE: 814
cagcgtaaag agaggt                                                    16

SEQ ID NO: 815         moltype = DNA  length = 15
FEATURE                Location/Qualifiers
misc_feature           1..15
                       note = Antisense oligonucleotide GalNAc conjugate
misc_feature           1
                       note = GalNAc2-C6
modified_base          1..3
                       mod_base = OTHER
                       note = Phosphodiester lnternucleoside linkages
modified_base          order(3..5,14,15)
                       mod_base = OTHER
                       note = LNA nucleosides
modified_base          4..15
                       mod_base = OTHER
                       note = Phosphorothiate Internucleoside linkages
source                 1..15
                       mol_type = other DNA
                       organism = synthetic construct
modified_base          4
                       mod_base = OTHER
                       note = 5-methyl C
SEQUENCE: 815
cagcgtaaag agagg                                                     15

SEQ ID NO: 816         moltype = DNA  length = 15
FEATURE                Location/Qualifiers
misc_feature           1..15
                       note = Antisense oligonucleotide GalNAc conjugate
misc_feature           1
                       note = GalNAc2-C6
modified_base          1..3
                       mod_base = OTHER
                       note = Phosphodiester lnternucleoside linkages
modified_base          order(3..5,14,15)
                       mod_base = OTHER
                       note = LNA nucleosides
modified_base          4..15
                       mod_base = OTHER
                       note = Phosphorothiate Internucleoside linkages
modified_base          13
                       mod_base = OTHER
                       note = 5-methyl C
source                 1..15
                       mol_type = other DNA
                       organism = synthetic construct
SEQUENCE: 816
cagaagtgca cacgg                                                     15

SEQ ID NO: 817         moltype = DNA  length = 15
FEATURE                Location/Qualifiers
misc_feature           1..15
                       note = Antisense oligonucleotide GalNAc conjugate
misc_feature           1
                       note = GalNAc2-C6
modified_base          1..3
                       mod_base = OTHER
                       note = Phosphodiester lnternucleoside linkages
modified_base          order(3..5,14,15)
                       mod_base = OTHER
                       note = LNA nucleosides
modified_base          4..15
```

|  |  |  |
|---|---|---|
| | mod_base = OTHER | |
| | note = Phosphorothiate Internucleoside linkages | |
| source | 1..15 | |
| | mol_type = other DNA | |
| | organism = synthetic construct | |
| modified_base | order(3,14) | |
| | mod_base = OTHER | |
| | note = 5-methyl C | |
| SEQUENCE: 817 | | |
| cacgaagtgc acacg | | 15 |

| | | |
|---|---|---|
| SEQ ID NO: 818 | moltype = DNA  length = 16 | |
| FEATURE | Location/Qualifiers | |
| misc_feature | 1..16 | |
| | note = Antisense oligonucleotide GalNAc conjugate | |
| misc_feature | 1 | |
| | note = GalNAc2-C6 | |
| modified_base | 1..3 | |
| | mod_base = OTHER | |
| | note = Phosphodiester lnternucleoside linkages | |
| modified_base | order(3..5,14..16) | |
| | mod_base = OTHER | |
| | note = LNA nucleosides | |
| modified_base | 4..16 | |
| | mod_base = OTHER | |
| | note = Phosphorothiate Internucleoside linkages | |
| modified_base | 11 | |
| | mod_base = OTHER | |
| | note = 5-methyl C | |
| source | 1..16 | |
| | mol_type = other DNA | |
| | organism = synthetic construct | |
| SEQUENCE: 818 | | |
| caaggtgaag cgaagt | | 16 |

| | | |
|---|---|---|
| SEQ ID NO: 819 | moltype = DNA  length = 17 | |
| FEATURE | Location/Qualifiers | |
| misc_feature | 1..17 | |
| | note = Antisense oligonucleotide GalNAc conjugate | |
| misc_feature | 1 | |
| | note = GalNAc2-C6 | |
| modified_base | 1..3 | |
| | mod_base = OTHER | |
| | note = Phosphodiester lnternucleoside linkages | |
| modified_base | order(3..5,14..17) | |
| | mod_base = OTHER | |
| | note = LNA nucleosides | |
| modified_base | 4..17 | |
| | mod_base = OTHER | |
| | note = Phosphorothiate Internucleoside linkages | |
| source | 1..17 | |
| | mol_type = other DNA | |
| | organism = synthetic construct | |
| modified_base | 14 | |
| | mod_base = OTHER | |
| | note = 5-methyl C | |
| SEQUENCE: 819 | | |
| cagaaccact gaacaaa | | 17 |

| | | |
|---|---|---|
| SEQ ID NO: 820 | moltype = DNA  length = 18 | |
| FEATURE | Location/Qualifiers | |
| misc_feature | 1..18 | |
| | note = Antisense oligonucleotide GalNAc conjugate | |
| misc_feature | 1 | |
| | note = GalNAc2-C6 | |
| modified_base | 1..3 | |
| | mod_base = OTHER | |
| | note = Phosphodiester lnternucleoside linkages | |
| modified_base | order(3..6,16..18) | |
| | mod_base = OTHER | |
| | note = LNA nucleosides | |
| modified_base | 4..18 | |
| | mod_base = OTHER | |
| | note = Phosphorothiate Internucleoside linkages | |
| source | 1..18 | |
| | mol_type = other DNA | |
| | organism = synthetic construct | |
| modified_base | 15 | |
| | mod_base = OTHER | |

```
                          note = 5-methyl C
SEQUENCE: 820
cacgaaccac tgaacaaa                                            18

SEQ ID NO: 821            moltype = DNA  length = 15
FEATURE                   Location/Qualifiers
misc_feature              1..15
                          note = Antisense oligonucleotide GalNAc conjugate
misc_feature              1
                          note = GalNAc2-C6
modified_base             1..3
                          mod_base = OTHER
                          note = Phosphodiester lnternucleoside linkages
modified_base             order(3..5,13..15)
                          mod_base = OTHER
                          note = LNA nucleosides
modified_base             4..15
                          mod_base = OTHER
                          note = Phosphorothiate Internucleoside linkages
source                    1..15
                          mol_type = other DNA
                          organism = synthetic construct
modified_base             13
                          mod_base = OTHER
                          note = 5-methyl C
SEQUENCE: 821
cagaagtgca cacgg                                               15

SEQ ID NO: 822            moltype = DNA  length = 17
FEATURE                   Location/Qualifiers
misc_feature              1..17
                          note = Antisense oligonucleotide GalNAc conjugate
misc_feature              1
                          note = GalNAc2-C6
modified_base             1..3
                          mod_base = OTHER
                          note = Phosphodiester lnternucleoside linkages
modified_base             order(3..5,15..17)
                          mod_base = OTHER
                          note = LNA nucleosides
modified_base             4..17
                          mod_base = OTHER
                          note = Phosphorothiate Internucleoside linkages
source                    1..17
                          mol_type = other DNA
                          organism = synthetic construct
modified_base             15..16
                          mod_base = OTHER
                          note = 5-methyl C
SEQUENCE: 822
catagtaaac tgagcca                                             17

SEQ ID NO: 823            moltype = DNA  length = 15
FEATURE                   Location/Qualifiers
misc_feature              1..15
                          note = Antisense oligonucleotide GalNAc conjugate
misc_feature              1
                          note = GalNAc2-C6
modified_base             1..3
                          mod_base = OTHER
                          note = Phosphodiester lnternucleoside linkages
modified_base             order(3..5,13..15)
                          mod_base = OTHER
                          note = LNA nucleosides
modified_base             4..15
                          mod_base = OTHER
                          note = Phosphorothiate Internucleoside linkages
source                    1..15
                          mol_type = other DNA
                          organism = synthetic construct
modified_base             order(3,15)
                          mod_base = OTHER
                          note = 5-methyl C
SEQUENCE: 823
cacgaaccac tgaac                                               15

SEQ ID NO: 824            moltype = DNA  length = 16
FEATURE                   Location/Qualifiers
misc_feature              1..16
```

```
                         note = Antisense oligonucleotide GalNAc conjugate
misc_feature             1
                         note = GalNAc2-C6
modified_base            1..3
                         mod_base = OTHER
                         note = Phosphodiester lnternucleoside linkages
modified_base            order(3..5,13..16)
                         mod_base = OTHER
                         note = LNA nucleosides
modified_base            4..16
                         mod_base = OTHER
                         note = Phosphorothiate Internucleoside linkages
source                   1..16
                         mol_type = other DNA
                         organism = synthetic construct
modified_base            order(3,15)
                         mod_base = OTHER
                         note = 5-methyl C
SEQUENCE: 824
cacgaaccac tgaaca                                                           16

SEQ ID NO: 825           moltype = DNA  length = 15
FEATURE                  Location/Qualifiers
misc_feature             1..15
                         note = Antisense oligonucleotide GalNAc conjugate
misc_feature             1
                         note = GalNAc2-C6
modified_base            1..3
                         mod_base = OTHER
                         note = Phosphodiester lnternucleoside linkages
modified_base            order(3..5,13..15)
                         mod_base = OTHER
                         note = LNA nucleosides
modified_base            4..15
                         mod_base = OTHER
                         note = Phosphorothiate Internucleoside linkages
source                   1..15
                         mol_type = other DNA
                         organism = synthetic construct
modified_base            4
                         mod_base = OTHER
                         note = 5-methyl C
SEQUENCE: 825
cagcgtaaag agagg                                                            15

SEQ ID NO: 826           moltype = DNA  length = 17
FEATURE                  Location/Qualifiers
misc_feature             1..17
                         note = Antisense oligonucleotide GalNAc conjugate
misc_feature             1
                         note = GalNAc2-C6
modified_base            1..3
                         mod_base = OTHER
                         note = Phosphodiester lnternucleoside linkages
modified_base            order(3,4,14..17)
                         mod_base = OTHER
                         note = LNA nucleosides
modified_base            4..17
                         mod_base = OTHER
                         note = Phosphorothiate Internucleoside linkages
modified_base            11
                         mod_base = OTHER
                         note = 5-methyl C
source                   1..17
                         mol_type = other DNA
                         organism = synthetic construct
SEQUENCE: 826
caaggtgaag cgaagtg                                                          17

SEQ ID NO: 827           moltype = DNA  length = 24
FEATURE                  Location/Qualifiers
misc_feature             1..24
                         note = oligonucleotide target sequence
source                   1..24
                         mol_type = other DNA
                         organism = synthetic construct
SEQUENCE: 827
acggggcgca cctctcttta cgcg                                                  24
```

-continued

```
SEQ ID NO: 828              moltype = DNA  length = 22
FEATURE                     Location/Qualifiers
misc_feature                1..22
                            note = oligonucleotide target sequence
source                      1..22
                            mol_type = other DNA
                            organism = synthetic construct
SEQUENCE: 828
cgtgtgcact tcgcttcacc tc                                              22

SEQ ID NO: 829              moltype = DNA  length = 16
FEATURE                     Location/Qualifiers
misc_feature                1..16
                            note = oligonucleotide target sequence
source                      1..16
                            mol_type = other DNA
                            organism = synthetic construct
SEQUENCE: 829
ccgtctgtgc cttctc                                                     16

SEQ ID NO: 830              moltype = DNA  length = 15
FEATURE                     Location/Qualifiers
misc_feature                1..15
                            note = oligonucleotide target sequence
source                      1..15
                            mol_type = other DNA
                            organism = synthetic construct
SEQUENCE: 830
cgatccatac tgcgg                                                      15

SEQ ID NO: 831              moltype = DNA  length = 15
FEATURE                     Location/Qualifiers
misc_feature                1..15
                            note = oligonucleotide target sequence
source                      1..15
                            mol_type = other DNA
                            organism = synthetic construct
SEQUENCE: 831
tggctcagtt tacta                                                      15

SEQ ID NO: 832              moltype = DNA  length = 15
FEATURE                     Location/Qualifiers
misc_feature                1..15
                            note = oligonucleotide sequence motif
source                      1..15
                            mol_type = other DNA
                            organism = synthetic construct
SEQUENCE: 832
ccgcagtatg gatcg                                                      15

SEQ ID NO: 833              moltype = DNA  length = 15
FEATURE                     Location/Qualifiers
misc_feature                1..15
                            note = oligonucleotide target sequence
source                      1..15
                            mol_type = other DNA
                            organism = synthetic construct
SEQUENCE: 833
ctagtgccat ttgtt                                                      15

SEQ ID NO: 834              moltype = DNA  length = 15
FEATURE                     Location/Qualifiers
misc_feature                1..15
                            note = oligonucleotide sequence motif
source                      1..15
                            mol_type = other DNA
                            organism = synthetic construct
SEQUENCE: 834
tagtaaactg agcca                                                      15

SEQ ID NO: 835              moltype = DNA  length = 16
FEATURE                     Location/Qualifiers
misc_feature                1..16
                            note = oligonucleotide sequence motif
source                      1..16
                            mol_type = other DNA
                            organism = synthetic construct
SEQUENCE: 835
ctagtaaact gagcca                                                     16
```

```
SEQ ID NO: 836          moltype = DNA   length = 15
FEATURE                 Location/Qualifiers
misc_feature            1..15
                        note = oligonucleotide sequence motif
source                  1..15
                        mol_type = other DNA
                        organism = synthetic construct
SEQUENCE: 836
ctagtaaact gagcc                                                       15

SEQ ID NO: 837          moltype = DNA   length = 15
FEATURE                 Location/Qualifiers
misc_feature            1..15
                        note = oligonucleotide sequence motif
source                  1..15
                        mol_type = other DNA
                        organism = synthetic construct
SEQUENCE: 837
gcactagtaa actga                                                       15

SEQ ID NO: 838          moltype = DNA   length = 16
FEATURE                 Location/Qualifiers
misc_feature            1..16
                        note = oligonucleotide sequence motif
source                  1..16
                        mol_type = other DNA
                        organism = synthetic construct
SEQUENCE: 838
ggcactagta aactga                                                      16

SEQ ID NO: 839          moltype = DNA   length = 15
FEATURE                 Location/Qualifiers
misc_feature            1..15
                        note = oligonucleotide sequence motif
source                  1..15
                        mol_type = other DNA
                        organism = synthetic construct
SEQUENCE: 839
caacggggta aaggt                                                       15

SEQ ID NO: 840          moltype = DNA   length = 15
FEATURE                 Location/Qualifiers
misc_feature            1..15
                        note = oligonucleotide sequence motif
source                  1..15
                        mol_type = other DNA
                        organism = synthetic construct
SEQUENCE: 840
cagtatggat cggca                                                       15

SEQ ID NO: 841          moltype = DNA   length = 16
FEATURE                 Location/Qualifiers
misc_feature            1..16
                        note = oligonucleotide sequence motif
source                  1..16
                        mol_type = other DNA
                        organism = synthetic construct
SEQUENCE: 841
ttccgcagta tggatc                                                      16

SEQ ID NO: 842          moltype = DNA   length = 15
FEATURE                 Location/Qualifiers
misc_feature            1..15
                        note = oligonucleotide sequence motif
source                  1..15
                        mol_type = other DNA
                        organism = synthetic construct
SEQUENCE: 842
ttccgcagta tggat                                                       15

SEQ ID NO: 843          moltype = DNA   length = 16
FEATURE                 Location/Qualifiers
misc_feature            1..16
                        note = oligonucleotide sequence motif
source                  1..16
                        mol_type = other DNA
                        organism = synthetic construct
SEQUENCE: 843
```

```
                                   -continued gttccgcagt atggat                                                    16

SEQ ID NO: 844          moltype = DNA  length = 15
FEATURE                 Location/Qualifiers
misc_feature            1..15
                        note = oligonucleotide sequence motif
source                  1..15
                        mol_type = other DNA
                        organism = synthetic construct SEQUENCE: 844
gttccgcagt atgga                                                     15

SEQ ID NO: 845          moltype = DNA  length = 16
FEATURE                 Location/Qualifiers
misc_feature            1..16
                        note = oligonucleotide sequence motif
source                  1..16
                        mol_type = other DNA
                        organism = synthetic construct SEQUENCE: 845
agttccgcag tatgga                                                    16

SEQ ID NO: 846          moltype = DNA  length = 15
FEATURE                 Location/Qualifiers
misc_feature            1..15
                        note = oligonucleotide sequence motif
source                  1..15
                        mol_type = other DNA
                        organism = synthetic construct SEQUENCE: 846
agttccgcag tatgg                                                     15

SEQ ID NO: 847          moltype = DNA  length = 16
FEATURE                 Location/Qualifiers
misc_feature            1..16
                        note = oligonucleotide sequence motif
source                  1..16
                        mol_type = other DNA
                        organism = synthetic construct SEQUENCE: 847
gagttccgca gtatgg                                                    16

SEQ ID NO: 848          moltype = DNA  length = 15
FEATURE                 Location/Qualifiers
misc_feature            1..15
                        note = oligonucleotide sequence motif
source                  1..15
                        mol_type = other DNA
                        organism = synthetic construct SEQUENCE: 848
gagttccgca gtatg                                                     15

SEQ ID NO: 849          moltype = DNA  length = 16
FEATURE                 Location/Qualifiers
misc_feature            1..16
                        note = oligonucleotide sequence motif
source                  1..16
                        mol_type = other DNA
                        organism = synthetic construct SEQUENCE: 849
ggagttccgc agtatg                                                    16

SEQ ID NO: 850          moltype = DNA  length = 16
FEATURE                 Location/Qualifiers
misc_feature            1..16
                        note = oligonucleotide sequence motif
source                  1..16
                        mol_type = other DNA
                        organism = synthetic construct SEQUENCE: 850
taaagagagg tgcgcc                                                    16

SEQ ID NO: 851          moltype = DNA  length = 15
FEATURE                 Location/Qualifiers
misc_feature            1..15
                        note = oligonucleotide sequence motif
source                  1..15
                        mol_type = other DNA
                        organism = synthetic construct
```

```
SEQUENCE: 851
taaagagagg tgcgc                                                          15

SEQ ID NO: 852           moltype = DNA  length = 16
FEATURE                  Location/Qualifiers
misc_feature             1..16
                         note = oligonucleotide sequence motif
source                   1..16
                         mol_type = other DNA
                         organism = synthetic construct
SEQUENCE: 852
gtaaagagag gtgcgc                                                         16

SEQ ID NO: 853           moltype = DNA  length = 15
FEATURE                  Location/Qualifiers
misc_feature             1..15
                         note = oligonucleotide sequence motif
source                   1..15
                         mol_type = other DNA
                         organism = synthetic construct
SEQUENCE: 853
gtaaagagag gtgcg                                                          15

SEQ ID NO: 854           moltype = DNA  length = 16
FEATURE                  Location/Qualifiers
misc_feature             1..16
                         note = oligonucleotide sequence motif
source                   1..16
                         mol_type = other DNA
                         organism = synthetic construct
SEQUENCE: 854
cgtaaagaga ggtgcg                                                         16

SEQ ID NO: 855           moltype = DNA  length = 15
FEATURE                  Location/Qualifiers
misc_feature             1..15
                         note = oligonucleotide sequence motif
source                   1..15
                         mol_type = other DNA
                         organism = synthetic construct
SEQUENCE: 855
cgtaaagaga ggtgc                                                          15

SEQ ID NO: 856           moltype = DNA  length = 16
FEATURE                  Location/Qualifiers
misc_feature             1..16
                         note = oligonucleotide sequence motif
source                   1..16
                         mol_type = other DNA
                         organism = synthetic construct
SEQUENCE: 856
gcgtaaagag aggtgc                                                         16

SEQ ID NO: 857           moltype = DNA  length = 15
FEATURE                  Location/Qualifiers
misc_feature             1..15
                         note = oligonucleotide sequence motif
source                   1..15
                         mol_type = other DNA
                         organism = synthetic construct
SEQUENCE: 857
gcgtaaagag aggtg                                                          15

SEQ ID NO: 858           moltype = DNA  length = 16
FEATURE                  Location/Qualifiers
misc_feature             1..16
                         note = oligonucleotide sequence motif
source                   1..16
                         mol_type = other DNA
                         organism = synthetic construct
SEQUENCE: 858
cgcgtaaaga gaggtg                                                         16

SEQ ID NO: 859           moltype = DNA  length = 16
FEATURE                  Location/Qualifiers
misc_feature             1..16
                         note = oligonucleotide sequence motif
source                   1..16
                         mol_type = other DNA
```

```
                    organism = synthetic construct
SEQUENCE: 859
tgagaaggca cagacg                                                     16

SEQ ID NO: 860       moltype = DNA  length = 15
FEATURE              Location/Qualifiers
misc_feature         1..15
                     note = oligonucleotide sequence motif
source               1..15
                     mol_type = other DNA
                     organism = synthetic construct
SEQUENCE: 860
gcctcaaggt cggtc                                                      15

SEQ ID NO: 861       moltype = DNA  length = 15
FEATURE              Location/Qualifiers
misc_feature         1..15
                     note = oligonucleotide sequence motif
source               1..15
                     mol_type = other DNA
                     organism = synthetic construct
SEQUENCE: 861
atgcctacag cctcc                                                      15

SEQ ID NO: 862       moltype = DNA  length = 16
FEATURE              Location/Qualifiers
misc_feature         1..16
                     note = oligonucleotide sequence motif
source               1..16
                     mol_type = other DNA
                     organism = synthetic construct
SEQUENCE: 862
accaatttat gcctac                                                     16
```